United States Patent
Cha et al.

(10) Patent No.: US 11,952,376 B2
(45) Date of Patent: *Apr. 9, 2024

(54) SUBSTITUTED AMINO ACIDS AS INTEGRIN INHIBITORS

(71) Applicant: Pliant Therapeutics, Inc., South San Francisco, CA (US)

(72) Inventors: Jacob Cha, San Bruno, CA (US); Manuel Muñoz, Vallejo, CA (US); Maureen Reilly, Burlingame, CA (US); Nicole Cooper, Oakland, CA (US); Katerina Leftheris, San Mateo, CA (US); David J. Morgans, Jr., South San Francisco, CA (US); Timothy Hom, Sunnyvale, CA (US); Yajun Zheng, Foster City, CA (US); Christopher Bailey, Mountain View, CA (US); Darren Finkelstein, Hillsborough, CA (US)

(73) Assignee: PLIANT THERAPEUTICS, INC., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/504,384

(22) Filed: Oct. 18, 2021

(65) Prior Publication Data

US 2022/0144829 A1 May 12, 2022

Related U.S. Application Data

(63) Continuation of application No. 16/596,649, filed on Oct. 8, 2019, now Pat. No. 11,180,494.

(60) Provisional application No. 62/742,901, filed on Oct. 8, 2018.

(51) Int. Cl.
| A61K 31/519 | (2006.01) |
| C07D 471/04 | (2006.01) |
| C07D 487/04 | (2006.01) |
| C07D 519/00 | (2006.01) |

(52) U.S. Cl.
CPC ......... *C07D 471/04* (2013.01); *C07D 519/00* (2013.01)

(58) Field of Classification Search
CPC .......................... A61K 31/519; C07D 487/04
USPC ....................................... 514/262.1; 544/262
See application file for complete search history.

(56) References Cited

U.S. PATENT DOCUMENTS

| 6,048,861 | A | 4/2000 | Askew, Jr. et al. |
| 10,131,658 | B2 | 11/2018 | Degrado |
| 10,214,522 | B2 | 2/2019 | Degrado |
| 10,604,520 | B2 | 3/2020 | Jiang |
| 10,696,672 | B2 | 6/2020 | Morgans, Jr. |
| 10,793,564 | B2 | 10/2020 | Cha |
| 11,180,494 | B2 | 11/2021 | Cha et al. |
| 2002/0010176 | A1 | 1/2002 | Askew |
| 2012/0289481 | A1 | 11/2012 | O'neil |
| 2014/0349968 | A1 | 11/2014 | O'neil |
| 2016/0264566 | A1 | 9/2016 | Degrado |
| 2016/0376266 | A1 | 12/2016 | Degrado |
| 2018/0008583 | A1 | 1/2018 | Fukunaga |
| 2018/0093984 | A1 | 4/2018 | Jiang |
| 2019/0276449 | A1 | 9/2019 | Cha |
| 2019/0322663 | A1 | 10/2019 | Morgans, Jr. |
| 2020/0109141 | A1 | 4/2020 | Cha |
| 2020/0123151 | A1 | 4/2020 | Leftheris et al. |
| 2020/0352942 | A1 | 11/2020 | Cha et al. |
| 2021/0017171 | A1 | 1/2021 | Cha et al. |
| 2021/0024516 | A1 | 1/2021 | Jiang |
| 2021/0122747 | A1 | 4/2021 | Morgans, Jr. et al. |

FOREIGN PATENT DOCUMENTS

| WO | 2008157162 A1 | 12/2008 |
| WO | 2015048819 A1 | 4/2015 |
| WO | 2016046226 A1 | 3/2016 |
| WO | 2016145258 A1 | 9/2016 |
| WO | 2016153054 A1 | 9/2016 |
| WO | 2018009501 A1 | 1/2018 |
| WO | 2018049068 A1 | 3/2018 |
| WO | 2018089355 A1 | 5/2018 |
| WO | 2018119087 A1 | 6/2018 |

(Continued)

OTHER PUBLICATIONS

Jordan, V. C. Nature Reviews: Drug Discovery, 2, 2003, 205.*

(Continued)

*Primary Examiner* — Douglas M Willis

(74) *Attorney, Agent, or Firm* — MORRISON & FOERSTER LLP; Kraig Anderson, Pliant; Johannes Hull, Pliant

(57) ABSTRACT

The invention relates to compounds of formula (I):

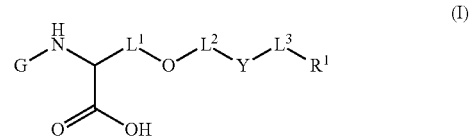

or a salt thereof, wherein $R^1$, G, $L^1$, $L^2$, $L^3$, and Y are as described herein. Compounds of formula (I) and pharmaceutical compositions thereof are inhibitors of one, or both of, $\alpha v \beta_1$ integrin and $\alpha v \beta_6$ integrin that are useful for treating fibrosis such as in nonalcoholic steatohepatitis (NASH), idiopathic pulmonary fibrosis (IPF) and nonspecific interstitial pneumonia (NSIP).

172 Claims, 23 Drawing Sheets

(56) References Cited

FOREIGN PATENT DOCUMENTS

| WO | 2018160521 A2 | 9/2018 | |
| WO | 2018160522 A1 | 9/2018 | |
| WO | 2018160521 A3 | 10/2018 | |
| WO | 2019173653 A1 | 9/2019 | |
| WO | 2019175776 A1 | 9/2019 | |
| WO | 2020006315 A1 | 1/2020 | |
| WO | 2020047207 A1 | 3/2020 | |
| WO | 2020047208 A1 | 3/2020 | |
| WO | 2020047239 A1 | 3/2020 | |
| WO | WO-2020076862 A1 * | 4/2020 | ......... A61K 31/4375 |
| WO | 2020210404 A1 | 10/2020 | |
| WO | 2021225912 A1 | 11/2021 | |

OTHER PUBLICATIONS

Dörwald, F. Zaragoza. Side Reactions in Organic Synthesis: A Guide to Successful Synthesis Design, Weinheim: Wiley-VCH Verlag GmbH & Co. KGaA, 2005, Preface.*

Extended European Search Report, dated Jun. 7, 2022, for European Patent Application No. 19870448.8, 14 pages.

Alphascreen® (2009). "Exclusive AlphaScreen and AlphaLISA Assay Technology," Perkin Elmer, Waltham, MA., 68 pages.

International Preliminary Report on Patentability, dated Apr. 8, 2021, for PCT Application No. PCT/US2019/55252, filed Oct. 8, 2019, 9 pages.

International Search Report and Written Opinion, dated Jan. 23, 2020, for PCT Application No. PCT/US2019/55252, filed Oct. 8, 2019, 16 pages.

Invitation to Pay Additional Fees, dated Nov. 21, 2019, for PCT Application No. PCT/US2019/55252, filed Oct. 8, 2019, 3 pages.

Kim, D.S. et al. (2006). "Classification and Natural History of the Idiopathic Interstitial Pneumonias," Proc. Am. Thorac. Soc. 3:285-292.

Kinder, B.W. et al. (Jun. 2007). "Idiopathic Nonspecific Interstitial Pneumonia. Lung Manifestation of Undifferentiated Connective Tissue Disease?," Am. J. Respir. Crit. Care Med. 176:691-697.

Remington: The Science and Practice of Pharmacy, 21st Edition, Journal of Pharmacy Technology, Mar.-Apr. 2006, 22:133-135.

Ullman, E.F. et al. (Jun. 7, 1994). "Luminescent Oxygen Channeling Immunoassay: Measurement of Particle Binding Kinetics by Chemiluminescence," Proc. Natl. Acad. Sci. USA 91(12):5426-5430.

* cited by examiner

Table 2*

*Reference to compound numbers in the table in some instances depicts a particular stereoisomeric form of the compound number, as will be evident from the chemical structure depicted.

Table B-2

| Example # | Compound # | Proximity-based assay | | Example # | Compound # | Proximity-based assay | |
|---|---|---|---|---|---|---|---|
| | | $\alpha_v\beta_1$ | $\alpha_v\beta_6$ | | | $\alpha_v\beta_1$ | $\alpha_v\beta_6$ |
| 1 | 1 | - | ≤50 | 31 | 38 | - | ≤50 |
| 2 | 8 | >50-250 | >500-1000 | 32 | 39 | - | ≤50 |
| 3 | 9 | >50-250 | >50-250 | 33 | 40 | - | ≤50 |
| 4 | 2 | - | >1000 | 34 | 41 | - | >50-250 |
| 5 | 3 | - | >50-250 | 35 | 42 | - | >50-250 |
| 6 | 4 | - | >250-500 | 36 | 43 | - | ≤50 |
| 7 | 5 | - | >50-250 | 37 | 44 | - | ≤50 |
| 8 | 6 | - | >250-500 | 38 | 45 | - | >50-250 |
| 9 | 7 | - | >50-250 | 39 | 46 | - | >50-250 |
| 10 | 15 | - | >50-250 | 40 | 47 | - | >50-250 |
| 11 | 18 | - | >50-250 | 41 | 48 | - | ≤50 |
| 12 | 19 | - | >50-250 | 42 | 49 | - | >50-250 |
| 13 | 22 | - | >250-500 | 43 | 49 | - | >500-1000 |
| 14 | 14 | - | ≤50 | 44 | 50 | - | >50-250 |
| 15 | 24 | - | ≤50 | 45 | 51 | - | >50-250 |
| 16 | 24 | - | ≤50 | 46 | 49 | - | >500-1000 |
| 17 | 25 | - | ≤50 | 47 | 49 | - | >250-500 |
| 18 | 19 | - | >50-250 | 48 | 52 | - | >250-500 |
| 19 | 26 | - | ≤50 | 49 | 53 | - | >50-250 |
| 20 | 27 | - | ≤50 | 50 | 54 | - | ≤50 |
| 21 | 28 | - | ≤50 | 51 | 55 | - | ≤50 |
| 22 | 29 | - | ≤50 | 52 | 56 | - | ≤50 |
| 23 | 30 | - | ≤50 | 53 | 57 | - | >50-250 |
| 24 | 31 | - | ≤50 | 54 | 58 | - | >50-250 |
| 25 | 32 | - | ≤50 | 55 | 59 | - | >250-500 |
| 26 | 33 | - | ≤50 | 56 | 60 | - | >50-250 |
| 27 | 34 | - | ≤50 | 57 | 61 | - | >500-1000 |
| 28 | 35 | - | ≤50 | 58 | 44 | - | >1000 |
| 29 | 36 | - | ≤50 | 59 | 51 | - | >1000 |
| 30 | 37 | - | ≤50 | 60 | 14 | - | >50-250 |

FIG. 2

| Example # | Compound # | Proximity-based assay | | Example # | Compound # | Proximity-based assay | |
|---|---|---|---|---|---|---|---|
| | | $\alpha_V\beta_1$ | $\alpha_V\beta_6$ | | | $\alpha_V\beta_1$ | $\alpha_V\beta_6$ |
| 61 | 53 | - | >1000 | 91 | 74 | ≤50 | >500-1000 |
| 62 | 44 | - | ≤50 | 92 | 75 | - | >500-1000 |
| 63 | 51 | - | ≤50 | 93 | 76 | - | >50-250 |
| 64 | 14 | - | ≤50 | 94 | 77 | - | >50-250 |
| 65 | 53 | - | ≤50 | 95 | 78 | - | >1000 |
| 66 | 36 | >50-250 | >50-250 | 96 | 78 | - | >250-500 |
| 67 | 51 | ≤50 | >50-250 | 97 | 66 | - | ≤50 |
| 68 | 44 | - | >250-500 | 98 | 67 | - | ≤50 |
| 69 | 53 | - | >250-500 | 99 | 68 | - | ≤50 |
| 70 | 49 | ≤50 | >50-250 | 100 | 69 | - | >50-250 |
| 71 | 49 | - | >1000 | 101 | 19 | ≤50 | ≤50 |
| 72 | 62 | - | ≤50 | 102 | 70 | - | ≤50 |
| 73 | 63 | - | >50-250 | 103 | 71 | - | ≤50 |
| 74 | 64 | >1000 | >1000 | 104 | 72 | - | ≤50 |
| 75 | 64 | - | >500-1000 | 105 | 73 | - | ≤50 |
| 76 | 64 | - | >500-1000 | 106 | 74 | - | ≤50 |
| 77 | 64 | - | >1000 | 107 | 75 | - | ≤50 |
| 78 | 65 | - | >1000 | 108 | 76 | - | ≤50 |
| 79 | 65 | - | >50-250 | 109 | 77 | - | ≤50 |
| 80 | 65 | - | >50-250 | 110 | 78 | - | >250-500 |
| 81 | 65 | - | >1000 | 111 | 78 | - | ≤50 |
| 82 | 66 | - | >250-500 | 112 | 79 | - | >50-250 |
| 83 | 67 | - | >1000 | 113 | 80 | - | ≤50 |
| 84 | 68 | - | ≤50 | 114 | 81 | - | ≤50 |
| 85 | 69 | - | >500-1000 | 115 | 82 | - | ≤50 |
| 86 | 19 | - | >250-500 | 116 | 83 | ≤50 | ≤50 |
| 87 | 70 | - | >250-500 | 117 | 84 | - | ≤50 |
| 88 | 71 | - | >50-250 | 118 | 85 | - | ≤50 |
| 89 | 72 | - | >500-1000 | 119 | 86 | - | >50-250 |
| 90 | 73 | - | >250-500 | 120 | 87 | - | ≤50 |

FIG. 2 (continued)

| Example # | Compound # | Proximity-based assay | | Example # | Compound # | Proximity-based assay | |
|---|---|---|---|---|---|---|---|
| | | $\alpha_V\beta_1$ | $\alpha_V\beta_6$ | | | $\alpha_V\beta_1$ | $\alpha_V\beta_6$ |
| 121 | 88 | - | ≤50 | 150 | 112 | - | >250-500 |
| 122 | 89 | - | >50-250 | 151 | 113 | - | ≤50 |
| 123 | 90 | - | ≤50 | 152 | 114 | - | ≤50 |
| 124 | 91 | - | ≤50 | 153 | 115 | - | ≤50 |
| 125 | 92 | - | >50-250 | 154 | 113 | - | >500-1000 |
| 126 | 93 | - | ≤50 | 155a | 115 | - | ≤50 |
| 127 | 94 | - | ≤50 | 155b | 115 | - | ≤50 |
| 128 | 95 | - | >50-250 | 156a | 116 | - | ≤50 |
| 129 | 96 | - | >50-250 | 156b | 116 | - | ≤50 |
| 130 | 97 | - | >50-250 | 157 | 117 | - | ≤50 |
| 131 | 98 | - | ≤50 | 158 | 118 | - | >50-250 |
| 132 | 99 | - | >50-250 | 159 | 119 | - | ≤50 |
| 133 | 100 | - | ≤50 | 160 | 120 | - | ≤50 |
| 134 | 101 | - | >50-250 | 161 | 121 | - | >50-250 |
| 135 | 102 | - | >50-250 | 162a | 122 | - | >50-250 |
| 136 | 103 | - | ≤50 | 162b | 122 | - | ≤50 |
| 137 | 104 | - | >500-1000 | 163a | 123 | - | ≤50 |
| 138 | 100 | - | >50-250 | 163b | 123 | - | >50-250 |
| 139 | 104 | - | >1000 | 164 | 124 | - | >50-250 |
| 140 | 105 | - | >250-500 | 165 | 125 | - | >50-250 |
| 141 | 105 | - | ≤50 | 166 | 126 | - | ≤50 |
| 142 | 106 | - | >50-250 | 167 | 127 | - | ≤50 |
| 143 | 107 | - | >500-1000 | 168 | 128 | - | ≤50 |
| 144 | 108 | - | >500-1000 | 169 | 129 | - | ≤50 |
| 145a | 109 | - | >500-1000 | 170 | 130 | - | ≤50 |
| 145b | 109 | - | >50-250 | 171 | 131 | - | ≤50 |
| 146 | 108 | - | >50-250 | 172 | 132 | - | ≤50 |
| 147 | 110 | - | ≤50 | 173 | 133 | - | ≤50 |
| 148 | 111 | - | >500-1000 | 174 | 134 | - | >50-250 |
| 149 | 111 | - | >50-250 | 175a | 135 | - | >50-250 |

FIG. 2 (continued)

| Example # | Compound # | Proximity-based assay | | Example # | Compound # | Proximity-based assay | |
|---|---|---|---|---|---|---|---|
| | | $\alpha_V\beta_1$ | $\alpha_V\beta_6$ | | | $\alpha_V\beta_1$ | $\alpha_V\beta_6$ |
| 175b | 135 | - | >50-250 | 203 | 157 | ≤50 | ≤50 |
| 176a | 136 | - | ≤50 | 204 | 158 | ≤50 | ≤50 |
| 176b | 136 | - | >50-250 | 205 | 159 | ≤50 | >500-1000 |
| 180a | 138 | ≤50 | ≤50 | 206 | 160 | ≤50 | >1000 |
| 180b | 138 | ≤50 | ≤50 | 207 | 161 | ≤50 | >250-500 |
| 177 | 137 | ≤50 | ≤50 | 208 | 162 | ≤50 | ≤50 |
| 178 | 124 | - | >50-250 | 209 | 162 | ≤50 | ≤50 |
| 179 | 124 | ≤50 | >50-250 | 210 | 163 | ≤50 | ≤50 |
| 181 | 139 | ≤50 | >1000 | 211 | 164 | ≤50 | >50-250 |
| 182 | 140 | ≤50 | >500-1000 | 212 | 165 | ≤50 | >1000 |
| 183 | 134 | ≤50 | >250-500 | 213 | 166 | ≤50 | >50-250 |
| 184 | 141 | ≤50 | >50-250 | 214 | 167 | ≤50 | >50-250 |
| 185 | 142 | - | ≤50 | 215 | 168 | ≤50 | >50-250 |
| 186 | 143 | ≤50 | >500-1000 | 216 | 169 | ≤50 | >50-250 |
| 187 | 144 | ≤50 | >500-1000 | 217 | 170 | ≤50 | >250-500 |
| 188 | 145 | ≤50 | >1000 | 218 | 171 | ≤50 | >500-1000 |
| 189 | 146 | ≤50 | >500-1000 | 219 | 172 | - | ≤50 |
| 190 | 147 | ≤50 | >250-500 | 220 | 173 | - | >250-500 |
| 191 | 124 | ≤50 | ≤50 | 221 | 174 | - | >500-1000 |
| 192 | 134 | ≤50 | >50-250 | 222 | 175 | - | >500-1000 |
| 193 | 148 | ≤50 | >50-250 | 223 | 148 | - | ≤50 |
| 194 | 149 | ≤50 | >50-250 | 224 | 178 | - | >50-250 |
| 195 | 150 | ≤50 | >1000 | 225 | 187 | ≤50 | >1000 |
| 196 | 151 | ≤50 | >50-250 | 226 | 188 | ≤50 | >1000 |
| 197 | 152 | ≤50 | >500-1000 | 227 | 178 | ≤50 | >50-250 |
| 198 | 153 | ≤50 | >1000 | 228 | 178 | ≤50 | ≤50 |
| 199 | 149 | ≤50 | >1000 | 229 | 186 | ≤50 | ≤50 |
| 200 | 154 | ≤50 | ≤50 | 230 | 210 | ≤50 | >50-250 |
| 201 | 155 | ≤50 | >50-250 | 231 | 211 | ≤50 | >1000 |
| 202 | 156 | ≤50 | ≤50 | 232 | 212 | ≤50 | >250-500 |

FIG. 2 (continued)

| Example # | Compound # | Proximity-based assay $\alpha_V\beta_1$ | Proximity-based assay $\alpha_V\beta_6$ | Example # | Compound # | Proximity-based assay $\alpha_V\beta_1$ | Proximity-based assay $\alpha_V\beta_6$ |
|---|---|---|---|---|---|---|---|
| 233 | 213 | ≤50 | >500-1000 | 263 | 243 | ≤50 | >1000 |
| 234 | 214 | ≤50 | >500-1000 | 264 | 244 | ≤50 | >50-250 |
| 235 | 215 | ≤50 | >50-250 | 265 | 245 | ≤50 | >50-250 |
| 236 | 216 | ≤50 | ≤50 | 266 | 246 | ≤50 | >50-250 |
| 237 | 217 | ≤50 | >1000 | 267 | 247 | ≤50 | >1000 |
| 238 | 218 | ≤50 | >50-250 | 268 | 248 | ≤50 | >1000 |
| 239 | 219 | ≤50 | >50-250 | 269 | 249 | ≤50 | ≤50 |
| 240 | 220 | ≤50 | ≤50 | 270 | 250 | ≤50 | >50-250 |
| 241 | 221 | ≤50 | >50-250 | 271 | 251 | ≤50 | >500-1000 |
| 242 | 222 | ≤50 | >1000 | 272 | 252 | ≤50 | >50-250 |
| 243 | 223 | ≤50 | >50-250 | 273 | 253 | ≤50 | >250-500 |
| 244 | 224 | ≤50 | >250-500 | 274 | 254 | ≤50 | >250-500 |
| 245 | 225 | ≤50 | >250-500 | 275 | 255 | ≤50 | >1000 |
| 246 | 226 | ≤50 | >50-250 | 276 | 256 | - | ≤50 |
| 247 | 227 | ≤50 | ≤50 | 277 | 257 | >50-250 | >50-250 |
| 248 | 228 | ≤50 | >1000 | 278 | 258 | ≤50 | >50-250 |
| 249 | 229 | ≤50 | >500-1000 | 279 | 259 | ≤50 | ≤50 |
| 250 | 230 | ≤50 | >50-250 | 280 | 260 | ≤50 | ≤50 |
| 251 | 231 | ≤50 | >1000 | 281 | 261 | ≤50 | ≤50 |
| 252 | 232 | ≤50 | ≤50 | 282 | 262 | ≤50 | >50-250 |
| 253 | 233 | ≤50 | >50-250 | 283 | 263 | ≤50 | >500-1000 |
| 254 | 234 | ≤50 | >50-250 | 284 | 264 | ≤50 | >50-250 |
| 255 | 235 | ≤50 | >1000 | 285 | 265 | ≤50 | ≤50 |
| 256 | 236 | >500-1000 | >1000 | 286 | 266 | ≤50 | >50-250 |
| 257 | 237 | ≤50 | >50-250 | 287 | 267 | ≤50 | ≤50 |
| 258 | 238 | ≤50 | >1000 | 288 | 268 | ≤50 | ≤50 |
| 259 | 239 | ≤50 | >1000 | 289 | 269 | >50-250 | ≤50 |
| 260 | 240 | ≤50 | >250-500 | 290 | 270 | ≤50 | ≤50 |
| 261 | 241 | ≤50 | ≤50 | 291 | 271 | ≤50 | ≤50 |
| 262 | 242 | ≤50 | >50-250 | 292 | 272 | ≤50 | ≤50 |

FIG. 2 (continued)

| Example # | Compound # | Proximity-based assay $\alpha_V\beta_1$ | Proximity-based assay $\alpha_V\beta_6$ | Example # | Compound # | Proximity-based assay $\alpha_V\beta_1$ | Proximity-based assay $\alpha_V\beta_6$ |
|---|---|---|---|---|---|---|---|
| 293 | 273 | ≤50 | ≤50 | 323 | 303 | ≤50 | >50-250 |
| 294 | 274 | ≤50 | >50-250 | 324 | 304 | ≤50 | >500-1000 |
| 295 | 275 | ≤50 | ≤50 | 325 | 305 | >50-250 | >1000 |
| 296 | 276 | ≤50 | >50-250 | 326 | 306 | ≤50 | >500-1000 |
| 297 | 277 | ≤50 | ≤50 | 327 | 307 | ≤50 | ≤50 |
| 298 | 278 | ≤50 | >1000 | 328 | 308 | ≤50 | >1000 |
| 299 | 279 | ≤50 | ≤50 | 329 | 309 | >250-500 | >1000 |
| 300 | 280 | ≤50 | ≤50 | 330 | 310 | >250-500 | >1000 |
| 301 | 281 | ≤50 | >50-250 | 331 | 311 | ≤50 | >500-1000 |
| 302 | 282 | ≤50 | >250-500 | 332 | 312 | ≤50 | >1000 |
| 303 | 283 | ≤50 | >1000 | 333 | 313 | ≤50 | >1000 |
| 304 | 284 | ≤50 | >500-1000 | 334 | 314 | >50-250 | >1000 |
| 305 | 285 | ≤50 | >1000 | 335 | 315 | ≤50 | >50-250 |
| 306 | 286 | ≤50 | >250-500 | 336 | 316 | ≤50 | >1000 |
| 307 | 287 | ≤50 | >500-1000 | 337 | 317 | ≤50 | >250-500 |
| 308 | 288 | >50-250 | >1000 | 338 | 318 | ≤50 | >1000 |
| 309 | 289 | ≤50 | >50-250 | 339 | 319 | >50-250 | >1000 |
| 310 | 290 | >50-250 | >1000 | 340 | 320 | >250-500 | >1000 |
| 311 | 291 | ≤50 | >500-1000 | 341 | 321 | ≤50 | ≤50 |
| 312 | 292 | ≤50 | >50-250 | 342 | 322 | >1000 | >1000 |
| 313 | 293 | ≤50 | >1000 | 343 | 323 | >1000 | >1000 |
| 314 | 294 | ≤50 | >50-250 | 344 | 324 | >500-1000 | >1000 |
| 315 | 295 | ≤50 | >50-250 | 345 | 325 | >1000 | >1000 |
| 316 | 296 | ≤50 | >50-250 | 346 | 326 | - | ≤50 |
| 317 | 297 | ≤50 | ≤50 | 347 | 327 | - | >50-250 |
| 318 | 298 | >50-250 | >1000 | 348 | 328 | - | ≤50 |
| 319 | 299 | ≤50 | ≤50 | 349 | 329 | - | ≤50 |
| 320 | 300 | >50-250 | >500-1000 | 350 | 10 | - | ≤50 |
| 321 | 301 | ≤50 | >1000 | 351 | 11 | - | ≤50 |
| 322 | 302 | ≤50 | ≤50 | 352 | 12 | - | ≤50 |

FIG. 2 (continued)

| Example # | Compound # | Proximity-based assay ||
|---|---|---|---|
| | | $\alpha_V\beta_1$ | $\alpha_V\beta_6$ |
| 353 | 13 | - | >50-250 |
| 354 | 16 | - | >500-1000 |
| 355 | 17 | - | - |
| 356 | 20 | - | - |
| 357 | 21 | - | ≤50 |
| 358 | 178 | - | >50-250 |
| 359 | 179 | - | ≤50 |
| 360 | 180 | - | ≤50 |
| 361 | 181 | - | ≤50 |
| 362 | 182 | - | ≤50 |
| 363 | 183 | - | ≤50 |
| 364 | 184 | - | >50-250 |
| 365 | 185 | - | >500-1000 |
| 12A | 19 | - | >50-250 |

FIG. 2 (continued)

SUBSTITUTED AMINO ACIDS AS INTEGRIN INHIBITORS

RELATED APPLICATIONS

This application is a Continuation Patent Application of U.S. patent application Ser. No. 16/596,649, filed Oct. 8, 2019 which claims the benefit of priority to U.S. Provisional Pat. App. No. 62/742,901, filed Oct. 8, 2018, the entire contents of which are incorporated by reference herein.

FIELD OF THE INVENTION

This disclosure relates generally to therapeutic agents that may be useful as αvβ6 integrin inhibitors. The therapeutic agents may be used in the treatment or prophylactic treatment of fibrosis such as idiopathic pulmonary fibrosis (IPF) and nonspecific interstitial pneumonia (NSIP).

BACKGROUND

Fibrosis, a pathologic feature of many diseases, is caused by a dysfunction in the body's natural ability to repair damaged tissues. If left untreated, fibrosis can result in scarring of vital organs causing irreparable damage and eventual organ failure.

Patients with nonalcoholic fatty liver disease (NAFLD) may progress from simple steatosis to nonalcoholic steatohepatitis (NASH) and then fibrosis. While liver fibrosis is reversible in its initial stages, progressive liver fibrosis can lead to cirrhosis.

Fibrosis in the kidney, characterized by glomerulosclerosis and tubulointerstitial fibrosis, is the final common manifestation of a wide variety of chronic kidney diseases (CKD). Irrespective of the initial causes, progressive CKD often results in widespread tissue scarring that leads to destruction of kidney parenchyma and end-stage renal failure, a devastating condition that requires dialysis or kidney replacement.

Scleroderma encompasses a spectrum of complex and variable conditions primarily characterized by fibrosis, vascular alterations, and autoimmunity. The scleroderma spectrum of disorders share the common feature of fibrosis, resulting in hardening or thickening of the skin. For some patients, this hardening occurs only in limited areas, but for others, it can spread to other major organs.

Following myocardial infarction, cardiac structural remodeling is associated with an inflammatory reaction, resulting in scar formation at the site of the infarction. This scar formation is a result of fibrotic tissue deposition which may lead to reduced cardiac function and disruption of electrical activity within the heart.

Crohn's Disease is a chronic disease of unknown etiology tending to progress even in the setting of medical or surgical treatment. Intestinal fibrosis is among the most common complications of Crohn's disease, resulting in stricture formation in the small intestine and colon.

Idiopathic pulmonary fibrosis (IPF) is a chronic, progressive, fibrosing disease of unknown etiology, occurring in adults and limited to the lungs. In IPF, the lung tissue becomes thickened, stiff, and scarred. As lung fibrosis progresses, it becomes more difficult for the lungs to transfer oxygen into the bloodstream and the organs do not receive the oxygen needed to function properly. IPF currently affects approximately 200,000 people in the U.S., resulting in 40,000 deaths per year. Patients diagnosed with IPF experience progressive breathlessness and eventually, complete respiratory failure.

Primary biliary cholangitis (PBC), also known as primary biliary cirrhosis, is a chronic disease of the liver that causes damage and fibrosis in the liver. It results from a slow, progressive destruction of the small bile ducts of the liver, causing bile and other toxins to build up in the liver, a condition called cholestasis. Over time, this leads to scarring and fibrosis in both the liver and biliary tract.

Nonspecific interstitial pneumonia (NSIP) is a rare disorder that affects the tissue that surrounds and separates the tiny air sacs of the lungs. These air sacs, called the alveoli, are where the exchange of oxygen and carbon dioxide takes place between the lungs and the bloodstream. Interstitial pneumonia is a disease in which the mesh-like walls of the alveoli become inflamed. The pleura (a thin covering that protects and cushions the lungs and the individual lobes of the lungs) might become inflamed as well. There are two primary forms of NSIP—cellular and fibrotic. The cellular form is defined mainly by inflammation of the cells of the interstitium. The fibrotic form is defined by thickening and scarring of lung tissue. This scarring is known as fibrosis and is irreversible. When the lung tissue thickens or becomes scarred, it does not function as effectively. Breathing becomes less efficient, and there are lower levels of oxygen in the blood. (Kim et al., Proc. Am. Thorac. Soc. (2006) 3:285-292; Lynch, D., Radiology (2001) 221:583-584; Kinder et al., Am. J. Respir. Crit. Care Med. (2007) 176: 691-697)

Available courses of treatment are scarce, as there are currently no options on the market proven to have an effect on long-term patient survival or symptomatology. There remains a need for treatment of fibrotic diseases.

The αvβ6 integrin is expressed in epithelial cells, and binds to the latency-associated peptide of transforming growth factor-β1 (TGFβ1) and mediates TGFβ1 activation. Its expression level is significantly increased after injury to lung and cholangiocytes, and plays a critical in vivo role in tissue fibrosis. Increased levels are also associated with increased mortality in IPF and NSIP patients.

Primary sclerosing cholangitis (PSC) involves bile duct inflammation, and fibrosis that obliterates the bile ducts. The resulting impediment to the flow of bile to the intestines can lead to cirrhosis of the liver and subsequent complications such as liver failure and liver cancer. Expression of αvβ6 is elevated in liver and bile duct of PSC patients.

The present disclosure provides for αvβ6 integrin inhibitors that may be useful for treatment of fibrosis.

SUMMARY

Disclosed are amino acid compounds that are αvβ6 integrin inhibitors, compositions containing these compounds and methods for treating diseases mediated by αvβ6 integrin such as a fibrotic disease.

In one aspect, provided is a compound of formula (I), or any variation thereof, or a salt thereof (e.g., a pharmaceutically acceptable salt thereof), as detailed herein.

Further provided is a pharmaceutical composition comprising a compound of formula (I), or any variation thereof detailed herein, or a salt thereof (e.g., a pharmaceutically acceptable salt thereof), and a pharmaceutically acceptable carrier or excipient.

In another aspect, provided is a method of treating a fibrotic disease or condition in an individual (such as a human) in need thereof comprising administering to the individual a therapeutically effective amount of a compound of formula (I), or any variation thereof detailed herein, or a pharmaceutically acceptable salt thereof. In some embodiments, the fibrotic disease or condition is pulmonary, liver, renal, cardiac, dermal, or gastrointestinal fibrosis. In other embodiments the fibrotic disease or condition is idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primarily biliary cholangitis (also known as primary biliary cirrhosis), systemic sclerosis associated interstitial lung disease, scleroderma (also known as systemic sclerosis), diabetic nephropathy, diabetic kidney disease, focal segmental glomerulosclerosis, chronic kidney disease, and Crohn's Disease.

In another aspect, provided is a method of delaying the onset and/or development of a fibrotic disease or condition in an individual (such as a human) who is at risk for developing a fibrotic disease or condition comprising administering to the individual a therapeutically effective amount of a compound of formula (I), or any variation thereof detailed herein, or a pharmaceutically acceptable salt thereof. In some embodiments, the disease or condition is pulmonary, liver, renal, cardiac, dermal, or gastrointestinal fibrosis. In other embodiments the fibrotic disease or condition is idiopathic pulmonary fibrosis, interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis, primarily biliary cholangitis (also known as primary biliary cirrhosis), systemic sclerosis associated interstitial lung disease, scleroderma (also known as systemic sclerosis), diabetic nephropathy, diabetic kidney disease, focal segmental glomerulosclerosis, chronic kidney disease, and Crohn's Disease.

Also provided is a compound of formula (I), or any variation thereof detailed herein, or a pharmaceutical composition thereof, for the treatment of a fibrotic disease.

Also provided is use of a compound of formula (I), or any variation thereof detailed herein, or a pharmaceutically acceptable salt thereof, in the manufacture of a medicament for the treatment of a fibrotic disease.

Further provided is a kit comprising a compound of formula (I), or any variation thereof detailed herein, or a pharmaceutically acceptable salt thereof. In some embodiments, the kit comprises instructions for use according to a method described herein, such as a method of treating a fibrotic disease in an individual.

In another aspect, provided is a method of making a compound of formula (I) or any variation thereof. Also provided are compound intermediates useful in synthesis of a compound of formula (I), or any variation thereof.

It is understood that aspects and variations described herein also include "consisting" and/or "consisting essentially of" aspects and variations.

BRIEF DESCRIPTION OF THE FIGURES

FIG. 2, Table B-2 shows biological data for various compounds disclosed herein.

DETAILED DESCRIPTION

Figure 1:
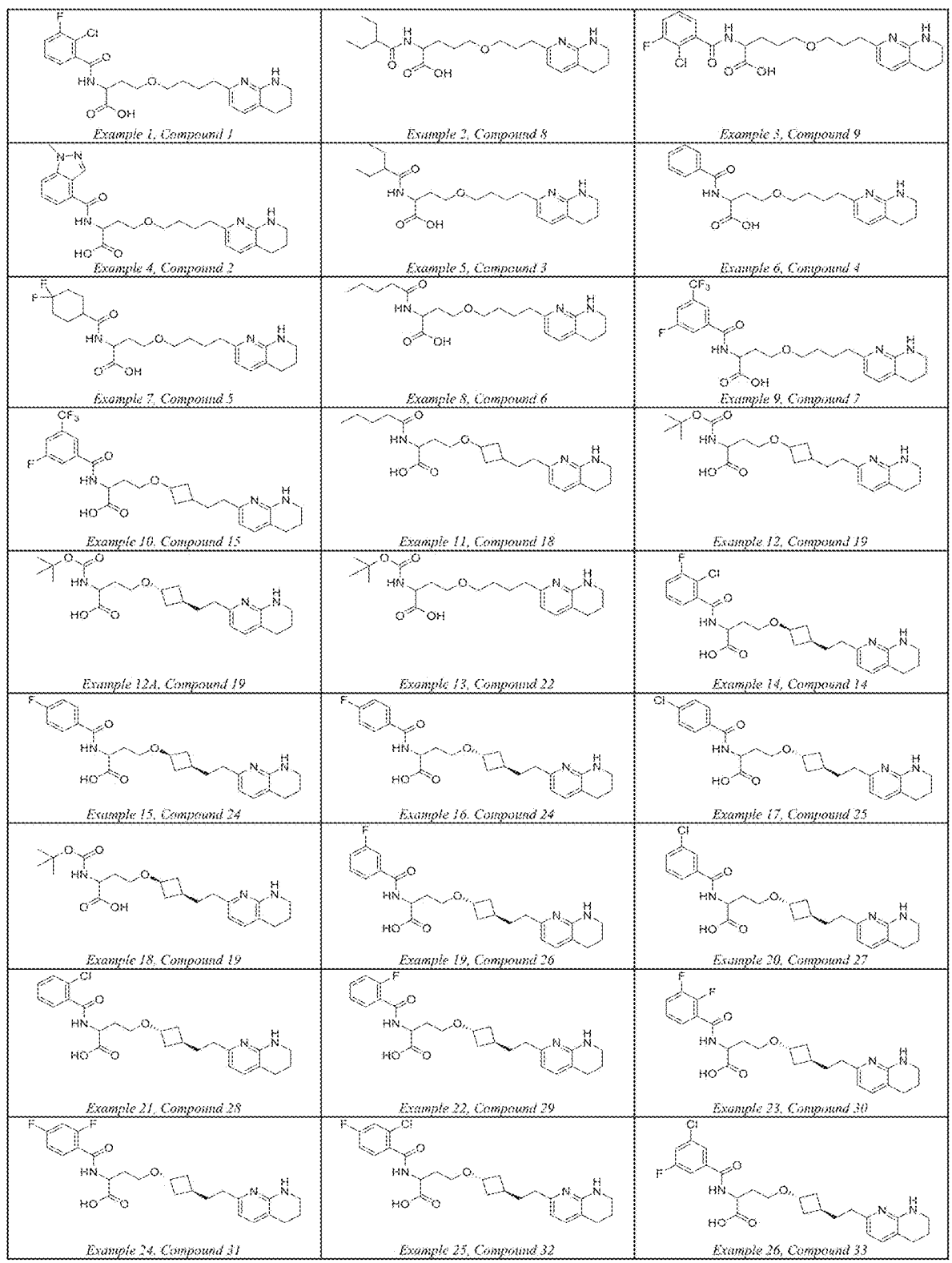
FIG. 1, Table 2 shows chemical structures for various compounds disclosed herein. Reference to compound numbers in the table in some instances depicts a particular stereoisomeric form of the compound number, as will be evident from the chemical structure depicted.
Figure 1:
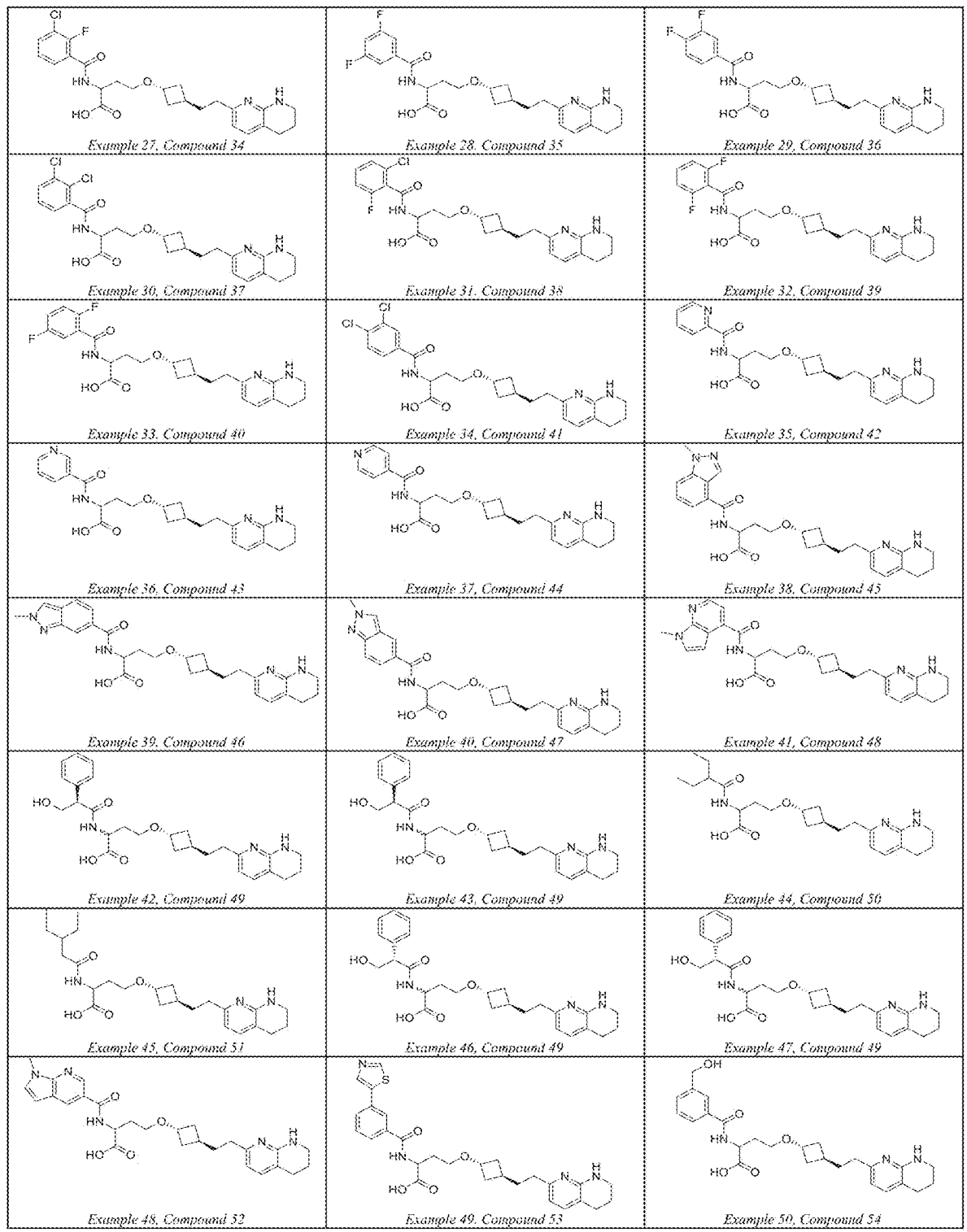
Figure 1:
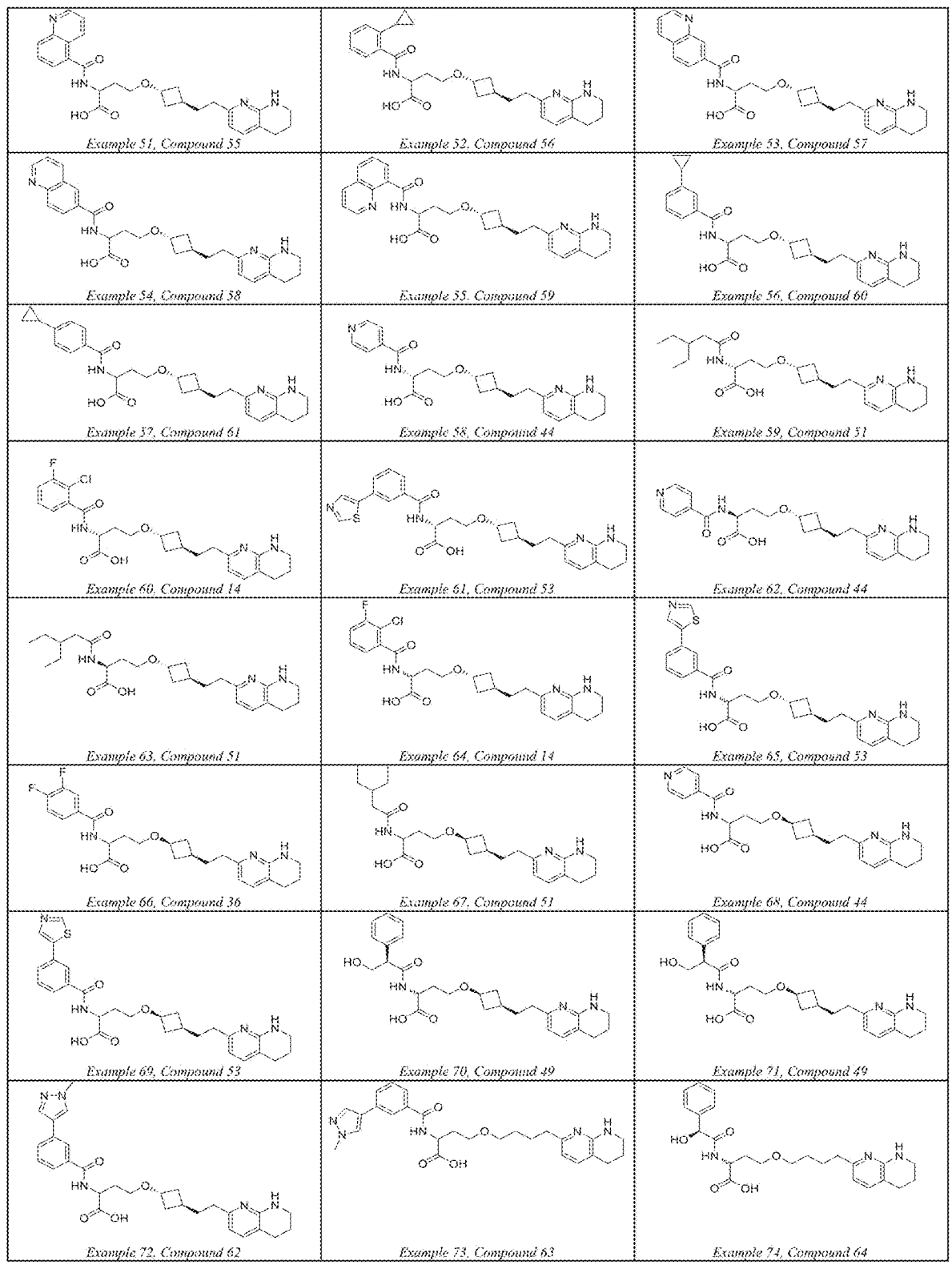
Figure 1:
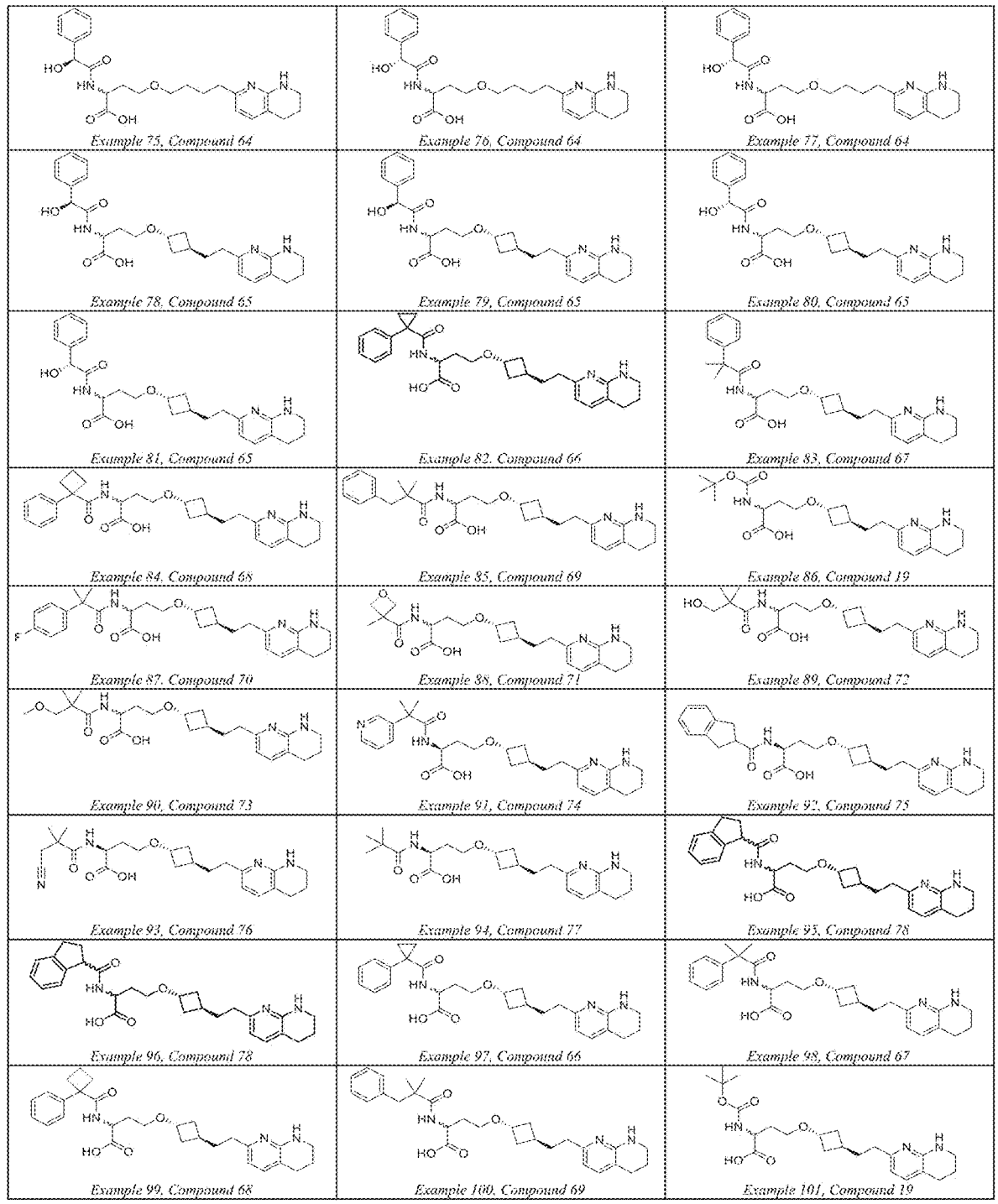
Figure 1:
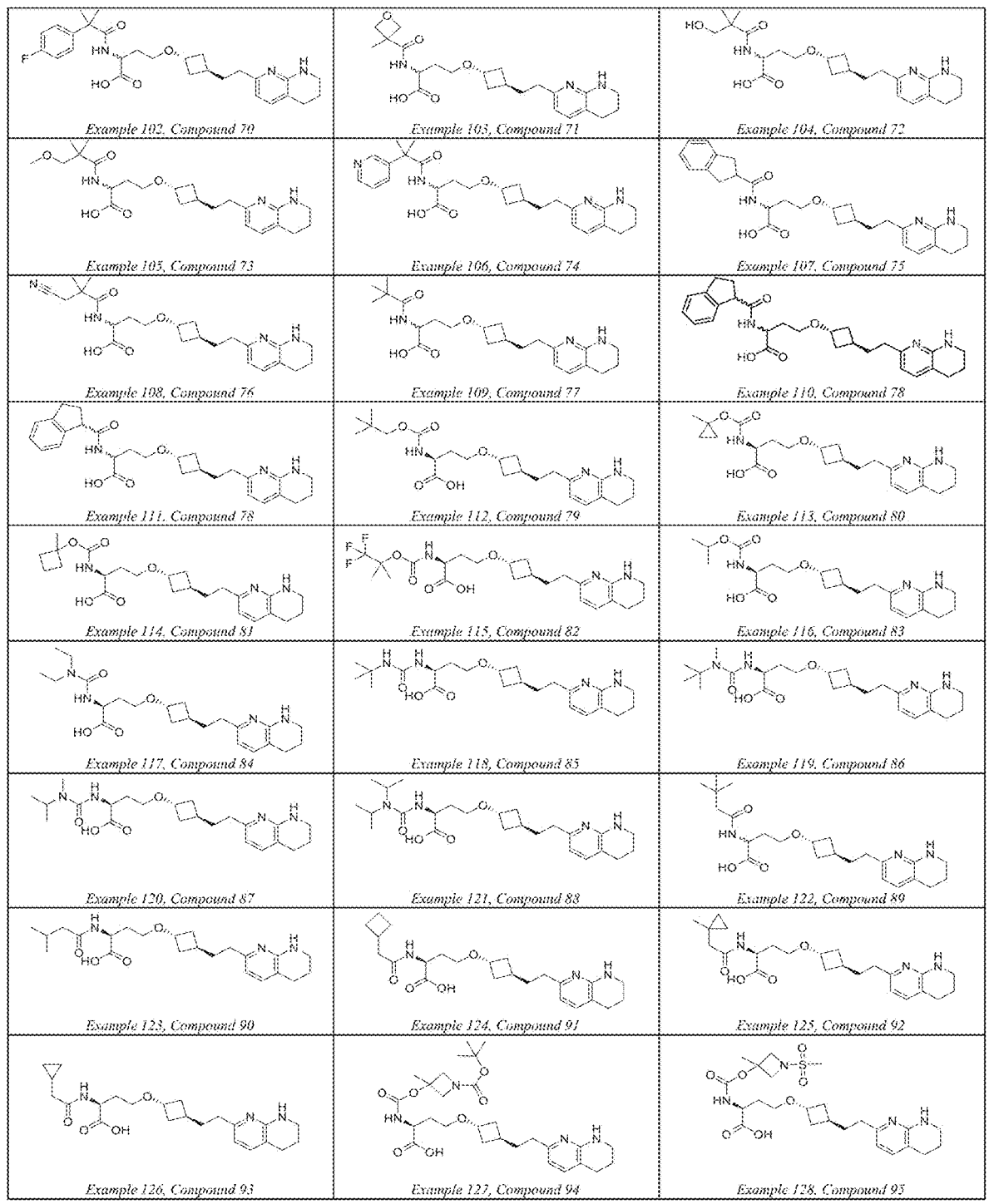
Figure 1:
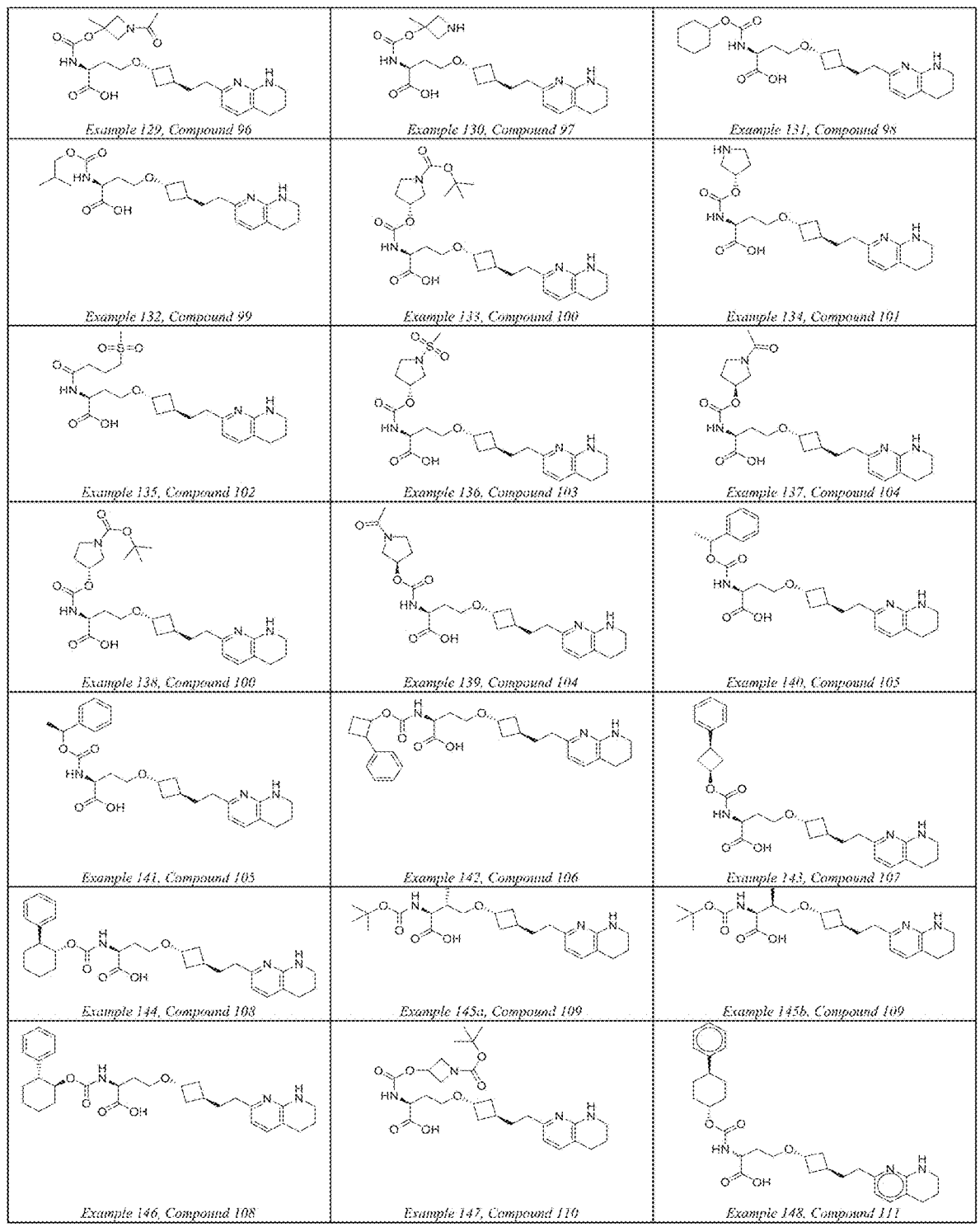
Figure 1:
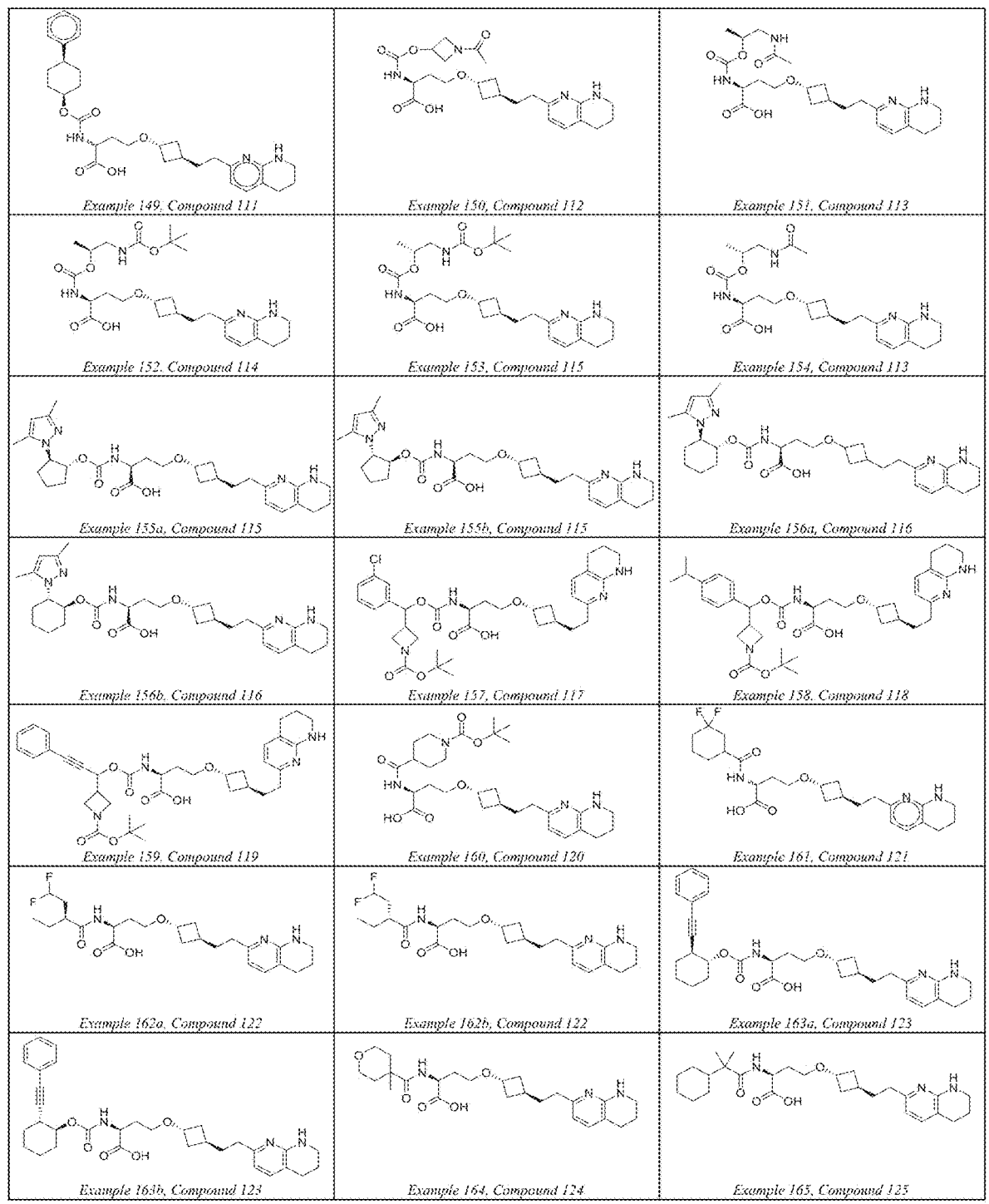
Figure 1:
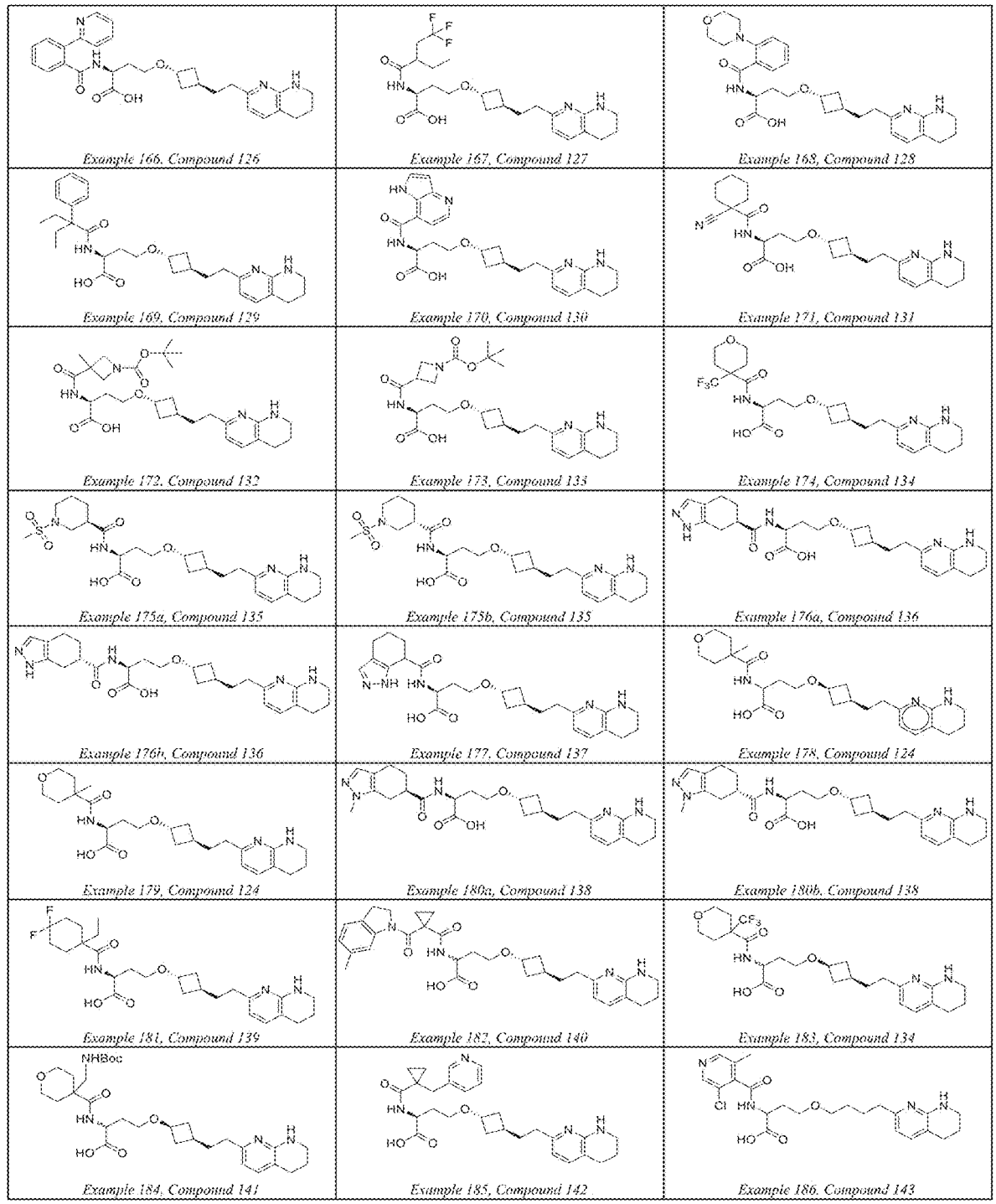
Figure 1:
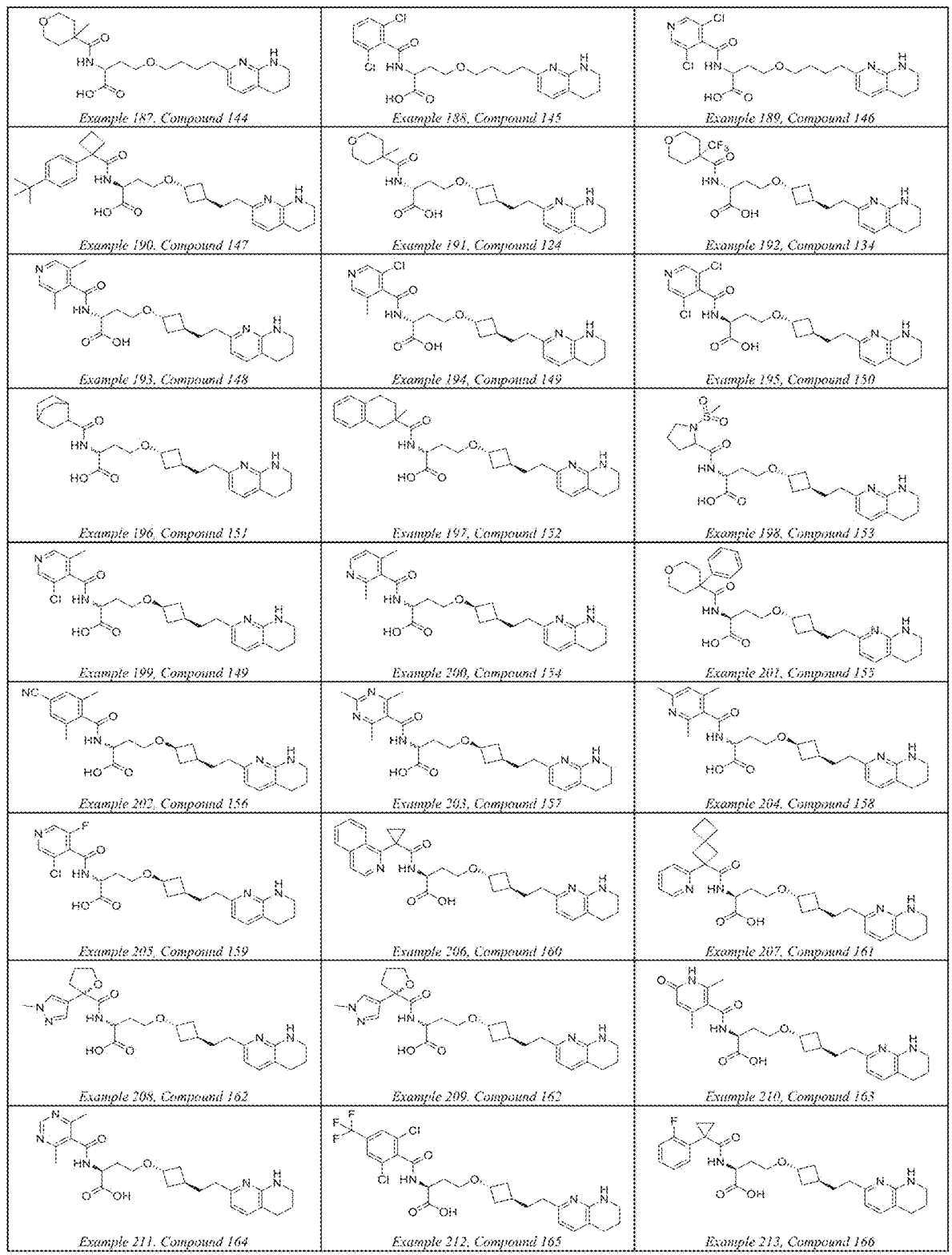
Figure 1:
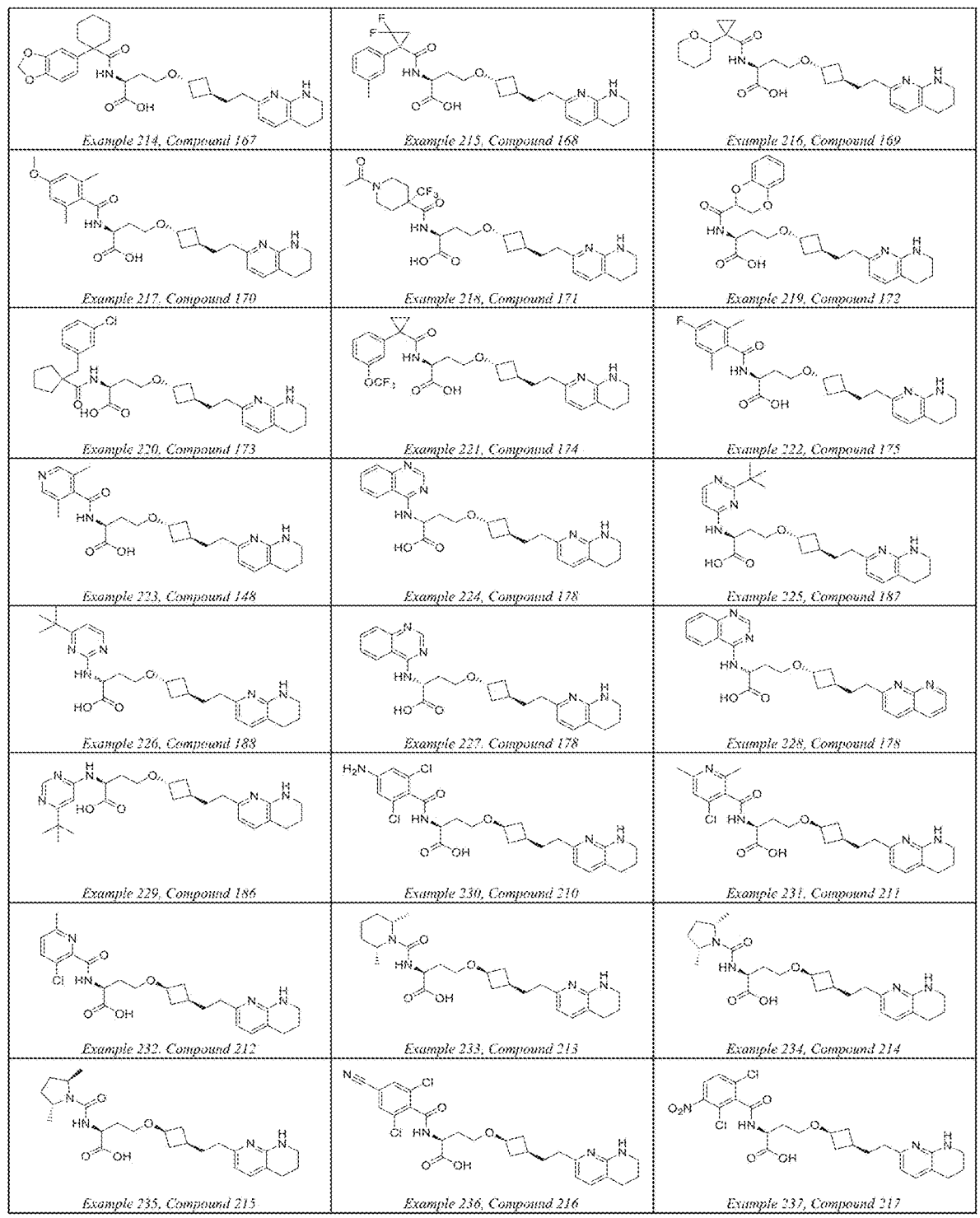
Figure 1:
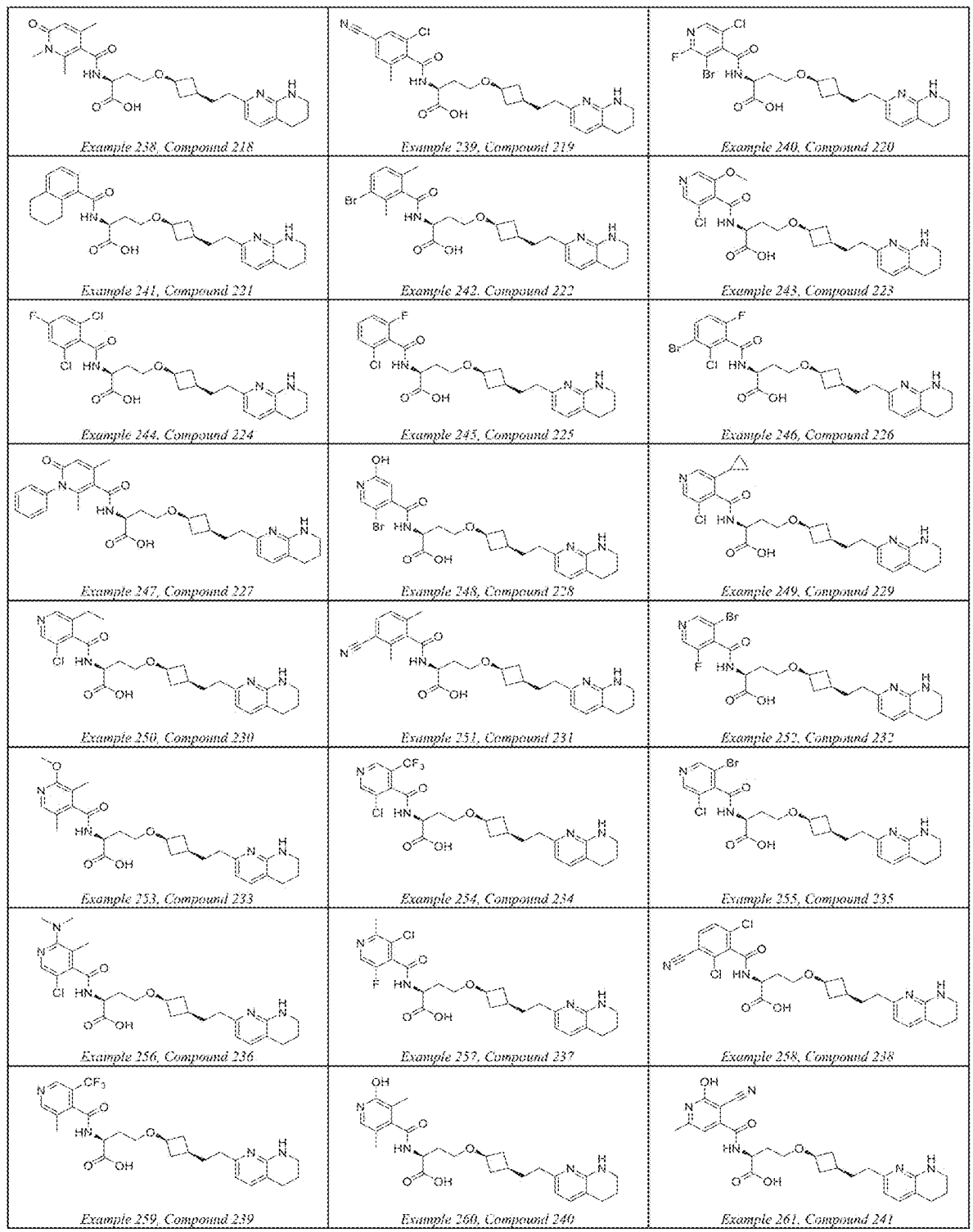
Figure 1:
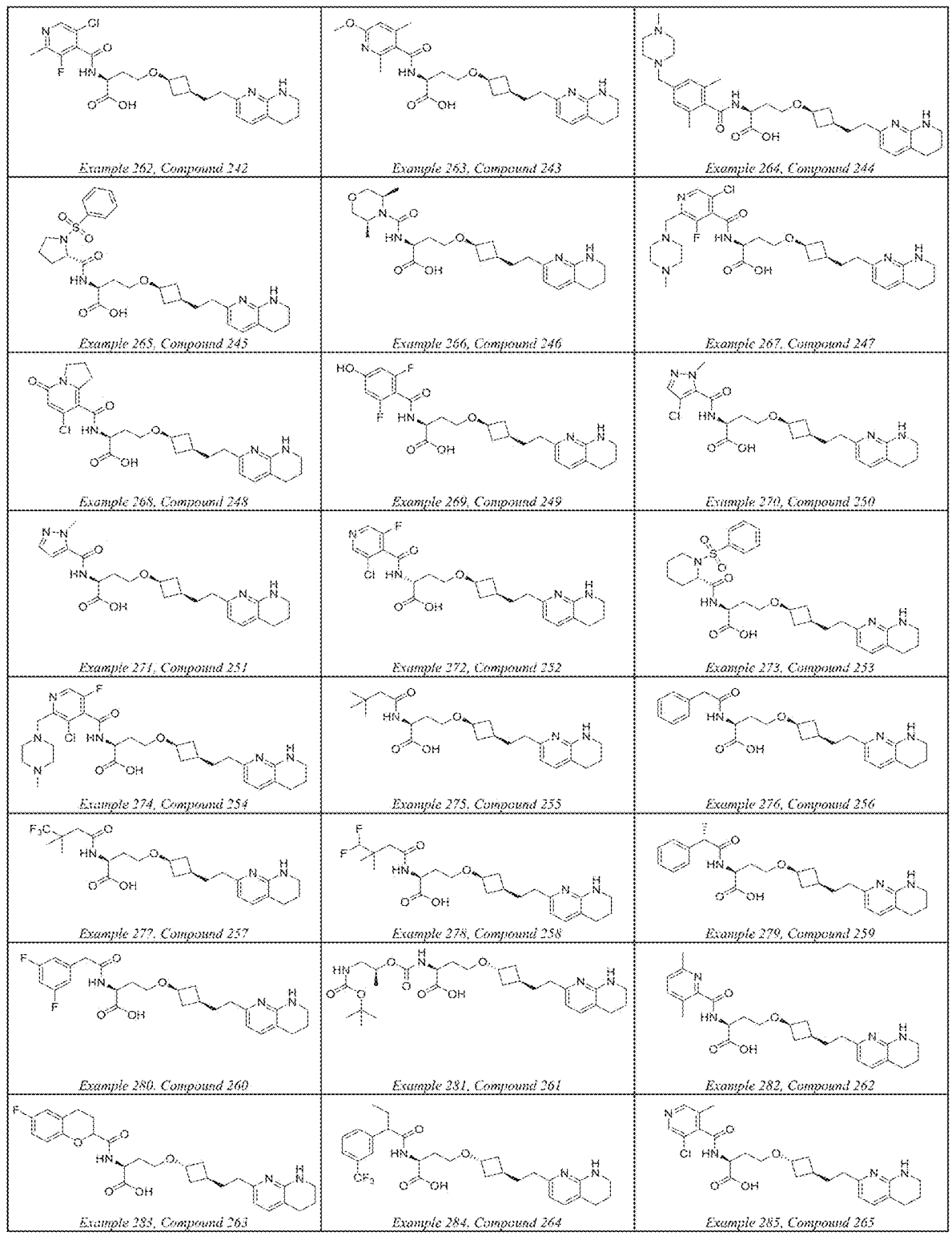
Figure 1:
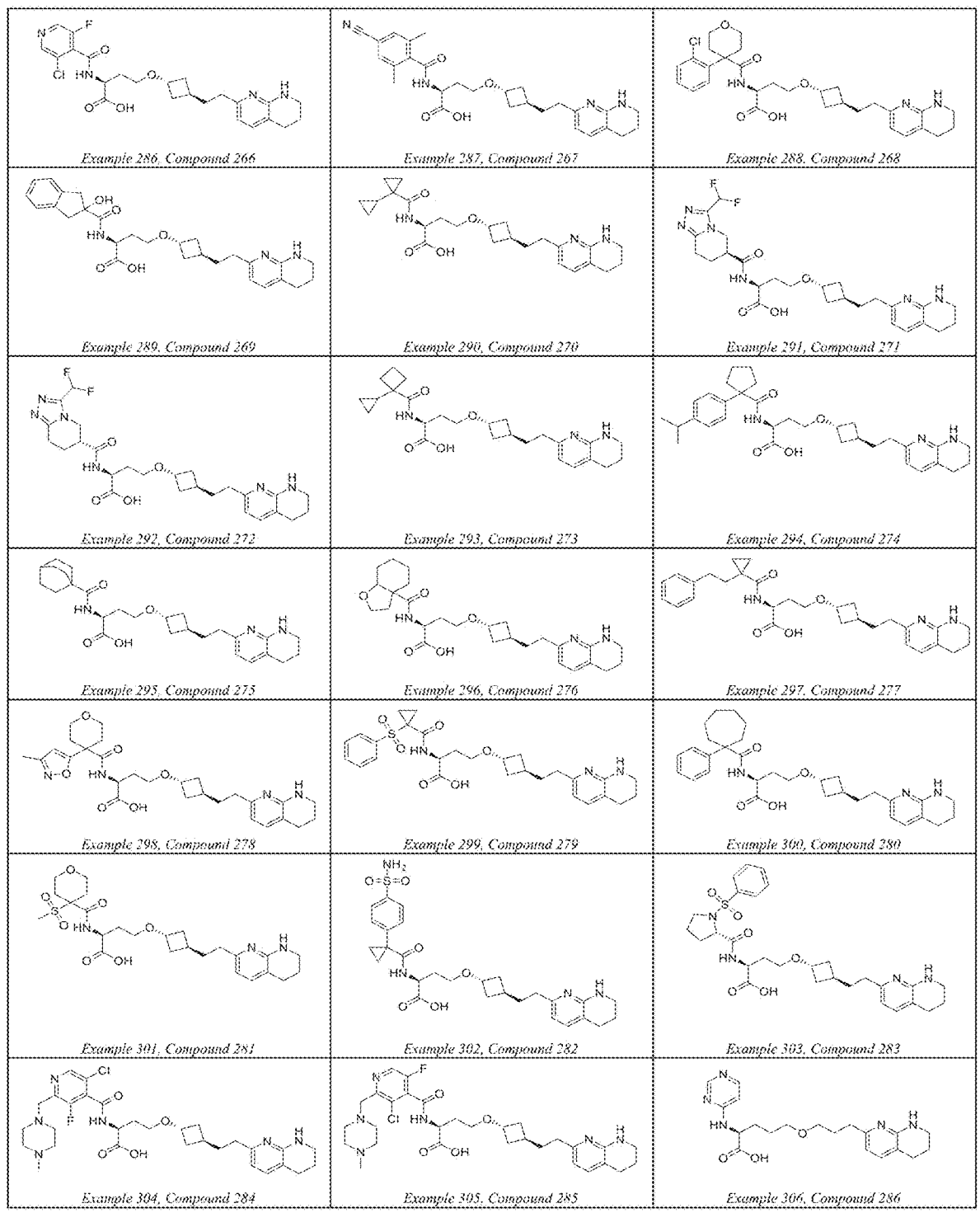
Figure 1:
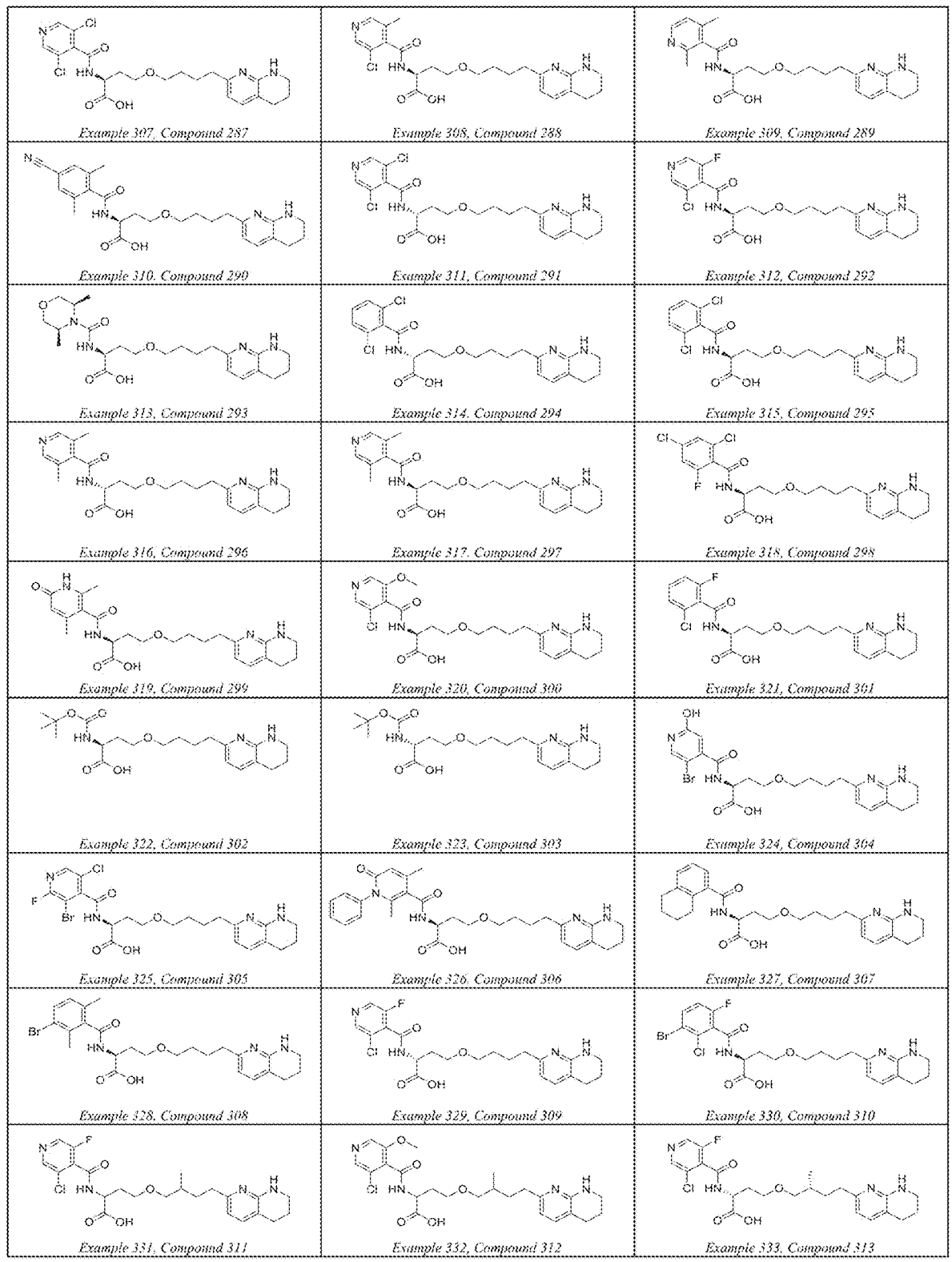
Figure 1:
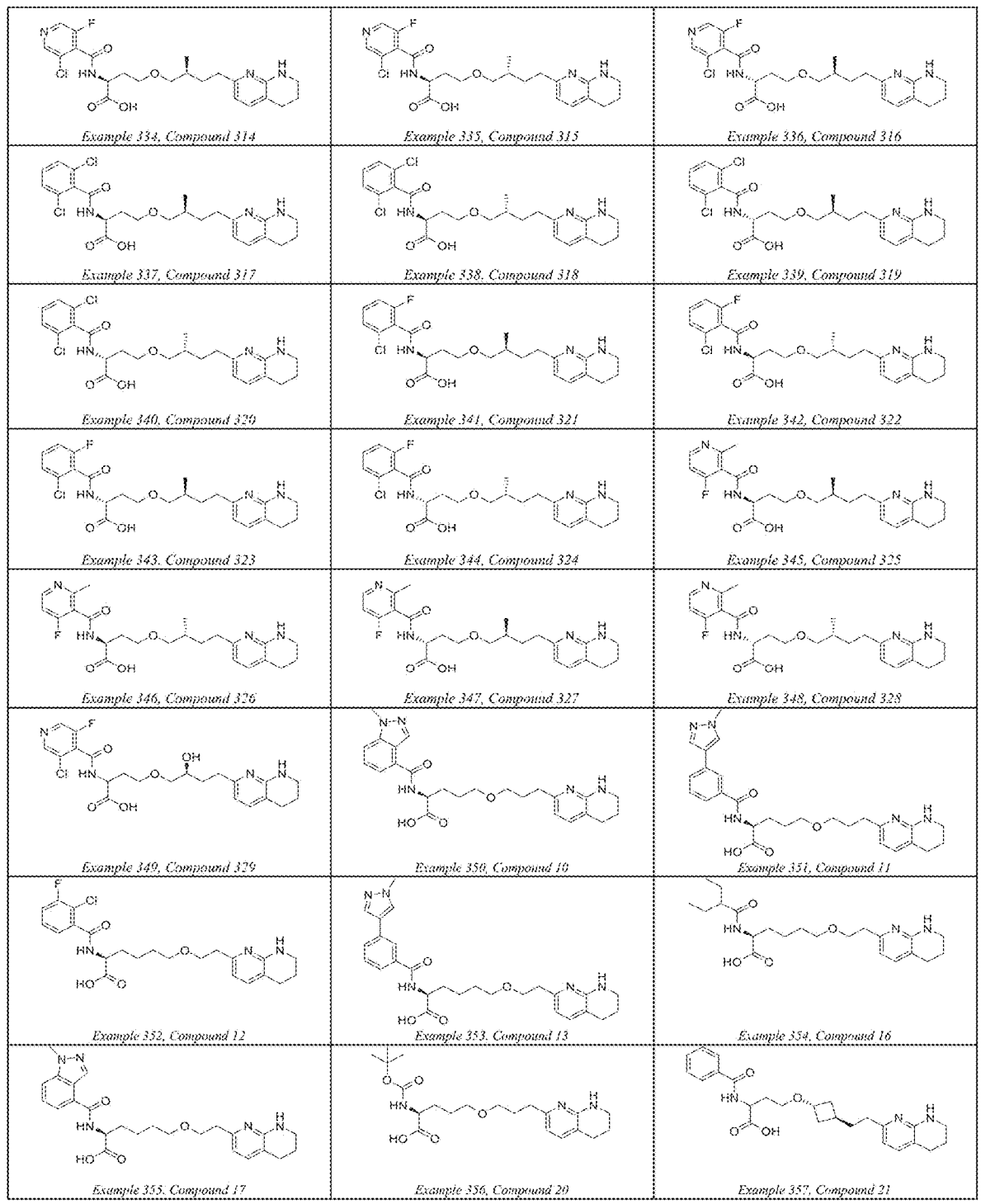
Figure 1:
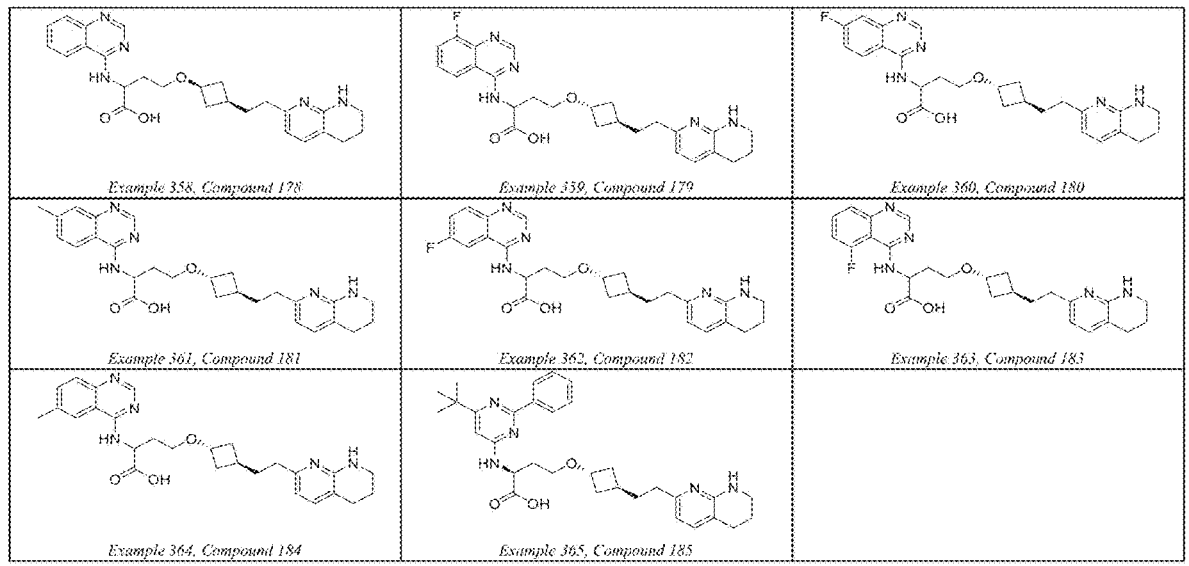

The invention provides, inter alia, compounds of formula (I), and variations thereof, pharmaceutical compositions comprising compounds of formula (I), and methods of using such compounds and compositions in treating fibrotic diseases. Compounds and pharmaceutical compositions comprising salts of compounds of formula (I) are provided as well.

Definitions

For use herein, unless clearly indicated otherwise, use of the terms "a", "an" and the like refers to one or more.

Reference to "about" a value or parameter herein includes (and describes) embodiments that are directed to that value or parameter per se. For example, description referring to "about X" includes description of "X". Likewise, reference to a value "X" also includes description of "about X".

"Alkyl" as used herein refers to and includes, unless otherwise stated, a saturated linear (i.e., unbranched) or branched univalent hydrocarbon chain or combination thereof, having the number of carbon atoms designated (i.e., $C_1$-$C_{10}$ means one to ten carbon atoms). Particular alkyl groups are those having 1 to 20 carbon atoms (a "$C_1$-$C_{20}$ alkyl"), having 1 to 10 carbon atoms (a "$C_1$-$C_{10}$ alkyl"), having 6 to 10 carbon atoms (a "$C_6$-$C_{10}$ alkyl"), having 1 to 6 carbon atoms (a "$C_1$-$C_6$ alkyl"), having 2 to 6 carbon atoms (a "$C_2$-$C_6$ alkyl"), or having 1 to 4 carbon atoms (a "$C_1$-$C_4$ alkyl"). Examples of alkyl groups include, but are not limited to, groups such as methyl, ethyl, n-propyl, isopropyl, n-butyl, t-butyl, isobutyl, sec-butyl, n-pentyl, n-hexyl, n-heptyl, n-octyl, n-nonyl, n-decyl, and the like.

"Alkylene" as used herein refers to the same residues as alkyl, but having bivalency. Particular alkylene groups are those having 1 to 20 carbon atoms (a "$C_1$-$C_{20}$ alkylene"), having 1 to 10 carbon atoms (a "$C_1$-$C_{10}$ alkylene"), having 6 to 10 carbon atoms (a "$C_6$-$C_{10}$ alkylene"), having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), isopropylene (—$CH_2CH(CH_3)$—), butylene (—$CH_2(CH_2)_2CH_2$—), isobutylene (—$CH_2CH(CH_3)CH_2$—), pentylene (—$CH_2(CH_2)_3CH_2$—), hexylene (—$CH_2(CH_2)_4CH_2$—), heptylene (—$CH_2(CH_2)_5CH_2$—), octylene (—$CH_2(CH_2)_6CH_2$—), and the like. It is understood that when alkylene is substituted (for example with a cycloalkyl group), the substituent is not one of the sites of bivalency. For example, propylene substitution with cyclopropyl may provide

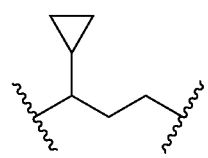 [SMILES: *CCC(*)C1CC1]

but does not provide

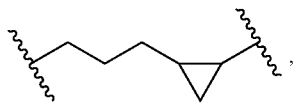 [SMILES: *CCCC1CC1*]

wherein the wavy line denotes a site of bivalency.

"Alkenyl" as used herein refers to and includes, unless otherwise stated, an unsaturated linear (i.e., unbranched) or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). An alkenyl group may have "cis" or "trans" configurations, or alternatively have "E" or "Z" configurations. Particular alkenyl groups are those having 2 to 20 carbon atoms (a "$C_2$-$C_{20}$ alkenyl"), having 6 to 10 carbon atoms (a "$C_6$-$C_{10}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl groups include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, pent-1-enyl, pent-2-enyl, hex-1-enyl, hex-2-enyl, hex-3-enyl, and the like.

"Alkenylene" as used herein refers to the same residues as alkenyl, but having bivalency. Particular alkenylene groups are those having 2 to 20 carbon atoms (a "$C_2$-$C_{20}$ alkenylene"), having 2 to 10 carbon atoms (a "$C_2$-$C_{10}$ alkenylene"), having 6 to 10 carbon atoms (a "$C_6$-$C_{10}$ alkenylene"), having 2 to 6 carbon atoms (a "$C_2$-$C_6$ alkenylene"), 2 to 4 carbon atoms (a "$C_2$-$C_4$ alkenylene") or 2 to 3 carbon atoms (a "$C_2$-$C_3$ alkenylene"). Examples of alkenylene include, but are not limited to, groups such as ethenylene (or vinylene) (—CH=CH—), propenylene (—CH=CHCH$_2$—), 1,4-but-1-enylene (—CH=CH—CH$_2$CH$_2$—), 1,4-but-2-enylene (—CH$_2$CH=CHCH$_2$—), 1,6-hex-1-enylene (—CH=CH—(CH$_2$)$_3$CH$_2$—), and the like.

"Alkynyl" as used herein refers to and includes, unless otherwise stated, an unsaturated linear (i.e., unbranched) or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 6 to 10 carbon atoms (a "$C_6$-$C_{10}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl group include, but are not limited to, groups such as ethynyl (or acetylenyl), prop-1-ynyl, prop-2-ynyl (or propargyl), but-1-ynyl, but-2-ynyl, but-3-ynyl, and the like.

"Alkynylene" as used herein refers to the same residues as alkynyl, but having bivalency. Particular alkynylene groups are those having 2 to 20 carbon atoms (a "$C_2$-$C_{20}$ alkynylene"), having 2 to 10 carbon atoms (a "$C_2$-$C_{10}$ alkynylene"), having 6 to 10 carbon atoms (a "$C_6$-$C_{10}$ alkynylene"), having 2 to 6 carbon atoms (a "$C_2$-$C_6$ alkynylene"), 2 to 4 carbon atoms (a "$C_2$-$C_4$ alkynylene") or 2 to 3 carbon atoms (a "$C_2$-$C_3$ alkynylene"). Examples of alkynylene include, but are not limited to, groups such as ethynylene (or acetylenylene) (—C≡C—), propynylene (—C≡CCH$_2$—), and the like.

"Cycloalkyl" as used herein refers to and includes, unless otherwise stated, saturated cyclic univalent hydrocarbon structures, having the number of carbon atoms designated (i.e., $C_3$-$C_{10}$ means three to ten carbon atoms). Cycloalkyl can consist of one ring, such as cyclohexyl, or multiple rings, such as adamantyl. A cycloalkyl comprising more than one ring may be fused, spiro or bridged, or combinations thereof. Particular cycloalkyl groups are those having from 3 to 12 annular carbon atoms. A preferred cycloalkyl is a cyclic hydrocarbon having from 3 to 8 annular carbon atoms (a "$C_3$-$C_8$ cycloalkyl"), having 3 to 6 annular carbon atoms (a "$C_3$-$C_6$ cycloalkyl"), or having from 3 to 4 annular carbon atoms (a "$C_3$-$C_4$ cycloalkyl"). Examples of cycloalkyl include, but are not limited to, cyclopropyl, cyclobutyl, cyclopentyl, cyclohexyl, cycloheptyl, norbornyl, and the like.

"Cycloalkylene" as used herein refers to the same residues as cycloalkyl, but having bivalency. Cycloalkylene can consist of one ring or multiple rings which may be fused, spiro or bridged, or combinations thereof. Particular cycloalkylene groups are those having from 3 to 12 annular carbon atoms. A preferred cycloalkylene is a cyclic hydrocarbon having from 3 to 8 annular carbon atoms (a "$C_3$-$C_8$ cycloalkylene"), having 3 to 6 carbon atoms (a "$C_3$-$C_6$ cycloalkylene"), or having from 3 to 4 annular carbon atoms (a "$C_3$-$C_4$ cycloalkylene"). Examples of cycloalkylene include, but are not limited to, cyclopropylene, cyclobutylene, cyclopentylene, cyclohexylene, cycloheptylene, norbornylene, and the like. A cycloalkylene may attach to the remaining structures via the same ring carbon atom (e.g., 1,1-cyclopropylene) or different ring carbon atoms (e.g., 1,2-cyclopropylene). When a cycloalkylene attaches to the remaining structures via two different ring carbon atoms, the connecting bonds may be cis or trans to each other (e.g., cis-1,2-cyclopropylene or trans-1,2-cyclopropylene). If points of attachment are not specified, the moiety can include any chemically possible attachments. For example, cyclopropylene can indicate 1,1-cyclopropylene or 1,2-cyclopropylene (e.g., cis-1,2-cyclopropylene, trans-1,2-cyclopropylene, or a mixture thereof), or a mixture thereof.

"Cycloalkenyl" refers to and includes, unless otherwise stated, an unsaturated cyclic non-aromatic univalent hydrocarbon structure, having at least one site of olefinic unsaturation (i.e., having at least one moiety of the formula C=C) and having the number of carbon atoms designated (i.e., $C_3$-$C_{10}$ means three to ten carbon atoms). Cycloalkenyl can consist of one ring, such as cyclohexenyl, or multiple rings, such as norbornenyl. A preferred cycloalkenyl is an unsaturated cyclic hydrocarbon having from 3 to 8 annular carbon atoms (a "$C_3$-$C_8$ cycloalkenyl"). Examples of cycloalkenyl groups include, but are not limited to, cyclopropenyl, cyclobutenyl, cyclopentenyl, cyclohexenyl, norbornenyl, and the like.

"Cycloalkenylene" as used herein refers to the same residues as cycloalkenyl, but having bivalency.

"Aryl" or "Ar" as used herein refers to an unsaturated aromatic carbocyclic group having a single ring (e.g., phenyl) or multiple condensed rings (e.g., naphthyl or anthryl) which condensed rings are carbocyclic and may or may not be aromatic, provided at least one ring in the multiple condensed ring structure is aromatic. Particular aryl groups are those having from 6 to 14 annular carbon atoms (a "$C_6$-$C_{14}$ aryl"). An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Arylene" as used herein refers to the same residues as aryl, but having bivalency. Particular arylene groups are those having from 6 to 14 annular carbon atoms (a "$C_6$-$C_{14}$ arylene").

"Heteroaryl" as used herein refers to an unsaturated aromatic cyclic group having from 1 to 14 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may be carbocyclic or may contain one or more annular heteroatom and which may or may not be aromatic, provided at least one ring in the multiple condensed ring structure is both aromatic and contains at least one annular heteroatom. Particular heteroaryl groups are 5 to 14-membered rings having 1 to 12 annular carbon atoms and 1 to 6 annular heteroatoms independently selected from nitrogen, oxygen and sulfur, 5 to 10-membered rings having 1 to 8 annular carbon atoms and 1 to 4 annular heteroatoms independently selected from nitrogen, oxygen and sulfur, or 5, 6 or 7-membered rings having 1 to 5 annular carbon atoms and 1 to 4 annular heteroatoms independently selected from nitrogen, oxygen and sulfur. In one variation, particular heteroaryl groups are monocyclic aromatic 5-, 6- or 7-membered rings having from 1 to 6 annular carbon atoms and 1 to 4 annular heteroatoms independently selected from nitrogen, oxygen and sulfur. In another variation, particular heteroaryl groups are polycyclic aromatic rings having from 1 to 12 annular carbon atoms and 1 to 6 annular heteroatoms independently selected from nitrogen, oxygen and sulfur. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position. A heteroaryl group may be connected to the parent structure at a ring carbon atom or a ring heteroatom.

"Heteroarylene" as used herein refers to the same residues as heteroaryl, but having bivalency.

"Heterocycle", "heterocyclic", or "heterocyclyl" as used herein refers to a saturated or an unsaturated non-aromatic cyclic group having from 1 to 14 annular carbon atoms and from 1 to 6 annular heteroatoms, such as nitrogen, sulfur or oxygen, and the like. A heterocyclic group may have a single ring (e.g., pyrrolidinyl) or multiple condensed rings (e.g., decahydroisoquinolin-1-yl), which condensed rings may or may not be aromatic and which may be carbocyclic or contain one or more annular heteroatoms, but which excludes heteroaryl rings. A heterocycle comprising more than one ring may be fused, bridged or spiro, or any combination thereof. In fused ring systems, one or more of the fused rings can be cycloalkyl or aryl, but excludes heteroaryl groups. The heterocyclyl group may be optionally substituted independently with one or more substituents described herein. Particular heterocyclyl groups are 3 to 14-membered rings having 1 to 13 annular carbon atoms and 1 to 6 annular heteroatoms independently selected from nitrogen, oxygen and sulfur, 3 to 12-membered rings having 1 to 11 annular carbon atoms and 1 to 6 annular heteroatoms independently selected from nitrogen, oxygen and sulfur, 3 to 10-membered rings having 1 to 9 annular carbon atoms and 1 to 4 annular heteroatoms independently selected from nitrogen, oxygen and sulfur, 3 to 8-membered rings having 1 to 7 annular carbon atoms and 1 to 4 annular heteroatoms independently selected from nitrogen, oxygen and sulfur, or 3 to 6-membered rings having 1 to 5 annular carbon atoms and 1 to 4 annular heteroatoms independently selected from nitrogen, oxygen and sulfur. In one variation, heterocyclyl includes monocyclic 3-, 4-, 5-, 6- or 7-membered rings having from 1 to 2, 1 to 3, 1 to 4, 1 to 5, or 1 to 6 annular carbon atoms and 1 to 2, 1 to 3, or 1 to 4 annular heteroatoms independently selected from nitrogen, oxygen and sulfur. In another variation, heterocyclyl includes polycyclic non-aromatic rings having from 1 to 12 annular carbon atoms and 1 to 6 annular heteroatoms independently selected from nitrogen, oxygen and sulfur.

"Heterocyclylene" as used herein refers to the same residues as heterocyclyl, but having bivalency.

"Halo" or "halogen" refers to elements of the Group 17 series having atomic number 9 to 85. Preferred halo groups include the radicals of fluorine, chlorine, bromine and iodine. Where a residue is substituted with one or more halogens, it may be referred to by using the prefix "halo," e.g., haloaryl, haloalkyl, etc. refer to aryl and alkyl substituted with one or more halo groups, which in the case of two or more halo groups may be, but are not necessarily the same halogen. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each hydrogen is replaced with a halo group is referred to as a "perhaloalkyl." A preferred haloalkyl, e.g., perhaloalkyl group is trifluoromethyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

"Carbonyl" refers to the group C=O.

"Thiocarbonyl" refers to the group C=S.

"Oxo" refers to the moiety =O.

"D" refers to deuterium ($^2H$).

"Boc" refers to tert-butyloxycarbonyl.

"Cbz" refers to carboxybenzyl.

"HATU" refers to 1-[bis(dimethylamino)methylene]-1H-1,2,3-triazolo[4,5-b]pyridinium 3-oxide hexafluorophosphate.

"BOP" refers to benzotriazol-1-yloxytris(dimethylamino)phosphonium hexafluorophosphate.

"PyBOP" refers to benzotriazol-1-yl-oxytripyrrolidinophosphonium hexafluorophosphate.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 1 to 3, 1 to 4, 1 to 5, 2 to 3, 2 to 4, or 2 to 5 substituents. In one embodiment, an optionally substituted group is unsubstituted.

Unless clearly indicated otherwise, "an individual" as used herein intends a mammal, including but not limited to a primate, human, bovine, horse, feline, canine, or rodent. In one variation, the individual is a human.

As used herein, "treatment" or "treating" is an approach for obtaining beneficial or desired results including clinical results. For purposes of this invention, beneficial or desired results include, but are not limited to, one or more of the following: decreasing one more symptoms resulting from the disease, diminishing the extent of the disease, stabilizing the disease (e.g., preventing or delaying the worsening of the disease), preventing or delaying the spread of the disease, delaying the occurrence or recurrence of the disease, delay or slowing the progression of the disease, ameliorating the disease state, providing a remission (whether partial or total) of the disease, decreasing the dose of one or more other medications required to treat the disease, enhancing effect of another medication, delaying the progression of the disease, increasing the quality of life, and/or prolonging survival. Also encompassed by "treatment" is a reduction of pathological consequence of fibrosis. The methods of the invention contemplate any one or more of these aspects of treatment.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents (e.g., a compound, or pharmaceutically acceptable salt thereof), and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

A "therapeutically effective amount" refers to an amount of a compound or salt thereof sufficient to produce a desired therapeutic outcome.

As used herein, "unit dosage form" refers to physically discrete units, suitable as unit dosages, each unit containing a predetermined quantity of active ingredient calculated to produce the desired therapeutic effect in association with the required pharmaceutical carrier. Unit dosage forms may contain a single or a combination therapy.

As used herein, the term "controlled release" refers to a drug-containing formulation or fraction thereof in which release of the drug is not immediate, i.e., with a "controlled release" formulation, administration does not result in immediate release of the drug into an absorption pool. The term encompasses depot formulations designed to gradually release the drug compound over an extended period of time. Controlled release formulations can include a wide variety of drug delivery systems, generally involving mixing the drug compound with carriers, polymers or other compounds having the desired release characteristics (e.g., pH-dependent or non-pH-dependent solubility, different degrees of water solubility, and the like) and formulating the mixture according to the desired route of delivery (e.g., coated capsules, implantable reservoirs, injectable solutions containing biodegradable capsules, and the like).

As used herein, by "pharmaceutically acceptable" or "pharmacologically acceptable" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug Administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine and the like. Acceptable inorganic bases which can be used to prepared salts include aluminum hydroxide, calcium hydroxide, potassium hydroxide, sodium carbonate, sodium hydroxide, and the like. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification.

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

Unless otherwise stated, "substantially pure" intends a composition that contains no more than 10% impurity, such as a composition comprising less than about 9%, 7%, 5%, 3%, 1%, 0.5% impurity.

It is understood that aspects and embodiments described herein as "comprising" include "consisting of" and "consisting essentially of" embodiments.

When a composition is described as "consisting essentially of" the listed components, the composition contains the components expressly listed, and may contain other components which do not substantially affect the disease or condition being treated such as trace impurities. However, the composition either does not contain any other components which do substantially affect the disease or condition being treated other than those components expressly listed; or, if the composition does contain extra components other than those listed which substantially affect the disease or condition being treated, the composition does not contain a sufficient concentration or amount of those extra components to substantially affect the disease or condition being treated. When a method is described as "consisting essentially of" the listed steps, the method contains the steps listed, and may contain other steps that do not substantially affect the disease or condition being treated, but the method does not contain any other steps which substantially affect the disease or condition being treated other than those steps expressly listed.

Compounds

In one aspect, provided is a compound of formula (I): or a salt thereof, wherein:

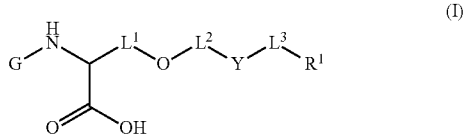

(I)

$R^1$ is 5,6,7,8-tetrahydro-1,8-naphthyridin-2-yl optionally substituted by $R^4$, 1,2,3,4-tetrahydro-1,8-naphthyridin-2-yl optionally substituted by $R^4$, 6-aminopyridin-2-yl optionally substituted by $R^4$, or (pyridin-2-yl)amino optionally substituted by $R^4$;

G is —C(O)$R^2$ or $R^3$;

$R^2$ is $C_1$-$C_6$ alkyl optionally substituted by $R^{2a}$, $C_3$-$C_5$ cycloalkyl optionally substituted by $R^{2b}$, 3- to 12-membered heterocyclyl optionally substituted by $R^{2c}$, $C_6$-$C_{14}$ aryl optionally substituted by $R^{2d}$, 5- to 10-membered heteroaryl optionally substituted by $R^{2e}$, —O$R^{2f}$, or —N$R^{2g}R^{2h}$.

$R^3$ is $C_1$-$C_6$ alkyl optionally substituted by $R^{3a}$, $C_3$-$C_8$ cycloalkyl optionally substituted by $R^{3b}$, 3- to 12-membered heterocyclyl optionally substituted by $R^{3c}$, $C_6$-$C_{14}$ aryl optionally substituted by $R^{3d}$, or 5- to 10-membered heteroaryl optionally substituted by $R^{3e}$;

$L^1$ is $C_2$-$C_4$ alkylene optionally substituted by $R^4$;

$L^2$ is a bond or $C_1$-$C_3$ alkylene optionally substituted by $R^4$;

$L^3$ is $C_2$-$C_4$ alkylene optionally substituted by $R^4$;

Y is a bond or $C_3$-$C_5$ cycloalkylene optionally substituted by $Y^a$;

$R^{2f}$ is $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, and 5- to 10-membered heteroaryl of $R^{2f}$ are independently optionally substituted by $R^{2i}$;

$R^{2g}$ and $R^{2h}$ are each independently hydrogen, deuterium, $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, and 5- to 10-membered heteroaryl of $R^{2g}$ and $R^{2h}$ are independently optionally substituted by $R^{2j}$;

each $R^{2a}$, $R^{2b}$, $R^{2c}$, $R^{2d}$, $R^{2e}$, $R^{2i}$, $R^{2j}$, $R^{3a}$, $R^{3b}$, $R^{3c}$, $R^{3d}$, $R^{3e}$ and $Y^a$ is independently oxo or $R^4$;

each $R^4$ is independently deuterium, halogen, $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, 5- to 10-membered heteroaryl, —CN, —O$R^5$, —S$R^5$, —N$R^6R^7$, —NO$_2$, —C=NH(O$R^5$), —C(O)$R^5$, —OC(O)$R^5$, —C(O)O$R^5$, —C(O)N$R^6R^7$, —N$R^5$C(O)$R^6$, —N$R^5$C(O)O$R^6$, —N$R^5$C(O)N$R^6R^7$, —S(O)$R^5$, —S(O)$_2R^5$, —N$R^5$S(O)$R^6$, —N$R^5$S(O)$_2R^6$, —S(O)N$R^6R^7$, —S(O)$_2$N$R^6R^7$, or —P(O)(O$R^5$)(O$R^6$), wherein the $C_1$-$C_6$ alkyl, $C_2$-$C_6$ alkenyl, $C_2$-$C_6$ alkynyl, $C_3$-$C_5$ cycloalkyl, 3- to 12-membered heterocyclyl, $C_6$-$C_{14}$ aryl, and 5- to 10-membered heteroaryl of $R^4$ are independently optionally substituted by $R^{4a}$;

each $R^{4a}$ is independently deuterium, halogen, oxo, —O$R^8$, —N$R^8R^9$, —C(O)$R^8$, —C(O)O$R^9$, —N$R^8$C(O)O$R^{10}$, —CN, —S(O)$R^8$, —S(O)$_2R^8$, —P(O)(O$R^8$)(O$R^9$), $C_3$-$C_8$ cycloalkyl, 3- to 12-membered heterocyclyl, 5- to 10-membered heteroaryl, $C_6$-$C_{14}$ aryl, or $C_1$-$C_6$ alkyl, wherein the 3- to 12-membered heterocyclyl, 5- to 10-membered heteroaryl, $C_6$-$C_{14}$ aryl, and $C_1$-$C_6$ alkyl of $R^{4a}$ are independently optionally substituted by $R^{4b}$;

each $R^{4b}$ is independently deuterium, oxo, —OH, —O($^2$H), halogen, or $C_1$-$C_6$ alkyl optionally substituted by deuterium, halogen, —OH, —O($^2$H), or oxo;

each $R^5$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 10-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 10-membered heterocyclyl of $R^5$ are each independently optionally substituted by $R^{5a}$;

each $R^{5a}$ is independently halogen, deuterium, oxo, —CN, —O$R^{10}$, —N$R^{11}R^{12}$, —P(O)(O$R^{11}$)(O$R^{12}$), 3- to 12-membered heterocyclyl, or $C_1$-$C_6$ alkyl optionally substituted by deuterium, halogen, —OH, —O($^2$H), or oxo;

each $R^6$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^6$ are independently optionally substituted by deuterium, halogen, oxo, —CN, —O$R^{10}$, —N$R^{11}R^{12}$, or $C_1$-$C_6$ alkyl optionally substituted by deuterium, halogen, —OH, —O($^2$H), or oxo;

each $R^7$ is independently hydrogen, deuterium, $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, or 3- to 6-membered heterocyclyl, wherein the $C_1$-$C_6$ alkyl, $C_2$-$C_6$ alkenyl, $C_2$-$C_6$ alkynyl, $C_3$-$C_6$ cycloalkyl, $C_6$-$C_{14}$ aryl, 5- to 10-membered heteroaryl, and 3- to 6-membered heterocyclyl of $R^7$ are independently optionally substituted by deuterium, halogen, oxo, —CN, —O$R^{10}$, —N$R^{11}R^{12}$, or $C_1$-$C_6$ alkyl optionally substituted by deuterium, halogen, —OH, —O($^2$H), or oxo;

or $R^6$ and $R^7$ are taken together with the atom to which they are attached to form a 3- to 10-membered heterocyclyl optionally substituted by deuterium, halogen, oxo, —OR$^{10}$, —NR$^{11}$R$^{12}$, or C$_1$-C$_6$ alkyl optionally substituted by deuterium, halogen, oxo, —OH, or —O($^2$H);

each R$^9$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{10}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{10}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

each R$^{11}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo; and each R$^{12}$ is independently hydrogen, deuterium, C$_1$-C$_6$ alkyl optionally substituted by deuterium, halogen, or oxo, C$_2$-C$_6$ alkenyl optionally substituted by deuterium, halogen, or oxo, or C$_2$-C$_6$ alkynyl optionally substituted by deuterium, halogen, or oxo;

or R$^{11}$ and R$^{12}$ are taken together with the atom to which they are attached to form a 3-6 membered heterocyclyl optionally substituted by deuterium, halogen, oxo or C$_1$-C$_6$ alkyl optionally substituted by deuterium, oxo, or halogen.

In one variation is provided a compound of the formula (I), or a salt thereof, wherein the carbon bearing the CO$_2$H and N(H)G moieties is in the "S" configuration. In another variation is provided a compound of the formula (I), or a salt thereof, wherein the carbon bearing the CO$_2$H and N(H)G moieties is in the "R" configuration. Mixtures of a compound of the formula (I) are also embraced, including racemic or non-racemic mixtures of a given compound, and mixtures of two or more compounds of different chemical formulae.

In the descriptions herein, it is understood that every description, variation, embodiment or aspect of a moiety may be combined with every description, variation, embodiment or aspect of other moieties the same as if each and every combination of descriptions is specifically and individually listed. For example, every description, variation, embodiment or aspect provided herein with respect to G of formula (I) may be combined with every description, variation, embodiment or aspect of L$^1$, L$^2$, Y, L$^2$ and/or R$^1$ the same as if each and every combination were specifically and individually listed. It is also understood that all descriptions, variations, embodiments or aspects of formula (I), where applicable, apply equally to other formulae detailed herein, and are equally described, the same as if each and every description, variation, embodiment or aspect were separately and individually listed for all formulae. For example, all descriptions, variations, embodiments or aspects of formula (I), where applicable, apply equally to any of formulae (IIa), (IIb), (IIIa), (IIIb), (IVa), (IVb), (Va), (Va-1), (Va-2), (Vb), (Vb-1), and (Vb-2) detailed herein, and are equally described, the same as if each and every description, variation, embodiment or aspect were separately and individually listed for all formulae.

In some embodiments of the compound of formula (I), or a salt thereof, L$^1$ is unsubstituted C$_2$-C$_4$ alkylene. In a particular variation, L$^1$ is —CH$_2$—CH$_2$—, —CH$_2$—CH$_2$—CH$_2$—, or —CH$_2$—CH$_2$—CH$_2$—CH$_2$—. In another variation, L$^1$ is —CH$_2$—CH$_2$—.

In some embodiments of the compound of formula (I), or a salt thereof, -L$^2$- is a bond.

In some embodiments of the compound of formula (I), or a salt thereof, —Y— is a bond.

In some embodiments of the compound of formula (I), or a salt thereof, —Y— is a C$_3$-C$_4$ cycloalkylene. In one aspect, Y is a C$_3$ cycloalkylene. In another aspect, Y is a C$_4$ cycloalkylene. In one variation, the point of attachment of the C$_3$-C$_4$ cycloalkylene to L$^2$ and L$^3$ are via the same carbon atom (e.g.,

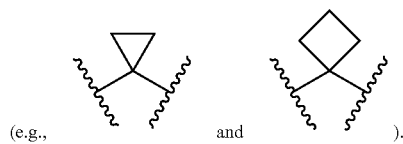 [SMILES: *C1(*)CC1 ; *C1(*)CCC1]

(e.g., and ).

In another variation, the point of attachment of the C$_3$-C$_4$ cycloalkylene to L$^2$ and L$^3$ are via two different carbon atoms (e.g.,

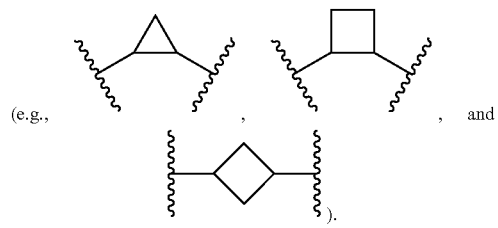

(e.g., , , and ).

In another variation, when the point of attachment of the C$_3$-C$_4$ cycloalkylene to L$^2$ and L$^3$ are via two different carbon atoms, the stereochemistry introduced at the C$_3$-C$_4$ cycloalkylene is trans (e.g.,

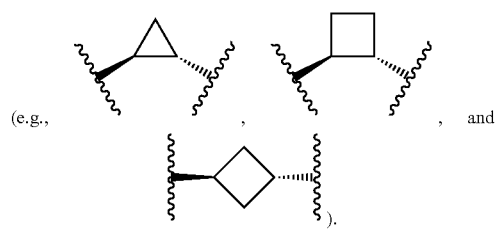

(e.g., , , and ).

In another variation, when the point of attachment of the C$_3$-C$_4$ cycloalkylene to L$^2$ and L$^3$ are via two different carbon atoms, the stereochemistry introduced at the C$_3$-C$_4$ cycloalkylene is cis (e.g.,

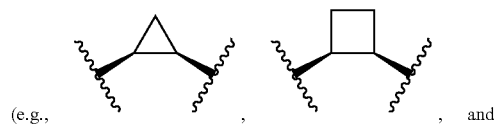

(e.g., , , and

-continued

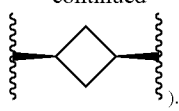).

In some embodiments of the compound of formula (I), or a salt thereof, at least one of $R^{2g}$, $R^{2h}$, $R^4$, $R^{4a}$, $R^{4b}$, $R^5$, $R^{5a}$, $R^6$, $R^7$, $R^8$, $R^9$, $R^{10}$, $R^{11}$, or $R^{12}$ is deuterium.

In some embodiments of the compound of formula (I), or a salt thereof, -$L^2$-Y-$L^3$- are taken together to form a moiety selected from the group consisting of: —CH$_2$CH$_2$CH$_2$—,

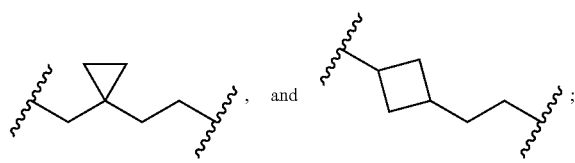 [SMILES: *CCC1(C*)CC1 ; *CCC1CC(*)C1]

wherein the wavy lines denote attachment points to the parent molecule.

In some embodiments of the compound of formula (I), or a salt thereof, -$L^1$-O-$L^2$-Y-$L^3$- are taken together to form a moiety selected from the group consisting of:

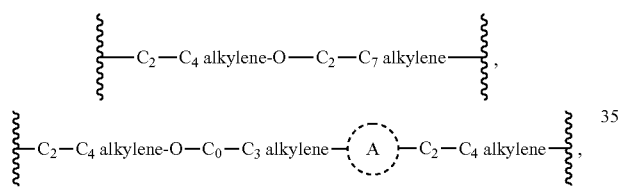

wherein

is a C$_3$-C$_5$ cycloalkylene optionally substituted by Y$^a$, and

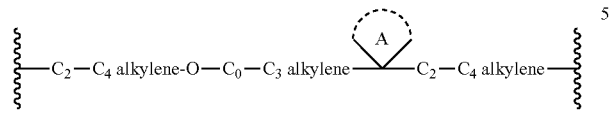

wherein

is a C$_3$-C$_5$ cycloalkylene optionally substituted by Y$^a$.

In some embodiments of the compound of formula (I), or a salt thereof, -$L^1$-O-$L^2$-Y-$L^3$- are taken together to form a moiety selected from the group consisting of:

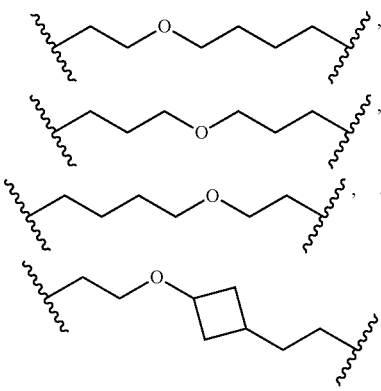

In another variation, -$L^1$-O-$L^2$-Y-$L^3$- are taken together to form a moiety selected from the group consisting of:

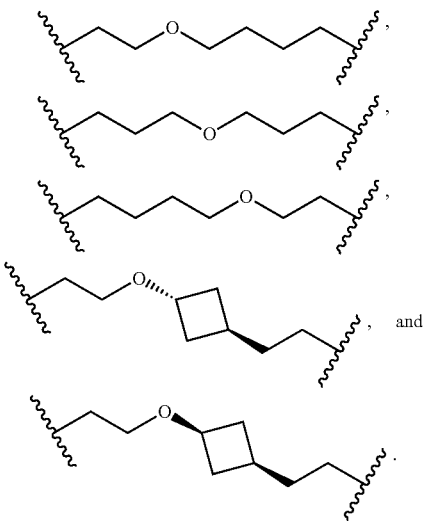

In another particular variation, -$L^1$-O-$L^2$-Y-$L^3$- are taken together to form a moiety selected from the group consisting of:

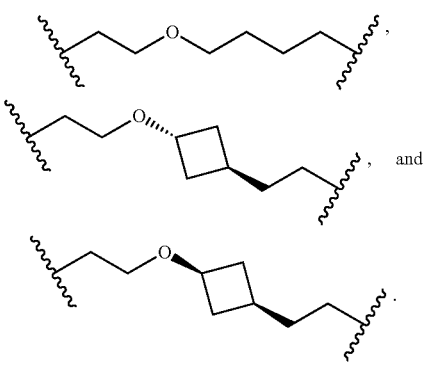

In an embodiment, the compound of formula (I) or a salt thereof is provided wherein: $R^1$ is 1,2,3,4-tetrahydro-1,8-naphthyridin-2-yl; $L^1$ is —CH$_2$CH$_2$—, Y is a bond, and L is —CH$_2$CH$_2$CH$_2$CH$_2$—; and G is —C(O)R$^2$, wherein R$^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2CH_2$—, Y is a bond, and $L^3$ is —$CH_2CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2CH_2CH_2$—, Y is a bond, and $L^3$ is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is 1,3-cyclobutyl, and L; is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is cis-1,3-cyclobutyl, and $L^3$ is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is trans-1,3-cyclobutyl, and $L^3$ is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2CH_2$—, Y is a bond, and $L^3$ is —$CH_2CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; L is —$CH_2CH_2CH_2$—, Y is a bond, and $L^3$ is —$CH_2CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; L is —$CH_2CH_2CH_2CH_2$—, Y is a bond, and L is —$CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is 1,3-cyclobutyl, and $L^3$ is —$CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is cis-1,3-cyclobutyl, and $L^3$ is —$CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 1,2,3,4-tetrahydro-1,8-naphthyridin-2-yl; $L^1$ is —$CH_2CH_2$—, Y is trans-1,3-cyclobutyl, and $L^3$ is —$CH_2CH_2$—; and G is —$R^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. For each individual preceding embodiment described in this paragraph, a further embodiment is disclosed in which among the substitutable ring atoms in $R^2$, one of: one saturated ring atom is substituted with $C_1$-$C_6$ haloalkyl, e.g., —$CF_3$; two aryl ring atoms are independently substituted with halogen; and 2 or 3 heteroaryl ring atoms are independently substituted with halogen or $C_1$-$C_6$ alkyl, e.g., methyl. Further, in various embodiments, each preceding embodiment described in this paragraph may be excluded from the compound represented by formula (I) and salts thereof.

In an embodiment, the compound of formula (I) or a salt thereof is provided wherein: $R^1$ is 5,6,7,8-tetrahydro-1,8-naphthyridin-2-yl; $L^1$ is —$CH_2CH_2$—, Y is a bond, and $L^3$ is —$CH_2CH_2CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —$CH_2CH_2CH_2$—, Y is a bond, and $L^3$ is —$CH_2CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —$CH_2CH_2CH_2CH_2$—, Y is a bond, and $L^3$ is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —$CH_2CH_2$—, Y is 1,3-cyclobutyl, and $L^3$ is —$CH_2CH_2$—; and G is —$C(O)R^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is cis-1,3-cyclobutyl, and $L^3$ is —CH$_2$CH$_2$—; and G is —C(O)R$^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is trans-1,3-cyclobutyl, and $L^3$ is —CH$_2$CH$_2$—; and G is —C(O)R$^2$, wherein $R^2$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is a bond, and $L^3$ is —CH$_2$CH$_2$CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$CH$_2$—, Y is a bond, and $L^3$ is —CH$_2$CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$CH$_2$CH$_2$—, Y is a bond, and $L^3$ is —CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is 1,3-cyclobutyl, and $L^3$ is —CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is cis-1,3-cyclobutyl, and $L^3$ is —CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. In an embodiment, the compound of formula (I) or a salt thereof is provided wherein: $R^1$ is 5,6,7,8-tetrahydro-1,8-naphthyridin-2-yl; $L^1$ is —CH$_2$CH$_2$—, Y is trans-1,3-cyclobutyl, and $L^3$ is —CH$_2$CH$_2$—; and G is —R$^3$, wherein $R^3$ is a six-membered heterocyclyl, aryl, or heteroaryl ring, wherein among the substitutable ring atoms in $R^2$, 1 saturated ring atom, or 2 or 3 unsaturated ring atoms are independently substituted with halogen, $C_1$-$C_6$ alkyl, or $C_1$-$C_6$ haloalkyl. For each individual preceding embodiment described in this paragraph, a further embodiment is disclosed in which among the substitutable ring atoms in $R^2$, one of: one saturated ring atom is substituted with $C_1$-$C_6$ haloalkyl, e.g., —CF$_3$; two aryl ring atoms are independently substituted with halogen; and 2 or 3 heteroaryl ring atoms are independently substituted with halogen or $C_1$-$C_6$ alkyl, e.g., methyl. Further, in various embodiments, each preceding embodiment described in this paragraph may be excluded from the compound represented by formula (I) and salts thereof.

In some embodiments, the compound of formula (I) is of the formula (IIa):

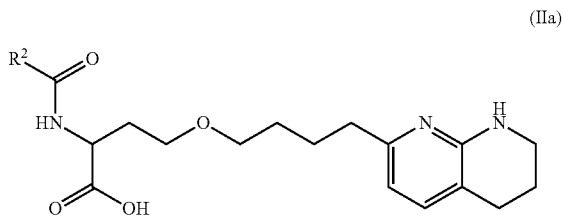

(IIa)

or a salt thereof, wherein $R^2$ is as defined for formula (I).

In some embodiments, the compound of formula (I) is of the formula (IIb):

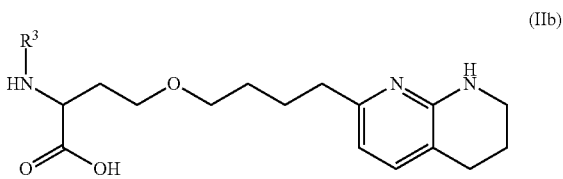

(IIb)

or a salt thereof, wherein $R^3$ is as defined for formula (I).

In some embodiments, the compound of formula (I) is of the formula (IIIa):

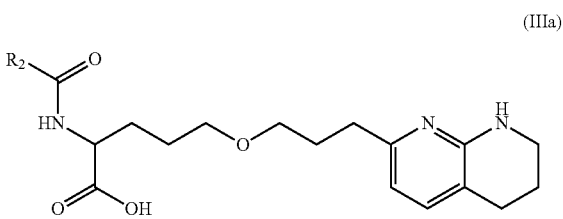

(IIIa)

or a salt thereof, wherein $R^2$ is as defined for formula (I).

In some embodiments, the compound of formula (I) is of the formula (IIIb):

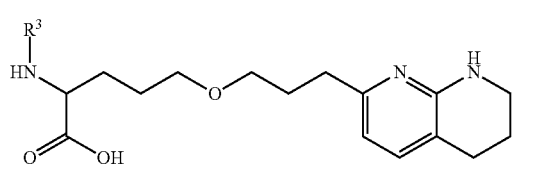

(IIIb)

or a salt thereof, wherein $R^3$ is as defined for formula (I).

In some embodiments, the compound of formula (I) is of the formula (IVa):

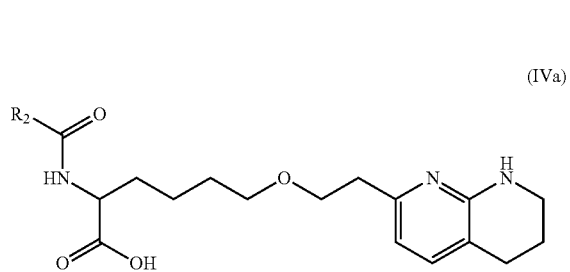

(IVa)

or a salt thereof, wherein R² is as defined for formula (I).

In some embodiments, the compound of formula (I) is of the formula (IVb):

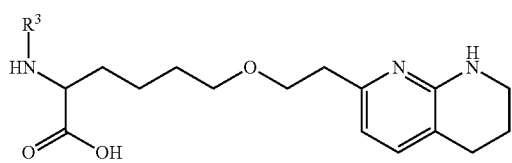

(IVb)

or a salt thereof, wherein R³ is as defined for formula (I).

In some embodiments, the compound of formula (I) is of the formula (Va):

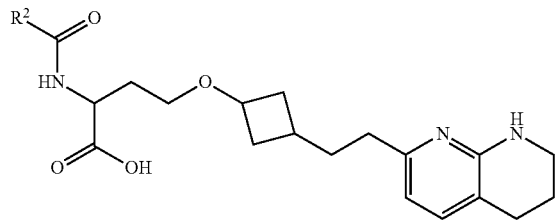

(Va)

or a salt thereof, wherein R² is as defined for formula (I).

In some embodiments, the compound of formula (Va) is of the formula (Va-1):

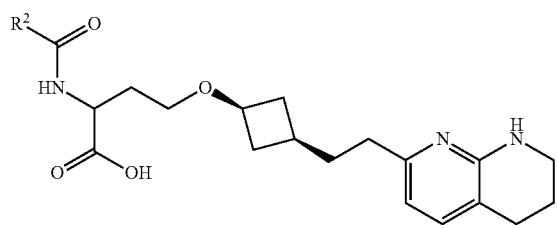

(Va-1)

or a salt thereof, wherein R² is as defined for formula (I).

In some embodiments, the compound of formula (Va) is of the formula (Va-2):

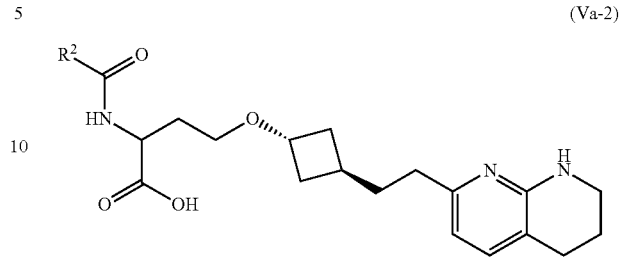

(Va-2)

or a salt thereof, wherein R² is as defined for formula (I).

In some embodiments, the compound of formula (I) is of the formula (Vb):

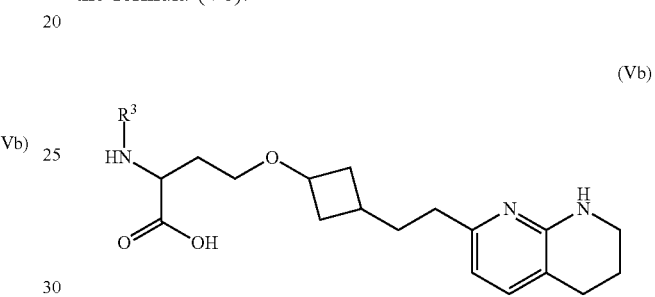

(Vb)

or a salt thereof, wherein R³ is as defined for formula (I).

In some embodiments, the compound of formula (Vb) is of the formula (Vb-1):

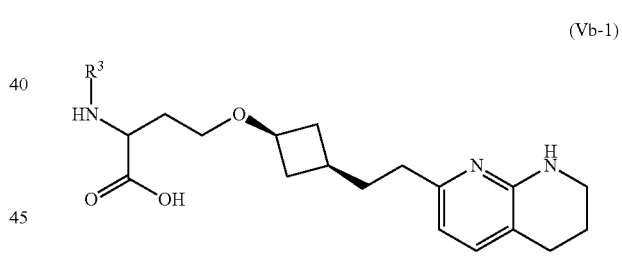

(Vb-1)

or a salt thereof, wherein R³ is as defined for formula (I).

In some embodiments, the compound of formula (Vb) is of the formula (Vb-2):

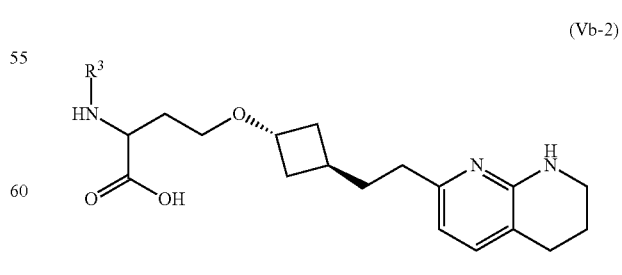

(Vb-2)

or a salt thereof, wherein R; is as defined for formula (I).

In some embodiments, the compound of formula (I) is of the formula:

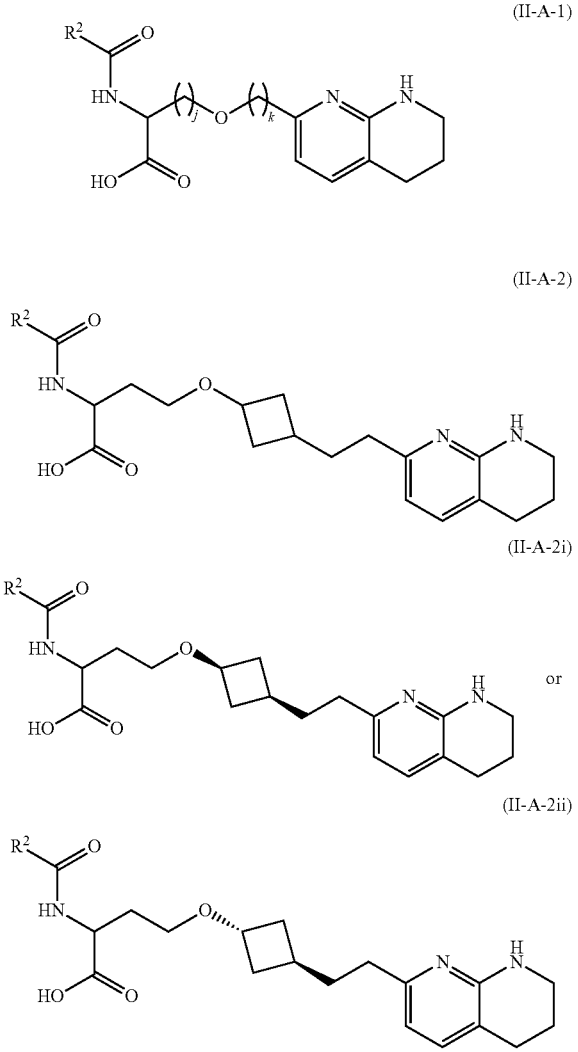

(II-A-1)

(II-A-2)

(II-A-2i)

(II-A-2ii)

wherein j and k are respectively 2 and 4, 3 and 3, or 4 and 2, or a salt thereof.

In some embodiments, the compound of formula (I) is of the formula:

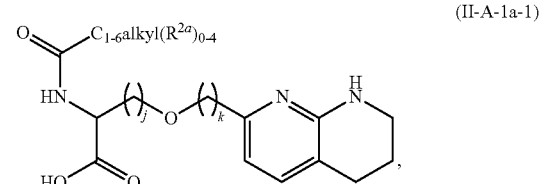

(II-A-1a-1)

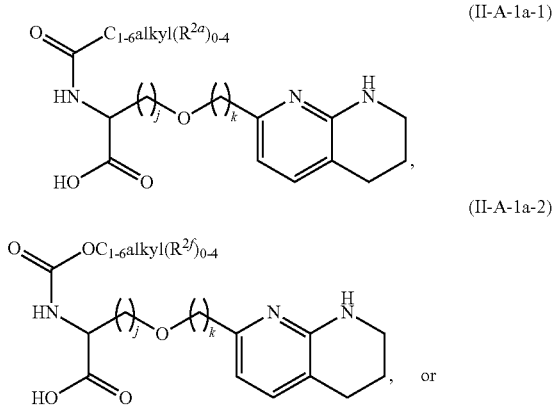

(II-A-1a-2)

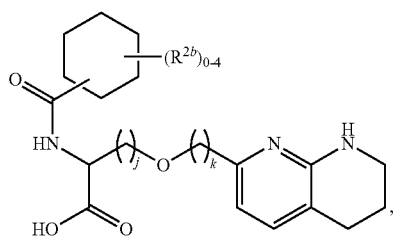

(II-A-1a-3)

or a salt thereof.

In some embodiments, the compound of formula (I) is of the formula:

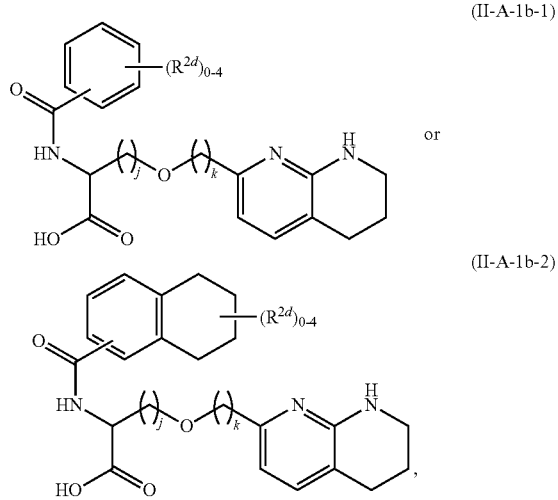

(II-A-1b-1)

(II-A-1b-2)

or a salt thereof.

In some embodiments, the compound of formula (I) is of the formula:

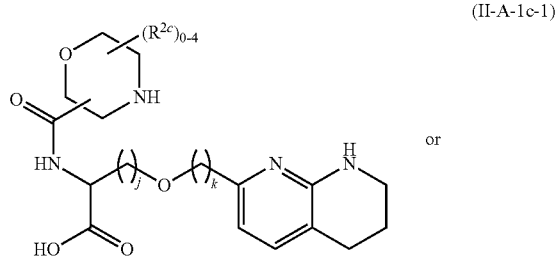

(II-A-1c-1)

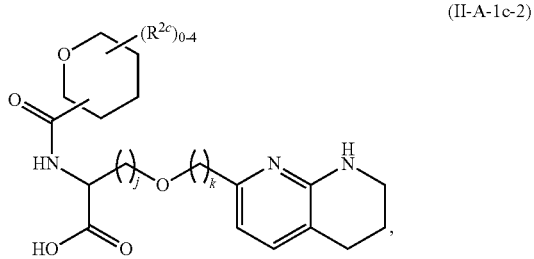

(II-A-1c-2)

or a salt thereof.

In some embodiments, the compound of formula (T) is of the formula:

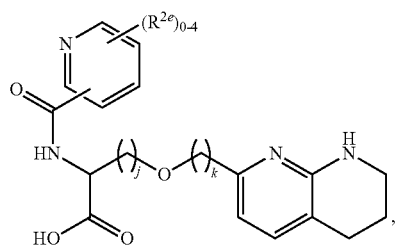
(II-A-1d-1)
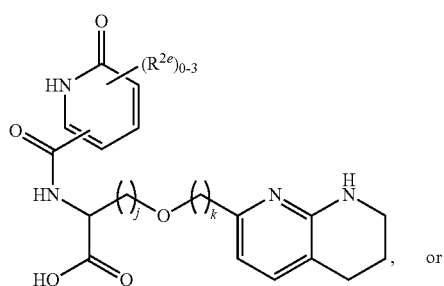
(II-A-1d-2)
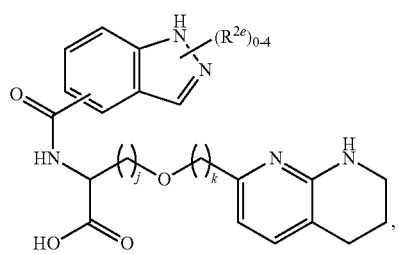
(II-A-1d-3)
or a salt thereof.
In some embodiments, the compound of formula (I) is of the formula:
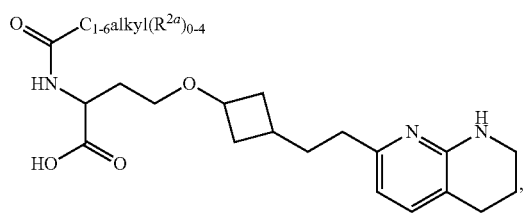
(II-A-2a-1)
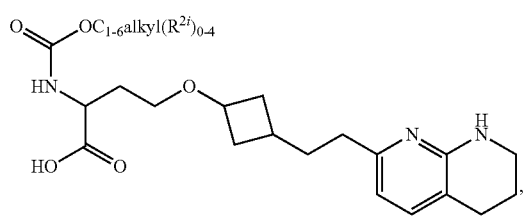
(II-A-2a-2)
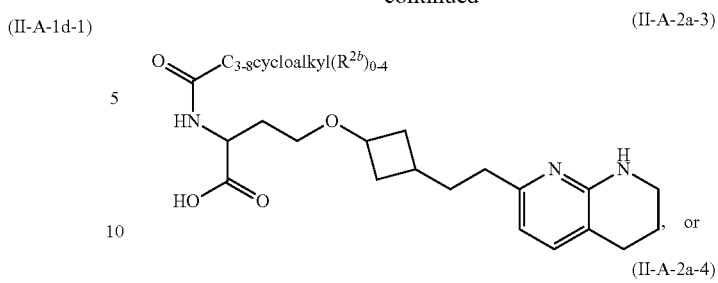
(II-A-2a-3)
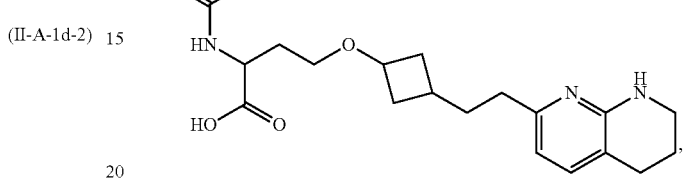
(II-A-2a-4)
or a salt thereof.
In some embodiments, the compound of formula (I) is of the formula:
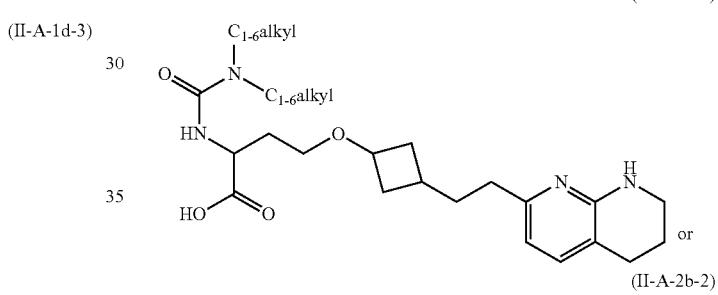
(II-A-2b-1)
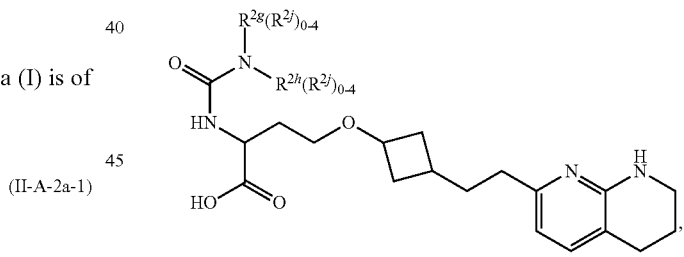
(II-A-2b-2)
or a salt thereof.
In some embodiments, the compound of formula (I) is of the formula:
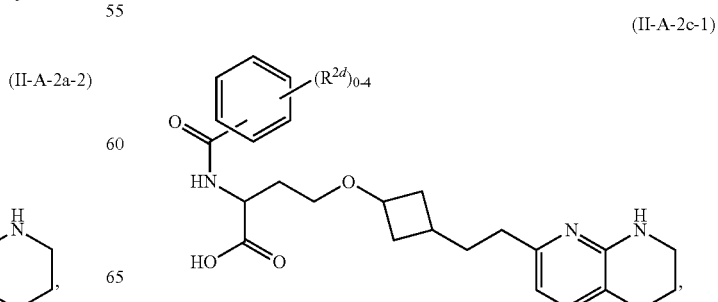
(II-A-2c-1)

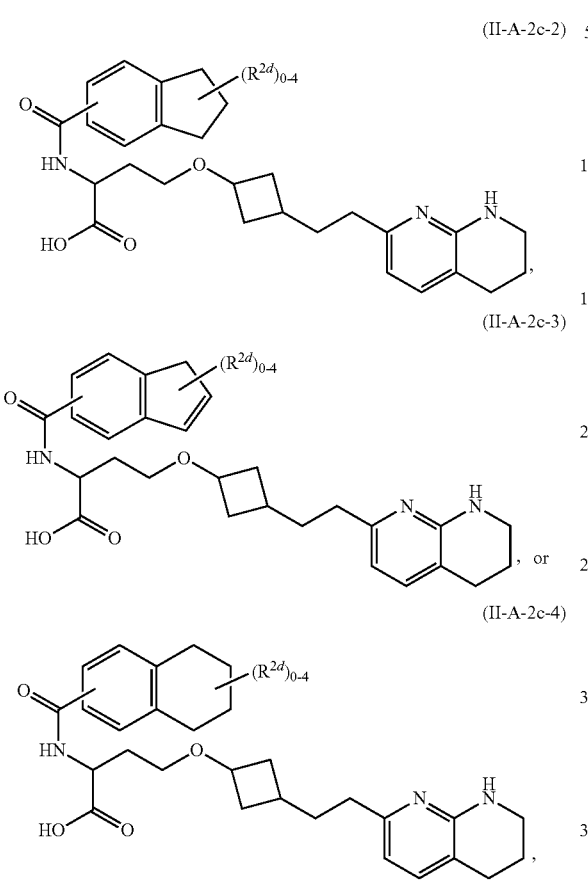
(II-A-2c-2)
(II-A-2c-3)
(II-A-2c-4)
or a salt thereof.
In some embodiments, the compound of formula (I) is of the formula:
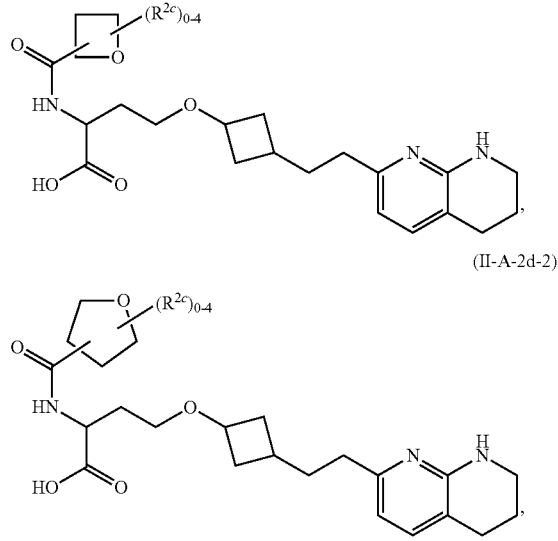
(II-A-2d-1)
(II-A-2d-2)
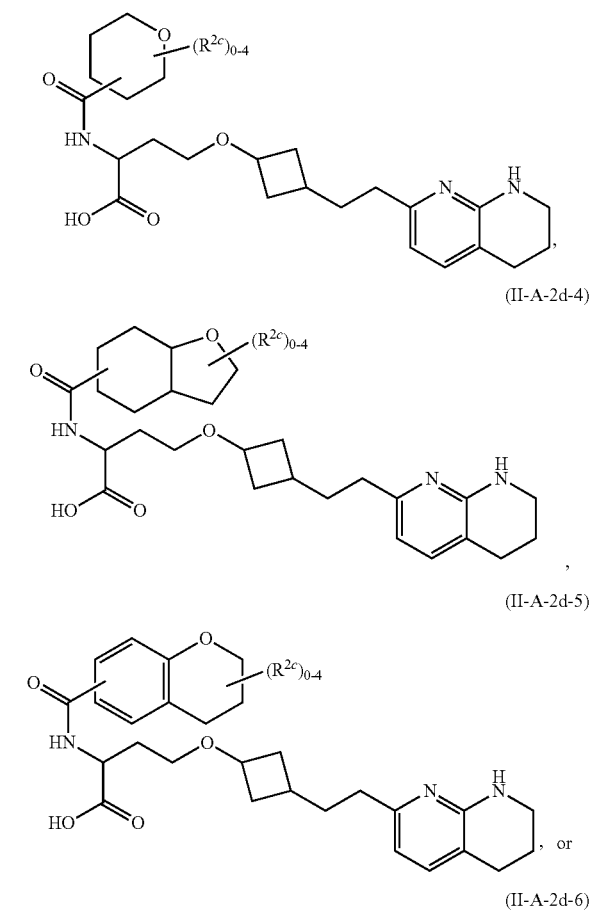
(II-A-2d-3)
(II-A-2d-4)
(II-A-2d-5)
(II-A-2d-6)
or a salt thereof.
In some embodiments, the compound of formula (I) is of the formula:
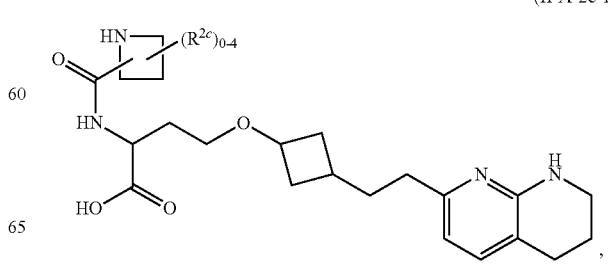
(II-A-2e-1)

(II-A-2e-2)
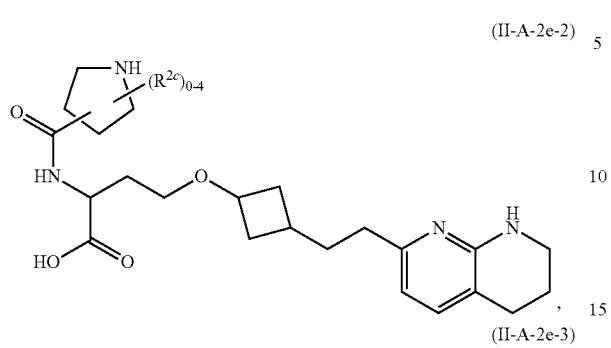
(II-A-2e-3)
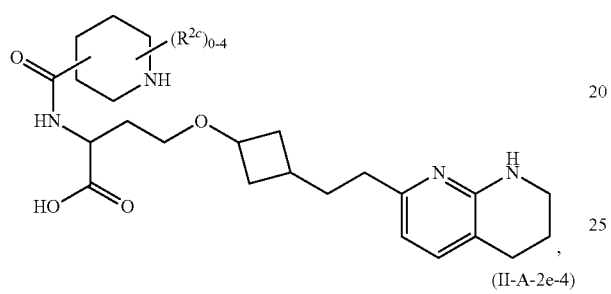
(II-A-2e-4)
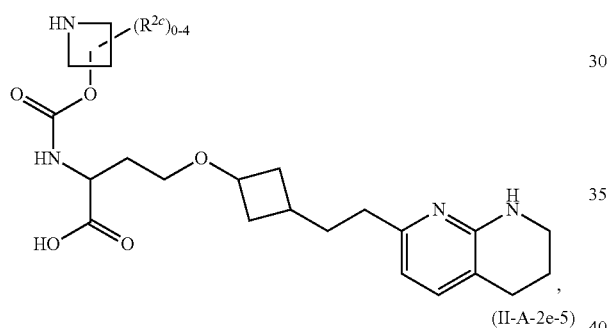
(II-A-2e-5)
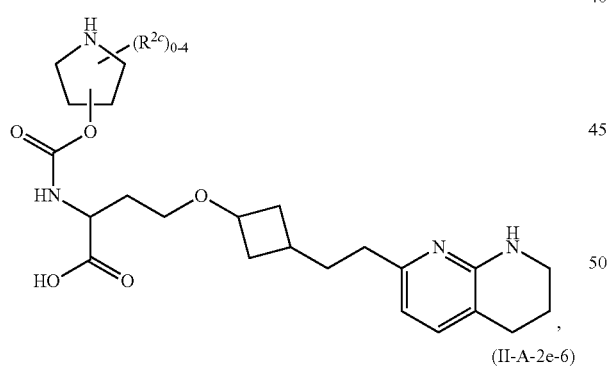
(II-A-2e-6)
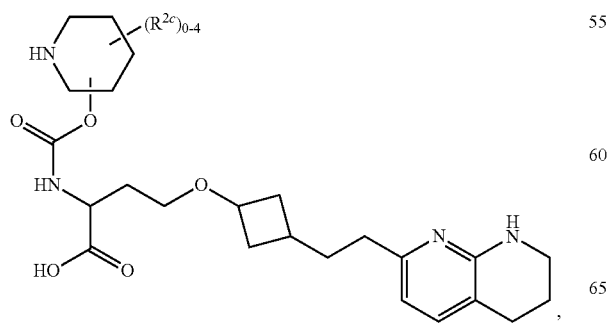
(II-A-2e-7)
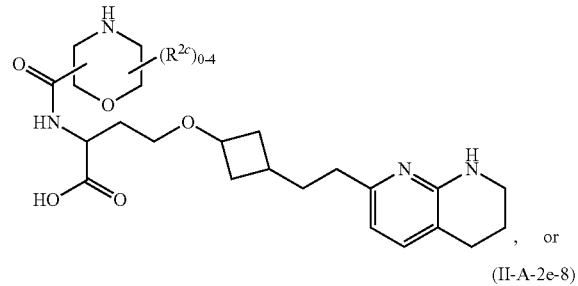
, or
(II-A-2e-8)
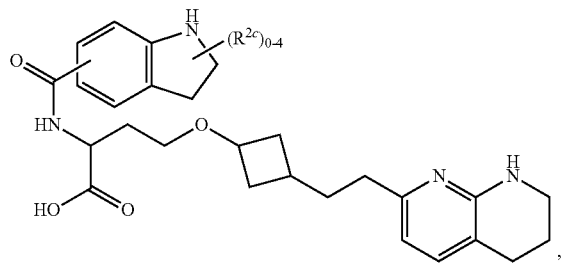
,
or a salt thereof.
In some embodiments, the compound of formula (I) is of the formula:
(II-A-2f-1)
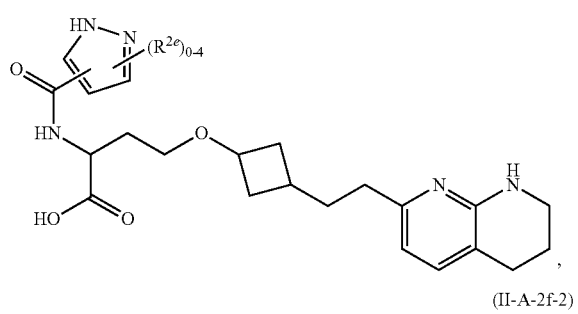
,
(II-A-2f-2)
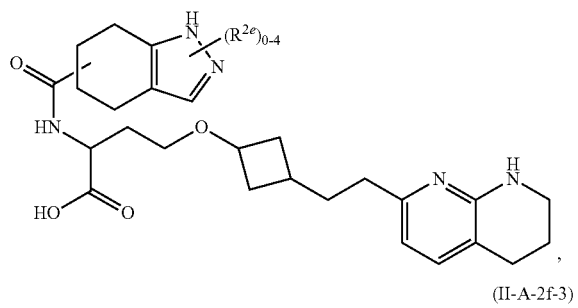
,
(II-A-2f-3)
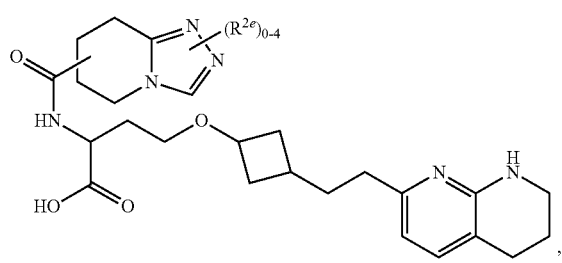
,

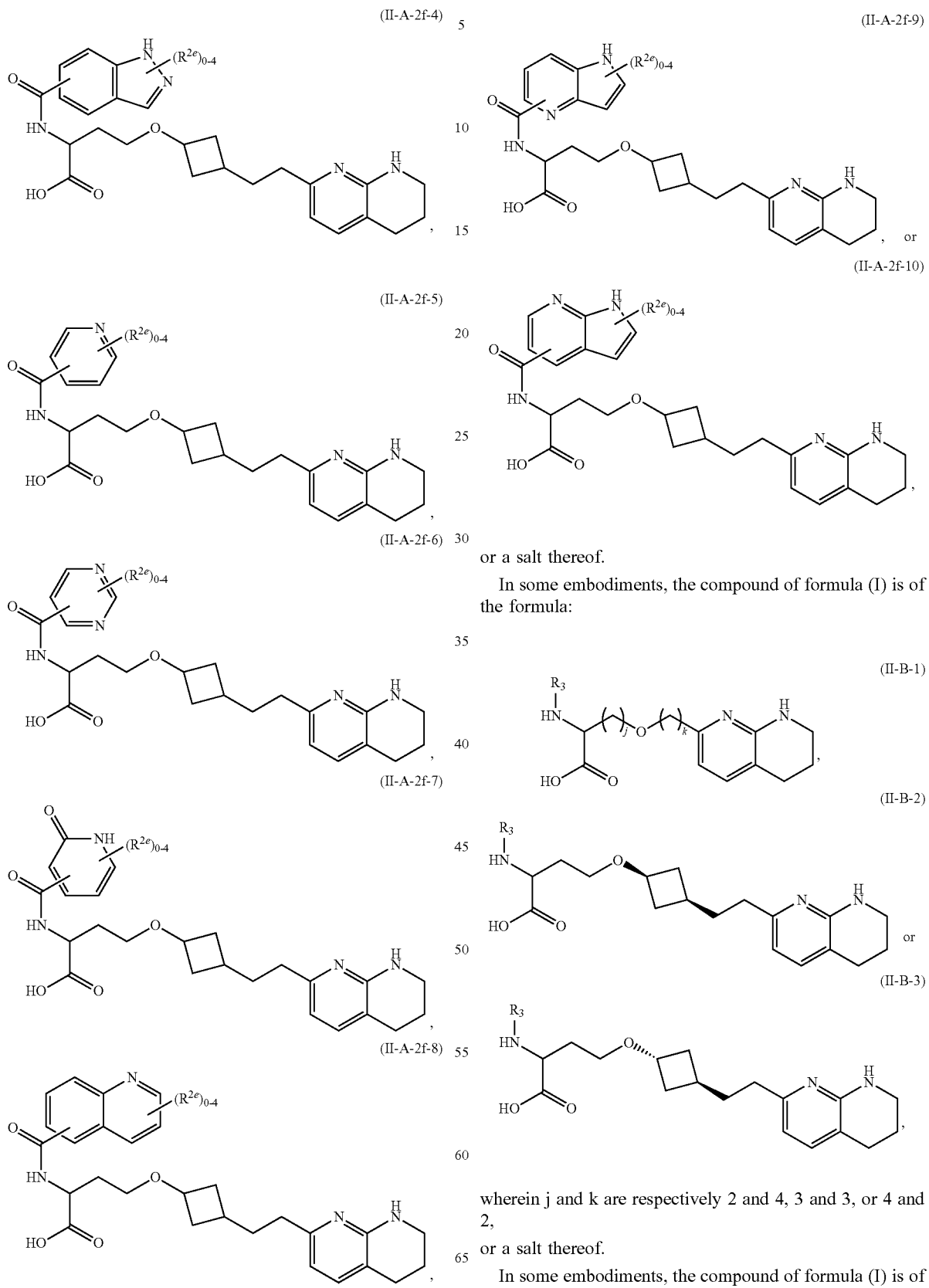
or a salt thereof.
In some embodiments, the compound of formula (I) is of the formula:
wherein j and k are respectively 2 and 4, 3 and 3, or 4 and 2,
or a salt thereof.
In some embodiments, the compound of formula (I) is of the formula:

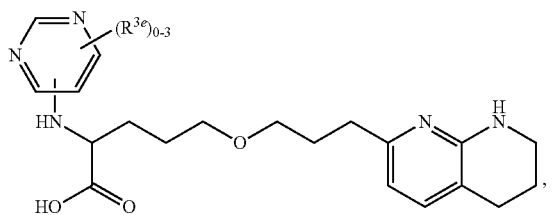

(II-B-1a)

or a salt thereof.

In some embodiments, the compound of formula (I) is of the formula:

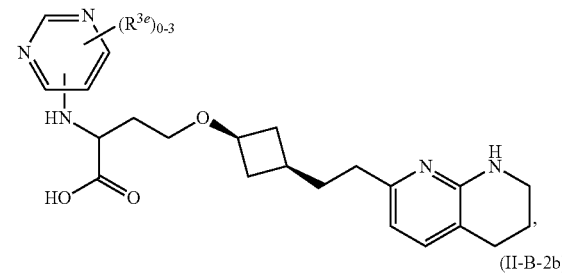

(II-B-2a)

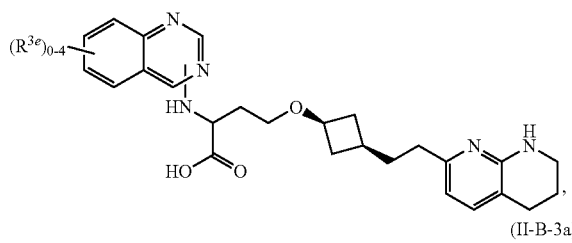

(II-B-2b)

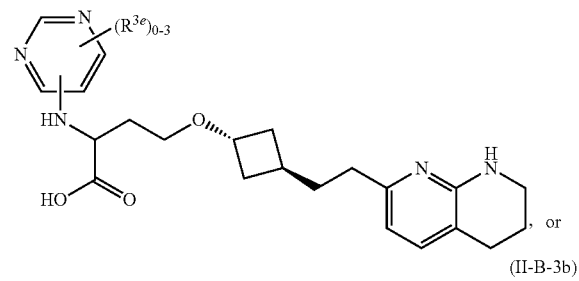

(II-B-3a)

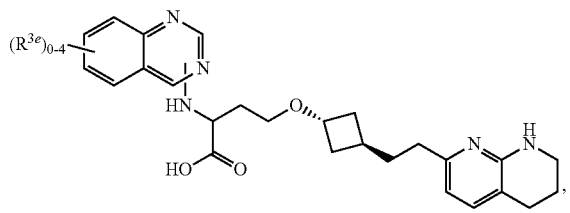

(II-B-3b)

or a salt thereof.

Reference to formula (I) or any variation thereof includes reference to (IIa), (IIb), (IIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound of Table 1 or Table 2, or any one of compounds 1-329.

In some embodiments of the compound of formula (I), or a salt thereof, the compound is selected from the group consisting of

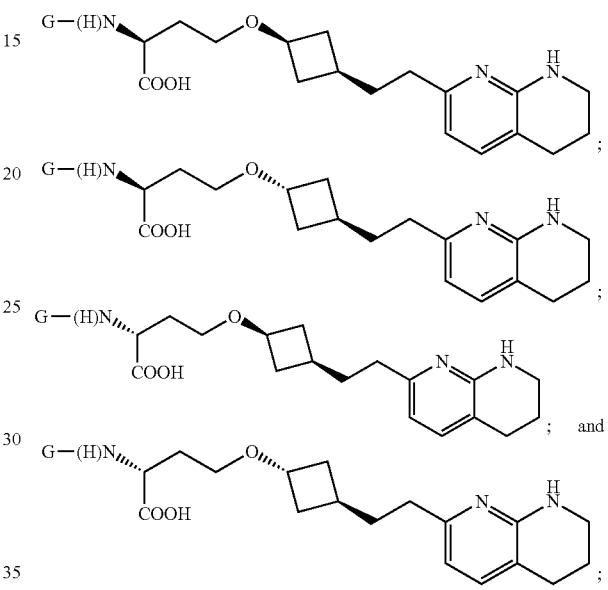

or a pharmaceutically acceptable salt thereof, wherein G is as defined for formula (I), or any applicable variation thereof, and the alpha-carbon of the amino acid can have either R or S absolute stereochemistry as indicated. In one such embodiment, the alpha-carbon of the amino acid is in the S absolute stereochemistry. When the alpha-carbon of the amino acid is in the S absolute stereochemical configuration, in some embodiments such a compound is substantially isolated from the corresponding compound in which the amino acid is in the R absolute stereochemical configuration, such as when a composition comprising the compound in the S absolute stereochemical configuration comprises no more than 5% or 3% or 1% or 0.5% or 0.1% by weight of the corresponding compound having the R absolute stereochemical configuration. In another such embodiment, the alpha-carbon of the amino acid is in the R absolute stereochemistry. When the alpha-carbon of the amino acid is in the R absolute stereochemical configuration, in some embodiments such a compound is substantially isolated from the corresponding compound in which the amino acid is in the S absolute stereochemical configuration, such as when a composition comprising the compound in the R absolute stereochemical configuration comprises no more than 5% or 3% or 1% or 0.5% or 0.1% by weight of the corresponding compound having the S absolute stereochemical configuration. In another embodiment is provided a composition comprising a foregoing compound, or a pharmaceutically acceptable salt thereof, and a pharmaceutically acceptable carrier. In one such embodiment is provided a composition comprising a mixture of a compound in which the alpha-carbon of the amino acid is in the S stereochemical configuration and a compound in which the alpha-carbon of the amino acid is in the R stereochemical configuration.

Also provided in another embodiment is a compound of formula (I), or a salt thereof, wherein G is —C(O)R² and R² is $C_1$-$C_6$ alkyl substituted by 0-5 $R^{2a}$ groups. In one aspect of the foregoing embodiment, R² is unsubstituted $C_1$-$C_6$ alkyl (e.g., unsubstituted $C_4$-$C_6$ alkyl). In one aspect of the foregoing embodiment, the $C_1$-$C_6$ alkyl of R² is straight-chain alkyl (e.g., n-butyl). In another aspect of the foregoing embodiment, the $C_1$-$C_6$ alkyl of R² is branched alkyl (e.g., isobutyl). In another aspect of the foregoing embodiment, R² is $C_1$-$C_5$ alkyl substituted by 1-5 $R^{2a}$ groups, wherein each $R^{2a}$ is independently selected from halogen, $C_1$-$C_6$ alkyl, $C_3$-$C_8$ cycloalkyl, 3- to 12-membered heterocyclyl, $C_6$-$C_{14}$ aryl, 5- to 10-membered heteroaryl, —CN, —OR⁵, —NR⁶R⁷, —NR⁵C(O)OR⁶, and —S(O)₂R⁵, wherein the $C_1$-$C_6$ alkyl, $C_3$-$C_5$ cycloalkyl, 3- to 12-membered heterocyclyl, $C_6$-$C_{14}$ aryl, and 5- to 10-membered heteroaryl of $R^{2a}$ are independently optionally substituted by $R^{4a}$. In another aspect of the foregoing embodiment, R² is $C_2$-$C_5$ alkyl substituted by 1-5 $R^{2a}$ groups, wherein at least one of the $R^{2a}$ groups is halogen (e.g., $R^2C_5$ alkyl substituted by 2-3 fluoro groups). In another aspect of the foregoing embodiment, R² is $C_1$-$C_5$ alkyl (e.g., $C_1$-$C_3$ alkyl) substituted by 1-5 $R^{2a}$ groups, wherein at least one of the $R^{2a}$ groups is $C_3$-$C_8$ cycloalkyl (e.g., cyclopropyl, cyclobutyl, and cyclohexyl). In another aspect of the foregoing embodiment, R² is $C_1$-$C_3$ alkyl substituted by $C_3$-$C_6$ cycloalkyl, wherein the $C_3$-$C_6$ cycloalkyl is substituted by 0-5 groups selected from the group consisting of halogen, $C_1$-$C_6$ alkyl (e.g., methyl), and —OR⁵ (e.g., —OH and —OCH₃). In another aspect of the foregoing embodiment, R² is $C_1$-$C_3$ alkyl substituted by $C_3$-$C_6$ cycloalkyl, wherein the $C_3$-$C_6$ cycloalkyl unsubstituted. In another aspect of the foregoing embodiment, R² is $C_1$-$C_5$ alkyl substituted by 1-5 $R^{2a}$ groups, wherein at least one of the $R^{2a}$ groups is 3- to 12-membered heterocyclyl (e.g. R² is $C_1$ alkyl substituted by 6-membered heterocyclyl). In another aspect of the foregoing embodiment, R² is $C_1$-$C_5$ alkyl substituted by 1-5 $R^{2a}$ groups, wherein at least one of the $R^{2a}$ groups is $C_6$-$C_{14}$ aryl, wherein the $C_6$-$C_{14}$ aryl is independently optionally substituted by halogen or $C_1$-$C_6$ alkyl substituted by 0-5 halogen (e.g., $R^{2a}$ is unsubstituted phenyl or phenyl substituted by 1-5 halogen. In another aspect of the foregoing embodiment, R² is $C_2$-$C_5$ alkyl (e.g., $C_5$ alkyl) substituted by 1-5 $R^{2a}$ groups, wherein at least one of the $R^{2a}$ groups is 5- to 10-membered heteroaryl substituted by 0-5 $R^{4a}$ groups (e.g., $R^{2a}$ is unsubstituted pyridinyl). In another aspect of the foregoing embodiment, R² is $C_1$-$C_5$ alkyl substituted by 1-5 $R^{2a}$ groups, wherein at least one of the $R^{2a}$ groups is —OR⁵, wherein each R⁵ is independently selected from hydrogen, $C_1$-$C_6$ alkyl, and $C_6$-$C_{14}$ aryl (e.g., R⁵ is $C_6$-$C_{14}$ aryl substituted by 0-5 halogen). In another aspect of the foregoing embodiment, R² is $C_1$-$C_5$ alkyl substituted by 1-5 $R^{2a}$ groups, wherein at least one of the $R^{2a}$ groups is —CN, —NR⁶R⁷, —NR⁵C(O)OR⁶, or —S(O)₂R⁵. In another aspect of the foregoing embodiment, R² is $C_1$-$C_5$ alkyl substituted by 2-5 $R^{2a}$ groups, wherein each $R^{2a}$ is independently selected from halogen, $C_1$-$C_6$ alkyl, $C_3$-$C_8$ cycloalkyl, 5- to 10-membered heteroaryl, $C_6$-$C_{14}$ aryl, —CN, —OR⁵, and —NR⁵C(O)OR⁶. In another aspect of the foregoing embodiment, R² is $C_1$-$C_5$ alkyl substituted by 2-5 $R^{2a}$ groups, wherein at least one $R^{2a}$ group is phenyl substituted by 0-5 halogen and at least one $R^{2a}$ group is OR⁵, wherein each R⁵ is independently selected from hydrogen and $C_1$-$C_6$ alkyl.

Also provided is a compound of formula (I), or a salt thereof, wherein G is —C(O)R² and R² is selected from the group consisting of:

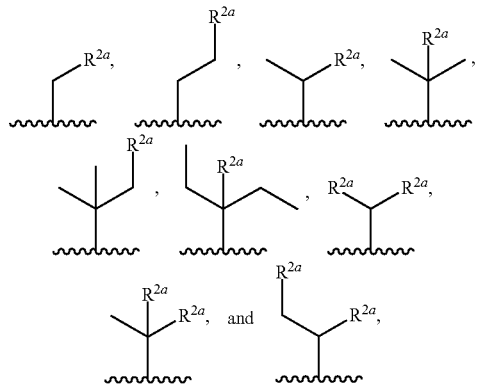

wherein each $R^{2a}$ is independently as defined for formula (I).

Also provided in another embodiment is a compound of formula (I), or a salt thereof, wherein G is —C(O)R² and R² is $C_3$-$C_5$ cycloalkyl substituted by 0-5 $R^{2b}$ groups. In one aspect of the foregoing embodiment, the $C_3$-$C_5$ cycloalkyl of R² is monocyclic. In another aspect, the $C_3$-$C_5$ cycloalkyl of R² is bicyclic (e.g., fused, spiro, or bridged). In another aspect, R² is unsubstituted $C_3$-$C_8$ cycloalkyl (e.g., bicycle [2.2.2]octanyl). In another aspect of the foregoing embodiment, R² is $C_3$-$C_5$ cycloalkyl substituted by 1-5 $R^{2b}$ groups, wherein each $R^{2b}$ is independently selected from halogen, $C_1$-$C_6$ alkyl, 3- to 12-membered heterocyclyl, $C_6$-$C_{14}$ aryl, 5- to 10-membered heteroaryl, and —OR⁵. In another aspect of the foregoing embodiment, R² is $C_3$-$C_6$ cycloalkyl (e.g., cyclopropyl or cyclohexyl) substituted by 1-5 $R^{2b}$ groups, wherein at least one of the $R^{2b}$ groups is halogen (e.g., fluoro). In another aspect of the foregoing embodiment, R² is $C_3$-$C_6$ cycloalkyl substituted by 1-5 $R^{2b}$ groups, wherein at least one of the $R^{2b}$ groups is $C_1$-$C_6$ alkyl, wherein the $C_1$-$C_6$ alkyl of $R^{2b}$ is substituted by 0-5 $R^{4a}$ groups (e.g., $R^{2b}$ is $C_1$-$C_2$ alkyl substituted by 1-5 $R^{4a}$ groups, wherein each $R^{4a}$ groups is independently selected from phenyl substituted by 0-5 halogen and 6-membered heteroaryl substituted by 0-5 halogen). In another aspect of the foregoing embodiment, R² is $C_3$-$C_6$ cycloalkyl substituted by 1-5 $R^{2b}$ groups, wherein at least one of the $R^{2b}$ groups is 3- to 12-membered heterocyclyl (e.g., tetrahydro-2H-pyranyl or benzodioxolyl). In another aspect of the foregoing embodiment, R² is $C_3$-$C_4$ cycloalkyl substituted by 1-5 $R^{2b}$ groups, wherein at least one of the $R^{2b}$ groups is $C_6$-$C_{14}$ aryl substituted by 0-5 $R^{4a}$ groups, wherein each $R^{4a}$ is independently selected from halogen, $C_1$-$C_6$ alkyl, and —OR⁸ (e.g., $R^{2b}$ is unsubstituted phenyl or $R^{2b}$ is phenyl substituted by fluoro, methyl, tert-butyl, or —OCF₃). In another aspect of the foregoing embodiment, R² is $C_3$-$C_7$ cycloalkyl substituted by 1-5 $R^{2b}$ groups, wherein at least one of the $R^{2b}$ groups is 5- to 10-membered heteroaryl (e.g., pyridinyl or isoquinolinyl). In another aspect of the foregoing embodiment, R² is $C_3$-$C_6$ cycloalkyl substituted by 2-5 $R^{2b}$ groups, wherein each $R^{2b}$ is independently selected from halogen (e.g., fluoro), $C_6$-$C_{14}$ aryl (e.g., phenyl), and —OR⁵ (e.g., —OH). In another aspect of the foregoing embodiment, R² is $C_3$-$C_6$ cycloalkyl substituted by 2-5 $R^{2b}$ groups, wherein at least one $R^{2b}$ group is halogen (e.g., fluoro) and at least one $R^{2b}$ group is phenyl substituted by 0-5 $C_1$-$C_6$ alkyl (e.g., —CH₃).

Also provided is a compound of formula (I), or a salt thereof, wherein G is —C(O)R² and R² is selected from the group consisting of:

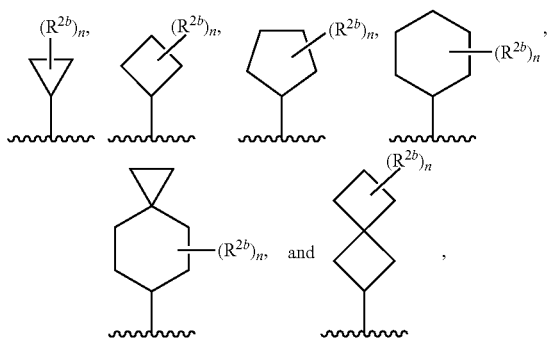

wherein R²ᵇ is as defined for formula (I), and n is 0, 1, 2, or 3. In one variation, n is 0. In another variation, n is 1. In another variation, n is 2. In yet another variation, n is 3.

Also provided in another embodiment is a compound of formula (I), or a salt thereof, wherein G is —C(O)R² and R² is 3- to 12-membered heterocyclyl substituted by 0-5 R²ᶜ groups. In another aspect of the foregoing embodiment, the 3- to 12-membered heterocyclyl of R² is monocyclic. In another aspect of the foregoing embodiment, the 3- to 12-membered heterocyclyl of R² is bicyclic (e.g., fused, spiro, or bridged). In another aspect of the foregoing embodiment, R² unsubstituted 4- to 10-membered heterocyclyl (e.g., azetidinyl, pyrrolidinyl, piperidinyl, oxetanyl, tetrahydrofuranyl, tetrahydropyranyl, oxabicyclohexanyl, oxabicyclooctanyl, tetrahydro-2H-thiopyranyl, morpholinyl, benzodioxanyl, 3-oxabicyclo[3.1.0]hexanyl, or 8-oxabicyclo[3.2.1]octanyl). In another aspect of the foregoing embodiment, R² is 3- to 12-membered heterocyclyl substituted by 1-5 R²ᶜ groups, wherein each R²ᶜ is independently selected from oxo, halogen, C₁-C₆ alkyl, C₆-C₁₄ aryl, 5- to 10-membered heteroaryl, —CN, —OR⁵, —C(O)R⁵, —C(O)OR⁵, and —S(O)₂R⁵. In another aspect of the foregoing embodiment, R² is 4- to 6-membered heterocyclyl (e.g., oxetanyl, tetrahydropyranyl, or azetidinyl) substituted by 1-5 R²ᶜ groups, wherein at least one of the R²ᶜ groups is C₁-C₆ alkyl, wherein the C₁-C₆ alkyl of R²ᶜ is substituted by 0-5 R⁴ᵃ groups. In another aspect of the foregoing embodiment, R²ᶜ is C₁-C₂ alkyl substituted by 1-5 R⁴ᵃ groups, wherein each R⁴ᵃ groups is independently selected from halogen; phenyl substituted by 0-5 halogen; 6-membered heteroaryl (e.g., pyridinyl or pyrimidinyl) substituted by 0-5 halogen; and —NR⁸C(O)OR¹⁰ (e.g., —NHC(O)O-t-butyl). In another aspect of the foregoing embodiment, R² is 4- to 6-membered heterocyclyl substituted by 1-5 R²ᶜ groups, wherein at least one of the R²ᶜ groups is unsubstituted C₆-C₁₄ aryl (e.g., phenyl). In another aspect of the foregoing embodiment, R² is 4- to 6-membered heterocyclyl (e.g., 5-membered heterocyclyl) substituted by 1-5 R²ᶜ groups, wherein at least one of the R²ᶜ groups is 5- to 10-membered heteroaryl substituted by 0-5 C₁-C₆ alkyl (e.g., R²ᶜ is pyrazolyl substituted by —CH₃). In another aspect of the foregoing embodiment, R² is 4- to 6-membered heterocyclyl substituted by 1-5 R²ᶜ groups, wherein at least one R²ᶜ group is —C(O)R⁵, —C(O)OR⁵, or —S(O)₂R⁵, wherein each R⁵ is independently C₁-C₆ alkyl. In another aspect of the foregoing embodiment, R² is 4- to 6-membered heterocyclyl (e.g., 1,2-dihydropyridinyl) substituted by 1-5 R²ᶜ groups, wherein at least one R²ᶜ group is oxo. In another aspect of the foregoing embodiment, R² is 4- to 6-membered heterocyclyl substituted by 2-5 R²ᶜ groups, wherein each R²ᶜ is independently selected from halogen, C₁-C₆ alkyl, —C(O)R⁵, and —C(O)OR⁵. In another aspect of the foregoing embodiment, R² is 4- to 6-membered heterocyclyl substituted by 2-5 R²ᶜ groups, wherein at least one R²ᶜ group is C₁-C₆ alkyl substituted by 0-5 halogen and at least one R²ᶜ group is —C(O)R¹ or —C(O)OR⁵. In another aspect of the foregoing embodiment, R² is azetidinyl, pyrrolidinyl, piperidinyl, oxetanyl, tetrahydrofuranyl, tetrahydropyranyl, oxabicyclohexanyl, oxabicyclooctanyl, tetrahydro-2H-thiopyranyl, morpholinyl, or benzodioxanyl, each of which is substituted by 0-5 R²ᶜ groups.

Also provided is a compound of formula (I), or a salt thereof, wherein G is —C(O)R² and R² is selected from the group consisting of:

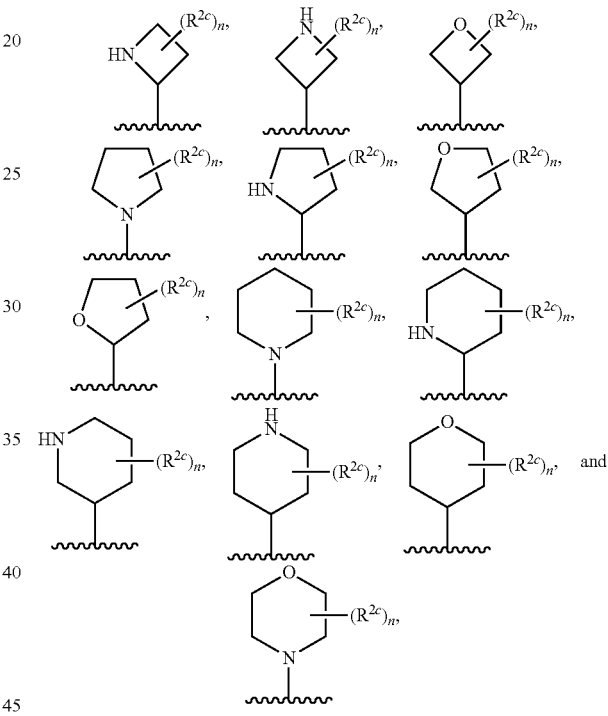

wherein R²ᶜ is as defined for formula (I), and n is 0, 1, 2, or 3. In one variation, n is 0. In another variation, n is 1. In another variation, n is 2. In yet another variation, n is 3. In the above structures that depict an —N(H)— moiety and n is 1, 2, or 3, it is understood that one of the R²ᶜ groups can replace the hydrogen atom of the —N(H)— moiety (e.g., n is 1 and R² is

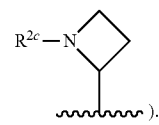).

Also provided in another embodiment is a compound of formula (I), or a salt thereof, wherein G is —C(O)R² and R² is C₆-C₁₄ aryl substituted by 0-5 R²ᵈ groups. In another aspect of the foregoing embodiment, R² is unsubstituted C₆-C₁₀ aryl (e.g., phenyl, indanyl, or 1,2,3,4-tetrahydronaphthalenyl). In another aspect of the foregoing embodiment, $R^2$ is $C_6$-$C_{10}$ aryl substituted by 1-5 $R^{2d}$ groups, wherein each $R^{2d}$ is independently selected from halogen, $C_1$-$C_6$ alkyl, $C_3$-$C_5$ cycloalkyl, 3- to 12-membered heterocyclyl, 5- to 10-membered heteroaryl, —CN, and —$OR^5$, wherein the $C_1$-$C_6$ alkyl, $C_3$-$C_5$ cycloalkyl, 3- to 12-membered heterocyclyl and 5- to 10-membered heteroaryl of $R^{2d}$ are each independently substituted by 0-5 halogen, $C_1$-$C_6$ alkyl or $OR^8$. In another aspect of the foregoing embodiment, $R^2$ is $C_6$-$C_{10}$ aryl substituted by 1-5 $R^{2d}$ groups, wherein at least one of the $R^{2d}$ groups is halogen (e.g., fluoro or chloro). In another aspect of the foregoing embodiment, $R^2$ is $C_6$-$C_{10}$ aryl substituted by 1-5 $R^{2d}$ groups, wherein at least one of the $R^{2d}$ groups is $C_1$-$C_6$ alkyl, wherein the $C_1$-$C_6$ alkyl of $R^{2d}$ is substituted by 0-5 $R^{4a}$ groups (e.g., $R^{2d}$ is —$CH_3$). In another aspect of the foregoing embodiment, $R^{2d}$ is $C_1$-$C_2$ alkyl substituted by 1-5 $R^{4a}$ groups, wherein each $R^{4a}$ groups is independently selected from halogen and $OR^8$ (e.g., $R^{2d}$ is —$CH_2(OH)$, or —$CF_3$). In another aspect of the foregoing embodiment, $R^2$ is $C_6$-$C_{10}$ aryl (e.g., phenyl) substituted by 1-5 $R^{2d}$ groups, wherein at least one of the $R^{2d}$ groups is $C_3$-$C_6$ cycloalkyl (e.g., cyclopropyl). In another aspect of the foregoing embodiment, $R^2$ is $C_6$-$C_{10}$ aryl (e.g., phenyl) substituted by 1-5 $R^{2d}$ groups, wherein at least one of the $R^{2d}$ groups is 6-membered heterocyclyl (e.g., morpholinyl). In another aspect of the foregoing embodiment, $R^2$ is $C_6$-$C_{10}$ aryl (e.g., phenyl) substituted by 1-5 $R^{2d}$ groups, wherein at least one of the $R^{2d}$ groups is 5- to 6-membered heteroaryl (e.g., pyrazolyl, thiazolyl, or pyridinyl), wherein the heteroaryl of $R^{2d}$ is substituted by 0-5 $C_1$-$C_6$ alkyl groups (e.g., —$CH_3$). In another aspect of the foregoing embodiment, $R^2$ is $C_6$-$C_{10}$ aryl (e.g., phenyl) substituted by 1-5 $R^{2d}$ groups, wherein at least one of the $R^{2d}$ groups is —$OR^5$, wherein each $R^5$ is independently selected from $C_1$-$C_2$ alkyl substituted by 0-5 groups selected from halogen (e.g., fluoro) and —$OR^{10}$ (e.g., —$OCH_3$). In another aspect of the foregoing embodiment, $R^2$ is $C_6$-$C_{10}$ aryl (e.g., phenyl) substituted by 2-5 $R^{2d}$ groups, wherein each $R^{2d}$ is independently selected from halogen, $C_1$-$C_6$ alkyl, —CN, and —$OR^5$. In another aspect of the foregoing embodiment, $R^2$ is $C_6$-$C_{10}$ aryl (e.g., phenyl) substituted by 2-5 $R^{2d}$ groups, wherein at least two of the $R^{2d}$ groups are halogen (e.g., fluoro or chloro). In another aspect of the foregoing embodiment, $R^2$ is $C_6$-$C_{10}$ aryl (e.g., phenyl) substituted by 2-5 $R^{2d}$ groups, wherein at least one of the $R^{2d}$ groups is $C_1$-$C_6$ alkyl and at least one of the $R^{2d}$ groups is selected from the group consisting of halogen, —CN, and —$OR^5$. In another aspect of the foregoing embodiment, $R^2$ is phenyl, indanyl, or 1,2,3,4-tetrahydronaphthalenyl, each of which is substituted by 0-5 $R^{2d}$ groups.

Also provided is a compound of formula (I), or a salt thereof, wherein G is —$C(O)R^2$ and $R^2$ is selected from the group consisting of:

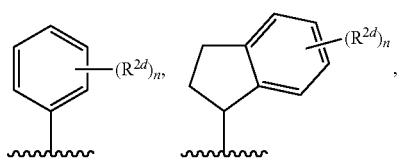

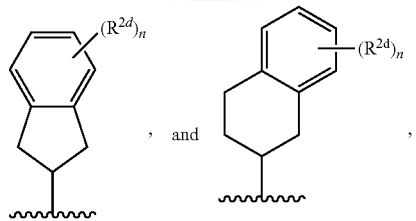

wherein $R^{2d}$ is as defined for formula (I), and n is 0, 1, 2, or 3. In one variation, n is 0. In another variation, n is 1. In another variation, n is 2. In yet another variation, n is 3.

Also provided in another embodiment is a compound of formula (I), or a salt thereof, wherein G is —$C(O)R^2$ and $R^2$ is 5- to 10-membered heteroaryl substituted by 0-5 $R^{2e}$ groups. In another aspect of the foregoing embodiment, $R^2$ is unsubstituted 5- to 10-membered heteroaryl (e.g., pyridinyl, pyrrolopyridinyl, quinolinyl, or 4,5,6,7-tetrahydro-indazolyl). In another aspect of the foregoing embodiment, $R^2$ is 5- to 10-membered heteroaryl substituted by 1-5 $R^{2e}$ groups, wherein each $R^{2e}$ is independently selected from halogen, $C_1$-$C_6$ alkyl, and —$OR^5$. In another aspect of the foregoing embodiment, $R^2$ is 5- to 10-membered heteroaryl (e.g., pyridinyl) substituted by 1-5 $R^{2e}$ groups, wherein at least one of the $R^{2e}$ groups is halogen. In another aspect of the foregoing embodiment, $R^2$ is 5- to 10-membered heteroaryl (e.g., pyridinyl, pyrimidinyl, pyrrolopyridinyl, or indazolyl) substituted by 1-5 $R^{2e}$ groups, wherein at least one of the $R^{2e}$ groups is $C_1$-$C_4$ alkyl, wherein the $C_1$-$C_4$ alkyl of $R^{2e}$ is substituted by 0-5 halogen groups (e.g., $R^{2e}$ is —$CH_3$ or —$CF_3$). In another aspect of the foregoing embodiment, $R^2$ is 5- to 10-membered heteroaryl substituted by 2-5 $R^{2e}$ groups, wherein each $R^{2e}$ is independently selected from halogen, $C_1$-$C_6$ alkyl, and —CN. In another aspect of the foregoing embodiment, $R^2$ is 5- to 10-membered heteroaryl substituted by 2-5 $R^{2e}$ groups, wherein at least two of the $R^{2e}$ groups are halogen. In another aspect of the foregoing embodiment, $R^2$ is 5- to 10-membered heteroaryl substituted by 2-5 $R^{2e}$ groups, wherein at least two of the $R^{2e}$ groups are $C_1$-$C_6$ alkyl. In another aspect of the foregoing embodiment, $R^2$ is 5- to 10-membered heteroaryl (e.g., pyridinyl or pyrimidinyl) substituted by 3-5 $R^{2e}$ groups, wherein each $R^{2e}$ is independently selected from halogen, $C_1$-$C_6$ alkyl, and —CN. In another aspect of the foregoing embodiment, $R^2$ is 5- to 10-membered heteroaryl (e.g., pyridinyl or pyrimidinyl) substituted by three —$CH_3$ groups. In another aspect of the foregoing embodiment, $R^2$ is 5- to 10-membered heteroaryl (e.g., pyridinyl or pyrimidinyl) substituted by two —$CH_3$ groups and one halogen group. In another aspect of the foregoing embodiment, $R^2$ is pyrazolyl, pyridyl, pyrimidinyl, indazolyl, pyrrolopyridinyl, quinolinyl, or 4,5,6,7-tetrahydro-indazolyl, each of which is substituted by 0-5 $R^{2e}$ groups.

Also provided is a compound of formula (I), or a salt thereof, wherein G is —$C(O)R^2$ and $R^2$ is selected from the group consisting of:

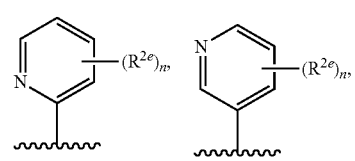

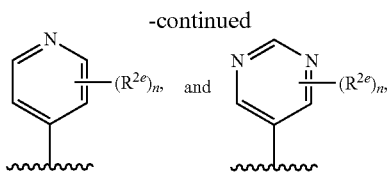

wherein $R^{2e}$ is as defined for formula (I), and n is 0, 1, 2, or 3. In one variation, n is 0. In another variation, n is 1. In another variation, n is 2. In yet another variation, n is 3.

Also provided in another embodiment is a compound of formula (I), or a salt thereof, wherein G is —C(O)$R^2$ and $R^2$ is —O$R^{2f}$. In another aspect of the foregoing embodiment, $R^{2f}$ is selected from the group consisting of $C_1$-$C_6$ alkyl, $C_3$-$C_8$ cycloalkyl, 3- to 12-membered heterocyclyl, $C_6$-$C_{14}$ aryl, and 5- to 10-membered heteroaryl.

Also provided in another embodiment is a compound of formula (I), or a salt thereof, wherein G is —C(O)$R^2$, $R^2$ is —O$R^{2f}$, and $R^{2f}$ is $C_1$-$C_6$ alkyl substituted by 0-5 $R^{2i}$ groups. In another aspect of the foregoing embodiment, $R^{2f}$ is unsubstituted $C_1$-$C_6$ alkyl. In another aspect of the foregoing embodiment, $R^{2f}$ is $C_1$-$C_6$ alkyl substituted by 1-5 $R^{2i}$ groups, wherein each $R^{2i}$ is independently selected from the group consisting of halogen, $C_1$-$C_6$ alkyl, $C_3$-$C_5$ cycloalkyl, 3- to 12-membered heterocyclyl, $C_6$-$C_{14}$ aryl, 5- to 10-membered heteroaryl, —O$R^5$—, —N$R^5$C(O)$R^6$, and —N$R^5$C(O)O$R^6$, wherein the $C_1$-$C_6$ alkyl, $C_3$-$C_8$ cycloalkyl, 3- to 12-membered heterocyclyl, $C_6$-$C_{14}$ aryl, and 5- to 10-membered heteroaryl of $R^{2i}$ is substituted by 0-5 groups selected from the group consisting of halogen, —CN, —O$R^8$, and $C_1$-$C_6$ alkyl optionally substituted by halogen. In another aspect of the foregoing embodiment, $R^{2f}$ is $C_1$-$C_6$ alkyl substituted by 1-5 $R^{2i}$ groups, wherein at least one of the $R^{2i}$ groups is halogen. In another aspect of the foregoing embodiment, $R^{2f}$ is $C_1$-$C_6$ alkyl substituted by 1-5 $R^{2i}$ groups, wherein at least one of the $R^{2i}$ groups is phenyl. In another aspect of the foregoing embodiment, $R^{2f}$ is $C_1$-$C_6$ alkyl substituted by 1-5 $R^{2i}$ groups, wherein at least one of the $R^{2i}$ groups is —N$R^5$C(O)O$R^6$, wherein $R^5$ is hydrogen and $R^6$ is $C_1$-$C_6$ alkyl (e.g., $R^{2i}$ is —NHC(O)O-t-butyl). In another aspect of the foregoing embodiment, $R^{2f}$ is $C_1$-$C_6$ alkyl substituted by 1-5 $R^{2i}$ groups, wherein at least one of the $R^{2i}$ groups is —N$R^5$C(O)$R^6$, wherein $R^5$ is hydrogen and $R^6$ is $C_1$-$C_6$ alkyl (e.g., $R^{2i}$ is —NHC(O)CH$_3$).

Also provided is a compound of formula (I), or a salt thereof, wherein G is —C(O)$R^2$ and $R^2$ is selected from the group consisting of:

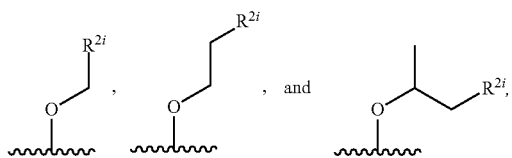

wherein $R^{2i}$ is as defined for formula (I).

Also provided in another embodiment is a compound of formula (I), or a salt thereof, wherein G is —C(O)$R^2$, $R^2$ is —O$R^{2f}$, and $R^{2f}$ is $C_3$-$C_8$ cycloalkyl substituted by 0-5 $R^{2i}$ groups. In another aspect of the foregoing embodiment, $R^{2f}$ is unsubstituted $C_3$-$C_8$ cycloalkyl (e.g., cyclopentyl, cyclohexyl, or spiro[2.3]hexanyl). In another aspect of the foregoing embodiment, $R^{2f}$ is $C_3$-$C_8$ cycloalkyl substituted by 1-5 $R^{2i}$ groups, wherein each $R^{2i}$ is independently selected from the group consisting of halogen, $C_1$-$C_6$ alkyl, $C_2$-$C_6$ alkynyl, $C_6$-$C_{14}$ aryl, and 5- to 10-membered heteroaryl, wherein the $C_1$-$C_6$ alkyl, $C_2$-$C_6$ alkynyl, $C_6$-$C_{14}$ aryl, and 5- to 10-membered heteroaryl of $R^{2i}$ are substituted by 0-5 groups selected from the group consisting of $C_1$-$C_6$ alkyl and $C_6$-$C_{14}$ aryl. In another aspect of the foregoing embodiment, $R^{2f}$ is $C_3$-$C_6$ cycloalkyl (e.g., cyclopropyl or cyclobutyl) substituted by 1-5 $R^2$ groups, wherein at least one $R^{2i}$ group is $C_1$ alkyl. In another aspect of the foregoing embodiment, $R^{2i}$ is $C_3$-$C_6$ cycloalkyl substituted by 1-5 $R^{2i}$ groups, wherein at least one $R^{2i}$ group is $C_2$ alkynyl substituted by 0-1 phenyl group. In another aspect of the foregoing embodiment, $R^{2f}$ is $C_3$-$C_6$ cycloalkyl substituted by 1-5 $R^{2i}$ groups, wherein at least one $R^{2i}$ group is phenyl substituted by 0-3 $C_1$-$C_6$ alkyl groups or is pyrazolyl substituted by 0-3 $C_1$-$C_6$ alkyl groups, which $C_1$-$C_6$ alkyl groups on phenyl or pyrazolyl of $R^{2i}$ may be the same or different.

Also provided is a compound of formula (I), or a salt thereof, wherein G is —C(O)$R^2$ and $R^2$ is selected from the group consisting of:

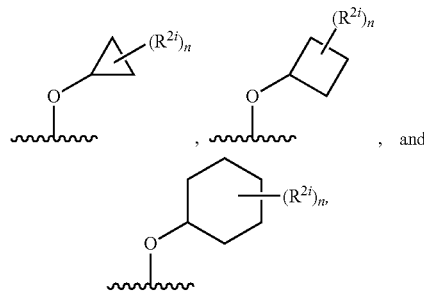

wherein $R^{2i}$ is as defined for formula (I) and n is 0, 1, or 2. In one variation, n is 0. In another variation, n is 1. In yet another variation, n is 2.

Also provided in another embodiment is a compound of formula (I), or a salt thereof, wherein G is —C(O)$R^2$, $R^2$ is —O$R^{2f}$, and $R^{2f}$ is 3- to 12-membered heterocyclyl substituted by 0-5 $R^{2i}$ groups. In another aspect of the foregoing embodiment, $R^{2f}$ is unsubstituted 3- to 12-membered heterocyclyl (e.g., azetidinyl or pyrrolidinyl). In another aspect of the foregoing embodiment, $R^{2f}$ is 3- to 12-membered heterocyclyl substituted by 1-5 $R^{2i}$ groups, wherein each $R^{2i}$ is independently selected from the group consisting of $C_1$-$C_6$ alkyl, $C_2$-$C_6$ alkynyl, $C_6$-$C_{14}$ aryl, —C(O)$R^5$, —C(O)O$R^5$, and —S(O)$_2$$R^5$. In another aspect of the foregoing embodiment, $R^{2f}$ is 3- to 12-membered heterocyclyl substituted by 1-5 $R^{2i}$ groups, wherein at least one $R^{2i}$ group is $C_1$-$C_6$ alkyl or $C_2$-$C_6$ alkynyl, each of which is unsubstituted or substituted by a phenyl group. In another aspect of the foregoing embodiment, $R^{2f}$ is 3- to 12-membered heterocyclyl substituted by 1-5 $R^{2i}$ groups, wherein at least one $R^{2i}$ group is $C_6$-$C_{14}$ aryl (e.g., phenyl) substituted by 0-5 $R^{4a}$ groups, wherein each $R^{4a}$ is independently selected from the group consisting of halogen and $C_1$-$C_6$ alkyl (e.g., isopropyl). In another aspect of the foregoing embodiment, $R^{2f}$ is 3- to 12-membered heterocyclyl (e.g., azetidinyl or pyrrolidinyl) substituted by 1-5 $R^{2i}$ groups, wherein at least one $R^{2i}$ group is —C(O)R, wherein $R^5$ is $C_1$-$C_6$ alkyl (e.g., $R^{2i}$ is —C(O)CH$_3$). In another aspect of the foregoing embodiment, $R^{2f}$ is 3- to 12-membered heterocyclyl substituted by 1-5 $R^{2i}$ groups, wherein at least one $R^{2i}$ group is —C(O)O$R^5$, wherein $R^5$ is $C_1$-$C_6$ alkyl (e.g., $R^{2i}$, is —C(O)O-t-butyl). In another aspect of the foregoing embodiment, $R^{2f}$ is 3- to 12-membered heterocyclyl (e.g., azetidinyl or pyrrolidinyl) substituted by 1-5 $R^{2i}$ groups, wherein at least one $R^{2i}$ group is —S(O)$_2$R$^5$, wherein $R^5$ is $C_1$-$C_6$ alkyl (e.g., $R^{2i}$ is —S(O)$_2$CH$_3$). In another aspect of the foregoing embodiment, $R^{2f}$ is 3- to 12-membered heterocyclyl substituted by 2-5 $R^{2i}$ groups, wherein at least one $R^{2i}$ group is —C(O)R$^5$, —C(O)OR$^5$, or —S(O)$_2$R$^5$, wherein $R^5$ is $C_1$-$C_6$ alkyl (e.g., $R^5$ is —CH$_3$ or t-butyl). In another aspect of the foregoing embodiment, $R^{2f}$ is azetidinyl, pyrrolidinyl, or tetrahydropyranyl, each of which is optionally substituted by 0-5 $R^{2i}$.

Also provided is a compound of formula (I), or a salt thereof, wherein G is —C(O)R$^2$ and R$^2$ is selected from the group consisting of:

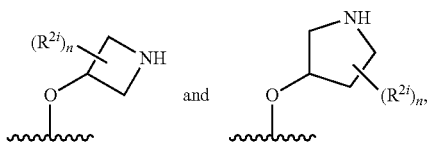

wherein $R^{2i}$ is as defined for formula (I) and n is 0, 1, or 2. In one variation, n is 0. In another variation, n is 1. In yet another variation, n is 2. In the above structures that depict an —N(H)— moiety and n is 1 or 2, it is understood that one of the $R^{2i}$ groups can replace the hydrogen atom of the —N(H)— moiety (e.g., n is 1 and R$^2$ is

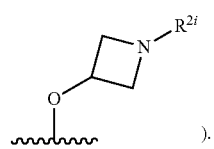

).

Also provided in another embodiment is a compound of formula (I), or a salt thereof, wherein G is —C(O)R$^2$, R$^2$ is —OR$^{2f}$, and $R^{2f}$ is $C_6$-$C_{14}$ aryl substituted by 0-5 $R^{2i}$ groups. In another aspect of the foregoing embodiment, $R^{2f}$ is unsubstituted $C_6$-$C_{14}$ aryl (e.g., indanyl or 1,2,3,4-tetrahydronaphthalenyl).

Also provided is a compound of formula (I), or a salt thereof, wherein G is —C(O)R$^2$ and R$^2$ is selected from the group consisting of:

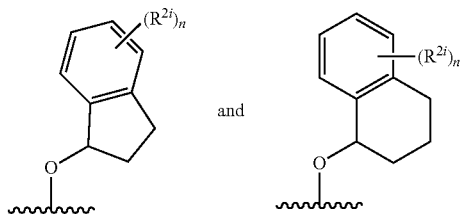

wherein $R^{2i}$ is as defined for formula (I) and n is 0, 1, or 2. In one variation, n is 0. In another variation, n is 1. In yet another variation, n is 2.

Also provided in another embodiment is a compound of formula (I), or a salt thereof, wherein G is —C(O)R$^2$, R$^2$ is —OR$^{2f}$, and $R^{2f}$ is 5- to 10-membered heteroaryl substituted by 0-5 $R^{2i}$ groups. In another aspect of the foregoing embodiment, $R^{2f}$ is unsubstituted 5- to 10-membered heteroaryl.

Also provided in another embodiment is a compound of formula (I), or a salt thereof, wherein G is —C(O)R$^2$ and R$^2$ is —NR$^{2g}$R$^{2h}$. In another aspect of the foregoing embodiment, $R^{2g}$ is hydrogen and $R^{2h}$ is $C_1$-$C_6$ alkyl substituted by 0-5 halogen. In another aspect of the foregoing embodiment, $R^{2g}$ is $C_1$-$C_6$ alkyl substituted by 0-5 halogen and $R^{2h}$ is $C_1$-$C_6$ alkyl substituted by 0-5 halogen.

Also provided is a compound of formula (I), or a salt thereof, wherein G is —C(O)R$^2$ and R$^2$ is selected from the group consisting of:

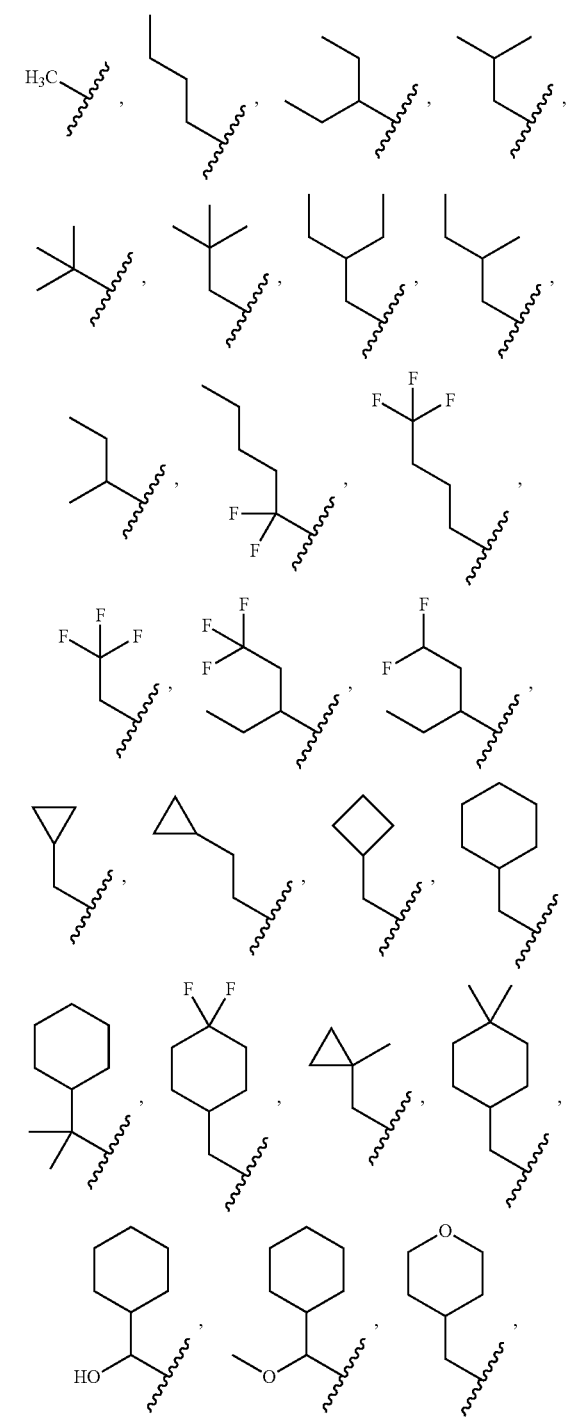

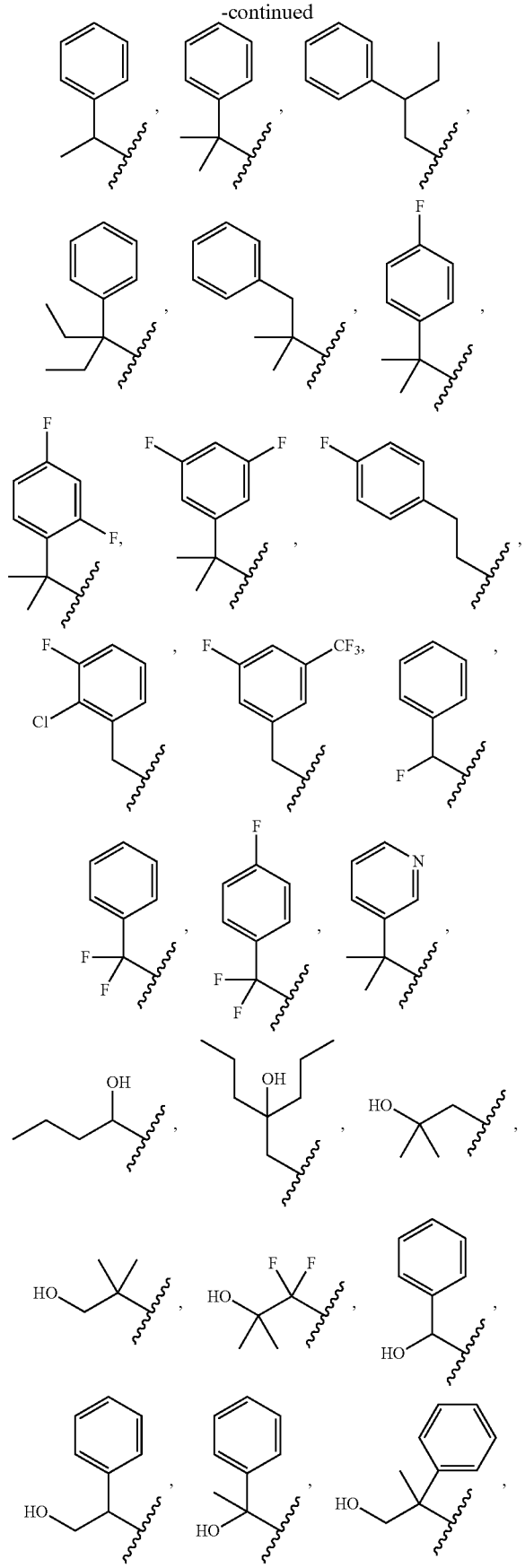
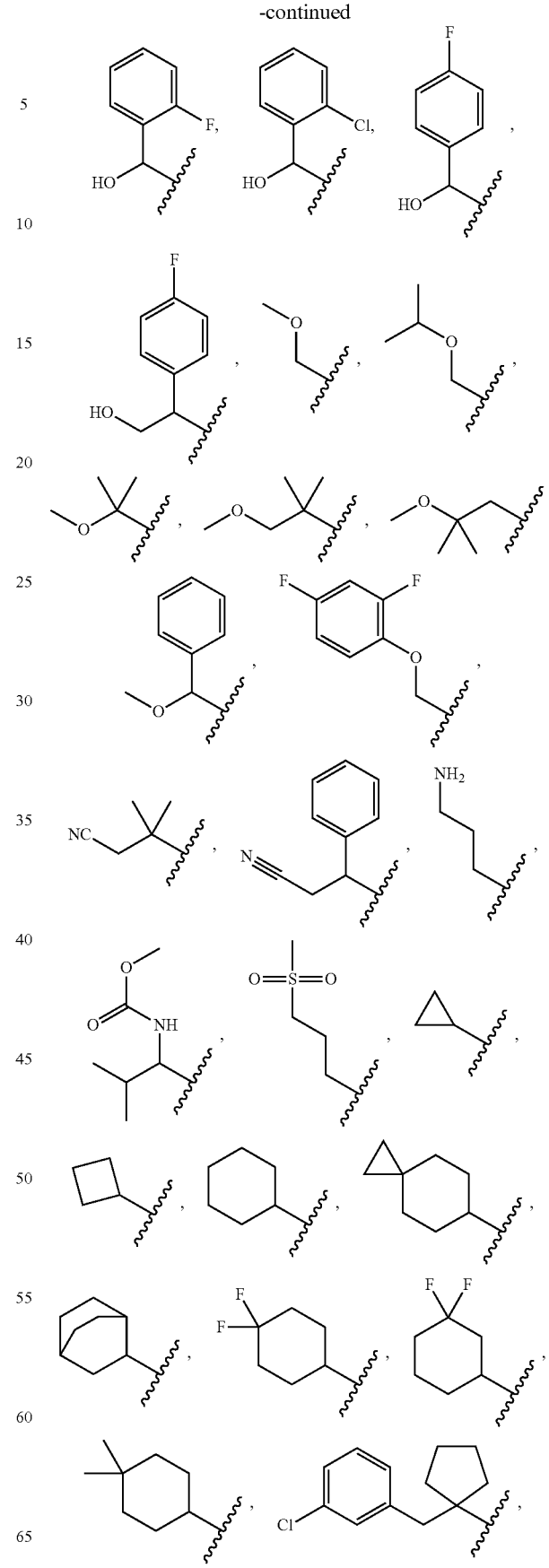

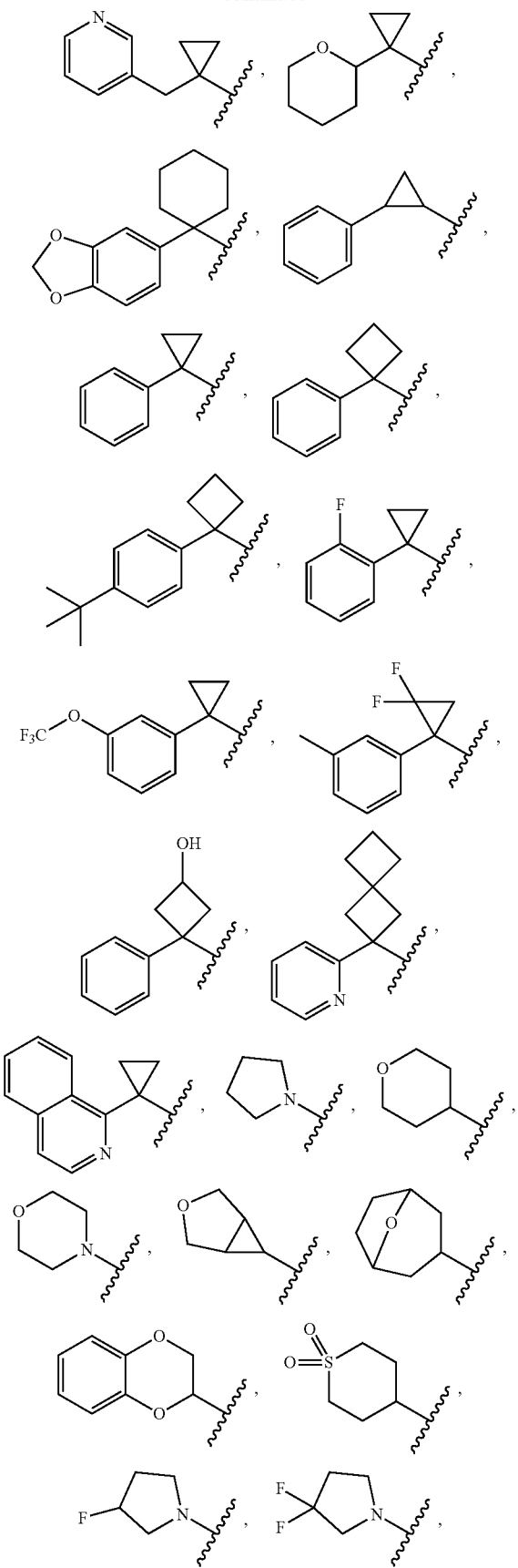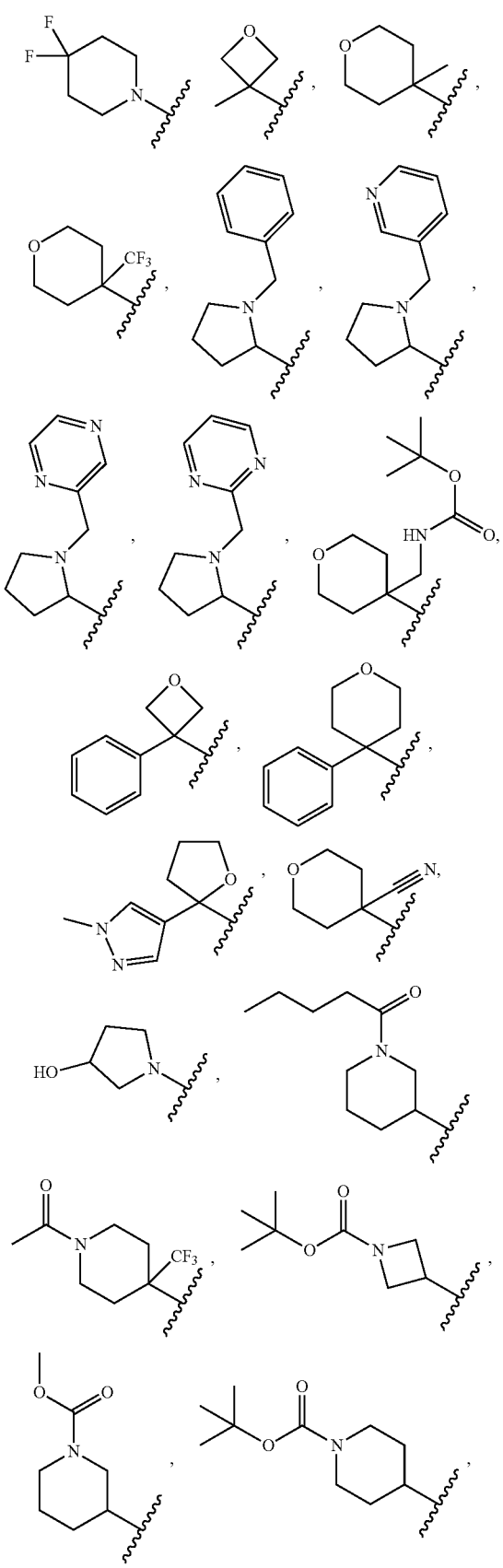

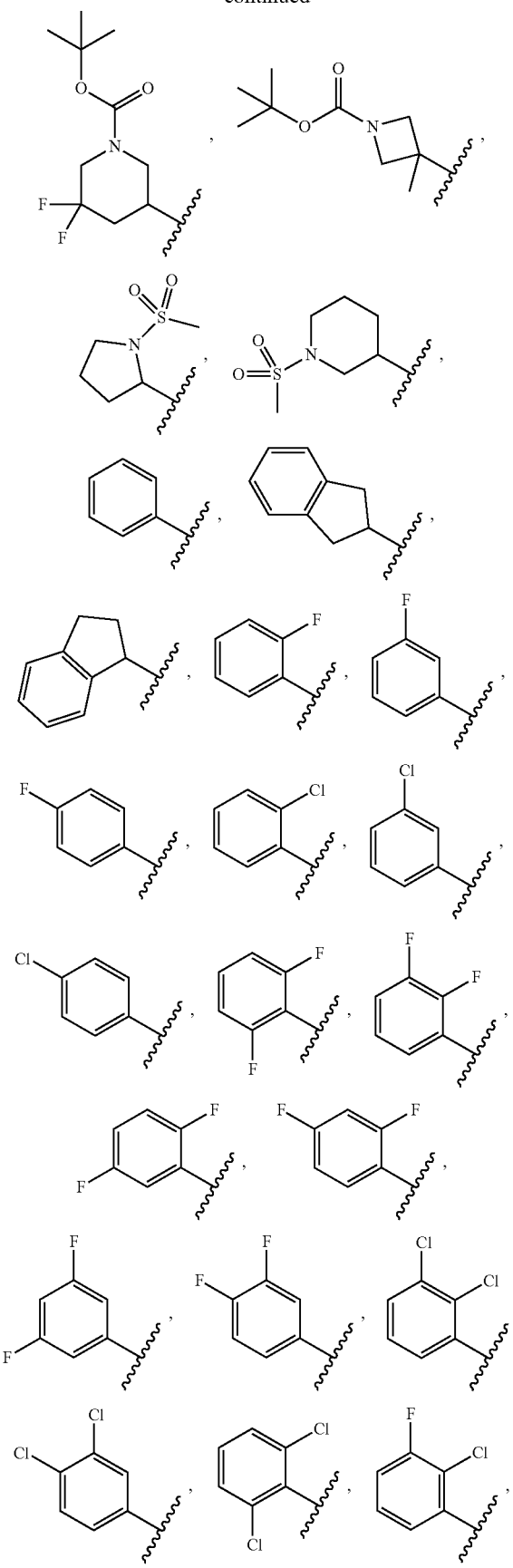
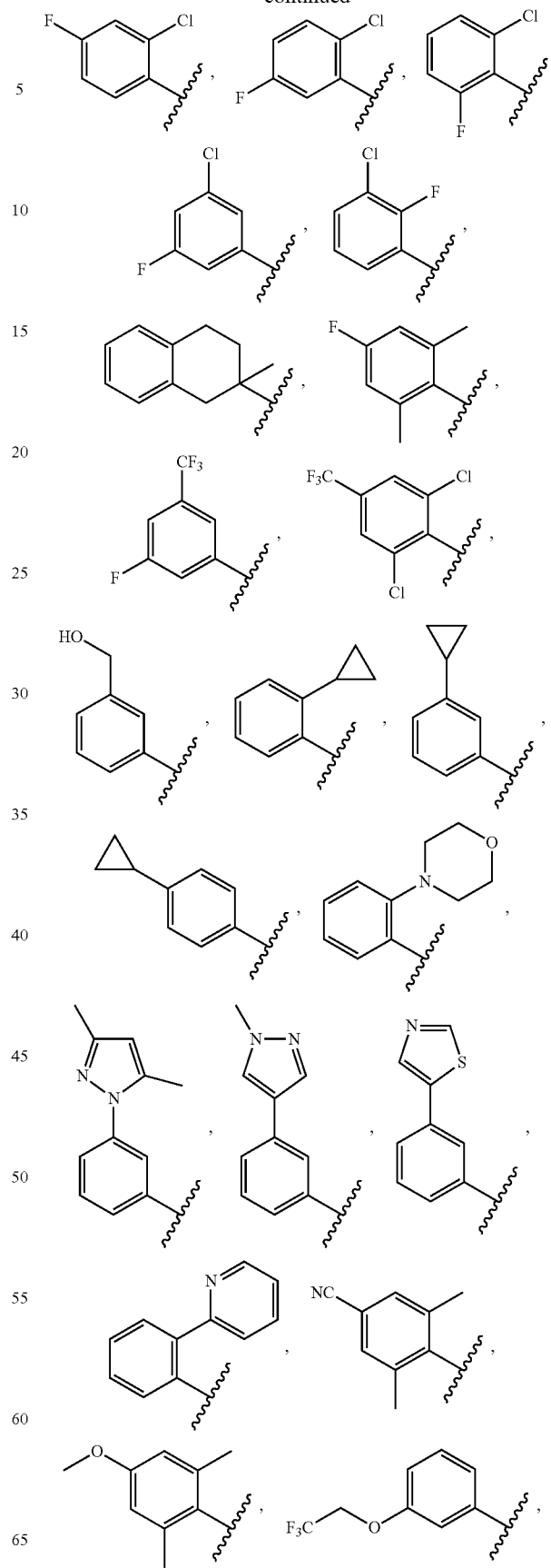

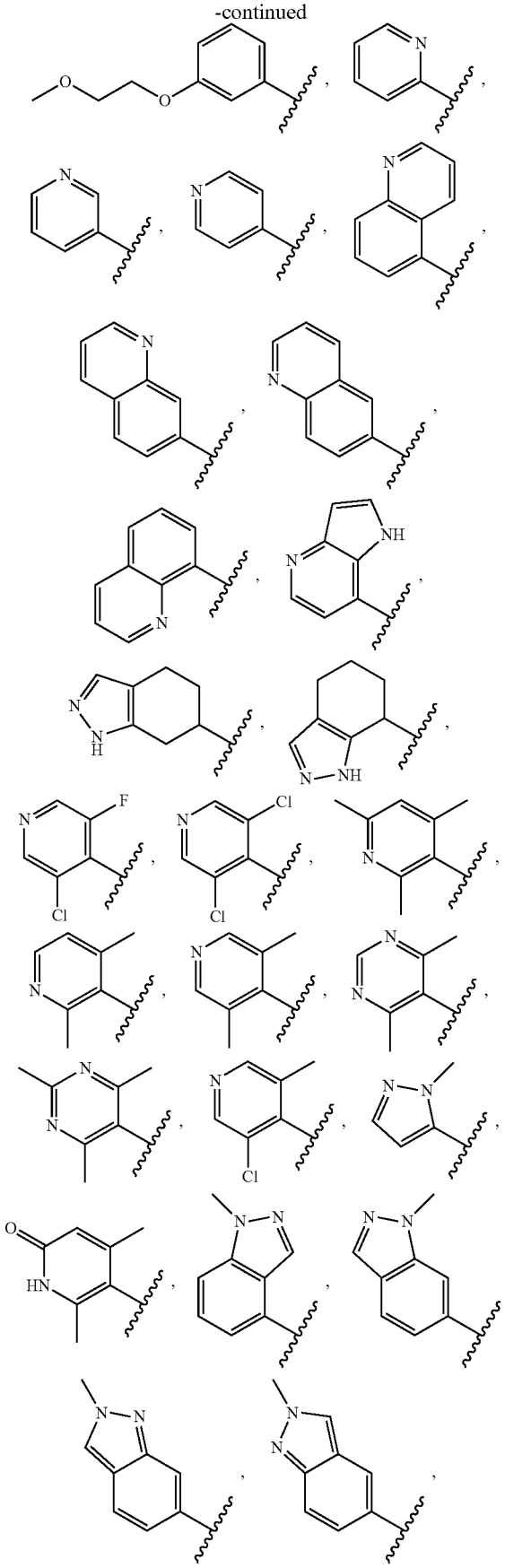
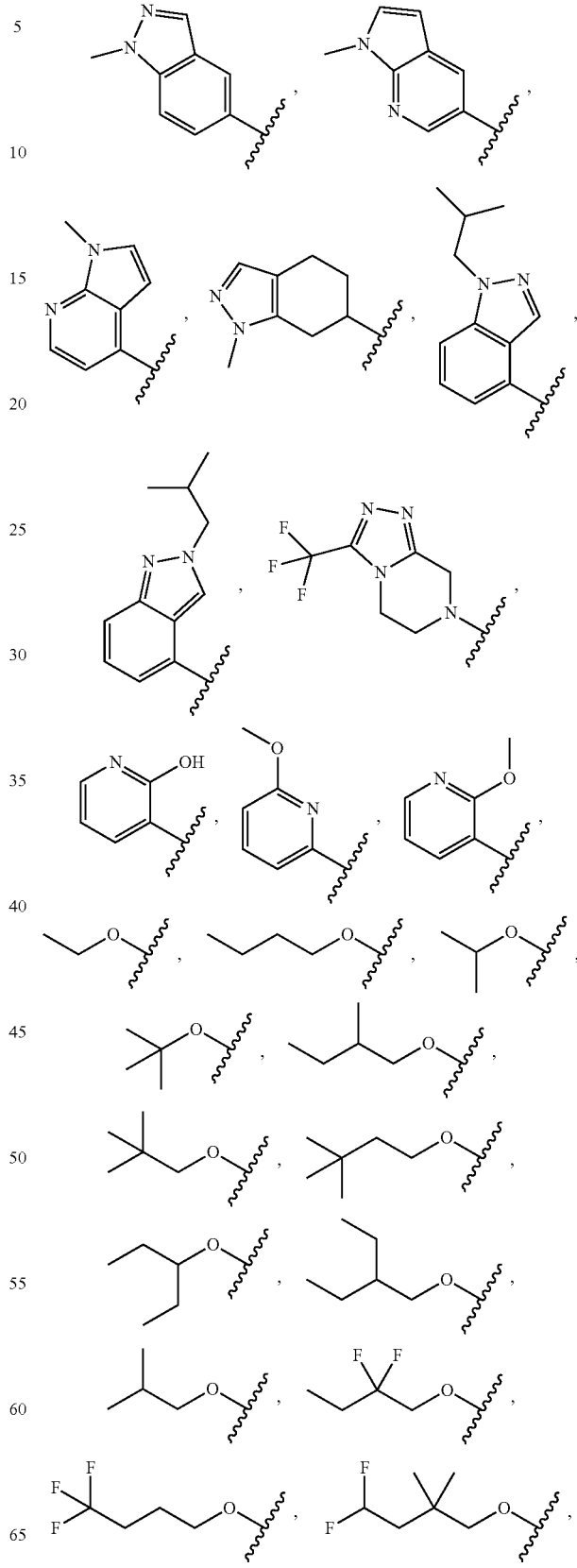

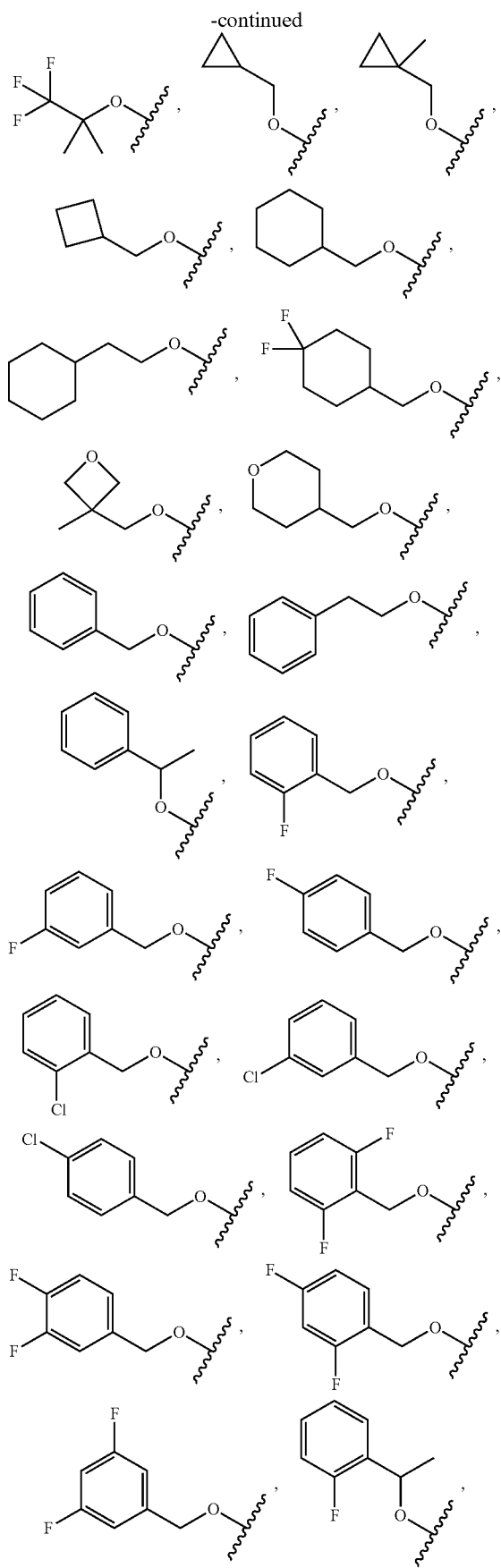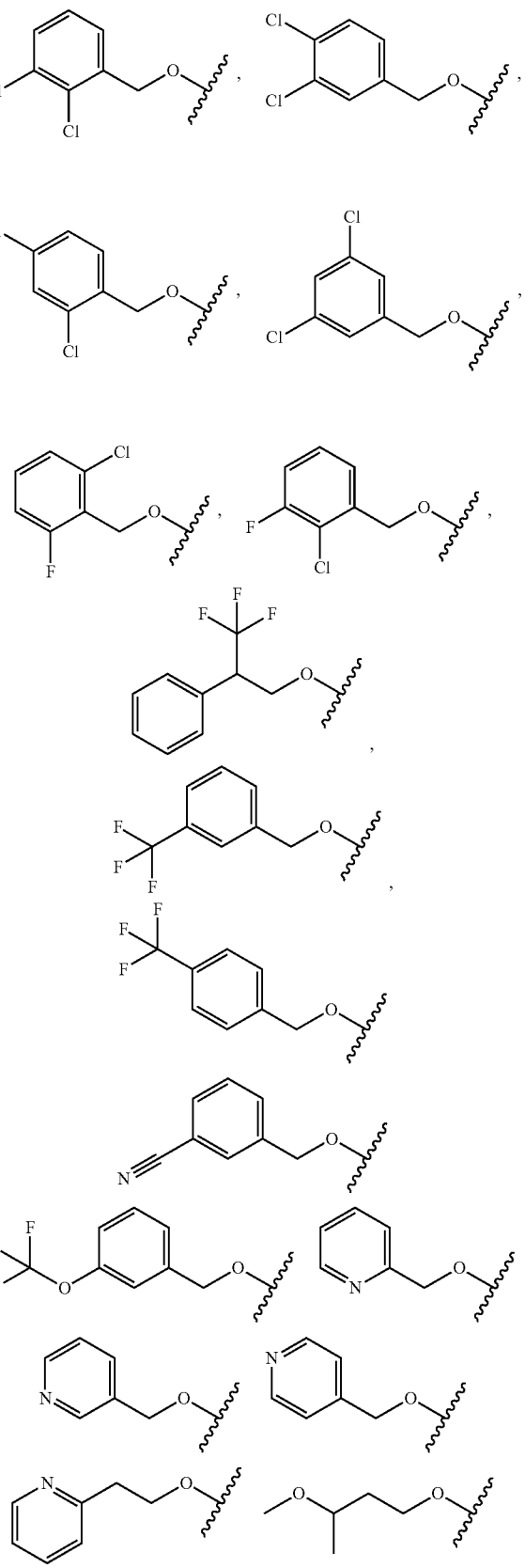

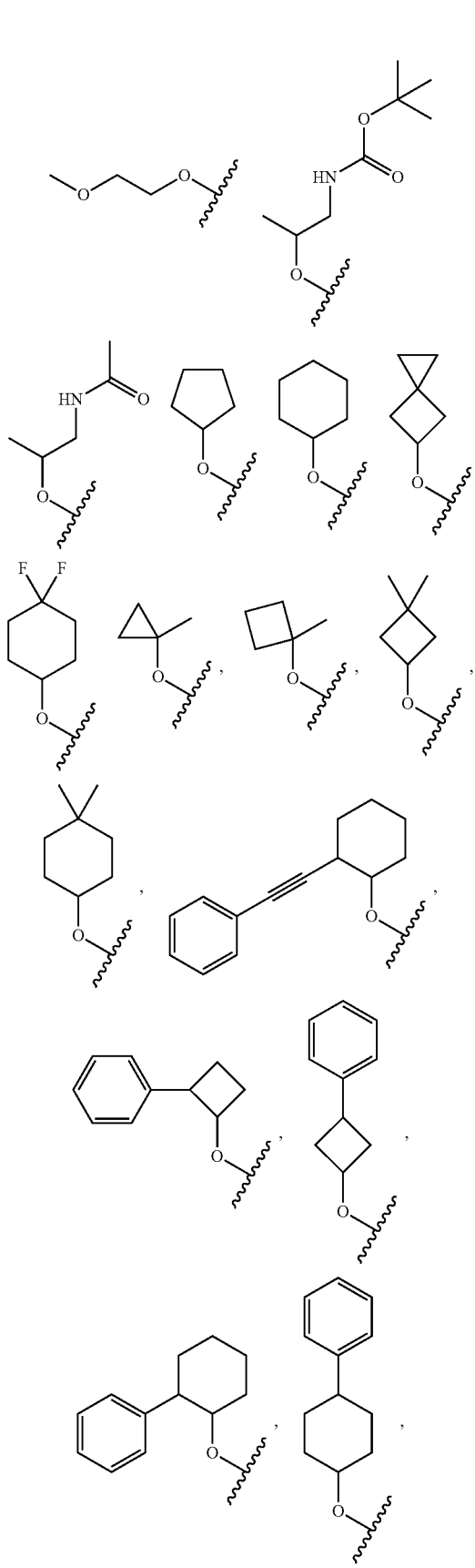
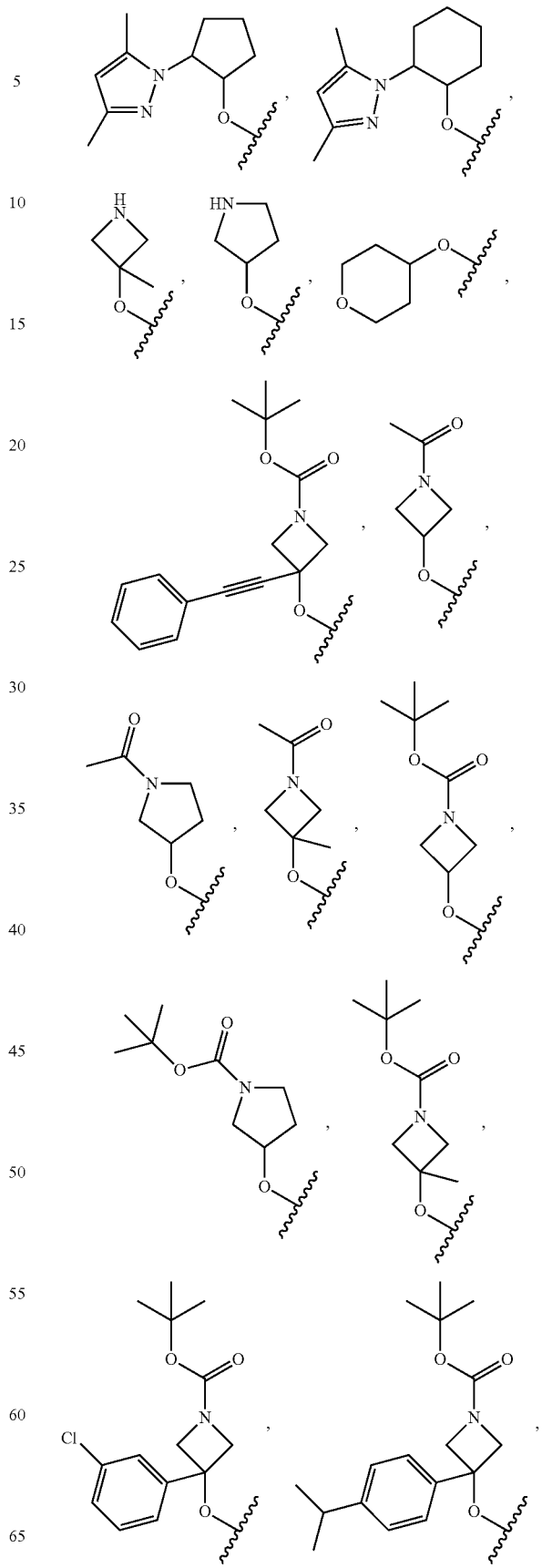

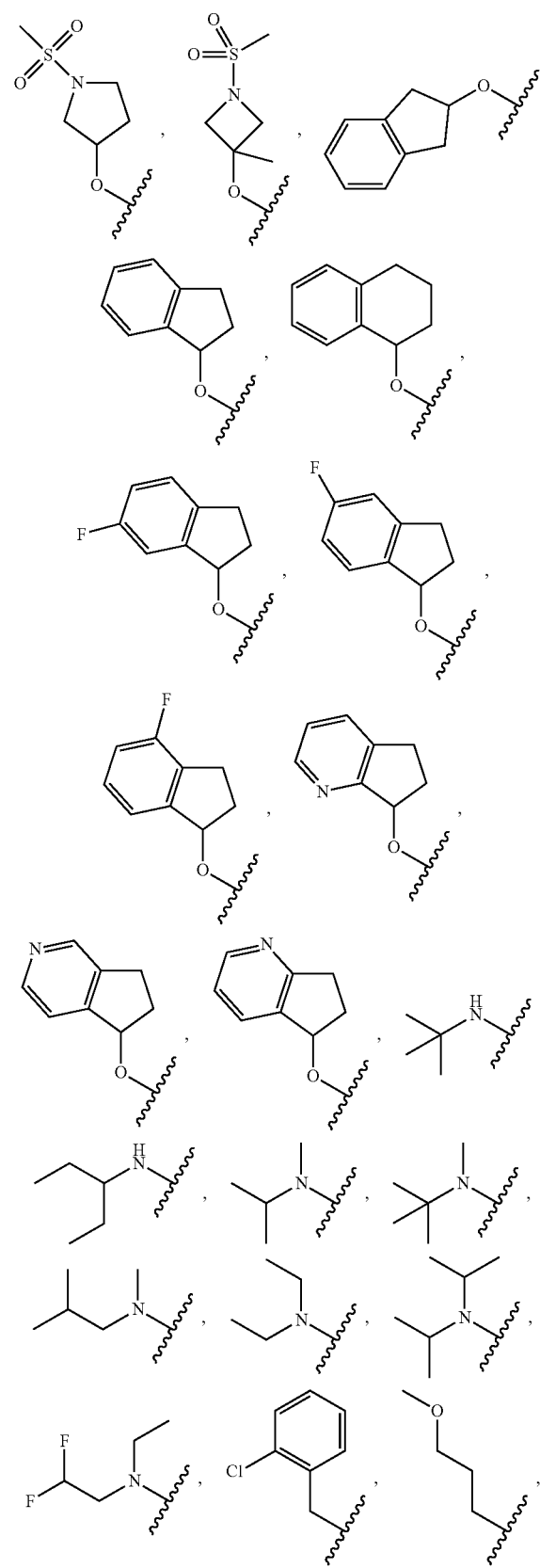
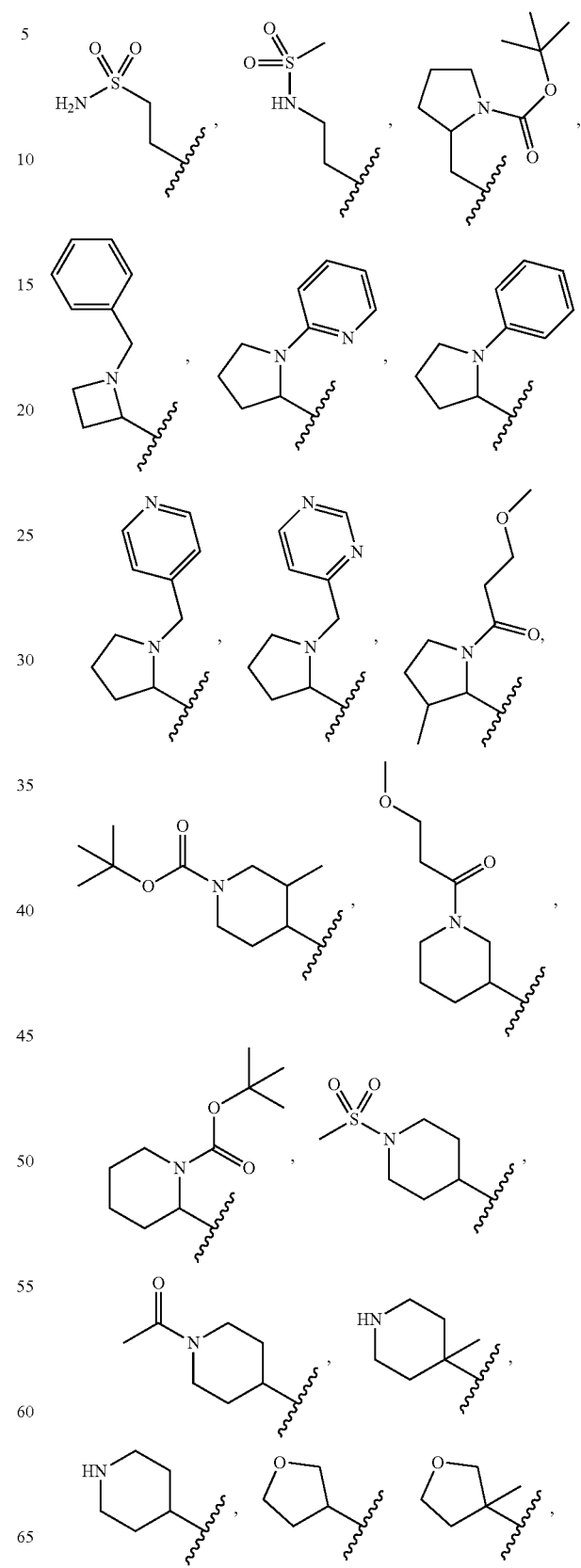

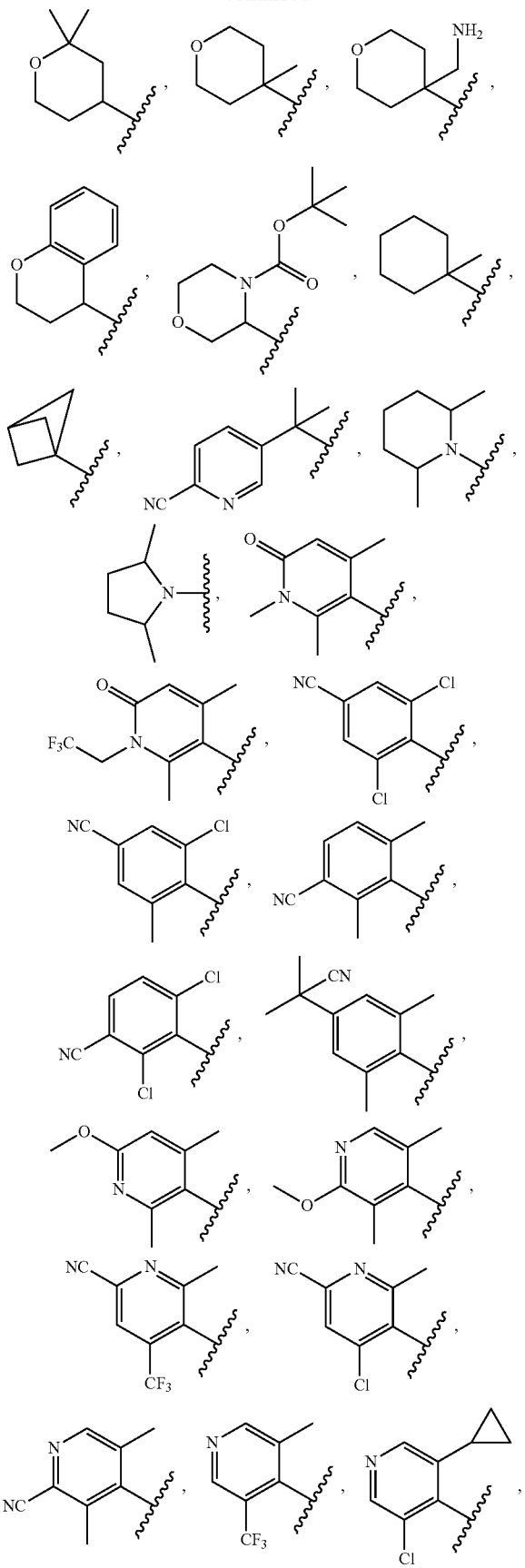
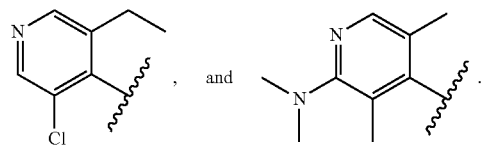
Also provided is a compound of formula (I), or a salt thereof, wherein G is —C(O)R² and R² is selected from the group consisting of:
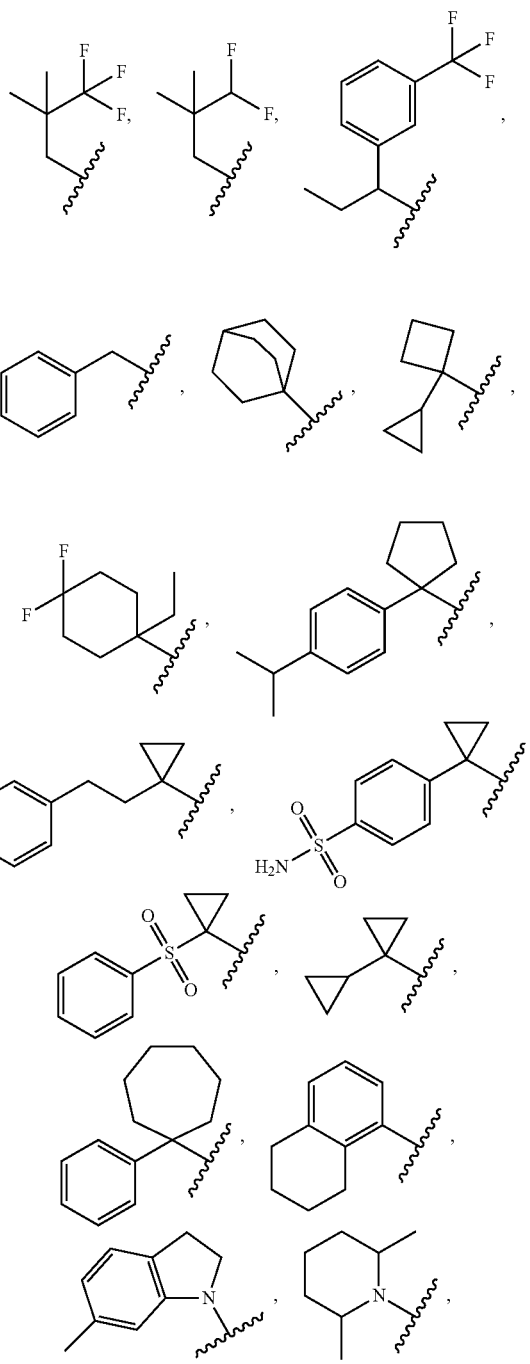

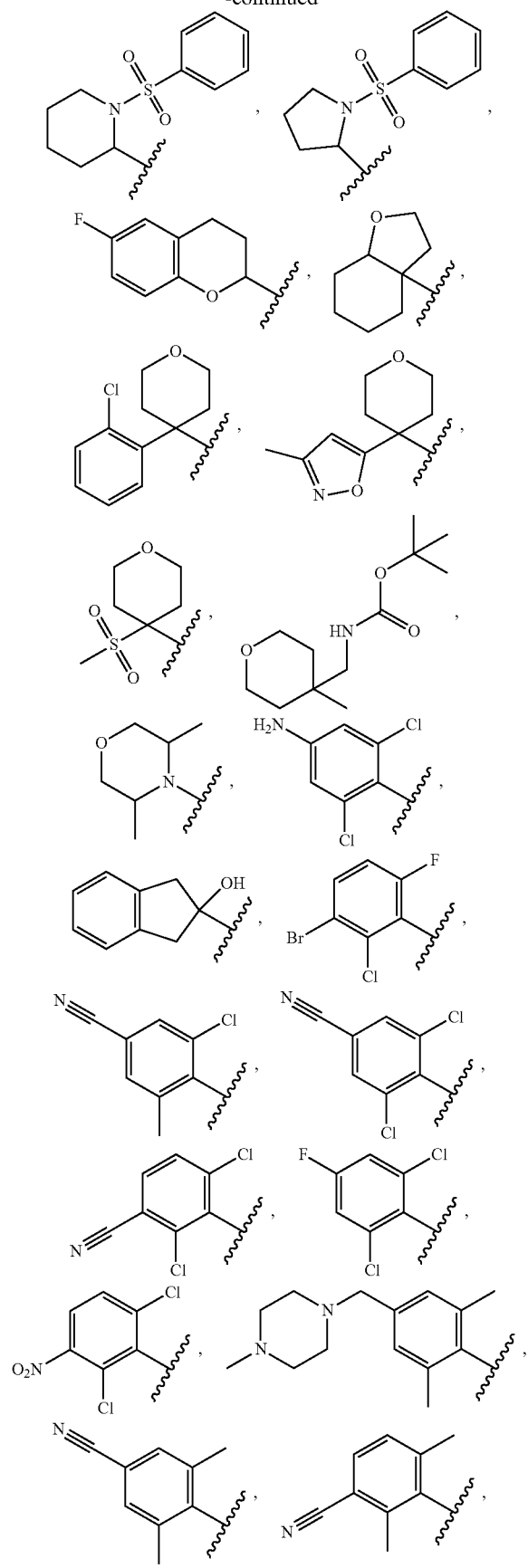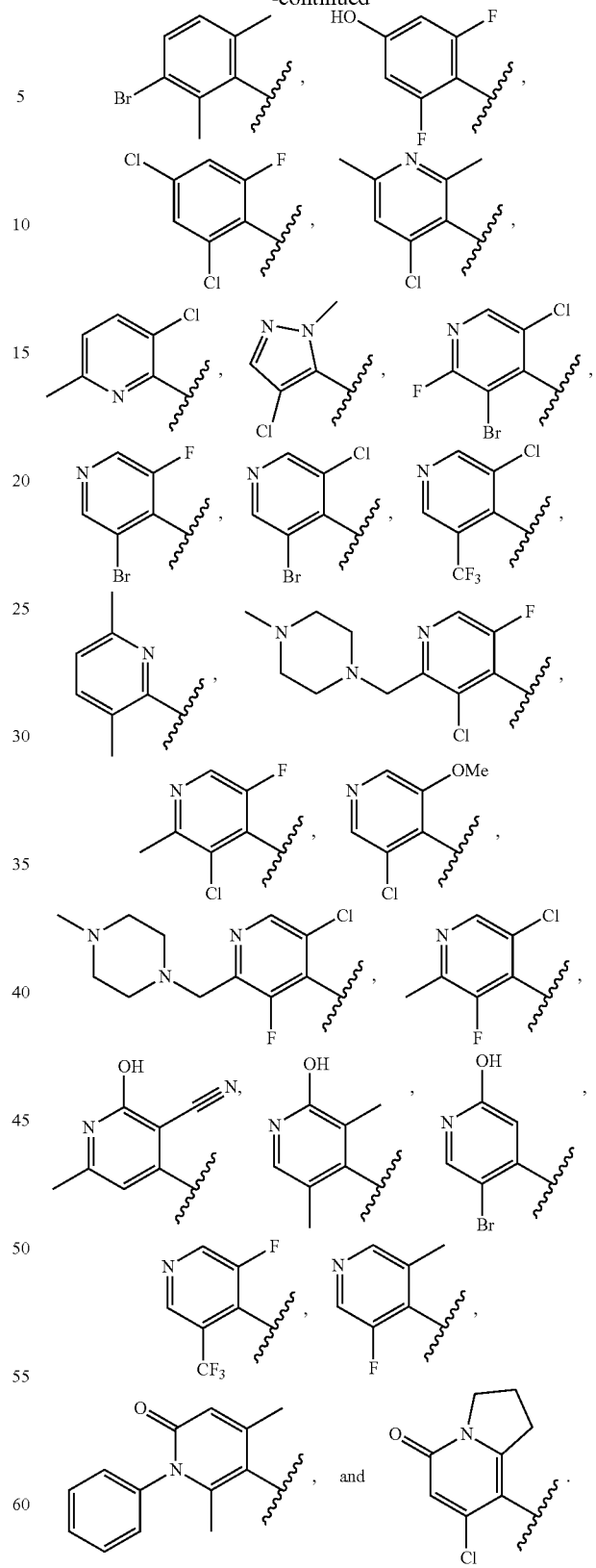
Also provided is a compound of formula (I), or a salt thereof, wherein G is —C(O)R$^2$ and R$^2$ is selected from the group consisting of:

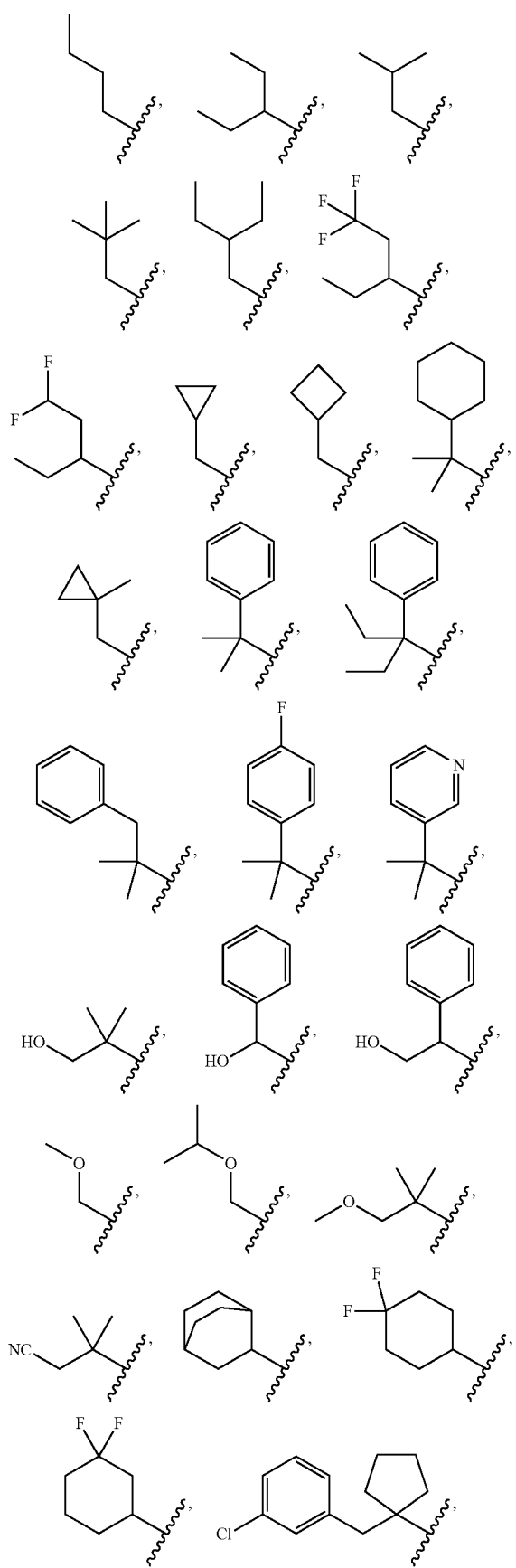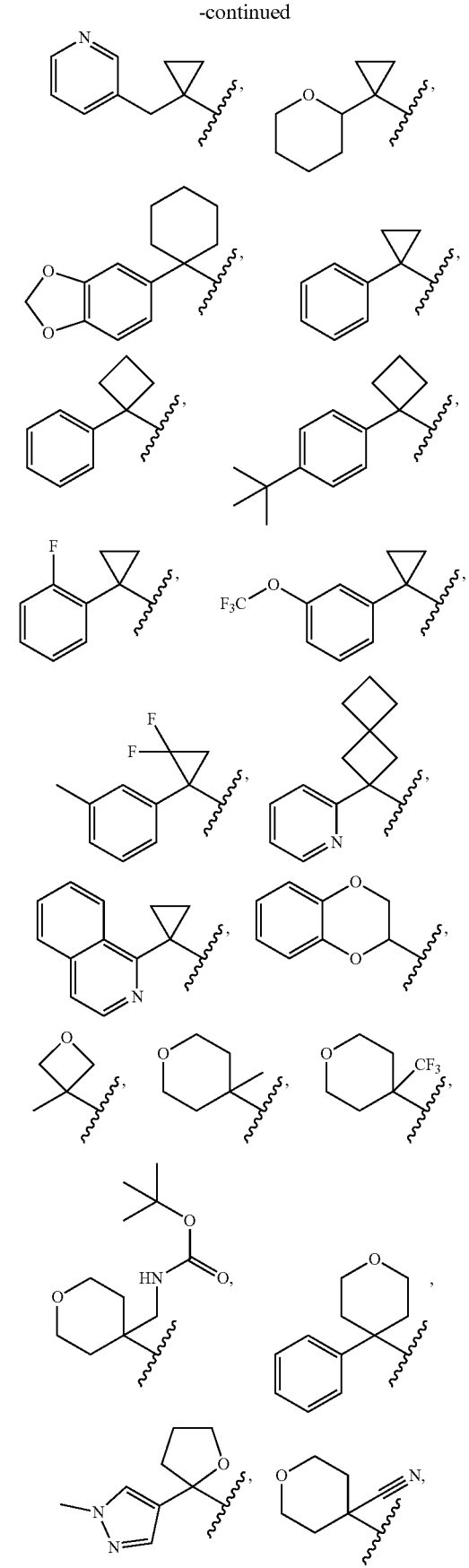

65
-continued
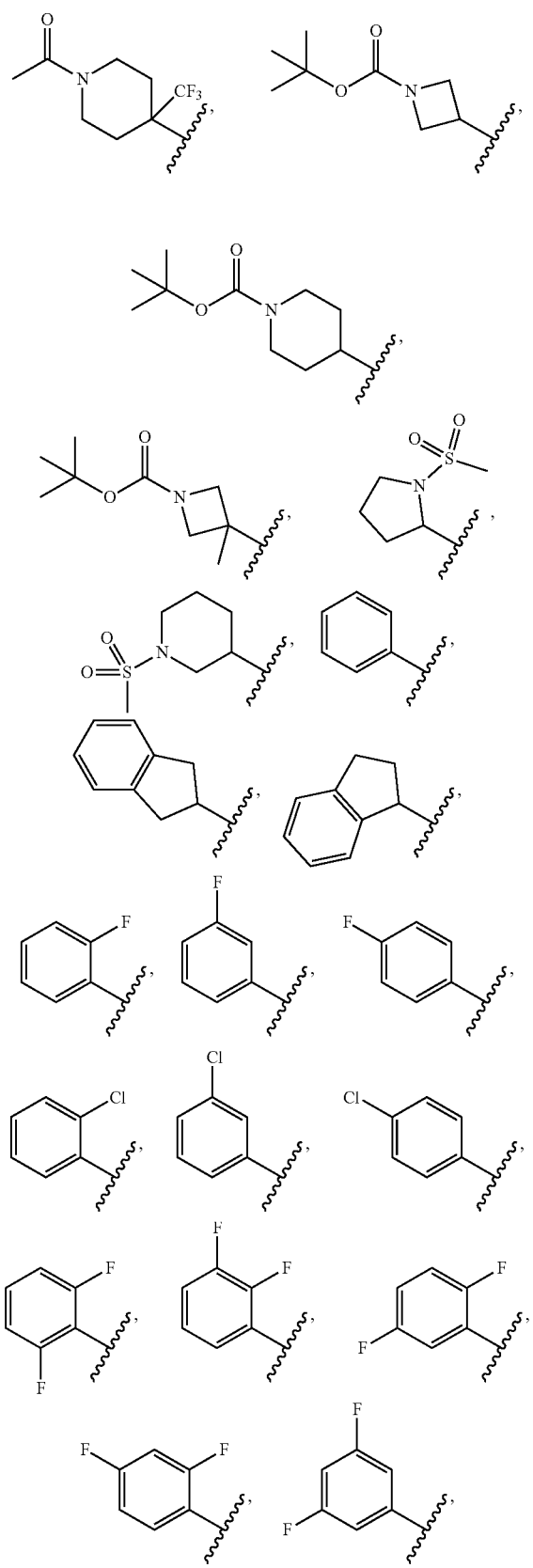
66
-continued
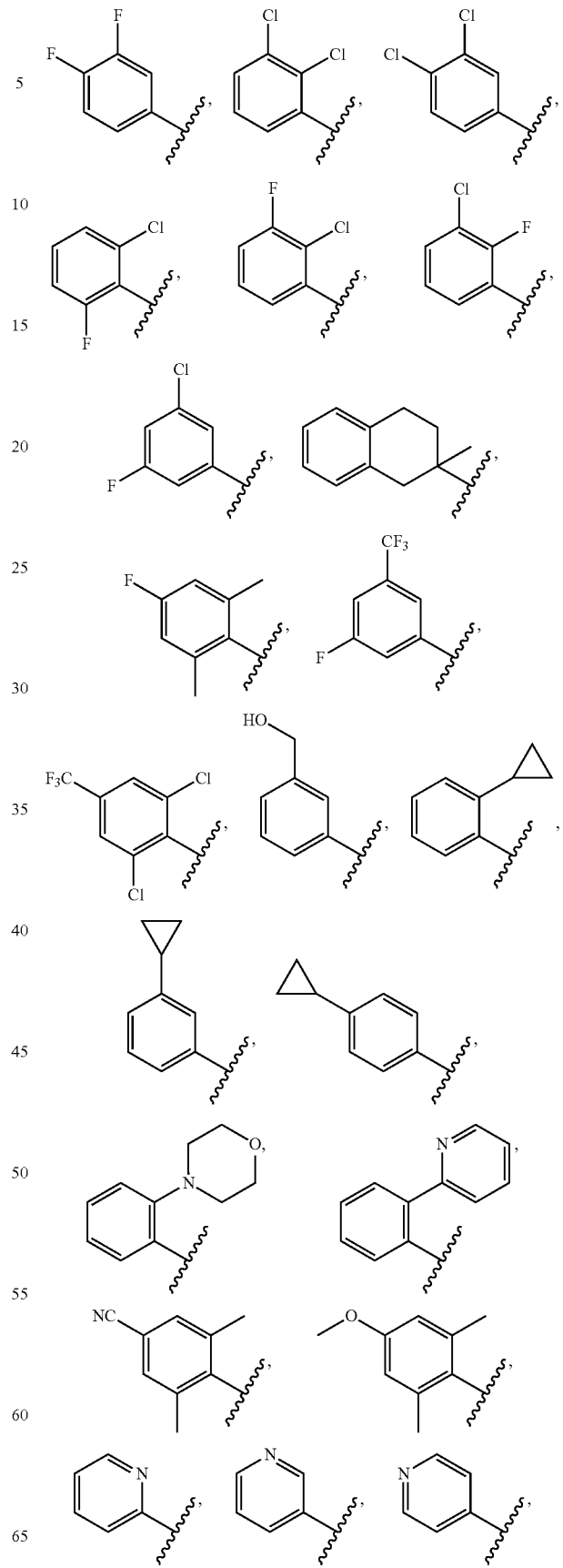

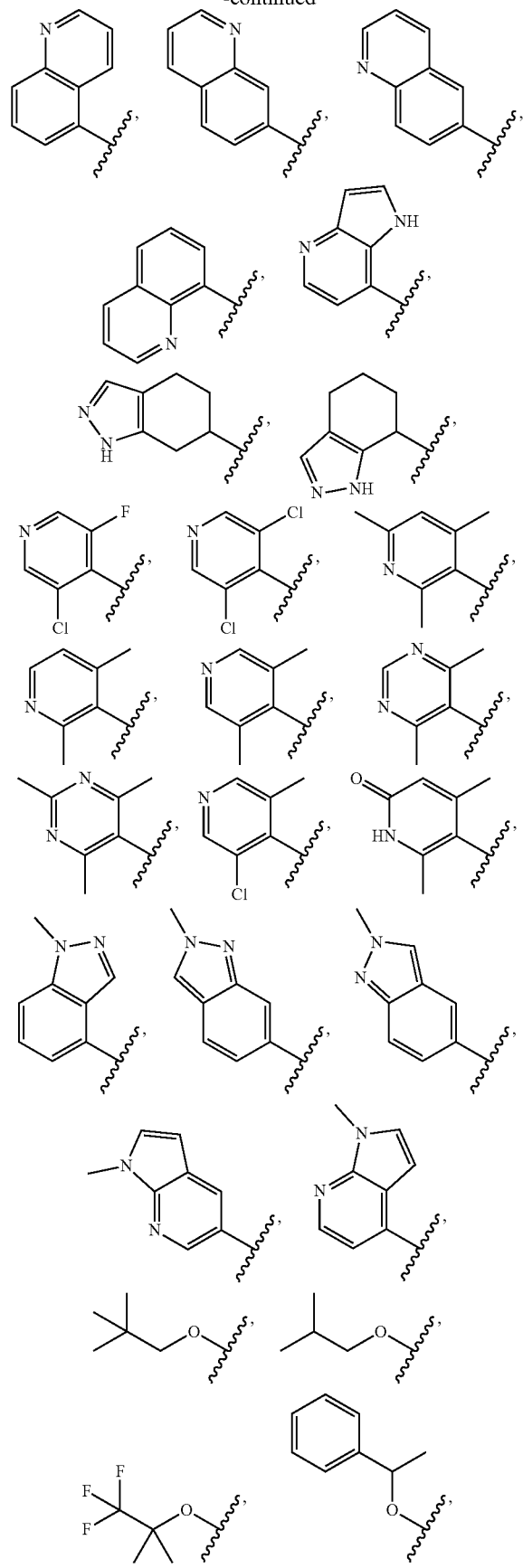
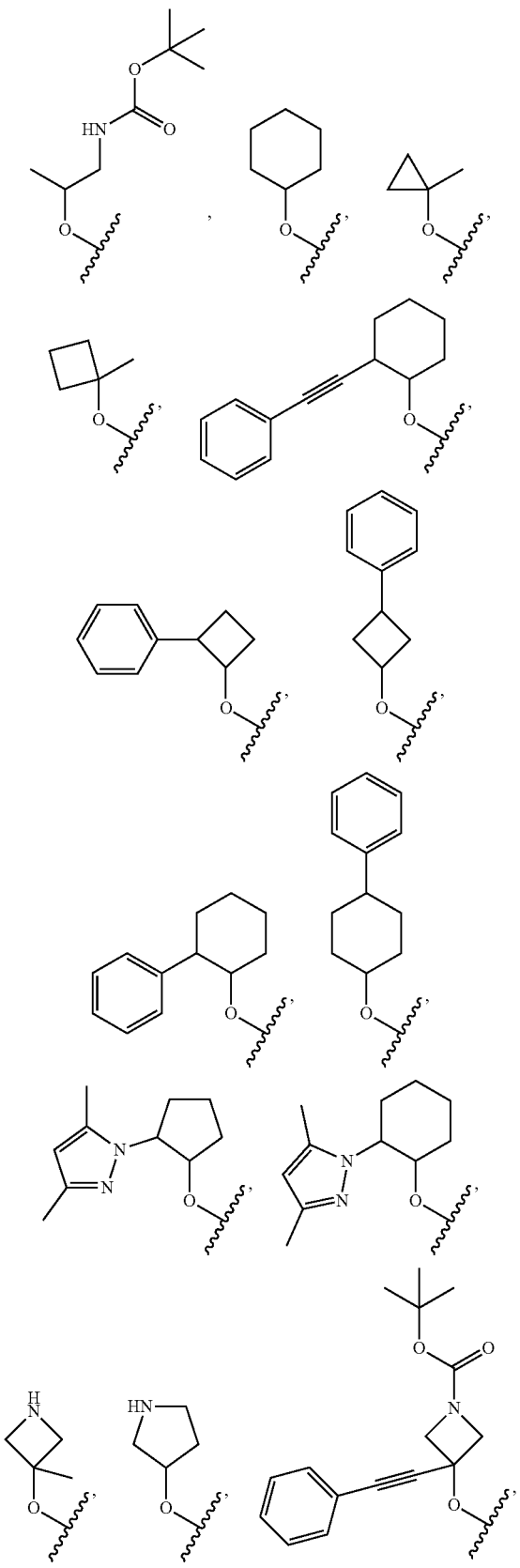

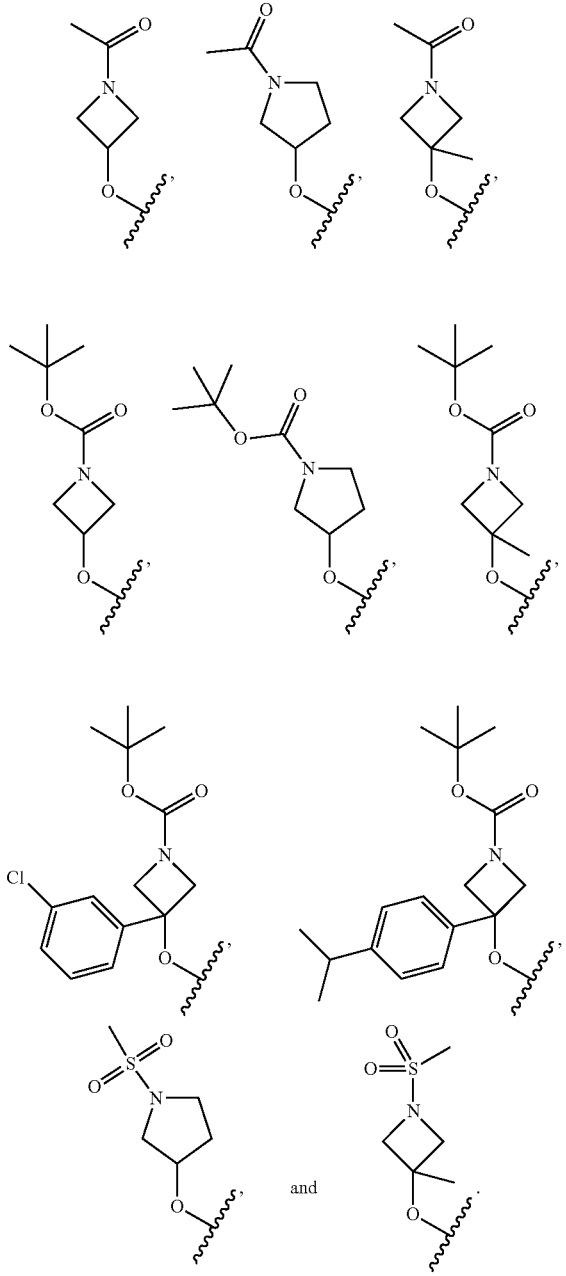

Also provided is a compound of formula (I), or a salt thereof, wherein G is —C(O)R² and R² s selected from the group consisting of:

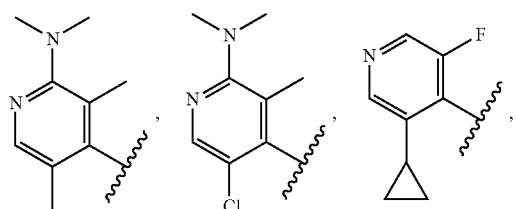

Also provided in another embodiment is a compound of formula (I), or a salt thereof, wherein G is $R^3$. In one aspect, $R^3$ is 5- to 10-membered heteroaryl (e.g., pyrimidinyl or quinazolinyl) substituted by 0-5 $R^{3e}$ groups, wherein each $R^{3e}$ group is independently selected from halogen; $C_1$-$C_6$ alkyl optionally substituted by halogen; 5- to 10-membered heteroaryl optionally substituted by halogen or $C_1$-$C_6$ alkyl; and $C_1$-$C_6$ alkoxy. In one aspect, $R^3$ is unsubstituted 5- to 10-membered heteroaryl. In one aspect, $R^3$ is 5- to 10-membered heteroaryl substituted by 1-5 $R^{3e}$ groups, wherein each $R^{3e}$ group is independently selected from halogen, $C_1$-$C_6$ alkyl, and $C_6$-$C_{14}$ aryl. In one aspect, $R^3$ is 5- to 10-membered heteroaryl substituted by 1-5 $R^{3e}$ groups, wherein at least one $R^{3e}$ group is halogen. In one aspect, $R^3$ is 5- to 10-membered heteroaryl substituted by 1-5 $R^{3e}$ groups, wherein at least one $R^{3e}$ group is $C_1$-$C_4$ alkyl. In one aspect, $R^3$ is 5- to 10-membered heteroaryl substituted by 1-5 $R^{3e}$ groups, wherein at least one $R^{3e}$ group is phenyl. In one aspect, $R^3$ is 5- to 10-membered heteroaryl substituted by 2-5 $R^{3e}$ groups, wherein at least one $R^{3e}$ group is $C_1$-$C_6$ alkyl, and wherein at least one $R^{3e}$ group is $C_6$-$C_{14}$ aryl.

Also provided is a compound of formula (I), or a salt thereof, wherein G is $R^3$ and $R^3$ is selected from the group consisting of:

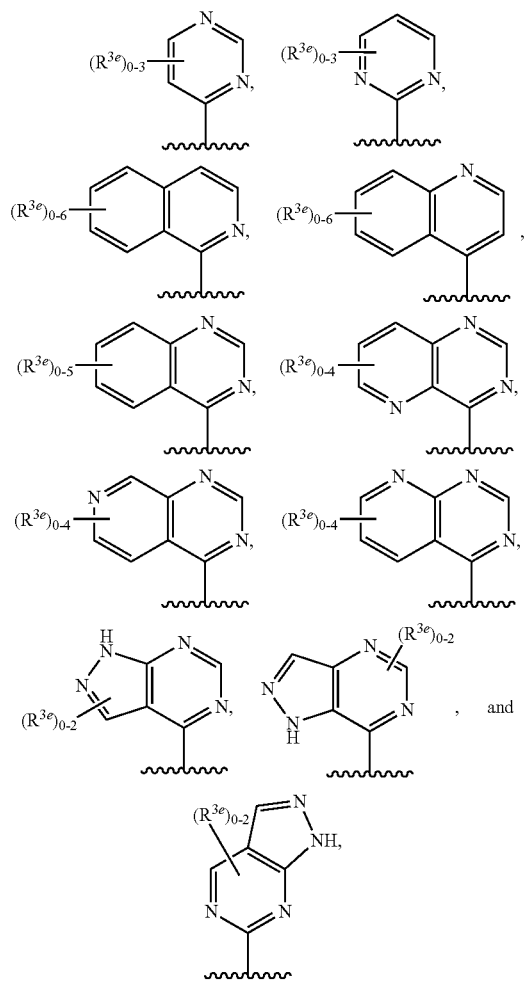

wherein each $R^{3e}$ is independently $R^4$. In the above structures wherein the —N(H)— moiety is present as shown and the structure it substituted by at least one $R^{3e}$ group, it is understood that one of the $R^{3e}$ groups can replace the hydrogen atom of the —N(H)— moiety (e.g., $R^3$ is

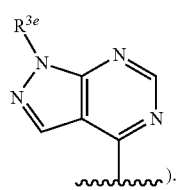

).

Also provided is a compound of formula (I), or a salt thereof, wherein G is $R^3$ and $R^3$ is selected from the group consisting of:

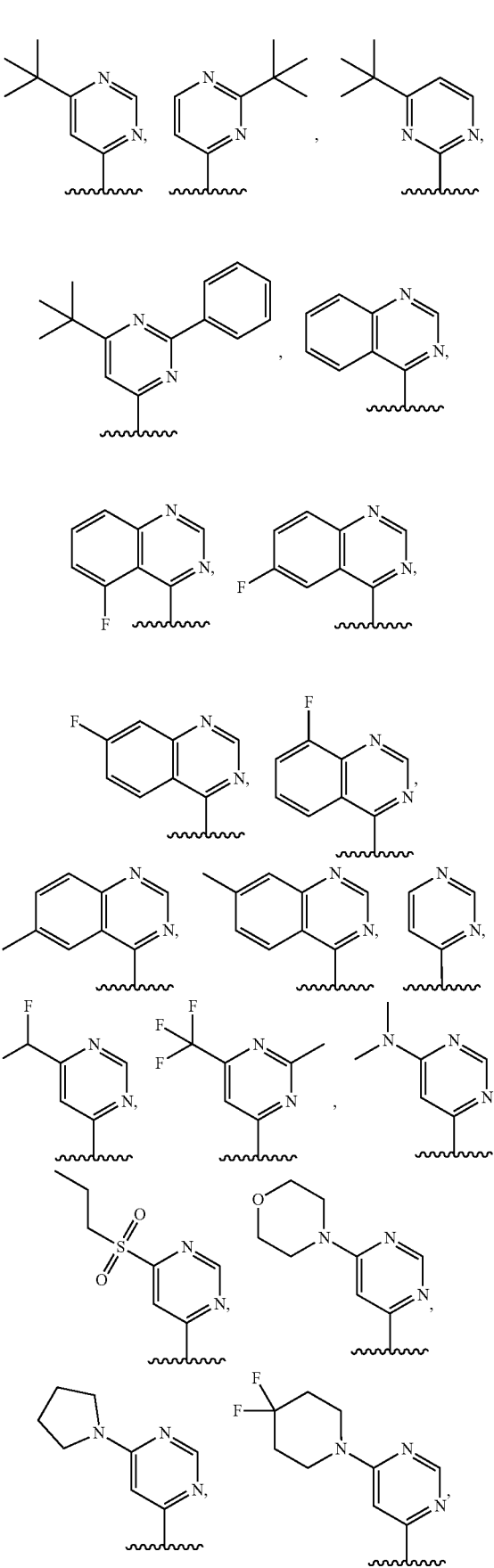

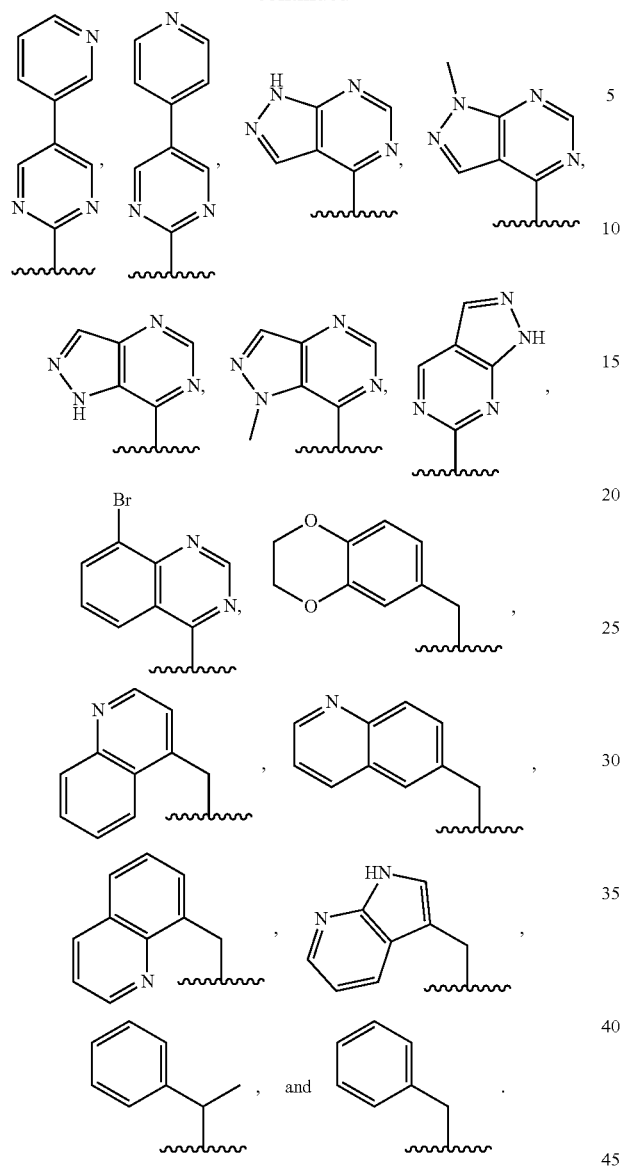
Also provided is a compound of formula (I), or a salt thereof, wherein G is R³ and R³ is selected from the group consisting of:
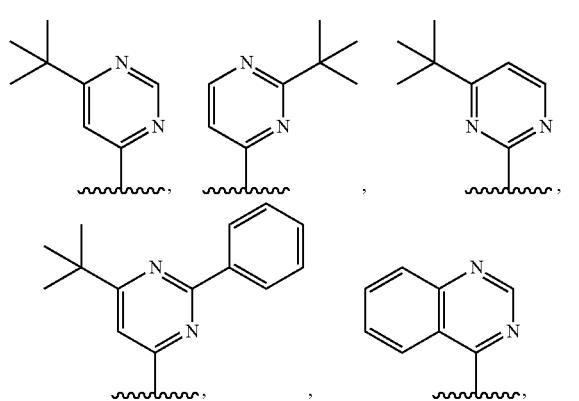
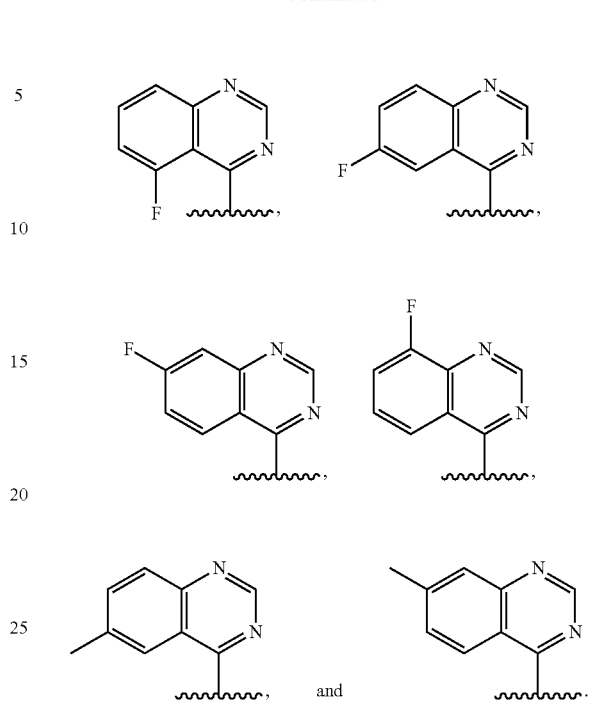
Also provided is a compound of formula (I), or a salt thereof, wherein G is R³ and R³ is selected from the group consisting of:
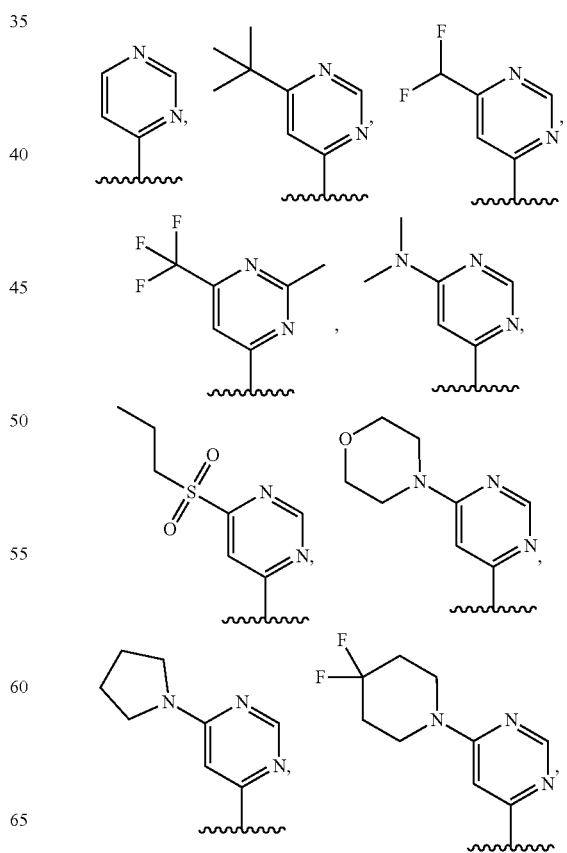

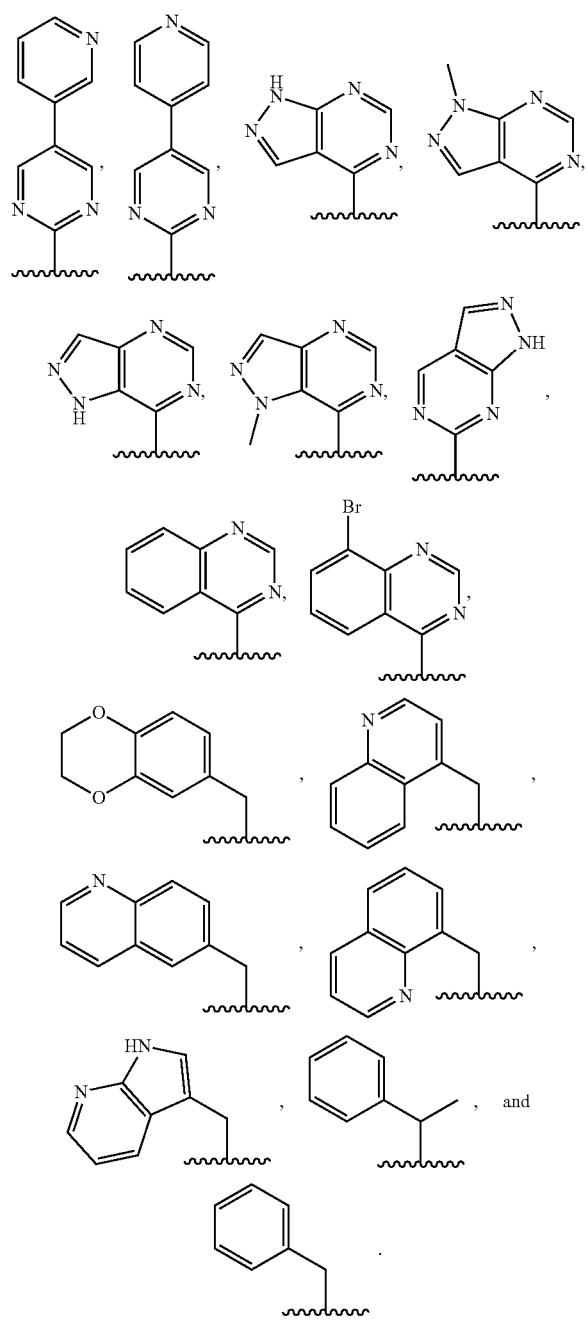
Also provided is a compound of formula (I), or a salt thereof, wherein G is selected from the group consisting of:
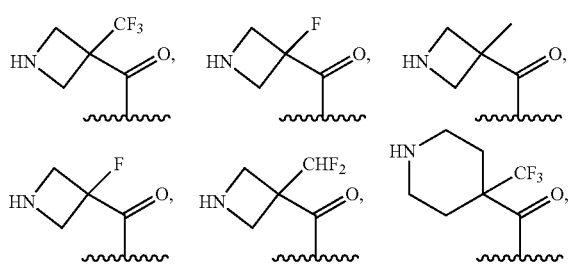
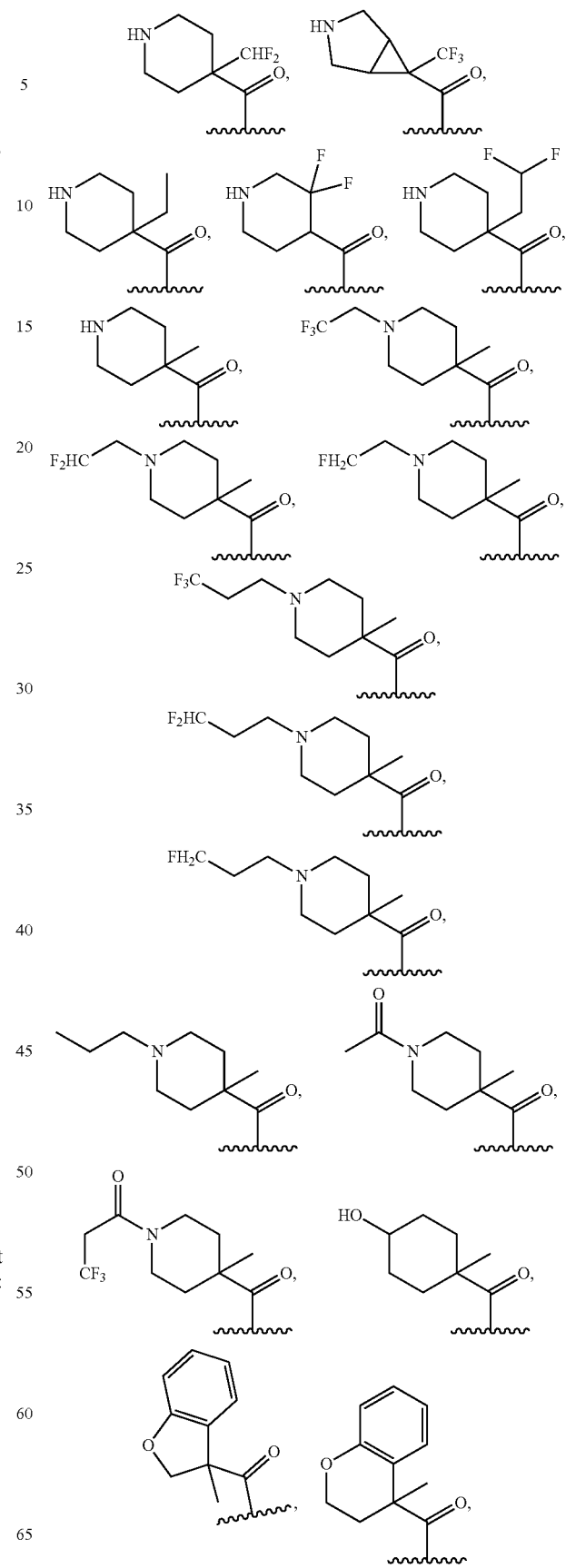

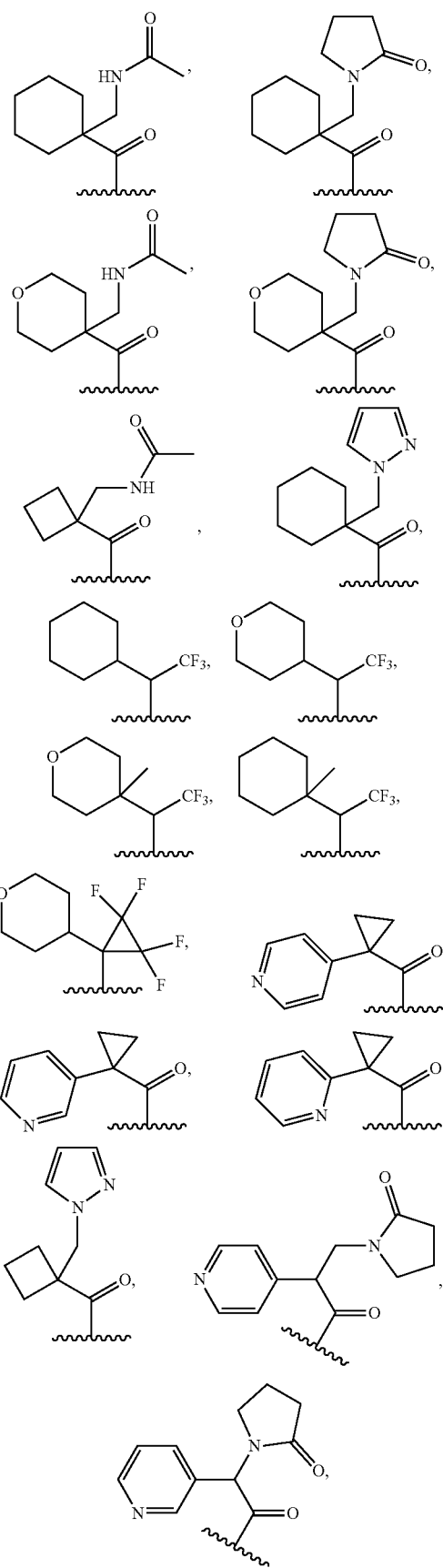
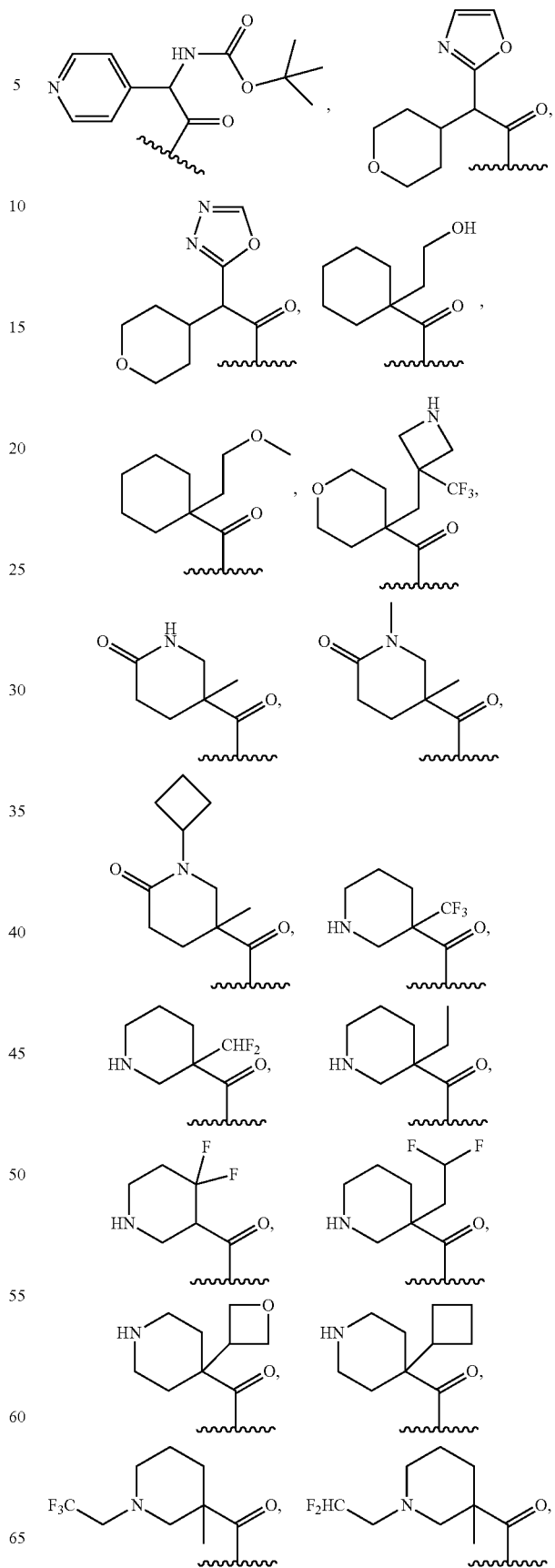

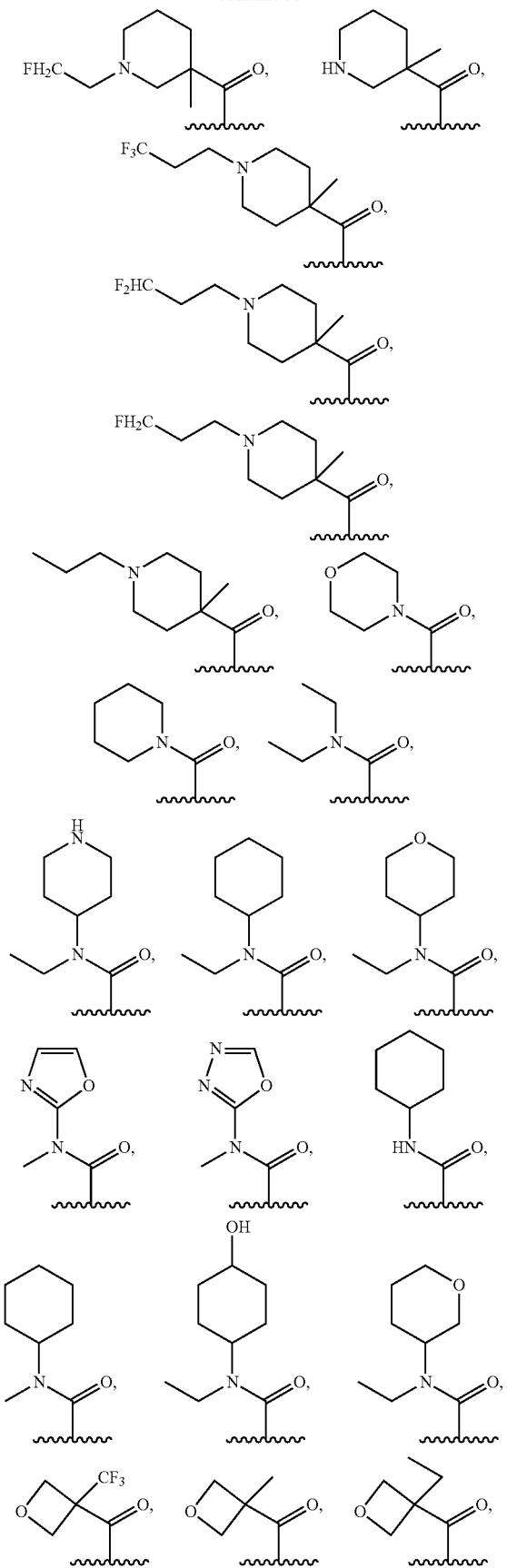
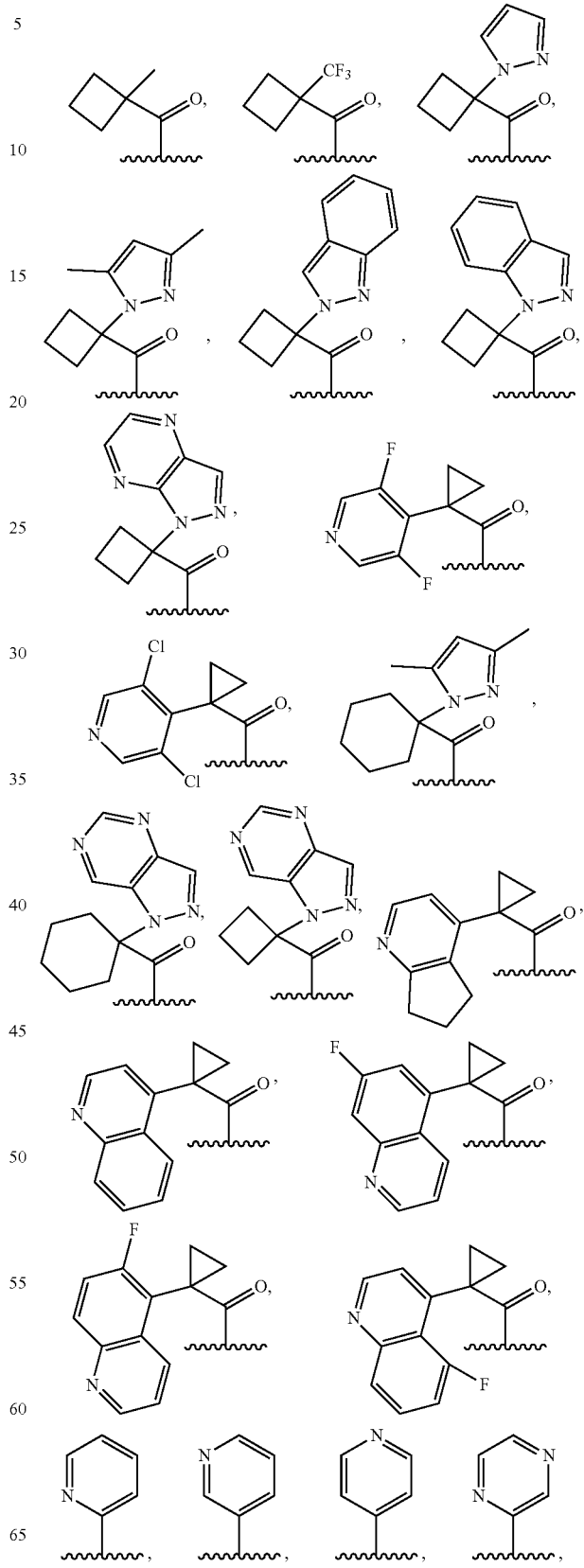

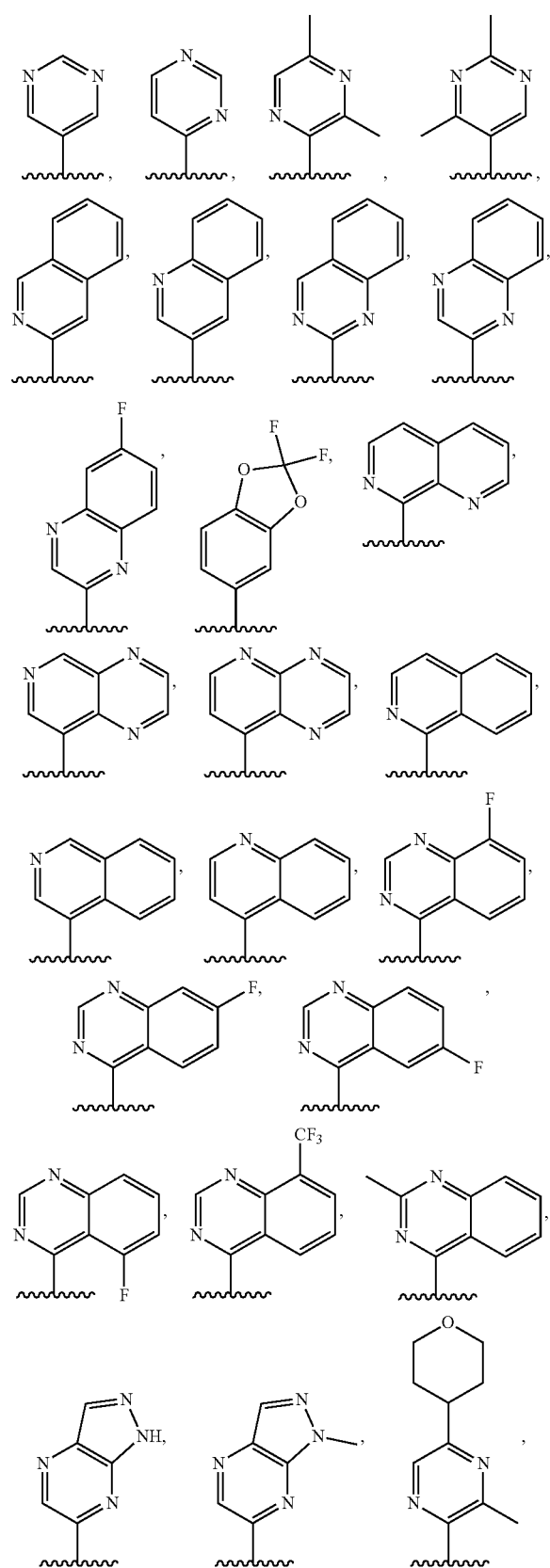
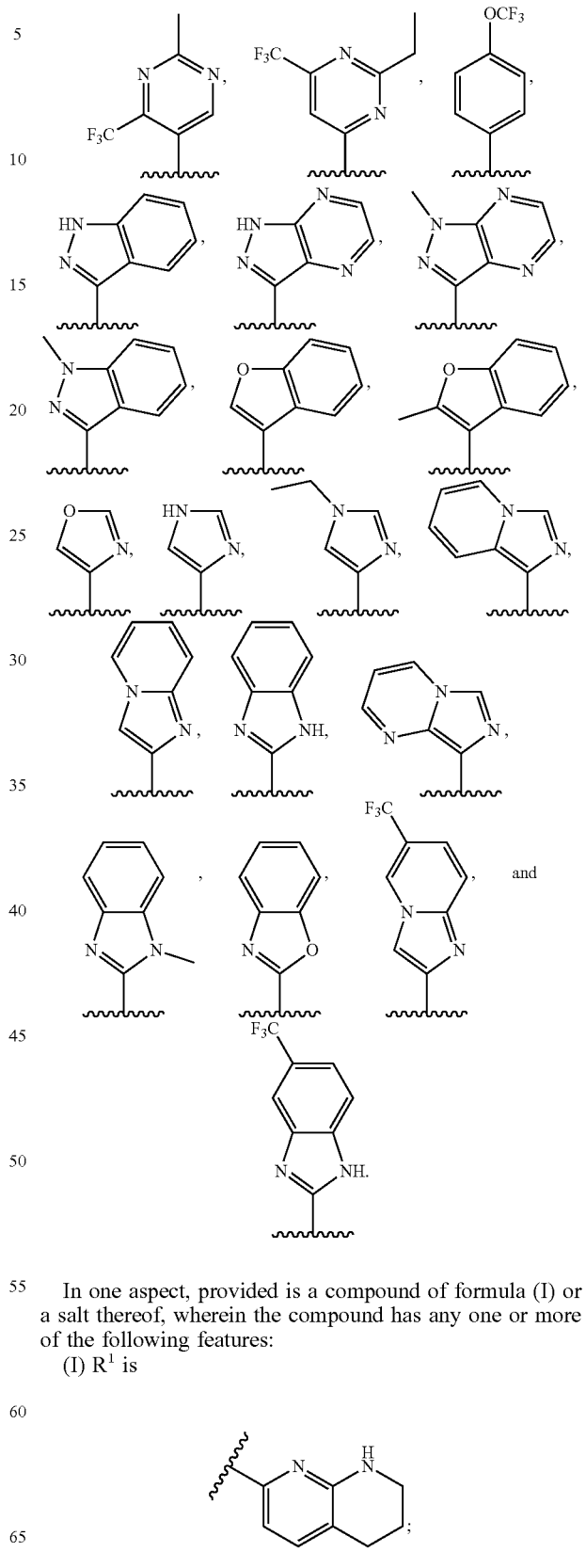
In one aspect, provided is a compound of formula (I) or a salt thereof, wherein the compound has any one or more of the following features:
(I) R[1] is (II) -L¹-O-L²-Y-L³- are taken together to form a moiety selected from the group consisting of:

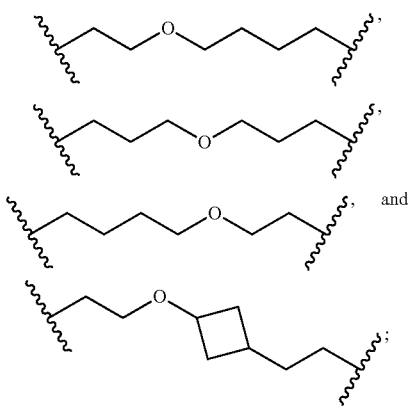

(III) G is —C(O)R² or R³ wherein.
(A) R² is:
(i) $C_1$-$C_6$ alkyl optionally substituted by $R^{2a}$, such as methyl, ethyl, isopropyl, or tert-butyl, each of which is substituted by 0-5 $R^{2a}$ groups,
(ii) $C_3$-$C_5$ cycloalkyl optionally substituted by $R^{2b}$, such as cyclopropyl, cyclobutyl, cyclopentyl, cyclohexyl, or spiro[3.3]heptanyl, each of which is substituted by 0-5 $R^{2b}$ groups;
(iii) 3- to 12-membered heterocyclyl optionally substituted by $R^{2c}$, such as 4- to 6-membered heterocyclyl containing 1 or 2 heteroatoms selected from O and N (e.g., azetidinyl, pyrrolidinyl, piperidinyl, oxetanyl, tetrahydrofuranyl, or tetrahydropyranyl), each of which is substituted by 0-5 $R^{2c}$ groups;
(iv) $C_6$-$C_{14}$ aryl optionally substituted by $R^{2d}$, such as phenyl substituted by 0-5 $R^{2d}$ groups; or
(v) 5- to 10-membered heteroaryl optionally substituted by $R^{2e}$, such as pyridinyl, pyrimidinyl, indazolyl, or quinolinyl, each of which is substituted by 0-5 $R^{2e}$ groups; and
wherein each $R^{2a}$, $R^{2b}$, $R^{2d}$, and $R^{2e}$ is independently $R^4$, $R^{2c}$ is oxo or $R^4$, and $R^4$ is halogen, $C_1$-$C_6$ alkyl, $C_3$-$C_5$ cycloalkyl, 3- to 12-membered heterocyclyl, $C_6$-$C_{14}$ aryl, 5- to 10-membered heteroaryl, —CN, —OR, —C(O)R⁵, —C(O)OR⁵, —C(O)NR⁶R⁷, —NR⁵C(O)OR⁶, or —S(O)₂R⁵, wherein the $C_1$-$C_6$ alkyl, $C_3$-$C_8$ cycloalkyl, 3- to 12-membered heterocyclyl, $C_6$-$C_{14}$ aryl, and 5- to 10-membered heteroaryl of $R^4$ are independently optionally substituted by $R^{4a}$, wherein $R^{4a}$ is halogen, —OR⁸, —NR⁸R⁹, —C(O)OR⁸, —NR⁸C(O)OR¹⁰, —CN, 5- to 10-membered heteroaryl, $C_6$-$C_{14}$ aryl, or $C_1$-$C_6$ alkyl, wherein
R⁸ is hydrogen or $C_1$-$C_6$ alkyl optionally substituted by halogen,
R⁹ is hydrogen, and
R¹⁰ is $C_1$-$C_6$ alkyl optionally substituted by halogen; and
(B) R³ is:
(vi) $C_1$-$C_6$ alkyl optionally substituted by $R^{3a}$, such as methyl or ethyl, each of which is substituted by 1 $R^{3a}$ group, wherein $R^{3a}$ is phenyl or quinazolinyl; or
(vii) 5- to 10-membered heteroaryl optionally substituted by $R^{3e}$, such as pyrimidinyl, quinazolinyl, or pyrazolopyrimidinyl, each of which is substituted by 0-5 $R^{3e}$ groups.

In one aspect of this variation, (I) and (II) apply, and G is —C(O)R². In another aspect of this variation, (I) and (II) apply, and G is R³. In another variation, (I) and (II) apply, G is —C(O)R², and (i) applies. In another variation, (I) and (II) apply, G is —C(O)R², and (ii) applies. In another variation, (I) and (II) apply, G is —C(O)R², and (iii) applies. In another variation, (I) and (II) apply, G is —C(O)R², and (iv) applies. In another variation, (I) and (II) apply, G is —C(O)R², and (v) applies. In another variation, (I) and (II) apply, G is R³, and (vi) applies. In another variation, (I) and (II) apply, G is R³, and (vii) applies.

Also provided is a compound of formula (I), or a salt thereof, wherein G is —C(O)R², R² is $C_1$-$C_6$ alkyl optionally substituted by $R^{2a}$, $C_3$-$C_5$ cycloalkyl optionally substituted by $R^{2b}$, 3- to 12-membered heterocyclyl optionally substituted by $R^{2c}$, $C_6$-$C_{14}$ aryl optionally substituted by $R^{2d}$, or 5- to 10-membered heteroaryl optionally substituted by $R^{2e}$, wherein each $R^{2a}$, $R^{2b}$, $R^{2c}$, $R^{2d}$, and $R^{2e}$ is independently $R^4$, wherein each $R^4$ is independently selected from the group consisting of:

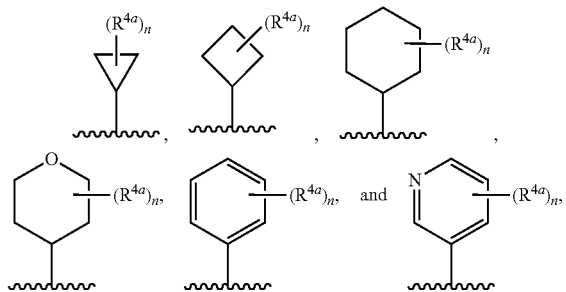

wherein each $R^{4a}$ is independently halogen, —OR⁸, —NR⁸R⁹, —C(O)OR⁸, —NR⁸C(O)OR¹⁰, —CN, 5- to 10-membered heteroaryl, $C_6$-$C_{14}$ aryl, or $C_1$-$C_6$ alkyl, wherein R⁸, R⁹, and R¹⁰ are as defined for formula (I), and n is 0, 1, or 2. In one variation, n is 0. In another variation, n is 1. In yet another variation, n is 2.

Also provided is a compound of formula (I), or a salt thereof, wherein G is —C(O)R², R² is $C_1$-$C_6$ alkyl optionally substituted by $R^{2a}$, $C_3$-$C_5$ cycloalkyl optionally substituted by $R^{2b}$, 3- to 12-membered heterocyclyl optionally substituted by $R^{2c}$, $C_6$-$C_{14}$ aryl optionally substituted by $R^{2d}$, or 5- to 10-membered heteroaryl optionally substituted by $R^{2e}$, wherein each $R^{2a}$, $R^{2b}$, $R^{2c}$, $R^{2d}$, and $R^{2e}$ is independently $R^4$, wherein each $R^4$ is independently selected from the group consisting of:

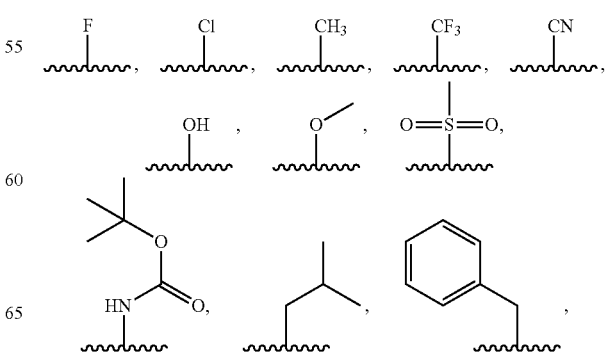

85
-continued

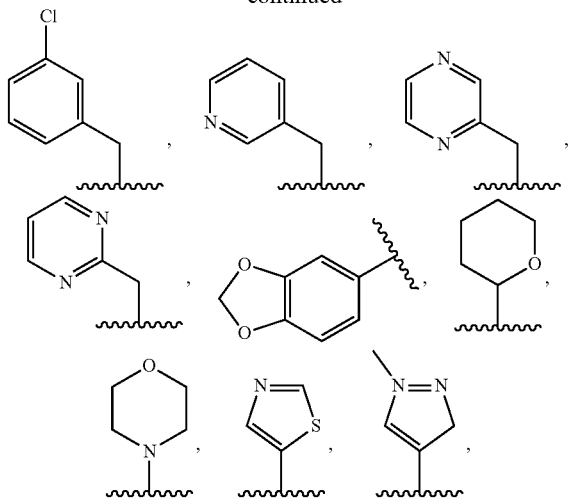

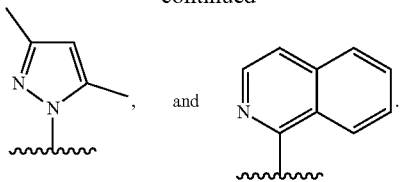

, and

When a moiety is contemplated, it is understood that the moiety can be attached to the rest of the structure at any available position. For example, 3-chloro-5-methylpyridinyl may be attached to the rest of the structure at the 2-, 4-, or 6-position (i.e., 3-chloro-5-methylpyridin-2-yl, 3-chloro-5-methylpyridin-4-yl or 3-chloro-5-methylpyridin-6-yl, respectively). The $R^2$ and $R^3$ groups described herein are shown as attached at specific positions (e.g., pyrimid-4-yl, quinazolin-4-yl, or isoquinolin-1-yl) but they can also be attached via any other available valence (e.g., pyrimid-2-yl, quinazolin-2-yl, or isoquinolin-3-yl, respectively).

Representative compounds are listed in Table 1.

TABLE 1

| Compound # | Structure |
| --- | --- |
| 1 | 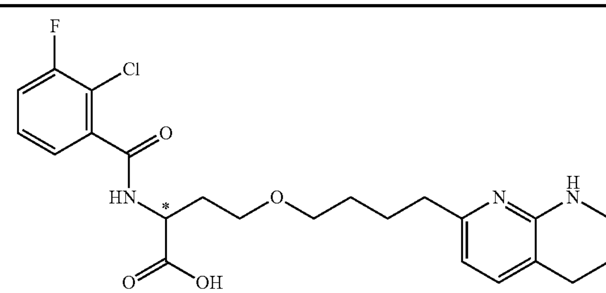 |
| 2 | 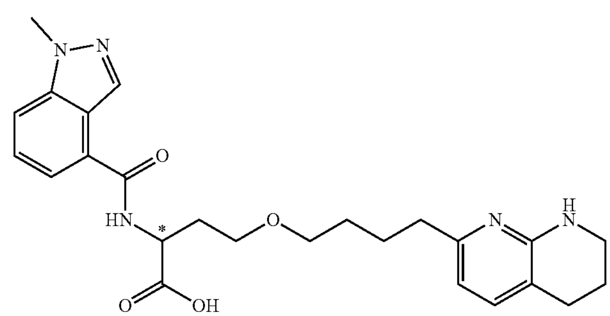 [SMILES: Cn1ncc2c(C(=O)NC(CCOCCCCc3ccc4c(n3)NCCC4)C(=O)O)cccc21] |
| 3 | 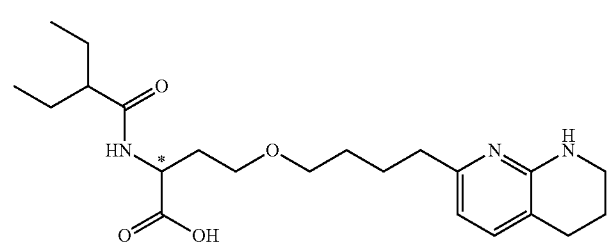 [SMILES: CCC(CC)C(=O)NC(CCOCCCCc1ccc2c(n1)NCCC2)C(=O)O] |
| 4 | 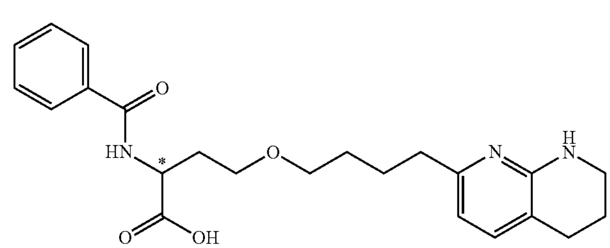 [SMILES: O=C(NC(CCOCCCCc1ccc2c(n1)NCCC2)C(=O)O)c1ccccc1] |

TABLE 1-continued
| Compound # | Structure |
|---|---|
| 5 | 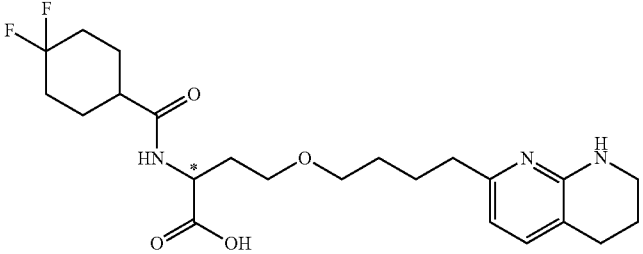 [SMILES: O=C(NC(CCOCCCCc1ccc2c(n1)NCCC2)C(=O)O)C1CCC(F)(F)CC1] |
| 6 | 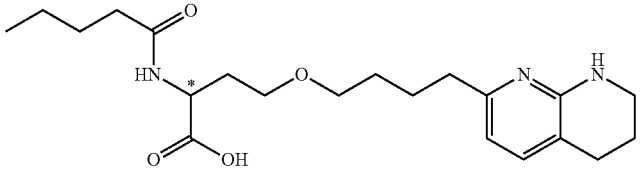 [SMILES: CCCCC(=O)NC(CCOCCCCc1ccc2c(n1)NCCC2)C(=O)O] |
| 7 | 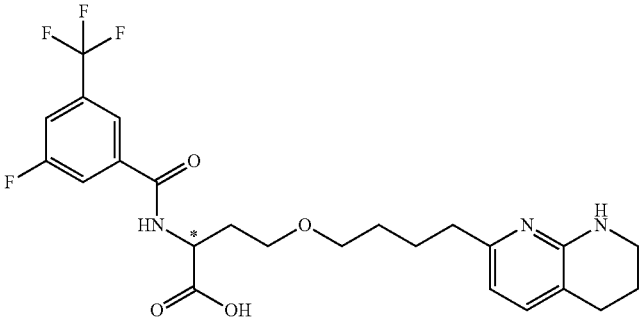 [SMILES: O=C(NC(CCOCCCCc1ccc2c(n1)NCCC2)C(=O)O)c1cc(F)cc(C(F)(F)F)c1] |
| 8 | 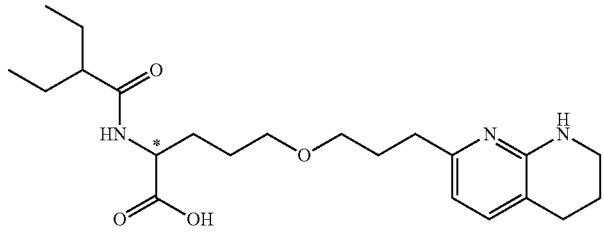 [SMILES: CCC(CC)C(=O)NC(CCCOCCCc1ccc2c(n1)NCCC2)C(=O)O] |
| 9 | 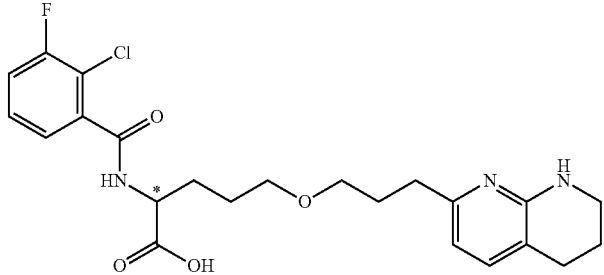 [SMILES: O=C(NC(CCCOCCCc1ccc2c(n1)NCCC2)C(=O)O)c1cccc(F)c1Cl] |

TABLE 1-continued
| Compound # | Structure |
|---|---|
| 10 | 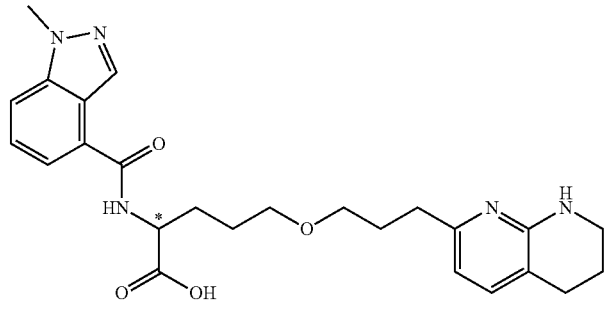 [SMILES: Cn1ncc2c(C(=O)NC(CCCOCCCc3ccc4c(n3)NCCC4)C(=O)O)cccc21] |
| 11 | 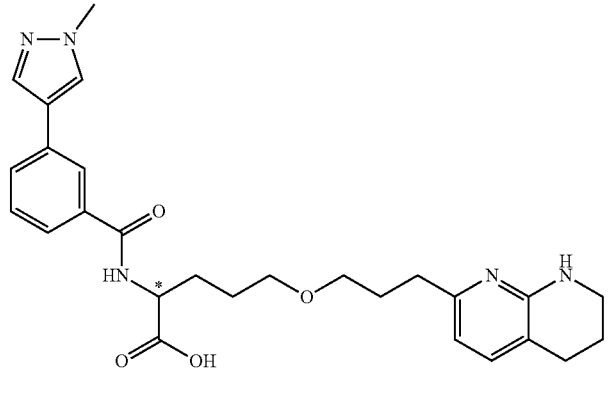 [SMILES: Cn1cc(-c2cccc(C(=O)NC(CCCCOCCc3ccc4c(n3)NCCC4)C(=O)O)c2)cn1] |
| 12 | 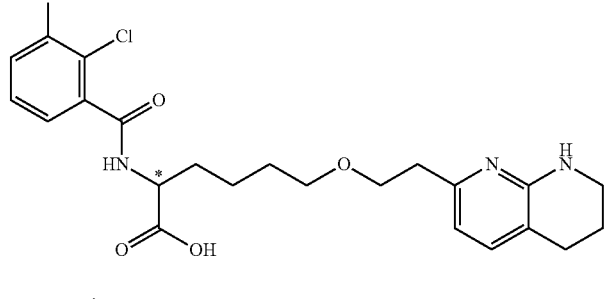 |
| 13 | 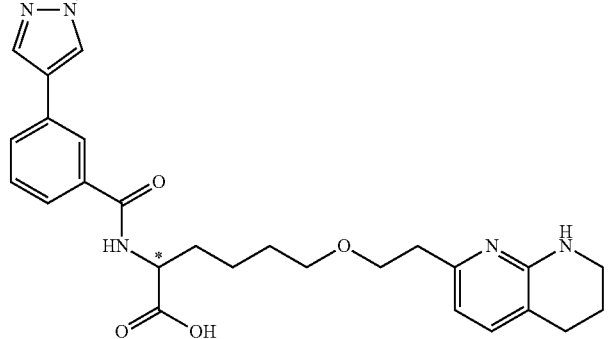 |

TABLE 1-continued

| Compound # | Structure |
|---|---|
| 14 | 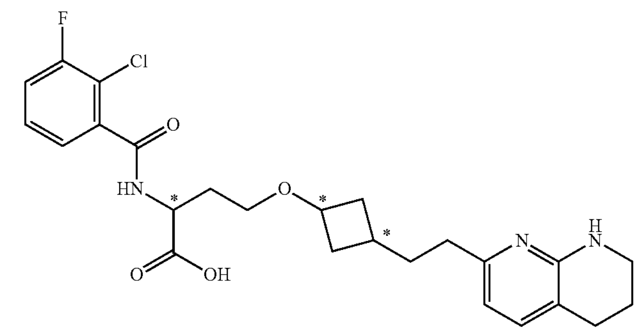 [SMILES: O=C(NC(CCOC1CC(CCc2ccc3c(n2)NCCC3)C1)C(=O)O)c1cccc(F)c1Cl] |
| 15 | 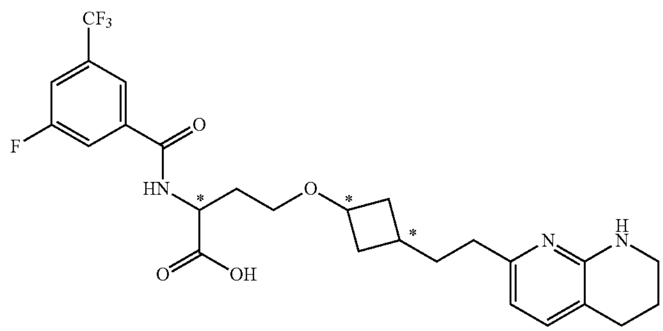 |
| 16 | 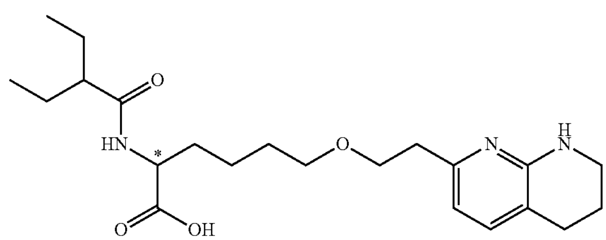 [SMILES: CCC(CC)C(=O)NC(CCCCOCCc1ccc2c(n1)NCCC2)C(=O)O] |
| 17 | 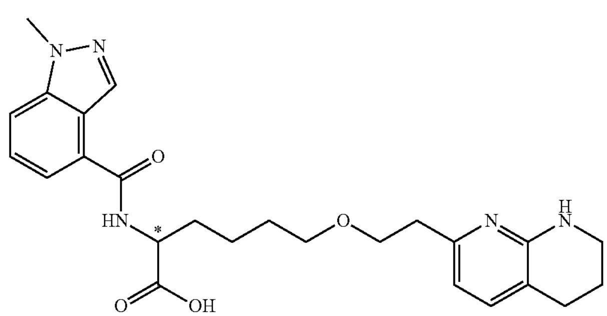 [SMILES: Cn1ncc2c(C(=O)NC(CCCCOCCc3ccc4c(n3)NCCC4)C(=O)O)cccc21] |
| 18 | 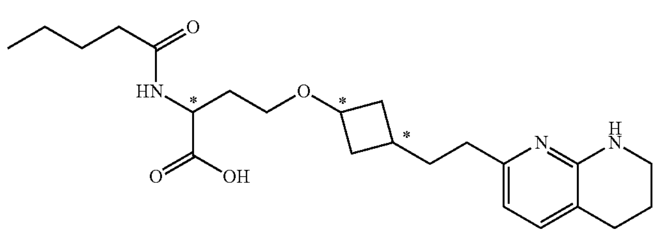 [SMILES: CCCCC(=O)NC(CCOC1CC(CCc2ccc3c(n2)NCCC3)C1)C(=O)O] |

TABLE 1-continued

| Compound # | Structure |
|---|---|
| 19 | 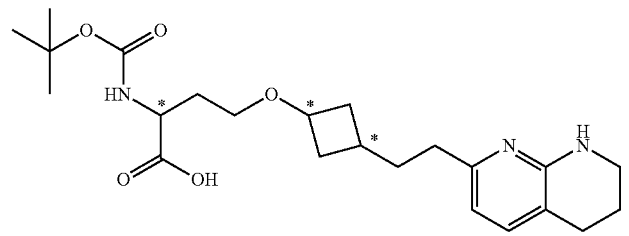 [SMILES: CC(C)(C)OC(=O)NC(CCOC1CC(CCc2ccc3c(n2)NCCC3)C1)C(=O)O] |
| 20 | 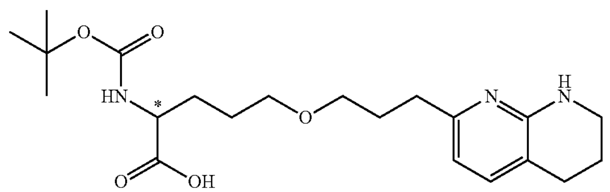 [SMILES: CC(C)(C)OC(=O)NC(CCCOCCCc1ccc2c(n1)NCCC2)C(=O)O] |
| 21 | 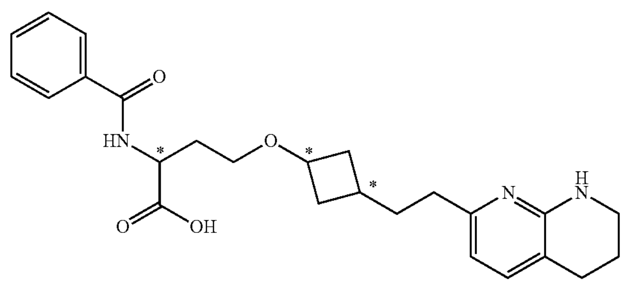 [SMILES: O=C(NC(CCOC1CC(CCc2ccc3c(n2)NCCC3)C1)C(=O)O)c1ccccc1] |
| 22 | 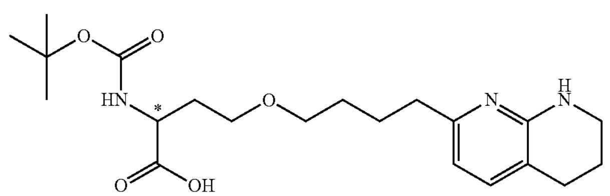 |
| 23 | 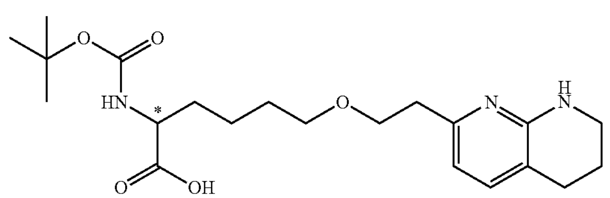 [SMILES: CC(C)(C)OC(=O)NC(CCCCOCCc1ccc2c(n1)NCCC2)C(=O)O] |
| 24 | 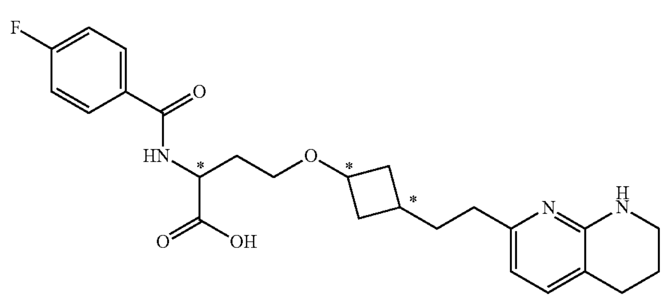 [SMILES: O=C(NC(CCOC1CC(CCc2ccc3c(n2)NCCC3)C1)C(=O)O)c1ccc(F)cc1] |

TABLE 1-continued

| Compound # | Structure |
|---|---|
| 25 | 4-chlorobenzamide linked to (S)-2-amino-4-((cis/trans)-3-(2-(5,6,7,8-tetrahydro-1,8-naphthyridin-2-yl)ethyl)cyclobutoxy)butanoic acid |
| 26 | 3-fluorobenzamide linked to (S)-2-amino-4-((cis/trans)-3-(2-(5,6,7,8-tetrahydro-1,8-naphthyridin-2-yl)ethyl)cyclobutoxy)butanoic acid |
| 27 | 3-chlorobenzamide linked to (S)-2-amino-4-((cis/trans)-3-(2-(5,6,7,8-tetrahydro-1,8-naphthyridin-2-yl)ethyl)cyclobutoxy)butanoic acid |
| 28 | 2-chlorobenzamide linked to (S)-2-amino-4-((cis/trans)-3-(2-(5,6,7,8-tetrahydro-1,8-naphthyridin-2-yl)ethyl)cyclobutoxy)butanoic acid |
| 29 | 2-fluorobenzamide linked to (S)-2-amino-4-((cis/trans)-3-(2-(5,6,7,8-tetrahydro-1,8-naphthyridin-2-yl)ethyl)cyclobutoxy)butanoic acid |

TABLE 1-continued

| Compound # | Structure |
|---|---|
| 30 | 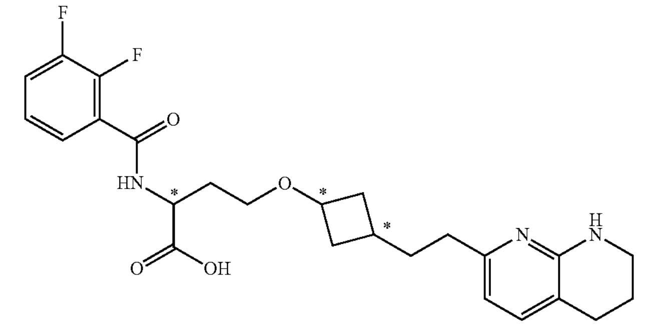 |
| 31 | 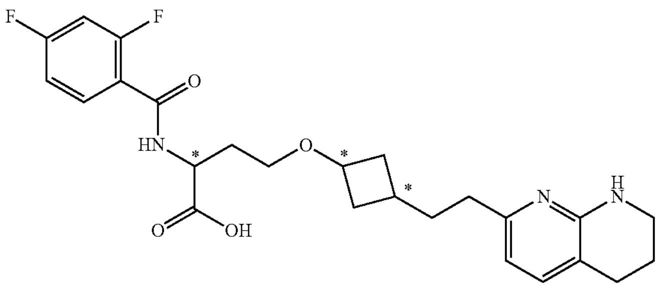 |
| 32 | 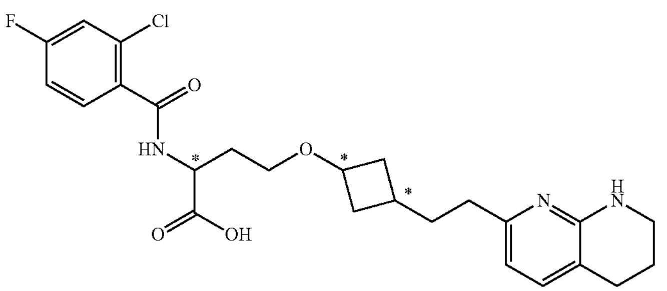 |
| 33 | 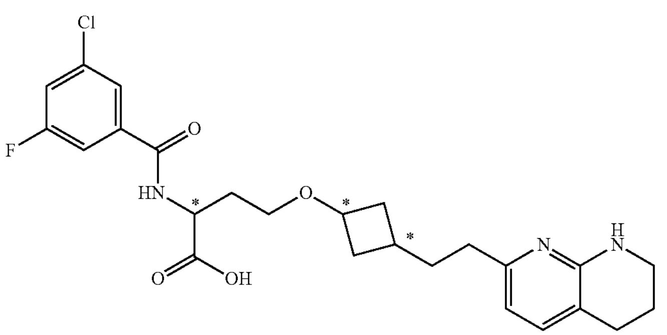 |
| 34 | 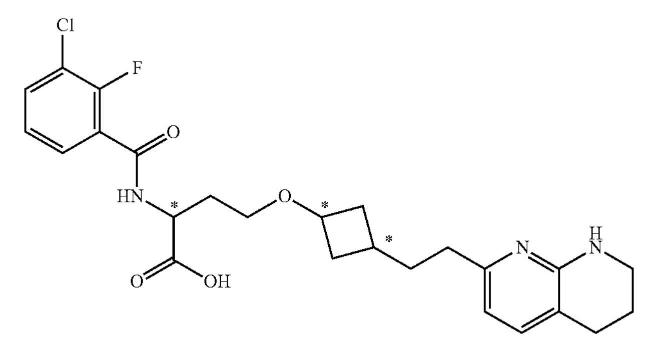 [SMILES: O=C(NC(CCOC1CC(CCc2ccc3c(n2)NCCC3)C1)C(=O)O)c1cccc(F)c1F] |

TABLE 1-continued
| Compound # | Structure |
|---|---|
| 35 | 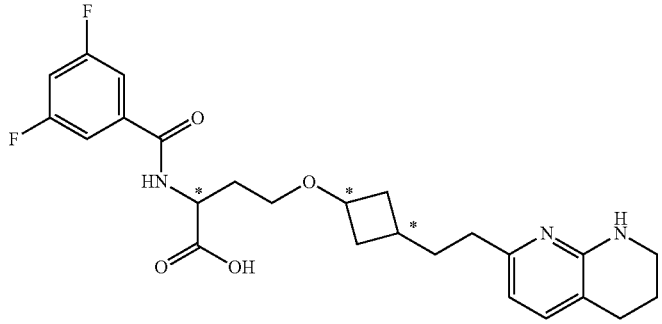 [SMILES: O=C(NC(CCOC1CC(CCc2ccc3c(n2)NCCC3)C1)C(=O)O)c1cc(F)cc(F)c1] |
| 36 | 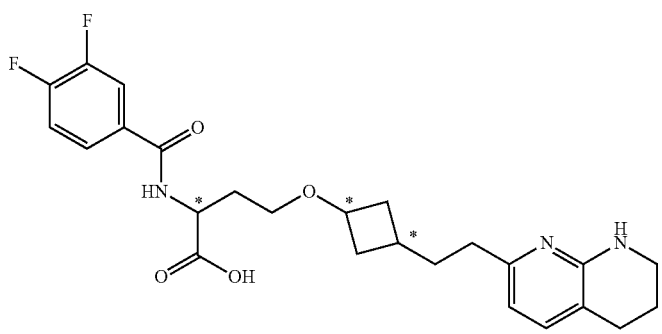 [SMILES: O=C(NC(CCOC1CC(CCc2ccc3c(n2)NCCC3)C1)C(=O)O)c1ccc(F)c(F)c1] |
| 37 | 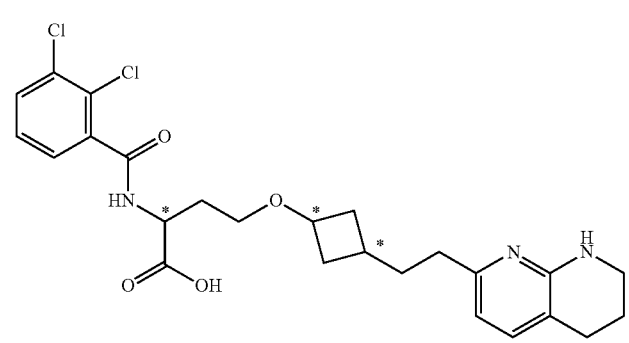 [SMILES: O=C(NC(CCOC1CC(CCc2ccc3c(n2)NCCC3)C1)C(=O)O)c1cccc(Cl)c1Cl] |
| 38 | 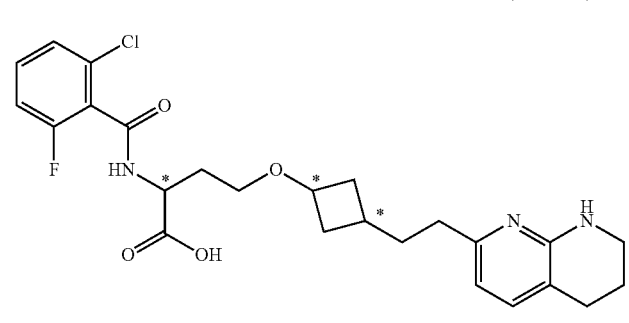 |
| 39 | 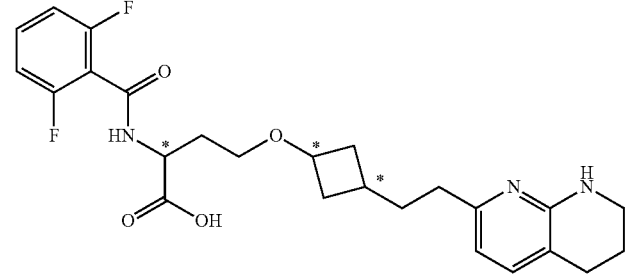 |

TABLE 1-continued
| Compound # | Structure |
|---|---|
| 40 | 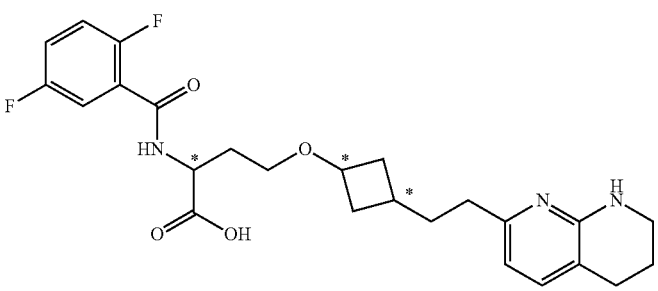 [SMILES: O=C(NC(CCOC1CC(CCc2ccc3c(n2)NCCC3)C1)C(=O)O)c1cc(F)ccc1F] |
| 41 | 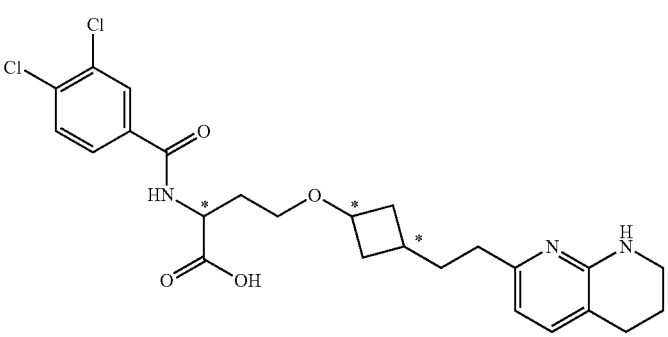 [SMILES: O=C(NC(CCOC1CC(CCc2ccc3c(n2)NCCC3)C1)C(=O)O)c1ccc(Cl)c(Cl)c1] |
| 42 | 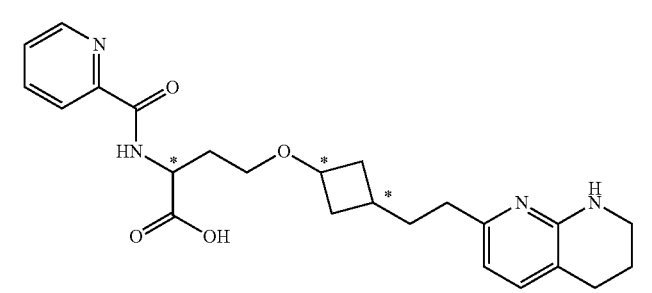 [SMILES: O=C(NC(CCOC1CC(CCc2ccc3c(n2)NCCC3)C1)C(=O)O)c1ccccn1] |
| 43 | 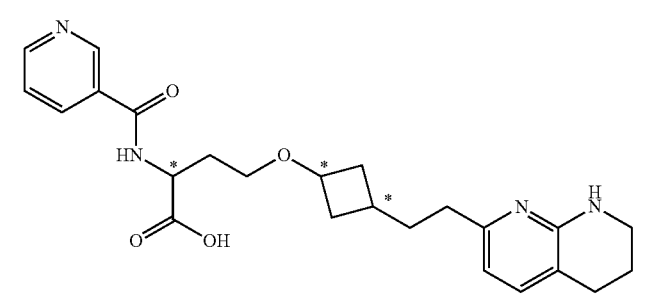 [SMILES: O=C(NC(CCOC1CC(CCc2ccc3c(n2)NCCC3)C1)C(=O)O)c1cccnc1] |
| 44 | 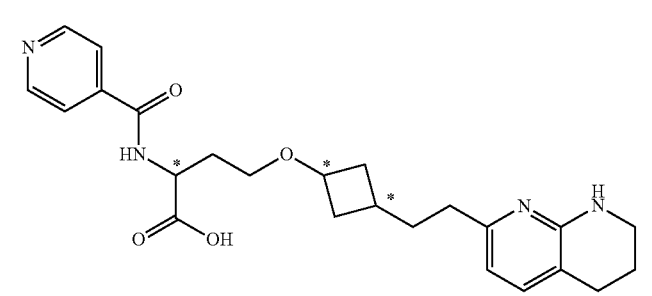 [SMILES: O=C(NC(CCOC1CC(CCc2ccc3c(n2)NCCC3)C1)C(=O)O)c1ccncc1] |

TABLE 1-continued
| Compound # | Structure |
|---|---|
| 45 | 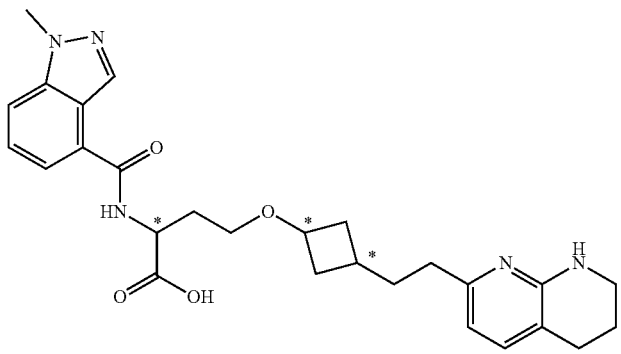 [SMILES: Cn1ncc2c(C(=O)NC(CCOC3CC(CCc4ccc5c(n4)NCCC5)C3)C(=O)O)cccc21] |
| 46 | 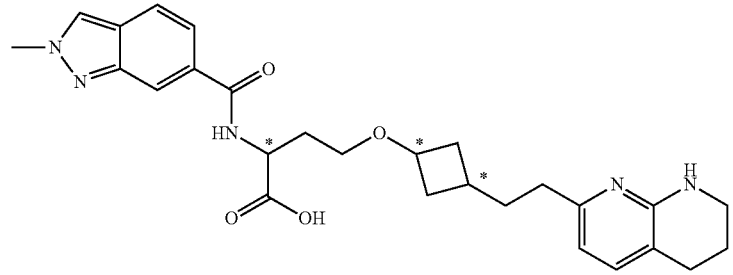 |
| 47 | 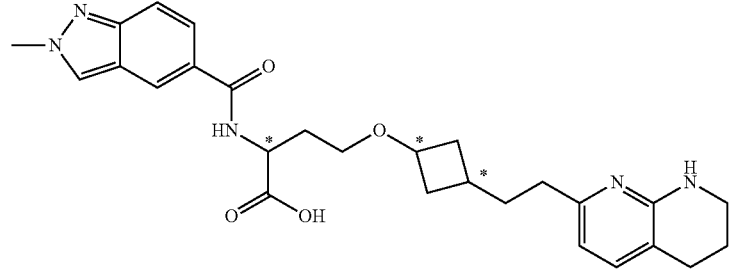 [SMILES: Cn1cc2cc(C(=O)NC(CCOC3CC(CCc4ccc5c(n4)NCCC5)C3)C(=O)O)ccc2n1] |
| 48 | 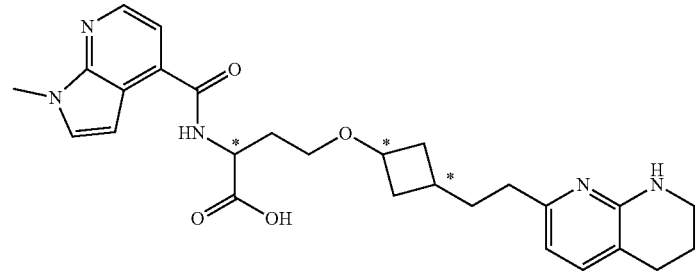 [SMILES: Cn1ccc2c(C(=O)NC(CCOC3CC(CCc4ccc5c(n4)NCCC5)C3)C(=O)O)ccnc21] |
| 49 | 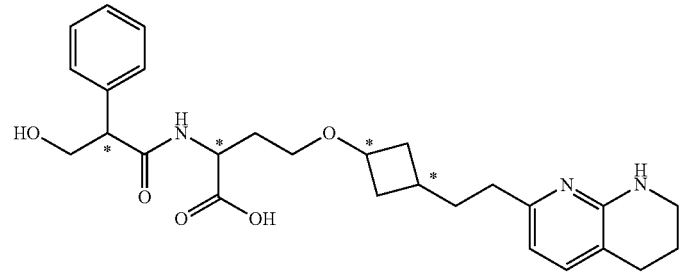 [SMILES: O=C(O)C(CCOC1CC(CCc2ccc3c(n2)NCCC3)C1)NC(=O)C(CO)c1ccccc1] |

TABLE 1-continued

| Compound # | Structure |
|---|---|
| 50 | 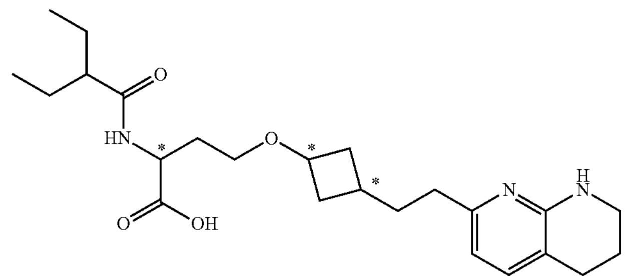 [SMILES: CCC(CC)C(=O)NC(CCOC1CC(CCc2ccc3c(n2)NCCC3)C1)C(=O)O] |
| 51 | 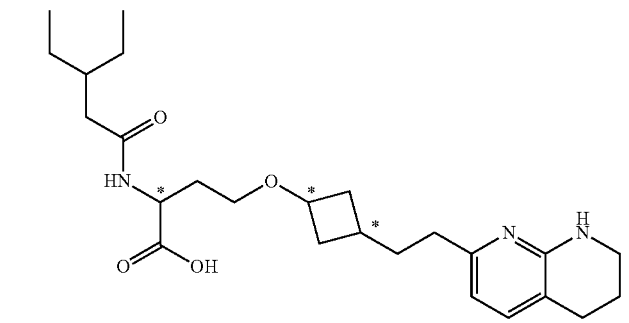 [SMILES: CCC(CC)CC(=O)NC(CCOC1CC(CCc2ccc3c(n2)NCCC3)C1)C(=O)O] |
| 52 | 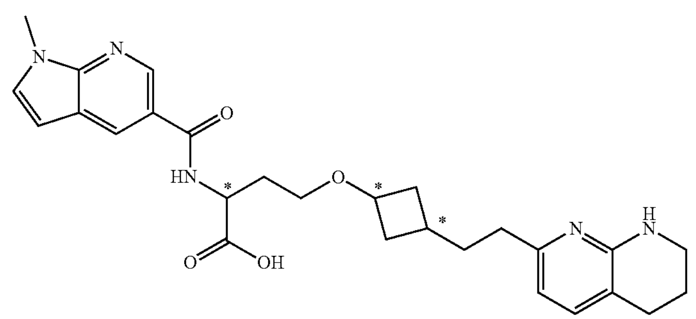 [SMILES: Cn1ccc2cc(C(=O)NC(CCOC3CC(CCc4ccc5c(n4)NCCC5)C3)C(=O)O)cnc21] |
| 53 | 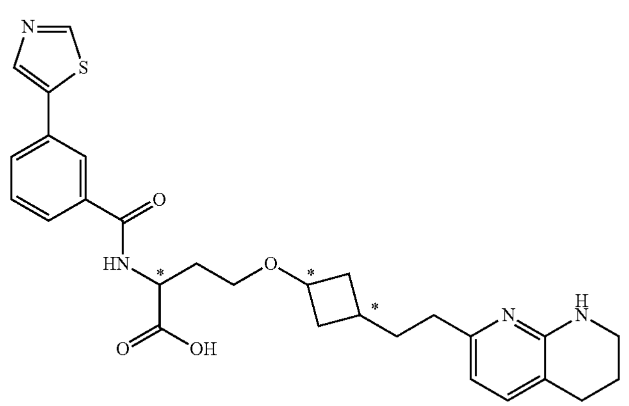 [SMILES: O=C(NC(CCOC1CC(CCc2ccc3c(n2)NCCC3)C1)C(=O)O)c1cccc(-c2cncs2)c1] |

TABLE 1-continued
| Compound # | Structure |
|---|---|
| 54 | 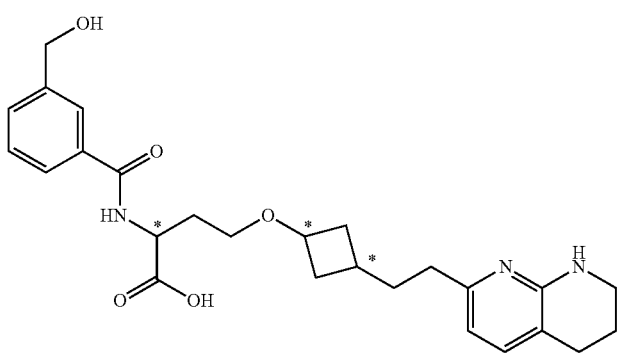 [SMILES: O=C(NC(CCOC1CC(CCc2ccc3c(n2)NCCC3)C1)C(=O)O)c1cccc(CO)c1] |
| 55 | 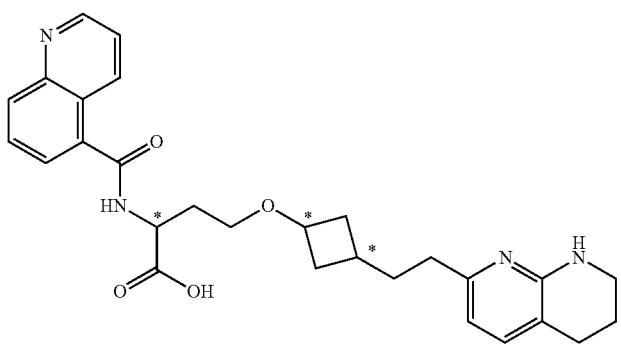 [SMILES: O=C(NC(CCOC1CC(CCc2ccc3c(n2)NCCC3)C1)C(=O)O)c1cccc2ncccc12] |
| 56 | 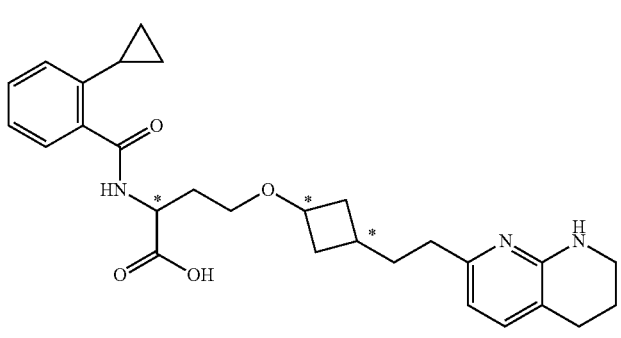 [SMILES: O=C(NC(CCOC1CC(CCc2ccc3c(n2)NCCC3)C1)C(=O)O)c1ccccc1C1CC1] |
| 57 | 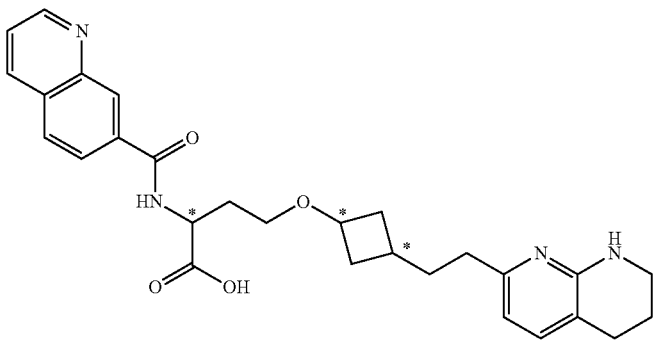 [SMILES: O=C(NC(CCOC1CC(CCc2ccc3c(n2)NCCC3)C1)C(=O)O)c1ccc2cccnc2c1] |

TABLE 1-continued

| Compound # | Structure |
|---|---|
| 58 | 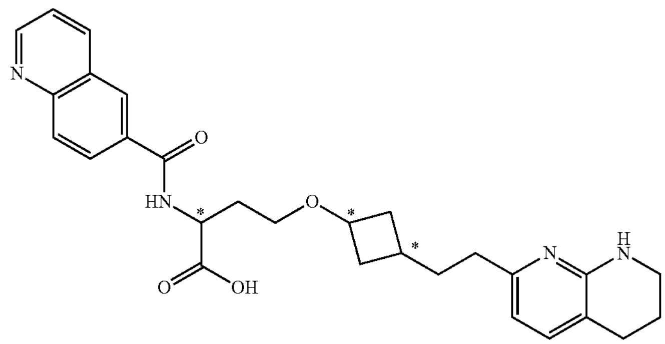 [SMILES: O=C(NC(CCOC1CC(CCc2ccc3c(n2)NCCC3)C1)C(=O)O)c1ccc2ncccc2c1] |
| 59 | 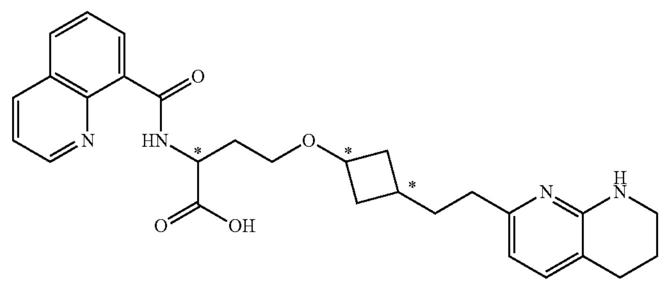 [SMILES: O=C(NC(CCOC1CC(CCc2ccc3c(n2)NCCC3)C1)C(=O)O)c1cccc2cccnc12] |
| 60 | 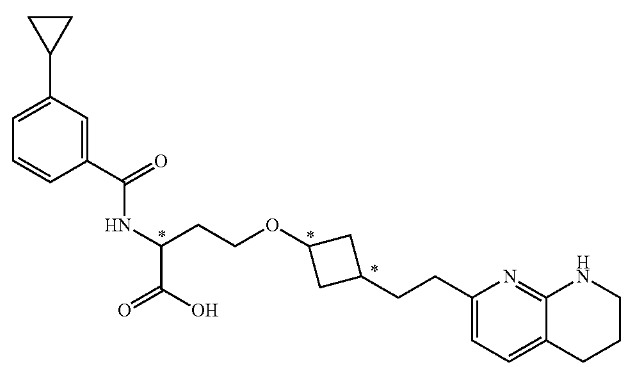 [SMILES: O=C(NC(CCOC1CC(CCc2ccc3c(n2)NCCC3)C1)C(=O)O)c1cccc(C2CC2)c1] |
| 61 | 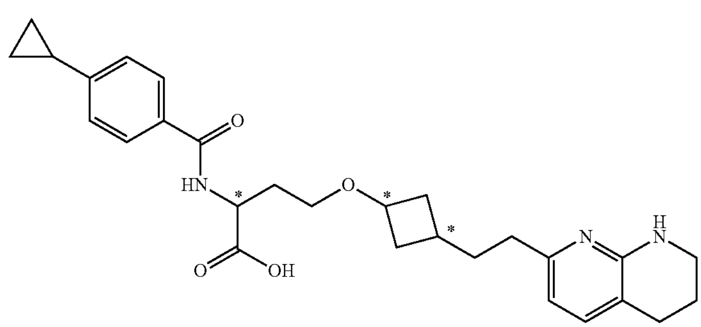 [SMILES: O=C(NC(CCOC1CC(CCc2ccc3c(n2)NCCC3)C1)C(=O)O)c1ccc(C2CC2)cc1] |

| Compound # | Structure |
|---|---|
| 62 | 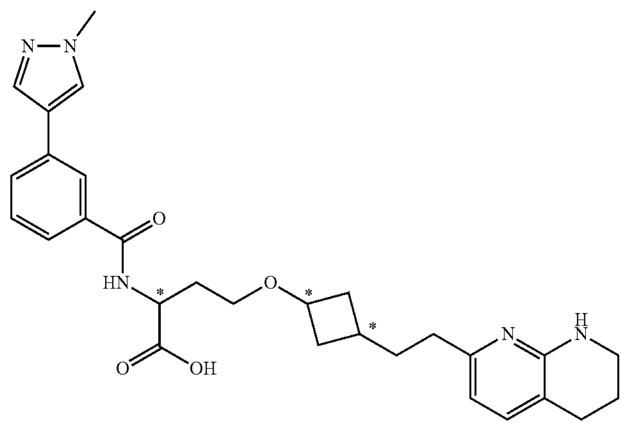 [SMILES: Cn1cc(-c2cccc(C(=O)NC(CCOC3CC(CCc4ccc5c(n4)NCCC5)C3)C(=O)O)c2)cn1] |
| 63 | 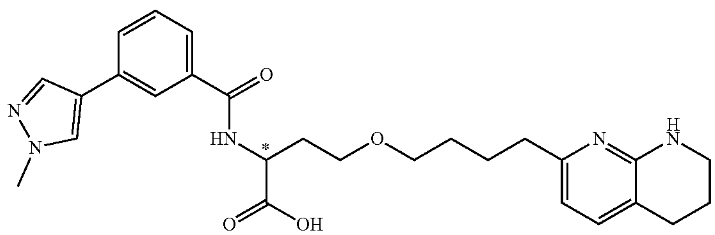 [SMILES: Cn1cc(-c2cccc(C(=O)NC(CCOCCCCc3ccc4c(n3)NCCC4)C(=O)O)c2)cn1] |
| 64 | 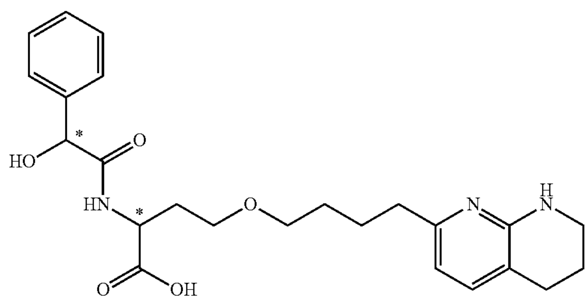 [SMILES: O=C(O)C(CCOCCCCc1ccc2c(n1)NCCC2)NC(=O)C(O)c1ccccc1] |
| 65 | 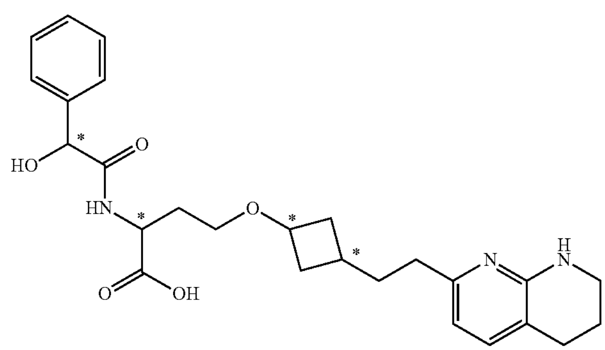 [SMILES: O=C(O)C(CCOC1CC(CCc2ccc3c(n2)NCCC3)C1)NC(=O)C(O)c1ccccc1] |
| 66 | 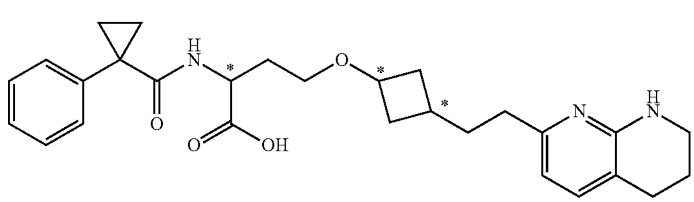 [SMILES: O=C(O)C(CCOC1CC(CCc2ccc3c(n2)NCCC3)C1)NC(=O)C1(c2ccccc2)CC1] |

US 11,952,376 B2
TABLE 1-continued
| Compound # | Structure |
|---|---|
| 67 | 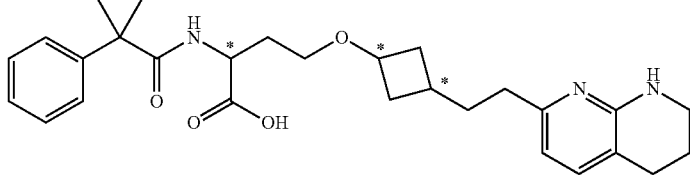 [SMILES: CC(C)(C(=O)NC(CCOC1CC(CCc2ccc3c(n2)NCCC3)C1)C(=O)O)c1ccccc1] |
| 68 | 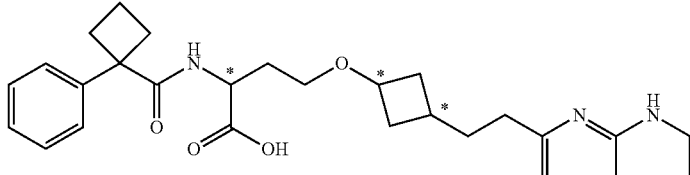 |
| 69 | 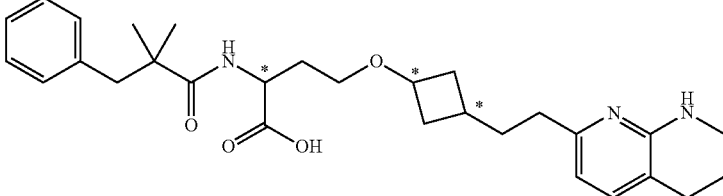 [SMILES: CC(C)(Cc1ccccc1)C(=O)NC(CCOC1CC(CCc2ccc3c(n2)NCCC3)C1)C(=O)O] |
| 70 | 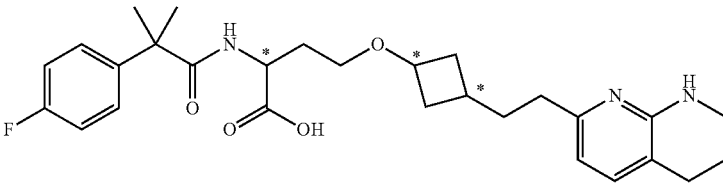 [SMILES: CC(C)(C(=O)NC(CCOC1CC(CCc2ccc3c(n2)NCCC3)C1)C(=O)O)c1ccc(F)cc1] |
| 71 | 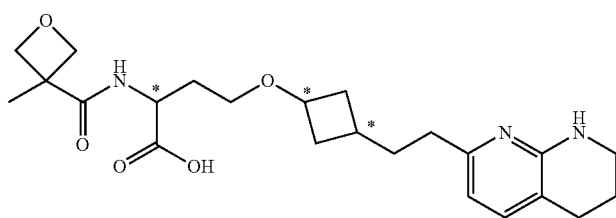 [SMILES: CC1(C(=O)NC(CCOC2CC(CCc3ccc4c(n3)NCCC4)C2)C(=O)O)COC1] |
| 72 | 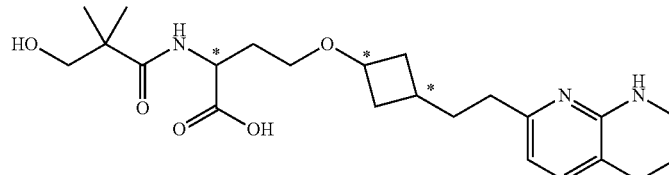 |
| 73 | 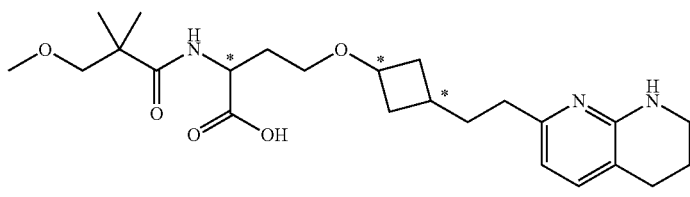 [SMILES: COCC(C)(C)C(=O)NC(CCOC1CC(CCc2ccc3c(n2)NCCC3)C1)C(=O)O] |

TABLE 1-continued

| Compound # | Structure |
| --- | --- |
| 74 | 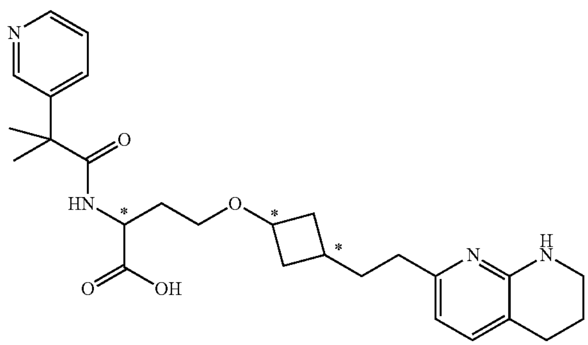 [SMILES: CC(C)(C(=O)NC(CCOC1CC(CCc2ccc3c(n2)NCCC3)C1)C(=O)O)c1cccnc1] |
| 75 | 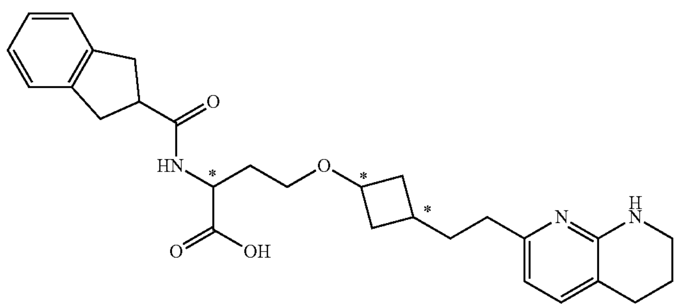 [SMILES: O=C(NC(CCOC1CC(CCc2ccc3c(n2)NCCC3)C1)C(=O)O)C1Cc2ccccc2C1] |
| 76 | 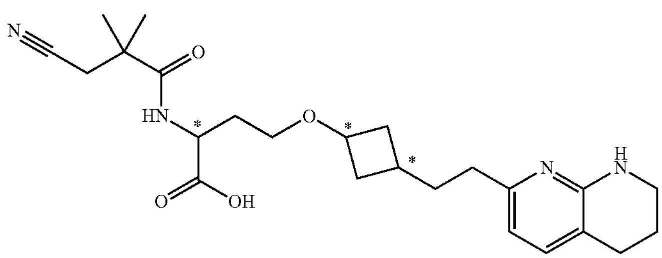 [SMILES: CC(C)(CC#N)C(=O)NC(CCOC1CC(CCc2ccc3c(n2)NCCC3)C1)C(=O)O] |
| 77 | 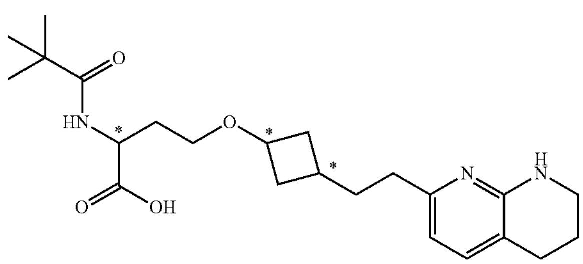 [SMILES: CC(C)(C)C(=O)NC(CCOC1CC(CCc2ccc3c(n2)NCCC3)C1)C(=O)O] |
| 78 | 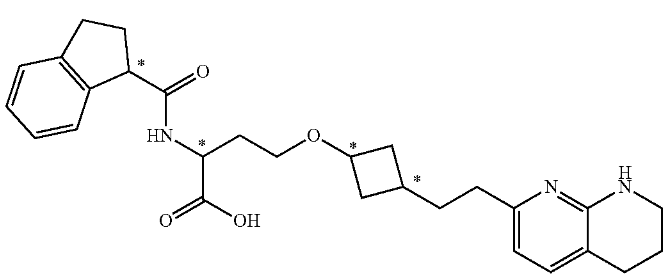 [SMILES: O=C(O)C(CCOC1CC(CCc2ccc3c(n2)NCCC3)C1)NC(=O)C1CCc2ccccc21] |

TABLE 1-continued

| Compound # | Structure |
|---|---|
| 79 | 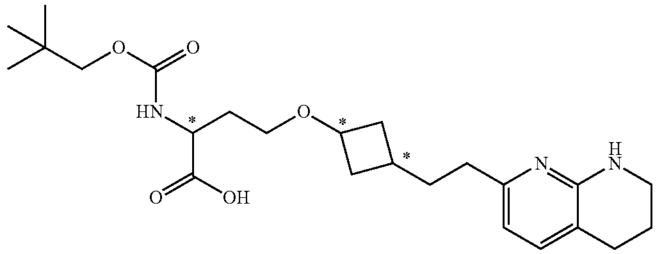 [SMILES: CC(C)(C)COC(=O)NC(CCOC1CC(CCc2ccc3c(n2)NCCC3)C1)C(=O)O] |
| 80 | 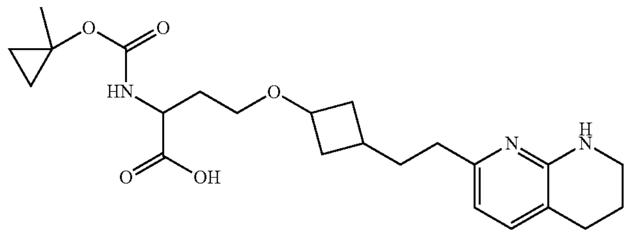 [SMILES: CC1(OC(=O)NC(CCOC2CC(CCc3ccc4c(n3)NCCC4)C2)C(=O)O)CC1] |
| 81 | 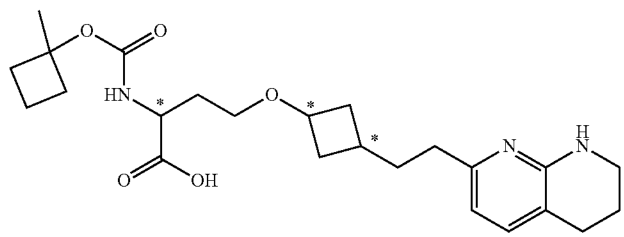 [SMILES: CC1(OC(=O)NC(CCOC2CC(CCc3ccc4c(n3)NCCC4)C2)C(=O)O)CCC1] |
| 82 | 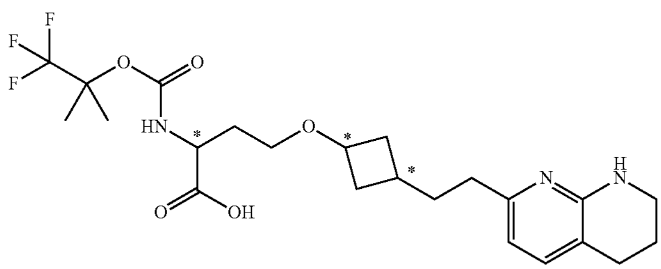 [SMILES: CC(C)(OC(=O)NC(CCOC1CC(CCc2ccc3c(n2)NCCC3)C1)C(=O)O)C(F)(F)F] |
| 83 | 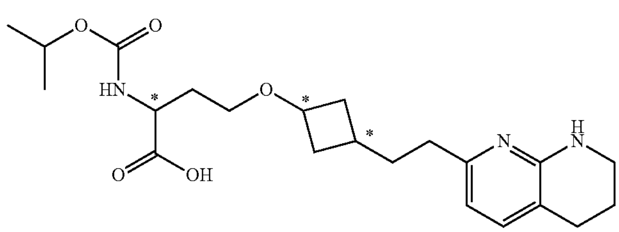 [SMILES: CC(C)OC(=O)NC(CCOC1CC(CCc2ccc3c(n2)NCCC3)C1)C(=O)O] |
| 84 | 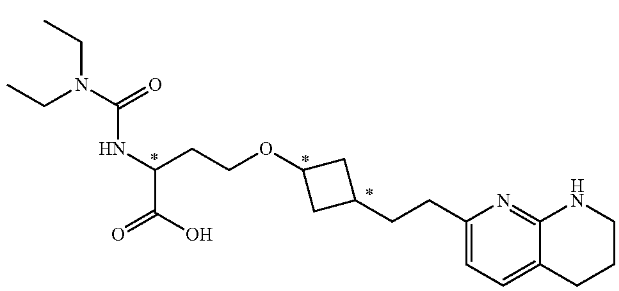 [SMILES: CCN(CC)C(=O)NC(CCOC1CC(CCc2ccc3c(n2)NCCC3)C1)C(=O)O] |

TABLE 1-continued

| Compound # | Structure |
|---|---|
| 85 | 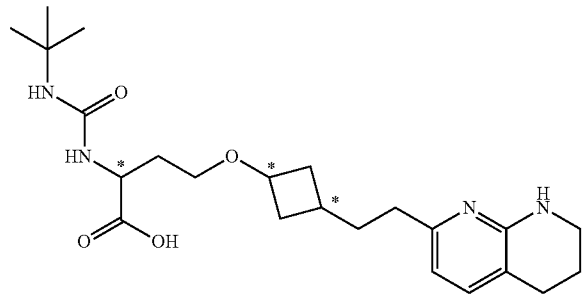 [SMILES: CC(C)(C)NC(=O)NC(CCOC1CC(CCc2ccc3c(n2)NCCC3)C1)C(=O)O] |
| 86 | 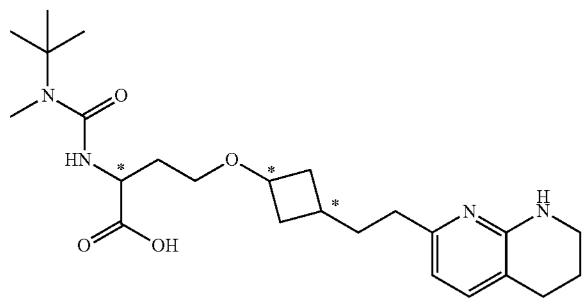 [SMILES: CN(C(=O)NC(CCOC1CC(CCc2ccc3c(n2)NCCC3)C1)C(=O)O)C(C)(C)C] |
| 87 | 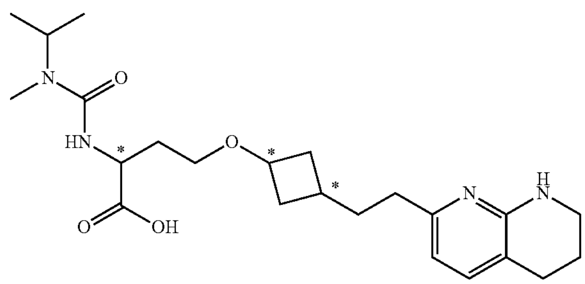 [SMILES: CC(C)N(C)C(=O)NC(CCOC1CC(CCc2ccc3c(n2)NCCC3)C1)C(=O)O] |
| 88 | 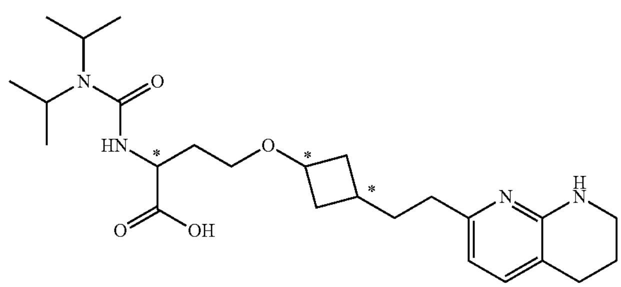 [SMILES: CC(C)N(C(=O)NC(CCOC1CC(CCc2ccc3c(n2)NCCC3)C1)C(=O)O)C(C)C] |
| 89 | 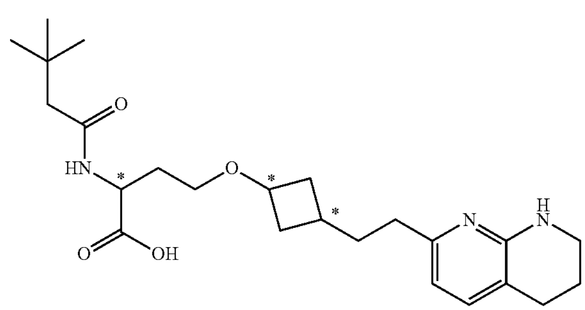 [SMILES: CC(C)(C)CC(=O)NC(CCOC1CC(CCc2ccc3c(n2)NCCC3)C1)C(=O)O] |

TABLE 1-continued
| Compound # | Structure |
|---|---|
| 90 | 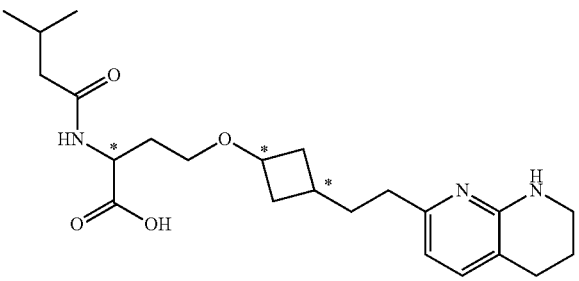 [SMILES: CC(C)CC(=O)NC(CCOC1CC(CCc2ccc3c(n2)NCCC3)C1)C(=O)O] |
| 91 | 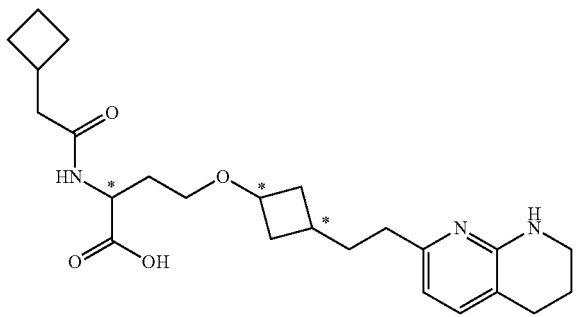 [SMILES: O=C(CC1CCC1)NC(CCOC1CC(CCc2ccc3c(n2)NCCC3)C1)C(=O)O] |
| 92 | 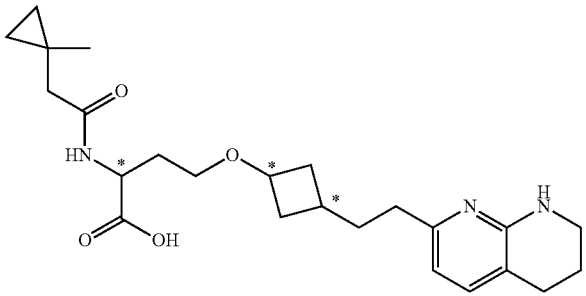 [SMILES: CC1(CC(=O)NC(CCOC2CC(CCc3ccc4c(n3)NCCC4)C2)C(=O)O)CC1] |
| 93 | 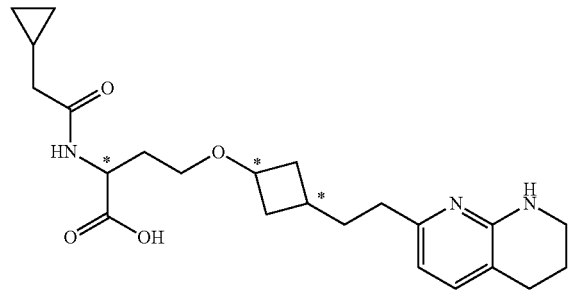 [SMILES: O=C(CC1CC1)NC(CCOC1CC(CCc2ccc3c(n2)NCCC3)C1)C(=O)O] |
| 94 | 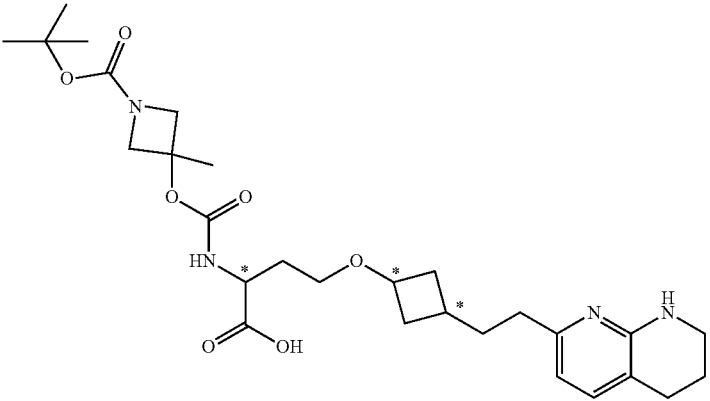 [SMILES: CC(C)(C)OC(=O)N1CC(C)(OC(=O)NC(CCOC2CC(CCc3ccc4c(n3)NCCC4)C2)C(=O)O)C1] |

TABLE 1-continued
| Compound # | Structure |
|---|---|
| 95 | 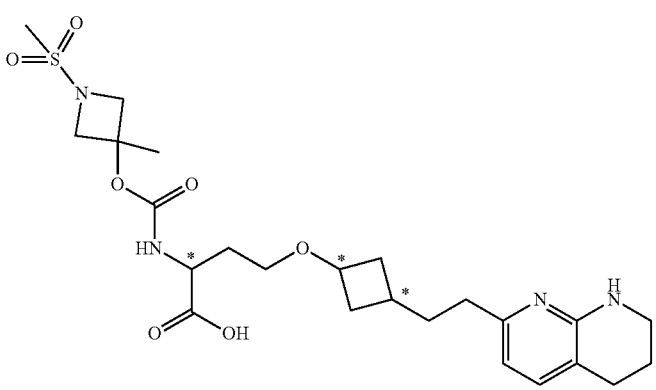 [SMILES: CC1(OC(=O)NC(CCOC2CC(CCc3ccc4c(n3)NCCC4)C2)C(=O)O)CN(S(C)(=O)=O)C1] |
| 96 | 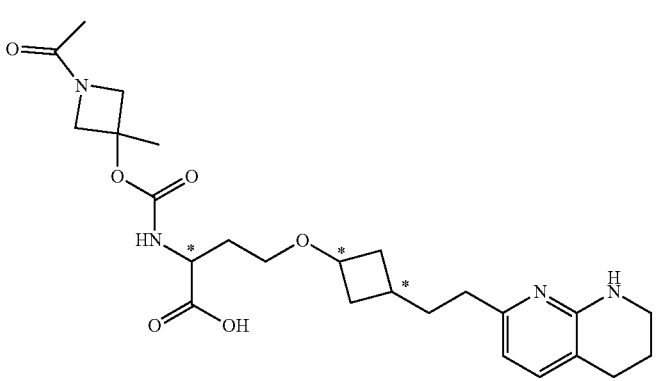 [SMILES: CC(=O)N1CC(C)(OC(=O)NC(CCOC2CC(CCc3ccc4c(n3)NCCC4)C2)C(=O)O)C1] |
| 97 | 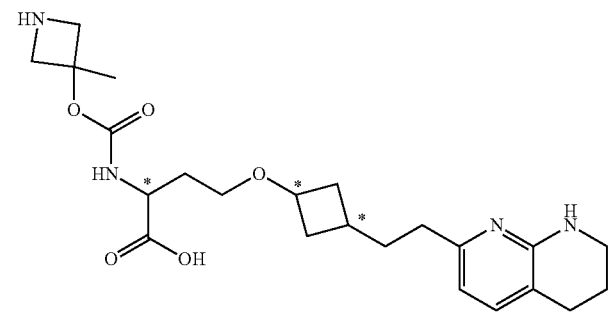 [SMILES: CC1(OC(=O)NC(CCOC2CC(CCc3ccc4c(n3)NCCC4)C2)C(=O)O)CNC1] |
| 98 | 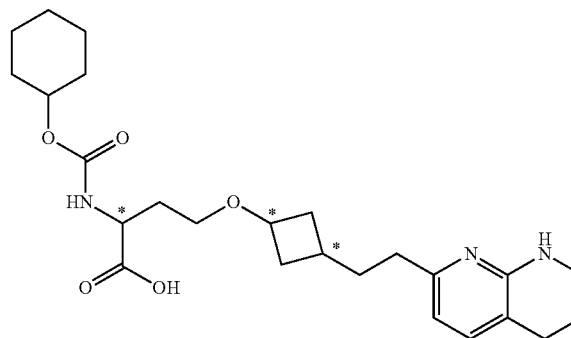 |

TABLE 1-continued
| Compound # | Structure |
|---|---|
| 99 | 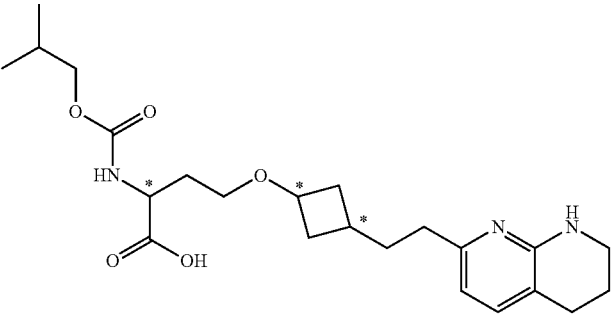 [SMILES: CC(C)COC(=O)NC(CCOC1CC(CCc2ccc3c(n2)NCCC3)C1)C(=O)O] |
| 100 | 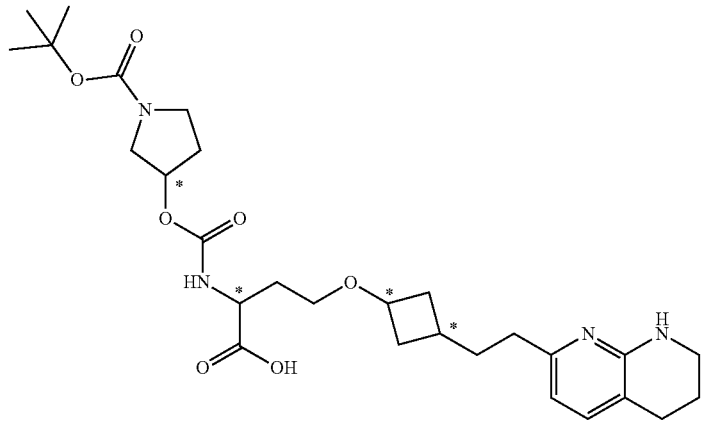 [SMILES: CC(C)(C)OC(=O)N1CCC(OC(=O)NC(CCOC2CC(CCc3ccc4c(n3)NCCC4)C2)C(=O)O)C1] |
| 101 | 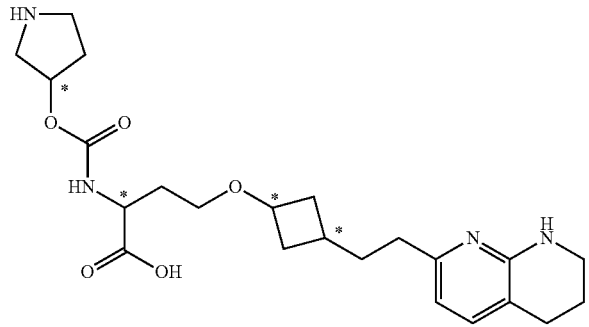 [SMILES: O=C(NC(CCOC1CC(CCc2ccc3c(n2)NCCC3)C1)C(=O)O)OC1CCNC1] |
| 102 | 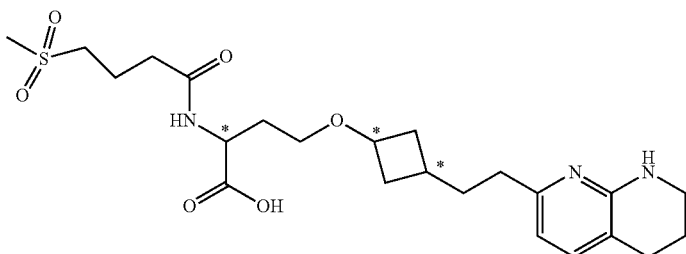 |
| 103 | 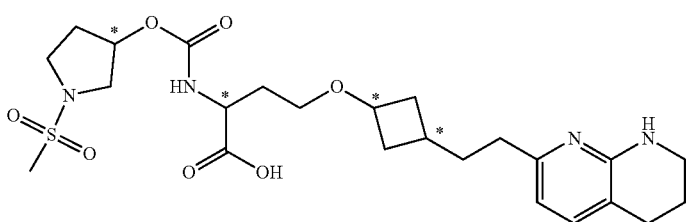 [SMILES: CS(=O)(=O)N1CCC(OC(=O)NC(CCOC2CC(CCc3ccc4c(n3)NCCC4)C2)C(=O)O)C1] |

TABLE 1-continued
| Compound # | Structure |
|---|---|
| 104 | 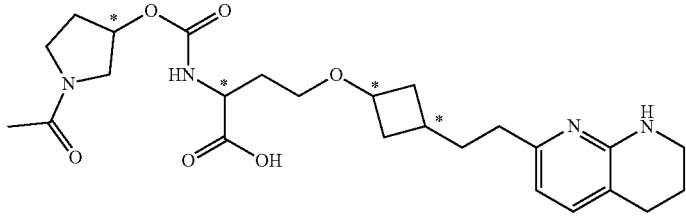 [SMILES: CC(=O)N1CCC(OC(=O)NC(CCOC2CC(CCc3ccc4c(n3)NCCC4)C2)C(=O)O)C1] |
| 105 | 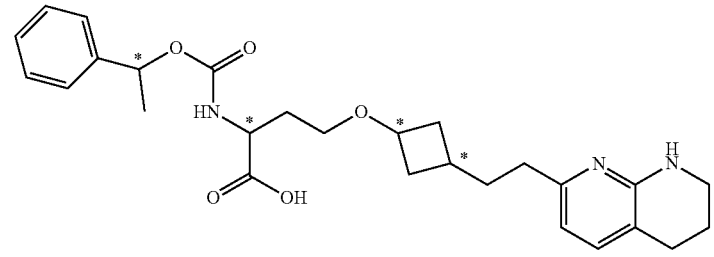 [SMILES: CC(OC(=O)NC(CCOC1CC(CCc2ccc3c(n2)NCCC3)C1)C(=O)O)c1ccccc1] |
| 106 | 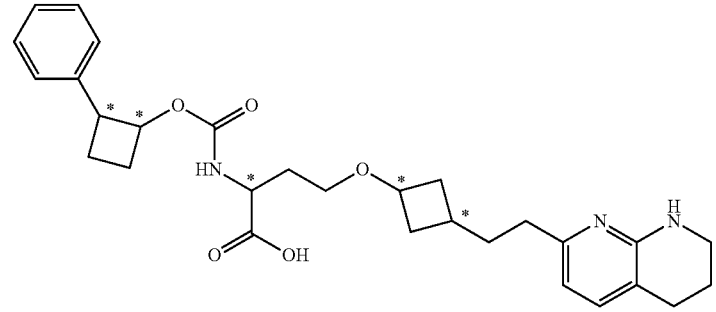 [SMILES: O=C(NC(CCOC1CC(CCc2ccc3c(n2)NCCC3)C1)C(=O)O)OC1CCC1c1ccccc1] |
| 107 | 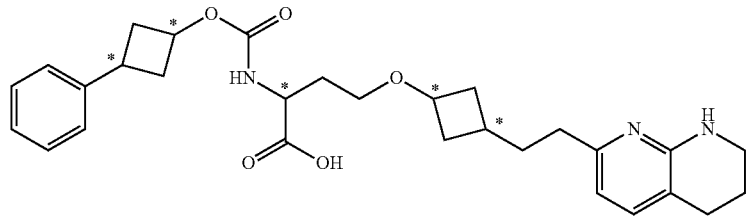 [SMILES: O=C(NC(CCOC1CC(CCc2ccc3c(n2)NCCC3)C1)C(=O)O)OC1CC(c2ccccc2)C1] |
| 108 | 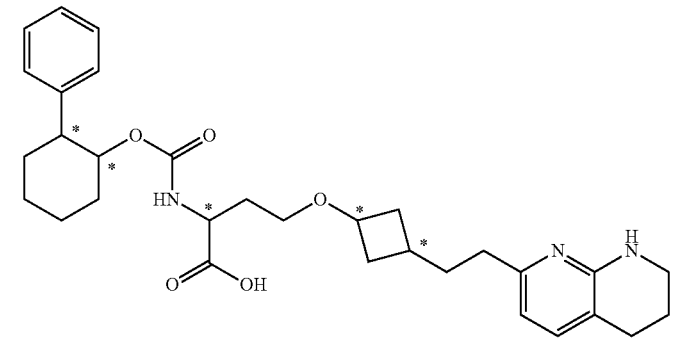 [SMILES: O=C(NC(CCOC1CC(CCc2ccc3c(n2)NCCC3)C1)C(=O)O)OC1CCCCC1c1ccccc1] |

TABLE 1-continued
| Compound # | Structure |
|---|---|
| 109 | 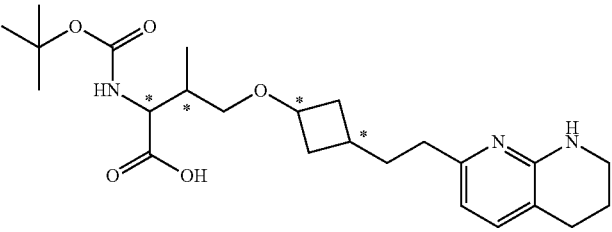 [SMILES: CC(COC1CC(CCc2ccc3c(n2)NCCC3)C1)C(NC(=O)OC(C)(C)C)C(=O)O] |
| 110 | 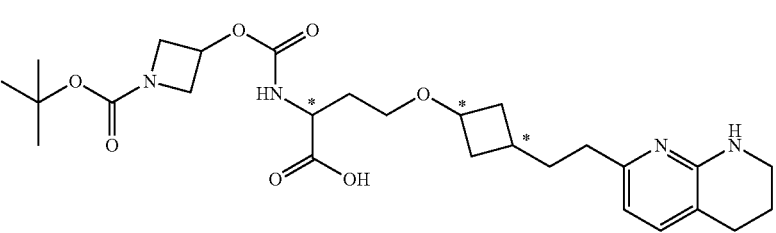 [SMILES: CC(C)(C)OC(=O)N1CC(OC(=O)NC(CCOC2CC(CCc3ccc4c(n3)NCCC4)C2)C(=O)O)C1] |
| 111 | 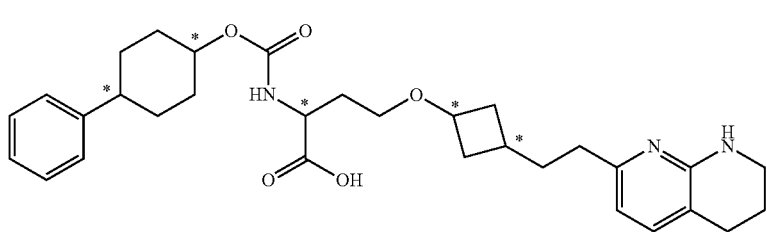 [SMILES: O=C(NC(CCOC1CC(CCc2ccc3c(n2)NCCC3)C1)C(=O)O)OC1CCC(c2ccccc2)CC1] |
| 112 | 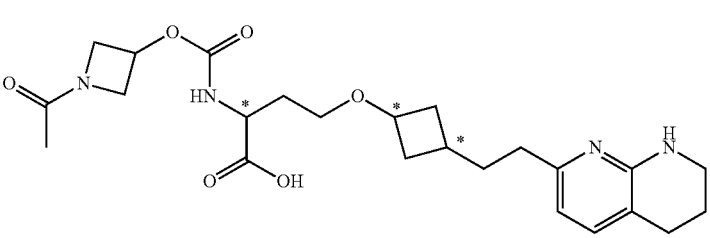 [SMILES: CC(=O)N1CC(OC(=O)NC(CCOC2CC(CCc3ccc4c(n3)NCCC4)C2)C(=O)O)C1] |
| 113 | 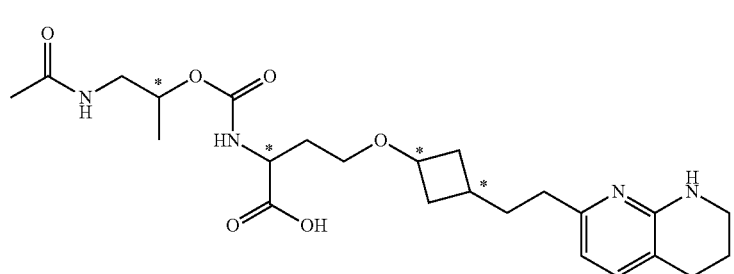 |
| 114 | 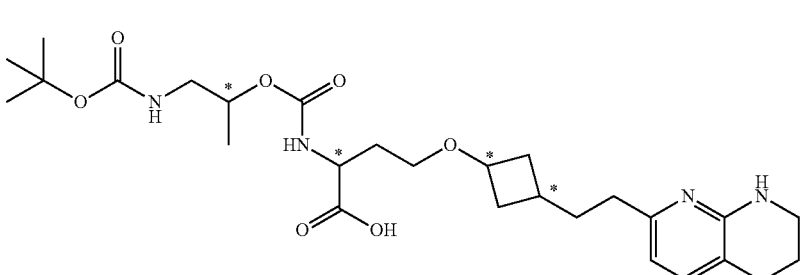 |

TABLE 1-continued
| Compound # | Structure |
|---|---|
| 115 | 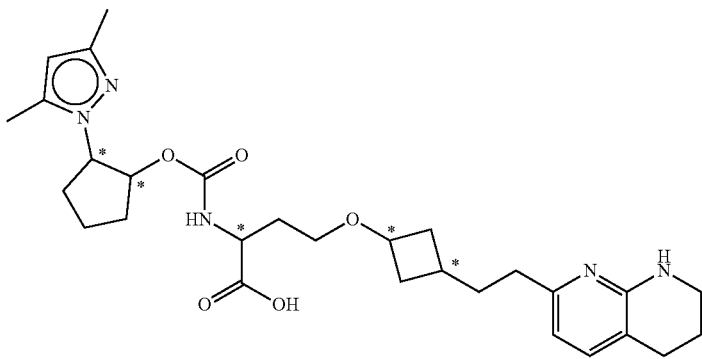 |
| 116 | 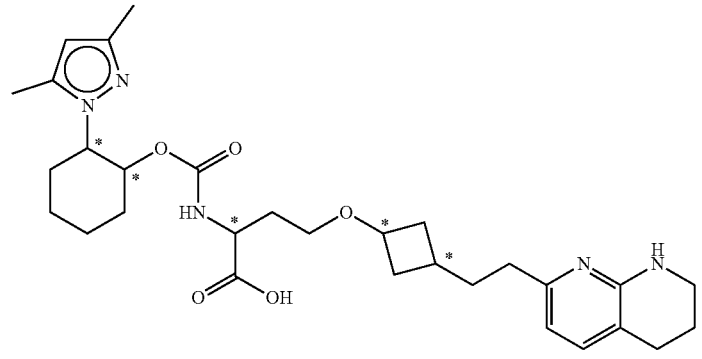 |
| 117 | 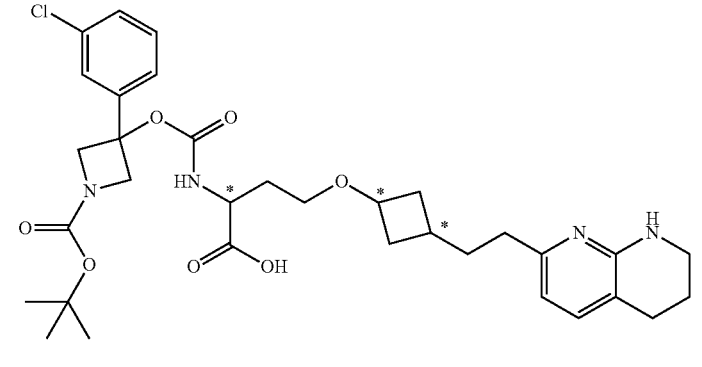 [SMILES: CC(C)(C)OC(=O)N1CC(OC(=O)NC(CCOC2CC(CCc3ccc4c(n3)NCCC4)C2)C(=O)O)(c2cccc(Cl)c2)C1] |
| 118 | 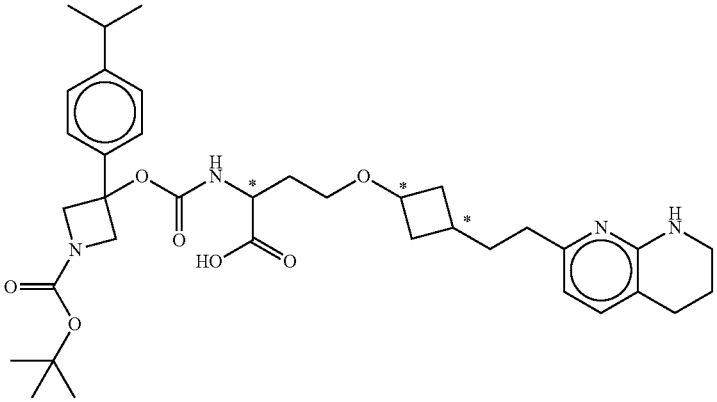 |

TABLE 1-continued
| Compound # | Structure |
|---|---|
| 119 | 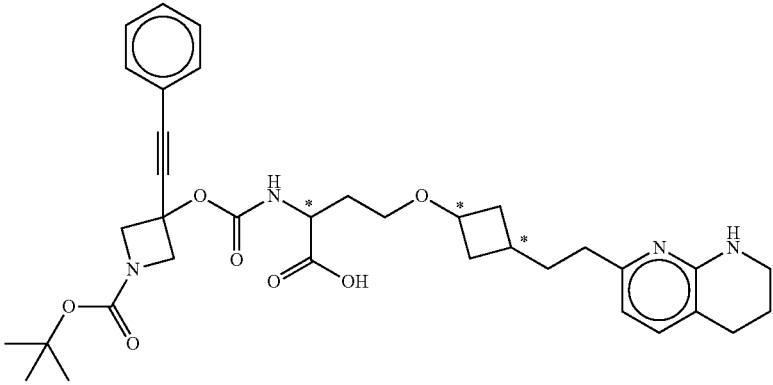 |
| 120 | 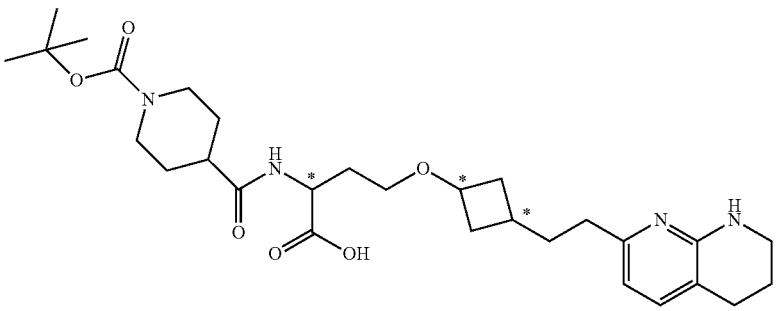 [SMILES: CC(C)(C)OC(=O)N1CCC(C(=O)NC(CCOC2CC(CCc3ccc4c(n3)NCCC4)C2)C(=O)O)CC1] |
| 121 | 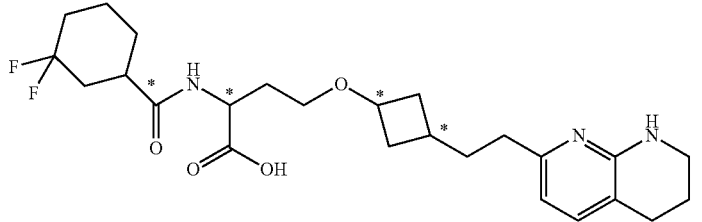 [SMILES: O=C(NC(CCOC1CC(CCc2ccc3c(n2)NCCC3)C1)C(=O)O)C1CCCC(F)(F)C1] |
| 122 | 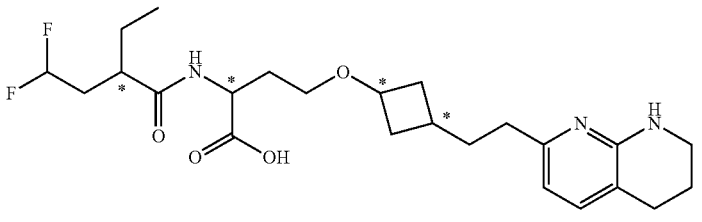 [SMILES: CCC(CC(F)F)C(=O)NC(CCOC1CC(CCc2ccc3c(n2)NCCC3)C1)C(=O)O] |
| 123 | 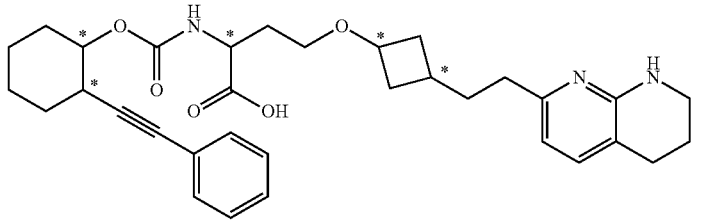 [SMILES: O=C(NC(CCOC1CC(CCc2ccc3c(n2)NCCC3)C1)C(=O)O)OC1CCCCC1C#Cc1ccccc1] |
| 124 | 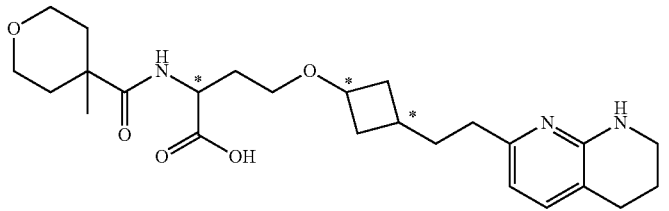 [SMILES: CC1(C(=O)NC(CCOC2CC(CCc3ccc4c(n3)NCCC4)C2)C(=O)O)CCOCC1] |

TABLE 1-continued

| Compound # | Structure |
|---|---|
| 125 | 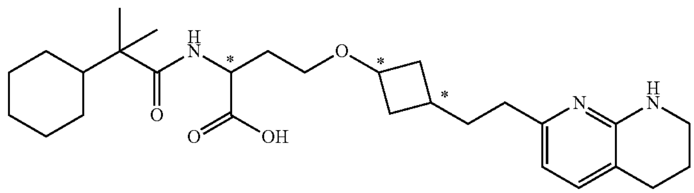 [SMILES: CC(C)(C(=O)NC(CCOC1CC(CCc2ccc3c(n2)NCCC3)C1)C(=O)O)C1CCCCC1] |
| 126 | 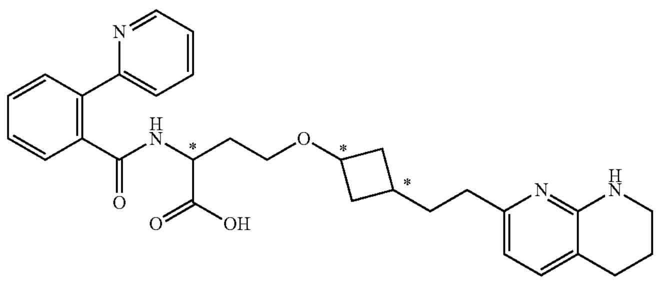 [SMILES: O=C(NC(CCOC1CC(CCc2ccc3c(n2)NCCC3)C1)C(=O)O)c1ccccc1-c1ccccn1] |
| 127 | 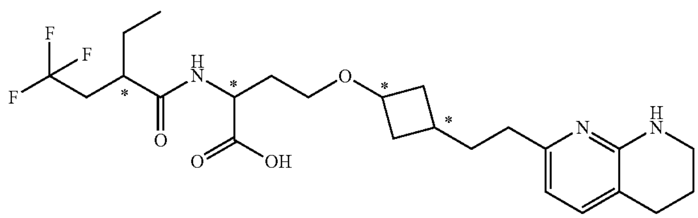 [SMILES: CCC(CC(F)(F)F)C(=O)NC(CCOC1CC(CCc2ccc3c(n2)NCCC3)C1)C(=O)O] |
| 128 | 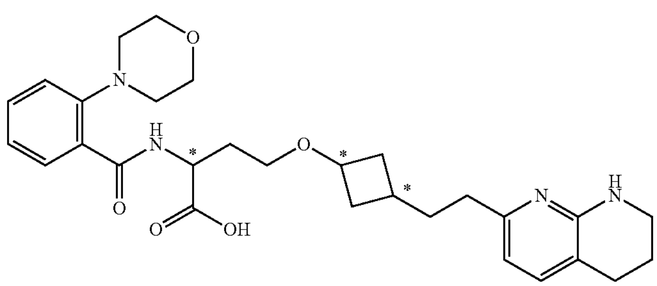 [SMILES: O=C(NC(CCOC1CC(CCc2ccc3c(n2)NCCC3)C1)C(=O)O)c1ccccc1N1CCOCC1] |
| 129 | 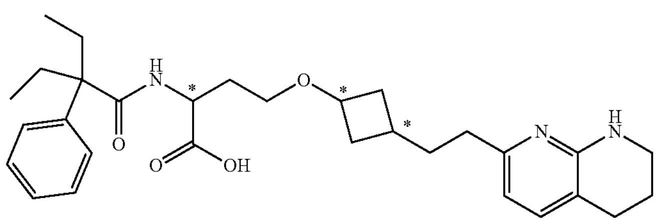 [SMILES: CCC(CC)(C(=O)NC(CCOC1CC(CCc2ccc3c(n2)NCCC3)C1)C(=O)O)c1ccccc1] |
| 130 | 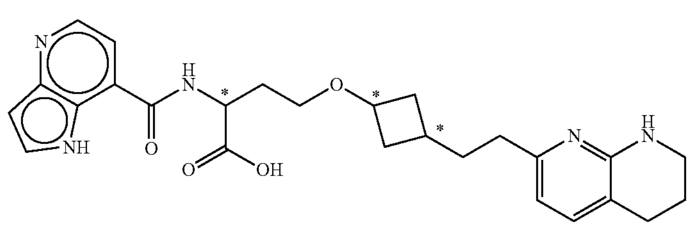 |

TABLE 1-continued

| Compound # | Structure |
|---|---|
| 131 | 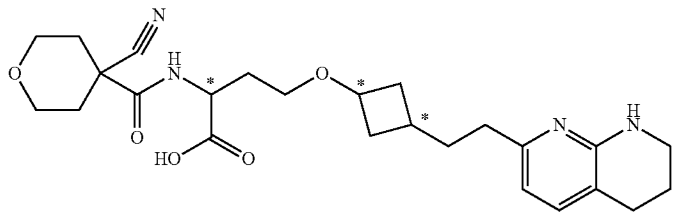 [SMILES: N#CC1(C(=O)NC(CCOC2CC(CCc3ccc4c(n3)NCCC4)C2)C(=O)O)CCOCC1] |
| 132 | 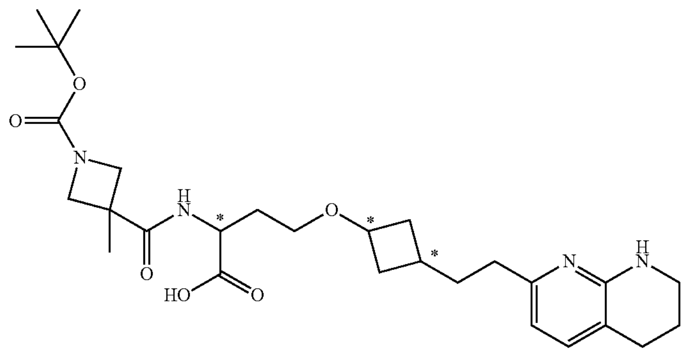 [SMILES: CC(C)(C)OC(=O)N1CC(C)(C(=O)NC(CCOC2CC(CCc3ccc4c(n3)NCCC4)C2)C(=O)O)C1] |
| 133 | 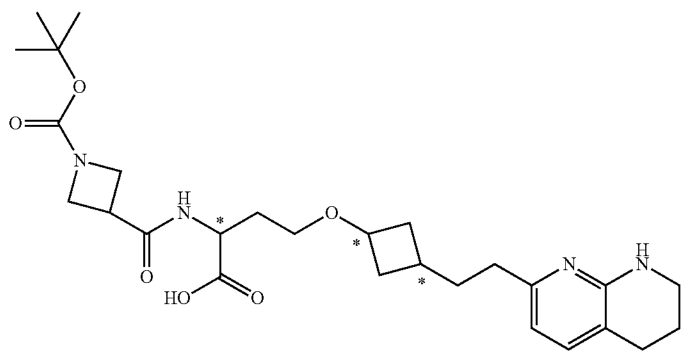 [SMILES: CC(C)(C)OC(=O)N1CC(C(=O)NC(CCOC2CC(CCc3ccc4c(n3)NCCC4)C2)C(=O)O)C1] |
| 134 | 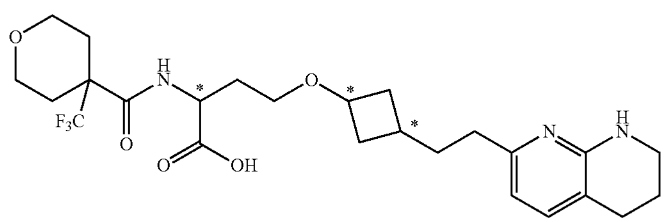 [SMILES: O=C(O)C(CCOC1CC(CCc2ccc3c(n2)NCCC3)C1)NC(=O)C1(C(F)(F)F)CCOCC1] |
| 135 | 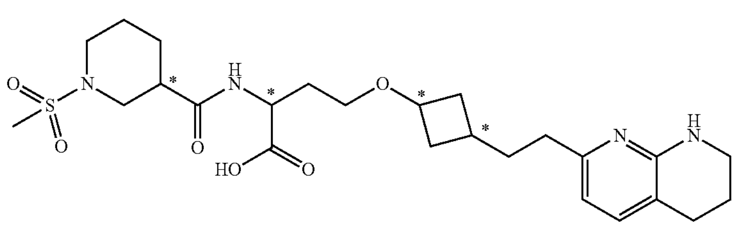 [SMILES: CS(=O)(=O)N1CCCC(C(=O)NC(CCOC2CC(CCc3ccc4c(n3)NCCC4)C2)C(=O)O)C1] |
| 136 | 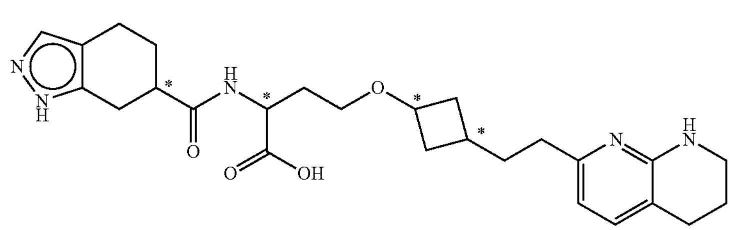 |

TABLE 1-continued
| Compound # | Structure |
|---|---|
| 137 | 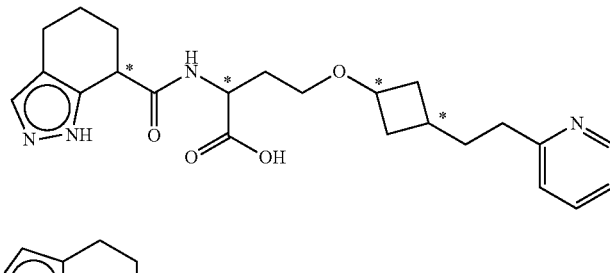 |
| 138 | 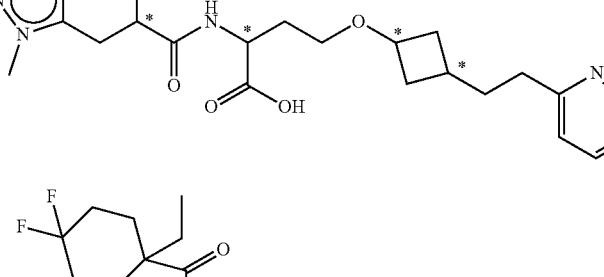 |
| 139 | 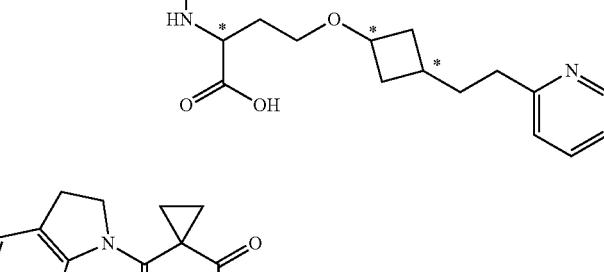 |
| 140 | 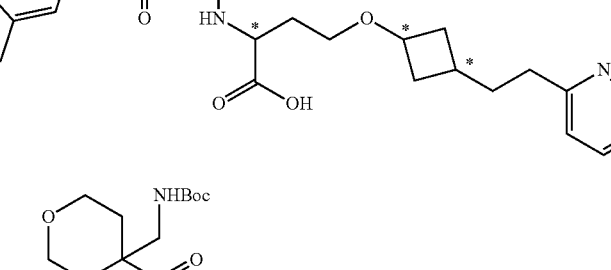 |
| 141 | 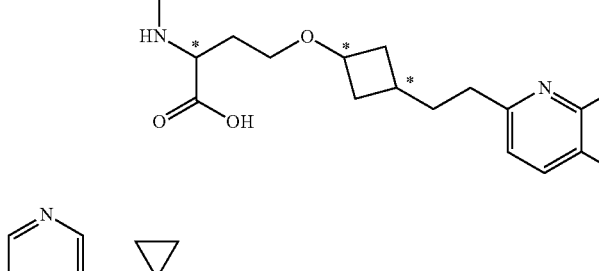 |
| 142 | 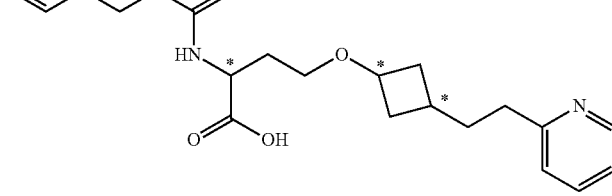 |

TABLE 1-continued

| Compound # | Structure |
|---|---|
| 143 | 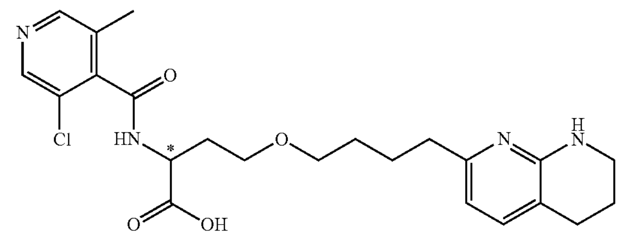 [SMILES: Cc1cncc(Cl)c1C(=O)NC(CCOCCCCc1ccc2c(n1)NCCC2)C(=O)O] |
| 144 | 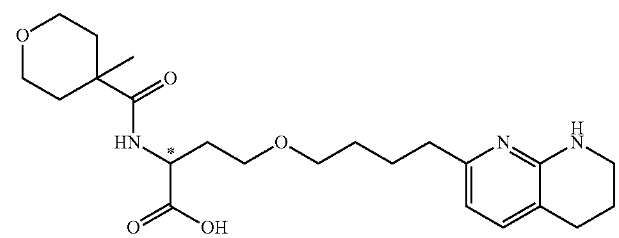 [SMILES: CC1(C(=O)NC(CCOCCCCc2ccc3c(n2)NCCC3)C(=O)O)CCOCC1] |
| 145 | 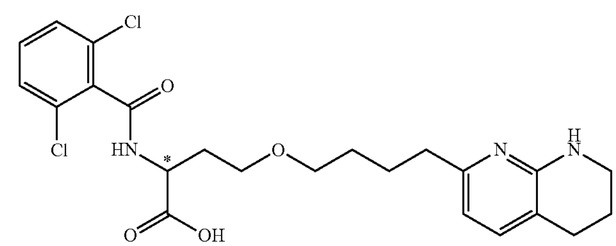 [SMILES: O=C(NC(CCOCCCCc1ccc2c(n1)NCCC2)C(=O)O)c1c(Cl)cccc1Cl] |
| 146 | 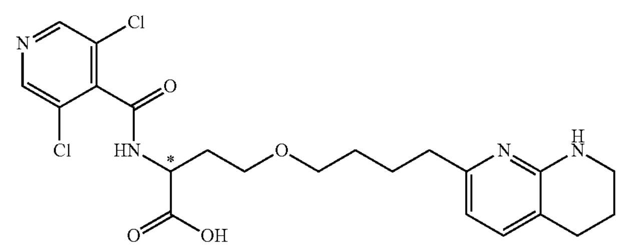 [SMILES: O=C(NC(CCOCCCCc1ccc2c(n1)NCCC2)C(=O)O)c1c(Cl)cncc1Cl] |
| 147 | 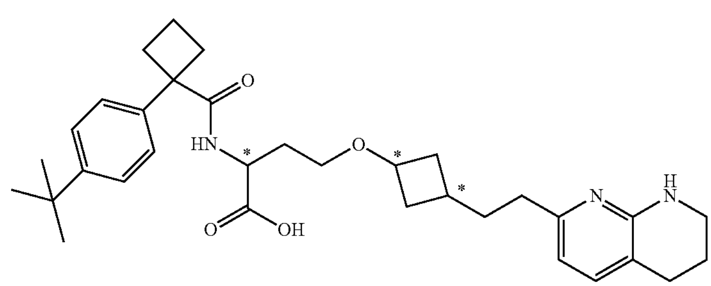 [SMILES: CC(C)(C)c1ccc(C2(C(=O)NC(CCOC3CC(CCc4ccc5c(n4)NCCC5)C3)C(=O)O)CCC2)cc1] |
| 148 | 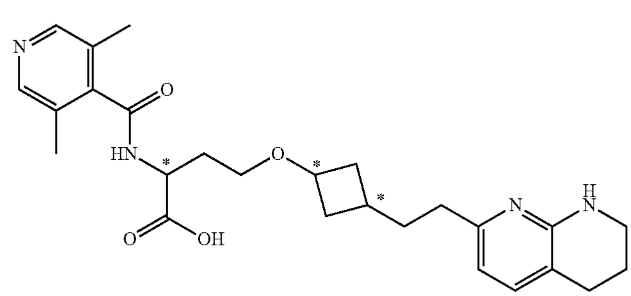 [SMILES: Cc1cncc(C)c1C(=O)NC(CCOC1CC(CCc2ccc3c(n2)NCCC3)C1)C(=O)O] |

TABLE 1-continued

| Compound # | Structure |
|---|---|
| 149 | 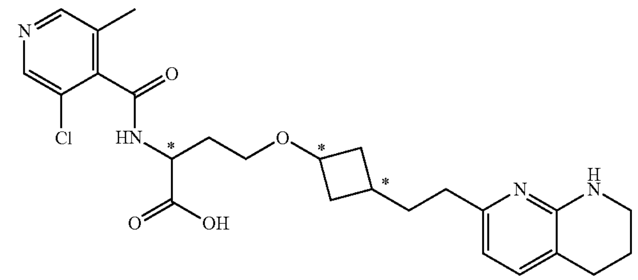 [SMILES: Cc1cncc(Cl)c1C(=O)NC(CCOC1CC(CCc2ccc3c(n2)NCCC3)C1)C(=O)O] |
| 150 | 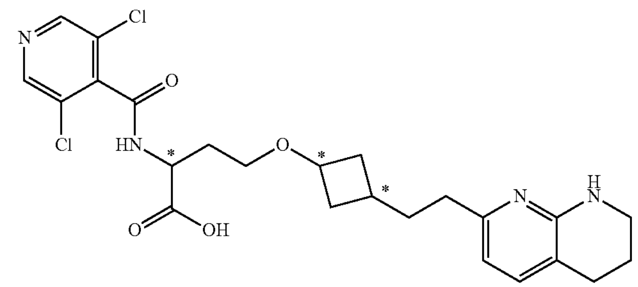 [SMILES: O=C(NC(CCOC1CC(CCc2ccc3c(n2)NCCC3)C1)C(=O)O)c1c(Cl)cncc1Cl] |
| 151 | 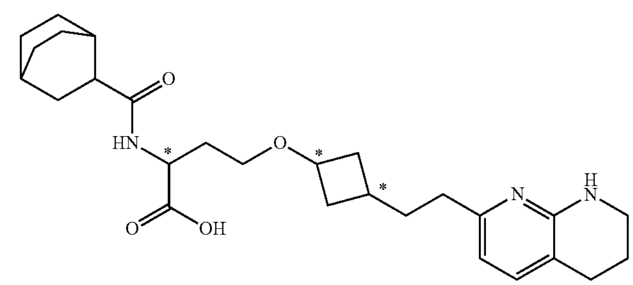 [SMILES: O=C(O)C(CCOC1CC(CCc2ccc3c(n2)NCCC3)C1)NC(=O)C1CC2CCC1CC2] |
| 152 | 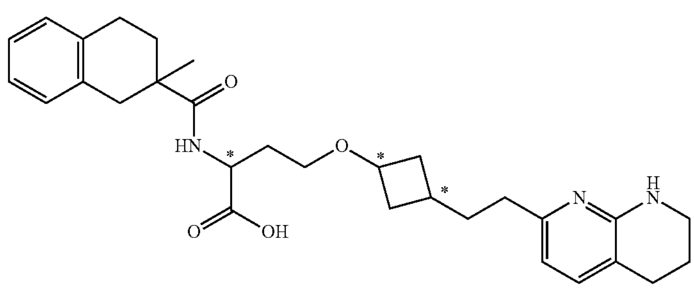 [SMILES: CC1(C(=O)NC(CCOC2CC(CCc3ccc4c(n3)NCCC4)C2)C(=O)O)CCc2ccccc2C1] |
| 153 | 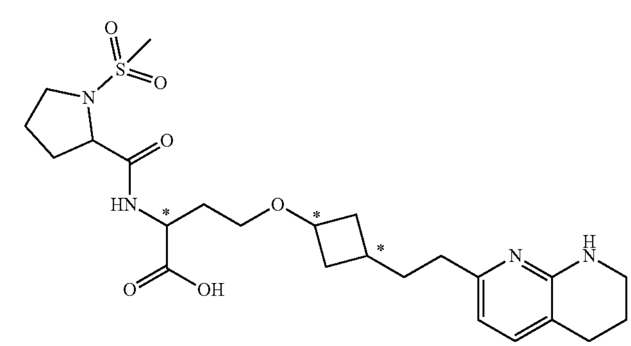 [SMILES: CS(=O)(=O)N1CCCC1C(=O)NC(CCOC1CC(CCc2ccc3c(n2)NCCC3)C1)C(=O)O] |

TABLE 1-continued

| Compound # | Structure |
|---|---|
| 154 | 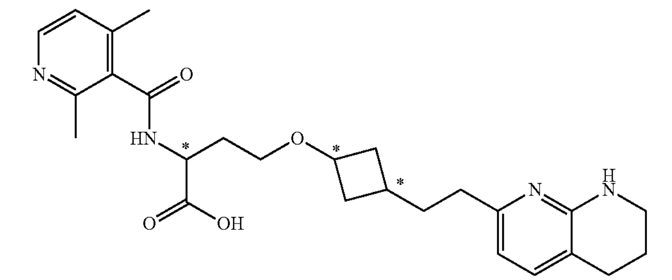 [SMILES: Cc1ccnc(C)c1C(=O)NC(CCOC1CC(CCc2ccc3c(n2)NCCC3)C1)C(=O)O] |
| 155 | 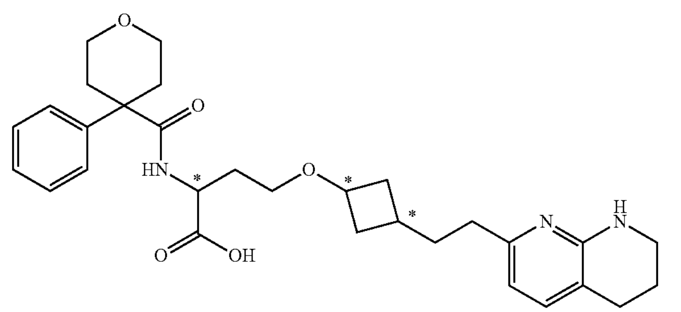 [SMILES: O=C(O)C(CCOC1CC(CCc2ccc3c(n2)NCCC3)C1)NC(=O)C1(c2ccccc2)CCOCC1] |
| 156 | 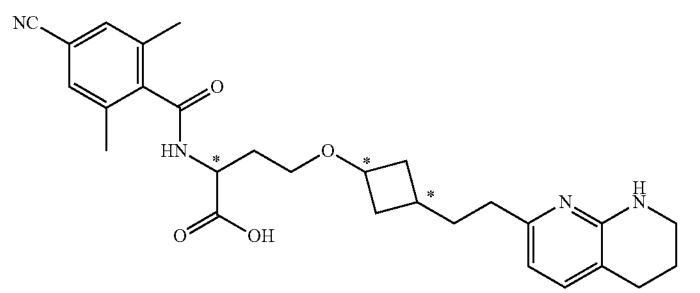 [SMILES: Cc1cc(C#N)cc(C)c1C(=O)NC(CCOC1CC(CCc2ccc3c(n2)NCCC3)C1)C(=O)O] |
| 157 | 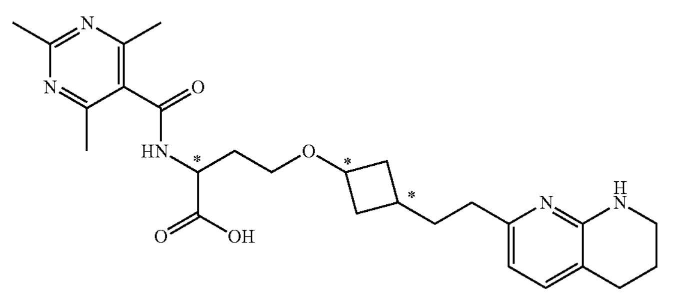 [SMILES: Cc1nc(C)c(C(=O)NC(CCOC2CC(CCc3ccc4c(n3)NCCC4)C2)C(=O)O)c(C)n1] |
| 158 | 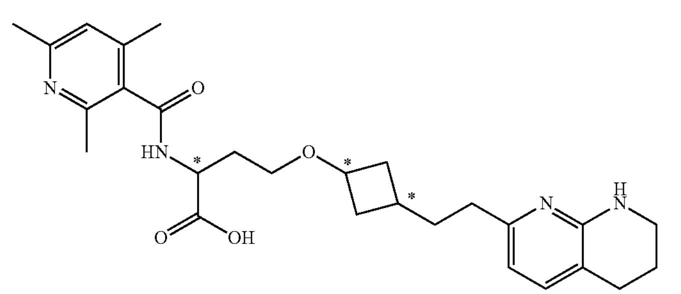 [SMILES: Cc1cc(C)c(C(=O)NC(CCOC2CC(CCc3ccc4c(n3)NCCC4)C2)C(=O)O)c(C)n1] |

TABLE 1-continued
| Compound # | Structure |
|---|---|
| 159 | 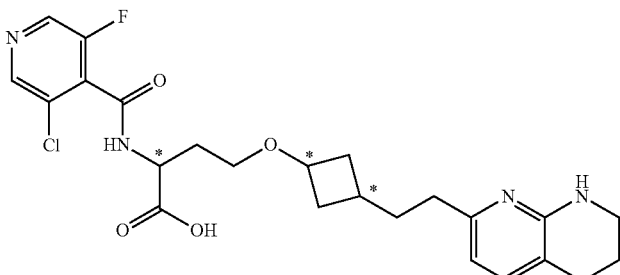 |
| 160 | 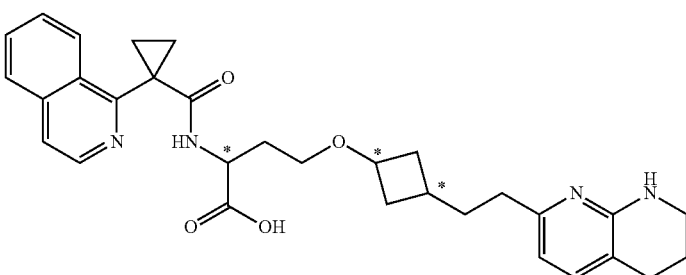 |
| 161 | 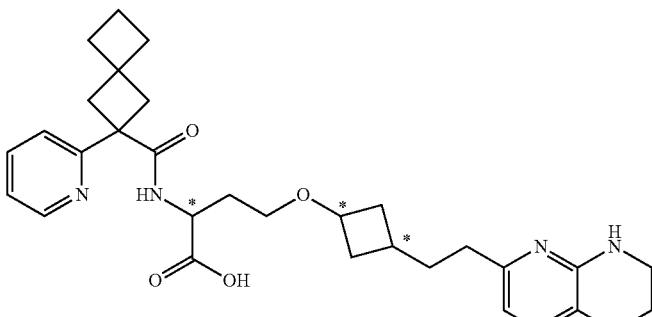 |
| 162 | 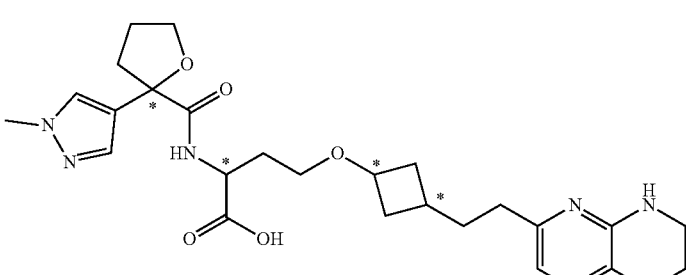 |
| 163 | 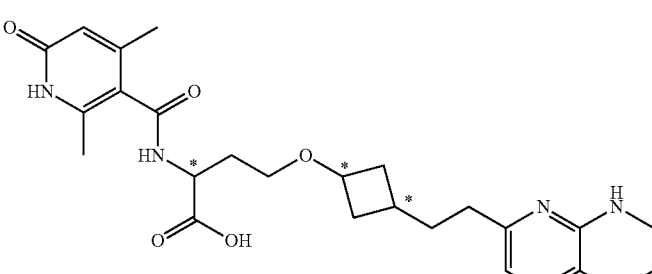 |

TABLE 1-continued

| Compound # | Structure |
|---|---|
| 164 | 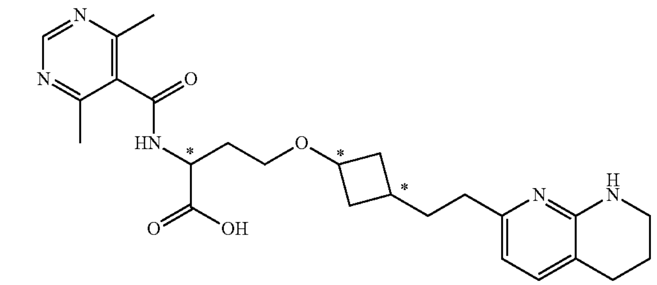 [SMILES: Cc1ncnc(C)c1C(=O)NC(CCOC1CC(CCc2ccc3c(n2)NCCC3)C1)C(=O)O] |
| 165 | 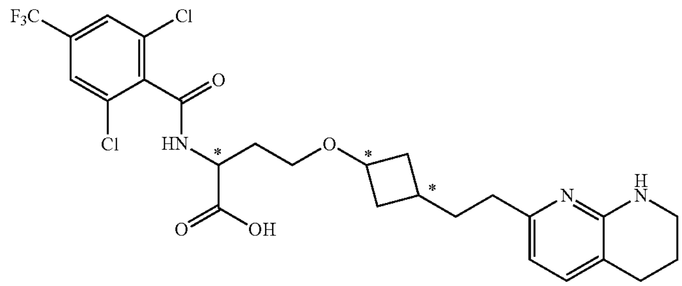 [SMILES: O=C(NC(CCOC1CC(CCc2ccc3c(n2)NCCC3)C1)C(=O)O)c1c(Cl)cc(C(F)(F)F)cc1Cl] |
| 166 | 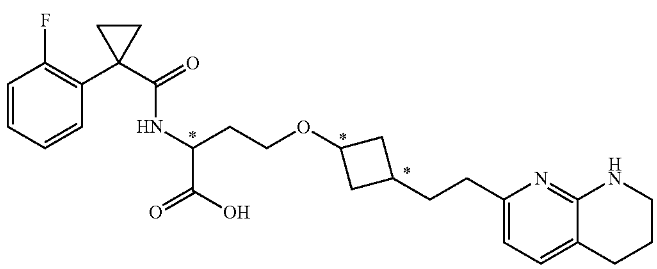 [SMILES: O=C(O)C(CCOC1CC(CCc2ccc3c(n2)NCCC3)C1)NC(=O)C1(c2ccccc2F)CC1] |
| 167 | 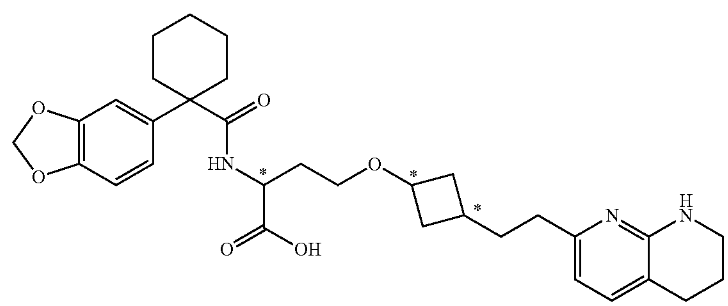 [SMILES: O=C(O)C(CCOC1CC(CCc2ccc3c(n2)NCCC3)C1)NC(=O)C1(c2ccc3c(c2)OCO3)CCCCC1] |
| 168 | 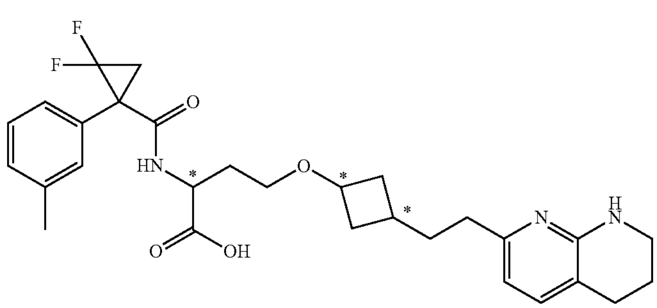 [SMILES: Cc1cccc(C2(C(=O)NC(CCOC3CC(CCc4ccc5c(n4)NCCC5)C3)C(=O)O)CC2(F)F)c1] |

TABLE 1-continued

| Compound # | Structure |
|---|---|
| 169 | 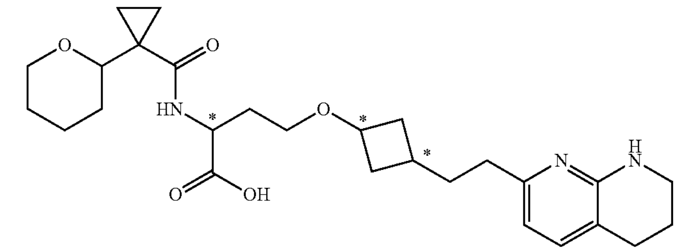 [SMILES: O=C(O)C(CCOC1CC(CCc2ccc3c(n2)NCCC3)C1)NC(=O)C1(C2CCCCO2)CC1] |
| 170 | 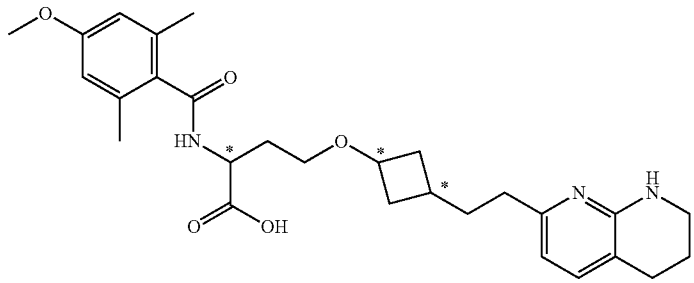 [SMILES: COc1cc(C)c(C(=O)NC(CCOC2CC(CCc3ccc4c(n3)NCCC4)C2)C(=O)O)c(C)c1] |
| 171 | 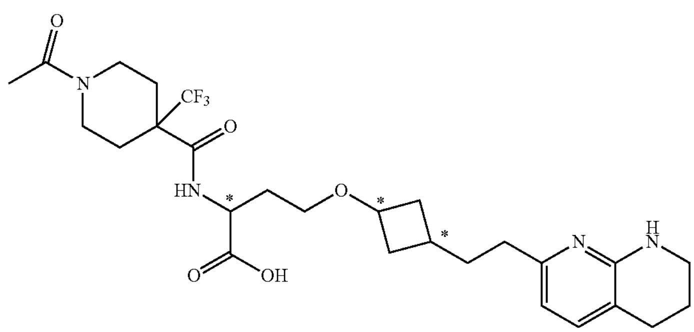 [SMILES: CC(=O)N1CCC(C(=O)NC(CCOC2CC(CCc3ccc4c(n3)NCCC4)C2)C(=O)O)(C(F)(F)F)CC1] |
| 172 | 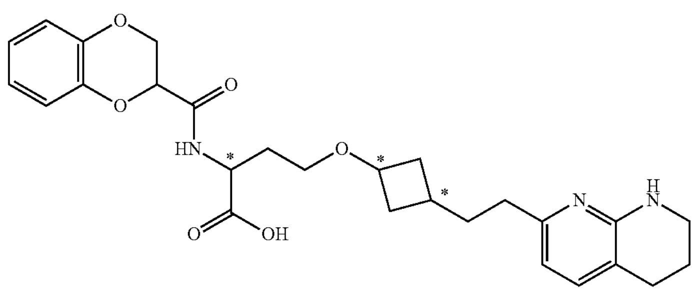 [SMILES: O=C(O)C(CCOC1CC(CCc2ccc3c(n2)NCCC3)C1)NC(=O)C1COc2ccccc2O1] |
| 173 | 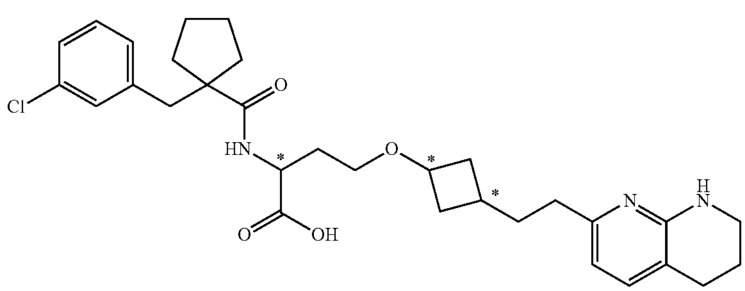 [SMILES: O=C(O)C(CCOC1CC(CCc2ccc3c(n2)NCCC3)C1)NC(=O)C1(Cc2cccc(Cl)c2)CCCC1] |

TABLE 1-continued
| Compound # | Structure |
|---|---|
| 174 | 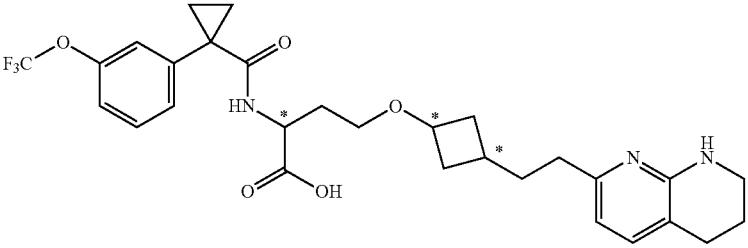 [SMILES: O=C(O)C(CCOC1CC(CCc2ccc3c(n2)NCCC3)C1)NC(=O)C1(c2cccc(OC(F)(F)F)c2)CC1] |
| 175 | 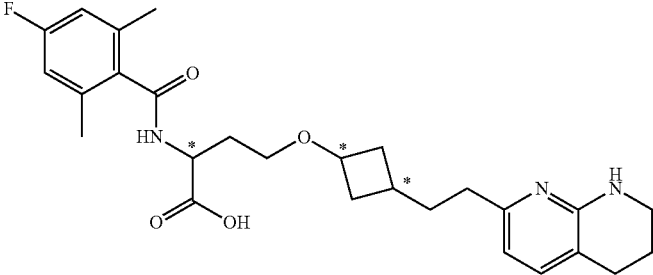 [SMILES: Cc1cc(F)cc(C)c1C(=O)NC(CCOC1CC(CCc2ccc3c(n2)NCCC3)C1)C(=O)O] |
| 176 | 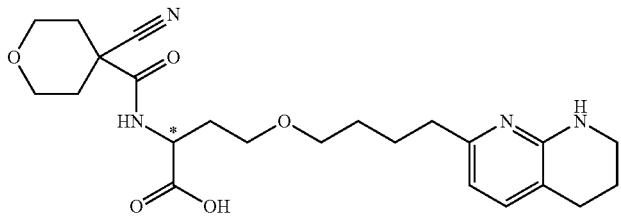 [SMILES: N#CC1(C(=O)NC(CCOCCCCc2ccc3c(n2)NCCC3)C(=O)O)CCOCC1] |
| 177 | 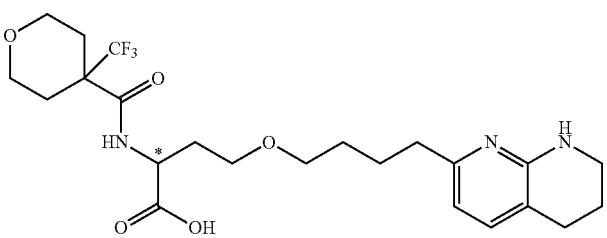 [SMILES: O=C(O)C(CCOCCCCc1ccc2c(n1)NCCC2)NC(=O)C1(C(F)(F)F)CCOCC1] |
| 178 | 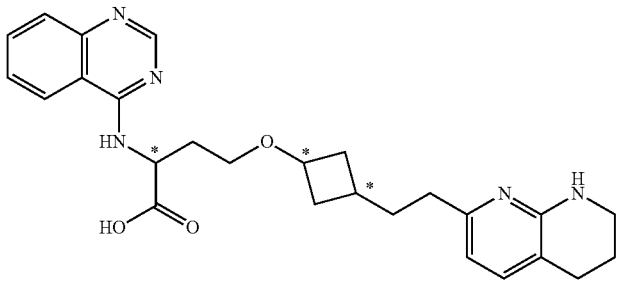 [SMILES: O=C(O)C(CCOC1CC(CCc2ccc3c(n2)NCCC3)C1)Nc1ncnc2ccccc12] |

TABLE 1-continued

| Compound # | Structure |
|---|---|
| 179 | 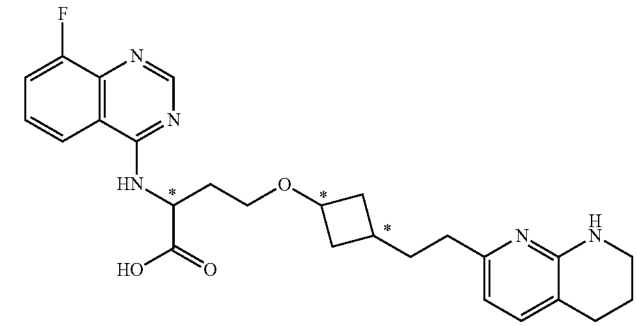 [SMILES: O=C(O)C(CCOC1CC(CCc2ccc3c(n2)NCCC3)C1)Nc1ncnc2c(F)cccc12] |
| 180 | 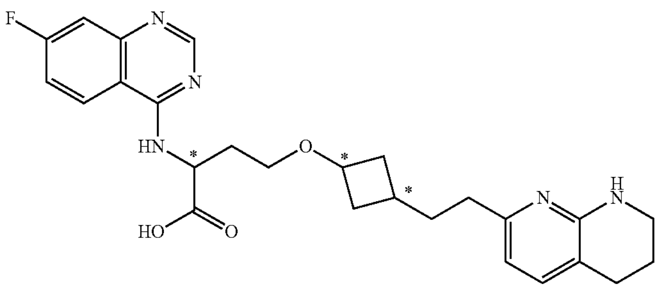 [SMILES: O=C(O)C(CCOC1CC(CCc2ccc3c(n2)NCCC3)C1)Nc1ncnc2cc(F)ccc12] |
| 181 | 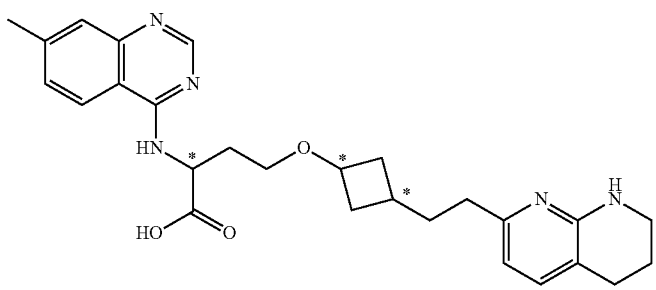 [SMILES: Cc1ccc2c(NC(CCOC3CC(CCc4ccc5c(n4)NCCC5)C3)C(=O)O)ncnc2c1] |
| 182 | 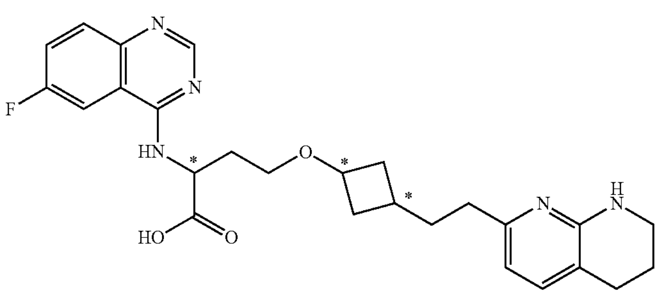 [SMILES: O=C(O)C(CCOC1CC(CCc2ccc3c(n2)NCCC3)C1)Nc1ncnc2ccc(F)cc12] |
| 183 | 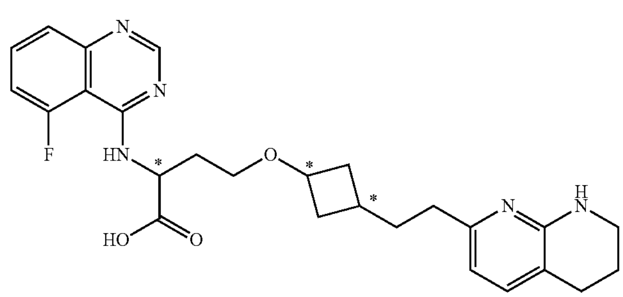 [SMILES: O=C(O)C(CCOC1CC(CCc2ccc3c(n2)NCCC3)C1)Nc1ncnc2cccc(F)c12] |

TABLE 1-continued

| Compound # | Structure |
|---|---|
| 184 | 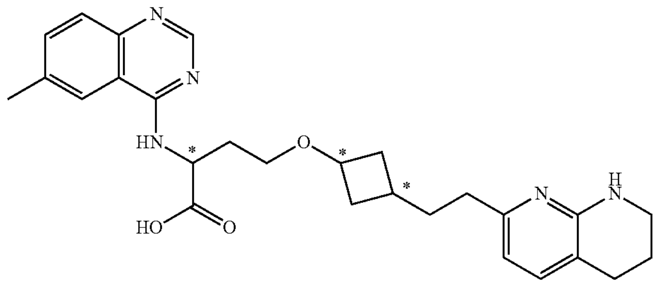 [SMILES: Cc1ccc2ncnc(NC(CCOC3CC(CCc4ccc5c(n4)NCCC5)C3)C(=O)O)c2c1] |
| 185 | 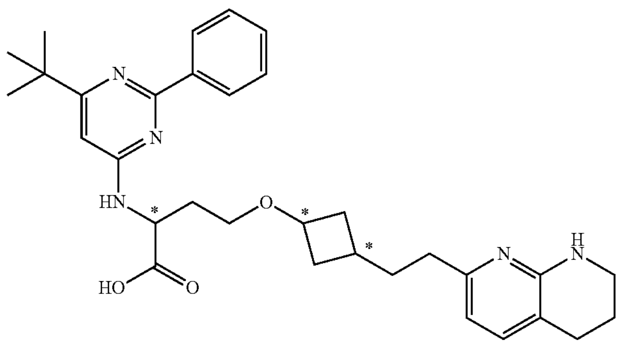 [SMILES: CC(C)(C)c1cc(NC(CCOC2CC(CCc3ccc4c(n3)NCCC4)C2)C(=O)O)nc(-c2ccccc2)n1] |
| 186 | 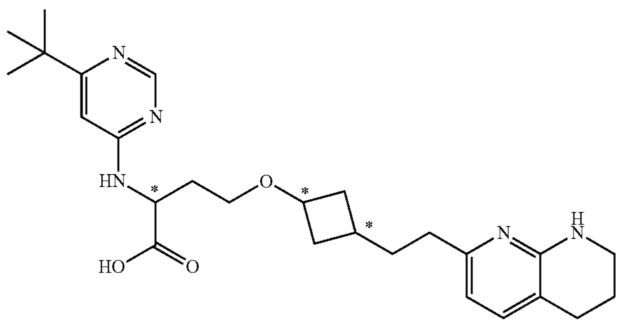 [SMILES: CC(C)(C)c1cc(NC(CCOC2CC(CCc3ccc4c(n3)NCCC4)C2)C(=O)O)ncn1] |
| 187 | 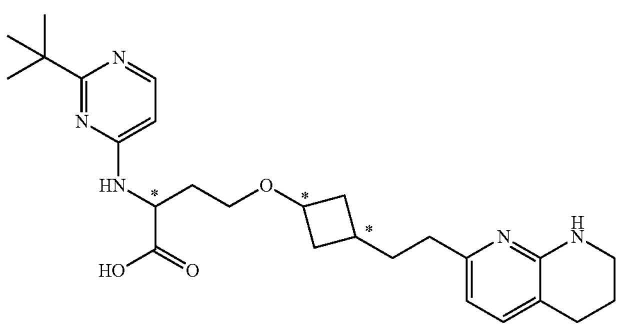 [SMILES: CC(C)(C)c1nccc(NC(CCOC2CC(CCc3ccc4c(n3)NCCC4)C2)C(=O)O)n1] |
| 188 | 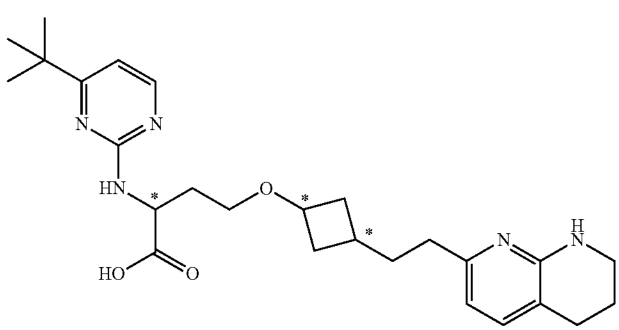 [SMILES: CC(C)(C)c1ccnc(NC(CCOC2CC(CCc3ccc4c(n3)NCCC4)C2)C(=O)O)n1] |

TABLE 1-continued
| Compound # | Structure |
|---|---|
| 189 | 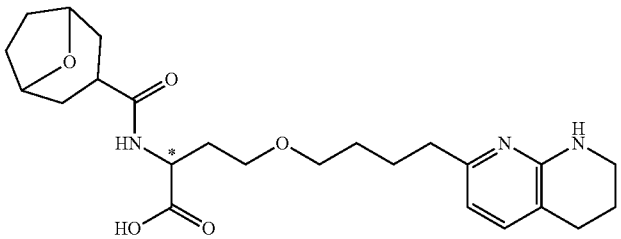 [SMILES: O=C(NC(CCOCCCCc1ccc2c(n1)NCCC2)C(=O)O)C1CC2CCC(C1)O2] |
| 190 | 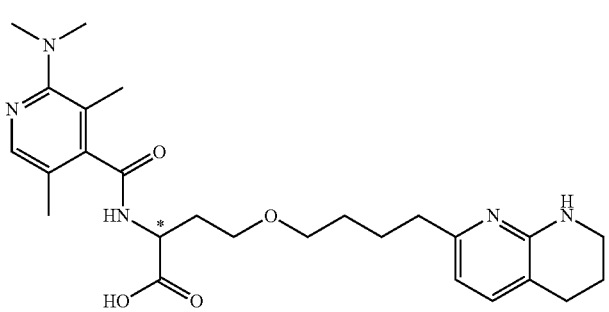 [SMILES: Cc1cnc(N(C)C)c(C)c1C(=O)NC(CCOCCCCc1ccc2c(n1)NCCC2)C(=O)O] |
| 191 | 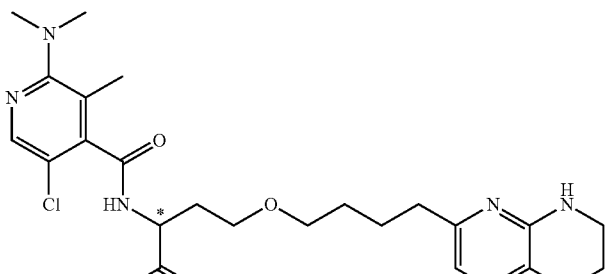 |
| 192 | 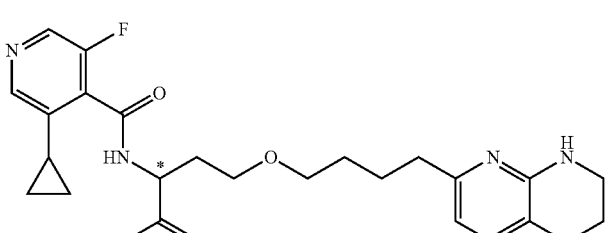 |
| 193 | 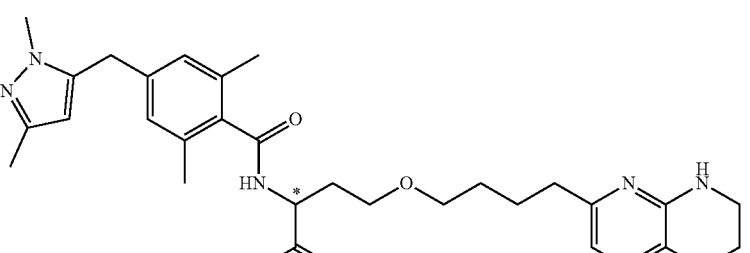 |

TABLE 1-continued
| Compound # | Structure |
|---|---|
| 194 | 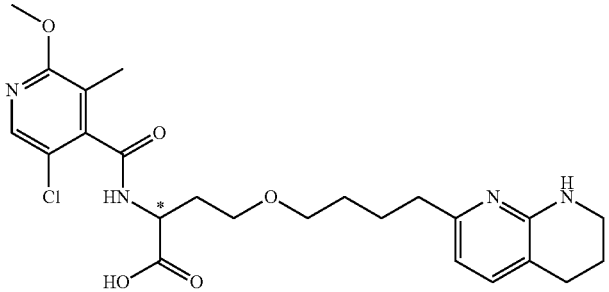 [SMILES: COc1ncc(Cl)c(C(=O)NC(CCOCCCCc2ccc3c(n2)NCCC3)C(=O)O)c1C] |
| 195 | 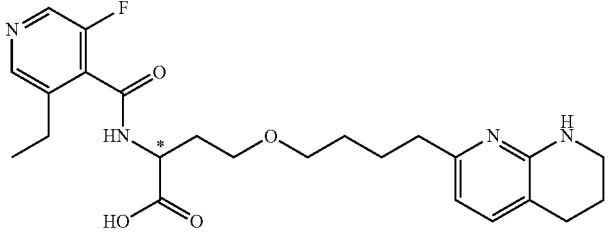 [SMILES: CCc1cncc(F)c1C(=O)NC(CCOCCCCc1ccc2c(n1)NCCC2)C(=O)O] |
| 196 | 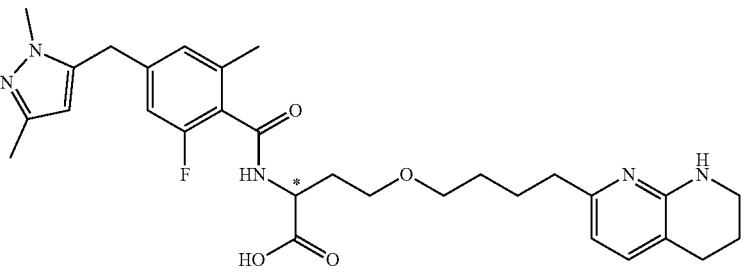 [SMILES: Cc1cc(Cc2cc(C)c(C(=O)NC(CCOCCCCc3ccc4c(n3)NCCC4)C(=O)O)c(F)c2)n(C)n1] |
| 197 | 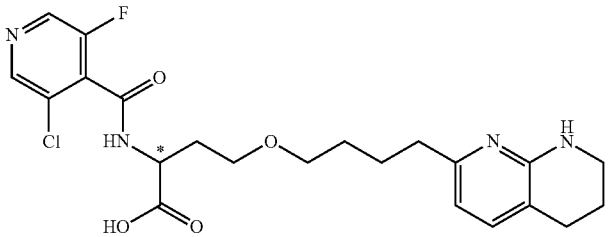 [SMILES: O=C(NC(CCOCCCCc1ccc2c(n1)NCCC2)C(=O)O)c1c(F)cncc1Cl] |
| 198 | 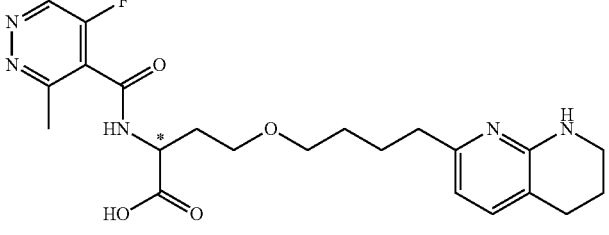 |
| 199 | 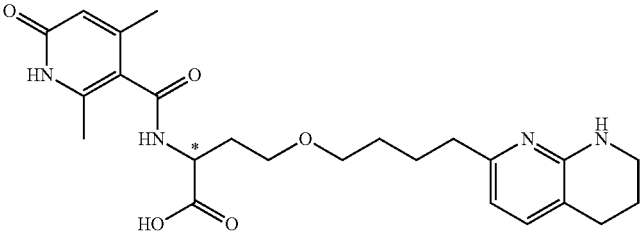 [SMILES: Cc1cc(=O)[nH]c(C)c1C(=O)NC(CCOCCCCc1ccc2c(n1)NCCC2)C(=O)O] |

TABLE 1-continued

| Compound # | Structure |
|---|---|
| 200 | 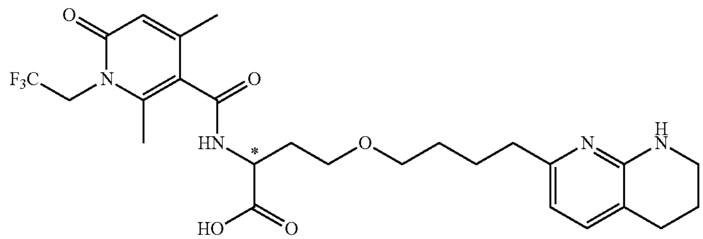 [SMILES: Cc1cc(=O)n(CC(F)(F)F)c(C)c1C(=O)NC(CCOCCCCc1ccc2c(n1)NCCC2)C(=O)O] |
| 201 | 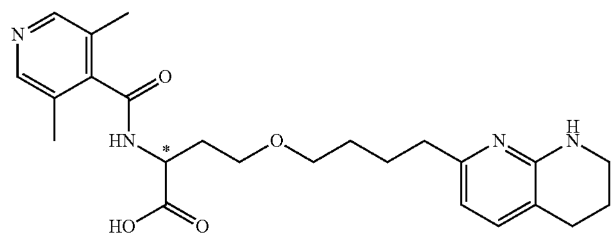 [SMILES: Cc1cncc(C)c1C(=O)NC(CCOCCCCc1ccc2c(n1)NCCC2)C(=O)O] |
| 202 | 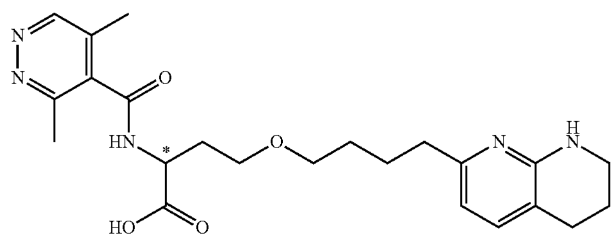 [SMILES: Cc1cnnc(C)c1C(=O)NC(CCOCCCCc1ccc2c(n1)NCCC2)C(=O)O] |
| 203 | 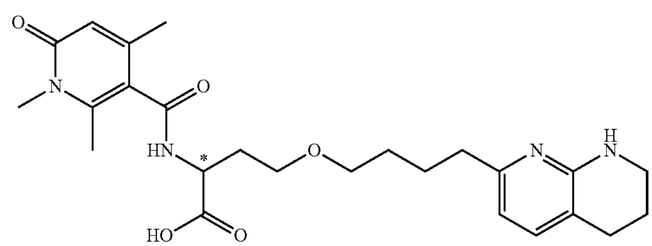 [SMILES: Cc1cc(=O)n(C)c(C)c1C(=O)NC(CCOCCCCc1ccc2c(n1)NCCC2)C(=O)O] |
| 204 | 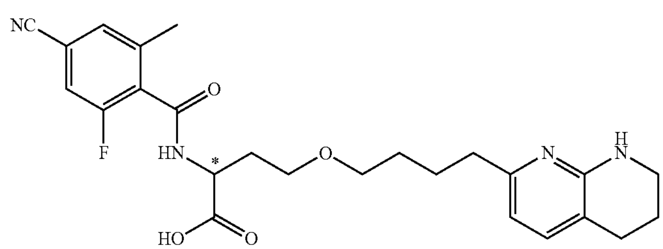 [SMILES: Cc1cc(C#N)cc(F)c1C(=O)NC(CCOCCCCc1ccc2c(n1)NCCC2)C(=O)O] |
| 205 | 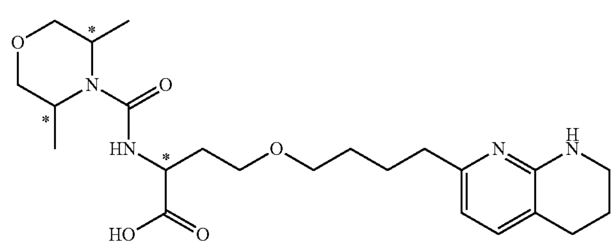 [SMILES: CC1COCC(C)N1C(=O)NC(CCOCCCCc1ccc2c(n1)NCCC2)C(=O)O] |

TABLE 1-continued

| Compound # | Structure |
|---|---|
| 206 | (structure: 4-chloro-3-methylpyridazine-carboxamide linked to amino acid with ether-butyl-tetrahydronaphthyridine chain) |
| 207 | (structure: 6-methoxy-2,4-dimethylpyridine-3-carboxamide linked to amino acid with ether-butyl-tetrahydronaphthyridine chain) |
| 208 | (structure: 2-chloro-6-fluoro-4-cyanobenzamide linked to amino acid with ether-butyl-tetrahydronaphthyridine chain) |
| 209 | (structure: 2,6-dichlorobenzamide linked to amino acid with ether-butyl-tetrahydronaphthyridine chain) |

The structures in Table 1 are drawn without stereochemistry. Atoms which can be stereocenters are noted by an asterisk (*). The structures are intended to embrace all possible stereoisomers of the compound depicted, as well as mixtures of stereoisomers in any proportion. Thus, racemic mixtures, scalemic mixtures, mixtures of enantiomers in any proportion, mixtures of diastereomers in any proportion, and mixtures of enantiomers and diastereomers in any proportion are embraced, as well as individual, stereochemically pure compounds.

In some embodiments, provided is a compound selected from the compounds depicted in Table 1, or a stereoisomer thereof (including a mixture of two or more stereoisomers thereof), or a salt thereof. In some embodiments, the compound is a salt of a compound selected from the compounds depicted in Table 1, or a stereoisomer thereof.

Additional representative compounds are shown in Table 2 (FIG. 1). In some embodiments, provided is a compound selected from the compounds depicted in Table 2, or a stereoisomer thereof (including a mixture of two or more stereoisomers thereof), or a salt thereof. In some embodiments, the compound is a salt of a compound selected from the compounds depicted in Table 2, or a stereoisomer thereof. The "flat" versions of all compounds depicted in Table 2 are also contemplated in this disclosure, including flat versions of any specific stereoisomeric forms in the Table.

Regarding the structures in FIG. 1, Table 2, reference to compound numbers in the table in some instances depicts a particular stereoisomeric form of the compound number, as will be evident from the chemical structure depicted. For example, Table 2 lists

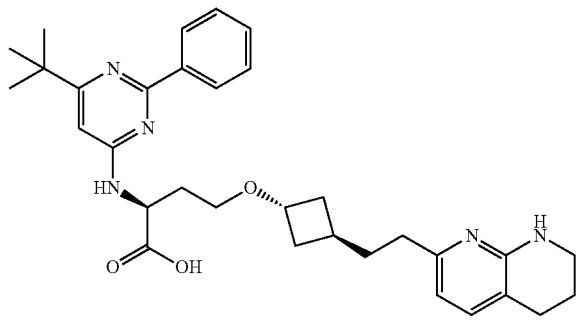 [SMILES: CC(C)(C)c1cc(N[C@@H](CCO[C@H]2C[C@H](CCc3ccc4c(n3)NCCC4)C2)C(=O)O)nc(-c2ccccc2)n1]

as Compound 185. It is appreciated that the compound depicted is a specific stereochemical form of Compound 185, in particular the form produced by Example 365.

In one variation, the compound detailed herein is selected from the group consisting of:

N-(1-methyl-1H-indazole-4-carbonyl)-O-(4-(5,6,7,8-tetrahydro-1,8-naphthyridin-2-yl)butyl)homoserine;
N-(2-chloro-3-fluorobenzoyl)-O-(4-(5,6,7,8-tetrahydro-1,8-naphthyridin-2-yl)butyl)homoserine;
N-(2-ethylbutanoyl)-O-(4-(5,6,7,8-tetrahydro-1,8-naphthyridin-2-yl)butyl)homoserine;
N-benzoyl-O-(4-(5,6,7,8-tetrahydro-1,8-naphthyridin-2-yl)butyl)homoserine;
N-(4,4-difluorocyclohexane-1-carbonyl)-O-(4-(5,6,7,8-tetrahydro-1,8-naphthyridin-2-yl)butyl)homoserine;
N-pentanoyl-O-(4-(5,6,7,8-tetrahydro-1,8-naphthyridin-2-yl)butyl)homoserine;
N-(3-fluoro-5-(trifluoromethyl)benzoyl)-O-(4-(5,6,7,8-tetrahydro-1,8-naphthyridin-2-yl)butyl)homoserine;
2-(2-ethylbutanamido)-5-(3-(5,6,7,8-tetrahydro-1,8-naphthyridin-2-yl)propoxy)pentanoic acid;
2-(2-chloro-3-fluorobenzamido)-5-(3-(5,6,7,8-tetrahydro-1,8-naphthyridin-2-yl)propoxy)pentanoic acid;
2-(1-methyl-1H-indazole-4-carboxamido)-5-(3-(5,6,7,8-tetrahydro-1,8-naphthyridin-2-yl)propoxy)pentanoic acid;
2-(3-(1-methyl-1H-pyrazol-4-yl)benzamido)-5-(3-(5,6,7,8-tetrahydro-1,8-naphthyridin-2-yl)propoxy)pentanoic acid;
2-(2-chloro-3-fluorobenzamido)-6-(2-(5,6,7,8-tetrahydro-1,8-naphthyridin-2-yl)ethoxy)hexanoic acid;
2-(3-(1-methyl-1H-pyrazol-4-yl)benzamido)-6-(2-(5,6,7,8-tetrahydro-1,8-naphthyridin-2-yl)ethoxy)hexanoic acid;
N-(2-chloro-3-fluorobenzoyl)-O-(3-(2-(5,6,7,8-tetrahydro-1,8-naphthyridin-2-yl)ethyl)cyclobutyl)homoserine;
N-(3-fluoro-5-(trifluoromethyl)benzoyl)-O-(3-(2-(5,6,7,8-tetrahydro-1,8-naphthyridin-2-yl)ethyl)cyclobutyl)homoserine;
2-(2-ethylbutanamido)-6-(2-(5,6,7,8-tetrahydro-1,8-naphthyridin-2-yl)ethoxy)hexanoic acid;
2-(1-methyl-1H-indazole-4-carboxamido)-6-(2-(5,6,7,8-tetrahydro-1,8-naphthyridin-2-yl)ethoxy)hexanoic acid;
N-pentanoyl-O-(3-(2-(5,6,7,8-tetrahydro-1,8-naphthyridin-2-yl)ethyl)cyclobutyl)homoserine;
N-(tert-butoxycarbonyl)-O-(3-(2-(5,6,7,8-tetrahydro-1,8-naphthyridin-2-yl)ethyl)cyclobutyl)homoserine;
2-((tert-butoxycarbonyl)amino)-5-(3-(5,6,7,8-tetrahydro-1,8-naphthyridin-2-yl)propoxy)pentanoic acid;
N-benzoyl-O-(3-(2-(5,6,7,8-tetrahydro-1,8-naphthyridin-2-yl)ethyl)cyclobutyl)homoserine;
N-(tert-butoxycarbonyl)-O-(4-(5,6,7,8-tetrahydro-1,8-naphthyridin-2-yl)butyl)homoserine;
2-((tert-butoxycarbonyl)amino)-6-(2-(5,6,7,8-tetrahydro-1,8-naphthyridin-2-yl)ethoxy)hexanoic acid;
N-(4-fluorobenzoyl)-O-(3-(2-(5,6,7,8-tetrahydro-1,8-naphthyridin-2-yl)ethyl)cyclobutyl)homoserine;
N-(4-chlorobenzoyl)-O-(3-(2-(5,6,7,8-tetrahydro-1,8-naphthyridin-2-yl)ethyl)cyclobutyl)homoserine;
N-(3-fluorobenzoyl)-O-(3-(2-(5,6,7,8-tetrahydro-1,8-naphthyridin-2-yl)ethyl)cyclobutyl)homoserine;
N-(3-chlorobenzoyl)-O-(3-(2-(5,6,7,8-tetrahydro-1,8-naphthyridin-2-yl)ethyl)cyclobutyl)homoserine;
N-(2-chlorobenzoyl)-O-(3-(2-(5,6,7,8-tetrahydro-1,8-naphthyridin-2-yl)ethyl)cyclobutyl)homoserine;
N-(2-fluorobenzoyl)-O-(3-(2-(5,6,7,8-tetrahydro-1,8-naphthyridin-2-yl)ethyl)cyclobutyl)homoserine;
N-(2,3-difluorobenzoyl)-O-(3-(2-(5,6,7,8-tetrahydro-1,8-naphthyridin-2-yl)ethyl)cyclobutyl)homoserine;
N-(2,4-difluorobenzoyl)-O-(3-(2-(5,6,7,8-tetrahydro-1,8-naphthyridin-2-yl)ethyl)cyclobutyl)homoserine;
N-(2-chloro-4-fluorobenzoyl)-O-(3-(2-(5,6,7,8-tetrahydro-1,8-naphthyridin-2-yl)ethyl)cyclobutyl)homoserine;
N-(3-chloro-5-fluorobenzoyl)-O-(3-(2-(5,6,7,8-tetrahydro-1,8-naphthyridin-2-yl)ethyl)cyclobutyl)homoserine;
N-(3-chloro-2-fluorobenzoyl)-O-(3-(2-(5,6,7,8-tetrahydro-1,8-naphthyridin-2-yl)ethyl)cyclobutyl)homoserine;
N-(3,5-difluorobenzoyl)-O-(3-(2-(5,6,7,8-tetrahydro-1,8-naphthyridin-2-yl)ethyl)cyclobutyl)homoserine;
N-(3,4-difluorobenzoyl)-O-(3-(2-(5,6,7,8-tetrahydro-1,8-naphthyridin-2-yl)ethyl)cyclobutyl)homoserine;
N-(2,3-dichlorobenzoyl)-O-(3-(2-(5,6,7,8-tetrahydro-1,8-naphthyridin-2-yl)ethyl)cyclobutyl)homoserine;
N-(2-chloro-6-fluorobenzoyl)-O-(3-(2-(5,6,7,8-tetrahydro-1,8-naphthyridin-2-yl)ethyl)cyclobutyl)homoserine;
N-(2,6-difluorobenzoyl)-O-(3-(2-(5,6,7,8-tetrahydro-1,8-naphthyridin-2-yl)ethyl)cyclobutyl)homoserine;
N-(2,5-difluorobenzoyl)-O-(3-(2-(5,6,7,8-tetrahydro-1,8-naphthyridin-2-yl)ethyl)cyclobutyl)homoserine;
N-(3,4-dichlorobenzoyl)-O-(3-(2-(5,6,7,8-tetrahydro-1,8-naphthyridin-2-yl)ethyl)cyclobutyl)homoserine;
N-picolinoyl-O-(3-(2-(5,6,7,8-tetrahydro-1,8-naphthyridin-2-yl)ethyl)cyclobutyl)homoserine;
N-nicotinoyl-O-(3-(2-(5,6,7,8-tetrahydro-1,8-naphthyridin-2-yl)ethyl)cyclobutyl)homoserine;
N-isonicotinoyl-O-(3-(2-(5,6,7,8-tetrahydro-1,8-naphthyridin-2-yl)ethyl)cyclobutyl)homoserine;
N-(1-methyl-1H-indazole-4-carbonyl)-O-(3-(2-(5,6,7,8-tetrahydro-1,8-naphthyridin-2-yl)ethyl)cyclobutyl)homoserine;
N-(2-methyl-2H-indazole-6-carbonyl)-O-(3-(2-(5,6,7,8-tetrahydro-1,8-naphthyridin-2-yl)ethyl)cyclobutyl)homoserine;
N-(2-methyl-2H-indazole-5-carbonyl)-O-(3-(2-(5,6,7,8-tetrahydro-1,8-naphthyridin-2-yl)ethyl)cyclobutyl)homoserine;
N-(1-methyl-1H-pyrrolo[2,3-b]pyridine-4-carbonyl)-O-(3-(2-(5,6,7,8-tetrahydro-1,8-naphthyridin-2-yl)ethyl)cyclobutyl)homoserine;
N-(3-hydroxy-2-phenylpropanoyl)-O-(3-(2-(5,6,7,8-tetrahydro-1,8-naphthyridin-2-yl)ethyl)cyclobutyl)homoserine;
N-(2-ethylbutanoyl)-O-(3-(2-(5,6,7,8-tetrahydro-1,8-naphthyridin-2-yl)ethyl)cyclobutyl)homoserine;
N-(3-ethylpentanoyl)-O-(3-(2-(5,6,7,8-tetrahydro-1,8-naphthyridin-2-yl)ethyl)cyclobutyl)homoserine;
N-(1-methyl-1H-pyrrolo[2,3-b]pyridine-5-carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(3-(thiazol-5-yl)benzoyl)homoserine;

N-(3-(hydroxymethyl)benzoyl)-O-(3-(2-(5,6,7,8-tetrahydro-1,8-naphthyridin-2-yl)ethyl)cyclobutyl)homoserine;

N-(quinoline-5-carbonyl)-O-(3-(2-(5,6,7,8-tetrahydro-1,8-naphthyridin-2-yl)ethyl)cyclobutyl)homoserine;

N-(2-cyclopropylbenzoyl)-O-(3-(2-(5,6,7,8-tetrahydro-1,8-naphthyridin-2-yl)ethyl)cyclobutyl)homoserine;

N-(quinoline-7-carbonyl)-O-(3-(2-(5,6,7,8-tetrahydro-1,8-naphthyridin-2-yl)ethyl)cyclobutyl)homoserine;

N-(quinoline-6-carbonyl)-O-(3-(2-(5,6,7,8-tetrahydro-1,8-naphthyridin-2-yl)ethyl)cyclobutyl)homoserine;

N-(quinoline-8-carbonyl)-O-(3-(2-(5,6,7,8-tetrahydro-1,8-naphthyridin-2-yl)ethyl)cyclobutyl)homoserine;

N-(3-cyclopropylbenzoyl)-O-(3-(2-(5,6,7,8-tetrahydro-1,8-naphthyridin-2-yl)ethyl)cyclobutyl)homoserine;

N-(4-cyclopropylbenzoyl)-O-(3-(2-(5,6,7,8-tetrahydro-1,8-naphthyridin-2-yl)ethyl)cyclobutyl)homoserine;

N-(3-(1-methyl-1H-pyrazol-4-yl)benzoyl)-O-(3-(2-(5,6,7,8-tetrahydro-1,8-naphthyridin-2-yl)ethyl)cyclobutyl)homoserine;

N-(2-hydroxy-2-phenylacetyl)-O-(4-(5,6,7,8-tetrahydro-1,8-naphthyridin-2-yl)butyl)homoserine;

N-(2-hydroxy-2-phenylacetyl)-O-(3-(2-(5,6,7,8-tetrahydro-1,8-naphthyridin-2-yl)ethyl)cyclobutyl)homoserine;

N-(3-(1-methyl-1H-pyrazol-4-yl)benzoyl)-O-(4-(5,6,7,8-tetrahydro-1,8-naphthyridin-2-yl)butyl)homoserine;

N-(1-phenylcyclopropane-1-carbonyl)-O-(3-(2-(5,6,7,8-tetrahydro-1,8-naphthyridin-2-yl)ethyl)cyclobutyl)homoserine;

N-(2-methyl-2-phenylpropanoyl)-O-(3-(2-(5,6,7,8-tetrahydro-1,8-naphthyridin-2-yl)ethyl)cyclobutyl)homoserine;

N-(1-phenylcyclobutane-1-carbonyl)-O-(3-(2-(5,6,7,8-tetrahydro-1,8-naphthyridin-2-yl)ethyl)cyclobutyl)homoserine;

N-(2,2-dimethyl-3-phenylpropanoyl)-O-(3-(2-(5,6,7,8-tetrahydro-1,8-naphthyridin-2-yl)ethyl)cyclobutyl)homoserine;

N-(2-(4-fluorophenyl)-2-methylpropanoyl)-O-(3-(2-(5,6,7,8-tetrahydro-1,8-naphthyridin-2-yl)ethyl)cyclobutyl)homoserine;

N-(3-methyloxetane-3-carbonyl)-O-(3-(2-(5,6,7,8-tetrahydro-1,8-naphthyridin-2-yl)ethyl)cyclobutyl)homoserine;

N-(3-hydroxy-2,2-dimethylpropanoyl)-O-(3-(2-(5,6,7,8-tetrahydro-1,8-naphthyridin-2-yl)ethyl)cyclobutyl)homoserine;

N-(3-methoxy-2,2-dimethylpropanoyl)-O-(3-(2-(5,6,7,8-tetrahydro-1,8-naphthyridin-2-yl)ethyl)cyclobutyl)homoserine;

N-(2-methyl-2-(pyridin-3-yl)propanoyl)-O-(3-(2-(5,6,7,8-tetrahydro-1,8-naphthyridin-2-yl)ethyl)cyclobutyl)homoserine;

N-(2,3-dihydro-1H-indene-2-carbonyl)-O-(3-(2-(5,6,7,8-tetrahydro-1,8-naphthyridin-2-yl)ethyl)cyclobutyl)homoserine;

N-(3-cyano-2,2-dimethylpropanoyl)-O-(3-(2-(5,6,7,8-tetrahydro-1,8-naphthyridin-2-yl)ethyl)cyclobutyl)homoserine;

N-pivaloyl-O-(3-(2-(5,6,7,8-tetrahydro-1,8-naphthyridin-2-yl)ethyl)cyclobutyl)homoserine;

N-(2,3-dihydro-1H-indene-1-carbonyl)-O-(3-(2-(5,6,7,8-tetrahydro-1,8-naphthyridin-2-yl)ethyl)cyclobutyl)homoserine;

N-((neopentyloxy)carbonyl)-O-(3-(2-(5,6,7,8-tetrahydro-1,8-naphthyridin-2-yl)ethyl)cyclobutyl)homoserine;

N-((1-methylcyclopropoxy)carbonyl)-O-(3-(2-(5,6,7,8-tetrahydro-1,8-naphthyridin-2-yl)ethyl)cyclobutyl)homoserine;

N-((1-methylcyclobutoxy)carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(((1,1,1-trifluoro-2-methylpropan-2-yl)oxy)carbonyl)homoserine;

N-(isopropoxycarbonyl)-O-(3-(2-(5,6,7,8-tetrahydro-1,8-naphthyridin-2-yl)ethyl)cyclobutyl)homoserine;

N-(diethylcarbamoyl)-O-(3-(2-(5,6,7,8-tetrahydro-1,8-naphthyridin-2-yl)ethyl)cyclobutyl)homoserine;

N-(tert-butylcarbamoyl)-O-(3-(2-(5,6,7,8-tetrahydro-1,8-naphthyridin-2-yl)ethyl)cyclobutyl)homoserine;

N-(tert-butyl(methyl)carbamoyl)-O-(3-(2-(5,6,7,8-tetrahydro-1,8-naphthyridin-2-yl)ethyl)cyclobutyl)homoserine;

N-(isopropyl(methyl)carbamoyl)-O-(3-(2-(5,6,7,8-tetrahydro-1,8-naphthyridin-2-yl)ethyl)cyclobutyl)homoserine;

N-(diisopropylcarbamoyl)-O-(3-(2-(5,6,7,8-tetrahydro-1,8-naphthyridin-2-yl)ethyl)cyclobutyl)homoserine;

N-(3,3-dimethylbutanoyl)-O-(3-(2-(5,6,7,8-tetrahydro-1,8-naphthyridin-2-yl)ethyl)cyclobutyl)homoserine;

N-(3-methylbutanoyl)-O-(3-(2-(5,6,7,8-tetrahydro-1,8-naphthyridin-2-yl)ethyl)cyclobutyl)homoserine;

N-(2-cyclobutylacetyl)-O-(3-(2-(5,6,7,8-tetrahydro-1,8-naphthyridin-2-yl)ethyl)cyclobutyl)homoserine;

N-(2-(1-methylcyclopropyl)acetyl)-O-(3-(2-(5,6,7,8-tetrahydro-1,8-naphthyridin-2-yl)ethyl)cyclobutyl)homoserine;

N-(2-cyclopropylacetyl)-O-(3-(2-(5,6,7,8-tetrahydro-1,8-naphthyridin-2-yl)ethyl)cyclobutyl)homoserine;

N-(((1-(tert-butoxycarbonyl)-3-methylazetidin-3-yl)oxy)carbonyl)-O-(3-(2-(5,6,7,8-tetrahydro-1,8-naphthyridin-2-yl)ethyl)cyclobutyl)homoserine;

N-(((3-methyl-1-(methylsulfonyl)azetidin-3-yl)oxy)carbonyl)-O-(3-(2-(5,6,7,8-tetrahydro-1,8-naphthyridin-2-yl)ethyl)cyclobutyl)homoserine;

N-(((1-acetyl-3-methylazetidin-3-yl)oxy)carbonyl)-O-(3-(2-(5,6,7,8-tetrahydro-1,8-naphthyridin-2-yl)ethyl)cyclobutyl)homoserine;

N-(((3-methylazetidin-3-yl)oxy)carbonyl)-O-(3-(2-(5,6,7,8-tetrahydro-1,8-naphthyridin-2-yl)ethyl)cyclobutyl)homoserine;

N-((cyclohexyloxy)carbonyl)-O-(3-(2-(5,6,7,8-tetrahydro-1,8-naphthyridin-2-yl)ethyl)cyclobutyl)homoserine;

N-(isobutoxycarbonyl)-O-(3-(2-(5,6,7,8-tetrahydro-1,8-naphthyridin-2-yl)ethyl)cyclobutyl)homoserine;

N-(((1-(tert-butoxycarbonyl)pyrrolidin-3-yl)oxy)carbonyl)-O-(3-(2-(5,6,7,8-tetrahydro-1,8-naphthyridin-2-yl)ethyl)cyclobutyl)homoserine;

N-((pyrrolidin-3-yloxy)carbonyl)-O-(3-(2-(5,6,7,8-tetrahydro-1,8-naphthyridin-2-yl)ethyl)cyclobutyl)homoserine;

N-(4-(methylsulfonyl)butanoyl)-O-(3-(2-(5,6,7,8-tetrahydro-1,8-naphthyridin-2-yl)ethyl)cyclobutyl)homoserine;

N-(((1-(methylsulfonyl)pyrrolidin-3-yl)oxy)carbonyl)-O-(3-(2-(5,6,7,8-tetrahydro-1,8-naphthyridin-2-yl)ethyl)cyclobutyl)homoserine;

N-(((1-acetylpyrrolidin-3-yl)oxy)carbonyl)-O-(3-(2-(5,6,7,8-tetrahydro-1,8-naphthyridin-2-yl)ethyl)cyclobutyl)homoserine;

N-((1-phenylethoxy)carbonyl)-O-(3-(2-(5,6,7,8-tetrahydro-1,8-naphthyridin-2-yl)ethyl)cyclobutyl)homoserine;
N-((2-phenylcyclobutoxy)carbonyl)-O-(3-(2-(5,6,7,8-tetrahydro-1,8-naphthyridin-2-yl)ethyl)cyclobutyl)homoserine;
N-((3-phenylcyclobutoxy)carbonyl)-O-(3-(2-(5,6,7,8-tetrahydro-1,8-naphthyridin-2-yl)ethyl)cyclobutyl)homoserine;
N-(((2-phenylcyclohexyl)oxy)carbonyl)-O-(3-(2-(5,6,7,8-tetrahydro-1,8-naphthyridin-2-yl)ethyl)cyclobutyl)homoserine;
2-((tert-butoxycarbonyl)amino)-3-methyl-4-(3-(2-(5,6,7,8-tetrahydro-1,8-naphthyridin-2-yl)ethyl)cyclobutoxy)butanoic acid;
N-(((1-(tert-butoxycarbonyl)azetidin-3-yl)oxy)carbonyl)-O-(3-(2-(5,6,7,8-tetrahydro-1,8-naphthyridin-2-yl)ethyl)cyclobutyl)homoserine;
N-(((4-phenylcyclohexyl)oxy)carbonyl)-O-(3-(2-(5,6,7,8-tetrahydro-1,8-naphthyridin-2-yl)ethyl)cyclobutyl)homoserine;
N-(((1-acetylazetidin-3-yl)oxy)carbonyl)-O-(3-(2-(5,6,7,8-tetrahydro-1,8-naphthyridin-2-yl)ethyl)cyclobutyl)homoserine;
N-(((1-acetamidopropan-2-yl)oxy)carbonyl)-O-(3-(2-(5,6,7,8-tetrahydro-1,8-naphthyridin-2-yl)ethyl)cyclobutyl)homoserine;
N-(((1-((tert-butoxycarbonyl)amino)propan-2-yl)oxy)carbonyl)-O-(3-(2-(5,6,7,8-tetrahydro-1,8-naphthyridin-2-yl)ethyl)cyclobutyl)homoserine;
N-(((2-(3,5-dimethyl-1H-pyrazol-1-yl)cyclopentyl)oxy)carbonyl)-O-(3-(2-(5,6,7,8-tetrahydro-1,8-naphthyridin-2-yl)ethyl)cyclobutyl)homoserine;
N-(((2-(3,5-dimethyl-1H-pyrazol-1-yl)cyclohexyl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(3-chlorophenyl)azetidin-3-yl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(4-isopropylphenyl)azetidin-3-yl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(phenylethynyl)azetidin-3-yl)oxy)carbonyl)-O-(3-(2-(5,6,7,8-tetrahydro-1,8-naphthyridin-2-yl)ethyl)cyclobutyl)homoserine;
N-(1-(tert-butoxycarbonyl)piperidine-4-carbonyl)-O-(3-(2-(5,6,7,8-tetrahydro-1,8-naphthyridin-2-yl)ethyl)cyclobutyl)homoserine;
N-(3,3-difluorocyclohexane-1-carbonyl)-O-(3-(2-(5,6,7,8-tetrahydro-1,8-naphthyridin-2-yl)ethyl)cyclobutyl)homoserine;
N-(2-ethyl-4,4-difluorobutanoyl)-O-(3-(2-(5,6,7,8-tetrahydro-1,8-naphthyridin-2-yl)ethyl)cyclobutyl)homoserine;
N-(((2-(phenylethynyl)cyclohexyl)oxy)carbonyl)-O-(3-(2-(5,6,7,8-tetrahydro-1,8-naphthyridin-2-yl)ethyl)cyclobutyl)homoserine;
N-(4-methyltetrahydro-2H-pyran-4-carbonyl)-O-(3-(2-(5,6,7,8-tetrahydro-1,8-naphthyridin-2-yl)ethyl)cyclobutyl)homoserine;
N-(2-cyclohexyl-2-methylpropanoyl)-O-(3-(2-(5,6,7,8-tetrahydro-1,8-naphthyridin-2-yl)ethyl)cyclobutyl)homoserine;
N-(2-(pyridin-2-yl)benzoyl)-O-(3-(2-(5,6,7,8-tetrahydro-1,8-naphthyridin-2-yl)ethyl)cyclobutyl)homoserine;
N-(2-ethyl-4,4,4-trifluorobutanoyl)-O-(3-(2-(5,6,7,8-tetrahydro-1,8-naphthyridin-2-yl)ethyl)cyclobutyl)homoserine;
N-(2-morpholinobenzoyl)-O-(3-(2-(5,6,7,8-tetrahydro-1,8-naphthyridin-2-yl)ethyl)cyclobutyl)homoserine;
N-(2-ethyl-2-phenylbutanoyl)-O-(3-(2-(5,6,7,8-tetrahydro-1,8-naphthyridin-2-yl)ethyl)cyclobutyl)homoserine;
N-(1H-pyrrolo[3,2-b]pyridine-7-carbonyl)-O-(3-(2-(5,6,7,8-tetrahydro-1,8-naphthyridin-2-yl)ethyl)cyclobutyl)homoserine;
N-(4-cyanotetrahydro-2H-pyran-4-carbonyl)-O-(3-(2-(5,6,7,8-tetrahydro-1,8-naphthyridin-2-yl)ethyl)cyclobutyl)homoserine;
N-(1-(tert-butoxycarbonyl)-3-methylazetidine-3-carbonyl)-O-(3-(2-(5,6,7,8-tetrahydro-1,8-naphthyridin-2-yl)ethyl)cyclobutyl)homoserine;
N-(1-(tert-butoxycarbonyl)azetidine-3-carbonyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine;
N-(1-(methylsulfonyl)piperidine-3-carbonyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(4,5,6,7-tetrahydro-1H-indazole-6-carbonyl)homoserine;
O-(3-(2-(5,6,7,8-tetrahydro-1,8-naphthyridin-2-yl)ethyl)cyclobutyl)-N-(4,5,6,7-tetrahydro-1H-indazole-7-carbonyl)homoserine;
N-(1-methyl-4,5,6,7-tetrahydro-1H-indazole-6-carbonyl)-O-(3-(2-(5,6,7,8-tetrahydro-1,8-naphthyridin-2-yl)ethyl)cyclobutyl)homoserine;
N-(1-ethyl-4,4-difluorocyclohexane-1-carbonyl)-O-(3-(2-(5,6,7,8-tetrahydro-1,8-naphthyridin-2-yl)ethyl)cyclobutyl)homoserine;
N-(1-(6-methylindoline-1-carbonyl)cyclopropane-1-carbonyl)-O-(3-(2-(5,6,7,8-tetrahydro-1,8-naphthyridin-2-yl)ethyl)cyclobutyl)homoserine;
N-(4-(((tert-butoxycarbonyl)amino)methyl)tetrahydro-2H-pyran-4-carbonyl)-O-(3-(2-(5,6,7,8-tetrahydro-1,8-naphthyridin-2-yl)ethyl)cyclobutyl)homoserine;
N-(1-(pyridin-3-ylmethyl)cyclopropane-1-carbonyl)-O-(3-(2-(5,6,7,8-tetrahydro-1,8-naphthyridin-2-yl)ethyl)cyclobutyl)homoserine;
N-(3-chloro-5-methylisonicotinoyl)-O-(4-(5,6,7,8-tetrahydro-1,8-naphthyridin-2-yl)butyl)homoserine;
N-(4-methyltetrahydro-2H-pyran-4-carbonyl)-O-(4-(5,6,7,8-tetrahydro-1,8-naphthyridin-2-yl)butyl)homoserine;
N-(2,6-dichlorobenzoyl)-O-(4-(5,6,7,8-tetrahydro-1,8-naphthyridin-2-yl)butyl)homoserine;
N-(3,5-dichloroisonicotinoyl)-O-(4-(5,6,7,8-tetrahydro-1,8-naphthyridin-2-yl)butyl)homoserine;
N-(1-(4-(tert-butyl)phenyl)cyclobutane-1-carbonyl)-O-(3-(2-(5,6,7,8-tetrahydro-1,8-naphthyridin-2-yl)ethyl)cyclobutyl)homoserine;
N-(3,5-dimethylisonicotinoyl)-O-(3-(2-(5,6,7,8-tetrahydro-1,8-naphthyridin-2-yl)ethyl)cyclobutyl)homoserine;
N-(3-chloro-5-methylisonicotinoyl)-O-(3-(2-(5,6,7,8-tetrahydro-1,8-naphthyridin-2-yl)ethyl)cyclobutyl)homoserine;
N-(3,5-dichloroisonicotinoyl)-O-(3-(2-(5,6,7,8-tetrahydro-1,8-naphthyridin-2-yl)ethyl)cyclobutyl)homoserine;
N-(bicyclo[2.2.2]octane-2-carbonyl)-O-(3-(2-(5,6,7,8-tetrahydro-1,8-naphthyridin-2-yl)ethyl)cyclobutyl)homoserine;
N-(2-methyl-1,2,3,4-tetrahydronaphthalene-2-carbonyl)-O-(3-(2-(5,6,7,8-tetrahydro-1,8-naphthyridin-2-yl)ethyl)cyclobutyl)homoserine;

N-((methylsulfonyl)prolyl)-O-(3-(2-(5,6,7,8-tetrahydro-1,8-naphthyridin-2-yl)ethyl)cyclobutyl)homoserine;

N-(2,4-dimethylnicotinoyl)-O-(3-(2-(5,6,7,8-tetrahydro-1,8-naphthyridin-2-yl)ethyl)cyclobutyl)homoserine;

N-(4-phenyltetrahydro-2H-pyran-4-carbonyl)-O-(3-(2-(5,6,7,8-tetrahydro-1,8-naphthyridin-2-yl)ethyl)cyclobutyl)homoserine;

N-(4-cyano-2,6-dimethylbenzoyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(2,4,6-trimethylpyrimidine-5-carbonyl)homoserine; O-(3-(2-(5,6,7,8-tetrahydro-1,8-naphthyridin-2-yl)ethyl)cyclobutyl)-N-(2,4,6-trimethylnicoinoyl)homoserine;

N-(3-chloro-5-fluoroisonicotinoyl)-O-(3-(2-(5,6,7,8-tetrahydro-1,8-naphthyridin-2-yl)ethyl)cyclobutyl)homoserine;

N-(1-(isoquinolin-1-yl)cyclopropane-1-carbonyl)-O-(3-(2-(5,6,7,8-tetrahydro-1,8-naphthyridin-2-yl)ethyl)cyclobutyl)homoserine;

N-(2-(pyridin-2-yl)spiro[3.3]heptane-2-carbonyl)-O-(3-(2-(5,6,7,8-tetrahydro-1,8-naphthyridin-2-yl)ethyl)cyclobutyl)homoserine;

N-(2-(1-methyl-1H-pyrazol-4-yl)tetrahydrofuran-2-carbonyl)-O-(3-(2-(5,6,7,8-tetrahydro-1,8-naphthyridin-2-yl)ethyl)cyclobutyl)homoserine;

N-(2,4-dimethyl-6-oxo-1,6-dihydropyridine-3-carbonyl)-O-(3-(2-(5,6,7,8-tetrahydro-1,8-naphthyridin-2-yl)ethyl)cyclobutyl)homoserine;

N-(4,6-dimethylpyrimidine-5-carbonyl)-O-(3-(2-(5,6,7,8-tetrahydro-1,8-naphthyridin-2-yl)ethyl)cyclobutyl)homoserine;

N-(2,6-dichloro-4-(trifluoromethyl)benzoyl)-O-(3-(2-(5,6,7,8-tetrahydro-1,8-naphthyridin-2-yl)ethyl)cyclobutyl)homoserine;

N-(1-(2-fluorophenyl)cyclopropane-1-carbonyl)-O-(3-(2-(5,6,7,8-tetrahydro-1,8-naphthyridin-2-yl)ethyl)cyclobutyl)homoserine;

N-(1-(benzo[d][1,3]dioxol-5-yl)cyclohexane-1-carbonyl)-O-(3-(2-(5,6,7,8-tetrahydro-1,8-naphthyridin-2-yl)ethyl)cyclobutyl)homoserine;

N-(2,2-difluoro-1-(m-tolyl)cyclopropane-1-carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(1-(tetrahydro-2H-pyran-2-yl)cyclopropane-1-carbonyl)homoserine;

N-(4-methoxy-2,6-dimethylbenzoyl)-O-(3-(2-(5,6,7,8-tetrahydro-1,8-naphthyridin-2-yl)ethyl)cyclobutyl)homoserine;

N-(1-acetyl-4-(trifluoromethyl)piperidine-4-carbonyl)-O-(3-(2-(5,6,7,8-tetrahydro-1,8-naphthyridin-2-yl)ethyl)cyclobutyl)homoserine;

N-(2,3-dihydrobenzo[b][1,4]dioxine-2-carbonyl)-O-(3-(2-(5,6,7,8-tetrahydro-1,8-naphthyridin-2-yl)ethyl)cyclobutyl)homoserine;

N-(1-(3-chlorobenzyl)cyclopentane-1-carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(1-(3-(trifluoromethoxy)phenyl)cyclopropane-1-carbonyl)homoserine;

N-(4-fluoro-2,6-dimethylbenzoyl)-O-(3-(2-(5,6,7,8-tetrahydro-1,8-naphthyridin-2-yl)ethyl)cyclobutyl)homoserine;

N-(4-cyanotetrahydro-2H-pyran-4-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(4-(trifluoromethyl)tetrahydro-2H-pyran-4-carbonyl)homoserine;

N-(quinazolin-4-yl)-O-(3-(2-(5,6,7,8-tetrahydro-1,8-naphthyridin-2-yl)ethyl)cyclobutyl)homoserine;

N-(8-fluoroquinazolin-4-yl)-O-(3-(2-(5,6,7,8-tetrahydro-1,8-naphthyridin-2-yl)ethyl)cyclobutyl)homoserine;

N-(7-fluoroquinazolin-4-yl)-O-(3-(2-(5,6,7,8-tetrahydro-1,8-naphthyridin-2-yl)ethyl)cyclobutyl)homoserine;

N-(7-methylquinazolin-4-yl)-O-(3-(2-(5,6,7,8-tetrahydro-1,8-naphthyridin-2-yl)ethyl)cyclobutyl)homoserine;

N-(6-fluoroquinazolin-4-yl)-O-(3-(2-(5,6,7,8-tetrahydro-1,8-naphthyridin-2-yl)ethyl)cyclobutyl)homoserine;

N-(5-fluoroquinazolin-4-yl)-O-(3-(2-(5,6,7,8-tetrahydro-1,8-naphthyridin-2-yl)ethyl)cyclobutyl)homoserine;

N-(6-methylquinazolin-4-yl)-O-(3-(2-(5,6,7,8-tetrahydro-1,8-naphthyridin-2-yl)ethyl)cyclobutyl)homoserine;

N-(6-(tert-butyl)-2-phenylpyrimidin-4-yl)-O-(3-(2-(5,6,7,8-tetrahydro-1,8-naphthyridin-2-yl)ethyl)cyclobutyl)homoserine;

N-(6-(tert-butyl)pyrimidin-4-yl)-O-(3-(2-(5,6,7,8-tetrahydro-1,8-naphthyridin-2-yl)ethyl)cyclobutyl)homoserine;

N-(2-(tert-butyl)pyrimidin-4-yl)-O-(3-(2-(5,6,7,8-tetrahydro-1,8-naphthyridin-2-yl)ethyl)cyclobutyl)homoserine;

N-(4-(tert-butyl)pyrimidin-2-yl)-O-(3-(2-(5,6,7,8-tetrahydro-1,8-naphthyridin-2-yl)ethyl)cyclobutyl)homoserine;

N-(8-oxabicyclo[3.2.1]octane-3-carbonyl)-O-(4-(5,6,7,8-tetrahydro-1,8-naphthyridin-2-yl)butyl)homoserine;

N-(2-(dimethylamino)-3,5-dimethylisonicotinoyl)-O-(4-(5,6,7,8-tetrahydro-1,8-naphthyridin-2-yl)butyl)homoserine;

N-(5-chloro-2-(dimethylamino)-3-methylisonicotinoyl)-O-(4-(5,6,7,8-tetrahydro-1,8-naphthyridin-2-yl)butyl)homoserine;

N-(3-cyclopropyl-5-fluoroisonicotinoyl)-O-(4-(5,6,7,8-tetrahydro-1,8-naphthyridin-2-yl)butyl)homoserine;

N-(4-((1,3-dimethyl-1H-pyrazol-5-yl)methyl)-2,6-dimethylbenzoyl)-O-(4-(5,6,7,8-tetrahydro-1,8-naphthyridin-2-yl)butyl)homoserine;

N-(5-chloro-2-methoxy-3-methylisonicotinoyl)-O-(4-(5,6,7,8-tetrahydro-1,8-naphthyridin-2-yl)butyl)homoserine;

N-(3-ethyl-5-fluoroisonicotinoyl)-O-(4-(5,6,7,8-tetrahydro-1,8-naphthyridin-2-yl)butyl)homoserine;

N-(4-((1,3-dimethyl-1H-pyrazol-5-yl)methyl)-2-fluoro-6-methylbenzoyl)-O-(4-(5,6,7,8-tetrahydro-1,8-naphthyridin-2-yl)butyl)homoserine;

N-(3-chloro-5-fluoroisonicotinoyl)-O-(4-(5,6,7,8-tetrahydro-1,8-naphthyridin-2-yl)butyl)homoserine;

N-(5-fluoro-3-methylpyridazine-4-carbonyl)-O-(4-(5,6,7,8-tetrahydro-1,8-naphthyridin-2-yl)butyl)homoserine;

N-(2,4-dimethyl-6-oxo-1,6-dihydropyridine-3-carbonyl)-O-(4-(5,6,7,8-tetrahydro-1,8-naphthyridin-2-yl)butyl)homoserine;

N-(2,4-dimethyl-6-oxo-1-(2,2,2-trifluoroethyl)-1,6-dihydropyridine-3-carbonyl)-O-(4-(5,6,7,8-tetrahydro-1,8-naphthyridin-2-yl)butyl)homoserine;

N-(3,5-dimethylisonicotinoyl)-O-(4-(5,6,7,8-tetrahydro-1,8-naphthyridin-2-yl)butyl)homoserine;

N-(3,5-dimethylpyridazine-4-carbonyl)-O-(4-(5,6,7,8-tetrahydro-1,8-naphthyridin-2-yl)butyl)homoserine;

O-(4-(5,6,7,8-tetrahydro-1,8-naphthyridin-2-yl)butyl)-N-(1, 2,4-trimethyl-6-oxo-1,6-dihydropyridine-3-carbonyl)homoserine;
N-(4-cyano-2-fluoro-6-methylbenzoyl)-O-(4-(5,6,7,8-tetrahydro-1,8-naphthyridin-2-yl)butyl)homoserine;
N-(3,5-dimethylmorpholine-4-carbonyl)-O-(4-(5,6,7,8-tetrahydro-1,8-naphthyridin-2-yl)butyl)homoserine;
N-(5-chloro-3-methylpyridazine-4-carbonyl)-O-(4-(5,6,7,8-tetrahydro-1,8-naphthyridin-2-yl)butyl)homoserine;
N-(6-methoxy-2,4-dimethylnicotinoyl)-O-(4-(5,6,7,8-tetrahydro-1,8-naphthyridin-2-yl)butyl)homoserine;
N-(2-chloro-4-cyano-6-fluorobenzoyl)-O-(4-(5,6,7,8-tetrahydro-1,8-naphthyridin-2-yl)butyl)homoserine; and
N-(2,6-dichlorobenzoyl)-O-(4-(5,6,7,8-tetrahydro-1,8-naphthyridin-2-yl)butyl)homoserine.

In one variation, the compound detailed herein is selected from the group consisting of: N-(2-chloro-3-fluorobenzoyl)-O-(4-(5,6,7,8-tetrahydro-1,8-naphthyridin-2-yl)butyl)homoserine; N-(1-methyl-1H-indazole-4-carbonyl)-O-(4-(5,6,7,8-tetrahydro-1,8-naphthyridin-2-yl)butyl)homoserine; N-(4,4-difluorocyclohexane-1-carbonyl)-O-(4-(5,6,7,8-tetrahydro-1,8-naphthyridin-2-yl)butyl)homoserine; N-pentanoyl-O-(4-(5,6,7,8-tetrahydro-1,8-naphthyridin-2-yl)butyl)homoserine; N-(3-fluoro-5-(trifluoromethyl)benzoyl)-O-(4-(5,6,7,8-tetrahydro-1,8-naphthyridin-2-yl)butyl)homoserine; N-(3-fluoro-5-(trifluoromethyl)benzoyl)-O-(3-(2-(5,6,7,8-tetrahydro-1,8-naphthyridin-2-yl)ethyl)cyclobutyl)homoserine; N-pentanoyl-O-(3-(2-(5,6,7,8-tetrahydro-1,8-naphthyridin-2-yl)ethyl)cyclobutyl)homoserine; N-(tert-butoxycarbonyl)-O-(4-(5,6,7,8-tetrahydro-1,8-naphthyridin-2-yl)butyl)homoserine; N-(4-fluorobenzoyl)-O-(3-(2-(5,6,7,8-tetrahydro-1,8-naphthyridin-2-yl)ethyl)cyclobutyl)homoserine; N-(4-chlorobenzoyl)-O-(3-(2-(5,6,7,8-tetrahydro-1,8-naphthyridin-2-yl)ethyl)cyclobutyl)homoserine; N-(3-fluorobenzoyl)-O-(3-(2-(5,6,7,8-tetrahydro-1,8-naphthyridin-2-yl)ethyl)cyclobutyl)homoserine; N-(3-chlorobenzoyl)-O-(3-(2-(5,6,7,8-tetrahydro-1,8-naphthyridin-2-yl)ethyl)cyclobutyl)homoserine; N-(2-chlorobenzoyl)-O-(3-(2-(5,6,7,8-tetrahydro-1,8-naphthyridin-2-yl)ethyl)cyclobutyl)homoserine; N-(2-fluorobenzoyl)-O-(3-(2-(5,6,7,8-tetrahydro-1,8-naphthyridin-2-yl)ethyl)cyclobutyl)homoserine; N-(2,3-difluorobenzoyl)-O-(3-(2-(5,6,7,8-tetrahydro-1,8-naphthyridin-2-yl)ethyl)cyclobutyl)homoserine; N-(2,4-difluorobenzoyl)-O-(3-(2-(5,6,7,8-tetrahydro-1,8-naphthyridin-2-yl)ethyl)cyclobutyl)homoserine; N-(2-chloro-4-fluorobenzoyl)-O-(3-(2-(5,6,7,8-tetrahydro-1,8-naphthyridin-2-yl)ethyl)cyclobutyl)homoserine; N-(3-chloro-5-fluorobenzoyl)-O-(3-(2-(5,6,7,8-tetrahydro-1,8-naphthyridin-2-yl)ethyl)cyclobutyl)homoserine; N-(3-chloro-2-fluorobenzoyl)-O-(3-(2-(5,6,7,8-tetrahydro-1,8-naphthyridin-2-yl)ethyl)cyclobutyl)homoserine; N-(3,5-difluorobenzoyl)-O-(3-(2-(5,6,7,8-tetrahydro-1,8-naphthyridin-2-yl)ethyl)cyclobutyl)homoserine; N-(2,3-dichlorobenzoyl)-O-(3-(2-(5,6,7,8-tetrahydro-1,8-naphthyridin-2-yl)ethyl)cyclobutyl)homoserine; N-(2-chloro-6-fluorobenzoyl)-O-(3-(2-(5,6,7,8-tetrahydro-1,8-naphthyridin-2-yl)ethyl)cyclobutyl)homoserine; N-(2,6-difluorobenzoyl)-O-(3-(2-(5,6,7,8-tetrahydro-1,8-naphthyridin-2-yl)ethyl)cyclobutyl)homoserine; N-(2,5-difluorobenzoyl)-O-(3-(2-(5,6,7,8-tetrahydro-1,8-naphthyridin-2-yl)ethyl)cyclobutyl)homoserine; N-(3,4-dichlorobenzoyl)-O-(3-(2-(5,6,7,8-tetrahydro-1,8-naphthyridin-2-yl)ethyl)cyclobutyl)homoserine; N-picolinoyl-O-(3-(2-(5,6,7,8-tetrahydro-1,8-naphthyridin-2-yl)ethyl)cyclobutyl)homoserine; N-nicotinoyl-O-(3-(2-(5,6,7,8-tetrahydro-1,8-naphthyridin-2-yl)ethyl)cyclobutyl)homoserine; N-(1-methyl-1H-indazole-4-carbonyl)-O-(3-(2-(5,6,7,8-tetrahydro-1,8-naphthyridin-2-yl)ethyl)cyclobutyl)homoserine; N-(2-methyl-2H-indazole-6-carbonyl)-O-(3-(2-(5,6,7,8-tetrahydro-1,8-naphthyridin-2-yl)ethyl)cyclobutyl)homoserine; N-(2-methyl-2H-indazole-5-carbonyl)-O-(3-(2-(5,6,7,8-tetrahydro-1,8-naphthyridin-2-yl)ethyl)cyclobutyl)homoserine; N-(1-methyl-1H-pyrrolo[2,3-b]pyridine-4-carbonyl)-O-(3-(2-(5,6,7,8-tetrahydro-1,8-naphthyridin-2-yl)ethyl)cyclobutyl)homoserine; N-(2-ethylbutanoyl)-O-(3-(2-(5,6,7,8-tetrahydro-1,8-naphthyridin-2-yl)ethyl)cyclobutyl)homoserine; N-(1-methyl-1H-pyrrolo[2,3-b]pyridine-5-carbonyl)-O-(3-(2-(5,6,7,8-tetrahydro-1,8-naphthyridin-2-yl)ethyl)cyclobutyl)homoserine; N-(3-(hydroxymethyl)benzoyl)-O-(3-(2-(5,6,7,8-tetrahydro-1,8-naphthyridin-2-yl)ethyl)cyclobutyl)homoserine; N-(quinoline-5-carbonyl)-O-(3-(2-(5,6,7,8-tetrahydro-1,8-naphthyridin-2-yl)ethyl)cyclobutyl)homoserine; N-(2-cyclopropylbenzoyl)-O-(3-(2-(5,6,7,8-tetrahydro-1,8-naphthyridin-2-yl)ethyl)cyclobutyl)homoserine; N-(quinoline-7-carbonyl)-O-(3-(2-(5,6,7,8-tetrahydro-1,8-naphthyridin-2-yl)ethyl)cyclobutyl)homoserine; N-(quinoline-6-carbonyl)-O-(3-(2-(5,6,7,8-tetrahydro-1,8-naphthyridin-2-yl)ethyl)cyclobutyl)homoserine; N-(quinoline-8-carbonyl)-O-(3-(2-(5,6,7,8-tetrahydro-1,8-naphthyridin-2-yl)ethyl)cyclobutyl)homoserine; N-(3-cyclopropylbenzoyl)-O-(3-(2-(5,6,7,8-tetrahydro-1,8-naphthyridin-2-yl)ethyl)cyclobutyl)homoserine; N-(4-cyclopropylbenzoyl)-O-(3-(2-(5,6,7,8-tetrahydro-1,8-naphthyridin-2-yl)ethyl)cyclobutyl)homoserine; N-isonicotinoyl-O-(3-(2-(5,6,7,8-tetrahydro-1,8-naphthyridin-2-yl)ethyl)cyclobutyl)-homoserine; N-(3-ethylpentanoyl)-O-(3-(2-(5,6,7,8-tetrahydro-1,8-naphthyridin-2-yl)ethyl)cyclobutyl)-homoserine; N-(2-chloro-3-fluorobenzoyl)-O-(3-(2-(5,6,7,8-tetrahydro-1,8-naphthyridin-2-yl)ethyl)cyclobutyl)homoserine; N-(3,4-difluorobenzoyl)-O-(3-(2-(5,6,7,8-tetrahydro-1,8-naphthyridin-2-yl)ethyl)cyclobutyl)homoserine; N-(3-ethylpentanoyl)-O-(3-(2-(5,6,7,8-tetrahydro-1,8-naphthyridin-2-yl)ethyl)cyclobutyl)homoserine; N-isonicotinoyl-O-(3-(2-(5,6,7,8-tetrahydro-1,8-naphthyridin-2-yl)ethyl)cyclobutyl)homoserine; O-(3-(2-(5,6,7,8-tetrahydro-1,8-naphthyridin-2-yl)ethyl)cyclobutyl)-N-(3-(thiazol-5-yl)benzoyl)homoserine; N-(3-hydroxy-2-phenylpropanoyl)-O-(3-(2-(5,6,7,8-tetrahydro-1,8-naphthyridin-2-yl)ethyl)cyclobutyl)homoserine; N-(3-(1-methyl-1H-pyrazol-4-yl)benzoyl)-O-(3-(4-(5,6,7,8-tetrahydro-1,8-naphthyridin-2-yl)butyl)cyclobutyl)homoserine; N-(3-(1-methyl-1H-pyrazol-4-yl)benzoyl)-O-(4-(5,6,7,8-tetrahydro-1,8-naphthyridin-2-yl)butyl)homoserine; N-(2-hydroxy-2-phenylacetyl)-O-(4-(5,6,7,8-tetrahydro-1,8-naphthyridin-2-yl)butyl)homoserine; N-(2-hydroxy-2-phenylacetyl)-O-(4-(5,6,7,8-tetrahydro-1,8-naphthyridin-2-yl)butyl)-homoserine; N-(2-hydroxy-2-phenylacetyl)-O-(3-(2-(5,6,7,8-tetrahydro-1,8-naphthyridin-2-yl)ethyl)cyclobutyl)homoserine; N-(1-phenylcyclopropane-1-carbonyl)-O-(3-(2-(5,6,7,8-tetrahydro-1,8-naphthyridin-2-yl)ethyl)cyclobutyl)homoserine; N-(2-methyl-2-phenylpropanoyl)-O-(3-(2-(5,6,7,8-tetrahydro-1,8-naphthyridin-2-yl)ethyl)cyclobutyl)homoserine; N-(1-phenylcyclobutane-1-carbonyl)-O-(3-(2-(5,6,7,8-tetrahydro-1,8-naphthyridin-2-yl)ethyl)cyclobutyl)homoserine; N-(2,2-dimethyl-3-phenylpropanoyl)-O-(3-(2-(5,6,7,8-tetrahydro-1,8-naphthyridin-2-yl)ethyl)cyclobutyl)homoserine; N-(tert-butoxycarbonyl)-O-(3-(2-(5,6,7,8-tetrahydro-1,8-naphthyridin-2-yl)ethyl)cyclobutyl)homoserine; N-(2-(4-fluorophenyl)-2-methylpropanoyl)-O-

(3-(2-(5,6,7,8-tetrahydro-1,8-naphthyridin-2-yl)ethyl) cyclobutyl)homoserine; N-(3-methyloxetane-3-carbonyl)-O-(3-(2-(5,6,7,8-tetrahydro-1,8-naphthyridin-2-yl)ethyl) cyclobutyl)homoserine; N-(3-hydroxy-2,2-dimethylpropanoyl)-O-(3-(2-(5,6,7,8-tetrahydro-1,8-naphthyridin-2-yl)ethyl)cyclobutyl)homoserine; N-(3-methoxy-2,2-dimethylpropanoyl)-O-(3-(2-(5,6,7,8-tetrahydro-1,8-naphthyridin-2-yl)ethyl)cyclobutyl) homoserine; N-(2-methyl-2-(pyridin-3-yl)propanoyl)-O-(3-(2-(5,6,7,8-tetrahydro-1,8-naphthyridin-2-yl)ethyl) cyclobutyl)homoserine; N-(2,3-dihydro-1H-indene-2-carbonyl)-O-(3-(2-(5,6,7,8-tetrahydro-1,8-naphthyridin-2-yl)ethyl)cyclobutyl)homoserine; N-(3-cyano-2,2-dimethylpropanoyl)-O-(3-(2-(5,6,7,8-tetrahydro-1,8-naphthyridin-2-yl)ethyl)cyclobutyl)homoserine; N-pivaloyl-O-(3-(2-(5,6,7,8-tetrahydro-1,8-naphthyridin-2-yl)ethyl)cyclobutyl)homoserine; N-(2,3-dihydro-1H-indene-1-carbonyl)-O-(3-(2-(5,6,7,8-tetrahydro-1,8-naphthyridin-2-yl)ethyl)cyclobutyl)homoserine; N-((neopentyloxy) carbonyl)-O-(3-(2-(5,6,7,8-tetrahydro-1,8-naphthyridin-2-yl)ethyl)cyclobutyl)homoserine; N-((1-methylcyclopropoxy)carbonyl)-O-(3-(2-(5,6,7,8-tetrahydro-1,8-naphthyridin-2-yl)ethyl)cyclobutyl) homoserine; N-((1-methylcyclobutoxy)carbonyl)-O-(3-(2-(5,6,7,8-tetrahydro-1,8-naphthyridin-2-yl)ethyl)cyclobutyl) homoserine; O-(3-(2-(5,6,7,8-tetrahydro-1,8-naphthyridin-2-yl)ethyl)cyclobutyl)-N-(((1,1,1-trifluoro-2-methylpropan-2-yl)oxy)carbonyl)homoserine; N-(isopropoxycarbonyl)-O-(3-(2-(5,6,7,8-tetrahydro-1,8-naphthyridin-2-yl)ethyl) cyclobutyl)homoserine; N-(diethylcarbamoyl)-O-(3-(2-(5,6,7,8-tetrahydro-1,8-naphthyridin-2-yl)ethyl)cyclobutyl) homoserine; N-(tert-butylcarbamoyl)-O-(3-(2-(5,6,7,8-tetrahydro-1,8-naphthyridin-2-yl)ethyl)cyclobutyl) homoserine; N-(tert-butyl(methyl)carbamoyl)-O-(3-(2-(5,6,7,8-tetrahydro-1,8-naphthyridin-2-yl)ethyl)cyclobutyl) homoserine; N-(isopropyl(methyl)carbamoyl)-O-(3-(2-(5,6,7,8-tetrahydro-1,8-naphthyridin-2-yl)ethyl)cyclobutyl) homoserine; N-(diisopropylcarbamoyl)-O-(3-(2-(5,6,7,8-tetrahydro-1,8-naphthyridin-2-yl)ethyl)cyclobutyl) homoserine; N-(3,3-dimethylbutanoyl)-O-(3-(2-(5,6,7,8-tetrahydro-1,8-naphthyridin-2-yl)ethyl)cyclobutyl) homoserine; N-(3-methylbutanoyl)-O-(3-(2-(5,6,7,8-tetrahydro-1,8-naphthyridin-2-yl)ethyl)cyclobutyl) homoserine; N-(2-cyclobutylacetyl)-O-(3-(2-(5,6,7,8-tetrahydro-1,8-naphthyridin-2-yl)ethyl)cyclobutyl) homoserine; N-(2-(1-methylcyclopropyl)acetyl)-O-(3-(2-(5,6,7,8-tetrahydro-1,8-naphthyridin-2-yl)ethyl)cyclobutyl) homoserine; N-(2-cyclopropylacetyl)-O-(3-(2-(5,6,7,8-tetrahydro-1,8-naphthyridin-2-yl)ethyl)cyclobutyl) homoserine; N-(((1-(tert-butoxycarbonyl)-3-methylazetidin-3-yl)oxy)carbonyl)-O-(3-(2-(5,6,7,8-tetrahydro-1,8-naphthyridin-2-yl)ethyl)cyclobutyl) homoserine; N-(((3-methyl-1-(methylsulfonyl)azetidin-3-yl)oxy)carbonyl)-O-(3-(2-(5,6,7,8-tetrahydro-1,8-naphthyridin-2-yl)ethyl)cyclobutyl)homoserine; N-(((1-acetyl-3-methylazetidin-3-yl)oxy)carbonyl)-O-(3-(2-(5,6,7,8-tetrahydro-1,8-naphthyridin-2-yl)ethyl)cyclobutyl) homoserine; N-(((3-methylazetidin-3-yl)oxy)carbonyl)-O-(3-(2-(5,6,7,8-tetrahydro-1,8-naphthyridin-2-yl)ethyl) cyclobutyl)homoserine; N-((cyclohexyloxy)carbonyl)-O-(3-(2-(5,6,7,8-tetrahydro-1,8-naphthyridin-2-yl)ethyl) cyclobutyl)homoserine; N-(isobutoxycarbonyl)-O-(3-(2-(5,6,7,8-tetrahydro-1,8-naphthyridin-2-yl)ethyl)cyclobutyl) homoserine; N-(((pyrrolidin-3-yl)oxy)carbonyl)-O-(3-(2-(5,6,7,8-tetrahydro-1,8-naphthyridin-2-yl)ethyl)cyclobutyl) homoserine; N-(4-(methylsulfonyl)butanoyl)-O-(3-(2-(5,6,7,8-tetrahydro-1,8-naphthyridin-2-yl)ethyl)cyclobutyl) homoserine; N-(((1-(methylsulfonyl)pyrrolidin-3-yl)oxy) carbonyl)-O-(3-(2-(5,6,7,8-tetrahydro-1,8-naphthyridin-2-yl)ethyl)cyclobutyl)homoserine; N-(((1-(tert-butoxycarbonyl)pyrrolidin-3-yl)oxy)carbonyl)-O-(3-(2-(5,6,7,8-tetrahydro-1,8-naphthyridin-2-yl)ethyl)cyclobutyl) homoserine; N-(((1-acetylpyrrolidin-3-yl)oxy)carbonyl)-O-(3-(2-(5,6,7,8-tetrahydro-1,8-naphthyridin-2-yl)ethyl) cyclobutyl)homoserine; N-((1-phenylethoxy)carbonyl)-O-(3-(2-(5,6,7,8-tetrahydro-1,8-naphthyridin-2-yl)ethyl) cyclobutyl)homoserine; N-((2-phenylcyclobutoxy) carbonyl)-O-(3-(2-(5,6,7,8-tetrahydro-1,8-naphthyridin-2-yl)ethyl)cyclobutyl)homoserine; N-((3-phenylcyclobutoxy) carbonyl)-O-(3-(2-(5,6,7,8-tetrahydro-1,8-naphthyridin-2-yl)ethyl)cyclobutyl)homoserine; 2-((tert-butoxycarbonyl) amino)-3-methyl-4-(3-(2-(5,6,7,8-tetrahydro-1,8-naphthyridin-2-yl)ethyl)cyclobutoxy)butanoic acid; N-(((2-phenylcyclohexyl)oxy)carbonyl)-O-(3-(2-(5,6,7,8-tetrahydro-1,8-naphthyridin-2-yl)ethyl)cyclobutyl) homoserine; N-(((1-(tert-butoxycarbonyl)azetidin-3-yl)oxy) carbonyl)-O-(3-(2-(5,6,7,8-tetrahydro-1,8-naphthyridin-2-yl)ethyl)cyclobutyl)homoserine; N-(((4-phenylcyclohexyl) oxy)carbonyl)-O-(3-(2-(5,6,7,8-tetrahydro-1,8-naphthyridin-2-yl)ethyl)cyclobutyl)homoserine; N-(((1-acetylazetidin-3-yl)oxy)carbonyl)-O-(3-(2-(5,6,7,8-tetrahydro-1,8-naphthyridin-2-yl)ethyl)cyclobutyl) homoserine; N-(((1-((tert-butoxycarbonyl)amino)propan-2-yl)oxy)carbonyl)-O-(3-(2-(5,6,7,8-tetrahydro-1,8-naphthyridin-2-yl)ethyl)cyclobutyl)homoserine; N-(((1-acetamidopropan-2-yl)oxy)carbonyl)-O-(3-(2-(5,6,7,8-tetrahydro-1,8-naphthyridin-2-yl)ethyl)cyclobutyl) homoserine; N-(((2-(3,5-dimethyl-1H-pyrazol-1-yl) cyclopentyl)oxy)carbonyl)-O-(3-(2-(5,6,7,8-tetrahydro-1,8-naphthyridin-2-yl)ethyl)cyclobutyl)-homoserine; N-(((2-(3,5-dimethyl-1H-pyrazol-1-yl)cyclohexyl)oxy)carbonyl)-O-(3-(2-(5,6,7,8-tetrahydro-1,8-naphthyridin-2-yl)ethyl) cyclobutyl)-homoserine; N-(((1-(tert-butoxycarbonyl)-3-(3-chlorophenyl)azetidin-3-yl)oxy)carbonyl)-O-(3-(2-(5,6,7,8-tetrahydro-1,8-naphthyridin-2-yl)ethyl)cyclobutyl) homoserine; N-(((1-(tert-butoxycarbonyl)-3-(4-isopropylphenyl)azetidin-3-yl)oxy)carbonyl)-O-(3-(2-(5,6,7,8-tetrahydro-1,8-naphthyridin-2-yl)ethyl)cyclobutyl) homoserine; N-(((1-(tert-butoxycarbonyl)-3-(phenylethynyl)azetidin-3-yl)oxy)carbonyl)-O-(3-(2-(5,6,7,8-tetrahydro-1,8-naphthyridin-2-yl)ethyl)cyclobutyl) homoserine; N-(1-(tert-butoxycarbonyl)piperidine-4-carbonyl)-O-(3-(2-(5,6,7,8-tetrahydro-1,8-naphthyridin-2-yl)ethyl)cyclobutyl)homoserine; N-(3,3-difluorocyclohexane-1-carbonyl)-O-(3-(2-(5,6,7,8-tetrahydro-1,8-naphthyridin-2-yl)ethyl)cyclobutyl) homoserine; N-(2-ethyl-4,4-difluorobutanoyl)-O-(3-(2-(5,6,7,8-tetrahydro-1,8-naphthyridin-2-yl)ethyl)cyclobutyl)-homoserine; N-(((2-(phenylethynyl)cyclohexyl)oxy) carbonyl)-O-(3-(2-(5,6,7,8-tetrahydro-1,8-naphthyridin-2-yl)ethyl)cyclobutyl)-homoserine; N-(2-cyclohexyl-2-methylpropanoyl)-O-(3-(2-(5,6,7,8-tetrahydro-1,8-naphthyridin-2-yl)ethyl)cyclobutyl)homoserine; N-(2-(pyridin-2-yl)benzoyl)-O-(3-(2-(5,6,7,8-tetrahydro-1,8-naphthyridin-2-yl)ethyl)cyclobutyl)homoserine; N-(2-ethyl-4,4,4-trifluorobutanoyl)-O-(3-(2-(5,6,7,8-tetrahydro-1,8-naphthyridin-2-yl)ethyl)cyclobutyl)homoserine; N-(2-morpholinobenzoyl)-O-(3-(2-(5,6,7,8-tetrahydro-1,8-naphthyridin-2-yl)ethyl)cyclobutyl)homoserine; N-(2-ethyl-2-phenylbutanoyl)-O-(3-(2-(5,6,7,8-tetrahydro-1,8-naphthyridin-2-yl)ethyl)cyclobutyl)homoserine; N-(1H-pyrrolo[3,2-b]pyridine-7-carbonyl)-O-(3-(2-(5,6,7,8-tetrahydro-1,8-naphthyridin-2-yl)ethyl)cyclobutyl) homoserine; N-(4-cyanotetrahydro-2H-pyran-4-carbonyl)-

O-(3-(2-(5,6,7,8-tetrahydro-1,8-naphthyridin-2-yl)ethyl)cyclobutyl)homoserine; N-(1-(tert-butoxycarbonyl)-3-methylazetidine-3-carbonyl)-O-(3-(2-(5,6,7,8-tetrahydro-1,8-naphthyridin-2-yl)ethyl)cyclobutyl)homoserine; N-(1-(tert-butoxycarbonyl)azetidine-3-carbonyl)-O-(3-(2-(5,6,7,8-tetrahydro-1,8-naphthyridin-2-yl)ethyl)cyclobutyl)homoserine; N-(1-(methylsulfonyl)piperidine-3-carbonyl)-O-(3-(2-(5,6,7,8-tetrahydro-1,8-naphthyridin-2-yl)ethyl)cyclobutyl)-homoserine; O-(3-(2-(5,6,7,8-tetrahydro-1,8-naphthyridin-2-yl)ethyl)cyclobutyl)-N-(4,5,6,7-tetrahydro-1H-indazole-6-carbonyl)-homoserine; O-(3-(2-(5,6,7,8-tetrahydro-1,8-naphthyridin-2-yl)ethyl)cyclobutyl)-N-(4,5,6,7-tetrahydro-1H-indazole-7-carbonyl)homoserine; N-(4-methyltetrahydro-2H-pyran-4-carbonyl)-O-(3-(2-(5,6,7,8-tetrahydro-1,8-naphthyridin-2-yl)ethyl)cyclobutyl)homoserine; N-(1-methyl-4,5,6,7-tetrahydro-1H-indazole-6-carbonyl)-O-(3-(2-(5,6,7,8-tetrahydro-1,8-naphthyridin-2-yl)ethyl)cyclobutyl)-homoserine; N-(1-ethyl-4,4-difluoro-cyclohexane-1-carbonyl)-O-(3-(2-(5,6,7,8-tetrahydro-1,8-naphthyridin-2-yl)ethyl)cyclobutyl)homoserine; N-(1-(6-methylindoline-1-carbonyl)cyclopropane-1-carbonyl)-O-(3-(2-(5,6,7,8-tetrahydro-1,8-naphthyridin-2-yl)ethyl)cyclobutyl)homoserine; N-(4-(((tert-butoxycarbonyl)amino)methyl)tetrahydro-2H-pyran-4-carbonyl)-O-(3-(2-(5,6,7,8-tetrahydro-1,8-naphthyridin-2-yl)ethyl)cyclobutyl)homoserine; N-(1-(pyridin-3-ylmethyl)cyclopropane-1-carbonyl)-O-(3-(2-(5,6,7,8-tetrahydro-1,8-naphthyridin-2-yl)ethyl)cyclobutyl)homoserine; N-(3-chloro-5-methylisonicotinoyl)-O-(4-(5,6,7,8-tetrahydro-1,8-naphthyridin-2-yl)butyl)homoserine; N-(4-methyltetrahydro-2H-pyran-4-carbonyl)-O-(4-(5,6,7,8-tetrahydro-1,8-naphthyridin-2-yl)butyl)homoserine; N-(2,6-dichlorobenzoyl)-O-(4-(5,6,7,8-tetrahydro-1,8-naphthyridin-2-yl)butyl)homoserine; N-(3,5-dichloroisonicotinoyl)-O-(4-(5,6,7,8-tetrahydro-1,8-naphthyridin-2-yl)butyl)homoserine; N-(1-(4-(tert-butyl)phenyl)cyclobutane-1-carbonyl)-O-(3-(2-(5,6,7,8-tetrahydro-1,8-naphthyridin-2-yl)ethyl)cyclobutyl)homoserine; N-(4-methyltetrahydro-2H-pyran-4-carbonyl)-O-(3-(2-(5,6,7,8-tetrahydro-1,8-naphthyridin-2-yl)ethyl)cyclobutyl)homoserine; O-(3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine; N-(3-chloro-5-methylisonicotinoyl)-O-(3-(2-(5,6,7,8-tetrahydro-1,8-naphthyridin-2-yl)ethyl)cyclobutyl)homoserine; N-(3,5-dichloroisonicotinoyl)-O-(3-(2-(5,6,7,8-tetrahydro-1,8-naphthyridin-2-yl)ethyl)cyclobutyl)homoserine; N-(bicyclo[2.2.2]octane-2-carbonyl)-O-(3-(2-(5,6,7,8-tetrahydro-1,8-naphthyridin-2-yl)ethyl)cyclobutyl)homoserine; N-(2-methyl-1,2,3,4-tetrahydronaphthalene-2-carbonyl)-O-(3-(2-(5,6,7,8-tetrahydro-1,8-naphthyridin-2-yl)ethyl)cyclobutyl)homoserine; N-((methylsulfonyl)prolyl)-O-(3-(2-(5,6,7,8-tetrahydro-1,8-naphthyridin-2-yl)ethyl)cyclobutyl)homoserine; N-(2,4-dimethylnicotinoyl)-O-(3-(2-(5,6,7,8-tetrahydro-1,8-naphthyridin-2-yl)ethyl)cyclobutyl)homoserine; N-(4-phenyltetrahydro-2H-pyran-4-carbonyl)-O-(3-(2-(5,6,7,8-tetrahydro-1,8-naphthyridin-2-yl)ethyl)cyclobutyl)homoserine; N-(4-cyano-2,6-dimethylbenzoyl)-O-(3-(2-(5,6,7,8-tetrahydro-1,8-naphthyridin-2-yl)ethyl)cyclobutyl)homoserine; O-(3-(2-(5,6,7,8-tetrahydro-1,8-naphthyridin-2-yl)ethyl)cyclobutyl)-N-(2,4,6-trimethylpyrimidine-5-carbonyl)homoserine; O-(3-(2-(5,6,7,8-tetrahydro-1,8-naphthyridin-2-yl)ethyl)cyclobutyl)-N-(2,4,6-trimethylnicotinoyl)homoserine; N-(3-chloro-5-fluoroisonicotinoyl)-O-(3-(2-(5,6,7,8-tetrahydro-1,8-naphthyridin-2-yl)ethyl)cyclobutyl)homoserine; N-(1-(isoquinolin-1-yl)cyclopropane-1-carbonyl)-O-(3-(2-(5,6,7,8-tetrahydro-1,8-naphthyridin-2-yl)ethyl)cyclobutyl)homoserine; N-(2-(pyridin-2-yl)spiro[3.3]heptane-2-carbonyl)-O-(3-(2-(5,6,7,8-tetrahydro-1,8-naphthyridin-2-yl)ethyl)cyclobutyl)homoserine; N-(2-(1-methyl-1H-pyrazol-4-yl)tetrahydrofuran-2-carbonyl)-O-(3-(2-(5,6,7,8-tetrahydro-1,8-naphthyridin-2-yl)ethyl)cyclobutyl)homoserine; N-(2,4-dimethyl-6-oxo-1,6-dihydropyridine-3-carbonyl)-O-(3-(2-(5,6,7,8-tetrahydro-1,8-naphthyridin-2-yl)ethyl)cyclobutyl)homoserine; N-(4,6-dimethylpyrimidine-5-carbonyl)-O-(3-(2-(5,6,7,8-tetrahydro-1,8-naphthyridin-2-yl)ethyl)cyclobutyl)homoserine; N-(2,6-dichloro-4-(trifluoromethyl)benzoyl)-O-(3-(2-(5,6,7,8-tetrahydro-1,8-naphthyridin-2-yl)ethyl)cyclobutyl)homoserine; N-(1-(2-fluorophenyl)cyclopropane-1-carbonyl)-O-(3-(2-(5,6,7,8-tetrahydro-1,8-naphthyridin-2-yl)ethyl)cyclobutyl)homoserine; N-(1-(benzo[d][1,3]dioxol-5-yl)cyclohexane-1-carbonyl)-O-(3-(2-(5,6,7,8-tetrahydro-1,8-naphthyridin-2-yl)ethyl)cyclobutyl)homoserine; N-(2,2-difluoro-1-(m-tolyl)cyclopropane-1-carbonyl)-O-(3-(2-(5,6,7,8-tetrahydro-1,8-naphthyridin-2-yl)ethyl)cyclobutyl)homoserine; O-(3-(2-(5,6,7,8-tetrahydro-1,8-naphthyridin-2-yl)ethyl)cyclobutyl)-N-(1-(tetrahydro-2H-pyran-2-yl)cyclopropane-1-carbonyl)homoserine; N-(4-methoxy-2,6-dimethylbenzoyl)-O-(3-(2-(5,6,7,8-tetrahydro-1,8-naphthyridin-2-yl)ethyl)cyclobutyl)homoserine; N-(1-acetyl-4-(trifluoromethyl)piperidine-4-carbonyl)-O-(3-(2-(5,6,7,8-tetrahydro-1,8-naphthyridin-2-yl)ethyl)cyclobutyl)homoserine; N-(2,3-dihydrobenzo[b][1,4]dioxine-2-carbonyl)-O-(3-(2-(5,6,7,8-tetrahydro-1,8-naphthyridin-2-yl)ethyl)cyclobutyl)homoserine; N-(1-(3-chlorobenzyl)cyclopentane-1-carbonyl)-O-(3-(2-(5,6,7,8-tetrahydro-1,8-naphthyridin-2-yl)ethyl)cyclobutyl)homoserine; O-(3-(2-(5,6,7,8-tetrahydro-1,8-naphthyridin-2-yl)ethyl)cyclobutyl)-N-(1-(3-(trifluoromethoxy)phenyl)cyclopropane-1-carbonyl)homoserine; N-(4-fluoro-2,6-dimethylbenzoyl)-O-(3-(2-(5,6,7,8-tetrahydro-1,8-naphthyridin-2-yl)ethyl)cyclobutyl)homoserine; N-(3,5-dimethylisonicotinoyl)-O-(3-(2-(5,6,7,8-tetrahydro-1,8-naphthyridin-2-yl)ethyl)cyclobutyl)homoserine; N-(2-(tert-butyl)pyrimidin-4-yl)-O-(3-(2-(5,6,7,8-tetrahydro-1,8-naphthyridin-2-yl)ethyl)cyclobutyl)homoserine; N-(4-(tert-butyl)pyrimidin-2-yl)-O-(3-(2-(5,6,7,8-tetrahydro-1,8-naphthyridin-2-yl)ethyl)cyclobutyl)homoserine; O-(3-(2-(1,8-naphthyridin-2-yl)ethyl)cyclobutyl)-N-(quinazolin-4-yl)homoserine; N-(6-(tert-butyl)pyrimidin-4-yl)-O-(3-(2-(5,6,7,8-tetrahydro-1,8-naphthyridin-2-yl)ethyl)cyclobutyl)homoserine; 2-[(4-amino-2,6-dichloro-benzoyl)amino]-4-[3-[2-(5,6,7,8-tetrahydro-1,8-naphthyridin-2-yl)ethyl]cyclobutoxy]butanoic acid; N-(4-chloro-2,6-dimethylnicotinoyl)-O-(3-(2-(5,6,7,8-tetrahydro-1,8-naphthyridin-2-yl)ethyl)cyclobutyl)-homoserine; 2-[(3-chloro-6-methyl-pyridine-2-carbonyl)amino]-4-[3-[2-(5,6,7,8-tetrahydro-1,8-naphthyridin-2-yl)ethyl]cyclobutoxy]butanoic acid; N-(2,6-dimethylpiperidine-1-carbonyl)-O-(3-(2-(5,6,7,8-tetrahydro-1,8-naphthyridin-2-yl)ethyl)cyclobutyl)-homoserine; N-(2,5-dimethylpyrrolidine-1-carbonyl)-O-(3-(2-(5,6,7,8-tetrahydro-1,8-naphthyridin-2-yl)ethyl)cyclobutyl)-homoserine; N-(2,6-dichloro-4-cyanobenzoyl)-O-(3-(2-(5,6,7,8-tetrahydro-1,8-naphthyridin-2-yl)ethyl)cyclobutyl)-homoserine; N-(2,6-dichloro-3-nitrobenzoyl)-O-(3-(2-(5,6,7,8-tetrahydro-1,8-naphthyridin-2-yl)ethyl)cyclobutyl)-homoserine; 4-[3-[2-(5,6,7,8-tetrahydro-1,8-naphthyridin-2-yl)ethyl]cyclobutoxy]-2-[(1,2,4-trimethyl-6-oxo-pyridine-3-carbonyl)amino]butanoic acid; N-(2-chloro-4-cyano-6-methylbenzoyl)-O-(3-(2-(5,6,7,8-tetrahydro-1,8-naphthyridin-2-yl)ethyl)cyclobutyl)-homoserine; N-(3-bromo-5-chloro-2- fluoroisonicotinoyl)-O-(3-(2-(5,6,7,8-tetrahydro-1,8-naphthyridin-2-yl)ethyl)cyclobutyl)-homoserine; O-(3-(2-(5,6,7,8-tetrahydro-1,8-naphthyridin-2-yl)ethyl)cyclobutyl)-N-(5,6,7,8-tetrahydronaphthalene-1-carbonyl)-homoserine; N-(3-bromo-2,6-dimethylbenzoyl)-O-(3-(2-(5,6,7,8-tetrahydro-1,8-naphthyridin-2-yl)ethyl)cyclobutyl)-homoserine; 2-[(3-chloro-5-methoxy-pyridine-4-carbonyl)amino]-4-[3-[2-(5,6,7,8-tetrahydro-1,8-naphthyridin-2-yl)ethyl]cyclobutoxy]butanoic acid; 2-[(2,6-dichloro-4-fluorobenzoyl)amino]-4-[3-[2-(5,6,7,8-tetrahydro-1,8-naphthyridin-2-yl)ethyl]cyclobutoxy]butanoic acid; 2-[(2-chloro-6-fluoro-benzoyl)amino]-4-[3-[2-(5,6,7,8-tetrahydro-1,8-naphthyridin-2-yl)ethyl]cyclobutoxy]butanoic acid; N-(3-bromo-2-chloro-6-fluorobenzoyl)-O-(3-(2-(5,6,7,8-tetrahydro-1,8-naphthyridin-2-yl)ethyl)cyclobutyl)-homoserine; N-(2,4-dimethyl-6-oxo-1-phenyl-1,6-dihydropyridine-3-carbonyl)-O-(3-(2-(5,6,7,8-tetrahydro-1,8-naphthyridin-2-yl)ethyl)cyclobutyl)-homoserine; N-(5-bromo-2-hydroxyisonicotinoyl)-O-(3-(2-(5,6,7,8-tetrahydro-1,8-naphthyridin-2-yl)ethyl)cyclobutyl)-homoserine; N-(3-chloro-5-cyclopropylisonicotinoyl)-O-(3-(2-(5,6,7,8-tetrahydro-1,8-naphthyridin-2-yl)ethyl)cyclobutyl)-homoserine; N-(3-chloro-5-ethylisonicotinoyl)-O-(3-(2-(5,6,7,8-tetrahydro-1,8-naphthyridin-2-yl)ethyl)cyclobutyl)-homoserine; N-(3-cyano-2,6-dimethylbenzoyl)-O-(3-(2-(5,6,7,8-tetrahydro-1,8-naphthyridin-2-yl)ethyl)cyclobutyl)-homoserine; N-(3-bromo-5-fluoroisonicotinoyl)-O-(3-(2-(5,6,7,8-tetrahydro-1,8-naphthyridin-2-yl)ethyl)cyclobutyl)-homoserine; N-(2-methoxy-3,5-dimethylisonicotinoyl)-O-(3-(2-(5,6,7,8-tetrahydro-1,8-naphthyridin-2-yl)ethyl)cyclobutyl)-homoserine; N-(3-chloro-5-(trifluoromethyl)isonicotinoyl)-O-(3-(2-(5,6,7,8-tetrahydro-1,8-naphthyridin-2-yl)ethyl)cyclobutyl)-homoserine; N-(3-bromo-5-chloroisonicotinoyl)-O-(3-(2-(5,6,7,8-tetrahydro-1,8-naphthyridin-2-yl)ethyl)cyclobutyl)-homoserine; N-(2-(dimethylamino)-3,5-dimethylisonicotinoyl)-O-(3-(2-(5,6,7,8-tetrahydro-1,8-naphthyridin-2-yl)ethyl)cyclobutyl)-homoserine; N-(3-chloro-5-fluoro-2-methylisonicotinoyl)-O-(3-(2-(5,6,7,8-tetrahydro-1,8-naphthyridin-2-yl)ethyl)cyclobutyl)-homoserine; N-(2,6-dichloro-3-cyanobenzoyl)-O-(3-(2-(5,6,7,8-tetrahydro-1,8-naphthyridin-2-yl)ethyl)cyclobutyl)-homoserine; N-(3-methyl-5-(trifluoromethyl)isonicotinoyl)-O-(3-(2-(5,6,7,8-tetrahydro-1,8-naphthyridin-2-yl)ethyl)cyclobutyl)-homoserine; N-(2-hydroxy-3,5-dimethylisonicotinoyl)-O-(3-(2-(5,6,7,8-tetrahydro-1,8-naphthyridin-2-yl)ethyl)cyclobutyl)-homoserine; N-(3-cyano-2-hydroxy-6-methylisonicotinoyl)-O-(3-(2-(5,6,7,8-tetrahydro-1,8-naphthyridin-2-yl)ethyl)cyclobutyl)-homoserine; N-(5-chloro-3-fluoro-2-methylisonicotinoyl)-O-(3-(2-(5,6,7,8-tetrahydro-1,8-naphthyridin-2-yl)ethyl)cyclobutyl)-homoserine; 2-[(6-methoxy-2,4-dimethyl-pyridine-3-carbonyl)amino]-4-[3-[2-(5,6,7,8-tetrahydro-1,8-naphthyridin-2-yl)ethyl]cyclobutoxy]butanoic acid; 2-[[2,6-dimethyl-4-[(4-methylpiperazin-1-yl)methyl]benzoyl]amino]-4-[3-[2-(5,6,7,8-tetrahydro-1,8-naphthyridin-2-yl)ethyl]cyclobutoxy]butanoic acid; N-(3,5-dimethylmorpholine-4-carbonyl)-O-(3-(2-(5,6,7,8-tetrahydro-1,8-naphthyridin-2-yl)ethyl)cyclobutyl)-homoserine; 2-[[5-chloro-3-fluoro-2-[(4-methylpiperazin-1-yl)methyl]pyridine-4-carbonyl]amino]-4-[3-[2-(5,6,7,8-tetrahydro-1,8-naphthyridin-2-yl)ethyl]cyclobutoxy]butanoic acid; methyl 2-[(7-chloro-5-oxo-2,3-dihydro-1H-indolizine-8-carbonyl)amino]-4-[3-[2-(5,6,7,8-tetrahydro-1,8-naphthyridin-2-yl)ethyl]cyclobutoxy]butanoate; 2-[(2,6-difluoro-4-hydroxy-benzoyl)amino]-4-[3-[2-(5,6,7,8-tetrahydro-1,8-naphthyridin-2-yl)ethyl]cyclobutoxy]butanoic acid; 2-[(4-chloro-2-methyl-pyrazole-3-carbonyl)amino]-4-[3-[2-(5,6,7,8-tetrahydro-1,8-naphthyridin-2-yl)ethyl]cyclobutoxy]butanoic acid; 2-[(2-methylpyrazole-3-carbonyl)amino]-4-[3-[2-(5,6,7,8-tetrahydro-1,8-naphthyridin-2-yl)ethyl]cyclobutoxy]butanoic acid; N-(1-(phenylsulfonyl)piperidine-2-carbonyl)-O-(3-(2-(5,6,7,8-tetrahydro-1,8-naphthyridin-2-yl)ethyl)cyclobutyl)-homoserine; 2-(3,3-dimethylbutanoylamino)-4-[3-[2-(5,6,7,8-tetrahydro-1,8-naphthyridin-2-yl)ethyl]cyclobutoxy]butanoic acid; 2-[(2-phenylacetyl)amino]-4-[3-[2-(5,6,7,8-tetrahydro-1,8-naphthyridin-2-yl)ethyl]cyclobutoxy]butanoic acid; 4-[3-[2-(5,6,7,8-tetrahydro-1,8-naphthyridin-2-yl)ethyl]cyclobutoxy]-2-[(4,4,4-trifluoro-3,3-dimethyl-butanoyl)amino]butanoic acid; 2-[(4,4-difluoro-3,3-dimethyl-butanoyl)amino]-4-[3-[2-(5,6,7,8-tetrahydro-1,8-naphthyridin-2-yl)ethyl]cyclobutoxy]butanoic acid; 2-[[2-phenylpropanoyl]amino]-4-[3-[2-(5,6,7,8-tetrahydro-1,8-naphthyridin-2-yl)ethyl]cyclobutoxy]butanoic acid; 2-[[2-(3,5-difluorophenyl)acetyl]amino]-4-[3-[2-(5,6,7,8-tetrahydro-1,8-naphthyridin-2-yl)ethyl]cyclobutoxy]butanoic acid; 2-[[2-(tert-butoxycarbonylamino)-1-methyl-ethoxy]carbonylamino]-4-[3-[2-(5,6,7,8-tetrahydro-1,8-naphthyridin-2-yl)ethyl]cyclobutoxy]butanoic acid; 2-[(3,6-dimethylpyridine-2-carbonyl)amino]-4-[3-[2-(5,6,7,8-tetrahydro-1,8-naphthyridin-2-yl)ethyl]cyclobutoxy]butanoic acid; 2-[(6-fluorochromane-2-carbonyl)amino]-4-[3-[2-(5,6,7,8-tetrahydro-1,8-naphthyridin-2-yl)ethyl]cyclobutoxy]butanoic acid; 4-[3-[2-(5,6,7,8-tetrahydro-1,8-naphthyridin-2-yl)ethyl]cyclobutoxy]-2-[2-[3-(trifluoromethyl)phenyl]butanoylamino]butanoic acid; 2-[(3-chloro-5-methyl-pyridine-4-carbonyl)amino]-4-[3-[2-(5,6,7,8-tetrahydro-1,8-naphthyridin-2-yl)ethyl]cyclobutoxy]butanoic acid; 2-[(3-chloro-5-fluoro-pyridine-4-carbonyl)amino]-4-[3-[2-(5,6,7,8-tetrahydro-1,8-naphthyridin-2-yl)ethyl]cyclobutoxy]butanoic acid; 2-[(4-cyano-2,6-dimethyl-benzoyl)amino]-4-[3-[2-(5,6,7,8-tetrahydro-1,8-naphthyridin-2-yl)ethyl]cyclobutoxy]butanoic acid; 2-[[4-(2-chlorophenyl)tetrahydropyran-4-carbonyl]amino]-4-[3-[2-(5,6,7,8-tetrahydro-1,8-naphthyridin-2-yl)ethyl]cyclobutoxy]butanoic acid; 2-[(2-hydroxyindane-2-carbonyl)amino]-4-[3-[2-(5,6,7,8-tetrahydro-1,8-naphthyridin-2-yl)ethyl]cyclobutoxy]butanoic acid; 2-[(1-cyclopropylcyclopropanecarbonyl)amino]-4-[3-[2-(5,6,7,8-tetrahydro-1,8-naphthyridin-2-yl)ethyl]cyclobutoxy]butanoic acid; 2-[[3-(difluoromethyl)-5,6,7,8-tetrahydro-[1,2,4]triazolo[4,3-a]pyridine-6-carbonyl]amino]-4-[3-[2-(5,6,7,8-tetrahydro-1,8-naphthyridin-2-yl)ethyl]cyclobutoxy]butanoic acid; 2-[(1-cyclopropylcyclobutanecarbonyl)amino]-4-[3-[2-(5,6,7,8-tetrahydro-1,8-naphthyridin-2-yl)ethyl]cyclobutoxy]butanoic acid; 2-[[1-(4-isopropylphenyl)cyclopentanecarbonyl]amino]-4-[3-[2-(5,6,7,8-tetrahydro-1,8-naphthyridin-2-yl)ethyl]cyclobutoxy]butanoic acid; 2-(bicyclo[2.2.2]octane-4-carbonylamino)-4-[3-[2-(5,6,7,8-tetrahydro-1,8-naphthyridin-2-yl)ethyl]cyclobutoxy]butanoic acid; 2-(3,4,5,6,7,7a-hexahydro-2H-benzofuran-3a-carbonylamino)-4-[3-[2-(5,6,7,8-tetrahydro-1,8-naphthyridin-2-yl)ethyl]cyclobutoxy]butanoic acid; 2-[[1-(2-phenylethyl)cyclopropanecarbonyl]amino]-4-[3-[2-(5,6,7,8-tetrahydro-1,8-naphthyridin-2-yl)ethyl]cyclobutoxy]butanoic acid; 2-[[4-(3-methylisoxazol-5-yl)tetrahydropyran-4-carbonyl]amino]-4-[3-[2-(5,6,7,8-tetrahydro-1,8-naphthyridin-2-yl)ethyl]cyclobutoxy]butanoic acid; 2-[[1-(benzenesulfonyl)cyclopropanecarbonyl]amino]-4-[3-[2-(5,6,7,8-tetrahydro-1,8-naphthyridin-2-yl)ethyl]cyclobutoxy]butanoic acid; 2-[(1-phenylcycloheptanecarbonyl)amino]-4-[3-[2-(5,6,7,8- tetrahydro-1,8-naphthyridin-2-yl)ethyl]cyclobutoxy]butanoic acid; 2-[(4-methylsulfonyltetrahydropyran-4-carbonyl)amino]-4-[3-[2-(5,6,7,8-tetrahydro-1,8-naphthyridin-2-yl)ethyl]cyclobutoxy]butanoic acid; 2-[[1-(4-sulfamoylphenyl)cyclopropanecarbonyl]amino]-4-[3-[2-(5,6,7,8-tetrahydro-1,8-naphthyridin-2-yl)ethyl]cyclobutoxy]butanoic acid; N-((phenylsulfonyl)prolyl)-O-(3-(2-(5,6,7,8-tetrahydro-1,8-naphthyridin-2-yl)ethyl)cyclobutyl)-homoserine; N-(5-chloro-3-fluoro-2-((4-methylpiperazin-1-yl)methyl)isonicotinoyl)-O-(3-(2-(5,6,7,8-tetrahydro-1,8-naphthyridin-2-yl)ethyl)cyclobutyl)-homoserine; N-(3-chloro-5-fluoro-2-((4-methylpiperazin-1-yl)methyl)isonicotinoyl)-O-(3-(2-(5,6,7,8-tetrahydro-1,8-naphthyridin-2-yl)ethyl)cyclobutyl)-homoserine; 2-(pyrimidin-4-ylamino)-5-(3-(5,6,7,8-tetrahydro-1,8-naphthyridin-2-yl)propoxy)pentanoic acid; 2-[(3-chloro-5-methyl-pyridine-4-carbonyl)amino]-4-[4-(5,6,7,8-tetrahydro-1,8-naphthyridin-2-yl)butoxy]butanoic acid; 2-[(2,4-dimethylpyridine-3-carbonyl)amino]-4-[4-(5,6,7,8-tetrahydro-1,8-naphthyridin-2-yl)butoxy]butanoic acid; 2-[(4-cyano-2,6-dimethyl-benzoyl)amino]-4-[4-(5,6,7,8-tetrahydro-1,8-naphthyridin-2-yl)butoxy]butanoic acid; 2-[(3,5-dichloropyridine-4-carbonyl)amino]-4-[4-(5,6,7,8-tetrahydro-1,8-naphthyridin-2-yl)butoxy]butanoic acid; 2-[(3-chloro-5-fluoro-pyridine-4-carbonyl)amino]-4-[4-(5,6,7,8-tetrahydro-1,8-naphthyridin-2-yl)butoxy]butanoic acid; N-(3,5-dimethylmorpholine-4-carbonyl)-O-(4-(5,6,7,8-tetrahydro-1,8-naphthyridin-2-yl)butyl)-homoserine; N-(2,6-dichlorobenzoyl)-O-(4-(5,6,7,8-tetrahydro-1,8-naphthyridin-2-yl)butyl)-homoserine; N-(3,5-dimethylisonicotinoyl)-O-(4-(5,6,7,8-tetrahydro-1,8-naphthyridin-2-yl)butyl)-homoserine; 2-[(2,4-dichloro-6-fluoro-benzoyl)amino]-4-[4-(5,6,7,8-tetrahydro-1,8-naphthyridin-2-yl)butoxy]butanoic acid; 2-[(2,4-dimethyl-6-oxo-1H-pyridine-3-carbonyl)amino]-4-[4-(5,6,7,8-tetrahydro-1,8-naphthyridin-2-yl)butoxy]butanoic acid; N-(3-chloro-5-methoxyisonicotinoyl)-O-(4-(5,6,7,8-tetrahydro-1,8-naphthyridin-2-yl)butyl)-homoserine; 2-[(2-chloro-6-fluoro-benzoyl)amino]-4-[4-(5,6,7,8-tetrahydro-1,8-naphthyridin-2-yl)butoxy]butanoic acid; N-(tert-butoxycarbonyl)-O-(4-(5,6,7,8-tetrahydro-1,8-naphthyridin-2-yl)butyl)-homoserine; N-(5-bromo-2-hydroxyisonicotinoyl)-O-(4-(5,6,7,8-tetrahydro-1,8-naphthyridin-2-yl)butyl)-homoserine; N-(3-bromo-5-chloro-2-fluoroisonicotinoyl)-O-(4-(5,6,7,8-tetrahydro-1,8-naphthyridin-2-yl)butyl)-homoserine; N-(2,4-dimethyl-6-oxo-1-phenyl-1,6-dihydropyridine-3-carbonyl)-O-(4-(5,6,7,8-tetrahydro-1,8-naphthyridin-2-yl)butyl)-homoserine; O-(4-(5,6,7,8-tetrahydro-1,8-naphthyridin-2-yl)butyl)-N-(5,6,7,8-tetrahydronaphthalene-1-carbonyl)-homoserine; N-(3-bromo-2,6-dimethylbenzoyl)-O-(4-(5,6,7,8-tetrahydro-1,8-naphthyridin-2-yl)butyl)-homoserine; N-(3-chloro-5-fluoroisonicotinoyl)-O-(4-(5,6,7,8-tetrahydro-1,8-naphthyridin-2-yl)butyl)-homoserine; N-(3-bromo-2-chloro-6-fluorobenzoyl)-O-(4-(5,6,7,8-tetrahydro-1,8-naphthyridin-2-yl)butyl)-homoserine; 2-[(3-chloro-5-methoxy-pyridine-4-carbonyl)amino]-4-[2-methyl-4-(5,6,7,8-tetrahydro-1,8-naphthyridin-2-yl)butoxy]butanoic acid; 2-[(3-chloro-5-fluoro-pyridine-4-carbonyl)amino]-4-[2-methyl-4-(5,6,7,8-tetrahydro-1,8-naphthyridin-2-yl)butoxy]butanoic acid; N-(3-chloro-5-fluoroisonicotinoyl)-O-(2-methyl-4-(5,6,7,8-tetrahydro-1,8-naphthyridin-2-yl)butyl)-homoserine; N-(2,6-dichlorobenzoyl)-O-(2-methyl-4-(5,6,7,8-tetrahydro-1,8-naphthyridin-2-yl)butyl)-homoserine; N-(2-chloro-6-fluorobenzoyl)-O-(2-methyl-4-(5,6,7,8-tetrahydro-1,8-naphthyridin-2-yl)butyl)-homoserine; N-(4-fluoro-2-methylnicotinoyl)-O-(2-methyl-4-(5,6,7,8-tetrahydro-1,8-naphthyridin-2-yl)butyl)-homoserine; 2-[(3-chloro-5-fluoro-pyridine-4-carbonyl)amino]-4-[2-hydroxy-4-(5,6,7,8-tetrahydro-1,8-naphthyridin-2-yl)butoxy]butanoic acid; 2-(1-methyl-1H-indazole-4-carboxamido)-5-(3-(5,6,7,8-tetrahydro-1,8-naphthyridin-2-yl)propoxy)pentanoic acid; 2-(3-(1-methyl-1H-pyrazol-4-yl)benzamido)-5-(3-(5,6,7,8-tetrahydro-1,8-naphthyridin-2-yl)propoxy)pentanoic acid; 2-(2-chloro-3-fluorobenzamido)-6-(2-(5,6,7,8-tetrahydro-1,8-naphthyridin-2-yl)ethoxy)hexanoic acid; 2-(3-(1-methyl-1H-pyrazol-4-yl)benzamido)-6-(2-(5,6,7,8-tetrahydro-1,8-naphthyridin-2-yl)ethoxy)hexanoic acid; 2-(2-ethylbutanamido)-6-(2-(5,6,7,8-tetrahydro-1,8-naphthyridin-2-yl)ethoxy)hexanoic acid; 2-(1-methyl-1H-indazole-4-carboxamido)-6-(2-(5,6,7,8-tetrahydro-1,8-naphthyridin-2-yl)ethoxy)hexanoic acid; 2-((tert-butoxycarbonyl)amino)-5-(3-(5,6,7,8-tetrahydro-1,8-naphthyridin-2-yl)propoxy)pentanoic acid; N-benzoyl-O-(3-(2-(5,6,7,8-tetrahydro-1,8-naphthyridin-2-yl)ethyl)cyclobutyl)homoserine; N-(quinazolin-4-yl)-O-(3-(2-(5,6,7,8-tetrahydro-1,8-naphthyridin-2-yl)ethyl)cyclobutyl)homoserine; N-(8-fluoroquinazolin-4-yl)-O-(3-(2-(5,6,7,8-tetrahydro-1,8-naphthyridin-2-yl)ethyl)cyclobutyl)homoserine; N-(7-fluoroquinazolin-4-yl)-O-(3-(2-(5,6,7,8-tetrahydro-1,8-naphthyridin-2-yl)ethyl)cyclobutyl)homoserine; N-(7-methylquinazolin-4-yl)-O-(3-(2-(5,6,7,8-tetrahydro-1,8-naphthyridin-2-yl)ethyl)cyclobutyl)homoserine; N-(6-fluoroquinazolin-4-yl)-O-(3-(2-(5,6,7,8-tetrahydro-1,8-naphthyridin-2-yl)ethyl)cyclobutyl)homoserine; N-(5-fluoroquinazolin-4-yl)-O-(3-(2-(5,6,7,8-tetrahydro-1,8-naphthyridin-2-yl)ethyl)cyclobutyl)homoserine; N-(6-methylquinazolin-4-yl)-O-(3-(2-(5,6,7,8-tetrahydro-1,8-naphthyridin-2-yl)ethyl)cyclobutyl)homoserine; and N-(6-(tert-butyl)-2-phenylpyrimidin-4-yl)-O-(3-(2-(5,6,7,8-tetrahydro-1,8-naphthyridin-2-yl)ethyl)cyclobutyl)-homoserine.

In some embodiments, a composition, such as a pharmaceutical composition, is provided wherein the composition comprises a compound selected from the group consisting of one or more of the compounds depicted in Table 1, or a stereoisomer thereof (including a mixture of two or more stereoisomers thereof), or a salt thereof. In some embodiments, the composition comprises a compound selected from the group consisting of a salt of one or more of the compounds depicted in Table 1. In one aspect, the composition is a pharmaceutical composition that further comprises a pharmaceutically acceptable carrier.

In some embodiments, a composition, such as a pharmaceutical composition, is provided wherein the composition comprises a compound selected from the group consisting of one or more of the compounds depicted in Table 2, or a stereoisomer thereof (including a mixture of two or more stereoisomers thereof), or a salt thereof. In some embodiments, the composition comprises a compound selected from the group consisting of a salt of one or more of the compounds depicted in Table 2. In one aspect, the composition is a pharmaceutical composition that further comprises a pharmaceutically acceptable carrier.

The invention also includes all salts of compounds referred to herein, such as pharmaceutically acceptable salts. The invention also includes any or all of the stereochemical forms, including any enantiomeric or diastereomeric forms, and any tautomers or other forms of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also described and embraced by the invention. All forms of the compounds are also embraced by the invention, such as crystalline or non-crystalline forms of the compounds. It is also understood that prodrugs, solvates and metabolites of the compounds are embraced by this disclosure. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced. Where one or more tertiary amine moiety is present in the compound, the N-oxides are also provided and described.

Compounds described herein are αvβ6 integrin inhibitors. In some instances, it is desirable for the compound to inhibit other integrins in addition to αvβ6 integrin. In some embodiments, the compound inhibits αvβ6 integrin and one or more of αvβ1, αvβ3, αvβ5, α2β1, α3β1, α6β1 integrin, α7β1 and α11β1. In some embodiments, the compound inhibits αvβ6 integrin and αvβ1 integrin. In some embodiments, the compound inhibits αvβ6 integrin, αvβ3 integrin and αvβ5 integrin. In some embodiments, the compound inhibits αvβ6 integrin and α2β1 integrin. In some embodiments, the compound inhibits αvβ6 integrin, α2β1 integrin and α3β1 integrin. In some embodiments, the compound inhibits αvβ6 integrin and α6β1 integrin. In some embodiments, the compound inhibits αvβ6 integrin and α7β1 integrin. In some embodiments, the compound inhibits αvβ6 integrin and α11β1 integrin.

In some instances, it is desirable to avoid inhibition of other integrins. In some embodiments, the compound is a selective αvβ6 integrin inhibitor. In some embodiments, the compound does not inhibit substantially α4β1, αvβ8 and/or α2β3 integrin. In some embodiments, the compound inhibits αvβ6 integrin but does not inhibit substantially α4β1 integrin. In some embodiments, the compound inhibits αvβ6 integrin but does not inhibit substantially αvβ8 integrin. In some embodiments, the compound inhibits αvβ6 integrin but does not inhibit substantially α2β3 integrin. In some embodiments, the compound inhibits αvβ6 integrin but does not inhibit substantially the αvβ8 integrin and the α4β1 integrin.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of the formula (I) or variations thereof described herein, where one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2$H, $^3$H, $^{11}$C, $^{13}$C, $^{14}$C, $^{13}$N, $^{15}$O, $^{17}$O, $^{32}$P, $^{35}$S, $^{18}$F, $^{36}$Cl. Incorporation of heavier isotopes such as deuterium ($^2$H or D) can afford certain therapeutic advantages resulting from greater metabolic stability, for example, increased in vivo half-life, or reduced dosage requirements and, hence may be preferred in some instances. In some embodiments, provided herein is an isotopically enriched form of any of the formulae described herein, wherein the compound comprises one or more deuterium atoms. In some embodiments, the compounds of formula (I) may have one or more of the hydrogen atoms replaced by deuterium, such as any of the hydrogens in one or more of the moieties G, $L^1$, $L^2$, Y, $L^3$, and $R^1$.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound.

Articles of manufacture comprising a compound of the invention, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms.

GENERAL SYNTHETIC METHODS

The compounds of the invention may be prepared by a number of processes as generally described below and more specifically in the Examples hereinafter (such as the schemes provides in the Examples below). In the following process descriptions, the symbols when used in the formulae depicted are to be understood to represent those groups described above in relation to the formulae herein.

Where it is desired to obtain a particular stereoisomer of a compound, this may be accomplished from a corresponding mixture of stereoisomers using any suitable conventional procedure for separating stereoisomers or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular stereoisomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

Compounds provided herein may be prepared according to General Schemes A, B, C, D-2, E-2, F-2, G-2, and H; Schemes D-1, E-1, F-1, and G-1; General Procedures A, B, C, D, E, F, G, H, I, J, K, L, M, N, O, P, Q, and R; and Examples 1-226.

Compounds of formula 18A can be prepared according to General Scheme A, wherein G, $R^2$, and $R^3$ are as defined for formula (I), or any applicable variations detailed herein; $X^1$ is a leaving group (e.g., —OH, —Cl,

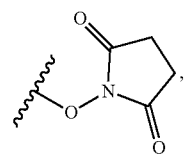 [SMILES: *ON1C(=O)CCC1=O]

and the like); and $X^2$ is another leaving group (e.g., —Cl, —Br, —I, —OTf, and the like).

General Scheme A

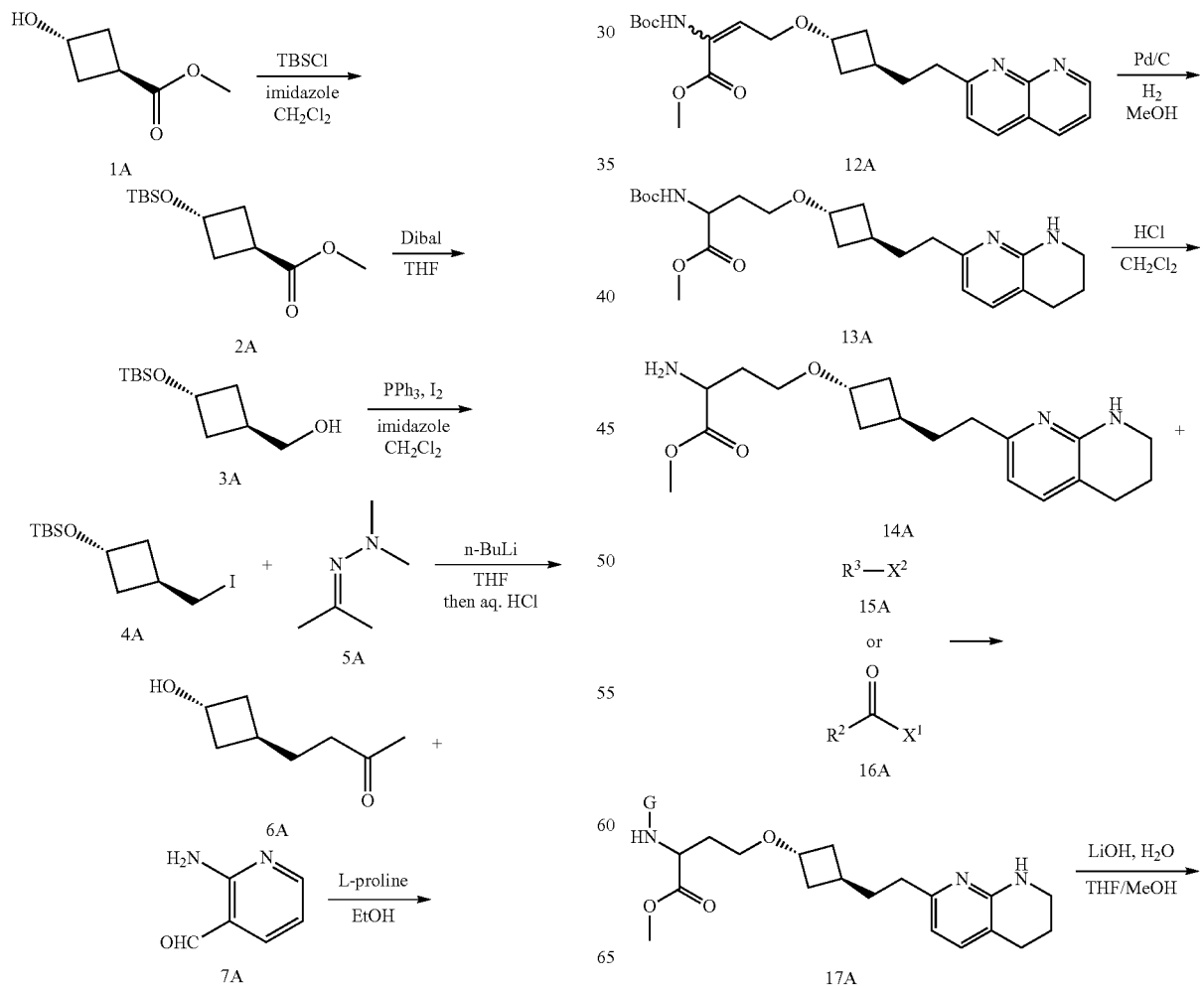

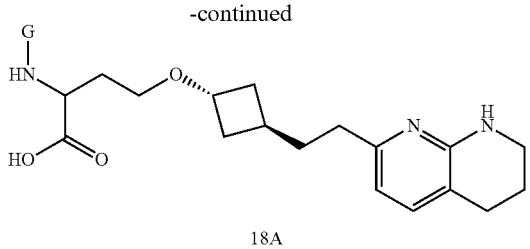

18A

Silylation of compound 1A gives compound 2A, which can be reduced with a suitable reducing agent to give compound 3A. Iodination of 3A gives compound 4A, which can be alkylated with compound 5A under basic conditions to give compound 6A. Condensation of compound 6A with compound 7A in the presence of an appropriate catalyst gives compound 8A, which can be alkylated with an alkyl halide to give compound 9A. Oxidative cleavage of 9A gives compound 10A, which can be treated with compound 11A under basic conditions to afford compound 12A. Reduction of compound 12A gives compound 13A, which can be exposed to an appropriate acid to give compound 14A. Coupling of compound 14A with compound of formula 15A or 16A gives rise to compound 17A, which can be hydrolyzed in the presence of a suitable hydroxide source to give compound 18A.

Reaction conditions for the transformations of General Scheme A are provided in the General Procedures that follow, in particular General Procedures D, E, F, H, I, K, and N. Exemplary reaction conditions for the transformations of General Scheme A are provided in General Procedure A, omitting the chiral separation step at the end of General Procedure A.

Compounds of formula 18B can be prepared according to General Scheme B, wherein G, $R^2$, and $R^3$ are as defined for formula (I), or any applicable variations detailed herein; $X^1$ is a leaving group (e.g., —OH, —Cl,

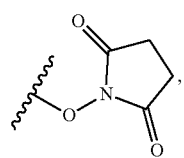 [SMILES: *ON1C(=O)CCC1=O]

and the like); and $X^2$ is another leaving group (e.g., —Cl, —Br, —I, —OTf, and the like).

General Scheme B

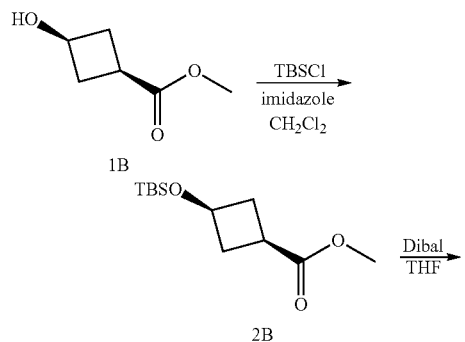

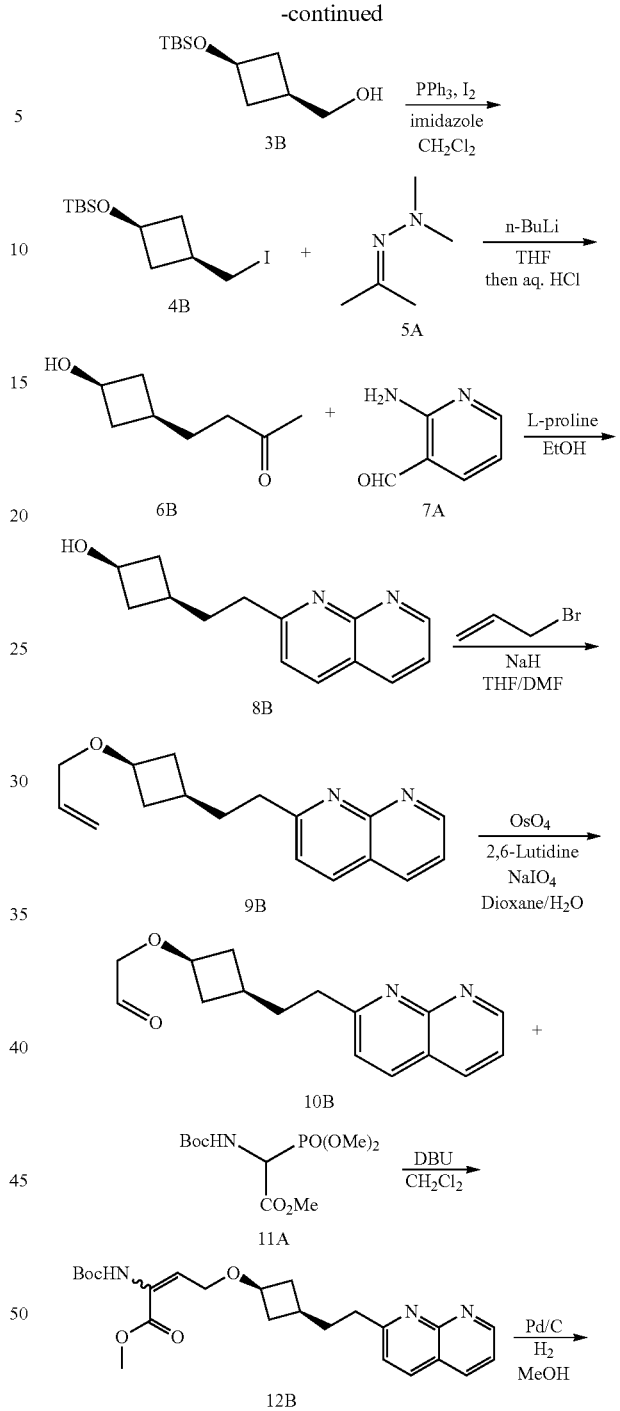

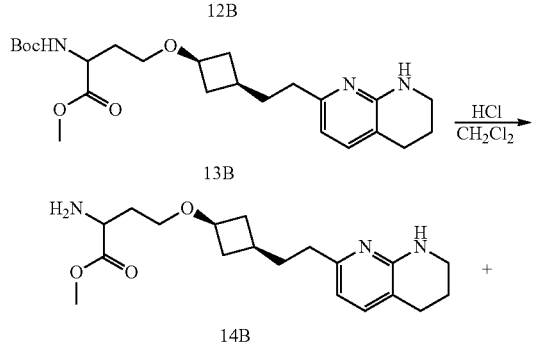

191

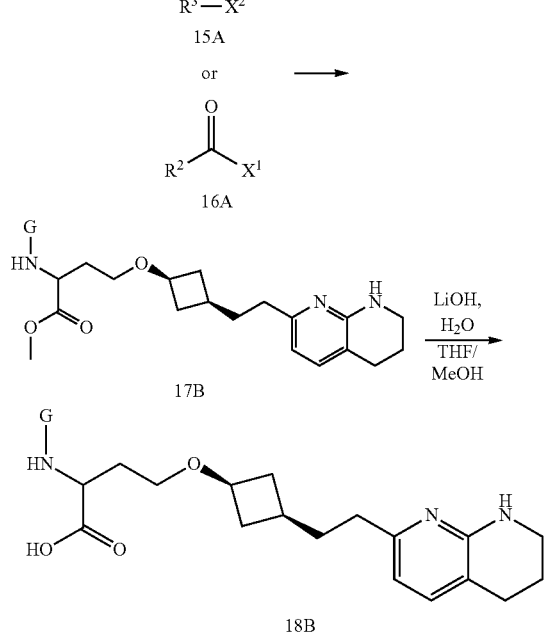

192

General Scheme C

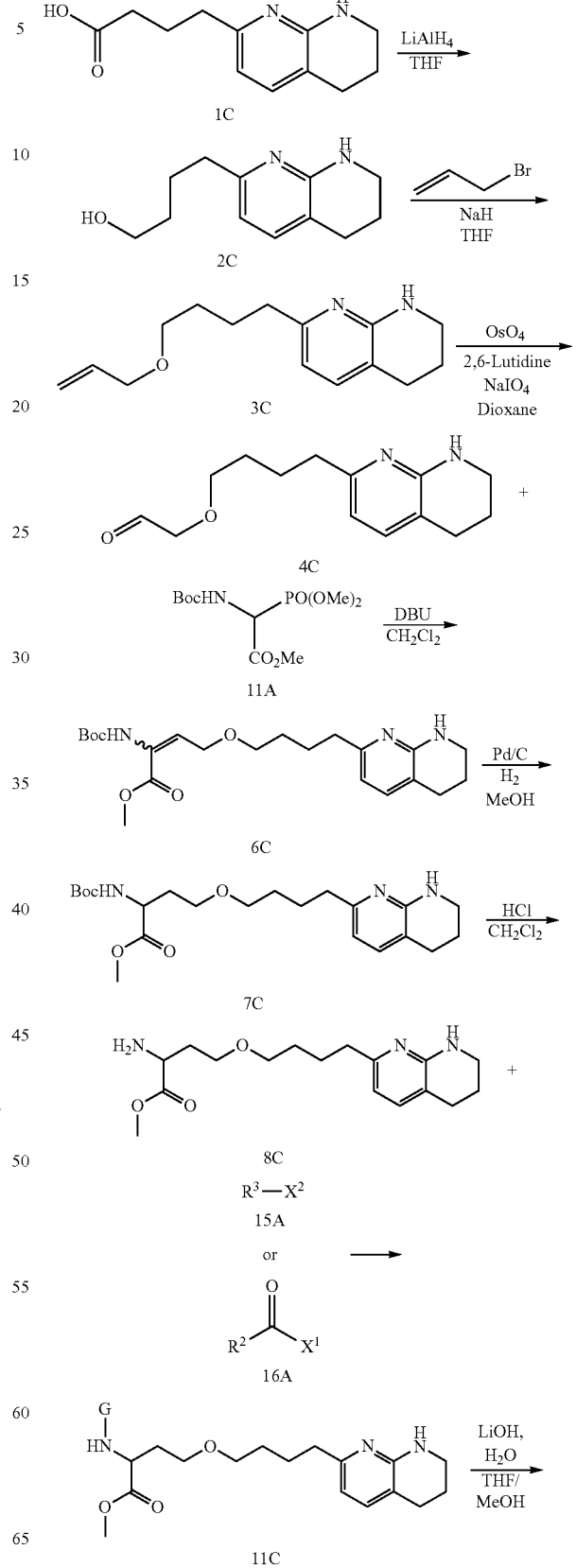

Silylation of compound B gives compound 210, which can be reduced with a suitable reducing agent to give compound 3B. Iodination of 3B gives compound 413, which can be alkylated with compound 5A under basic conditions to give compound 6B. Condensation of compound 6B with compound 7A in the presence of an appropriate catalyst gives compound 8b, which can be alkylated with an alkyl halide to give compound 9B. Oxidative cleavage of 9B gives compound 10B, which can be treated with compound 11A under basic conditions to afford compound 12B. Reduction of compound 12B gives compound 13B, which can be exposed to an appropriate acid to give compound 14B. Coupling of compound 14B with compound of formula 15A or 16A gives rise to compound 17B, which can be hydrolyzed in the presence of a suitable hydroxide source to give compound 18B.

Reaction conditions for the transformations of General Scheme B are provided in the General Procedures that follow in particular General Procedures D, E, F, H, I, K, and N. Exemplary reaction conditions for the transformations of General Scheme B are provided in General Procedure B, omitting the chiral separation step at the end of General Procedure B.

Compounds of formula 12C can be prepared according to General Scheme C, wherein G, $R^2$ and $R^3$ are as defined for formula (I), or any applicable variations detailed herein; $X^1$ is a leaving group (e.g., —OH, —Cl,

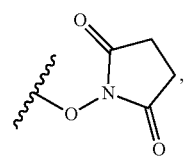 [SMILES: *ON1C(=O)CCC1=O]

and the like); and $X^2$ is another leaving group (e.g., —Cl, —Br, —I, —OTf, and the like).

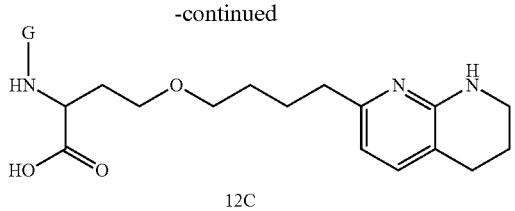

12C

Reduction of compound 1C gives compound 2C, which can be alkylated with an alkyl halide to give compound 3C. Oxidative cleavage of 3C gives compound 4C, which can be treated with compound 11A under basic conditions to afford compound 6C. Reduction of compound 6C gives compound 7C, which can be exposed to an appropriate acid to give compound 8C. Coupling of compound 8C with compound of formula 15A or 16A gives rise to compound of formula 11C, which can be hydrolyzed in the presence of a suitable hydroxide source to give compound 12C.

Reaction conditions for the transformations of General Scheme C are provided in the General Procedures that follow, in particular General Procedures D, E, F, H, I, K, and N. Exemplary reaction conditions for the transformations of General Scheme C are provided in General Procedure C, omitting the chiral separation step at the end of General Procedure C.

Compounds of formula 18D can be prepared according to Scheme D-1 followed by General Scheme D-2, wherein G, $R^2$ and $R^3$ are as defined for formula (I), or any applicable variations detailed herein; $X^1$ is a leaving group (e.g., —OH, —Cl,

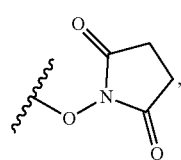 [SMILES: *ON1C(=O)CCC1=O]

and the like); and $X^2$ is another leaving group (e.g., —Cl, —Br, —I, —OTf, and the like).

Scheme D-1

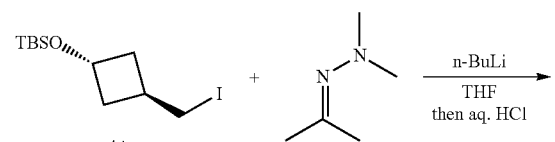

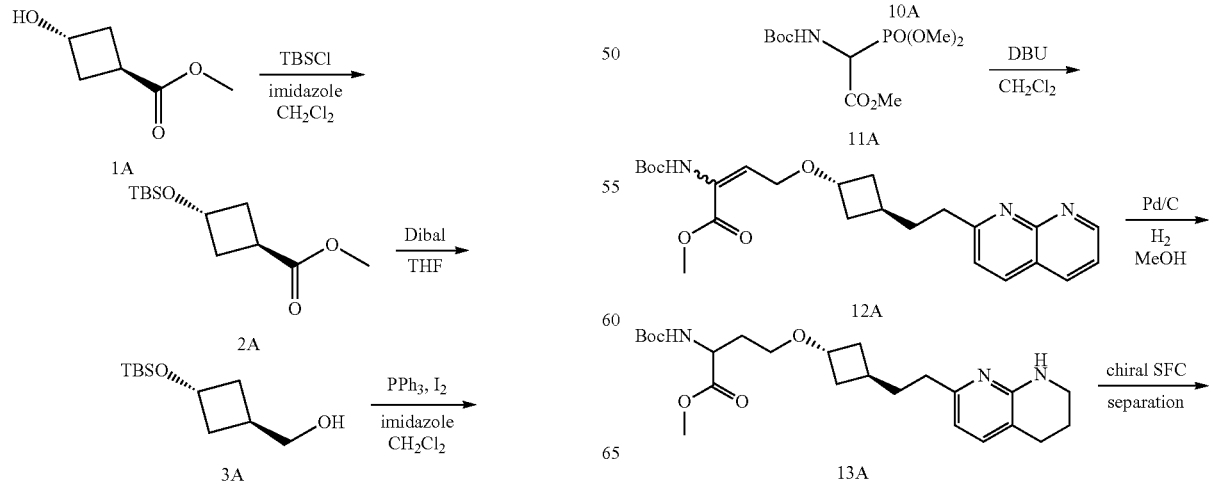

-continued

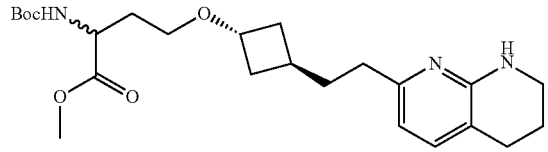

first eluting isomer
Isomer D1

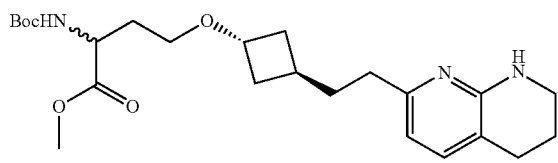

second eluting isomer
Isomer D2

Silylation of compound 1A gives compound 2A, which can be reduced with a suitable reducing agent to give compound 3A. Iodination of 3A gives compound 4A, which can be alkylated with compound 5A under basic conditions to give compound 6A. Condensation of compound 6A with compound 7A in the presence of an appropriate catalyst gives compound 8A, which can be alkylated with an alkyl halide to give compound 9A. Oxidative cleavage of 9A gives compound 10A, which can be treated with compound 11A under basic conditions to afford compound 12A. Reduction of compound 12A gives compound 13A, which can be separated using chiral SFC to afford Isomer D1 and Isomer D2.

General Scheme D-2

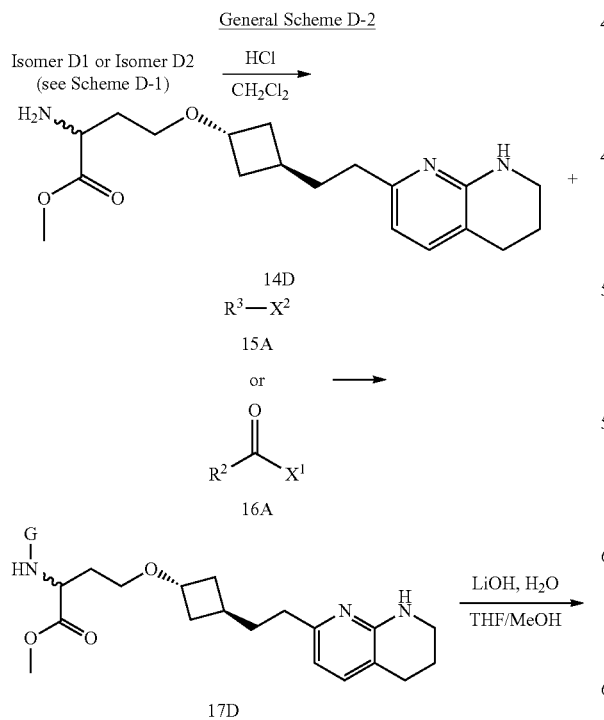

-continued

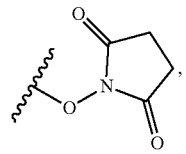 [SMILES: *ON1C(=O)CCC1=O]

18D

Exposure of Isomer D1 (i.e., first eluting isomer from Scheme D-1) or Isomer D2 (i.e., second eluting isomer from Scheme D-1) to an appropriate acid gives compound 14D, wherein the wavy line in compound 14D refers to the isomer obtained when either Isomer D1 or Isomer D2 is reacted. Coupling of compound 14D with compound of formula 15A or 16A gives rise to compound 17D, which can be hydrolyzed in the presence of a suitable hydroxide source to give compound 18D.

Reaction conditions for the transformations of General Scheme D-2 are provided in the General Procedures that follow, in particular General Procedures D, E, F, H, I, K, and N. Exemplary reaction conditions for the transformations of Scheme D-1 are provided in General Procedure A.

Compounds of formula 18E can be prepared according to Scheme E-1 followed by General Scheme E-2, wherein G, $R^2$ and $R^3$ are as defined for formula (I), or any applicable variations detailed herein; $X^1$ is a leaving group (e.g., —OH, —Cl, and the like); and $X^2$ is another leaving group (e.g., —Cl, —Br, —I, —OTf, and the like).

Scheme E-1

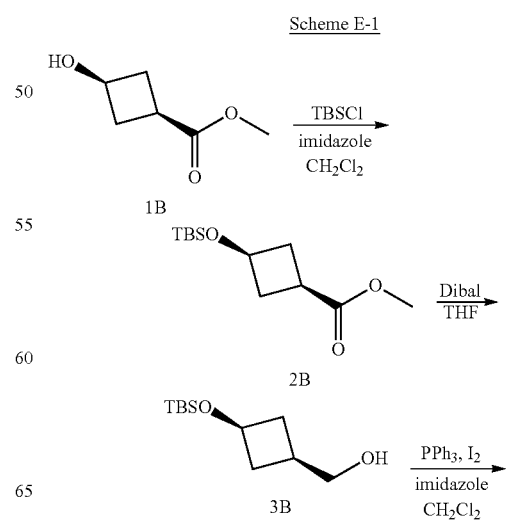

197
-continued

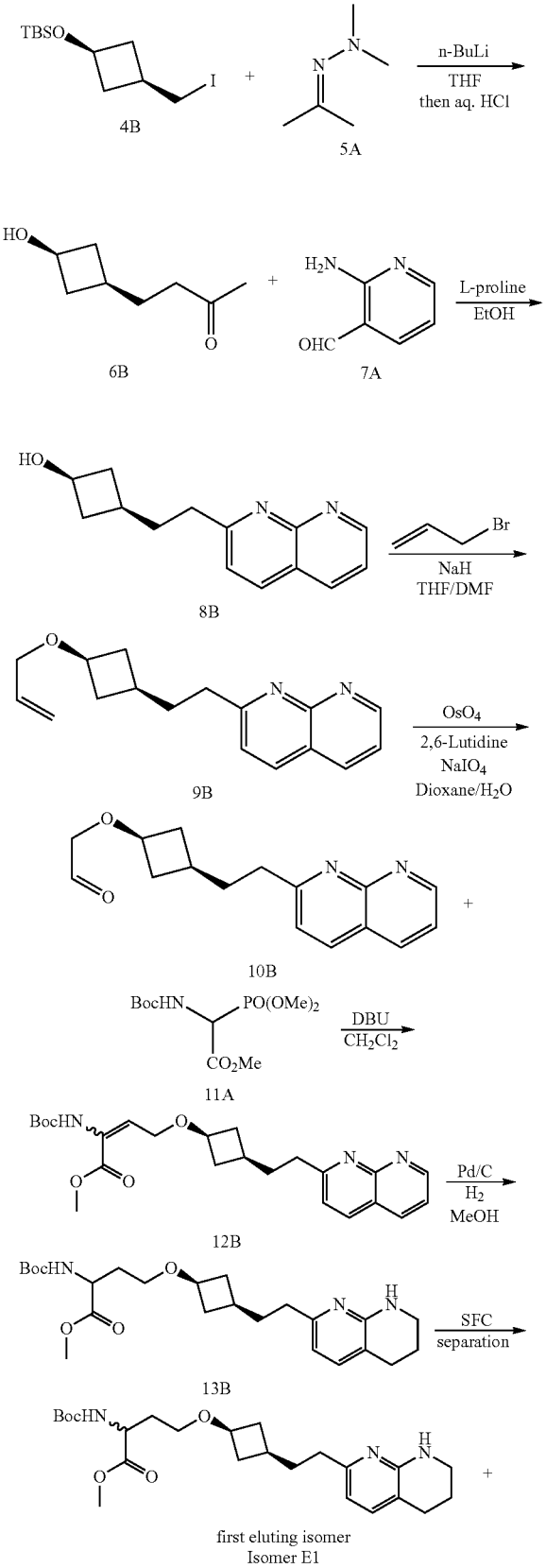

198
-continued

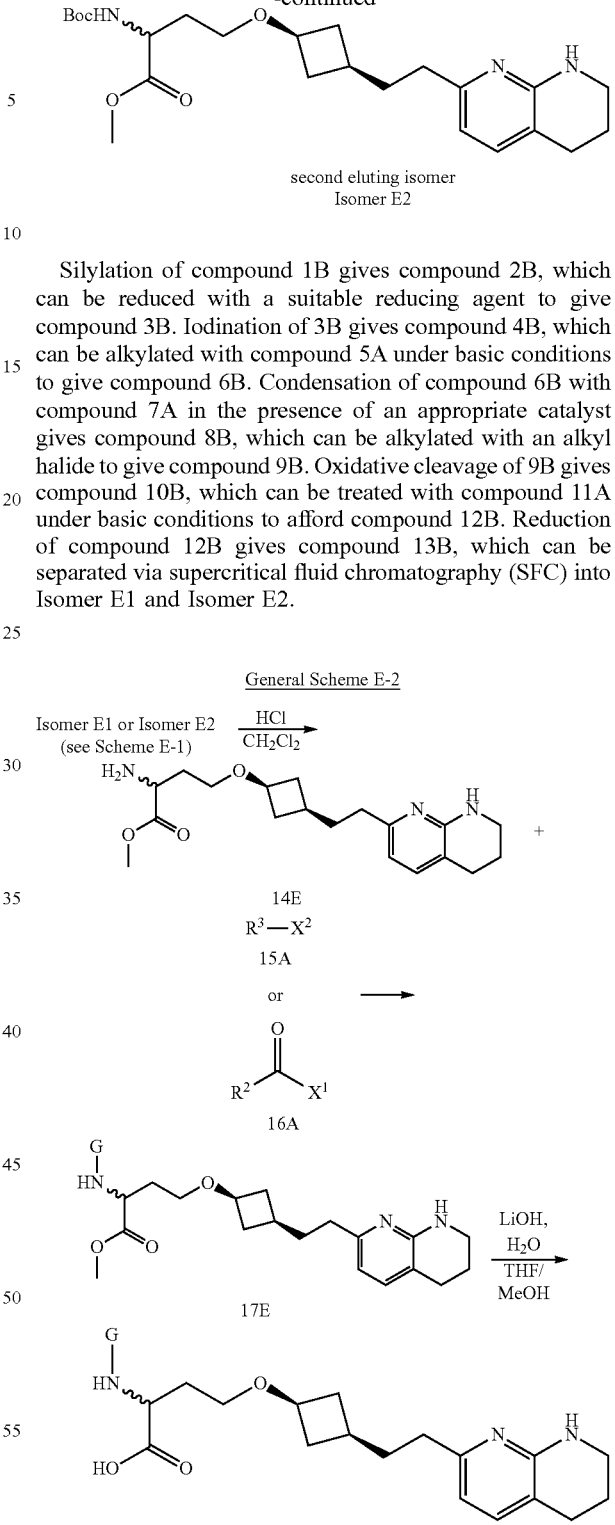

Silylation of compound 1B gives compound 2B, which can be reduced with a suitable reducing agent to give compound 3B. Iodination of 3B gives compound 4B, which can be alkylated with compound 5A under basic conditions to give compound 6B. Condensation of compound 6B with compound 7A in the presence of an appropriate catalyst gives compound 8B, which can be alkylated with an alkyl halide to give compound 9B. Oxidative cleavage of 9B gives compound 10B, which can be treated with compound 11A under basic conditions to afford compound 12B. Reduction of compound 12B gives compound 13B, which can be separated via supercritical fluid chromatography (SFC) into Isomer E1 and Isomer E2.

Exposure of Isomer E1 (i.e., first eluting isomer from Scheme E-1) or Isomer E2 (i.e., second eluting isomer from Scheme E-1) to an appropriate acid gives compound 14E, wherein the wavy line in compound 14E refers to the isomer obtained when either Isomer E1 or Isomer E2 is reacted. Coupling of compound 14E with compound of formula 15A or 16A gives rise to compound 17E, which can be hydrolyzed in the presence of a suitable hydroxide source to give compound 18E.

Reaction conditions for the transformations of General Scheme E-2 are provided in the General Procedures that follow, in particular General Procedures D, E, F, H, I, K, and N. Exemplary reaction conditions for the transformations of Scheme E-1 are provided in General Procedure B.

Compounds of formula 12F can be prepared according to Scheme F-1 followed by General Scheme F-2, wherein G, $R^2$ and $R^3$ are as defined for formula (I), or any applicable variations detailed herein; $X^1$ is a leaving group (e.g., —OH, —Cl,

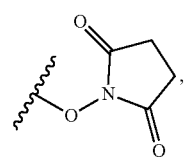 [SMILES: *ON1C(=O)CCC1=O]

and the like); and $X^2$ is another leaving group (e.g., —Cl, —Br, —I, —OTf, and the like).

Scheme F-1

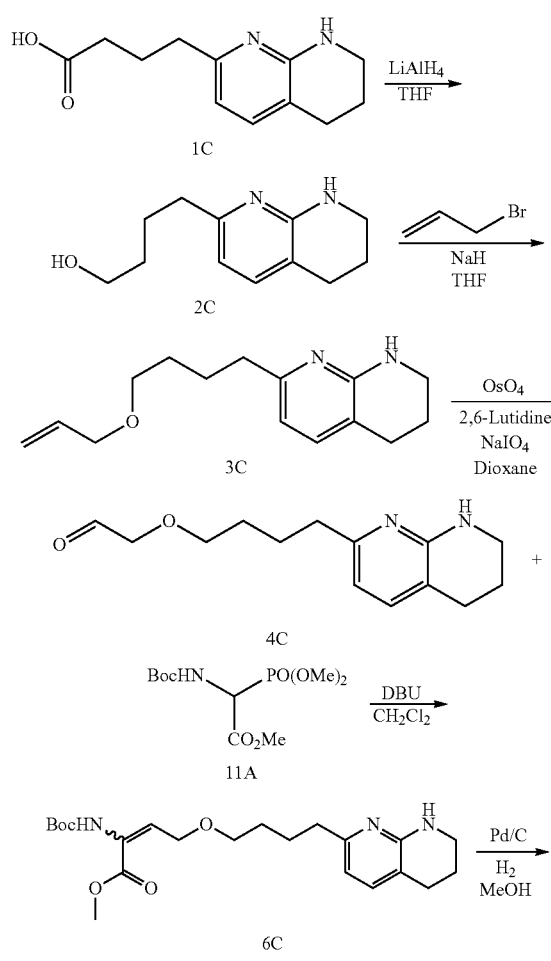

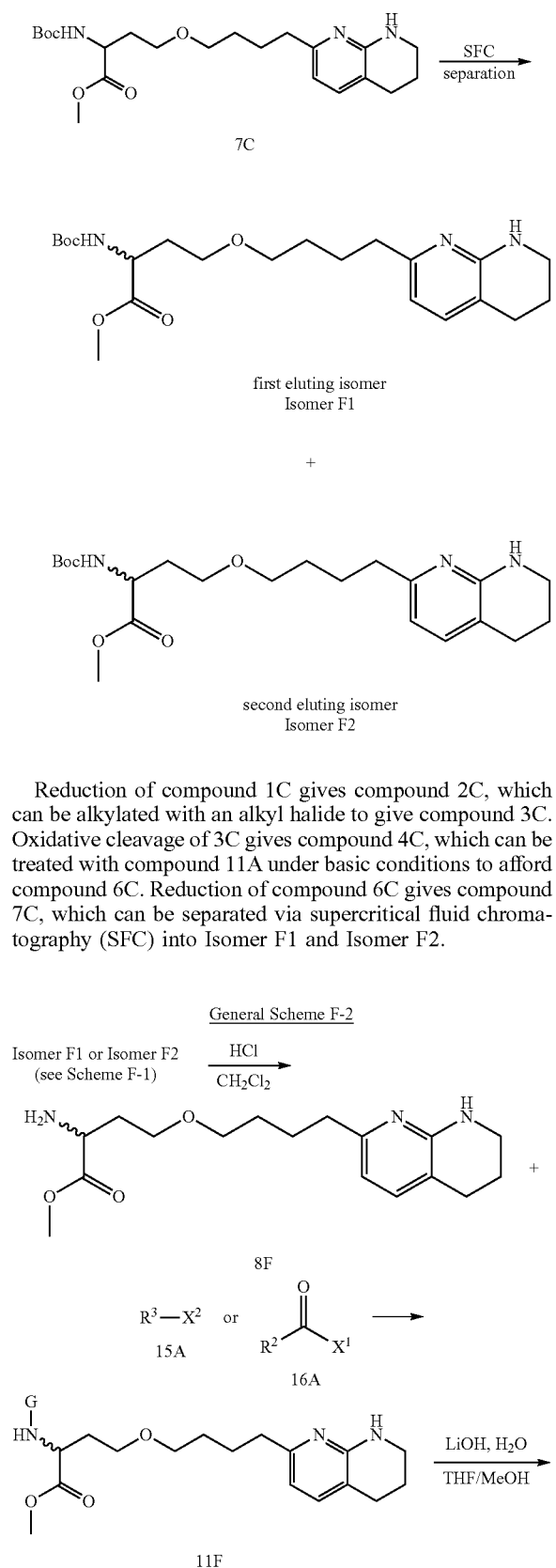

Reduction of compound 1C gives compound 2C, which can be alkylated with an alkyl halide to give compound 3C. Oxidative cleavage of 3C gives compound 4C, which can be treated with compound 11A under basic conditions to afford compound 6C. Reduction of compound 6C gives compound 7C, which can be separated via supercritical fluid chromatography (SFC) into Isomer F1 and Isomer F2.

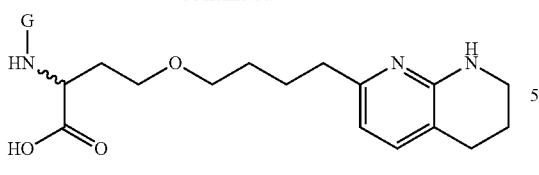

12F

Exposure of Isomer F1 (i.e., first eluting isomer from Scheme F-1) or Isomer F2 (i.e., second eluting isomer from Scheme F-1) to an appropriate acid gives compound 8F, wherein the wavy line in compound 8F refers to the isomer obtained when either Isomer F1 or Isomer F2 is reacted. Coupling of compound 8F with compound of formula 15A or 16A gives rise to compound of formula 11F, which can be hydrolyzed in the presence of a suitable hydroxide source to give compound 12F.

Reaction conditions for the transformations of General Scheme F-2 are provided in the General Procedures that follow, in particular General Procedures D, E, F, H, I, K, and N. Exemplary reaction conditions for the transformations of Scheme F-1 are provided in General Procedure C.

Compounds of formula 18G can be prepared according to Scheme G-1 followed by General Scheme G-2, wherein G, $R^2$ and $R^3$ are as defined for formula (I), or any applicable variations detailed herein; $X^1$ is a leaving group (e.g., —OH, —Cl,

and the like); and $X^2$ is another leaving group (e.g., —Cl, —Br, —I, —OTf, and the like).

Scheme G-1

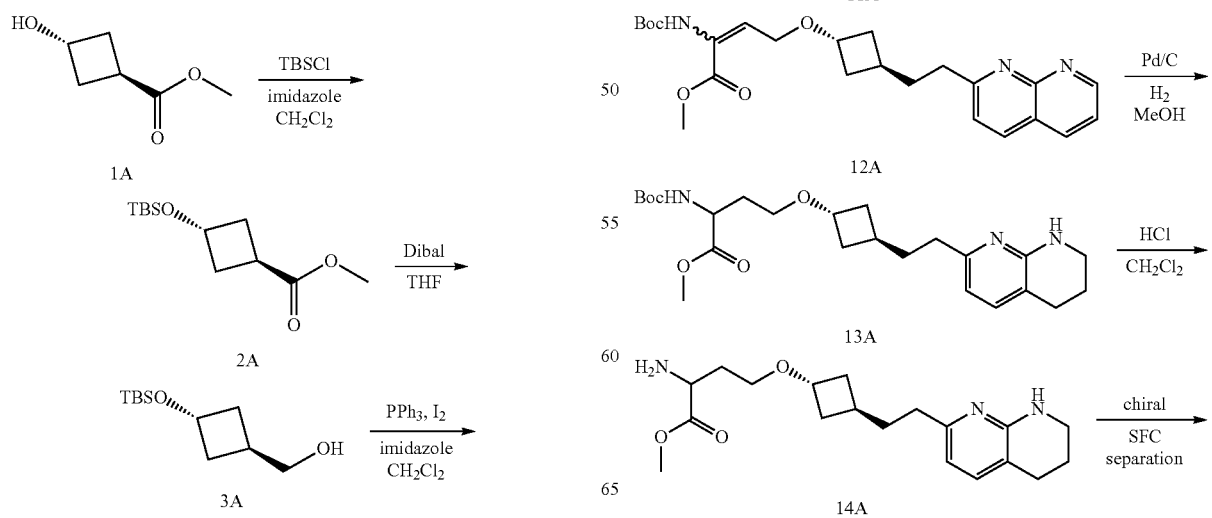

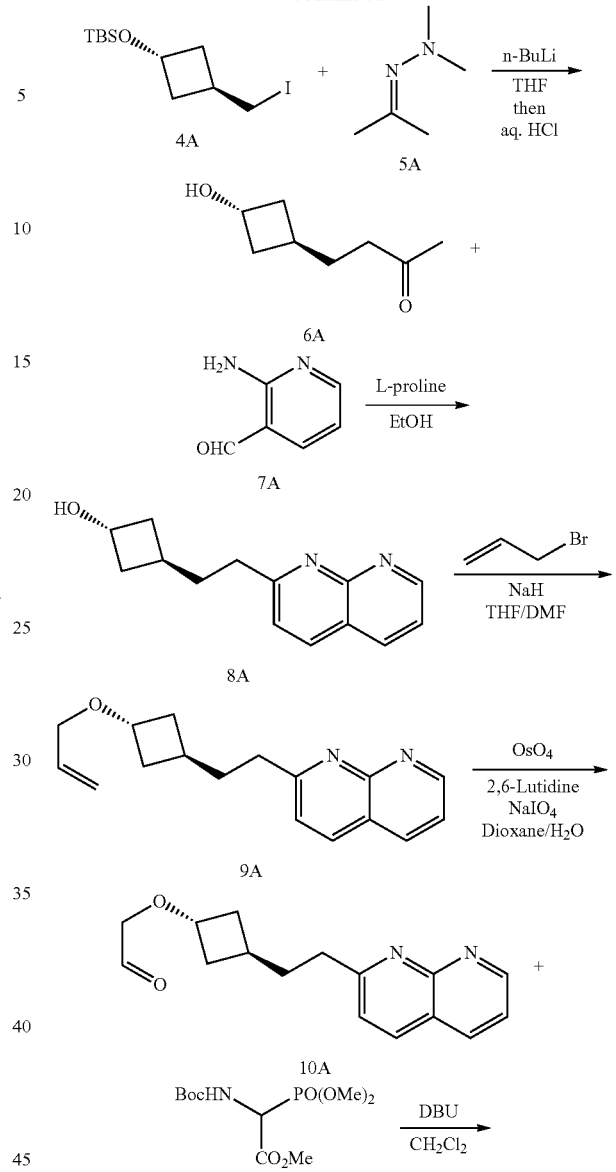

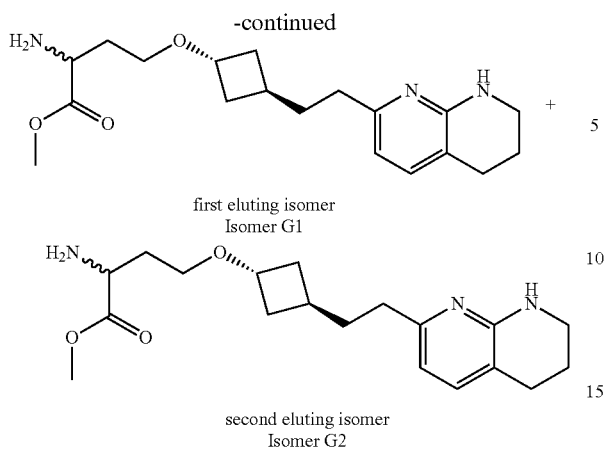

first eluting isomer
Isomer G1 second eluting isomer
Isomer G2

Silylation of compound 1A gives compound 2A, which can be reduced with a suitable reducing agent to give compound 3A. Iodination of 3A gives compound 4A, which can be alkylated with compound 5A under basic conditions to give compound 6A. Condensation of compound 6A with compound 7A in the presence of an appropriate catalyst gives compound 8A, which can be alkylated with an alkyl halide to give compound 9A. Oxidative cleavage of 9A gives compound 10A, which can be treated with compound 11A under basic conditions to afford compound 12A. Reduction of compound 12A gives compound 13A, which can be exposed to an appropriate acid to give compound 14A. Compound 14A can be separated using chiral SFC to afford Isomer G1 and Isomer G2.

General Scheme G-2

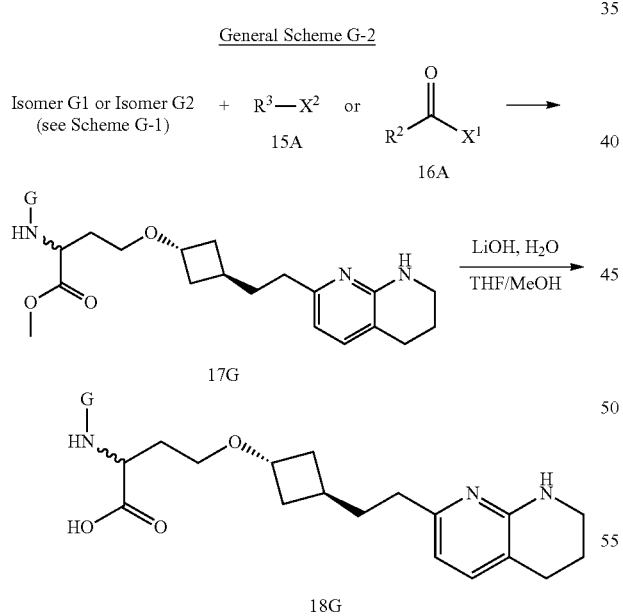

Coupling of Isomer G1 (i.e., first eluting isomer from Scheme G-1) or Isomer G2 (i.e., second eluting isomer from Scheme G-1) with compound of formula 15A or 16A gives compound 17G, wherein the wavy line in compound 17G refers to the isomer obtained when either Isomer G1 or Isomer G2 is reacted. Compound 17G can be hydrolyzed in the presence of a suitable hydroxide source to give compound 18G.

Reaction conditions for the transformations of Scheme G-1 and General Scheme G-2 are provided in the General Procedures that follow, in particular General Procedures D, E, F, H, I, K, and N. Exemplary reaction conditions for the transformations of Scheme G-1 are provided in General Procedure A.

Compounds of formula 18H can be prepared according to General Scheme H, wherein G, $R^2$ and $R^3$ are as defined for formula (I), or any applicable variations detailed herein; $X^1$ is a leaving group (e.g., —OH, —Cl,

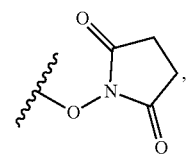 [SMILES: *ON1C(=O)CCC1=O]

and the like); and $X^2$ is another leaving group (e.g., —Cl, —Br, —I, —OTf, and the like).

General Scheme H

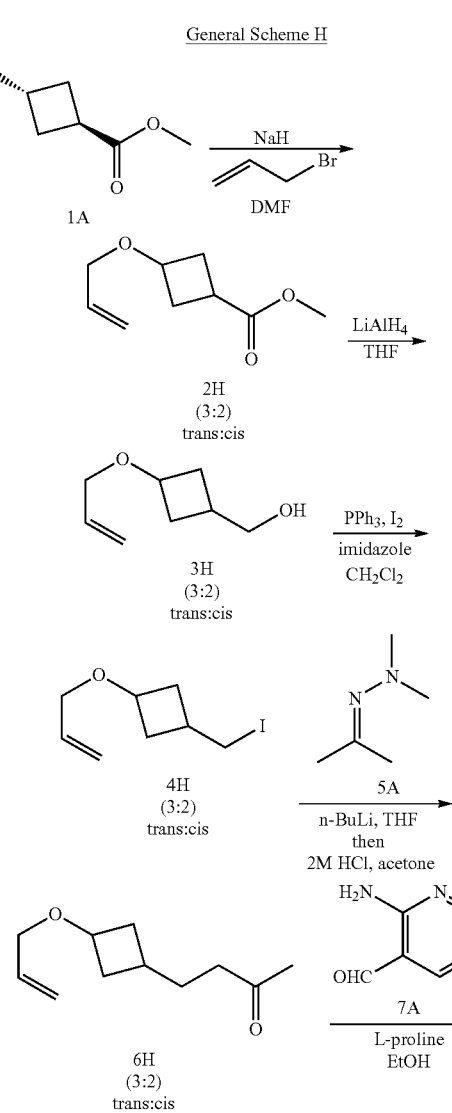

-continued

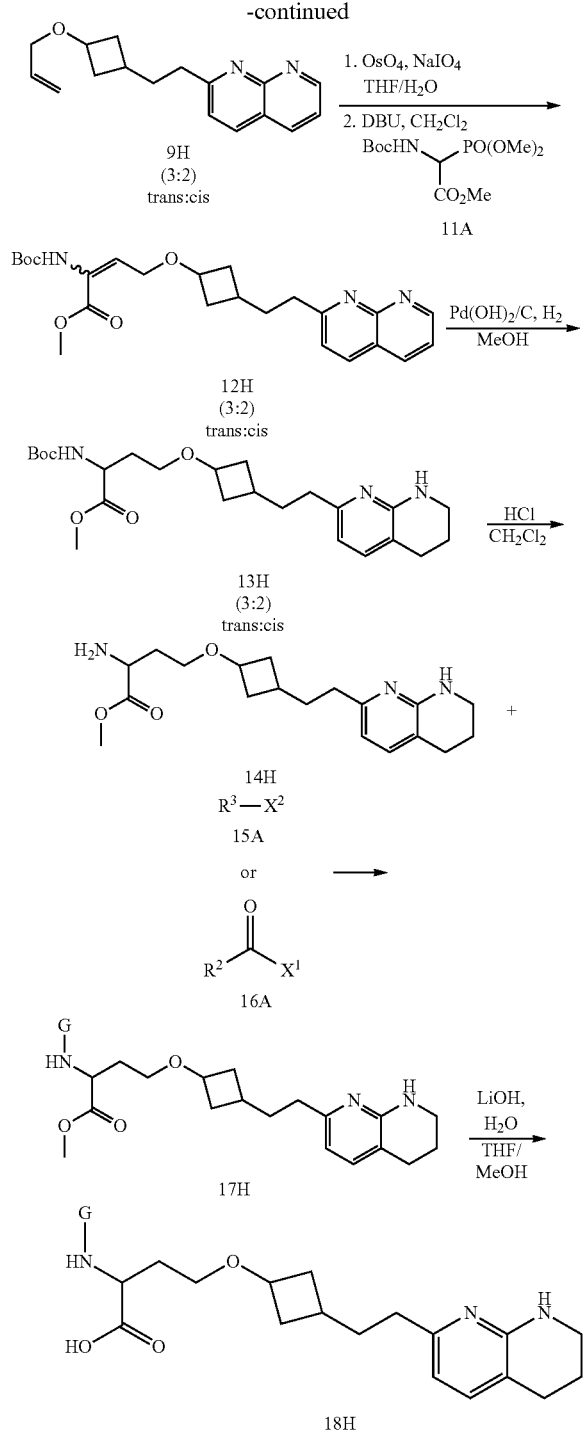

appropriate acid to give compound 14H. Coupling of compound 14H with compound of formula 15A or 16A gives rise to compound 17H, which can be hydrolyzed in the presence of a suitable hydroxide source to give compound 18H.

Reaction conditions for the transformations of General Scheme H are provided in the General Procedures that follow, in particular General Procedures D, E, F, H, I, K, and N.

It is understood that the schemes above may be modified to arrive at various compounds of the invention by selection of appropriate reagents and starting materials. For a general description of protecting groups and their use, see P. G. M. Wuts and T. W. Greene, Greene's Protective Groups in Organic Synthesis 4$^{th}$ edition, Wiley-Interscience, New York, 2006.

Additional methods of preparing compounds according to formula (I), and salts thereof, are provided in the Examples. As a skilled artisan would recognize, the methods of preparation taught herein may be adapted to provide additional compounds within the scope of formula (I), for example, by selecting starting materials which would provide a desired compound.

Pharmaceutical Compositions and Formulations

Pharmaceutical compositions of any of the compounds detailed herein, including compounds of the formulae (I), (IIa), (IIb), (IIIa), (IIIb), (IVa), (IVb), (Va), (Va-1), (Va-2), (Vb), (Vb-1), and (Vb-2), or a salt thereof, or compounds depicted in Table 1, or a salt thereof, or mixtures thereof, are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation. In one embodiment, the pharmaceutical composition are prepared from mixtures of any of the compounds detailed herein, or salts thereof. In one embodiment, the pharmaceutical composition is a composition for controlled release of any of the compounds detailed herein.

Pharmaceutical compositions of any of the compounds detailed herein, including compounds of the formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (1-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (1-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound of Table 1 or Table 2, or any one of compounds 1-329; or a salt thereof, or mixtures thereof, are also embraced by this invention.

A compound as detailed herein may in one aspect be in a purified form and compositions comprising a compound in purified forms are detailed herein. In one embodiment, compositions may have no more than 35% impurity, wherein the impurity denotes a compound other than the compound comprising the majority of the composition or a salt thereof, Allylation of compound 1A gives compound 2H, which can be reduced with a suitable reducing agent to give compound 3H. Iodination of 3H gives compound 4H, which can be alkylated with compound 5A under basic conditions to give compound 6H. Condensation of compound 6H with compound 7A in the presence of an appropriate catalyst gives compound 9H, which can be alkylated with an alkyl halide to give compound 9H. Oxidative cleavage of 9H followed by treating with compound 1 IA under basic conditions affords compound 12H. Reduction of compound 12H gives compound 13H, which can be exposed to an for example, a composition of a compound selected from a compound of Table 1 may contains no more than 35% impurity, wherein the impurity denotes a compound other than the compound of Table 1 or a salt thereof. In one embodiment, compositions may contain no more than 25% impurity. In one embodiment, compositions may contains no more than 20% impurity. In still further embodiments, compositions comprising a compound as detailed herein or a salt thereof are provided as compositions of substantially pure compounds. "Substantially pure" compositions comprise no more than 10% impurity, such as a composition comprising less than 9%, 7%, 5%, 3%, 1%, or 0.5% impurity. In some embodiments, a composition containing a compound as detailed herein or a salt thereof is in substantially pure form. In still another variation, a composition of substantially pure compound or a salt thereof is provided wherein the composition contains or no more than 10% impurity. In a further variation, a composition of substantially pure compound or a salt thereof is provided wherein the composition contains or no more than 9% impurity. In a further variation, a composition of substantially pure compound or a salt thereof is provided wherein the composition contains or no more than 7% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 10% or preferably no more than 5% or more preferably no more than 3% or even more preferably no more than 1% impurity or most preferably no more than 0.5% impurity, which impurity may be the compound in a different stereochemical form. For instance, a composition of substantially pure (S) compound means that the composition contains no more than 10% or no more than 5% or no more than 3% or no more than 1% or no more than 0.5% of the (R) form of the compound.

In further embodiments, the purified forms and substantially pure forms of the compounds apply to any compounds of the formulae (I), (IIa), (IIb), (IIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound of Table 1 or Table 2, or any one of compounds 1-329.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, $21^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound and a pharmaceutically acceptable carrier or excipient. In another variation, a composition of substantially pure compound is provided. In some embodiments, the composition is for use as a human or veterinary medicament. In some embodiments, the composition is for use in a method described herein. In some embodiments, the composition is for use in the treatment of a disease or disorder described herein.

Methods of Use

Compounds and compositions of the invention, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

In one aspect, provided is a method of treating a fibrotic disease in an individual in need thereof comprising administering to the individual a therapeutically effective amount of a compound of formula (I), or any variation thereof, e.g., a compound of formula (I), (IIa), (IIb), (IIIa), (IIIb), (IVa), (IVb), (Va), (Va-1), (Va-2), (Vb), (Vb-1), or (Vb-2), a compound selected from the compounds depicted in Table 1, or a stereoisomer thereof, or a pharmaceutically acceptable salt thereof. In one aspect, the individual is a human. The individual, such as a human, may be in need of treatment, such as a human who has or is suspected of having a fibrotic disease. In one embodiment, a variation of the compounds includes any stereoisomer thereof.

In a further aspect, provided is a method of treating a fibrotic disease in an individual in need thereof comprising administering to the individual a therapeutically effective amount of a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof. In one aspect, the individual is a human. The individual, such as a human, may be in need of treatment, such as a human who has or is suspected of having a fibrotic disease. In one embodiment, a variation of the compounds includes any stereoisomer thereof.

In another aspect, provided is a method of delaying the onset and/or development of a fibrotic disease in an individual (such as a human) who is at risk for developing a fibrotic disease. It is appreciated that delayed development may encompass prevention in the event the individual does not develop the fibrotic disease. An individual at risk of developing a fibrotic disease in one aspect has or is suspected of having one or more risk factors for developing a fibrotic disease. Risk factors for fibrotic disease may include an individual's age (e.g., middle-age or older adults), the presence of inflammation, having one or more genetic component associated with development of a fibrotic disease, medical history such as treatment with a drug or procedure believed to be associated with an enhanced susceptibility to fibrosis (e.g., radiology) or a medical condition believed to be associated with fibrosis, a history of smoking, the presence of occupational and/or environmental factors such as exposure to pollutants associated with development of a fibrotic disease. In some embodiments, the individual at risk for developing a fibrotic disease is an individual who has or is suspected of having NAFLD, NASH, CKD, scleroderma, Crohn's Disease, NSIP, PSC, PBC, or is an individual who has had or is suspected of having had a myocardial infarction.

In some embodiments, the fibrotic disease is fibrosis of a tissue such as the lung (pulmonary fibrosis), the liver, the skin, the heart (cardiac fibrosis), the kidney (renal fibrosis), or the gastrointestinal tract (gastrointestinal fibrosis).

In some embodiments, the fibrotic disease is pulmonary fibrosis (such as IPF), liver fibrosis, skin fibrosis, scleroderma, cardiac fibrosis, renal fibrosis, gastrointestinal fibrosis, primary sclerosing cholangitis, or biliary fibrosis (such as PBC).

In some embodiments, the fibrotic disease is a pulmonary fibrosis, e.g., idiopathic pulmonary fibrosis (IPF), interstitial lung disease, systemic sclerosis-associated interstitial lung disease, or radiation-induced pulmonary fibrosis. In some embodiments, the individual at risk for developing a fibrotic disease is an individual who has or is suspected of having a history of viral lung infections.

In some embodiments, the fibrotic disease is a primary sclerosing cholangitis, or biliary fibrosis.

In some embodiments, the fibrotic disease is fibrotic nonspecific interstitial pneumonia (NSIP).

In some embodiments, the fibrotic disease is a liver fibrosis, e.g., infectious liver fibrosis (from pathogens such as HCV, HBV or parasites such as schistosomiasis), NASH, alcoholic liver disease induced fibrosis, alcoholic steatosis induced liver fibrosis, nonalcoholic fatty liver disease, and cirrhosis.

In some embodiments, the fibrotic disease is biliary tract fibrosis.

In some embodiments, the fibrotic disease is renal fibrosis, e.g., diabetic kidney disease, diabetic nephrosclerosis, hypertensive nephrosclerosis, diabetic nephropathy, focal segmental glomerulosclerosis ("FSGS"), Alport syndrome, chronic kidney disease, and acute kidney injury from contrast induced nephropathy.

In some embodiments, the fibrotic disease is systemic and local sclerosis or scleroderma, keloids and hypertrophic scars, or post surgical adhesions.

In some embodiments, the fibrotic disease is atherosclerosis or restenosis.

In some embodiments, the fibrotic disease is a gastrointestinal fibrosis, e.g., Crohn's disease.

In some embodiments, the fibrotic disease is cardiac fibrosis, e.g., post myocardial infarction induced fibrosis and inherited cardiomyopathy.

In one aspect, provided is a compound of formula (I), or any variation thereof, e.g., a compound of formula (I), (IIa), (IIb), (Ia), (IIb), (IVa), (IVb), (Va), (Va-1), (Va-2), (Vb), (Vb-1), or (Vb-2), a compound selected from the compounds depicted in Table 1, or a stereoisomer thereof, or a pharmaceutically acceptable salt thereof, for use in the treatment of a fibrotic disease.

Also provided is use of a compound of formula (I), or any variation thereof, e.g., a compound of formula (II), a compound selected from the compounds depicted in Table 1, or a stereoisomer thereof, or a pharmaceutically acceptable salt thereof, in the manufacture of a medicament for the treatment of a fibrotic disease.

In another aspect, provided is a method of inhibiting αvβ6 integrin in an individual comprising administering a compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a stereoisomer thereof, or a compound selected from the compounds depicted in Table 1, or a pharmaceutically acceptable salt thereof.

Also provided is a method of inhibiting TGFβ activation in a cell comprising administering to the cell a compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a compound selected from the compounds depicted in Table 1, or a stereoisomer thereof, or a pharmaceutically acceptable salt thereof.

Also provided is a method of inhibiting αvβ6 integrin in an individual in need thereof, comprising administering to the individual a compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a compound selected from the compounds depicted in Table 1, or a stereoisomer thereof, or a pharmaceutically acceptable salt thereof. In one such method, the compound is a selective αvβ6 integrin inhibitor. In another such method, the compound does not inhibit substantially α4β1, αvβ8 and/or α2β3 integrin. In yet another such method, the compound inhibits αvβ6 integrin but does not inhibit substantially α4β1 integrin. In still another such method, the compound inhibits αvβ6 integrin but does not inhibit substantially αvβ8 integrin. In a further such method, the compound inhibits αvβ6 integrin but does not inhibit substantially α2β3 integrin. In one embodiment is provided a method of inhibiting αvβ6 integrin and one or more of αvβ1, αvβ3, αvβ5, α2β1, α3β1, α6β1 integrin, α7β1 and α11β1 in an individual in need thereof. In another embodiment is provided a method of inhibiting αvβ6 integrin and αvβ1 integrin. In another embodiment is provided a method of inhibiting αvβ6 integrin, αvβ3 integrin and αvβ5 integrin. In another embodiment is provided a method of inhibiting αvβ6 integrin and α2β1 integrin. In another embodiment is provided a method of inhibiting αvβ6 integrin, α2β1 integrin and α3β1 integrin. In another embodiment is provided a method of inhibiting αvβ6 integrin and α6β1 integrin. In another embodiment is provided a method of inhibiting αvβ6 integrin and α7β1 integrin. In another embodiment is provided a method of inhibiting αvβ6 integrin and α11β1 integrin. In all such embodiments, in one aspect the method of inhibition is for an individual in need thereof, such as an individual who has or is suspected of having a fibrotic disease, and wherein the method comprises administering to the individual a compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a compound selected from the compounds depicted in Table 1, or a stereoisomer thereof, or a pharmaceutically acceptable salt thereof.

Also provided is a method of modulating at least one integrin in a subject, the at least one integrin comprising an αv subunit, the method comprising administering to the subject an effective amount of the compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a stereoisomer thereof, or a compound selected from the compounds depicted in Table 1, or a pharmaceutically acceptable salt thereof. In another aspect, the modulating comprising inhibiting the at least one integrin in the subject. In another aspect, the at least one integrin comprising at least one of αvβ$_1$ integrin and αvβ$_6$ integrin. In another aspect, the subject has or is at risk of a fibrotic disease selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease; and the method comprises inhibiting one or both of αvβ$_1$ integrin and αvβ$_6$ integrin in the subject, thereby treating the fibrotic disease in the subject. In another aspect, the subject being in need of treatment for NASH, the effective amount administered to the subject being effective to inhibit at least αvβ$_1$ integrin, thereby treating the subject for NASH. In another aspect, the subject being in need of treatment for IPF, the effective amount administered to the subject being effective to inhibit at least αvβ$_6$ integrin, thereby treating the subject for IPF. In another aspect, the subject being in need of treatment for PSC, the effective amount administered to the subject being effective to inhibit at least one of αvβ$_1$ integrin and αvβ$_6$ integrin, thereby treating the subject for PSC.

Also provided is a method of modulating TGFβ activation in a cell, comprising contacting the cell with the compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a stereoisomer thereof, or a compound selected from the compounds depicted in Table 1, or a pharmaceutically acceptable salt thereof. In another aspect, the modulating comprising inhibiting TGFβ activation in the cell. In another aspect, the TGFβ activation being mediated in the cell by at least one of αvβ$_1$ integrin and αvβ$_6$ integrin.

Also provided is a method of treating a subject in need thereof, comprising: administering to the subject a therapeutically effective amount of the compound of formula (I), or any variation thereof, e.g., a compound of formula (IIa), (IIb), (IIIa), (IIIb), (IVa), (IVb), (Va), (Va-1), (Va-2), (Vb), (Vb-1), or (Vb-2), a stereoisomer thereof, or a compound selected from the compounds depicted in Table 1, or a pharmaceutically acceptable salt thereof, wherein the subject has at least one tissue in need of therapy and the tissue has at least one elevated level of: TGFβ activation and/or expression; αvβ$_1$ integrin activity and/or expression; or αvβ$_6$ integrin activity and/or expression; wherein the at least one elevated level is elevated compared to a healthy state of the tissue. In some aspects, the method selectively inhibits αvβ$_1$ integrin compared to αvβ$_6$ integrin in the subject. In some aspects, the method selectively inhibits αvβ$_6$ integrin compared to αvβ$_1$ integrin in the subject. In some aspects, the method inhibits both of αvβ$_1$ integrin and αvβ$_6$ integrin in the subject. In some aspects, the method selectively inhibits both αvβ$_1$ integrin and αvβ$_6$ integrin compared to at least one other αv-containing integrin in the subject. In some aspects, the αvβ$_1$ integrin is inhibited in one or more fibroblasts in the subject. In some aspects, the αvβ$_6$ integrin is inhibited in one or more epithelial cells in the subject. In some aspects, the at least one tissue in the subject comprises one or more of: lung tissue, liver tissue, skin tissue, cardiac tissue, kidney tissue, gastrointestinal tissue, gall bladder tissue, and bile duct tissue.

In one aspect, provided is a compound of formula (I), or any variation thereof, e.g., a compound of formulae (I), (IIa), (IIb), (IIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (l-A-2b-1), (II-A-2b-2), (II-A-2c-1), (II-A-2c-2), (II-A-2c-3), (II- A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof, for use in the treatment of a fibrotic disease.

Also provided is use of a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof, in the manufacture of a medicament for the treatment of a fibrotic disease.

In another aspect, provided is a method of inhibiting αvβ6 integrin in an individual comprising administering a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (It-A-2f-8), (II-A-2f-9), (It-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof.

Also provided is a method of inhibiting TGFβ activation in a cell comprising administering to the cell a compound of formulae (I), (IIa), (IIb), (IIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof.

Also provided is a method of inhibiting αvβ6 integrin in an individual in need thereof, comprising administering to the individual a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof. In one such method, the compound is a selective αvβ6 integrin inhibitor. In another such method, the compound does not inhibit substantially α4β1, αvβ8 and/or α2β3 integrin. In yet another such method, the compound inhibits αvβ6 integrin but does not inhibit substantially α4β1 integrin. In still another such method, the compound inhibits αvβ6 integrin but does not inhibit substantially αvβ8 integrin. In a further such method, the compound inhibits αvβ6 integrin but does not inhibit substantially α2β3 integrin. In one embodiment is provided a method of inhibiting αvβ6 integrin and one or more of αvβ1, αvβ3, αvβ5, α2β1, α3β1, α6β1 integrin, α7β1 and α11β1 in an individual in need thereof. In another embodiment is provided a method of inhibiting αvβ6 integrin and αvβ1 integrin. In another embodiment is provided a method of inhibiting αvβ6 integrin, αvβ3 integrin and αvβ5 integrin. In another embodiment is provided a method of inhibiting αvβ6 integrin and α2β1 integrin. In another embodiment is provided a method of inhibiting αvβ6 integrin, α2β1 integrin and α3β1 integrin. In another embodiment is provided a method of inhibiting αvβ6 integrin and α6β1 integrin. In another embodiment is provided a method of inhibiting αvβ6 integrin and α7β1 integrin. In another embodiment is provided a method of inhibiting αvβ6 integrin and α11β1 integrin. In all such embodiments, in one aspect the method of inhibition is for an individual in need thereof, such as an individual who has or is suspected of having a fibrotic disease, and wherein the method comprises administering to the individual a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (1-A-2e-7), (1-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof.

Also provided is a method of modulating at least one integrin in a subject, the at least one integrin comprising an αv subunit, the method comprising administering to the subject an effective amount of the compound of formulae (I), (IIa), (IIb), (IIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof. In another aspect, the modulating comprising inhibiting the at least one integrin in the subject. In another aspect, the at least one integrin comprising at least one of $\alpha v \beta_1$ integrin and $\alpha v \beta_6$ integrin. In another aspect, the subject has or is at risk of a fibrotic disease selected from the group consisting of: idiopathic pulmonary fibrosis (IPF), interstitial lung disease, radiation-induced pulmonary fibrosis, nonalcoholic fatty liver disease (NAFLD), nonalcoholic steatohepatitis (NASH), alcoholic liver disease induced fibrosis, Alport syndrome, primary sclerosing cholangitis (PSC), primary biliary cholangitis, biliary atresia, systemic sclerosis associated interstitial lung disease, scleroderma, diabetic nephropathy, diabetic kidney disease, focal segmental glomerulosclerosis, chronic kidney disease, and Crohn's Disease; and the method comprises inhibiting one or both of $\alpha v \beta_1$ integrin and $\alpha v \beta_6$ integrin in the subject, thereby treating the fibrotic disease in the subject. In another aspect, the subject being in need of treatment for NASH, the effective amount administered to the subject being effective to inhibit at least $\alpha v \beta_1$ integrin, thereby treating the subject for NASH. In another aspect, the subject being in need of treatment for IPF, the effective amount administered to the subject being effective to inhibit at least $\alpha v \beta_6$ integrin, thereby treating the subject for IPF. In another aspect, the subject being in need of treatment for PSC, the effective amount administered to the subject being effective to inhibit at least one of $\alpha v \beta_1$ integrin and $\alpha v \beta_6$ integrin, thereby treating the subject for PSC.

Also provided is a method of modulating TGFβ activation in a cell, comprising contacting the cell with the compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (II-A-1b-1), (II-A-1b-2), (II-A-1c-1), (II-A-1c-2), (II-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof. In another aspect, the modulating comprising inhibiting TGFβ activation in the cell. In another aspect, the TGFβ activation being mediated in the cell by at least one of $\alpha v \beta_1$ integrin and $\alpha v \beta_6$ integrin.

Also provided is a method of treating a subject in need thereof, comprising: administering to the subject a therapeutically effective amount of the compound of formula (I), or any variation thereof, e.g., a compound of formulae (I), (IIa), (IIb), (IIIa), (IIIb), (IVa), (IVb), (Va), (Va-1), (Va-2), (Vb), (Vb-1), (Vb-2), (II-A-1), (II-A-2), (II-A-2i), (II-A-2ii), (II-A-1a-1), (II-A-1a-2), (II-A-1a-3), (1-A-1b-1), (II-A-1b-2), (II-A-1c-1), (II-A-1c-2), (1-A-1d-1), (II-A-1d-2), (II-A-1d-3), (II-A-2a-1), (II-A-2a-2), (II-A-2a-3), (II-A-2a-4), (II-A-2b-1), (II-A-2b-2), (II-A-2c-1), (II-A-2c-2), (II-A-2c-3), (II-A-2c-4), (II-A-2d-1), (II-A-2d-2), (II-A-2d-3), (II-A-2d-4), (II-A-2d-5), (II-A-2d-6), (II-A-2e-1), (II-A-2e-2), (II-A-2e-3), (II-A-2e-4), (II-A-2e-5), (II-A-2e-6), (II-A-2e-7), (II-A-2e-8), (II-A-2f-1), (II-A-2f-2), (II-A-2f-3), (II-A-2f-4), (II-A-2f-5), (II-A-2f-6), (II-A-2f-7), (II-A-2f-8), (II-A-2f-9), (II-A-2f-10), (II-B-1), (II-B-2), (II-B-3), (II-B-1a), (II-B-2a), (II-B-2b), (II-B-3a), or (II-B-3b), a compound selected from the compounds depicted in Table 1 or Table 2, or any one of compounds 1-329, or a stereoisomer thereof, or a pharmaceutically acceptable salt thereof, wherein the subject has at least one tissue in need of therapy and the tissue has at least one elevated level of: TGFβ activation and/or expression; $\alpha v \beta_1$ integrin activity and/or expression; or $\alpha v \beta_6$ integrin activity and/or expression; wherein the at least one elevated level is elevated compared to a healthy state of the tissue. In some aspects, the method selectively inhibits $\alpha v \beta_1$ integrin compared to $\alpha v \beta_6$ integrin in the subject. In some aspects, the method selectively inhibits $\alpha v \beta_6$ integrin compared to $\alpha v \beta_1$ integrin in the subject. In some aspects, the method inhibits both of $\alpha v \beta_1$ integrin and $\alpha v \beta_6$ integrin in the subject. In some aspects, the method selectively inhibits both $\alpha v \beta_1$ integrin and $\alpha v \beta_6$ integrin compared to at least one other αv-containing integrin in the subject. In some aspects, the $\alpha v \beta_1$ integrin is inhibited in one or more fibroblasts in the subject. In some aspects, the $\alpha v \beta_6$ integrin is inhibited in one or more epithelial cells in the subject. In some aspects, the at least one tissue in the subject comprises one or more of: lung tissue, liver tissue, skin tissue, cardiac tissue, kidney tissue, gastrointestinal tissue, gall bladder tissue, and bile duct tissue.

In any of the described methods, in one aspect the individual is a human, such as a human in need of the method. The individual may be a human who has been diagnosed with or is suspected of having a fibrotic disease. The individual may be a human who does not have detectable disease but who has one or more risk factors for developing a fibrotic disease.

Kits

The invention further provides kits for carrying out the methods of the invention, which comprises one or more compounds described herein, or a salt thereof, or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for use in the treatment of a fibrotic disease.

Kits generally comprise suitable packaging. The kits may comprise one or more containers comprising any compound described herein. Each component (if there is more than one component) can be packaged in separate containers or some components can be combined in one container where cross-reactivity and shelf life permit. One or more components of a kit may be sterile and/or may be contained within sterile packaging.

The kits may be in unit dosage forms, bulk packages (e.g., multi-dose packages) or sub-unit doses. For example, kits may be provided that contain sufficient dosages of a compound as disclosed herein (e.g., a therapeutically effective amount) and/or a second pharmaceutically active compound useful for a disease detailed herein (e.g., fibrosis) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

GENERAL PROCEDURES

Compounds provided herein may be prepared according to General Schemes, as exemplified by the General Procedures and Examples.

When a specific stereoisomer, or an unspecified stereoisomer, or a mixture of stereoisomers is shown in the following general procedures, it is understood that similar chemical transformations can be performed on other specific stereoisomers, or an unspecified stereoisomer, or mixtures thereof. For example, a hydrolysis reaction of an L-homoserinate ester to an L-homoserine (i.e., free acid) can also be performed on a D-homoserinate ester to prepare a D-homoserine, or on a mixture of an L-homoserinate ester and a D-homoserinate ester to prepare a mixture of an L-homoserine and a D-homoserine. As another example, reactions of functional groups on a compound containing a trans-cyclobutyl group can also be performed on a compound containing a cis-cyclobutyl group, or on a mixture of a compound containing a cis-cyclobutyl group and a compound containing a trans-cyclobutyl group. As another example, reactions of functional groups on a compound containing a cycloalkyl Y group can also be performed on a compound lacking a Y group (i.e., where the linker is -$L_1$-O-$L_2$-$L_3$- as defined in Formula (I)), or on a mixture of a compound containing a cycloalkyl group and a compound lacking a Y group.

Some of the following general procedures use specific compounds to illustrate a general reaction (e.g., deprotection of a compound having a Boc-protected amine to a compound having a deprotected amine using acid). The general reaction can be carried out on other specific compounds having the same functional group (e.g., a different compound having a protected amine where the Boc-protecting group can be removed using acid in the same manner) as long as such other specific compounds do not contain additional functional groups affected by the general reaction (i.e., such other specific compounds do not contain acid-sensitive functional groups), or if the effect of the general reaction on those additional functional groups is desired (e.g., such other specific compounds have another group that is affected by acid, and the effect of the acid on that other group is a desirable reaction).

Where specific reagents or solvents are specified for reactions in the general procedures, the skilled artisan will recognize that other reagents or solvents can be substituted as desired. For example, acetylation is performed in the general examples with acetic anhydride, but an active ester of acetic acid can also be used. As another example, where hydrochloric acid is used to remove a Boc group, trifluoroacetic acid can be used instead. As another example, where HATU is used as a coupling reagent, BOP or PyBOP can be used instead.

General Procedure A

Detailed Procedures for General Scheme A and Scheme D-1

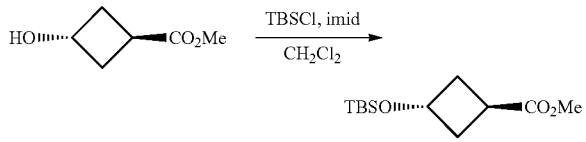

methyl (1r,3r)-3-((tert-butyldimethylsilyl)oxy)cyclobutane-1-carboxylate. To a solution of methyl (1r,3r)-3-hydroxycyclobutane-1-carboxylate (5.0 g, 38.42 mmol) in $CH_2Cl_2$ (100 mL) was added imidazole (3.92 g, 57.63 mmol) then TBSCl (6.95 g, 46.10 mmol) at room temperature and the resulting heterogeneous mixture was vigorously stirred for 30 minutes. The reaction mixture was diluted with sat. $NaHCO_3$ and water and stirred for 5 minutes. The layers were separated and the organic layer was washed with water (50 mL), dried over $MgSO_4$, filtered and concentrated in vacuo. The crude residue was purified by normal phase silica gel chromatography to give methyl (1r,3r)-3-((tert-butyldimethylsilyl)oxy)cyclobutane-1-carboxylate.

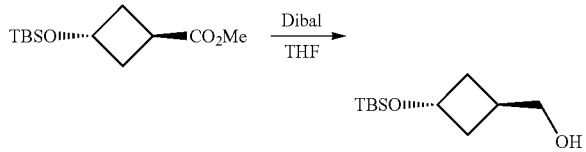

((1r,3r)-3-((tert-butyldimethylsilyl)oxy)cyclobutyl)methanol. To a solution of methyl (1r,3r)-3-((tert-butyldimethylsilyl)oxy)cyclobutane-1-carboxylate (9.19 g, 37.60 mmol) at −78° C. in THF (92 mL) was added Dibal-H (1.0 M in heptane, 94 mL, 94.00 mmol) dropwise and the resulting solution was allowed to stir for 1 hr at −78° C. The mixture was then warmed to 0° C. and then to this was slowly added EtOAc (100 mL) followed by a saturated aqueous solution of sodium potassium tartrate (250 mL) and water (100 mL) and the resulting mixture was then allowed to warm to room temperature and stirred vigorously for 4 hrs. The layers were separated and the aqueous layer was extracted with EtOAc. The combined organic extracts were dried over MgSO4, filtered, and concentrated in vacuo. The crude residue was purified by normal phase silica gel chromatography to give ((1r,3r)-3-((tert-butyldimethylsilyl)oxy)cyclobutyl)methanol.

tert-butyl((1r,3r)-3-(iodomethyl)cyclobutoxy)dimethylsilane. To a solution of $PPh_3$ (13.09 g, 49.91 mmol) and imidazole (4.53 g, 66.54 mmol) in CH$_2$Cl$_2$ (78 mL) at 0° C. was slowly added I$_2$ (12.24 g, 48.24 mmol) and the mixture was stirred an additional 30 minutes and then allowed to warm to room temperature. A solution of ((1r,3r)-3-((tert-butyldimethylsilyl)oxy)cyclobutyl)methanol (7.2 g, 33.27 mmol) in CH$_2$Cl$_2$ (20 mL) was then added to the reaction mixture and stirred for 6 hrs at room temperature. The reaction mixture was then diluted with sat. NaHCO$_3$ and stirred for 15 minutes. The layers were separated and the organic layer was washed with H$_2$O, dried over MgSO$_4$, filtered, and concentrated in vacuo. The crude residue was purified by normal phase silica gel chromatography to give tert-butyl((1r,3r)-3-(iodomethyl)cyclobutoxy)dimethylsilane.

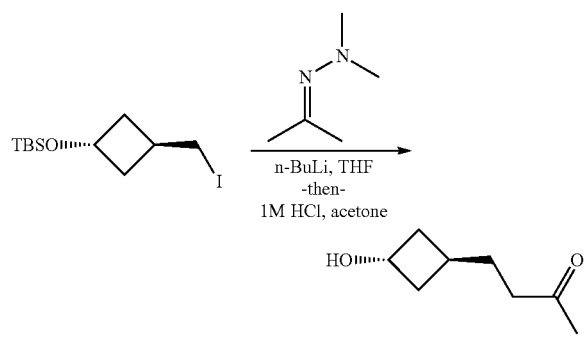

4-((1r,3s)-3-hydroxycyclobuyl)butan-2-one. To a solution of acetone dimethylhydrazone (8.33 g, 83.13 mmol) at −78° C. in THF (83 mL) was slowly added n-BuLi (2.5 M in hexanes, 32.59 mL, 81.46 mmol) causing a pale yellow suspension to occur. Upon completion of the addition, the resulting suspension was stirred an additional 15 minutes, at which time, a solution of tert-butyl((1r,3r)-3-(iodomethyl)cyclobutoxy)dimethylsilane (10.85 g, 33.25 mmol) in THF (20 mL) was slowly added dropwise. The resulting mixture was warmed to 0° C. and stirred for 30 minutes and then carefully quenched with aq 1M HCl (250 mL) and acetone (50 mL). The resulting mixture was allowed to stir at room temperature overnight and then was extracted with EtOAc. The combined organic extracts were dried over MgSO$_4$, filtered, and concentrated in vacuo. The crude residue was purified by normal phase column chromatography to give 4-((1r,3s)-3-hydroxycyclobutyl)butan-2-one.

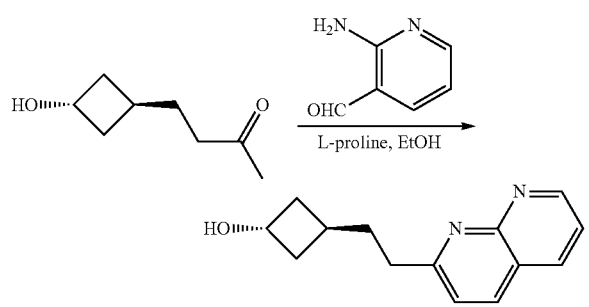

(1s,3r)-3-(2-(1,8-naphthyridin-2-yl)ethyl)cyclobutan-1-ol. A sealed tube containing 4-((1r,3s)-3-hydroxycyclobutyl)butan-2-one (2.46 g, 17.30 mmol) was charged with L-proline (996 mg, 8.65 mmol) and 2-aminonicotinaldehyde (2.53 g, 20.76 mmol) and then diluted with 200 proof EtOH (50 mL) and then sealed and placed in an aluminum block and heated to 95° C. overnight. The reaction mixture was allowed to cool to room temperature and then concentrated in vacuo. The crude residue was purified by normal phase column chromatography to give (1s,3r)-3-(2-(1,8-naphthyridin-2-yl)ethyl)cyclobutan-1-ol.

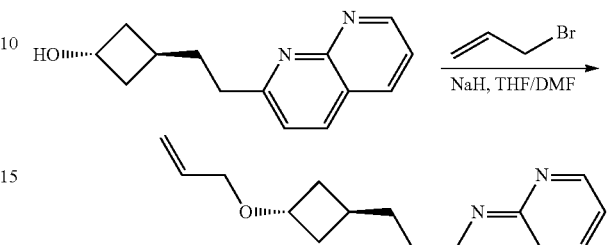

2-(2-((1r,3s)-3-(allyloxy)cyclobutyl)ethyl)-1,8-naphthyridine. To a solution of (1s,3r)-3-(2-(1,8-naphthyridin-2-yl)ethyl)cyclobutan-1-ol (3.36 g, 14.72 mmol) in 2:1 THF/DMF (34 mL) at room temperature was slowly added NaH (60% dispersion in mineral oil, 883 mg, 22.08 mmol) and the resulting mixture was stirred for 30 minutes, at which time, allyl bromide (1.91 mL, 22.08 mmol) was added and the resulting mixture was warmed to 50° C. for 1 hr. The reaction mixture was cooled to room temperature and then carefully diluted with sat NaHCO$_3$ and H$_2$O. The resulting mixture was extracted with 4:1 DCM/iPrOH and the combined organic extracts were dried over MgSO$_4$, filtered, and concentrated in vacuo. The crude residue was purified by normal phase column chromatography to give 2-(2-((1r,3s)-3-(allyloxy)cyclobutyl)ethyl)-1,8-naphthyridine.

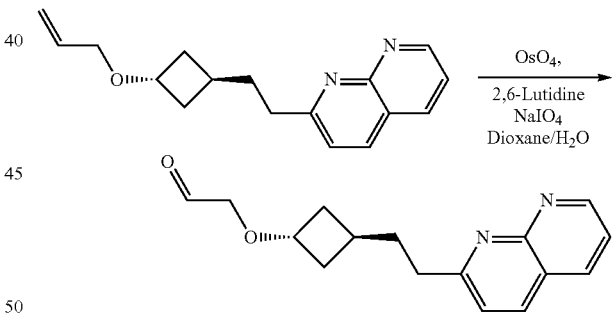

2-((1s,3r)-3-(2-(1,8-naphthyridin-2-yl)ethyl)cyclobutoxy)acetaldehyde. To a solution of 2-(2-((1r,3s)-3-(allyloxy)cyclobutyl)ethyl)-1,8-naphthyridine (1.38 g, 5.14 mmol) in 3:1 Dioxane/H$_2$O (14 mL) was added 2,6-lutidine (1.2 mL, 10.28 mmol), NaIO$_4$ (4.40 g, 20.56 mmol), then OsO$_4$ (2.5 wt % in 1-BuOH, 1.05 mL, 0.10 mmol) and the resulting mixture was allowed to stir at room temperature for 4 hrs. The reaction mixture was diluted with sat NaHCO$_3$ and H$_2$O and stirred for 15 minutes and then filtered through a coarse fritted funnel and the filter cake was rinsed with 4:1 DCM/iPrOH. The layers were separated and the aqueous layer was extracted with 4:1 DCM/iPrOH and the combined organic extracts were dried over MgSO$_4$, filtered, and concentrated in vacuo to give 2-((1s,3r)-3-(2-(1,8-naphthyridin-2-yl)ethyl)cyclobutoxy)acetaldehyde.

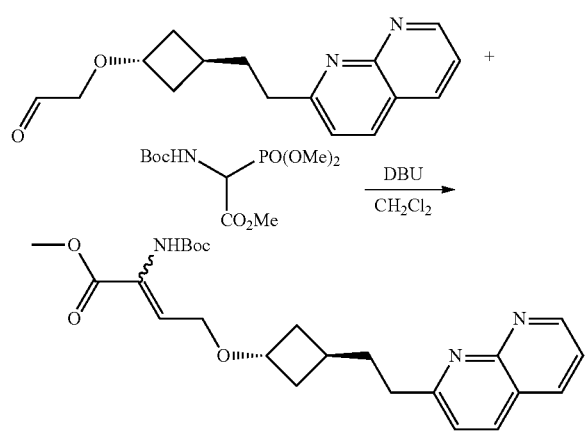

methyl 4-((1s,3r)-3-(2-(1,8-naphthyridin-2-yl)ethyl)cyclobutoxy)-2-((tert-butoxycarbonyl)amino)but-2-enoate. To a solution of 2-((1s,3r)-3-(2-(1,8-naphthyridin-2-yl)ethyl)cyclobutoxy)acetaldehyde in CH₂Cl₂ (14 mL) and to this was added methyl 2-((tert-butoxycarbonyl)amino)-2-(dimethoxyphosphoryl)acetate (2.29 g, 7.71 mmol) then DBU (1.16 mL, 7.71 mmol) and the resulting mixture was allowed to stir at room temperature for 30 minutes and then concentrated in vacuo. The crude residue was purified by normal phase column chromatography to give methyl 4-((1s,3r)-3-(2-(1,8-naphthyridin-2-yl)ethyl)cyclobutoxy)-2-((tert-butoxycarbonyl)amino)but-2-enoate.

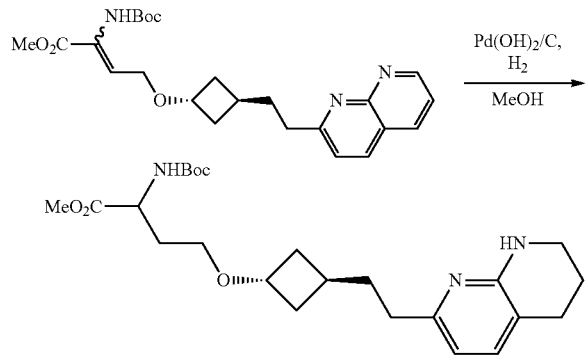

methyl N-(tert-butoxycarbonyl)-O-((1s,3r)-3-(2-(5,6,7,8-tetrahydro-1,8-naphthyridin-2-yl)ethyl)cyclobutyl)homoserinate. A flask containing methyl 4-((1s,3r)-3-(2-(1,8-naphthyridin-2-yl)ethyl)cyclobutoxy)-2-((tert-butoxycarbonyl)amino)but-2-enoate (2.27 g, 5.14 mmol) was charged with Pd(OH)₂/C (20 wt % on carbon, 454 mg) and then diluted with MeOH (23 mL). The flask was then evacuated and backfilled with H₂ for 3 cycles and then stirred under an H₂ atmosphere overnight. The reaction mixture was then filtered through a pad of Celite and then concentrated in vacuo. The crude residue was purified by normal phase column chromatography to give methyl N-(tert-butoxycarbonyl)-O-((1s,3r)-3-(2-(5,6,7,8-tetrahydro-1,8-naphthyridin-2-yl)ethyl)cyclobutyl)homoserinate.

After the synthesis of the racemic material as shown in the previous step, a chiral separation can be performed to afford two single enantiomers using chiral SFC with the following method: Chiralpak AY-H, 250*25 mm i.d. 10 u; Mobile phase: A for CO2 and B for EtOH (0.1% NH3H2O); Gradient: B %=45%; Flow rate: 80 g/min; Wavelength: 220 nm; Column temperature: 40° C.; System back pressure: 100 bar.

General Procedure B

Detailed Procedures for General Scheme B and Scheme E-1

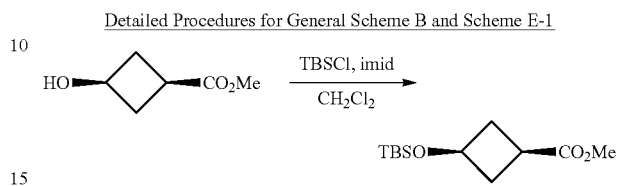

methyl (1s,3s)-3-((tert-butyldimethylsilyl)oxy)cyclobutane-1-carboxylate. To a solution of methyl (1s,3s)-3-hydroxycyclobutane-1-carboxylate (5.0 g, 38.16 mmol) in CH₂Cl₂ (100 mL) was added imidazole (3.92 g, 57.63 mmol) then TBSCl (6.95 g, 49.61 mmol) at room temperature and the resulting heterogeneous mixture was vigorously stirred for 30 minutes. The reaction mixture was diluted with sat. NaHCO₃ (50 mL) and water (50 mL) and stirred for 5 minutes. The layers were separated and the organic layer was washed with water (50 mL), dried over MgSO₄, filtered and concentrated in vacuo. The crude residue was purified by normal phase silica gel chromatography to give methyl (1s,3s)-3-((tert-butyldimethylsilyl)oxy)cyclobutane-1-carboxylate.

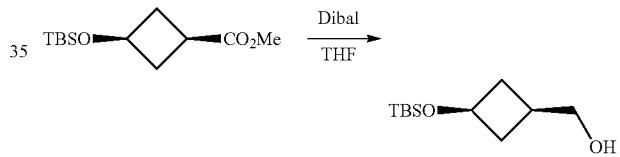

((1s,3s)-3-((tert-butyldimethylsilyl)oxy)cyclobutyl) methanol. To a solution of methyl (1s,3s)-3-((tert-butyldimethylsilyl)oxy)cyclobutane-1-carboxylate (9.20 g, 37.76 mmol) at −78° C. in THF (92 mL) was added Dibal-H (1.0 M in heptane, 113 mL, 113.00 mmol) dropwise and the resulting solution was allowed to stir for 1 hr at −78° C. The mixture was then warmed to 0° C. and then to this was slowly added EtOAc (100 mL) followed by a saturated aqueous solution of sodium potassium tartrate (250 mL) and water (100 mL) and the resulting mixture was then allowed to warm to room temperature and stirred vigorously for 4 hrs. The layers were separated and the aqueous layer was extracted with EtOAc. The combined organic extracts were dried over MgSO4, filtered, and concentrated in vacuo. The crude residue was purified by normal phase silica gel chromatography to give ((1s,3s)-3-((tert-butyldimethylsilyl)oxy)cyclobutyl)methanol.

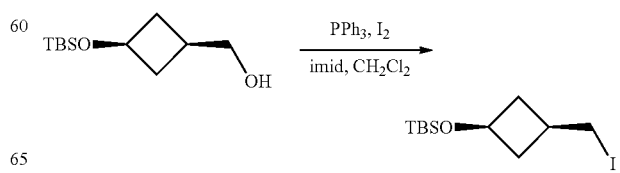

tert-butyl((1s,3s)-3-(iodomethyl)cyclobutoxy)dimethylsilane. To a solution of PPh₃ (12.80 g, 48.79 mmol) and imidazole (4.43 g, 65.05 mmol) in CH₂Cl₂ (72 mL) at 0° C. was slowly added I2 (11.97 g, 47.16 mmol) and the mixture was stirred an additional 30 minutes and then allowed to warm to room temperature. A solution of ((1s,3s)-3-((tert-butyldimethylsilyl)oxy)cyclobutyl)methanol (7.04 g, 32.53 mmol) in CH₂Cl₂ (20 mL) was then added to the reaction mixture and stirred for 6 hrs at room temperature. The reaction mixture was then diluted with sat. NaHCO₃ and stirred for 15 minutes. The layers were separated and the organic layer was washed with H₂O, dried over MgSO₄, filtered, and concentrated in vacuo. The crude residue was purified by normal phase silica gel chromatography to give tert-butyl((1s,3s)-3-(iodomethyl)cyclobutoxy)dimethylsilane.

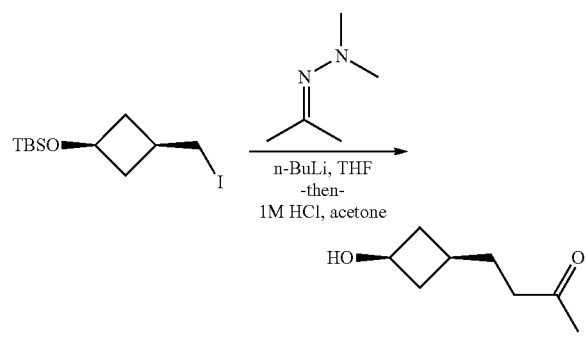

4-((1s,3r)-3-hydroxycyclobutyl)butan-2-one. To a solution of acetone dimethylhydrazone (8.15 g, 81.39 mmol) at −78° C. in THF (82 mL) was slowly added n-BuLi (2.5 M in hexanes, 31.25 mL, 78.13 mmol) causing a pale yellow suspension to occur. Upon completion of the addition, the resulting suspension was stirred an additional 15 minutes, at which time, a solution of tert-butyl((1s,3s)-3-(iodomethyl) cyclobutoxy)dimethylsilane (10.62 g, 32.55 mmol) in THF (20 mL) was slowly added dropwise. The resulting mixture was warmed to 0° C. and stirred for 30 minutes and then carefully quenched with aq 1M HCl (250 mL) and acetone (50 mL). The resulting mixture was allowed to stir at room temperature overnight and then was extracted with EtOAc. The combined organic extracts were dried over MgSO₄, filtered, and concentrated in vacuo. The crude residue was purified by normal phase column chromatography to give 4-((1s,3r)-3-hydroxycyclobutyl)butan-2-one.

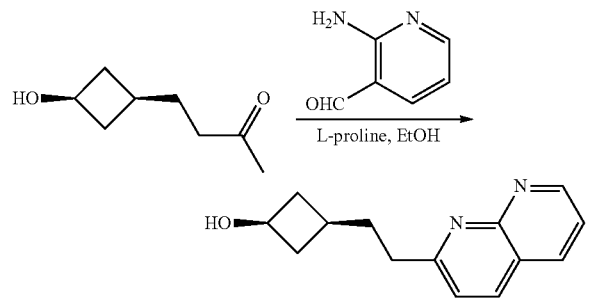

(1r,3s)-3-(2-(1,8-naphthyridin-2-yl)ethyl)cyclobutan-1-ol. A sealed tube containing 4-((1s,3r)-3-hydroxycyclobutyl)butan-2-one (2.72 g, 19.18 mmol) was charged with L-proline (1.10 g, 9.59 mmol) and 2-aminonicotinaldehyde (3.51 g, 28.77 mmol) and then diluted with 200 proof EtOH (50 mL) and then sealed and placed in an aluminum block and heated to 95° C. overnight. The reaction mixture was allowed to cool to room temperature and then concentrated in vacuo. The crude residue was purified by normal phase column chromatography to give (1r,3s)-3-(2-(1,8-naphthyridin-2-yl)ethyl)cyclobutan-1-ol.

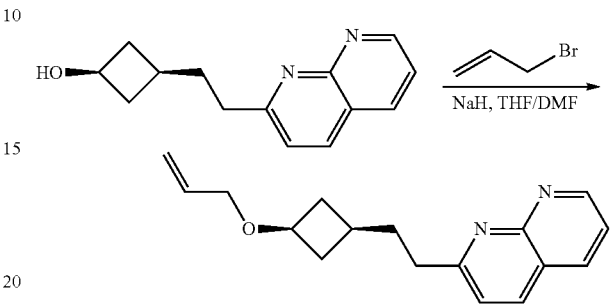

2-(2-((1s,3r)-3-(allyloxy)cyclobutyl)ethyl)-1,8-naphthyridine. To a solution of (1r,3s)-3-(2-(1,8-naphthyridin-2-yl) ethyl)cyclobutan-1-ol (3.72 g, 16.30 mmol) in 2:1 THF/DMF (37 mL) at room temperature was slowly added NaH (60% dispersion in mineral oil, 847 mg, 21.18 mmol) and the resulting mixture was stirred for 30 minutes, at which time, allyl bromide (1.83 mL, 21.18 mmol) was added and the resulting mixture was warmed to 50° C. for 1 hr. The reaction mixture was cooled to room temperature and then carefully diluted with sat NaHCO₃ and H₂O. The resulting mixture was extracted with 4:1 DCM/iPrOH and the combined organic extracts were dried over MgSO₄, filtered, and concentrated in vacuo. The crude residue was purified by normal phase column chromatography to give 2-(2-((1s,3r)-3-(allyloxy)cyclobutyl)ethyl)-1,8-naphthyridine.

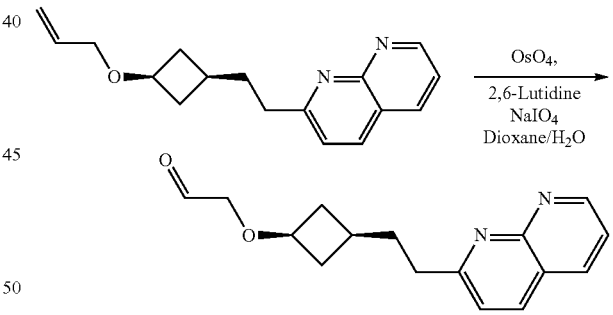

2-((1r,3s)-3-(2-(1,8-naphthyridin-2-yl)ethyl)cyclobutoxy)acetaldehyde. To a solution of 2-(2-((1s,3r)-3-(allyloxy)cyclobutyl)ethyl)-1,8-naphthyridine (946 mg, 3.53 mmol) in 3:1 Dioxane/H₂O (10 mL) was added 2,6-lutidine (0.82 mL, 7.05 mmol), NaIO₄ (3.02 g, 14.10 mmol), then OsO₄ (2.5 wt % in t-BuOH, 0.88 mL, 0.07 mmol) and the resulting mixture was allowed to stir at room temperature for 4 hrs. The reaction mixture was diluted with sat NaHCO₃ and H₂O and stirred for 15 minutes and then filtered through a coarse fritted funnel and the filter cake was rinsed with 4:1 DCM/iPrOH. The layers were separated and the aqueous layer was extracted with 4:1 DCM/iPrOH and the combined organic extracts were dried over MgSO₄, filtered, and concentrated in vacuo to give 2-((1r,3s)-3-(2-(1,8-naphthyridin-2-yl)ethyl)cyclobutoxy)acetaldehyde.

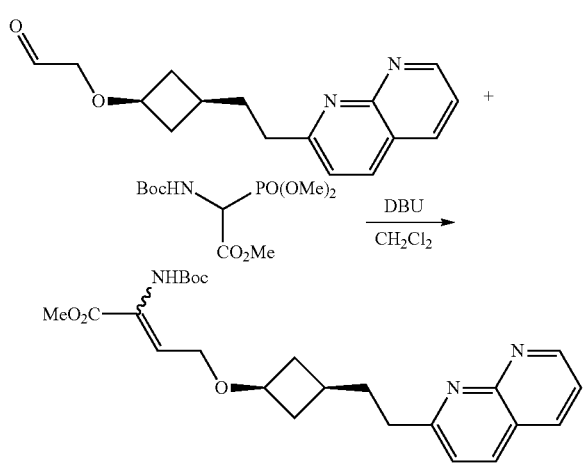

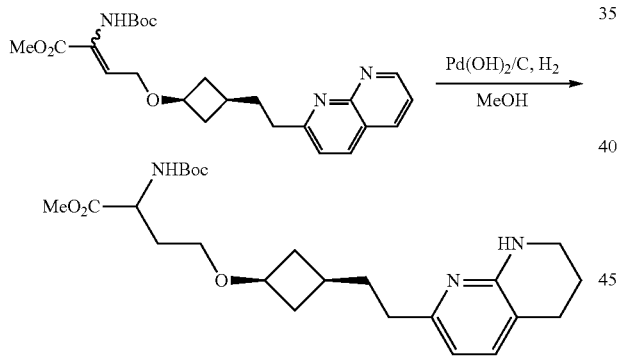

methyl 4-((1r,3s)-3-(2-(1,8-naphthyridin-2-yl)ethyl)cyclobutoxy)-2-((tert-butoxycarbonyl)amino)but-2-enoate. To a solution of 2-((1r,3s)-3-(2-(1,8-naphthyridin-2-yl)ethyl)cyclobutoxy)acetaldehyde (953 mg, 3.53 mmol) in $CH_2Cl_2$ (10 mL) and to this was added methyl 2-((tert-butoxycarbonyl)amino)-2-(dimethoxyphosphoryl)acetate (1.57 g, 5.29 mmol) then DBU (0.64 mL, 4.23 mmol) and the resulting mixture was allowed to stir at room temperature for 30 minutes and then concentrated in vacuo. The crude residue was purified by normal phase column chromatography to give methyl 4-((1r,3s)-3-(2-(1,8-naphthyridin-2-yl)ethyl)cyclobutoxy)-2-((tert-butoxycarbonyl)amino)but-2-enoate.

methyl N-(tert-butoxycarbonyl)-O-((1r,3s)-3-(2-(5,6,7,8-tetrahydro-1,8-naphthyridin-2-yl)ethyl)cyclobutyl)homoserinate. A flask containing methyl 4-((1r,3s)-3-(2-(1,8-naphthyridin-2-yl)ethyl)cyclobutoxy)-2-((tert-butoxycarbonyl)amino)but-2-enoate (846 mg, 1.92 mmol) was charged with Pd(OH)/C (20 wt % on carbon, 169 mg) and then diluted with MeOH (9 mL). The flask was then evacuated and backfilled with $H_2$ for 3 cycles and then stirred under an $H_2$ atmosphere overnight. The reaction mixture was then filtered through a pad of Celite and then concentrated in vacuo. The crude residue was purified by normal phase column chromatography to give methyl N-(tert-butoxycarbonyl)-O-((1r,3s)-3-(2-(5,6,7,8-tetrahydro-1,8-naphthyridin-2-yl)ethyl)cyclobutyl)homoserinate.

After the synthesis of the racemic material as shown in the previous step, a chiral separation can be performed to afford two single enantiomers using chiral SFC with the following method: Chiralpak AY-H 250*30 mm i.d. 5 u; mobile phase: A for CO2 and B for EtOH (0.1% $NH_3H_2O$); gradient: B %=50%; flow rate: 80 g/min; wavelength: 220 nm; column temperature: 40° C.; system back pressure: 100 bar.

General Procedure C

Detailed Procedures for General Scheme C and Scheme F-1

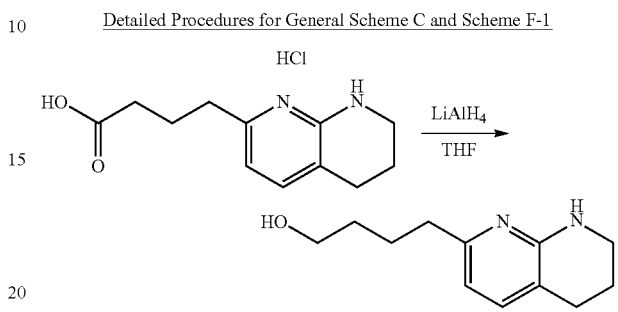

4-(5,6,7,8-tetrahydro-1,8-naphthyridin-2-yl)butan-1-ol. To a suspension of 4-(5,6,7,8-tetrahydro-1,8-naphthyridin-2-yl)butanoic acid hydrochloride (1.23 g, 4.79 mmol, 1.0 equiv) in THF was added $LiAlH_4$ (1.0 M in THF, 10.6 mL, 10.6 mmol) dropwise and the resulting mixture was refluxed overnight. The mixture was then cooled in an ice bath and to this was slowly added $H_2O$ (400 µL), then aqueous 1.0 M NaOH (400 µL), then $H_2O$ (400 µL) again and stirred for 15 minutes and then a large excess of $MgSO_4$ was added and stirred for an additional 30 minutes. The resulting organic mixture was filtered and then concentrated in vacuo to provide 4-(5,6,7,8-tetrahydro-1,8-naphthyridin-2-yl)butan-1-ol.

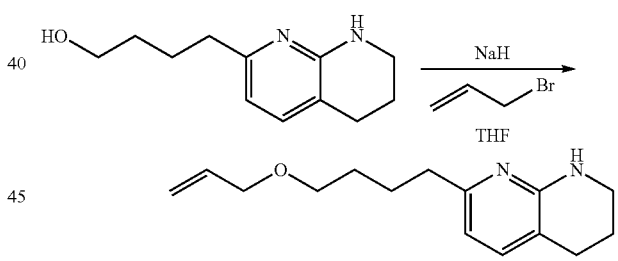

7-(4-(allyloxy)butyl)-1,2,3,4-tetrahydro-1,8-naphthyridine. To a stirring suspension of NaH (60 wt % dispersion in mineral oil, 238 mg, 5.96 mmol) in THF (8.2 mL) at 0° C. was added a solution of 4-(5,6,7,8-tetrahydro-1,8-naphthyridin-2-yl)butan-1-ol (820 mg, 3.98 mmol) in THF (4.1 mL) dropwise. Upon completion of the addition, the ice bath was removed and the resulting mixture was stirred at room temperature for 30 minutes, at which time, allyl bromide (400 µL, 4.62 mmol) was added dropwise. The suspension was stirred for an additional 6 hrs at room temperature and then carefully diluted with $H_2O$ and EtOAc. The layers were separated and the aqueous layer was extracted with EtOAc. The combined organic extracts were dried over $MgSO_4$, filtered, and concentrated in vacuo. The crude residue was purified by silica gel chromatography to provide 7-(4-(allyloxy)butyl)-1,2,3,4-tetrahydro-1,8-naphthyridine.

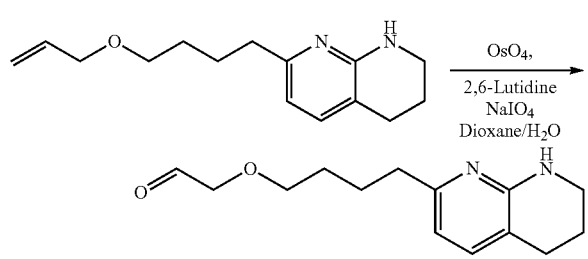

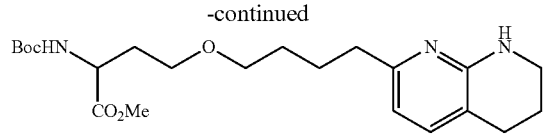

2-(4-(5,6,7,8-tetrahydro-1,8-naphthyridin-2-yl)butoxy) acetaldehyde. To a solution of 7-(4-(allyloxy)butyl)-1,2,3,4-tetrahydro-1,8-naphthyridine (582 mg, 2.36 mmol) in 3:1 THF/H$_2$O (6 mL) at room temperature was added NaIO$_4$ (2.02 g, 9.44 mmol) followed by OsO$_4$ (2.5 wt % in t-BuOH, 480 μL, 0.05 mmol). The resulting suspension was stirred at room temperature for 5 hrs and then diluted with 1:1 sat. aq. NaHCO$_3$/sat. aq. Na$_2$S$_2$O$_3$ and EtOAc and then stirred for 1 hr at room temperature. The biphasic mixture was filtered through a small pad of Celite and then the layers were separated. The aqueous layer was extracted with EtOAc and the combined organic extracts were dried over MgSO$_4$, filtered, and concentrated in vacuo to provide 2-(4-(5,6,7,8-tetrahydro-1,8-naphthyridin-2-yl)butoxy)acetaldehyde that was used without further purification.

methyl N-(tert-butoxycarbonyl)-O-(4-(5,6,7,8-tetrahydro-1,8-naphthyridin-2-yl)butyl)homoserinate. A flask containing methyl 2-((tert-butoxycarbonyl)amino)-4-(4-(5,6,7,8-tetrahydro-1,8-naphthyridin-2-yl)butoxy)but-2-enoate (497 mg, 1.10 mmol) and 20 wt % Pd(OH)$_2$ on carbon (100 mg) was diluted with MeOH (5 ml) and then evacuated and backfilled with H$_2$ for 3 cycles and then stirred under an H$_2$ atmosphere for 3 hrs. The resulting mixture was filtered through a pad of Celite and then concentrated in vacuo to give methyl N-(tert-butoxycarbonyl)-O-(4-(5,6,7,8-tetrahydro-1,8-naphthyridin-2-yl)butyl)homoserinate (352 mg) that was used without further purification.

After the synthesis of the racemic material as shown in the previous step, a chiral separation can be performed to afford two single enantiomers using chiral SFC with the following method: Chiralpak AY-H 250*30 mm i.d. 5 u; mobile phase: A for CO2 and B for IPA (0.1% NH3H2O); gradient: B %=40%; flow rate: 70 g/min; wavelength: 220 nm; column temperature: 40° C.; system back pressure: 100 bar.

General Procedure D

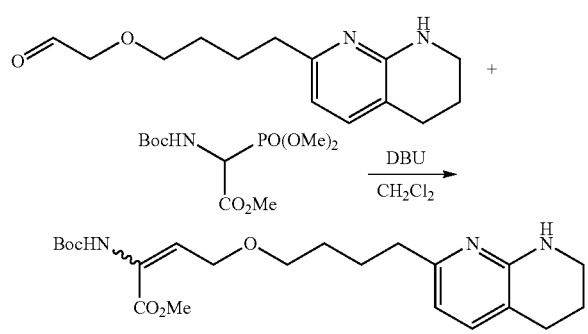

methyl 2-((tert-butoxycarbonyl)amino)-4-(4-(5,6,7,8-tetrahydro-1,8-naphthyridin-2-yl)butoxy)but-2-enoate. To a solution of 2-(4-(5,6,7,8-tetrahydro-1,8-naphthyridin-2-yl)butoxy)acetaldehyde (586 mg, 2.36 mmol) in CH$_2$Cl$_2$ (6 mL) at room temperature was added methyl 2-(((benzyloxy) carbonyl)amino)-2-(dimethoxyphosphoryl)acetate (860 mg, 2.60 mmol) followed by DBU (391 μL, 2.60 mmol) and stirred for 30 minutes at room temperature. The mixture was diluted with sat. aq. NH$_4$Cl and stirred for 5 minutes at room temperature. The layers were separated and the aqueous layer was extracted with EtOAc. The combined organic extracts were dried over MgSO$_4$, filtered, and concentrated in vacuo. The crude residue was purified by silica gel chromatography to provide methyl 2-((tert-butoxycarbonyl) amino)-4-(4-(5,6,7,8-tetrahydro-1,8-naphthyridin-2-yl)butoxy)but-2-enoate.

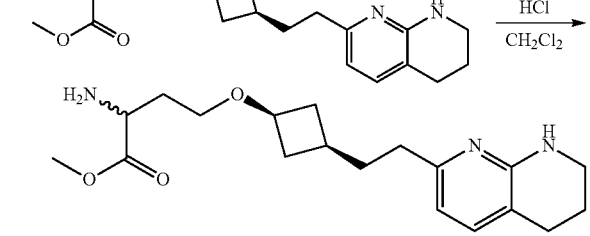

Methyl O-(cis-3-(2-(5,6,7,8-tetrahydro-1,8-naphthyridin-2-yl)ethyl)cyclobutyl)homoserinate. To a solution of methyl N-(tert-butoxycarbonyl)-O-(cis-3-(2-(5,6,7,8-tetrahydro-1,8-naphthyridin-2-yl)ethyl)cyclobutyl)homoserinate (2.26 g, 5.05 mmol) in DCM (13 mL) was added 4 N HCl in 1,4-dioxane (10 mL, 40 mmol). The reaction was allowed to stir at rt overnight. LCMS then showed the consumption of starting material. The reaction was concentrated and used in the next step without further purification.

General Procedure E

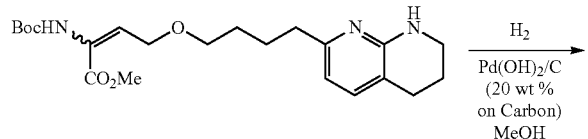

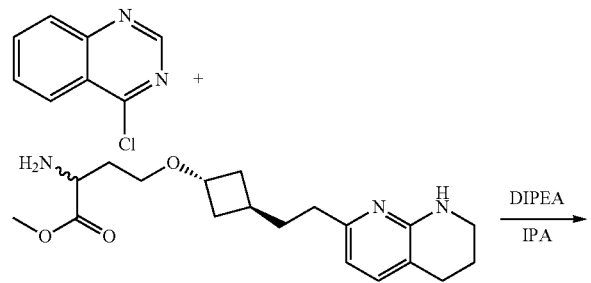

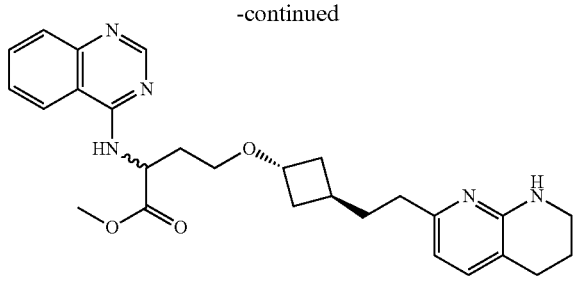

Methyl N-(quinazolin-4-yl)-O-(trans-3-(2-(5,6,7,8-tetrahydro-1,8-naphthyridin-2-yl)ethyl)cyclobutyl)homoserinate. To a solution of methyl O-(trans-3-(2-(5,6,7,8-tetrahydro-1,8-naphthyridin-2-yl)ethyl)cyclobutyl)homoserinate (14 mg, 0.040 mmol) in IPA (2 mL) was added 4-chloroquinazoline (9.9 mg, 0.060 mmol) and DIPEA (0.035 mL, 0.20 mmol). The reaction was heated at 60 C for 18 h. The reaction mixture was then concentrated and used directly in the next step.

General Procedure E can be used in the coupling step of compound 14A, or a similar compounds, with compound 15A in General Scheme A, General Scheme B, General Scheme C, General Scheme D-2, General Scheme E-2, General Scheme F-2, General Scheme G-2, or General Scheme H.

General Procedure F

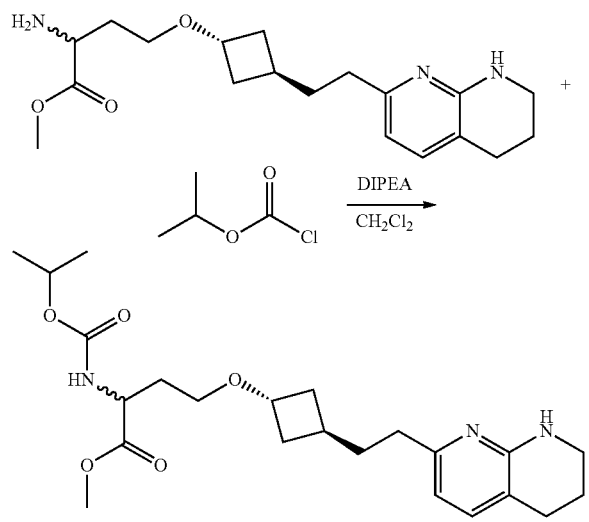

methyl N-(isopropoxycarbonyl)-O-(trans-3-(2-(5,6,7,8-tetrahydro-1,8-naphthyridin-2-yl)ethyl)cyclobutyl)homoserinate. Methyl O-(trans-3-(2-(5,6,7,8-tetrahydro-1,8-naphthyridin-2-yl)ethyl)cyclobutyl)homoserinate (54 mg, 0.16 mmol) in $CH_2Cl_2$ (2.0 mL) was added DIPEA (60 mg, 0.47 mmol) was added isopropyl carbonochloridate (23 mg, 0.19 mmol) and the resulting mixture was stirred at room temperature overnight and then concentrated in vacuo. The crude product was used without further purification.

General Procedure F can be used in the coupling step of compound 14A, or a similar compounds, with compound 16A in General Scheme A, General Scheme B, General Scheme C, General Scheme D-2, General Scheme E-2, General Scheme F-2, General Scheme G-2, or General Scheme H.

General Procedure G

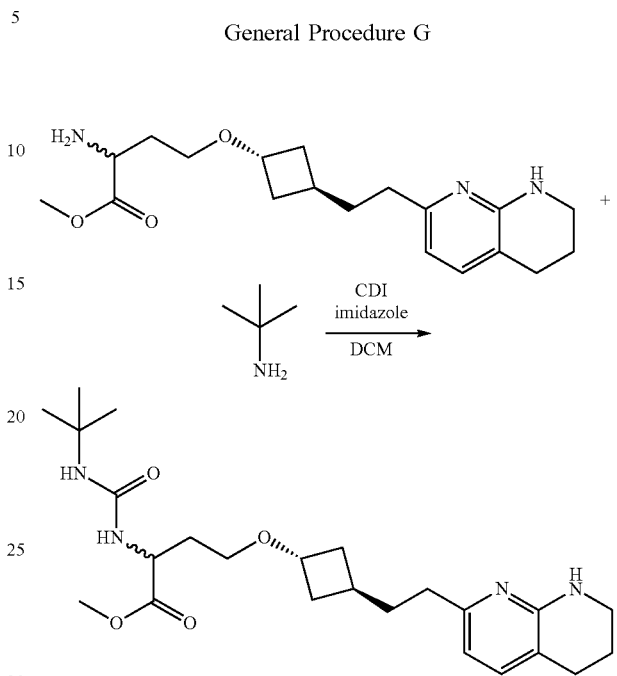

methyl N-(tert-butylcarbamoyl)-O-(trans-3-(2-(5,6,7,8-tetrahydro-1,8-naphthyridin-2-yl)ethyl)cyclobutyl)homoserinate. To a solution of methyl O-(trans-3-(2-(5,6,7,8-tetrahydro-1,8-naphthyridin-2-yl)ethyl)cyclobutyl) homoserinate (71 mg, 0.20 mmol) in DCM (2.4 mL) was added imidazole (15 mg, 0.22 mmol) and CDI (36 mg, 0.22 mmol). This mixture was allowed to stir at rt for 30 min before adding tert-butylamine (22 mg, 0.31 mmol). The reaction was stirred at rt for 18 h. LCMS indicated that methyl O-(trans-3-(2-(5,6,7,8-tetrahydro-1,8-naphthyridin-2-yl)ethyl)cyclobutyl)homoserinate remained, and imidazole (15 mg, 0.22 mmol), CDI (36 mg, 0.22 mmol), and tert-butylamine (22 mg, 0.31 mmol) were added. After 5 h, the reaction was concentrated in vacuo and the resulting crude residue was purified by normal phase silica gel chromatography to give methyl N-(tert-butylcarbamoyl)-O-(trans-3-(2-(5,6,7,8-tetrahydro-1,8-naphthyridin-2-yl)ethyl) cyclobutyl)homoserinate.

General Procedure H

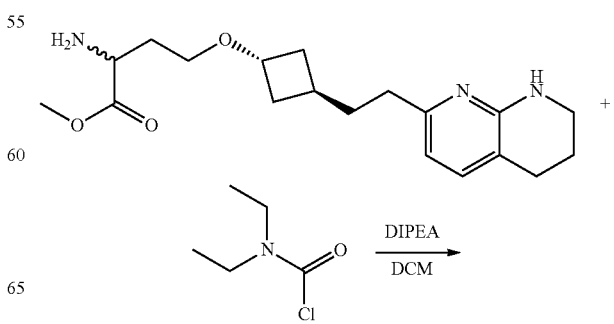

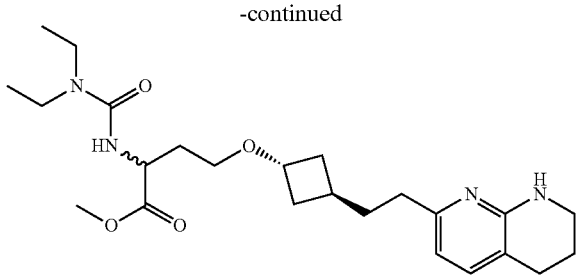

methyl N-(diethylcarbamoyl)-O-(trans-3-(2-(5,6,7,8-tetrahydro-1,8-naphthyridin-2-yl)ethyl)cyclobutyl)homoserinate. To a mixture of methyl O-(trans-3-(2-(5,6,7,8-tetrahydro-1,8-naphthyridin-2-yl)ethyl)cyclobutyl)homoserinate (57 mg, 0.16 mmol) in DCM (2.4 mL) at rt was added DIPEA (0.23 mL, 1.3 mmol) then diethylcarbamoyl chloride (0.10 mL, 0.82 mmol) and the resulting reaction mixture was stirred at rt overnight. The mixture was concentrated in vacuo and the resulting crude residue was purified by preparative reverse phase HPLC to give methyl N-(diethylcarbamoyl)-O-(trans-3-(2-(5,6,7,8-tetrahydro-1,8-naphthyridin-2-yl)ethyl)cyclobutyl)homoserinate.

General Procedure H can be used in the coupling step of compound 14A, or a similar compounds, with compound 16A in General Scheme A, General Scheme B, General Scheme C, General Scheme D-2, General Scheme E-2, General Scheme F-2, General Scheme G-2, or General Scheme H.

General Procedure I

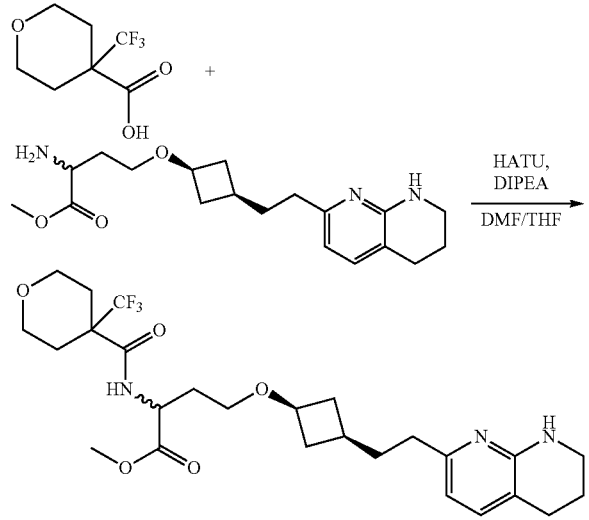

Methyl O-(cis-3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserinate. To a solution of methyl O-(cis-3-(2-(5,6,7,8-tetrahydro-1,8-naphthyridin-2-yl)ethyl)cyclobutyl)homoserinate (1.62 g, 4.68 mmol) in DMF (10 mL) was added DIPEA (5.7 mL, 32 mmol), HATU (2.0 g, 5.1 mmol), and 4-(trifluoromethyl)tetrahydro-2H-pyran-4-carboxylic acid (1.0 g, 5.1 mmol). The reaction was allowed to stir at rt for 18 h. LCMS showed product mass, and the reaction was concentrated, diluted with EtOAc and aqueous sat. sodium bicarbonate solution. The layers were separated, and the aqueous layer was extracted two times. Combined organic layers were dried over sodium sulfate, filtered, and concentrated to afford crude product, which was purified by silica gel chromatography to afford methyl O-(cis-3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserinate.

General Procedure I can be used in the coupling step of compound 14A, or a similar compounds, with compound 16A in General Scheme A, General Scheme B, General Scheme C, General Scheme D-2, General Scheme E-2, General Scheme F-2, General Scheme G-2, or General Scheme H.

General Procedure J

The following transformation:

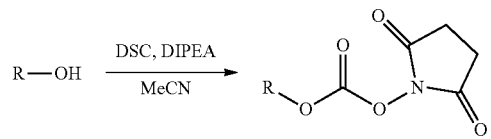

wherein R is $R^{2f}$ as defined for formula (I), or any applicable variations detailed herein, can be performed as exemplified below.

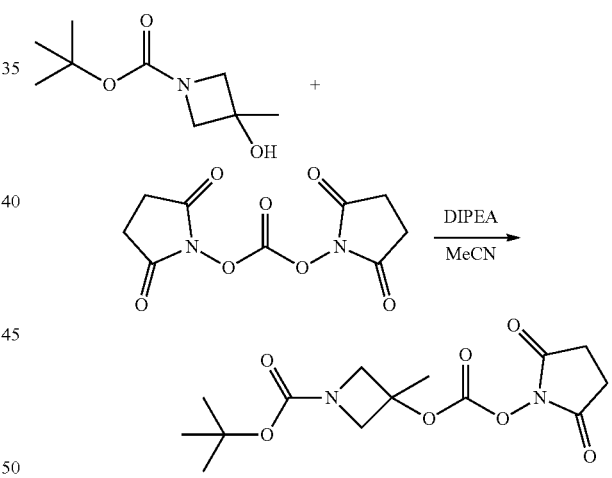

tert-butyl 3-((((2,5-dioxopyrrolidin-1-yl)oxy)carbonyl)oxy)-3-methylazetidine-1-carboxylate. To a mixture of tert-butyl 3-hydroxy-3-methylazetidine-1-carboxylate (1.1 g, 5.8 mmol) and N,N-diisopropylethylamine (2.02 mL, 11.6 mmol) in acetonitrile (10 mL) was added disuccinimidyl carbonate (3.0 g, 11.6 mmol) and the resulting mixture was stirred at room temperature for 14 hours. The reaction mixture was diluted with water and extracted with EtOAc. The combined organic layers were dried over sodium sulfate, filtered, and concentrated in vacuo. The crude residue was purified by normal phase silica gel chromatography to afford tert-butyl 3-((((((2,5-dioxopyrrolidin-1-yl)oxy)carbonyl)oxy)carbonyl)oxy)-3-methylazetidine-1-carboxylate.

General Procedure J can be used to make the appropriate reagent for use in General Procedure K

General Procedure K

The following transformation:

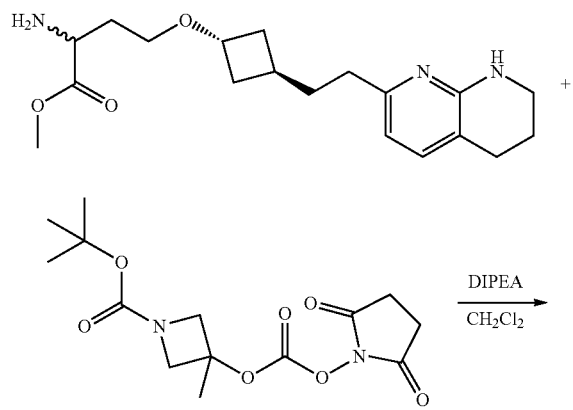

wherein R[2f] is as defined for formula (I), or any applicable variations detailed herein, can be performed as exemplified below.

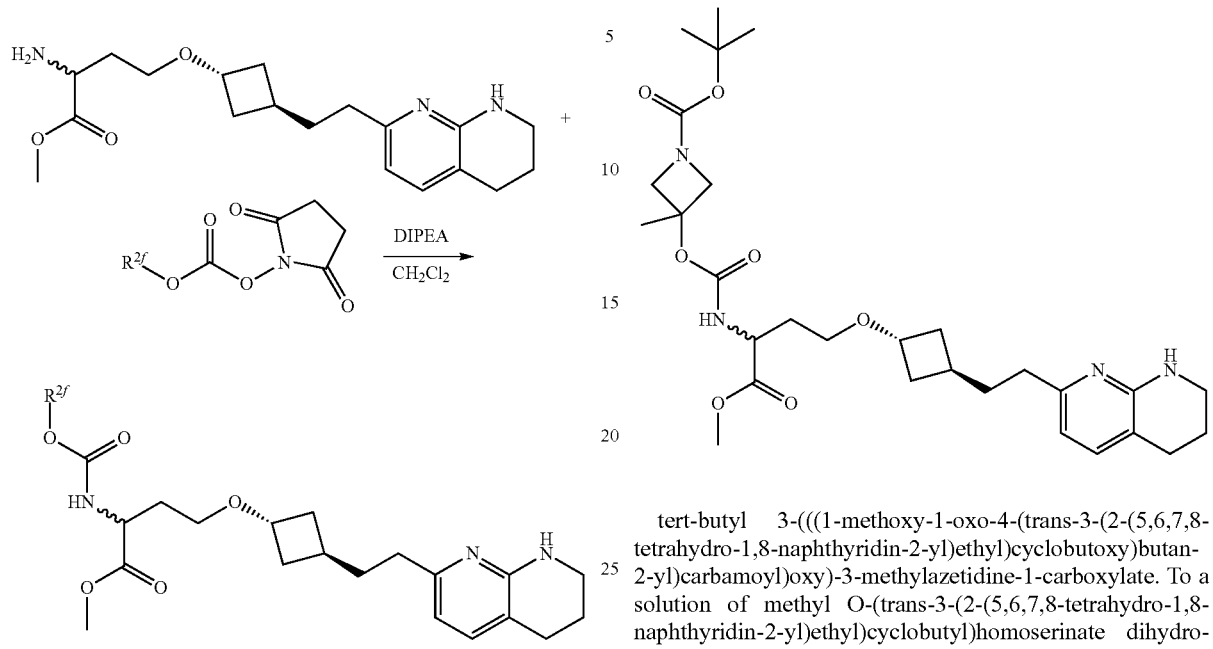

tert-butyl 3-(((1-methoxy-1-oxo-4-(trans-3-(2-(5,6,7,8-tetrahydro-1,8-naphthyridin-2-yl)ethyl)cyclobutoxy)butan-2-yl)carbamoyl)oxy)-3-methylazetidine-1-carboxylate. To a solution of methyl O-(trans-3-(2-(5,6,7,8-tetrahydro-1,8-naphthyridin-2-yl)ethyl)cyclobutyl)homoserinate dihydrochloride (220.0 mg, 0.63 mmol) and N,N-diisopropylethylamine (0.4 mL, 2.5 mmol) in dichloromethane (2.0 mL) was added tert-butyl 3-((((2,5-dioxopyrrolidin-1-yl)oxy)carbonyl)oxy)-3-methylazetidine-1-carboxylate (249.5 mg, 0.8 mmol) and the resulting mixture was stirred at room temperature for 1 hour. The reaction mixture was concentrated in vacuo and purified by normal phase silica gel column chromatography to afford tert-butyl 3-(((1-methoxy-1-oxo-4-(trans-3-(2-(5,6,7,8-tetrahydro-1,8-naphthyridin-2-yl)ethyl)cyclobutoxy)butan-2-yl)carbamoyl)oxy)-3-methylazetidine-1-carboxylate.

General Procedure K can be used in the coupling step of compound 14A, or a similar compounds, with compound 16A in General Scheme A, General Scheme B, General Scheme C, General Scheme D-2, General Scheme E-2, General Scheme F-2, General Scheme G-2, and General Scheme H.

General Procedure L

The following transformation:

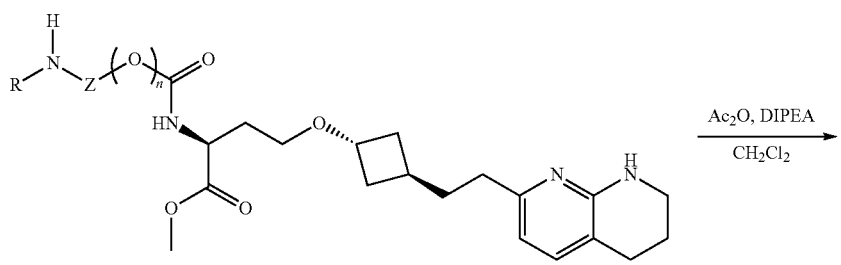

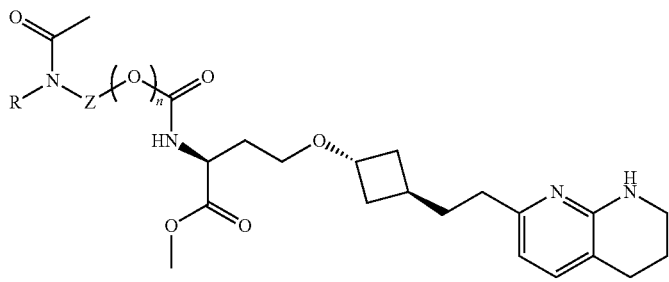

wherein Z refers to that portion of the molecule which links the —(O)$_n$C(O)N(H)CH(COOCH$_3$)L$^1$- portion of the molecule with the remainder of the R$^2$ moiety, wherein n is 0 or 1, L$^1$ and R$^2$ are as defined for formula (I), or any applicable variations detailed herein, can be performed as exemplified below. In some variations, Z is an alkylene moiety and R is hydrogen. In some variations, Z is taken together with the adjacent "NR" group to form a heterocyclic ring.

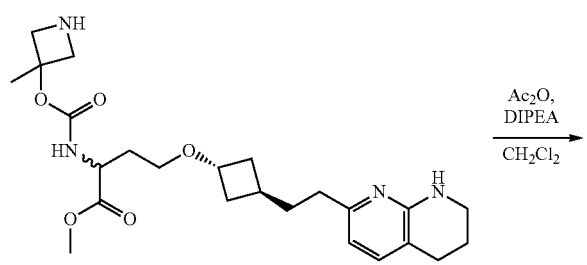

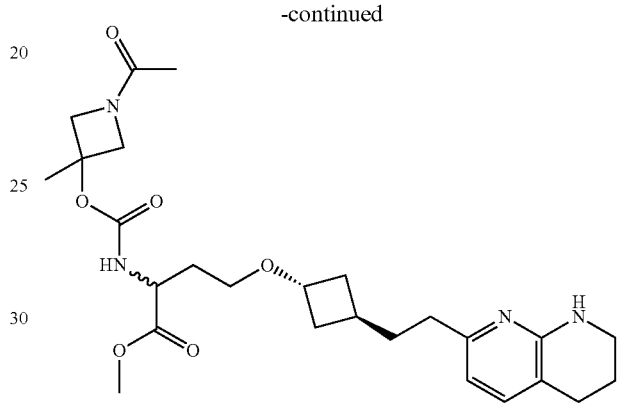

methyl N-(((1-acetyl-3-methylazetidin-3-yl)oxy)carbonyl)-O-(trans-3-(2-(5,6,7,8-tetrahydro-1,8-naphthyridin-2-yl)ethyl)cyclobutyl)homoserinate. To a solution of methyl N-(((3-methylazetidin-3-yl)oxy)carbonyl)-O-(trans-3-(2-(5,6,7,8-tetrahydro-1,8-naphthyridin-2-yl)ethyl)cyclobutyl)homoserinate bis(2,2,2-trifluoroacetate) (35.0 mg, 0.05 mmol) and N,N-diisopropylethylamine (52.9 µL, 0.304 mmol) in dichloromethane (2.0 mL) at 0° C. was added acetic anhydride (8.6 µL, 0.091 mmol). The reaction mixture was removed from the ice bath and allowed to warm to room temperature. After 20 minutes the reaction mixture was concentrated in vacuo and used without further purification.

General Procedure M

The following transformation:

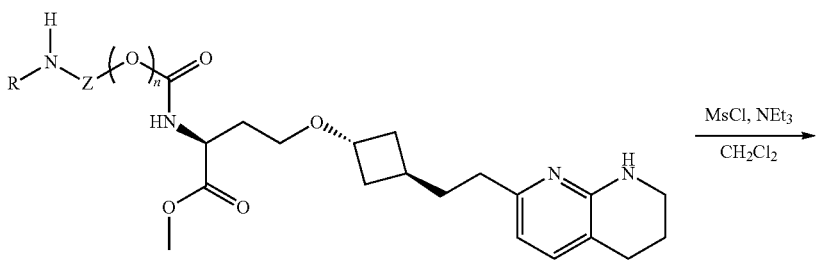

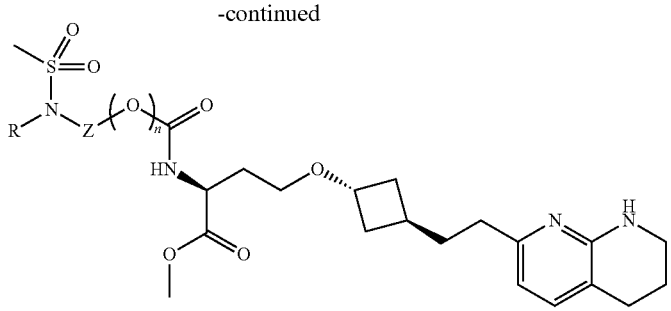

wherein Z refers to that portion of the molecule which links the —(O)$_n$C(O)N(H)CH(COOCH$_3$)L$^1$- portion of the molecule with the remainder of the R$^2$ moiety, wherein n is 0 or 1, L$^1$ and R$^2$ are as defined for formula (I), or any applicable variations detailed herein, can be performed as exemplified below. In some variations, Z is an alkylene moiety and R is hydrogen. In some variations, Z is taken together with the adjacent "NR" group to form a heterocyclic ring.

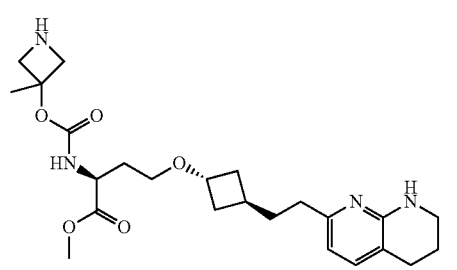

MsCl, NEt$_3$
CH$_2$Cl$_2$

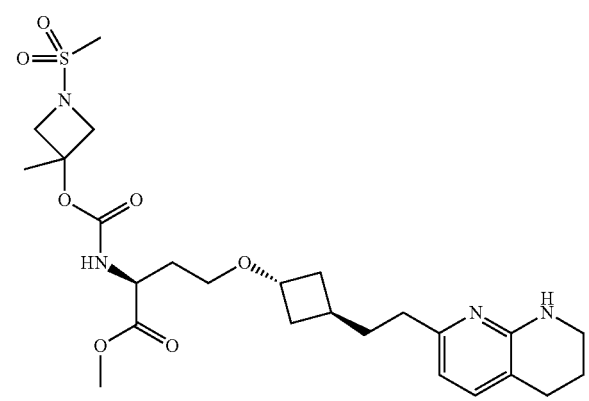

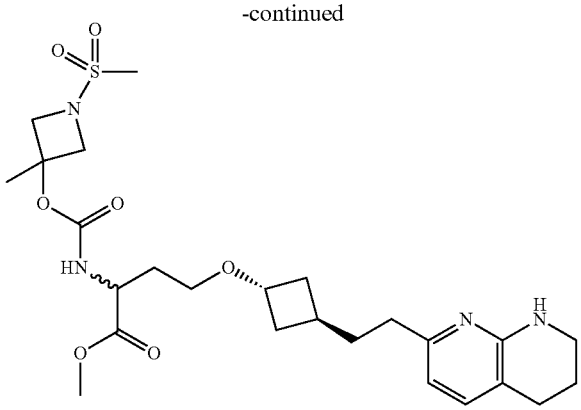

methyl N-(((3-methyl-1-(methylsulfonyl)azetidin-3-yl)oxy)carbonyl)-O-(trans-3-(2-(5,6,7,8-tetrahydro-1,8-naphthyridin-2-yl)ethyl)cyclobutyl)homoserinate. To a solution of methyl N-(((3-methylazetidin-3-yl)oxy)carbonyl)-O-(trans-3-(2-(5,6,7,8-tetrahydro-1,8-naphthyridin-2-yl)ethyl)cyclobutyl)homoserinate bis(2,2,2-trifluoroacetate) (28.0 mg, 0.04 mmol) and N,N-Diisopropylethylamine (42.4 µL, 0.24 mmol) in dichloromethane (2.0 mL) at 0° C. was added methanesulfonyl chloride (5.6 µL, 0.073 mmol). The reaction mixture was removed from the ice bath and allowed to warm to room temperature. After 20 minutes the reaction mixture was concentrated in vacuo and used without further purification.

General Procedure N

LiOH
THF/
MeOH/
H$_2$O
rt

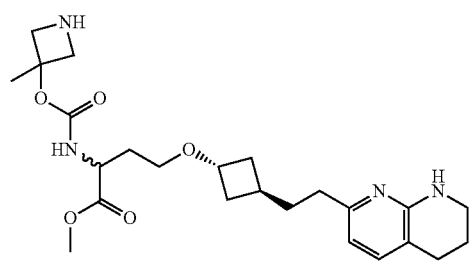

Ac$_2$O,
DIPEA
CH$_2$Cl$_2$

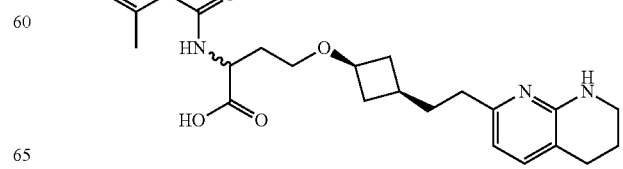

N-(4-cyano-2,6-dimethylbenzoyl)-O-(cis-3-(2-(5,6,7,8-tetrahydro-1,8-naphthyridin-2-yl)ethyl)cyclobutyl)homoserine. To a solution of methyl N-(4-cyano-2,6-dimethylbenzoyl)-O-(cis-3-(2-(5,6,7,8-tetrahydro-1,8-naphthyridin-2-yl)ethyl)cyclobutyl)homoserinate (427 mg, 0.846 mmol) in THF/MeOH/H2O 3:1:1 was added LiOH (81.0 mg, 3.38 mmol). The reaction was allowed to stir at rt for 4 h. LCMS showed conversion to product, and the reaction mixture was diluted with water and purified by reverse phase preparative HPLC to afford N-(4-cyano-2,6-dimethylbenzoyl)-O-(cis-3-(2-(5,6,7,8-tetrahydro-1,8-naphthyridin-2-yl)ethyl)cyclobutyl)homoserine as a TFA salt.

General Procedure O

Synthesis of tert-butyl 7-(4-oxobutyl)-3,4-dihydro-1,8-naphthyridine-1(2H)-carboxylate

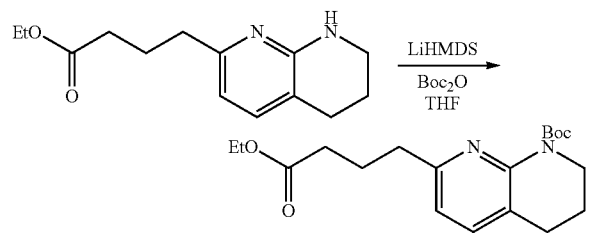

tert-butyl 7-(4-ethoxy-4-oxobutyl)-3,4-dihydro-1,8-naphthyridine-1(2H)-carboxylate. To a solution of ethyl 4-(5,6,7,8-tetrahydro-1,8-naphthyridin-2-yl)butanoate (5.25 g, 21.1 mmol) and di-tert-butyl dicarbonate (5.89 mL, 25.4 mmol in THF (70 mL) was added lithium bis(trimethylsilyl) amide (25.4 mL, 25.4 mmol) was added at 0° C. After 2 hr, the reaction was diluted with EtOAc (50 mL) and was quenched with sat NH4Cl (50 mL). After 30 min of stirring, the layers were separated and the organic layer was washed with brine (20 mL), dried over Na2SO4, and concentrated in vacuo. The resulting crude residue was purified by normal phase silica gel chromatography to give tert-butyl 7-(4-ethoxy-4-oxobutyl)-3,4-dihydro-1,8-naphthyridine-1(2H)-carboxylate.

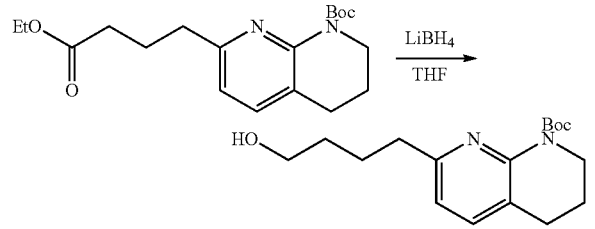

tert-butyl 7-(4-hydroxybutyl)-3,4-dihydro-1,8-naphthyridine-1(2H)-carboxylate. To a solution of tert-butyl 7-(4-ethoxy-4-oxobutyl)-3,4-dihydro-1,8-naphthyridine-1(2H)-carboxylate (6.81 g, 19.5 mmol) in THF (50 mL) was added LiBH4 (1.0M in THF, 19.5 mL, 19.5 mmol) at rt. The mixture was stirred overnight and then quenched with sat. NH4Cl and diluted with EtOAc. The layers were separated and the aqueous layer was extracted with EtOAc. The combined organic extracts were washed with H2O, dried over Na2SO4, filtered, and concentrated in vacuo. The resulting crude residue was purified by normal phase silica gel chromatography to give tert-butyl 7-(4-hydroxybutyl)-3,4-dihydro-1,8-naphthyridine-1(2H)-carboxylate.

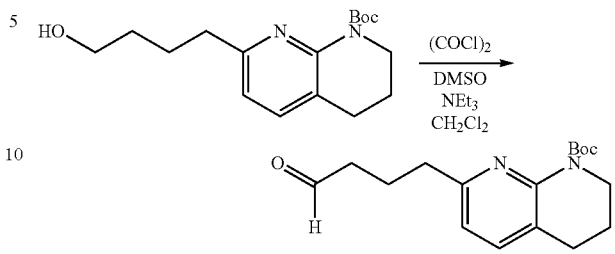

tert-butyl 7-(4-oxobutyl)-3,4-dihydro-1,8-naphthyridine-1(2H)-carboxylate. A solution of oxalyl chloride (2.57 mL, 29.3 mmol) in CH2Cl2 (69 mL) was cooled to −78° C. for 5 minutes, at which time, dimethyl sulfoxide (4.2 mL, 58.6 mmol) was added and the mixture was stirred for 30 min. A solution of tert-butyl 7-(4-hydroxybutyl)-3,4-dihydro-2H-1,8-naphthyridine-1-carboxylate (6.9 g, 22.6 mmol) in CH2Cl2 (10.5 mL) was added and stirred at −78° C. for 1 hr. Triethylamine (10.5 mL, 75.1 mmol) was then added to the reaction mixture and stirred for 30 mins. The reaction was quenched with water and extracted with CH2Cl2. The organic layer was collected and dried over sodium sulfate. The organic layer was concentrate to give tert-butyl 7-(4-oxobutyl)-3,4-dihydro-1,8-naphthyridine-1(2H)-carboxylate that was used without further purification.

General Procedure P

Synthesis of 3-(thiazol-5-yl)benzoic acid

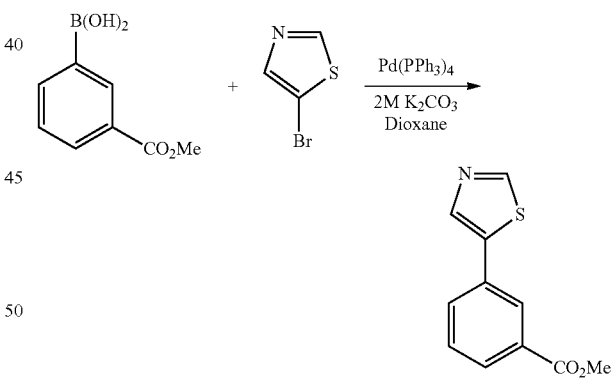

methyl 3-(thiazol-5-yl)benzoate. A microwave vial was charged with (3-(methoxycarbonyl)phenyl)boronic acid (513 mg, 2.85 mmol), 5-bromothiazole (513 mg, 3.13 mmol), and Pd(PPh3)4 (132 mg, 0.11 mmol) and then diluted with dioxane (5 mL) and 2M aq. K2CO3 (4.25 mL). The mixture was degassed by bubbling N2 through the solution while vigorously stirring at rt and then sealed and heated to 100° C. for 30 min. The reaction mixture was cooled to rt and diluted with EtOAc and H2O. The layers were separated and the organic layer was dried over Na2SO4, filtered and concentrated in vacuo. The crude residue was purified by normal phase silica gel chromatography to give methyl 3-(thiazol-5-yl)benzoate.

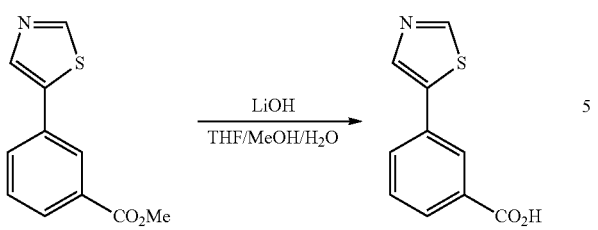

3-(thiazol-5-yl)benzoic acid. To a mixture of methyl 3-(thiazol-5-yl)benzoate (600 mg, 2.74 mmol) in 4:1:1 THF/MeOH/H$_2$O (6 mL) was added UGH (98 mg, 4.10 mmol) and the resulting mixture was stirred at rt for 3 hr. The mixture was partially concentrated in vacuo to remove the volatile organics and then acidified with 1M HCl to pH=1 causing a precipitate to form. The suspension was filtered and the solid that was collected was washed with H$_2$O and dried under high vacuum to give 3-(thiazol-5-yl)benzoic acid.

General Procedure Q

Synthesis of racemic trans-2-(3,5-dimethyl-1H-pyrazol-1-yl)cyclopentan-1-ol

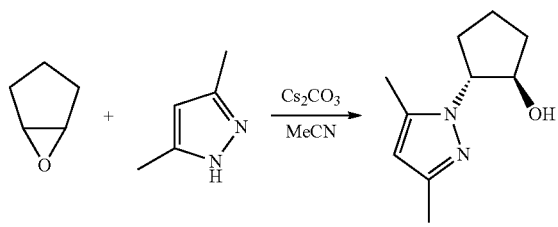

trans-2-(3,5-dimethyl-JH-pyrazol-1-yl)cyclopentan-1-ol (racemic). To a solution of cyclopentene oxide (2.03 g, 24.1 mmol) in MeCN (10 mL) was added 3,5-dimethyl-1H-pyrazole (2.78 g, 28.96 mmol) then Cs$_2$CO$_3$ (9.43 g, 28.96 mmol) and the resulting mixture was heated to reflux for 16 hours. The mixture was allowed to cool to room temperature and then filtered and concentrated in vacuo. The crude residue was purified by normal phase silica gel chromatography to give trans-2-(3,5-dimethyl-1H-pyrazol-1-yl)cyclopentan-1-ol (racemic).

General Procedure R

Preparation of tert-butyl 3-hydroxy-3-(4-isopropylphenyl)azetidine-1-carboxylate

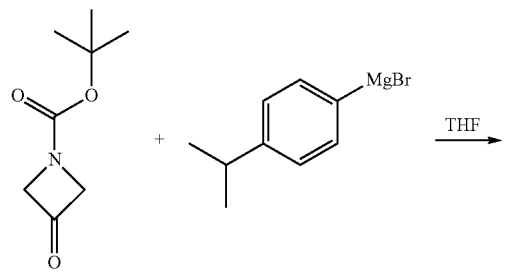

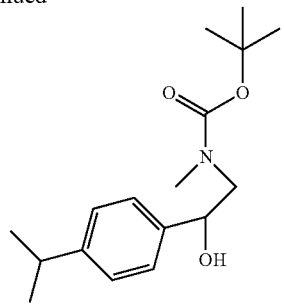

tert-butyl 3-hydroxy-3-(4-isopropylphenyl)azetidine-1-carboxylate. A solution of tert-butyl 3-oxoazetidine-1-carboxylate (793 mg, 4.63 mmol) in THF (4 mL) at −78° C. was added (4-isopropylphenyl)magnesium bromide (0.5 M in THF, 5 mL, 5.0 mmol) dropwise and the resulting mixture was stirred for 30 minutes at −78° C. The mixture was diluted with sat. aq. NH$_4$Cl and extracted with EtOAc. The combined organic extracts were dried over Na$_2$SO$_4$, filtered, and concentrated in vacuo. The crude residues was purified by normal phase silica gel chromatography to give tert-butyl 3-hydroxy-3-(4-isopropylphenyl)azetidine-1-carboxylate.

SYNTHETIC EXAMPLES

The chemical reactions in the Synthetic Examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, e.g., by appropriately protecting interfering groups, by utilizing other suitable reagents known in the art other than those described, or by making routine modifications of reaction conditions. Alternatively, other reactions disclosed herein or known in the art will be recognized as having applicability for preparing other compounds of the invention. In the following Examples, certain compounds are noted as racemic, as separated isomers, or with unassigned absolute stereochemistry at some stereocenters, and the like. For some compounds, further separation of isomers and/or assignment of absolute stereochemistry was performed. The assigned stereochemistry of such compounds is shown in the structures as depicted in FIG. 1, Table 2.

Example 1, Compound 1

Two Syntheses of N-(2-chloro-3-fluorobenzoyl)-O-(4-(5,6,7,8-tetrahydro-1,8-naphthyridin-2-yl)butyl) homoserine Example 1a

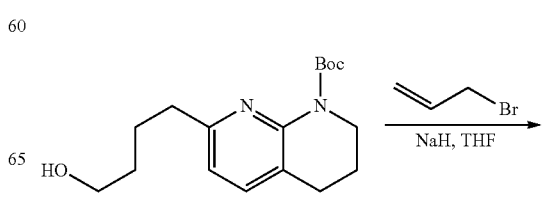

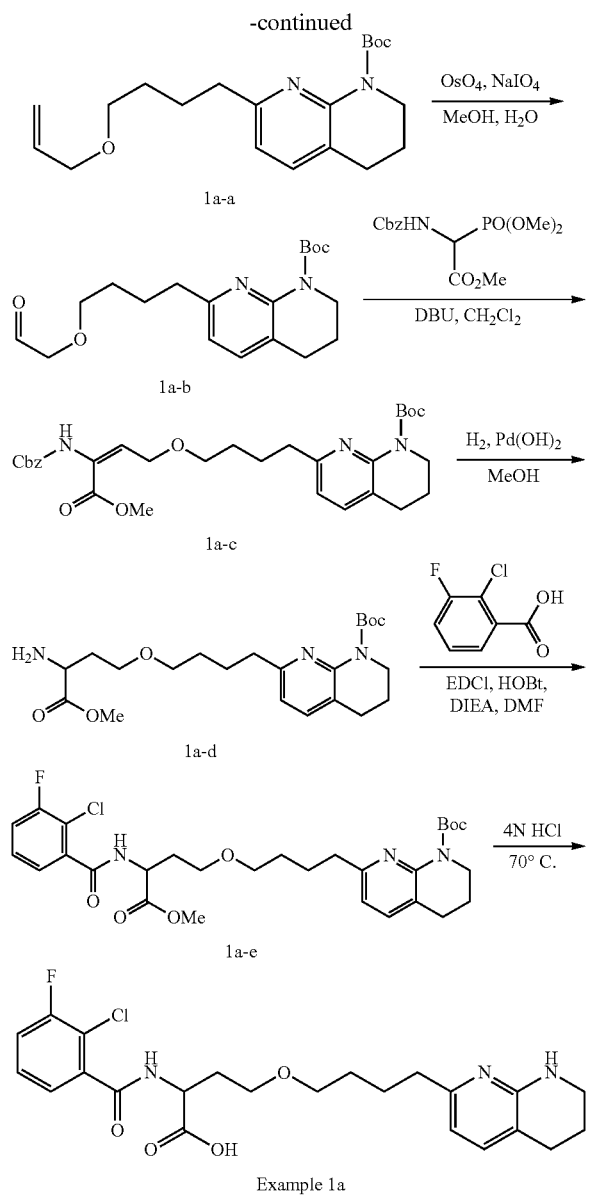

Example 1a

Compound 1a-a: To a solution of tert-butyl 7-(4-hydroxybutyl)-3,4-dihydro-2H-1,8-naphthyridine-1-carboxylate (11 g, 35.90 mmol) in DMF (150 mL) was added NaH (2.15 g, 53.85 mmol, 60% suspension in mineral oil) at 0° C. under $N_2$. The mixture was stirred for 30 min at 0° C., then 3-bromoprop-1-ene (5.21 g, 43.08 mmol, 1.2 eq) was added into the mixture at 0° C. The mixture was stirred for 10 hrs at 20° C. TLC (Petroleum ether/Ethyl acetate=3/1, $R_f$=0.1) indicated tert-butyl 7-(4-hydroxybutyl)-3,4-dihydro-2H-1,8-naphthyridine-1-carboxylate (11 g, 35.90 mmol) was consumed completely. LCMS indicated desired M+H⁺ was detected. The mixture was quenched by $NH_4Cl$ solution and extracted by EtOAc (3×50 mL). The organic layer was dried by brine and $Na_2SO_4$, filtered and concentrated under reduced pressure to give a residue. The crude product was purified by column chromatography ($SiO_2$, Petroleum ether/Ethyl acetate=50/1 to 5:1) to give compound 1a-a (6 g, 16.64 mmol, 46.36% yield) as a colourless oil. LCMS (ESI+): m/z=347.3 (M+H)⁺, RT=0.943 min.

¹H NMR (400 MHz, CDCl3) δ ppm 7.29 (s, 1H) 6.82 (d, J=7.50 Hz, 1H) 5.92 (td, J=11.19, 5.18 Hz, 1H) 5.11-5.32 (m, 2H) 3.96 (br d, J=5.51 Hz, 2H) 3.75 (t, J=5.95 Hz, 2H) 3.47 (t, J=6.50 Hz, 2H) 2.70-2.77 (m, 4H) 1.89-1.95 (m, 2H) 1.81 (br t, J=7.83 Hz, 2H) 1.64-1.72 (m, 2H) 1.52 (s, 9H).

Compound 1a-b: To a solution of compound 1a-a (3 g, 8.66 mmol) in MeOH (25 mL) and $H_2O$ (25 mL) at 20° C. was added $NaIO_4$ (4.63 g, 21.65 mmol, 1.2 mL) and $OsO_4$ (44.03 mg, 173.18 umol, 8.99 uL). The resulting suspension was stirred at 20° C. for 10 hrs. TLC (Petroleum ether/Ethyl acetate=1/1, $R_f$=0.6) indicated compound 1a-a was consumed completely and a new spot was detected. The mixture was quenched by $Na_2SO_3$ solution (150 mL) and extracted by EtOAc (3×60 mL). The organic layer was dried by brine and $Na_2SO_4$, filtered and concentrated under reduced pressure to give compound 1a-b (2.7 g, 7.75 mmol, 89.5% yield) as a yellow oil. The crude product was used for next step without further purification.

¹H NMR (400 MHz, CDCl3) δ ppm 9.73 (s, 1H) 7.29 (br d, J=7.72 Hz, 1H) 6.80-6.83 (m, 1H) 3.74 (br d, J=5.95 Hz, 2H) 3.57 (br t, J=6.39 Hz, 2H) 3.44-3.49 (m, 2H) 2.72 (br t, J=6.28 Hz, 4H) 1.90-1.94 (m, 2H) 1.70-1.84 (m, 4H) 1.52 (s, 9H)

Compound 1a-c: To a solution of compound 1a-b (2.7 g, 7.75 mmol) in DCM (30 mL) was added methyl 2-(benzyloxycarbonylamino)-2-dimethoxyphosphoryl-acetate (2.82 g, 8.52 mmol) followed by DBU (1.30 g, 8.52 mmol, 1.28 mL). The resulting suspension was stirred at 20° C. for 1 hr. TLC (Petroleum ether/Ethyl acetate=1/1, $R_f$=0.26) indicated compound 1a-b was consumed completely and one major new spot was detected. The mixture was quenched by $NH_4Cl$ solution and extracted with EtOAc (3×40 mL). The organic layer was dried by brine and $Na_2SO_4$, filtered and concentrated under reduced pressure to give a residue. The crude product was purified by column chromatography ($SiO_2$, Petroleum ether/Ethyl acetate=10/1 to 1:1). The product compound 1a-c (3 g, 5.42 mmol, 94.40% yield) was obtained as a brown oil.

¹H NMR (400 MHz, CDCl3) δ ppm 7.32-7.39 (m, 5H) 6.80 (d, J=7.50 Hz, 1H) 6.68 (br s, 1H) 6.57 (t, J=5.62 Hz, 1H) 5.14 (s, 2H) 4.15 (d, J=5.51 Hz, 2H) 3.79 (s, 3H) 3.74 (d, J=5.95 Hz, 2H) 3.47 (t, J=6.50 Hz, 2H) 2.70-2.75 (m, 4H) 1.92 (quin, J=6.34 Hz, 2H) 1.76-1.84 (m, 2H) 1.63-1.68 (m, 2H) 1.52 (s, 10H).

Compound 1a-d: The solvent MeOH (30 mL) was added $Pd(OH)_2$/C (507.31 mg, 722.48 umol, 20% purity) and degassed under vacuum and purged with $H_2$ several times. The mixture was stirred under $H_2$ (50 psi) at 50° C. for 4 hrs. Then compound 1a-c (2 g, 3.61 mmol) was added into the mixture. The suspension was degassed under vacuum and purged with $H_2$ for 3 times. The mixture was stirred under $H_2$ (50 psi) at 50° C. for 4 hrs. LCMS indicated desired MS was detected. The mixture was filtered and concentrated under reduced pressure. The product compound 1a-d (1.4 g, crude) was obtained as a yellow oil, which was used for next step without further purification. LCMS (ESI+): m/z=422.3 (M+H)⁺; RT=0.752 min.

Compound 1a-e: To a mixture of 2-chloro-3-fluoro-benzoic acid (807.50 mg, 4.63 mmol) in DMF (15 mL) was added HOBt (721.25 mg, 5.34 mmol), EDCI (1.02 g, 5.34 mmol) and DIEA (1.38 g, 10.68 mmol, 1.86 mL). Then compound 1a-d (1.5 g, 3.56 mmol) was added into the mixture. The mixture was stirred at 20° C. for 5 hrs. TLC (Petroleum ether/Ethyl acetate=0/1, $R_f$=0.2) indicated compound 1a-d was consumed completely. The mixture was extracted by $H_2O$ (40 mL) and EtOAc (3×20 mL). The organic layer was dried by brine and $Na_2SO_4$, filtered and concentrated under reduced pressure. The crude product was purified by prep-HPLC (neutral conditions) to give compound 1a-e (1.3 g, 2.2 mmol, 61.69% yield, 97.61% purity) as a brown oil. HPLC purification conditions: column: Phenomenex Gemini C18 250×50 mm×10 um; mobile phase: [water (10 mM NH4HCO3)-ACN]; B %: 40%-70%, 20 min. LCMS (ESI+): m/z=578.4 (M+H)+; RT=1.038 min.

Example 1a: To a mixture of compound 1a-e (500 mg, 864.94 umol) was added HCl (4 M, 3.24 mL, 15 eq). The mixture was stirred at 70° C. for 10 hrs. LCMS indicated desired M+H+ was detected. The mixture was freeze-dried directly to give Example 1a (304.47 mg, 587.12 umol, 67.88% yield, 96.492% purity, HCl) which was delivered without any further purification. LCMS (ESI+): m/z=464.1 (M+H)+, RT=2.450 min; HPLC purity: 96.492%, RT=6.566 min; Chiral SFC purity: 52.72%, ee value: 0%, RT=3.447 min.

$^1$H NMR (400 MHz, MeOH-$d_4$) δ ppm 7.57 (d, J=7.28 Hz, 1H) 7.32-7.47 (m, 3H) 6.65 (d, J=7.28 Hz, 1H) 3.54-3.64 (m, 3H) 3.43-3.50 (m, 3H) 2.80 (t, J=6.28 Hz, 2H) 2.70-2.77 (m, 2H) 2.29 (ddt, J=14.08, 9.40, 4.80, 4.80 Hz, 1H) 1.62-2.00 (m, 8H).

Example 1b

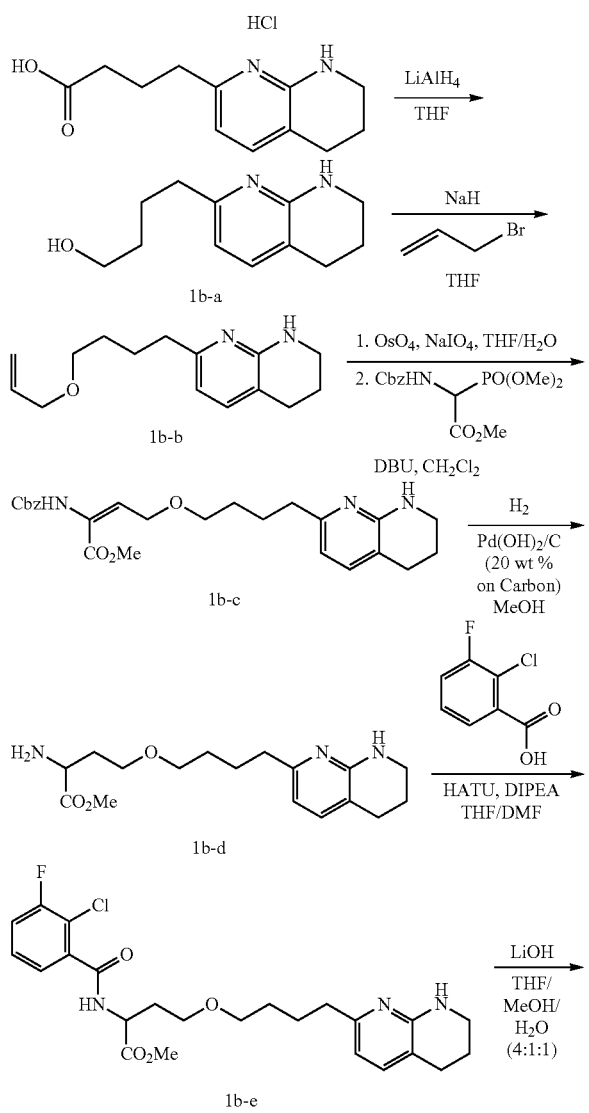

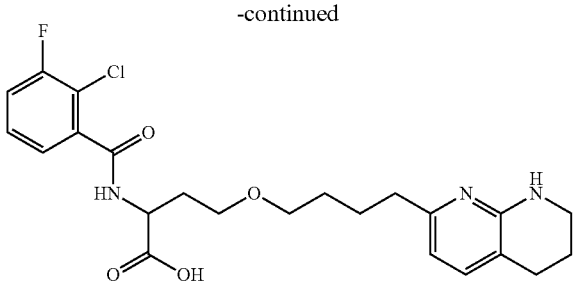

Example 1b

Compound 1b-a: To a suspension of 4-(5,6,7,8-tetrahydro-1,8-naphthyridin-2-yl)butanoic acid hydrochloride (1.23 g, 4.79 mmol, 1.0 equiv) in THF was added LiAlH4 (1.0M in THF, 10.6 mL, 10.6 mmol) dropwise and the resulting mixture was refluxed overnight. The mixture was then cooled in an ice bath and to this was slowly added $H_2O$ (400 μL), then aqueous 1.0 M NaOH (400 μL), then $H_2O$ (400 μL) again and stirred for 15 minutes and then a large excess of MgSO4 was added and stirred for an additional 30 minutes. The resulting organic mixture was filtered and then concentrated in vacuo to provide compound 1b-a.

Compound 1b-b: To a stirring suspension of NaH (60 wt % dispersion in mineral oil, 238 mg, 5.96 mmol) in THF (8.2 mL) at 0° C. was added a solution of 1b-a (820 mg, 3.98 mmol) in THF (4.1 mL) dropwise. Upon completion of the addition, the ice bath was removed and the resulting mixture was stirred at room temperature for 30 minutes, at which time, allyl bromide (400 μL, 4.62 mmol) was added dropwise. The suspension was stirred for an additional 6 hrs at room temperature and then carefully diluted with $H_2O$ and EtOAc. The layers were separated and the aqueous layer was extracted with EtOAc. The combined organic extracts were dried over MgSO4, filtered, and concentrated in vacuo. The crude residue was purified by silica gel chromatography to provide compound 1b-b.

Compound 1b-c: To a solution of 1b-b (582 mg, 2.36 mmol) in 3:1 THF/$H_2O$ (6 mL) at room temperature was added NaIO4 (2.02 g, 9.44 mmol) followed by OsO4 (2.5 wt % in t-BuOH, 480 μL, 0.05 mmol). The resulting suspension was stirred at room temperature for 5 hrs and then diluted with 1:1 sat. aq. NaHCO$_3$/sat. aq. Na2S2O3 and EtOAc and then stirred for 1 hr at room temperature. The biphasic mixture was filtered through a small pad of Celite and then the layers were separated. The aqueous layer was extracted with EtOAc and the combined organic extracts were dried over MgSO4, filtered, and concentrated in vacuo to provide a crude residue that was used without further purification.

To the crude residue obtained from the previous reaction (586 mg, 2.36 mmol) in $CH_2Cl2$ (6 mL) at room temperature was added methyl 2-(((benzyloxy)carbonyl)amino)-2-(dimethoxyphosphoryl)acetate (860 mg, 2.60 mmol) followed by DBU (391 μL, 2.60 mmol) and stirred for 30 minutes at room temperature. The mixture was diluted with sat. aq. NH4Cl and stirred for 5 minutes at room temperature. The layers were separated and the aqueous layer was extracted with EtOAc. The combined organic extracts were dried over MgSO4, filtered, and concentrated in vacuo. The crude residue was purified by silica gel chromatography to provide compound 1b-c.

Compound 1b-d: A flask containing 1b-c (497 mg, 1.10 mmol) and 20 wt % Pd(OH)$_2$ on carbon (100 mg) was diluted with MeOH (5 ml) and then evacuated and backfilled with H2 for 3 cycles and then stirred under an H2 atmosphere for 3 hrs. The resulting mixture was filtered through a pad of Celite and then concentrated in vacuo to give compound 1b-d (352 mg) that was used without further purification.

Compound 1b-e: A flask containing 1b-d (50.0 mg, 0.15 mmol) was charged with 2-chloro-3-fluorobenzoic acid (40.7 mg, 0.23 mmol) and then diluted with 10:1 THF/DMF (2.0 mL). To this was then added DIPEA (81 μL, 0.47 mmol) followed by HATU (89 mg, 0.23 mmol) and stirred for 30 minutes at room temperature and then concentrated in vacuo. The crude residue was purified by silica gel chromatography to provide compound 1b-e.

Example 1b: To a solution of 1b-e (61 mg, 0.13 mmol) in 4:1:1 THF/MeOH/H$_2$O (2.0 mL) was added LiOH (9 mg, 0.39 mmol) and the resulting mixture was stirred at room temperature for 30 minutes. The mixture was then neutralized with AcOH and then and purified by preparative reverse phase HPLC to give Example 1b as the trifluoroacetate salt. LCMS theoretical m/z=464.9 [M+H]+. found: 464.9.

Example 2, Compound 8

2-(2-ethylbutanamido)-5-(3-(5,6,7,8-tetrahydro-1,8-naphthyridin-2-yl)propoxy)pentanoic acid

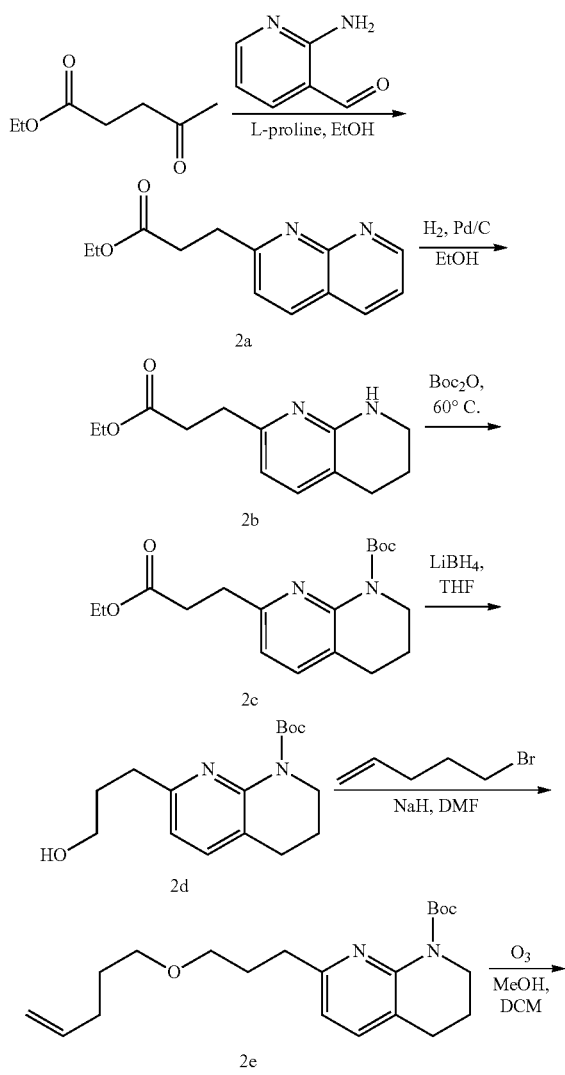

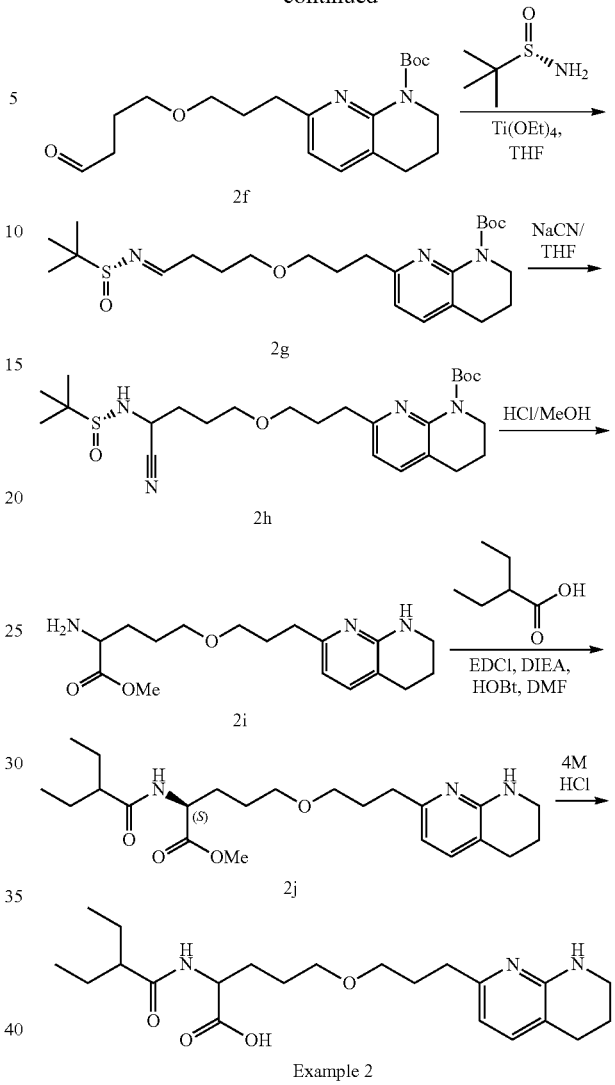

Compound 2a: two batches in parallel: To a mixture of ethyl 4-oxopentanoate (50 g, 346.82 mmol, 49.50 mL) and 2-aminopyridine-3-carbaldehyde (42.35 g, 346.82 mmol) in EtOH (800 mL) was added L-proline (19.96 g, 173.41 mmol). The mixture was refluxed at 85° C. for 12 hrs. LCMS indicated the reaction was completed. TLC (Petroleum ether/Ethyl acetate=2:1, R$_f$=0.31) was the spot of product. The mixture was combined and concentrated under reduced pressure. The mixture was extracted by H$_2$O (1000 mL) and EtOAc (3×800 mL), washed with brine and dried with Na$_2$SO$_4$, filtered and concentrated under reduced pressure. The crude product was purified by column chromatography (SiO$_2$, Petroleum ether/Ethyl acetate=10/1 to 1:1) to give compound 2a (60 g, 240.85 mmol, 34.72% yield, 92.4% purity) as a yellow solid. LCMS (ESI+): m/z=231.1 (M+H)$^+$, RT=0.68 min. $^1$H NMR (400 MHz, CDCl3) δ ppm 9.08 (dd, J=4.19, 1.98 Hz, 1H) 8.07-8.19 (m, 2H) 7.42-7.48 (m, 2H) 4.12 (q, J=7.06 Hz, 2H) 3.32-3.39 (m, 2H) 3.06 (t, J=7.28 Hz, 2H) 1.23 (t, 0.1=7.17 Hz, 3H).

Compound 2b: two batches were processed in parallel: To a solution of compound 2a (26 g, 112.91 mmol) in EtOH (300 mL) was added Pd/C (3 g, 10%) under N$_2$. The suspension was degassed under vacuum and purged with H$_2$ several times. The mixture was stirred under $H_2$ (50 psi) at 20° C. for 10 hrs. TLC (Petroleum ether/Ethyl acetate=0:1, $R_f$=0.3) indicated the compound 5a was consumed completely and a new spot was detected. LCMS indicated desired MS was detected. The mixture was filtered and concentrated under reduced pressure to give compound 2b (46 g, 196.33 mmol, 86.94% yield) as a white solid. The crude product was used for next step with further purification. LCMS (ESI+): m/z=235.1 (M+H)~, RT=0.772 min.

Compound 2c: A mixture of compound 2b (46 g, 196.33 mmol) and $Boc_2O$ (100 mL) was stirred at 40° C. for 15 hrs. TLC (Petroleum ether/Ethyl acetate=2:1, $R_f$=0.11) indicated compound 2c was formed. The mixture was not worked up but evaporated and applied to a column of silica gel. The crude product was purified by column chromatography ($SiO_2$, Petroleum ether/Ethyl acetate=100/1 to 5:1) to give compound 2c (32 g, 95.69 mmol, 48.74% yield) as a white solid. $^1$H NMR (400 MHz, CDCl3) δ ppm 7.33 (d, J=7.72 Hz, 1H) 6.88 (d, J=7.72 Hz, 1H) 4.17 (q, J=7.06 Hz, 2H) 3.76-3.81 (m, 2H) 3.04-3.10 (m, 2H) 2.81-2.86 (m, 2H) 2.76 (t, J=6.62 Hz, 2H) 1.95 (quin, J=6.34 Hz, 2H) 1.51 (s, 9H) 1.28 (t, J=7.06 Hz, 3H).

Compound 2d: To a solution of compound 2c (14 g, 41.86 mmol) in THF (140 mL) was added $LiBH_4$ (1.82 g, 83.73 mmol) in several portions at 0° C. under N2. The reaction mixture was warmed to 15° C. for 1 hr. The reaction mixture was stirred at 40° C. for 12 hrs. TLC (Petroleum ether/Ethyl acetate=1:1, $R_f$=0.61) indicated compound 2c was consumed completely. The mixture was poured into the saturated $NH_4Cl$ solution (500 mL) and was extracted by EtOAc (3×300 mL). The organic layer was dried by brine and $Na_2SO_4$, filtered and concentrated under reduced pressure. The crude product was purified by column chromatography ($SiO_2$, Petroleum ether/Ethyl acetate=0:1) to give compound 2d (18 g, 61.57 mmol, 73.53% yield) as a white solid. $^1$H NMR (400 MHz, CDCl3) δ ppm 7.31 (d, J=7.72 Hz, 1H) 6.83 (d, J=7.72 Hz, 1H) 3.74-3.78 (m, 2H) 3.69 (br t, J=5.62 Hz, 2H) 2.88-2.93 (m, 2H) 2.73 (t, J=6.50 Hz, 2H) 1.89-1.96 (m, 4H) 1.54 (s, 9H).

Compound 2e: To a mixture of compound 2d (3 g, 10.26 mmol) in DMF (30 mL) was added NaH (2.46 g, 61.57 mmol, 60% purity) at 0° C. Then the mixture was stirred at 0° C. for 0.5 hr. Then 5-bromopent-1-ene (6.12 g, 41.04 mmol) was added into the mixture at 0° C. The mixture was warmed to 15° C. for 12 hrs. LCMS indicated desired MS was detected. TLC (Petroleum ether/Ethyl acetate=3/1, $R_f$=0.18) indicated compound 2d was consumed. The mixture was poured into $NH_4Cl$ solution (50 mL) and extracted by EtOAc (3×30 mL). The organic layer was dried by brine and $Na_2SO_4$, filtered and concentrated under reduced pressure. The crude product was purified by column chromatography ($SiO_2$, Petroleum ether/Ethyl acetate=100/1 to 10:1) to give compound 2e (2.8 g, 7.77 mmol, 75.70% yield) as a yellow oil. LCMS (ESI+): m/z=361.3 (M+H)$^+$; RT: 1.016 min. $^1$H NMR (400 MHz, CDCl3) δ ppm 7.25 (d, J=3.09 Hz, 1H) 6.80 (d, J=7.72 Hz, 1H) 5.80 (ddt, J=17.03, 10.31, 6.61, 6.61 Hz, 1H) 4.92-5.02 (m, 2H) 3.72 (d, J=5.95 Hz, 2H) 3.40-3.44 (m, 4H) 2.69-2.77 (m, 4H) 2.08-2.13 (m, 2H) 1.97-2.02 (m, 2H) 1.88-1.92 (m, 2H) 1.62-1.67 (m, 2H) 1.49 (s, 9H).

Compound 2f: Ozone was bubbled into a solution of Compound 2e (2.8 g, 7.77 mmol) in DCM (20 mL) and MeOH (10 mL) at −78° C. for 30 minutes. After excess O3 was purged by O2, $Me_2S$ (4.83 g, 77.67 mmol, 5.70 mL) was added at −78° C. The mixture was stirred for 12 hrs at 20° C. LCMS indicated desired MS was detected. TLC (Petroleum ether/Ethyl acetate=1:1, $R_f$=0.6) indicated compound 2e was consumed completely. The mixture was concentrated under reduced pressure. The crude product was purified by column chromatography ($SiO_2$, Petroleum ether/Ethyl acetate=30:1 to 8:1) to give compound 2f (1.4 g, 3.86 mmol, 49.73% yield) as a brown oil. LCMS (ESI+): m/z=363.3 (M+H); RT=0.853 min.

Compound 2g: To a solution of compound 2f (1.4 g, 3.86 mmol, 1 eq) in THF (10 mL) was added 2-methylpropane-2-sulfinamide (514.95 mg, 4.25 mmol) and tetraethoxytitanium (2.64 g, 11.59 mmol, 2.40 mL). The mixture was stirred at 50° C. for 12 hrs. LCMS indicated the desired MS. The mixture was concentrated under reduced pressure to give compound 2g (1.7 g, crude) as brown oil. The crude product was used directly for next step without purification. LCMS (ESI+): m/z=466.3 (M+H)+, RT: 0.991 min.

Compound 2h: To a mixture of compound 2g (1.7 g, 3.65 mmol) in dried THF (20 mL) was added NaCN (536.75 mg, 10.95 mmol). The mixture was stirred at 40° C. for 12 hrs. NaCN (536.75 mg, 10.95 mmol) and i-PrOH (658.19 mg, 10.95 mmol, 838.46 uL) was added into the mixture with stirring for 16 hrs at 55° C. LCMS indicated desired M+H was detected. TLC (Petroleum ether/Ethyl acetate=1:1, $R_f$=0.72) indicated compound 2g was consumed. The mixture was extracted by $H_2O$ (50 mL) and EtOAc (3×30 mL). The organic layer was dried by brine and $Na_2SO_4$, filtered and concentrated under reduced pressure. The $H_2O$ layer was quenched by NaClO solution. The crude product was purified by column chromatography ($SiO_2$, Petroleum ether/Ethyl acetate=10:1 to 1:1) to give compound 2h (450 mg, 850.45 umol, 23.29% yield) as yellow oil. LCMS (ESI+): m/z=493.4 (M+H)$^+$, RT=0.958 min.

Compound 2i: To a mixture of compound 2h (450 mg, 913.38 umol) in HCl/MeOH (5 mL) was stirred at 50° C. for 16 hrs. LCMS indicated desired MS was detected. The mixture was concentrated under reduced pressure to give the crude compound 2i (360 mg, crude) as a brown oil, which was used directly for next step without further purification. LCMS (ESI+): m/z=322.3 (M+H)$^+$, RT=0.628 min.

Compound 2j: To a mixture of 2-ethylbutanoic acid (79.53 mg, 684.7 umol, 86.26 uL) in DMF (3 mL) was added HOBt (92.52 mg, 684.70 umol), EDCI (131.26 mg, 684.7 umol) and DIEA (176.98 mg, 1.37 mmol, 238.52 uL). Then compound 2i (180 mg, 456.46 umol) was added into the mixture. The mixture was stirred at 15° C. for 10 hrs. LCMS indicated desired MS was detected. The mixture was extracted by $H_2O$ (20 mL) and EtOAc (3×10 mL). The organic layer was dried by brine and $Na_2SO_4$, filtered and concentrated under reduced pressure. The crude product was purified by prep-TLC ($SiO_2$, Ethyl acetate/MeOH=10:1) to give compound 2j (65 mg, 154.93 umol, 33.94% yield) as a yellow oil. LCMS (ESI+): m/z=419.56 (M+H)$^+$, RT=0.855 min.

Example 2: To a mixture of compound 2j (65 mg, 154.92 umol) was added HCl (4 M, 193.66 uL). The mixture was stirred at 70° C. for 12 hrs. LCMS indicated desired MS was detected. The mixture was concentrated under reduced pressure. The crude product was purified by prep-HPLC (TFA condition) to give Example 2 (40 mg, 76.13 umol, 49.14% yield, 98.887% purity, TFA) as a colourless oil.

HPLC purification conditions: column: Luna C18 100×30 5 u; mobile phase: [water (0.1% TFA)-ACN]; B %: 1%-40%, 5 min.

$^1$H NMR (400 MHz, MeOH-d$_4$) δ ppm 7.59 (d, J=7.50 Hz, 1H) 6.64 (d, J=7.28 Hz, 1H) 4.46 (dd, J=9.26, 4.85 Hz, 1H) 3.44-3.53 (m, 6H) 2.78-2.85 (m, 4H) 2.14 (tt, J=9.59, 4.96 Hz, 1H) 1.91-1.98 (m, 5H) 1.44-1.75 (m, 7H) 0.87-0.95 (m, 6H); LCMS (ESI+): m/z=406.2 (M+H)$^+$, RT=2.336 min;

HPLC purity: 98.887%, RT=6.242 min; Chiral SFC purity: 52.72%, ee value: 5.44%, RT=2.013 min.

Example 3, Compound 9

2-(2-chloro-3-fluorobenzamido)-5-(3-(5,6,7,8-tetrahydro-1,8-naphthyridin-2-yl)propoxy)pentanoic acid

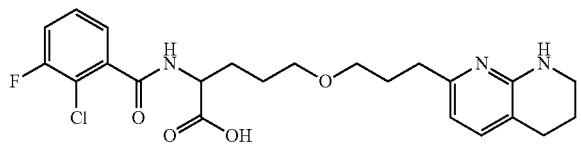 [SMILES: O=C(NC(CCCOCCCc1ccc2c(n1)NCCC2)C(=O)O)c1cccc(F)c1Cl]

Example 3 was prepared by the same procedure used to prepare Example 2 with the exception that the acid was replaced by 2-chloro-3-fluorobenzoic acid in the reaction with intermediate 2i.

HPLC purification conditions: column: Phenomenex Synergi C18 100*21.2 mm*4 um; mobile phase: [water (0.1% TFA)-ACN]; B %; 15%-45%, 10 min $^1$H NMR (400 MHz, MeOH-d$_4$) δ ppm 7.57 (d, J=7.50 Hz, 1H) 7.30-7.43 (m, 3H) 6.63 (d, J=7.28 Hz, 1H) 4.63 (dd, J=9.26, 4.85 Hz, 1H) 3.47-3.52 (m, 6H) 2.78-2.83 (m, 4H) 2.01-2.09 (m, 1H) 1.92-1.97 (m, 4H) 1.71-1.87 (m, 3H); HPLC purity: 99.041%, RT: 6.480 min; LCMS (ESI+): m/z=464.1 (M+H)$^+$, RT=2.399 min; Chiral SFC purity: 52.42%, ee value; 4.84%, RT=3.870 min.

Example 4, Compound 2

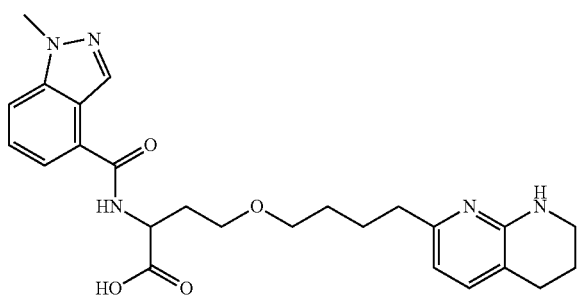 [SMILES: Cn1ncc2c(C(=O)NC(CCOCCCCc3ccc4c(n3)NCCC4)C(=O)O)cccc21]

N-(1-methyl-1H-indazole-4-carbonyl)-O-(4-(5,6,7,8-tetrahydro-1,8-naphthyridin-2-yl)butyl)homoserine. Prepared according to General Scheme C using General Procedure I with 1-methyl-1H-indazole-4-carboxylic acid. LCMS theoretical m/z=466.2. [M+H]+. found 466.2.

Example 5, Compound 3

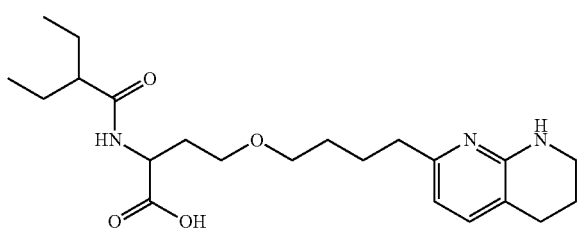 [SMILES: CCC(CC)C(=O)NC(CCOCCCCc1ccc2c(n1)NCCC2)C(=O)O]

N-(2-ethylbutanoyl)-O-(4-(5,6,7,8-tetrahydro-1,8-naphthyridin-2-yl)butyl)homoserine. Prepared according to General Scheme C using General Procedure I with 2-ethylbutanoic acid. LCMS theoretical m/z=406.3 [M+H]+. found: 406.3.

Example 6, Compound 4

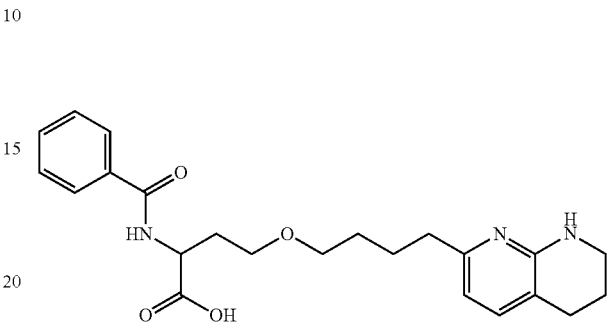

N-benzoyl-O-(4-(5,6,7,8-tetrahydro-1,8-naphthyridin-2-yl)butyl)homoserine. Prepared according to General Scheme C using General Procedure I with benzoic acid. LCMS theoretical m/z=412.2 [M+H]+. found: 412.2.

Example 7, Compound 5

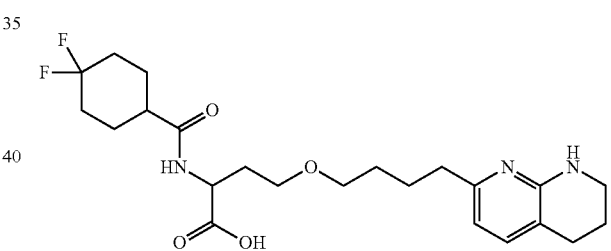

N-(4,4-difluorocyclohexane-1-carbonyl)-O-(4-(5,6,7,8-tetrahydro-1,8-naphthyridin-2-yl)butyl)homoserine. Prepared according to General Scheme C using General Procedure I with 4,4-difluorocyclohexane-1-carboxylic acid. LCMS theoretical m/z=454.3 [M+H]+. found: 454.3.

Example 8, Compound 6

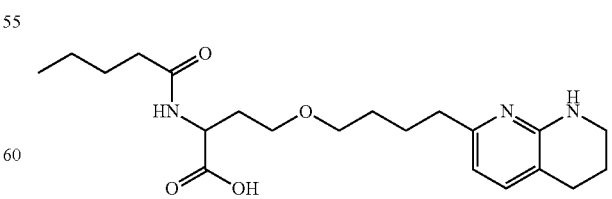

N-pentanoyl-O-(4-(5,6,7,8-tetrahydro-1,8-naphthyridin-2-yl)butyl)homoserine. Prepared according to General Scheme C using General Procedure I with butanoic acid. LCMS theoretical m/z=392.3 [M+H]+. found: 392.3.

Example 9, Compound 7

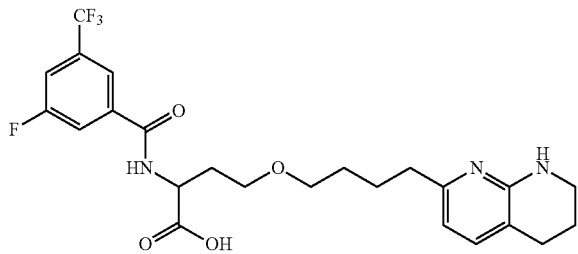 [SMILES: O=C(NC(CCOCCCCc1ccc2c(n1)NCCC2)C(=O)O)c1cc(F)cc(C(F)(F)F)c1]

N-(3-fluoro-5-(trifluoromethyl)benzoyl)-O-(4-(5,6,7,8-tetrahydro-1,8-naphthyridin-2-yl)butyl)homoserine Prepared according to General Scheme C using General Procedure I with 3-fluoro-5-(trifluoromethyl)benzoic acid. LCMS theoretical m/z=498.2 [M+H]+. found: 498.2.

Example 10, Compound 15

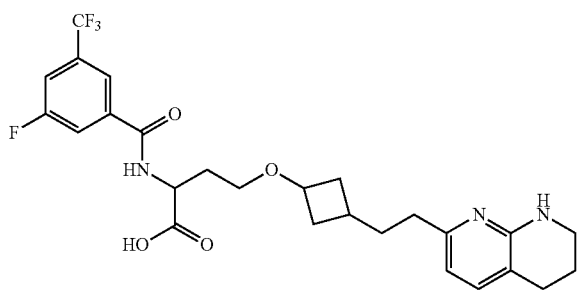 [SMILES: O=C(NC(CCOC1CC(CCc2ccc3c(n2)NCCC3)C1)C(=O)O)c1cc(F)cc(C(F)(F)F)c1]

N-(3-fluoro-5-(trifluoromethyl)benzoyl)-O-(3-(2-(5,6,7,8-tetrahydro-1,8-naphthyridin-2-yl)ethyl)cyclobutyl)homoserine. Prepared according to General Scheme H using General Procedure I with 3-fluoro-5-(trifluoromethyl)benzoic acid. LCMS theoretical m/z=524.2 [M+H]+. found 524.3.

Example 11, Compound 18

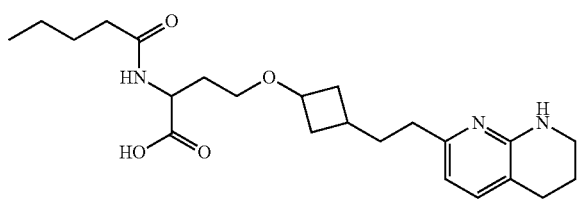 [SMILES: CCCCC(=O)NC(CCOC1CC(CCc2ccc3c(n2)NCCC3)C1)C(=O)O]

N-pentanoyl-O-(3-(2-(5,6,7,8-tetrahydro-1,8-naphthyridin-2-yl)ethyl)cyclobutyl)homoserine. Prepared according to General Scheme H using General Procedure I with pentanoic acid. LCMS theoretical m/z=418.3 [M+H]+. found 418.3.

Example 12, Compound 19

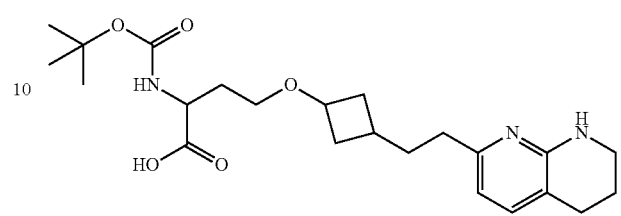

N-(tert-butoxycarbonyl)-O-(3-(2-(5,6,7,8-tetrahydro-1,8-naphthyridin-2-yl)ethyl)cyclobutyl)homoserine. Prepared according to General Scheme H through intermediate 13H, followed by General Procedure N. LCMS theoretical m/z=434.3 [M+H]+. found 434.3.

Example 12A, Compound 19

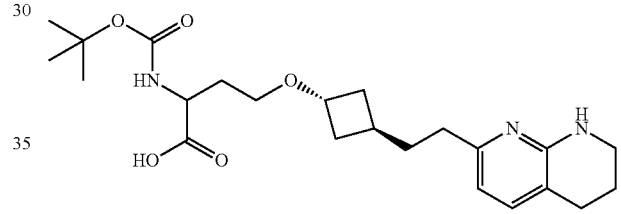

N-(tert-butoxycarbonyl)-O-(trans-3-(2-(5,6,7,8-tetrahydro-1,8-naphthyridin-2-yl)ethyl)cyclobutyl)homoserine. Prepared according to General Scheme A through intermediate 13A, followed by General Procedure N. LCMS theoretical m/z=434.3 [M+H]+. found 434.3.

Example 13, Compound 22

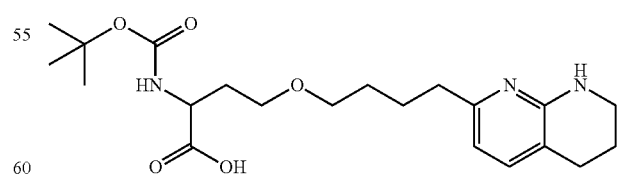

N-(tert-butoxycarbonyl)-O-(4-(5,6,7,8-tetrahydro-1,8-naphthyridin-2-yl)butyl)homoserine. Prepared according to General Scheme C through intermediate 7C, followed by General Procedure N. LCMS theoretical m/z=408.2 [M+H]+. found: 408.2.

Example 14, Compound 14

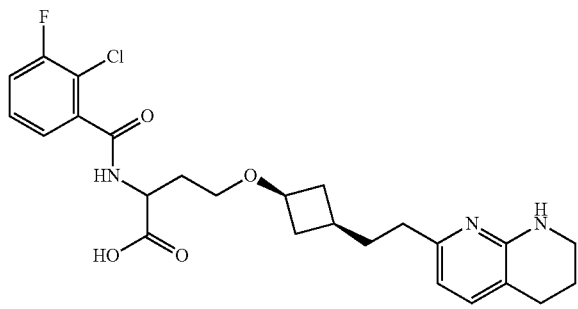 [SMILES: O=C(NC(CCO[C@H]1C[C@@H](CCc2ccc3c(n2)NCCC3)C1)C(=O)O)c1cccc(F)c1Cl]

N-(2-chloro-3-fluorobenzoyl)-O-(cis-3-(2-(5,6,7,8-tetrahydro-1,8-naphthyridin-2-yl)ethyl)cyclobutyl)homoserine. Prepared according to General Scheme B using General Procedure I with 2-chloro-3-fluorobenzoic acid. LCMS theoretical m/z=490.2 [M+H]+. found 490.2.

Example 15, Compound 24

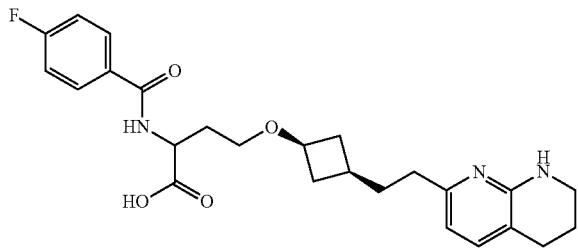 [SMILES: O=C(NC(CCO[C@H]1C[C@@H](CCc2ccc3c(n2)NCCC3)C1)C(=O)O)c1ccc(F)cc1]

N-(4-fluorobenzoyl)-O-(cis-3-(2-(5,6,7,8-tetrahydro-1,8-naphthyridin-2-yl)ethyl)cyclobutyl)homoserine. Prepared according to General Scheme B using General Procedure I with 4-fluorobenzoic acid. LCMS theoretical m/z=456.2 [M+H]+. found 456.2.

Example 16, Compound 24

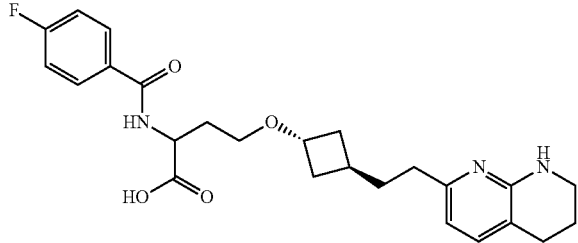 [SMILES: O=C(NC(CCO[C@H]1C[C@H](CCc2ccc3c(n2)NCCC3)C1)C(=O)O)c1ccc(F)cc1]

N-(4-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 4-fluorobenzoic acid. LCMS theoretical m/z=456.2 [M+H]+. found 456.2.

Example 17, Compound 25

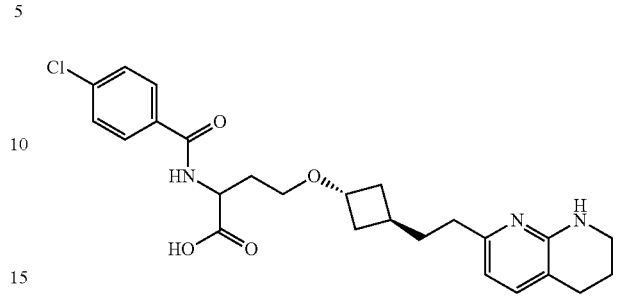

N-(4-chlorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 4-chlorobenzoic acid. LCMS theoretical m/z=472.2 [M+H]+. found 472.2.

Example 18, Compound 19

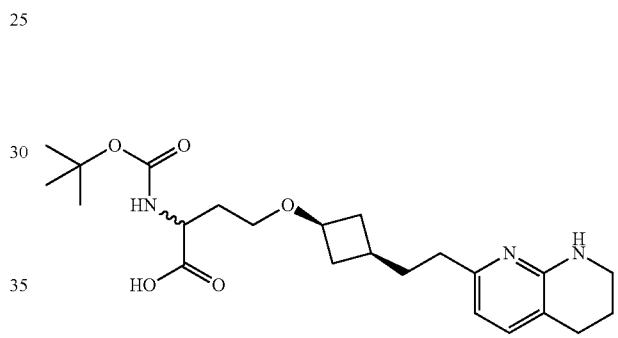

N-(tert-butoxycarbonyl)-O-(cis-3-(2-(5,6,7,8-tetrahydro-1,8-naphthyridin-2-yl)ethyl)cyclobutyl)homoserine. Isomer E2 was used in General Procedure N. LCMS theoretical m/z=434.3 [M+H]+. found 434.3.

Example 19, Compound 26

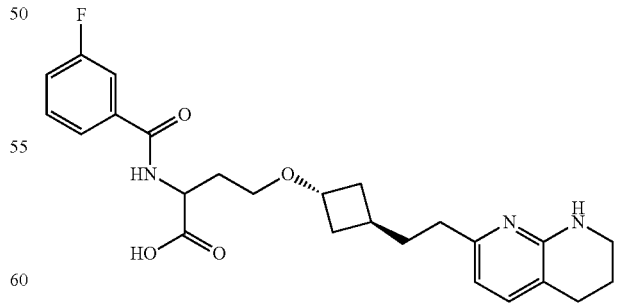

N-(3-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-fluorobenzoic acid. LCMS theoretical m/z=456.2 [M+H]+. found 456.2.

Example 20, Compound 27

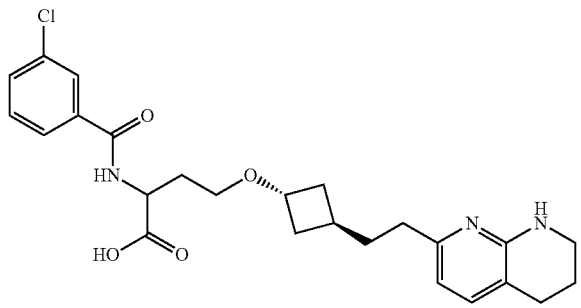 [SMILES: O=C(NC(CCO[C@H]1C[C@H](CCc2ccc3c(n2)NCCC3)C1)C(=O)O)c1cccc(Cl)c1]

N-(3-chlorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-chlorobenzoic acid. LCMS theoretical m/z=472.2 [M+H]+. found 472.2.

Example 21, Compound 28

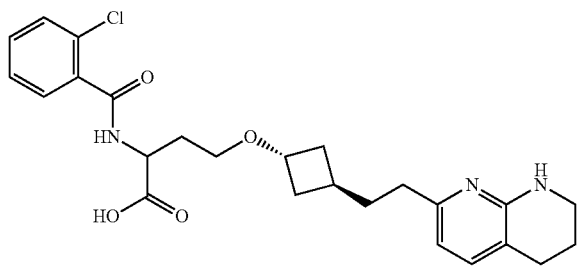 [SMILES: O=C(NC(CCO[C@H]1C[C@H](CCc2ccc3c(n2)NCCC3)C1)C(=O)O)c1ccccc1Cl]

N-(2-chlorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2-chlorobenzoic acid. LCMS theoretical m/z=472.2 [M+H]+. found 472.2.

Example 22. Compound 29

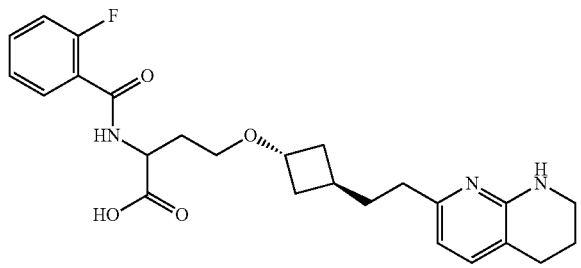 [SMILES: O=C(NC(CCO[C@H]1C[C@H](CCc2ccc3c(n2)NCCC3)C1)C(=O)O)c1ccccc1F]

N-(2-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2-fluorobenzoic acid. LCMS theoretical m/z=456.2 [M+H]+. found 456.2.

Example 23, Compound 30

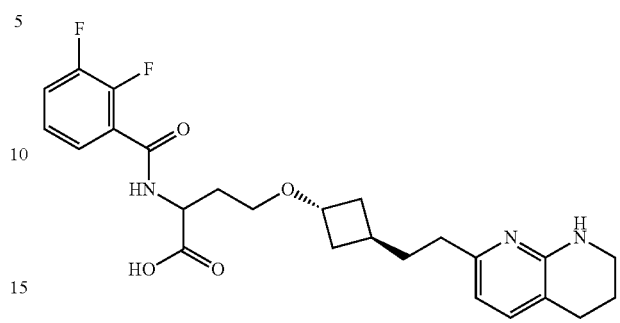

N-(2,3-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2,3-difluorobenzoic acid. LCMS theoretical m/z=474.2 [M+H]+. found 474.2.

Example 24, Compound 31

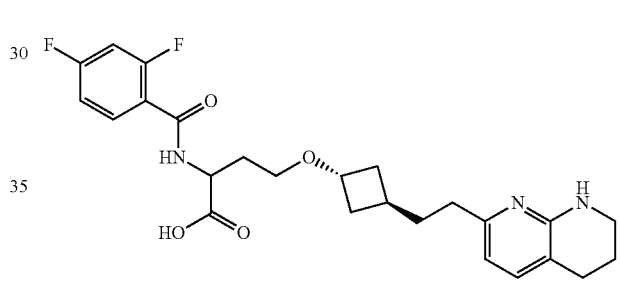

N-(2,4-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2,4-difluorobenzoic acid. LCMS theoretical m/z=474.2 [M+H]+. found 474.2.

Example 25, Compound 32

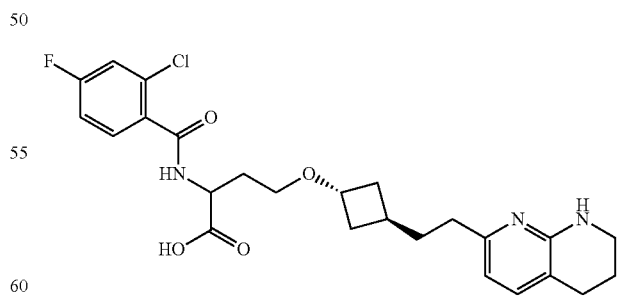

N-(2-chloro-4-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2-chloro-4-difluorobenzoic acid. LCMS theoretical m/z=490.2 [M+H]+. found 490.2.

Example 26, Compound 33

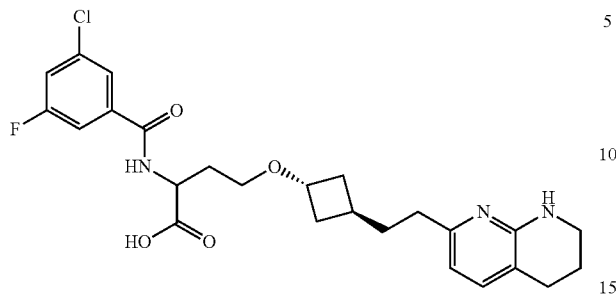

N-(3-chloro-5-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-chloro-5-fluorobenzoic acid. LCMS theoretical m/z=490.2 [M+H]+. found 490.2.

Example 27, Compound 34

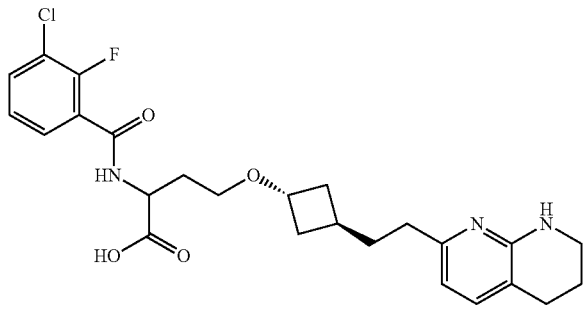 [SMILES: O=C(NC(CCO[C@H]1C[C@H](CCc2ccc3c(n2)NCCC3)C1)C(=O)O)c1cccc(F)c1F]

N-(3-chloro-2-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-chloro-2-fluorobenzoic acid. LCMS theoretical m/z=490.2 [M+H]+. found 490.2.

Example 28, Compound 35

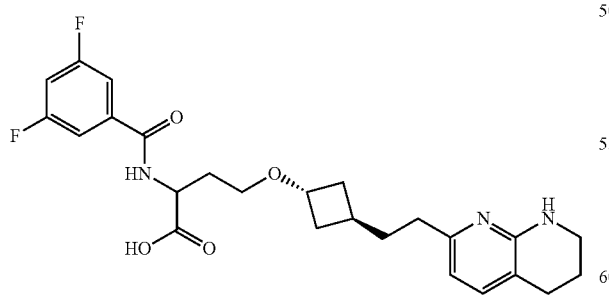

N-(3,5-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3,5-difluorobenzoic acid. LCMS theoretical m/z=474.2 [M+H]+. found 474.2.

Example 29, Compound 36

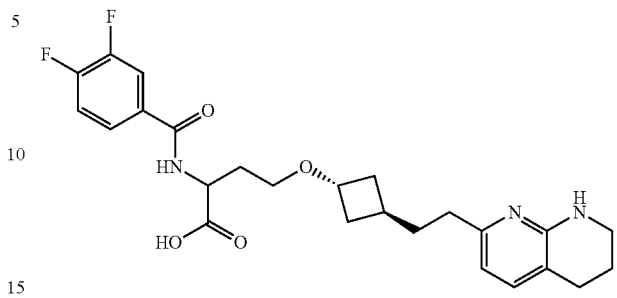

N-(3,4-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3,4-difluorobenzoic acid. LCMS theoretical m/z=474.2 [M+H]+. found 474.2.

Example 30, Compound 37

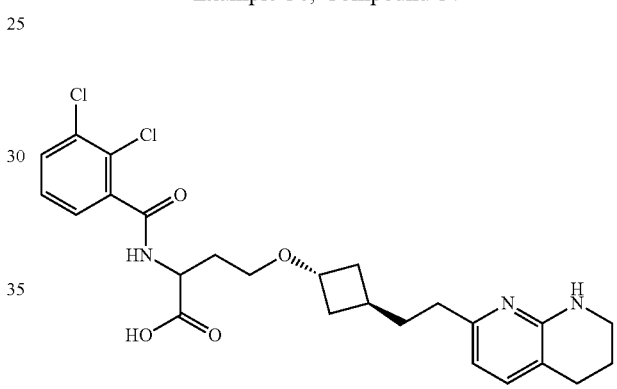

N-(2,3-dichlorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2,3-dichlorobenzoic acid. LCMS theoretical m/z=506.2 [M+H]+. found 506.2.

Example 31, Compound 38

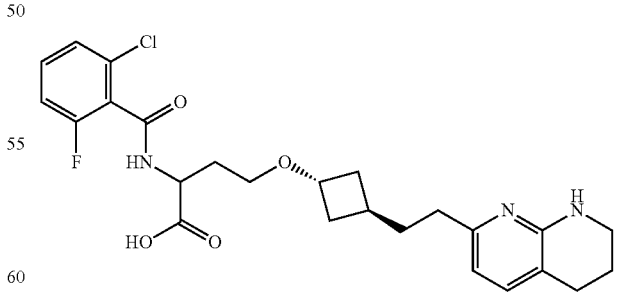

N-(2-chloro-6-fluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2-chloro-5-fluorobenzoic acid. LCMS theoretical m/z=490.2 [M+H]+. found 490.2.

Example 32, Compound 39

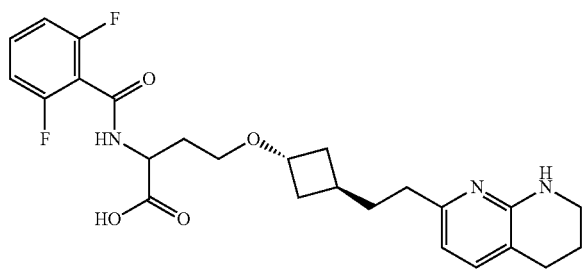 [SMILES: O=C(NC(CCO[C@H]1C[C@H](CCc2ccc3c(n2)NCCC3)C1)C(=O)O)c1c(F)cccc1Cl]

N-(2,6-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2,6-difluorobenzoic acid. LCMS theoretical m/z=474.2 [M+H]+. found 474.2.

Example 33, Compound 40

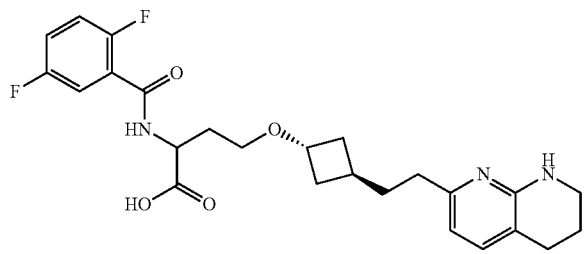 [SMILES: O=C(NC(CCO[C@H]1C[C@H](CCc2ccc3c(n2)NCCC3)C1)C(=O)O)c1cc(F)ccc1F]

N-(2,5-difluorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2,5-difluorobenzoic acid. LCMS theoretical m/z=474.2 [M+H]+. found 474.2.

Example 34, Compound 41

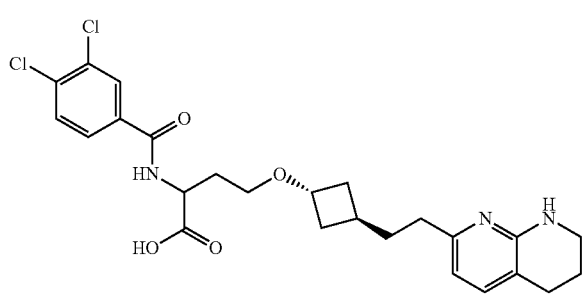 [SMILES: O=C(NC(CCO[C@H]1C[C@H](CCc2ccc3c(n2)NCCC3)C1)C(=O)O)c1ccc(Cl)c(Cl)c1]

N-(3,4-dichlorobenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3,4-dichlorobenzoic acid. LCMS theoretical m/z=506.2 [M+H]+. found 506.2.

Example 35, Compound 42

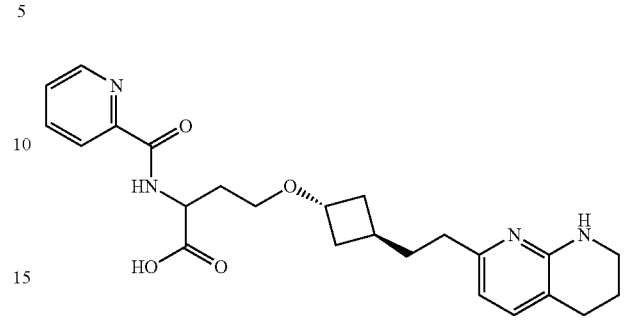

N-picolinoyl-O-(trans-3-(2-(5,6,7,8-tetrahydro-1,8-naphthyridin-2-yl)ethyl)cyclobutyl)homoserine. Prepared according to General Scheme A using General Procedure I with picolinic acid. LCMS theoretical m/z=439.2 [M+H]+. found 439.2.

Example 36, Compound 43

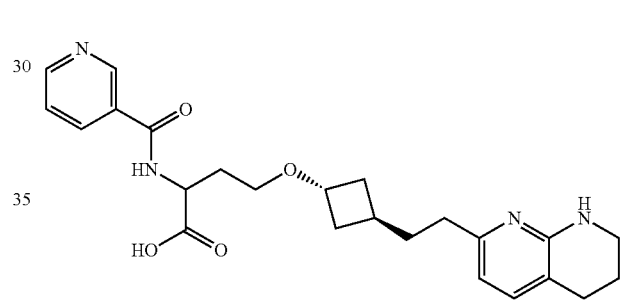

N-nicotinoyl-O-(trans-3-(2-(5,6,7,8-tetrahydro-1,8-naphthyridin-2-yl)ethyl)cyclobutyl)homoserine. Prepared according to General Scheme A using General Procedure I with nicotinic acid. LCMS theoretical m/z=439.2 [M+H]+. found 439.3.

Example 37, Compound 44

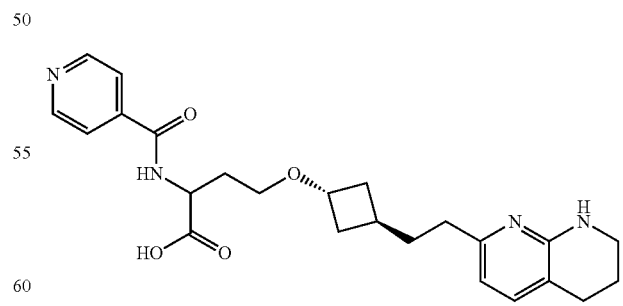

N-isonicotinoyl-O-(trans-3-(2-(5,6,7,8-tetrahydro-1,8-naphthyridin-2-yl)ethyl)cyclobutyl)homoserine. Prepared according to General Scheme A using General Procedure I with isonicotinic acid. LCMS theoretical m/z=439.2 [M+H]+. found 439.3.

Example 38, Compound 45

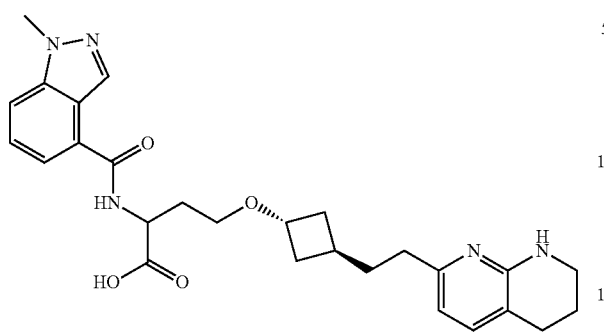

N-(1-methyl-1H-indazole-4-carbonyl)-O-(trans-3-(2-(5,6,7,8-tetrahydro-1,8-naphthyridin-2-yl)ethyl)cyclobutyl)homoserine. Prepared according to General Scheme A using General Procedure I with 1-methyl-1H-indazole-4-carboxylic acid. LCMS theoretical m/z=492.3 [M+H]+. found 492.3.

Example 39, Compound 46

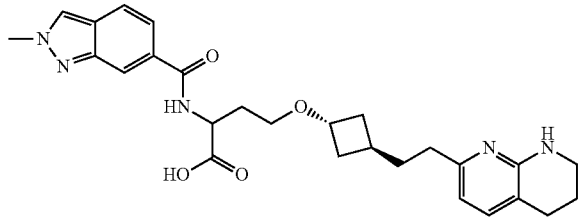 [SMILES: Cn1cc2ccc(C(=O)NC(CCO[C@H]3C[C@H](CCc4ccc5c(n4)NCCC5)C3)C(=O)O)cc2n1]

N-(2-methyl-2H-indazole-6-carbonyl)-O-(trans-3-(2-(5,6,7,8-tetrahydro-1,8-naphthyridin-2-yl)ethyl)cyclobutyl)homoserine. Prepared according to General Scheme A using General Procedure I with 2-methyl-2H-indazole-6-carboxylic acid. LCMS theoretical m/z=492.3 [M+H]+. found 492.3.

Example 40, Compound 47

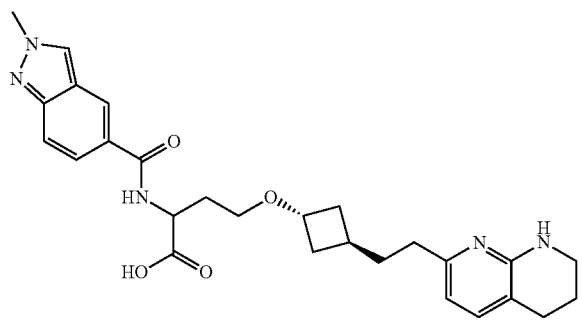 [SMILES: Cn1cc2cc(C(=O)NC(CCO[C@H]3C[C@H](CCc4ccc5c(n4)NCCC5)C3)C(=O)O)ccc2n1]

N-(2-methyl-2H-indazole-5-carbonyl)-O-(trans-3-(2-(5,6,7,8-tetrahydro-1,8-naphthyridin-2-yl)ethyl)cyclobutyl)homoserine. Prepared according to General Scheme A using General Procedure I with 2-methyl-2H-indazole-5-carboxylic acid. LCMS theoretical m/z=492.3 [M+H]+. found 492.3.

Example 41, Compound 48

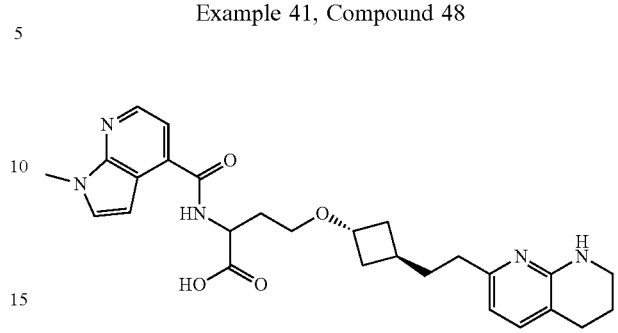

N-(1-methyl-1H-pyrrolo[2,3-b]pyridine-4-carbonyl)-O-(trans-3-(2-(5,6,7,8-tetrahydro-1,8-naphthyridin-2-yl)ethyl)cyclobutyl)homoserine. Prepared according to General Scheme A using General Procedure I with 1-methyl-1H-pyrrolo[2,3-b]pyridine-4-carboxylic acid. LCMS theoretical m/z=492.3 [M+H]+. found 492.3.

Example 42, Compound 49

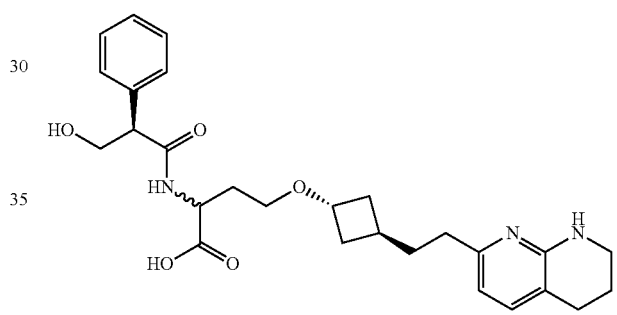

N—((R)-3-hydroxy-2-phenylpropanoyl)-O-(trans-3-(2-(5,6,7,8-tetrahydro-1,8-naphthyridin-2-yl)ethyl)cyclobutyl)homoserine. Prepared according to General Scheme A using General Procedure I with (R)-3-hydroxy-2-phenylpropanoic acid and General Procedure N followed by preparative HPLC to afford the first eluting of two diastereomers as a single stereoisomer. The amino acid stereochemistry was unassigned. LCMS theoretical m/z=482.3 [M+H]+. found 482.3.

Example 43, Compound 49

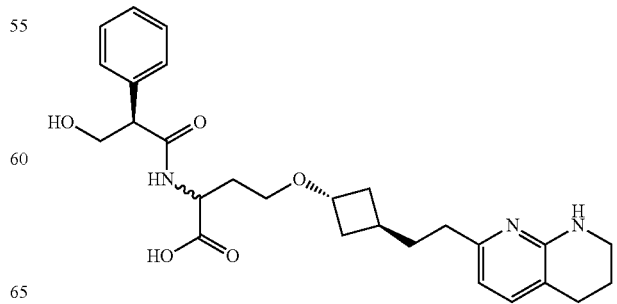

N—((R)-3-hydroxy-2-phenylpropanoyl)-O-(trans-3-(2-(5,6,7,8-tetrahydro-1,8-naphthyridin-2-yl)ethyl)cyclobutyl)homoserine. Prepared according to General Scheme A using General Procedure I with (R)-3-hydroxy-2-phenylpropanoic acid and General Procedure N followed by preparative HPLC to afford the second eluting of two diastereomers as a single stereoisomer. The amino acid stereochemistry was unassigned. LCMS theoretical m/z=482.3 [M+H]+. found 482.3.

Example 44, Compound 50

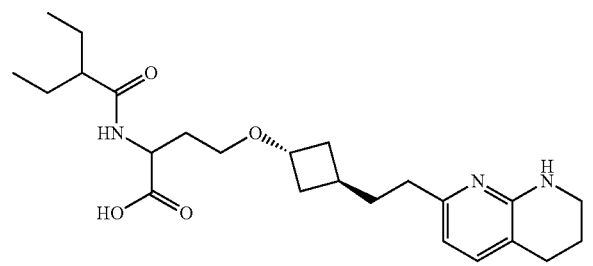 [SMILES: CCC(CC)C(=O)NC(CCO[C@H]1C[C@H](CCc2ccc3c(n2)NCCC3)C1)C(=O)O]

N-(2-ethylbutanoyl)-O-(trans-3-(2-(5,6,7,8-tetrahydro-1,8-naphthyridin-2-yl)ethyl)cyclobutyl)homoserine. Prepared according to General Scheme A using General Procedure I with 2-ethylbutanoic acid. LCMS theoretical m/z=432.3 [M+H]+. found 432.3.

Example 45, Compound 51

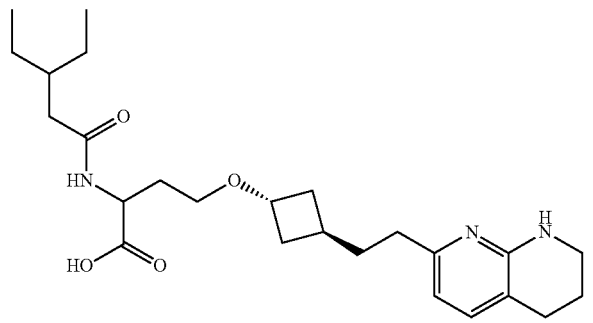 [SMILES: CCC(CC)CC(=O)NC(CCO[C@H]1C[C@H](CCc2ccc3c(n2)NCCC3)C1)C(=O)O]

N-(3-ethylpentanoyl)-O-(trans-3-(2-(5,6,7,8-tetrahydro-1,8-naphthyridin-2-yl)ethyl)cyclobutyl)homoserine. Prepared according to General Scheme A using General Procedure I with 3-ethylpentanoic acid. LCMS theoretical m/z=446.3 [M+H]+. found 446.3.

Example 46, Compound 49

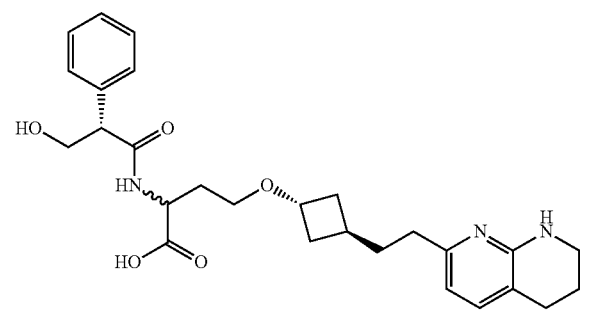 [SMILES: O=C(O)C(CCO[C@H]1C[C@H](CCc2ccc3c(n2)NCCC3)C1)NC(=O)[C@H](CO)c1ccccc1]

N—((S)-3-hydroxy-2-phenylpropanoyl)-O-(trans-3-(2-(5,6,7,8-tetrahydro-1,8-naphthyridin-2-yl)ethyl)cyclobutyl)homoserine. Prepared according to General Scheme A using General Procedure I with (S)-3-hydroxy-2-phenylpropanoic acid and General Procedure N followed by preparative HPLC to afford the first eluting of two diastereomers as a single stereoisomer. The amino acid stereochemistry was unassigned. LCMS theoretical m/z=482.3 [M+H]+. found 482.3.

Example 47, Compound 49

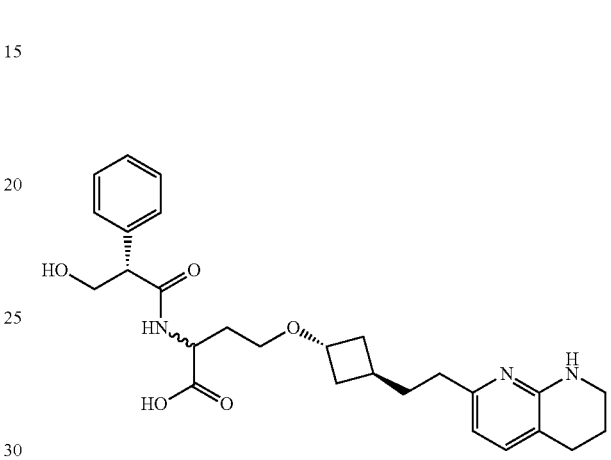

N—((S)-3-hydroxy-2-phenylpropanoyl)-O-(trans-3-(2-(5,6,7,8-tetrahydro-1,8-naphthyridin-2-yl)ethyl)cyclobutyl)homoserine. Prepared according to General Scheme A using General Procedure I with (S)-3-hydroxy-2-phenylpropanoic acid and General Procedure N followed by preparative HPLC to afford the second eluting of two diastereomers as a single stereoisomer. The amino acid stereochemistry was unassigned. LCMS theoretical m/z=482.3 [M+H]+. found 482.3.

Example 48, Compound 52

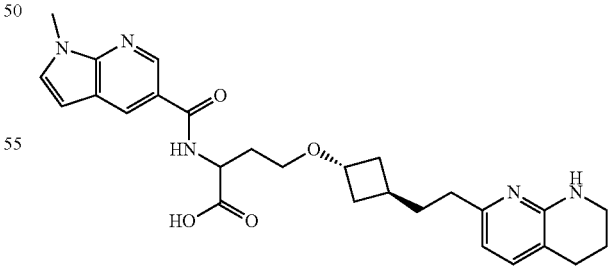

N-(1-methyl-1H-pyrrolo[2,3-b]pyridine-5-carbonyl)-O-(trans-3-(2-(5,6,7,8-tetrahydro-1,8-naphthyridin-2-yl)ethyl)cyclobutyl)homoserine. Prepared according to General Scheme A using General Procedure I with 1-methyl-1H-pyrrolo[2,3-b]pyridine-5-carboxylic acid. LCMS theoretical m/z=492.3 [M+H]+. found 492.3.

Example 49, Compound 53

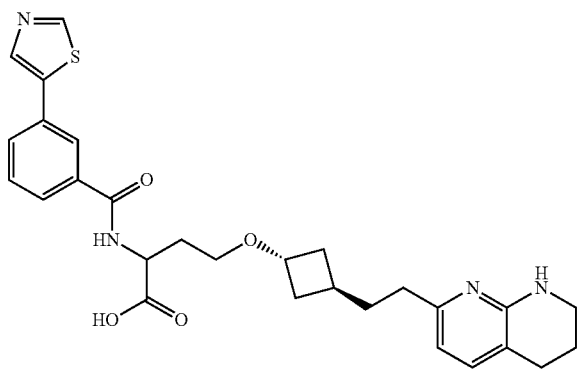 [SMILES: O=C(NC(CCO[C@H]1C[C@H](CCc2ccc3c(n2)NCCC3)C1)C(=O)O)c1cccc(-c2cncs2)c1]

O-(trans-3-(2-(5,6,7,8-tetrahydro-1,8-naphthyridin-2-yl)ethyl)cyclobutyl)-N-(3-(thiazol-5-yl)benzoyl)homoserine. Prepared according to General Scheme A using General Procedure I with 3-(thiazol-5-yl)benzoic acid. LCMS theoretical m/z=521.2 [M+H]+. found 521.2.

Example 50, Compound 54

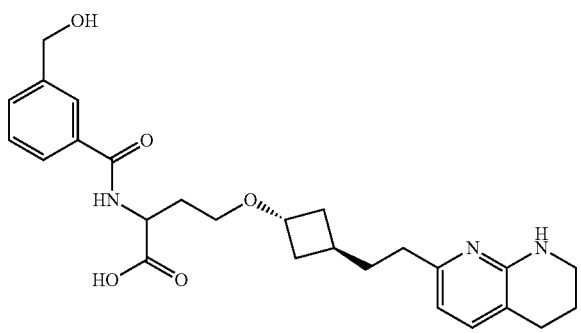 [SMILES: O=C(NC(CCO[C@H]1C[C@H](CCc2ccc3c(n2)NCCC3)C1)C(=O)O)c1cccc(CO)c1]

N-(3-(hydroxymethyl)benzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-(hydroxymethyl)benzoic acid. LCMS theoretical m/z=468.2. [M+H]+. found 468.3.

Example 51, Compound 55

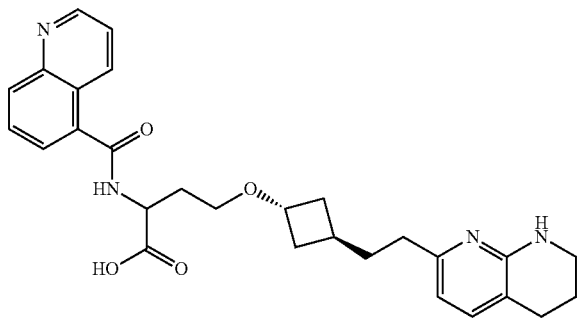 [SMILES: O=C(NC(CCO[C@H]1C[C@H](CCc2ccc3c(n2)NCCC3)C1)C(=O)O)c1cccc2ncccc12]

N-(quinoline-5-carbonyl)-O-(trans-3-(2-(5,6,7,8-tetrahydro-1,8-naphthyridin-2-yl)ethyl)cyclobutyl)homoserine. Prepared according to General Scheme A using General Procedure I with quinoline-5-carboxylic acid. LCMS theoretical m/z=489.2. [M+H]+. found 489.3.

Example 52, Compound 56

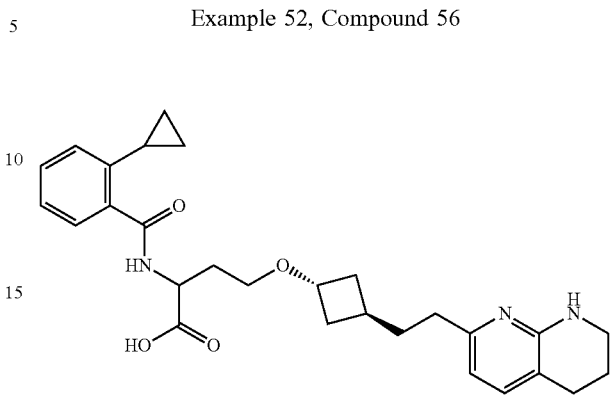

N-(2-cyclopropylbenzoyl)-O-(trans-3-(2-(5,6,7,8-tetrahydro-1,8-naphthyridin-2-yl)ethyl)cyclobutyl)homoserine. Prepared according to General Scheme A using General Procedure I with 2-cyclopropylbenzoic acid. LCMS theoretical m/z=478.3. [M+H]+. found 478.3.

Example 53, Compound 57

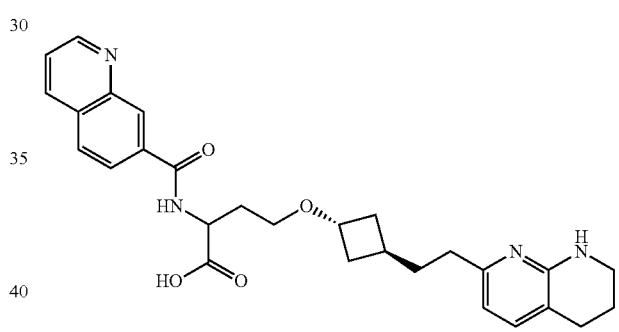

N-(quinoline-7-carbonyl)-O-(trans-3-(2-(5,6,7,8-tetrahydro-1,8-naphthyridin-2-yl)ethyl)cyclobutyl)homoserine. Prepared according to General Scheme A using General Procedure I with quinoline-7-carboxylic acid. LCMS theoretical m/z=489.2. [M+H]+. found 489.3.

Example 54, Compound 58

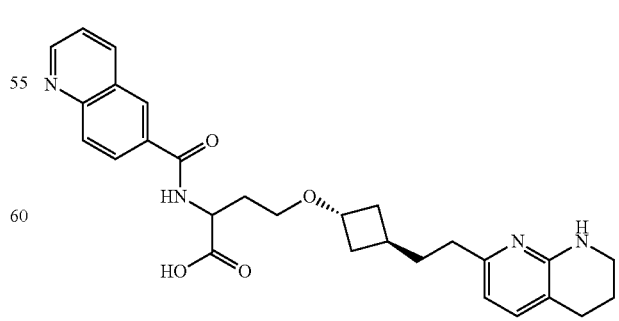

N-(quinoline-6-carbonyl)-O-(trans-3-(2-(5,6,7,8-tetrahydro-1,8-naphthyridin-2-yl)ethyl)cyclobutyl)homoserine.

Prepared according to General Scheme A using General Procedure I with quinoline-6-carboxylic acid. LCMS theoretical m/z=489.2. [M+H]+. found 489.3.

Example 55, Compound 59

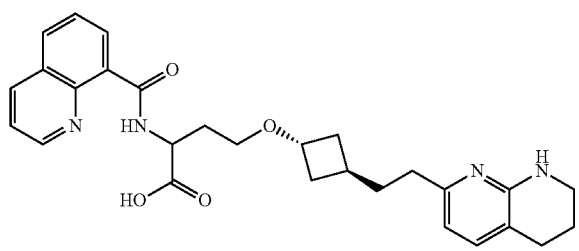 [SMILES: O=C(NC(CCO[C@H]1C[C@H](CCc2ccc3c(n2)NCCC3)C1)C(=O)O)c1cccc2cccnc12]

N-(quinoline-8-carbonyl)-O-(trans-3-(2-(5,6,7,8-tetrahydro-1,8-naphthyridin-2-yl)ethyl)cyclobutyl)homoserine. Prepared according to General Scheme A using General Procedure I with quinoline-8-carboxylic acid. LCMS theoretical m/z=489.2. [M+H]+. found 489.3.

Example 56, Compound 60

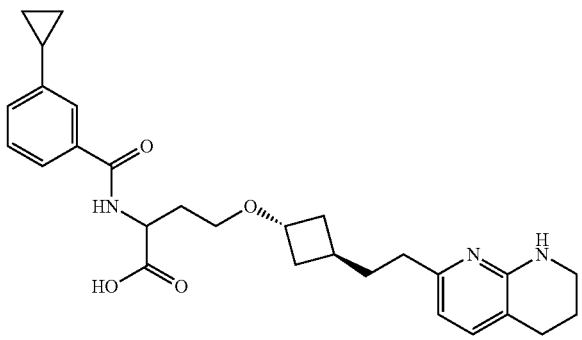 [SMILES: O=C(NC(CCO[C@H]1C[C@H](CCc2ccc3c(n2)NCCC3)C1)C(=O)O)c1cccc(C2CC2)c1]

N-(3-cyclopropylbenzoyl)-O-(trans-3-(2-(5,6,7,8-tetrahydro-1,8-naphthyridin-2-yl)ethyl)cyclobutyl)homoserine. Prepared according to General Scheme A using General Procedure I with 3-cyclopropylbenzoic acid. LCMS theoretical m/z=478.3. [M+H]+. found 478.3.

Example 57, Compound 61

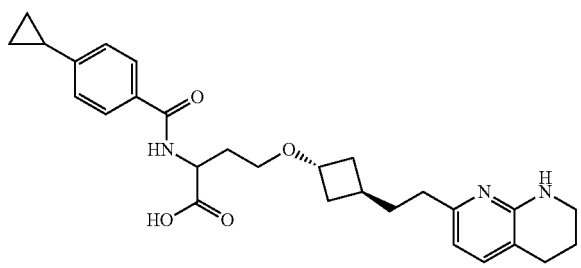 [SMILES: O=C(NC(CCO[C@H]1C[C@H](CCc2ccc3c(n2)NCCC3)C1)C(=O)O)c1ccc(C2CC2)cc1]

N-(4-cyclopropylbenzoyl)-O-(trans-3-(2-(5,6,7,8-tetrahydro-1,8-naphthyridin-2-yl)ethyl)cyclobutyl)homoserine. Prepared according to General Scheme A using General Procedure I with 4-cyclopropylbenzoic acid. LCMS theoretical m/z=478.3. [M+H]+. found 478.3.

Example 58, Compound 44

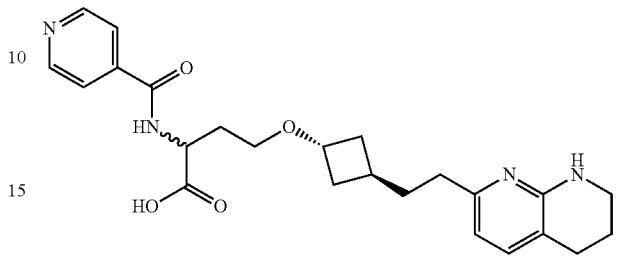

N-isonicotinoyl-O-(trans-3-(2-(5,6,7,8-tetrahydro-1,8-naphthyridin-2-yl)ethyl)cyclobutyl)-1-homoserine. Isomer D1 was employed in General Scheme D-2 using General Procedure I with isonicotinic acid. LCMS theoretical m/z=439.2. [M+H]+. found 439.3.

Example 59, Compound 51

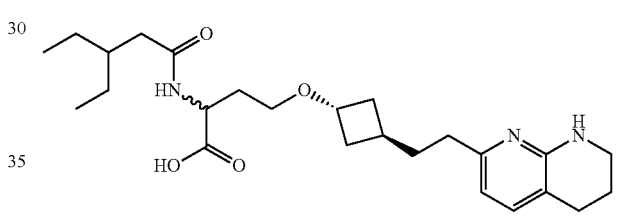

N-(3-ethylpentanoyl)-O-(trans-3-(2-(5,6,7,8-tetrahydro-1,8-naphthyridin-2-yl)ethyl)cyclobutyl)-D-homoserine. Isomer D1 was employed in General Scheme D-2 using General Procedure I with 3-ethylpentanoic acid. LCMS theoretical m/z=446.3. [M+H]+. found 446.3.

Example 60, Compound 14

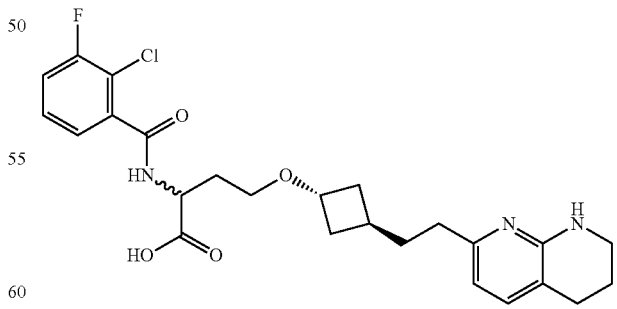

N-(2-chloro-3-fluorobenzoyl)-O-(trans-3-(2-(5,6,7,8-tetrahydro-1,8-naphthyridin-2-yl)ethyl)cyclobutyl)homoserine. Isomer D1 was employed in General Scheme D-2 using General Procedure I with 2-chloro-3-fluorobenzoic acid. LCMS theoretical m/z=490.2. [M+H]+. found 490.2.

Example 61, Compound 53

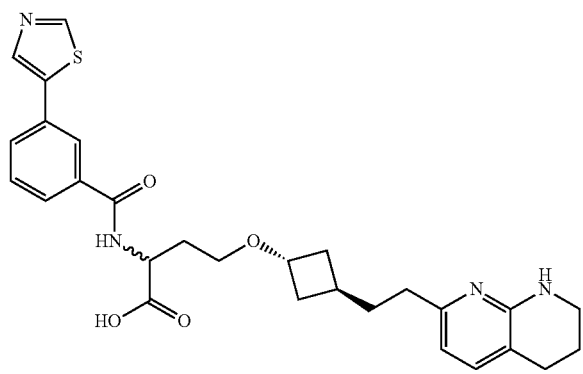 [SMILES: O=C(NC(CCO[C@H]1C[C@H](CCc2ccc3c(n2)NCCC3)C1)C(=O)O)c1cccc(-c2cncs2)c1]

O-(trans-3-(2-(5,6,7,8-tetrahydro-1,8-naphthyridin-2-yl)ethyl)cyclobutyl)-N-(3-(thiazol-5-yl)benzoyl)homoserine. Isomer D1 was employed in General Scheme D-2 using General Procedure I with 3-(thiazol-5-yl)benzoic acid. LCMS theoretical m/z=521.2. [M+H]+. found 521.2

Example 62, Compound 44

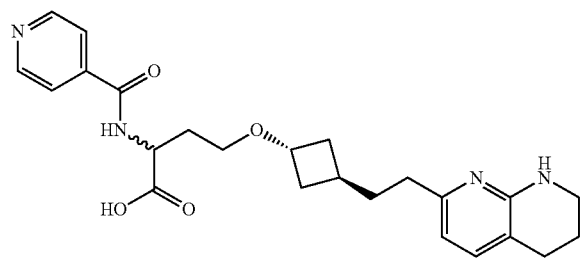 [SMILES: O=C(NC(CCO[C@H]1C[C@H](CCc2ccc3c(n2)NCCC3)C1)C(=O)O)c1ccncc1]

N-isonicotinoyl-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with isonicotinic acid. LCMS theoretical m/z=439.2. [M+H]+. found 439.3.

Example 63, Compound 51

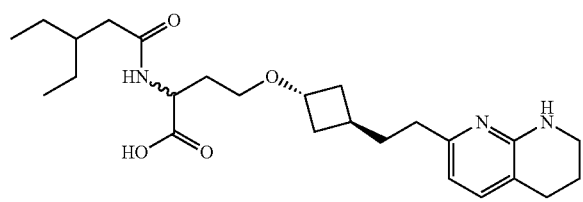 [SMILES: CCC(CC)CC(=O)NC(CCO[C@H]1C[C@H](CCc2ccc3c(n2)NCCC3)C1)C(=O)O]

N-(3-ethylpentanoyl)-O-(trans-3-(2-(5,6,7,8-tetrahydro-1,8-naphthyridin-2 yl)ethyl)cyclobutyl)homoserine. Isomer D2 was employed in General Scheme D-2 using General Procedure I with 3-ethylpentanoic acid. LCMS theoretical m/z=446.3. [M+H]+. found 446.3.

Example 64, Compound 14

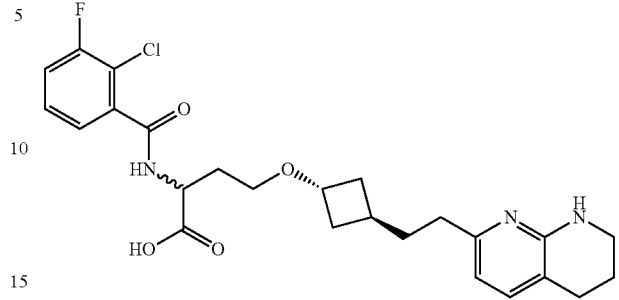

N-(2-chloro-3-fluorobenzoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-chloro-3-fluorobenzoic acid. LCMS theoretical m/z=490.2. [M+H]+. found 490.2.

Example 65, Compound 53

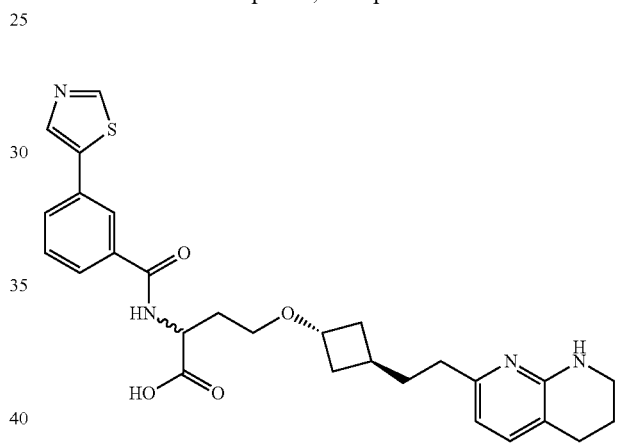

O-(trans-3-(2-(5,6,7,8-tetrahydro-1,8-naphthyridin-2-yl)ethyl)cyclobutyl)-N-(3-(thiazol-5-yl)benzoyl)homoserine. Isomer D2 was employed in General Scheme D-2 using General Procedure I with 3-(thiazol-5-yl)benzoic acid. LCMS theoretical m/z=521.2. [M+H]+. found 521.2.

Example 66, Compound 36

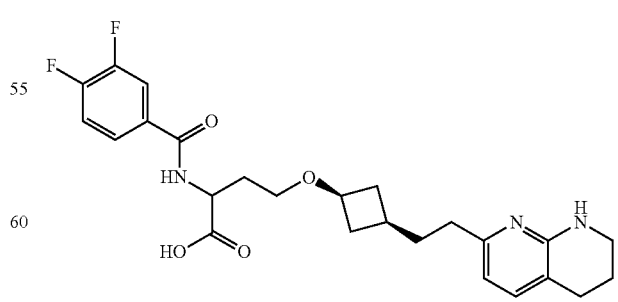

N-(3,4-difluorobenzoyl)-O-(cis-3-(2-(5,6,7,8-tetrahydro-1,8-naphthyridin-2-yl)ethyl)cyclobutyl)homoserine. Prepared according to General Scheme B using General Procedure I with 3,4-difluorobenzoic acid. LCMS theoretical m/z=474.2. [M+H]+. found 474.2.

Example 67, Compound 51

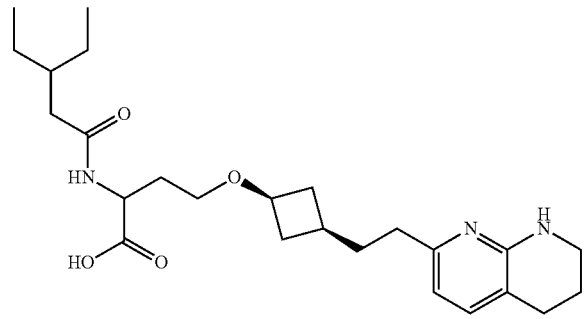 [SMILES: CCC(CC)CC(=O)NC(CCO[C@H]1C[C@@H](CCc2ccc3c(n2)NCCC3)C1)C(=O)O]

N-(3-ethylpentanoyl)-O-(cis-3-(2-(5,6,7,8-tetrahydro-1,8-naphthyridin-2-yl)ethyl)cyclobutyl)homoserine. Prepared according to General Scheme B using General Procedure I with 3-ethylpentanoic acid. LCMS theoretical m/z=446.3. [M+H]+. found 446.3.

Example 68, Compound 44

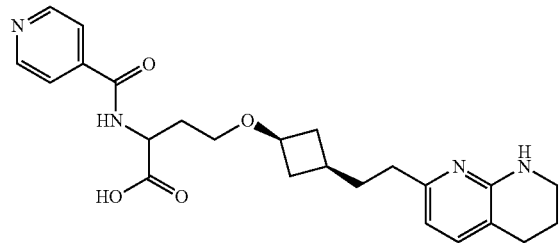 [SMILES: O=C(NC(CCO[C@H]1C[C@@H](CCc2ccc3c(n2)NCCC3)C1)C(=O)O)c1ccncc1]

N-isonicotinoyl-O-(cis-3-(2-(5,6,7,8-tetrahydro-1,8-naphthyridin-2-yl)ethyl)cyclobutyl)homoserine. Prepared according to General Scheme B using General Procedure I with isonicotinic acid. LCMS theoretical m/z=439.2. [M+H]+. found 439.2.

Example 69, Compound 53

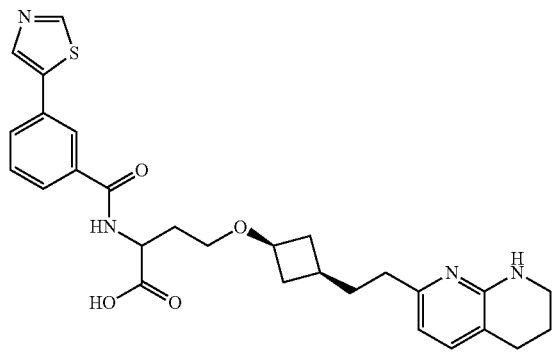 [SMILES: O=C(NC(CCO[C@H]1C[C@@H](CCc2ccc3c(n2)NCCC3)C1)C(=O)O)c1cccc(-c2cncs2)c1]

O-(cis-3-(2-(5,6,7,8-tetrahydro-1,8-naphthyridin-2-yl)ethyl)cyclobutyl)-N-(3-(thiazol-5-yl)benzoyl)homoserine.

Prepared according to General Scheme B using General Procedure I with 3-(thiazol-5-yl)benzoic acid. LCMS theoretical m/z=521.2. [M+H]+. found 521.2.

Example 70, Compound 49


N—((R)-3-hydroxy-2-phenylpropanoyl)-O-(cis-3-(2-(5,6,7,8-tetrahydro-1,8-naphthyridin-2-yl)ethyl)cyclobutyl)homoserine. Prepared according to General Scheme B using General Procedure I with (R)-3-hydroxy-2-phenylpropanoic acid, and General Procedure N to afford the title compound as the first eluting isomer. LCMS theoretical m/z=482.3. [M+H]+. found 482.3.

Example 71, Compound 49

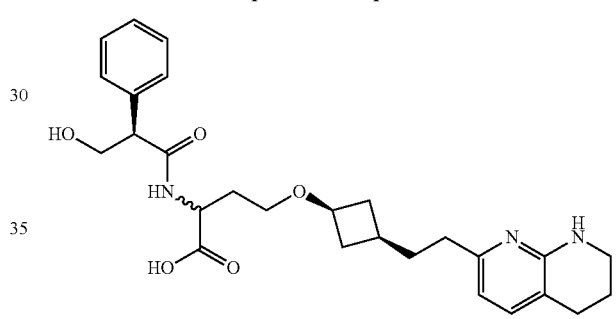

N—((R)-3-hydroxy-2-phenylpropanoyl)-O-(cis-3-(2-(5,6,7,8-tetrahydro-1,8-naphthyridin-2-yl)ethyl)cyclobutyl)homoserine. Prepared according to General Scheme B using General Procedure I with (R)-3-hydroxy-2-phenylpropanoic acid, and General Procedure N to afford the title compound as the second eluting isomer. LCMS theoretical m/z=482.3. [M+H]+. found 482.3.

Example 72. Compound 62

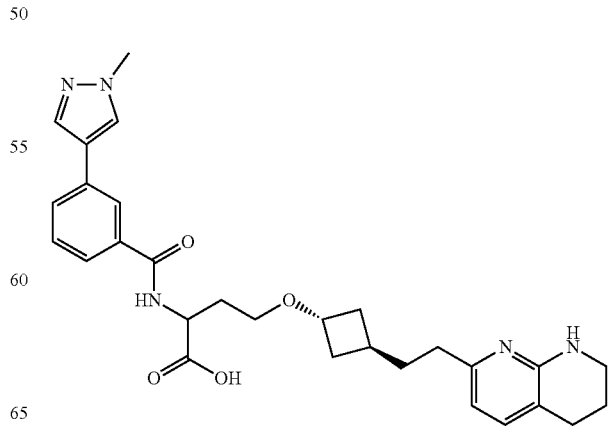

N-(3-(1-methyl-1H-pyrazol-4-yl)benzoyl)-O-(trans-3-(4-(5,6,7,8-tetrahydro-1,8-naphthyridin-2-yl)butyl)cyclobutyl)homoserine. Prepared according to General Scheme A using General Procedure I with 3-(1-methyl-1H-pyrazol-4-yl)benzoic acid. LCMS theoretical m/z=518.2. [M+H]+. found 518.2.

Example 73, Compound 63

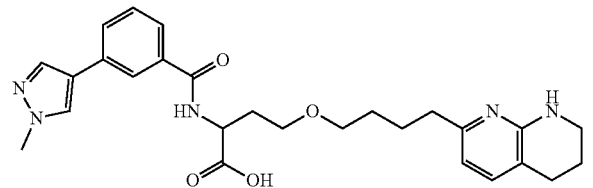 [SMILES: Cn1cc(-c2cccc(C(=O)NC(CCOCCCCc3ccc4c(n3)NCCC4)C(=O)O)c2)cn1]

N-(3-(1-methyl-1H-pyrazol-4-yl)benzoyl)-O-(4-(5,6,7,8-tetrahydro-1,8-naphthyridin-2-yl)butyl)homoserine. Prepared according to General Scheme C using General Procedure I with 3-(1-methyl-1H-pyrazol-4-yl)benzoic acid. LCMS theoretical m/z=492.3. [M+H]+. found 492.3.

Example 74, Compound 64

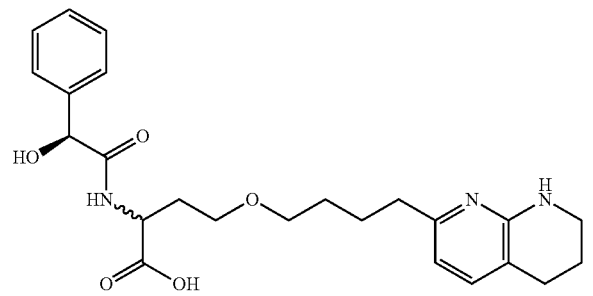 [SMILES: O=C(O)C(CCOCCCCc1ccc2c(n1)NCCC2)NC(=O)[C@@H](O)c1ccccc1]

N—((S)-2-hydroxy-2-phenylacetyl)-O-(4-(5,6,7,8-tetrahydro-1,8-naphthyridin-2-yl)butyl)homoserine. Prepared according to General Scheme C using General Procedure I with (S)-2-hydroxy-2-phenylacetic acid, and General Procedure N to afford the title compound as the first eluting isomer. LCMS theoretical m/z=442.2. [M+H]+. found 442.2.

Example 75, Compound 64

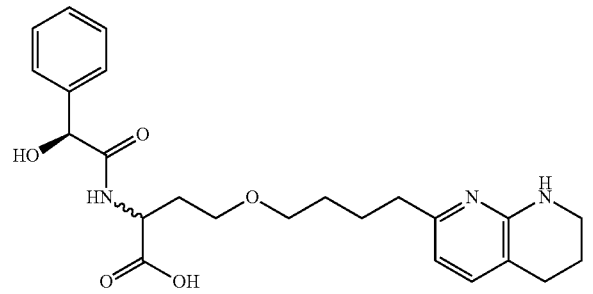 [SMILES: O=C(O)C(CCOCCCCc1ccc2c(n1)NCCC2)NC(=O)[C@@H](O)c1ccccc1]

N—((S)-2-hydroxy-2-phenylacetyl)-O-(4-(5,6,7,8-tetrahydro-1,8-naphthyridin-2-yl)butyl)homoserine. Prepared according to General Scheme C using General Procedure I with (S)-2-hydroxy-2-phenylacetic acid, and General Procedure N to afford the title compound as the second eluting isomer. LCMS theoretical m/z=442.2. [M+H]+. found 442.2.

Example 76, Compound 64

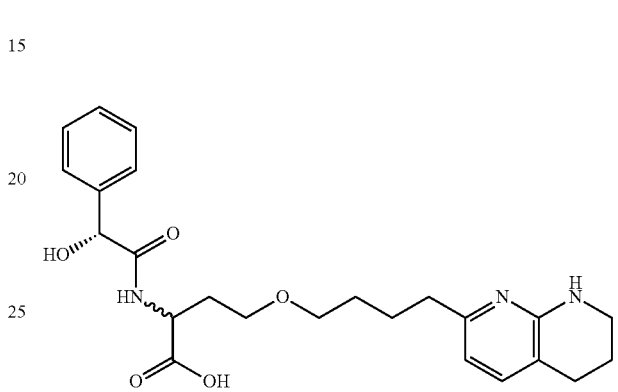

N—((R)-2-hydroxy-2-phenylacetyl)-O-(4-(5,6,7,8-tetrahydro-1,8-naphthyridin-2-yl)butyl)homoserine. Prepared according to General Scheme C using General Procedure I with (R)-2-hydroxy-2-phenylacetic acid, and General Procedure N to afford the title compound as the first eluting isomer. LCMS theoretical m/z=442.2. [M+H]+. found 442.2.

Example 77, Compound 64

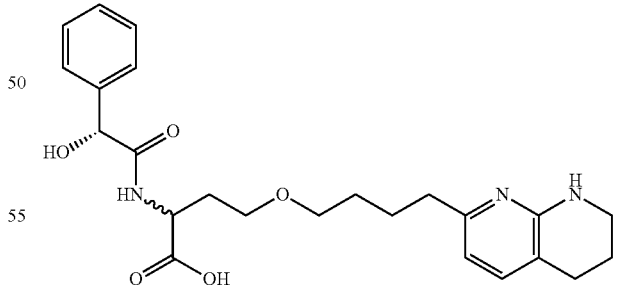

N—((R)-2-hydroxy-2-phenylacetyl)-O-(4-(5,6,7,8-tetrahydro-1,8-naphthyridin-2-yl)butyl)-D-homoserine. Prepared according to General Scheme C using General Procedure I with (R)-2-hydroxy-2-phenylacetic acid, and General Procedure N to afford the title compound as the second eluting isomer. LCMS theoretical m/z=442.2. [M+H]+. found 442.2.

Example 78, Compound 65

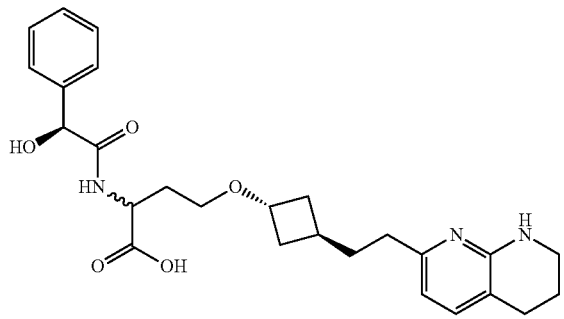 [SMILES: O=C(O)C(CCO[C@H]1C[C@H](CCc2ccc3c(n2)NCCC3)C1)NC(=O)[C@@H](O)c1ccccc1]

N—((S)-2-hydroxy-2-phenylacetyl)-O-(trans-3-(2-(5,6,7,8-tetrahydro-1,8-naphthyridin-2-yl)ethyl)cyclobutyl)homoserine. Prepared according to General Scheme A using General Procedure I with (S)-2-hydroxy-2-phenylacetic acid and General Procedure N to afford the title compound as the first eluting isomer. LCMS theoretical m/z=468.3. [M+H]+. found 468.3.

Example 79, Compound 65

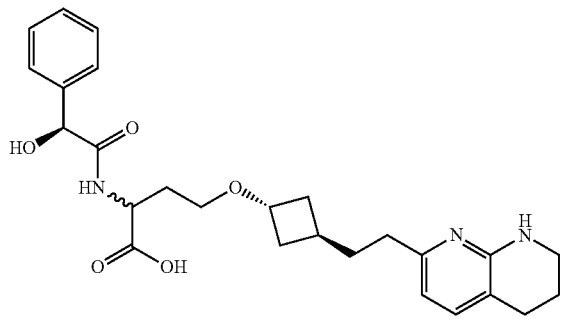 [SMILES: O=C(O)C(CCO[C@H]1C[C@H](CCc2ccc3c(n2)NCCC3)C1)NC(=O)[C@@H](O)c1ccccc1]

N—((S)-2-hydroxy-2-phenylacetyl)-O-(trans-3-(2-(5,6,7,8-tetrahydro-1,8-naphthyridin-2-yl)ethyl)cyclobutyl)homoserine. Prepared according to General Scheme A using General Procedure I with (S)-2-hydroxy-2-phenylacetic acid, and General Procedure N to afford the title compound as the second eluting isomer. LCMS theoretical m/z=468.3. [M+H]+. found 468.3.

Example 80, Compound 65

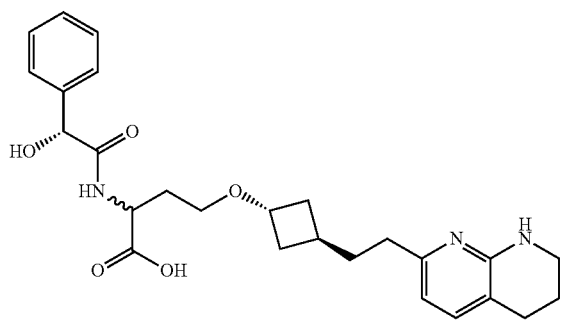 [SMILES: O=C(O)C(CCO[C@H]1C[C@H](CCc2ccc3c(n2)NCCC3)C1)NC(=O)[C@H](O)c1ccccc1]

N—((R)-2-hydroxy-2-phenylacetyl)-O-(trans-3-(2-(5,6,7,8-tetrahydro-1,8-naphthyridin-2-yl)ethyl)cyclobutyl)homoserine. Prepared according to General Scheme A using General Procedure I with (R)-2-hydroxy-2-phenylacetic acid, and General Procedure N to afford the title compound as the second eluting isomer. LCMS theoretical m/z=468.3. [M+H]+. found 468.3.

Example 81. Compound 65

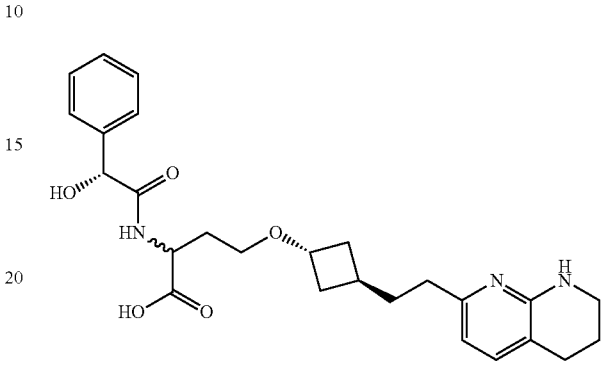

N—((R)-2-hydroxy-2-phenylacetyl)-O-(trans-3-(2-(5,6,7,8-tetrahydro-1,8-naphthyridin-2-yl)ethyl)cyclobutyl)homoserine. Prepared according to General Scheme A using General Procedure I with (R)-2-hydroxy-2-phenylacetic acid, and General Procedure N to afford the title compound as the second eluting isomer. LCMS theoretical m/z=468.3. [M+H]+. found 468.3.

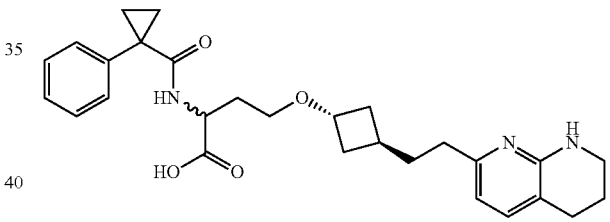

N-(1-phenylcyclopropane-1-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 1-phenylcyclopropane-1-carboxylic acid. LCMS theoretical m/z=478.3. [M+H]+. found 478.3.

Example 83, Compound 67

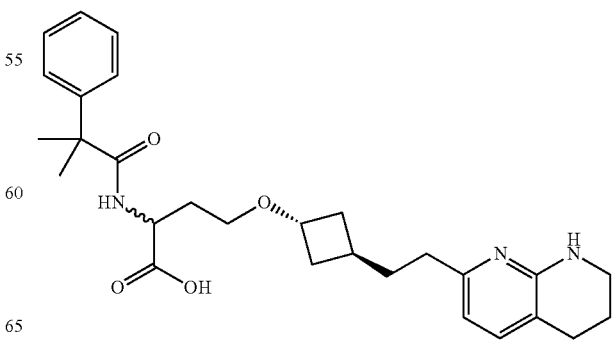

N-(2-methyl-2-phenylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2-methyl-2-phenylpropanoic acid. LCMS theoretical m/z=480.3. [M+H]+. found 480.1.

Example 84, Compound 68

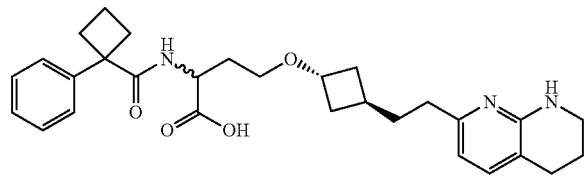 [SMILES: O=C(O)C(CCO[C@H]1C[C@H](CCc2ccc3c(n2)NCCC3)C1)NC(=O)C1(c2ccccc2)CCC1]

N-(1-phenylcyclobutane-1-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 1-phenylcyclobutane-1-carboxylic acid. LCMS theoretical m/z=492.3. [M+H]+. found 492.2.

Example 85, Compound 69

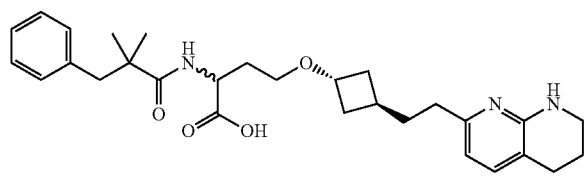 [SMILES: CC(C)(Cc1ccccc1)C(=O)NC(CCO[C@H]1C[C@H](CCc2ccc3c(n2)NCCC3)C1)C(=O)O]

N-(2,2-dimethyl-3-phenylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2,2-dimethyl-3-phenylpropanoic acid. LCMS theoretical m/z=494.3. [M+H]+. found 494.2.

Example 86, Compound 19

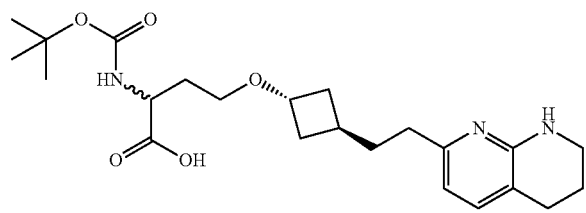 [SMILES: CC(C)(C)OC(=O)NC(CCO[C@H]1C[C@H](CCc2ccc3c(n2)NCCC3)C1)C(=O)O]

N-(tert-butoxycarbonyl)-O-(trans-3-(2-(5,6,7,8-tetrahydro-1,8-naphthyridin-2-yl)ethyl)cyclobutyl)homoserine. Prepared using Scheme G-1 to afford Isomer G1, then using di-tert-butyl dicarbonate and triethylamine in DCM afforded methyl N-(tert-butoxycarbonyl)-O-(trans-3-(2-(5,6,7,8-tetrahydro-1,8-naphthyridin-2-yl)ethyl)cyclobutyl)homoserinate, which was subjected to General Procedure N. LCMS theoretical m/z=434.3. [M+H]+. found 434.3.

Example 87, Compound 70

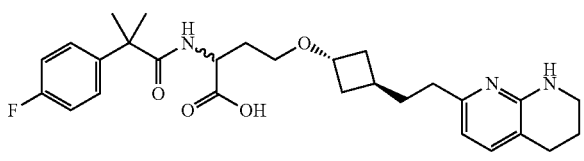 [SMILES: CC(C)(C(=O)NC(CCO[C@H]1C[C@H](CCc2ccc3c(n2)NCCC3)C1)C(=O)O)c1ccc(F)cc1]

N-(2-(4-fluorophenyl)-2-methylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2-(4-fluorophenyl)-2-methylpropanoic acid. LCMS theoretical m/z=498.3. [M+H]+. found 498.3.

Example 88, Compound 71

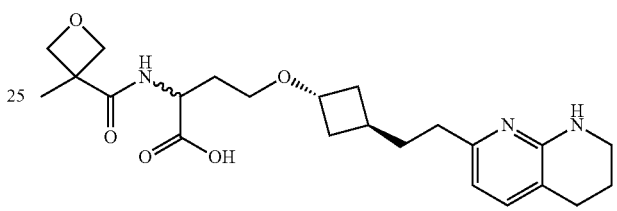

N-(3-methyloxetane-3-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 3-methyloxetane-3-carboxylic acid. LCMS theoretical m/z=432.2. [M+H]+. found 432.2.

Example 89, Compound 72

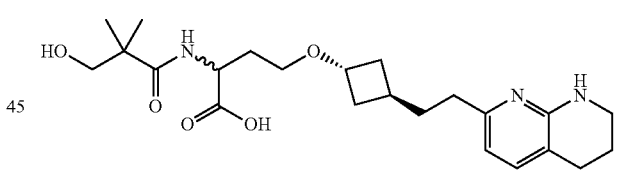

N-(3-hydroxy-2,2-dimethylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 3-hydroxy-2,2-dimethylpropanoic acid. LCMS theoretical m/z=434.3. [M+H]+. found 434.2.

Example 90, Compound 73

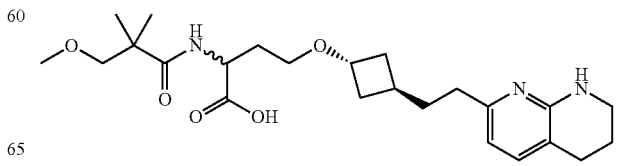

N-(3-methoxy-2,2-dimethylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 3-methoxy-2,2-dimethylpropanoic acid. LCMS theoretical m/z=448.3. [M+H]+. found 448.3.

Example 91, Compound 74

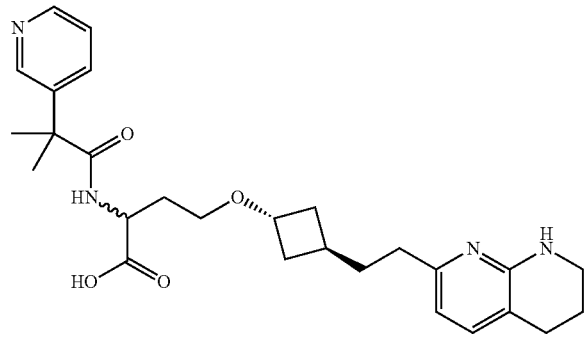 [SMILES: CC(C)(C(=O)NC(CCO[C@H]1C[C@H](CCc2ccc3c(n2)NCCC3)C1)C(=O)O)c1cccnc1]

N-(2-methyl-2-(pyridin-3-yl)propanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2-methyl-2-(pyridin-3-yl)propanoic acid. LCMS theoretical m/z=481.3. [M+H]+. found 481.3.

Example 92, Compound 75

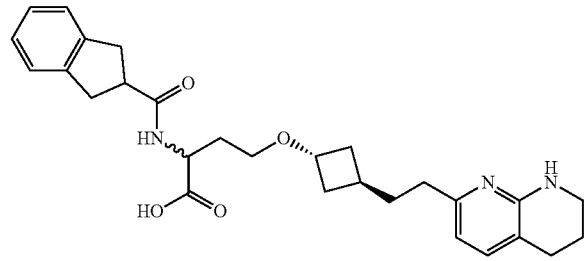 [SMILES: O=C(NC(CCO[C@H]1C[C@H](CCc2ccc3c(n2)NCCC3)C1)C(=O)O)C1Cc2ccccc2C1]

N-(2,3-dihydro-1H-indene-2-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2,3-dihydro-1H-indene-2-carboxylic acid. LCMS theoretical m/z=478.3. [M+H]+. found 478.1.

Example 93, Compound 76

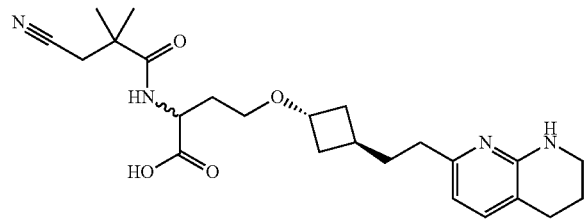 [SMILES: CC(C)(CC#N)C(=O)NC(CCO[C@H]1C[C@H](CCc2ccc3c(n2)NCCC3)C1)C(=O)O]

N-(3-cyano-2,2-dimethylpropanoyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 3-cyano-2,2-dimethylpropanoic acid. LCMS theoretical m/z=443.3. [M+H]+. found 443.1.

Example 94, Compound 77

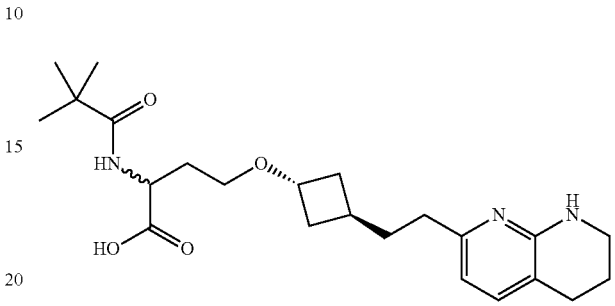

N-pivaloyl-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with pivalic acid. LCMS theoretical m/z=418.3. [M+H]+. found 418.4.

Example 95, Compound 78

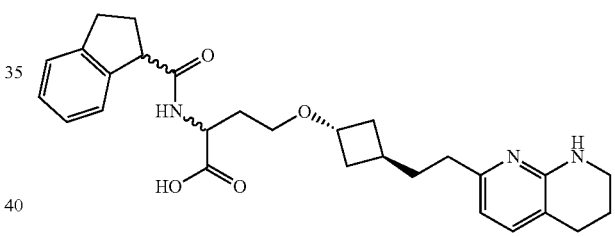

N-(2,3-dihydro-JH-indene-1-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2,3-dihydro-1H-indene-1-carboxylic acid, and General Procedure N followed by separation of the diastereomers by chiral SFC to afford title compound as the first eluting isomer as a single enantiomer. LCMS theoretical m/z=478.3. [M+H]+. found 478.2.

Example 96, Compound 78

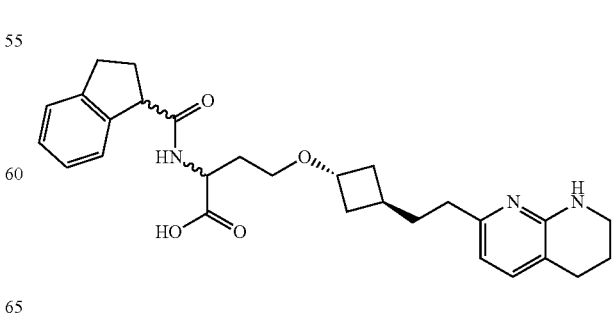

N-(2,3-dihydro-1H-indene-1-carbonyl)-O-(trans-3-(2-(5,6,7,8-tetrahydro-1,8-naphthyridin-2-yl)ethyl)cyclobutyl)homoserine. Isomer G1 was employed in General Scheme G-2 using General Procedure I with 2,3-dihydro-1H-indene-1-carboxylic acid, and General Procedure N followed by separation of the diastereomers by chiral SFC to afford title compound as the second eluting isomer as a single enantiomer. LCMS theoretical m/z=478.3. [M+H]+. found 478.2.

Example 97, Compound 66

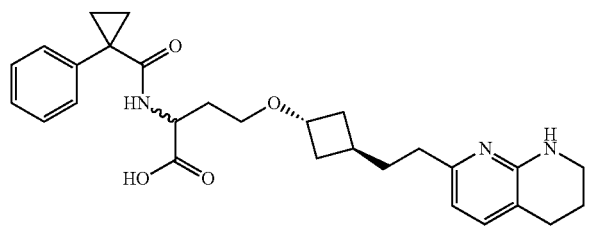 [SMILES: O=C(O)C(CCO[C@H]1C[C@H](CCc2ccc3c(n2)NCCC3)C1)NC(=O)C1(c2ccccc2)CC1]

N-(1-phenylcyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-phenylcyclopropane-1-carboxylic acid. LCMS theoretical m/z=478.3. [M+H]+. found 478.3.

Example 98, Compound 67

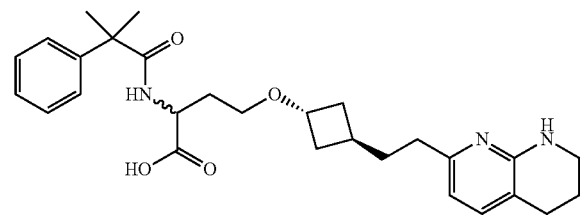 [SMILES: CC(C)(C(=O)NC(CCO[C@H]1C[C@H](CCc2ccc3c(n2)NCCC3)C1)C(=O)O)c1ccccc1]

N-(2-methyl-2-phenylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-methyl-2-phenylpropanoic acid. LCMS theoretical m/z=480.3. [M+H]+. found 480.3.

Example 99, Compound 68

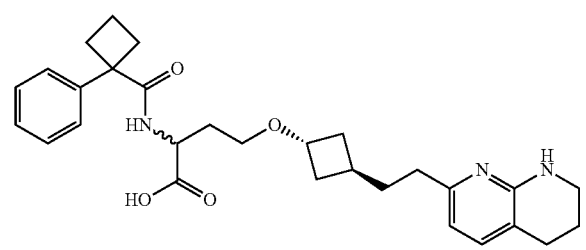 [SMILES: O=C(O)C(CCO[C@H]1C[C@H](CCc2ccc3c(n2)NCCC3)C1)NC(=O)C1(c2ccccc2)CCC1]

N-(1-phenylcyclobutane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-phenylcyclobutane-1-carboxylic acid. LCMS theoretical m/z=492.3. [M+H]+. found 492.3.

Example 100, Compound 69

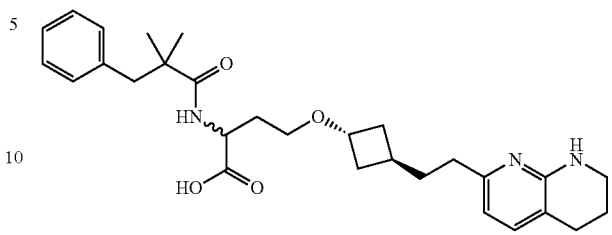

N-(2,2-dimethyl-3-phenylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,2-dimethyl-3-phenylpropanoic acid. LCMS theoretical m/z=494.3. [M+H]+. found 494.4.

Example 101, Compound 19

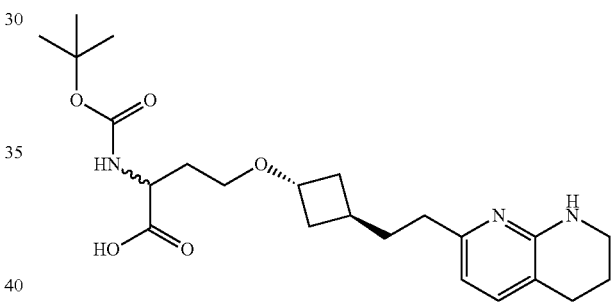

N-(tert-butoxycarbonyl)-O-(trans-3-(2-(5,6,7,8-tetrahydro-1,8-naphthyridin-2-yl)ethyl)cyclobutyl)homoserine. Isomer D2 was used in General Procedure N. LCMS theoretical m/z=434.3. [M+H]+. found 434.2.

Example 102, Compound 70

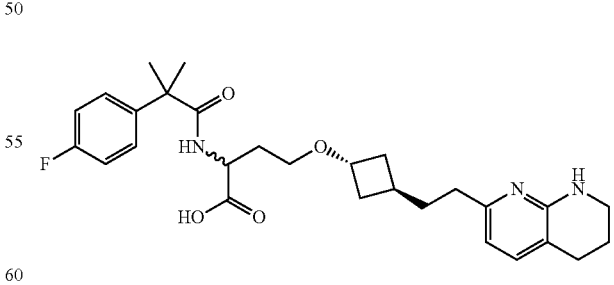

N-(2-(4-fluorophenyl)-2-methylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(4-fluorophenyl)-2-methylpropanoic acid. LCMS theoretical m/z=498.3. [M+H]+. found 498.3.

Example 103, Compound 71

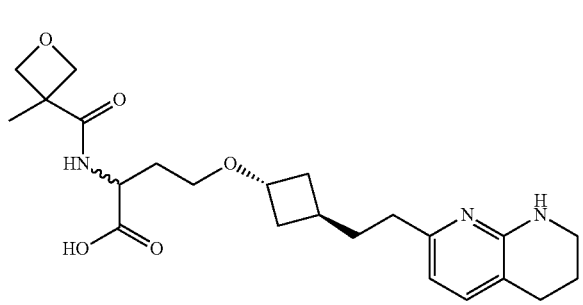 [SMILES: CC1(C(=O)NC(CCO[C@H]2C[C@H](CCc3ccc4c(n3)NCCC4)C2)C(=O)O)COC1]

N-(3-methyloxetane-3-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3-methyloxetane-3-carboxylic acid. LCMS theoretical m/z=432.2. [M+H]+. found 432.2.

Example 104, Compound 72

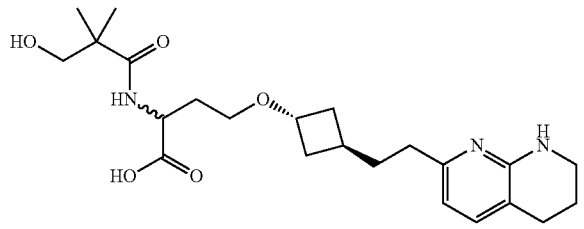 [SMILES: CC(C)(CO)C(=O)NC(CCO[C@H]1C[C@H](CCc2ccc3c(n2)NCCC3)C1)C(=O)O]

N-(3-hydroxy-2,2-dimethylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3-hydroxy-2,2-dimethylpropanoic acid. LCMS theoretical m/z=434.3. [M+H]+. found 434.4.

Example 105, Compound 73

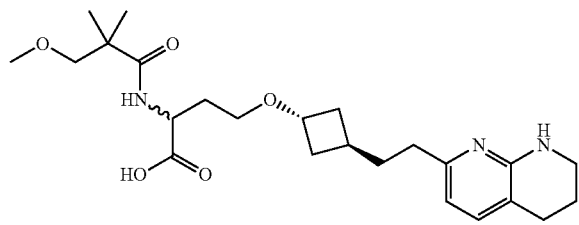 [SMILES: COCC(C)(C)C(=O)NC(CCO[C@H]1C[C@H](CCc2ccc3c(n2)NCCC3)C1)C(=O)O]

N-(3-methoxy-2,2-dimethylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3-methoxy-2,2-dimethylpropanoic acid. LCMS theoretical m/z=448.3. [M+H]+. found 448.4.

Example 106, Compound 74

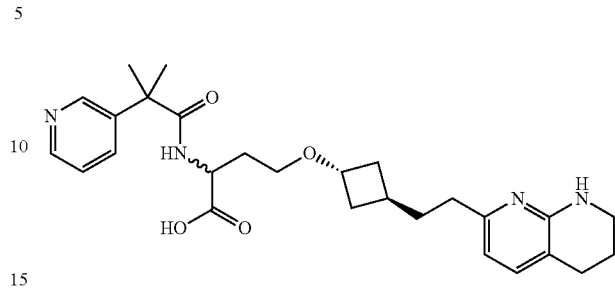

N-(2-methyl-2-(pyridin-3-yl)propanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-methyl-2-(pyridin-3-yl)propanoic acid. LCMS theoretical m/z=481.3. [M+H]+. found 481.4.

Example 107, Compound 75

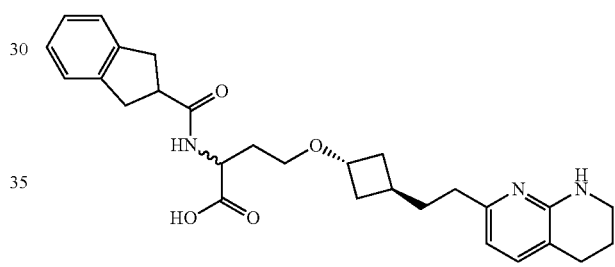

N-(2,3-dihydro-JH-indene-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,3-dihydro-1H-indene-2-carboxylic acid. LCMS theoretical m/z=478.3. [M+H]+. found 478.4.

Example 108, Compound 76

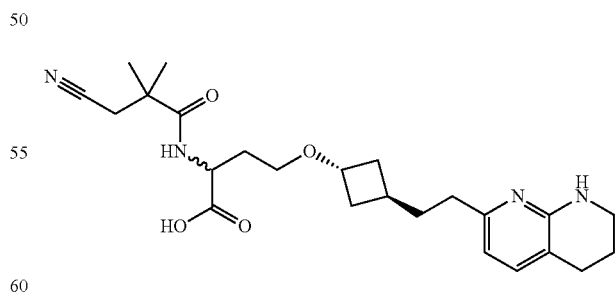

N-(3-cyano-2,2-dimethylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3-cyano-2,2-dimethylpropanoic acid. LCMS theoretical m/z=443.3. [M+H]+. found 443.3.

Example 109, Compound 77

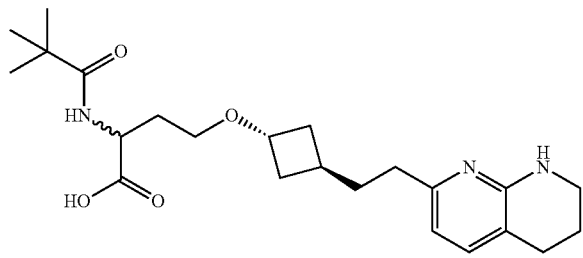 [SMILES: CC(C)(C)C(=O)NC(CCO[C@H]1C[C@H](CCc2ccc3c(n2)NCCC3)C1)C(=O)O]

N-pivaloyl-O-(trans-3-(2-(5,6,7,8-tetrahydro-1,8-naphthyridin-2-yl)ethyl)cyclobutyl)homoserine. Prepared using General Scheme D-2 beginning with Isomer D2 using General Procedure I with pivalic acid. LCMS theoretical m/z=418.3. [M+H]+. found 418.3.

Example 110, Compound 78

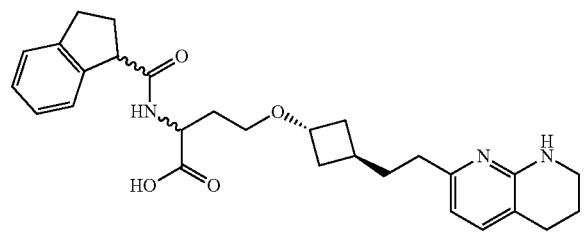 [SMILES: O=C(O)C(CCO[C@H]1C[C@H](CCc2ccc3c(n2)NCCC3)C1)NC(=O)C1CCc2ccccc21]

N-(2,3-dihydro-JH-indene-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,3-dihydro-1H-indene-1-carboxylic acid, and General Procedure N to afford the title compound as the first eluting isomer as a single enantiomer. LCMS theoretical m/z=478.3. [M+H]+. found 478.3.

Example 111, Compound 78

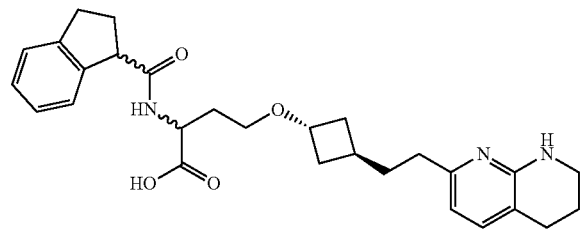 [SMILES: O=C(O)C(CCO[C@H]1C[C@H](CCc2ccc3c(n2)NCCC3)C1)NC(=O)C1CCc2ccccc21]

N-(2,3-dihydro-1H-indene-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,3-dihydro-1H-indene-1-carboxylic acid, and General Procedure N to afford the title compound as the second eluting isomer as a single enantiomer. LCMS theoretical m/z=478.3. [M+H]+. found 478.2.

Example 112, Compound 79

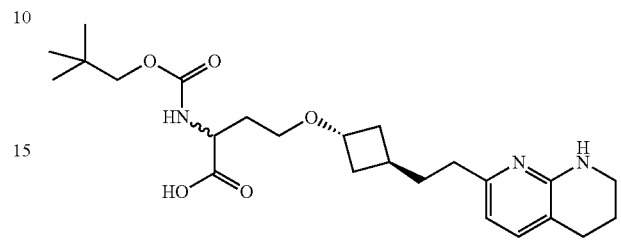

N-((neopentyloxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure F with neopentyl chloroformate. LCMS theoretical m/z=448.3. [M+H]+. found 448.3.

Example 113, Compound 80

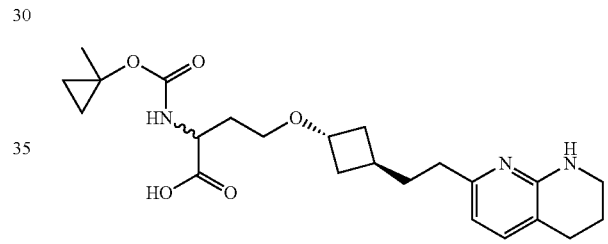

N-((1-methylcyclopropoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure J with 1-methylcyclopropan-1-ol, General Procedure K, and General Procedure N. LCMS theoretical m/z=432.3. [M+H]+. found 432.2.

Example 114, Compound 81

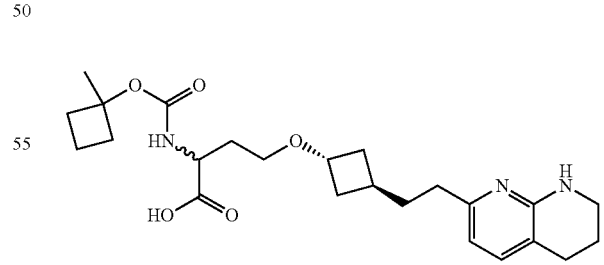

N-((1-methylcyclobutoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure J with 1-methylcyclobutan-1-ol, General Procedure K, and General Procedure N. LCMS theoretical m/z=446.3. [M+H]+. found 446.3.

Example 15, Compound 82

Example 118, Compound 85

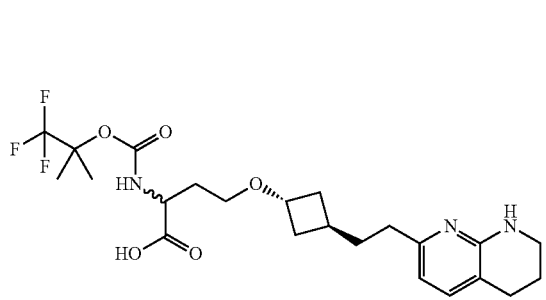 [SMILES: CC(C)(OC(=O)NC(CCO[C@H]1C[C@H](CCc2ccc3c(n2)NCCC3)C1)C(=O)O)C(F)(F)F]

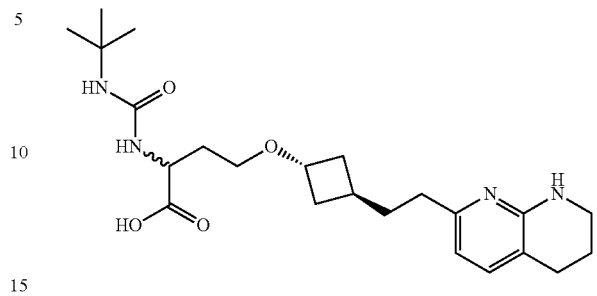

O-(trans-3-(2-(5,6,7,8-tetrahydro-1,8-naphthyridin-2-yl)ethyl)cyclobutyl)-N-(((1,1,1-trifluoro-2-methylpropan-2-yl)oxy)carbonyl)homoserine. Isomer D2 was employed in General Scheme D-2 using General Procedure J with 1,1,1-trifluoro-2-methylpropan-2-ol, General Procedure K, and General Procedure N. LCMS theoretical m/z=488.2. [M+H]+. found 488.2.

N-(tert-butylcarbamoyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure G with tert-butylamine, and General Procedure N. LCMS theoretical m/z=433.3. [M+H]+. found 433.3.

Example 119, Compound 86

Example 116, Compound 83

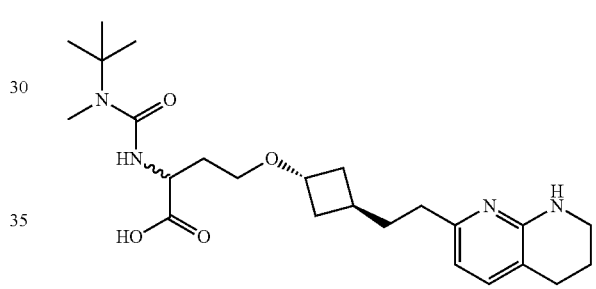

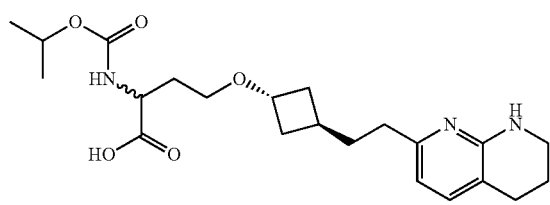 [SMILES: CC(C)OC(=O)NC(CCO[C@H]1C[C@H](CCc2ccc3c(n2)NCCC3)C1)C(=O)O]

N-(tert-butyl(methyl)carbamoyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure G with N,2-dimethylpropan-2-amine, and General Procedure N. LCMS theoretical m/z=447.3. [M+H]+. found 447.3.

N-(isopropoxycarbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure F with isopropyl chloroformate. LCMS theoretical m/z=420.3. [M+H]+. found 420.2.

Example 120, Compound 87

Example 117, Compound 84

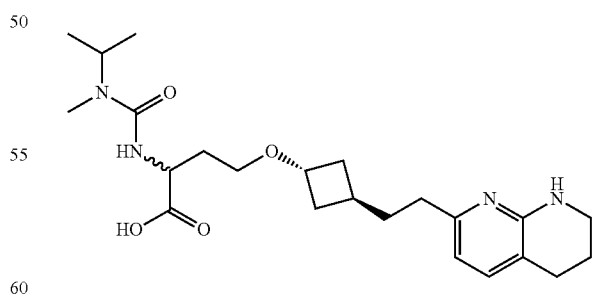

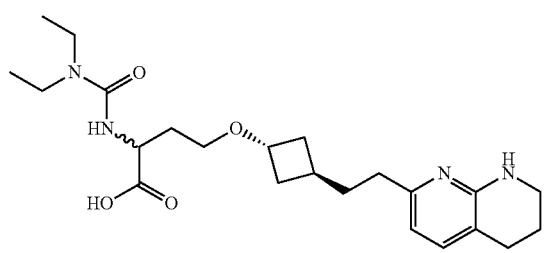 [SMILES: CCN(CC)C(=O)NC(CCO[C@H]1C[C@H](CCc2ccc3c(n2)NCCC3)C1)C(=O)O]

N-(diethylcarbamoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure H with diethylcarbamoyl chloride. LCMS theoretical m/z=433.3. [M+H]+. found 433.3.

N-(isopropyl(methyl)carbamoyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure G with N-methylpropan-2-amine, and General Procedure N. LCMS theoretical m/z=433.3. [M+H]+. found 433.3.

Example 121, Compound 88

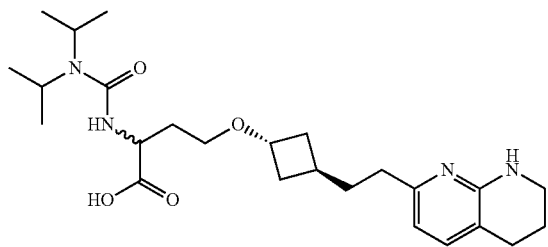 [SMILES: CC(C)N(C(=O)NC(CCO[C@H]1C[C@H](CCc2ccc3c(n2)NCCC3)C1)C(=O)O)C(C)C]

N-(diisopropylcarbamoyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure G with diisopropylamine, and General Procedure N. LCMS theoretical m/z=461.3. [M+H]+. found 461.3.

Example 122, Compound 89

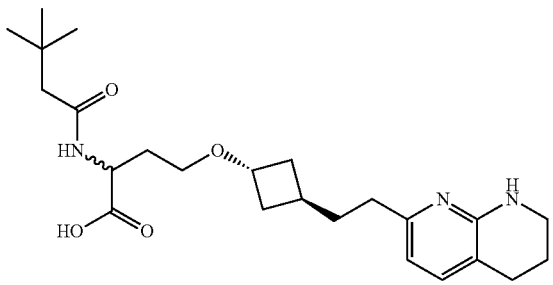 [SMILES: CC(C)(C)CC(=O)NC(CCO[C@H]1C[C@H](CCc2ccc3c(n2)NCCC3)C1)C(=O)O]

N-(3,3-dimethylbutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3,3-dimethylbutanoic acid. LCMS theoretical m/z=432.3. [M+H]+. found 432.3.

Example 123, Compound 90

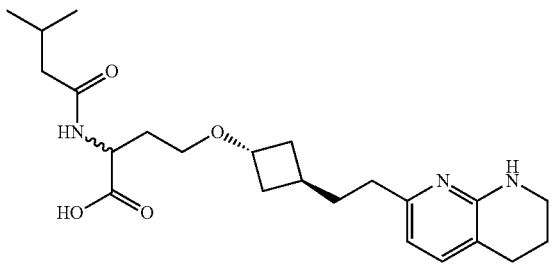 [SMILES: CC(C)CC(=O)NC(CCO[C@H]1C[C@H](CCc2ccc3c(n2)NCCC3)C1)C(=O)O]

N-(3-methylbutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3-methylbutanoic acid. LCMS theoretical m/z=418.3. [M+H]+. found 418.3.

Example 124, Compound 91

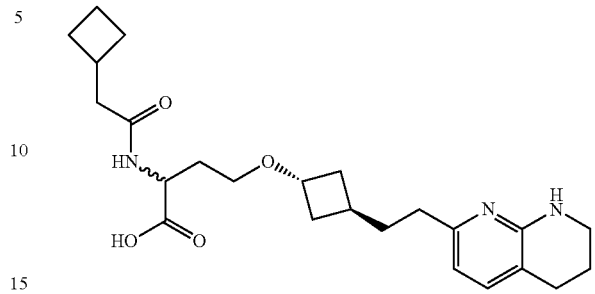

N-(2-cyclobutylacetyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-cyclobutylacetic acid. LCMS theoretical m/z=430.3. [M+H]+. found 430.3.

Example 125, Compound 92

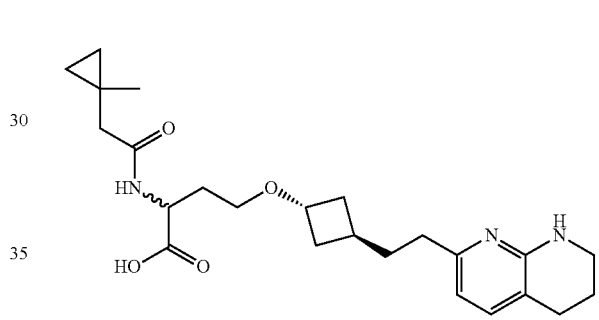

N-(2-(1-methylcyclopropyl)acetyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(1-methylcyclopropyl)acetic acid. LCMS theoretical m/z=430.3. [M+H]+. found 430.3.

Example 126, Compound 93

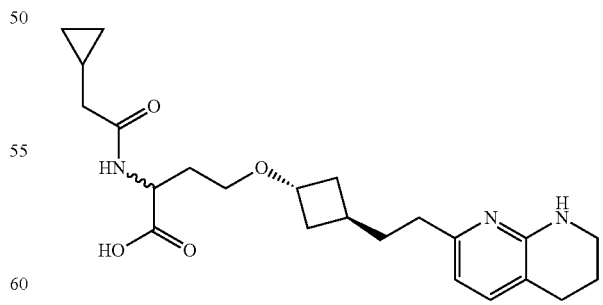

N-(2-cyclopropylacetyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-cyclopropylacetic acid. LCMS theoretical m/z=416.3. [M+H]+. found 416.3.

Example 127, Compound 94

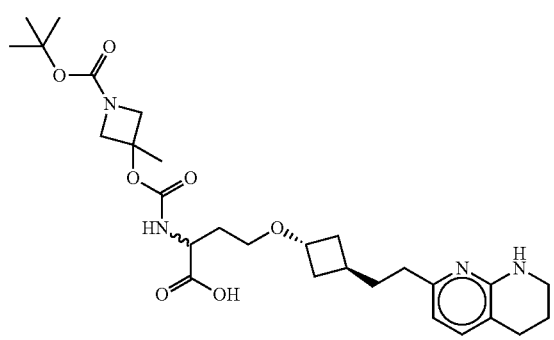

N-(((1-(tert-butoxycarbonyl)-3-methylazetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)-3-methylazetidine-1-carboxylate (prepared using General Procedure J with tert-butyl 3-hydroxy-3-methylazetidine-1-carboxylate), and General Procedure N. LCMS theoretical m/z=547.31. [M+H]+. found 547.3.

Example 128, Compound 95

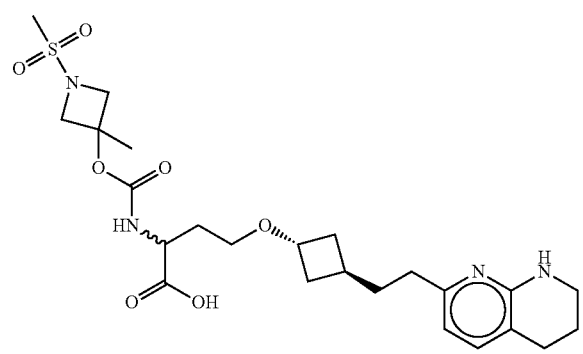

N-(((3-methyl-1-(methylsulfonyl)azetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)-3-methylazetidine-1-carboxylate (prepared using General Procedure J with tert-butyl 3-hydroxy-3-methylazetidine-1-carboxylate), General Procedure D, General Procedure M, then General Procedure N. LCMS theoretical m/z=525.24. [M+H]+. found 525.2.

Example 129, Compound 96

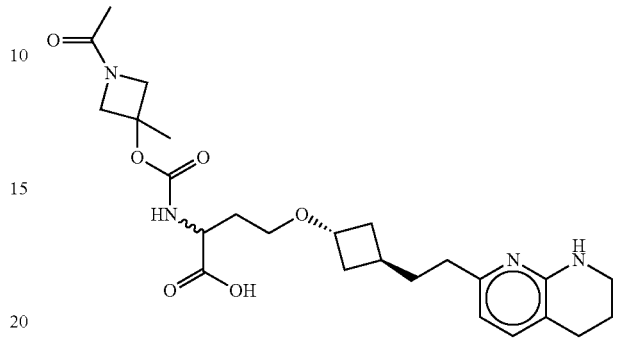

N-(((1-acetyl-3-methylazetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)-3-methylazetidine-1-carboxylate (prepared using General Procedure J with tert-butyl 3-hydroxy-3-methylazetidine-1-carboxylate), General Procedure D, General Procedure L, then General Procedure N. LCMS theoretical m/z=489.27. [M+H]+. found 489.3.

Example 130, (Compound 97

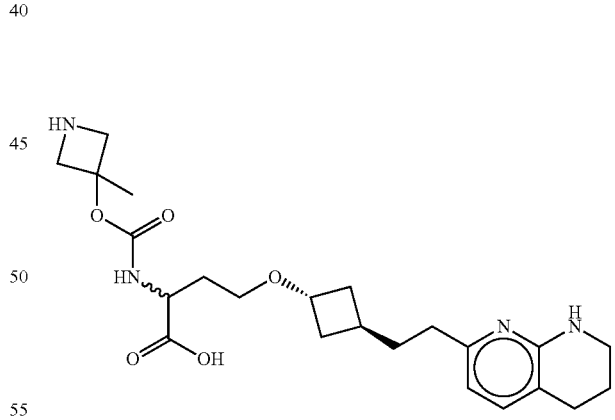

N-(((3-methylazetidin-3-yl)oxy)carbonyl)-O-(trans-3-(2-(5,6,7,8-tetrahydro-1,8-naphthyridin-2-yl)ethyl)cyclobutyl) homoserine. Isomer D2 was sequentially used in General Procedure D, General Procedure K with tert-butyl 3-((((2,5-dioxopyrrolidin-1-yl)oxy)carbonyl)oxy)-3-methylazetidine-1-carboxylate (prepared using General Procedure J with tert-butyl 3-hydroxy-3-methylazetidine-1-carboxylate), General Procedure D, then General Procedure N. LCMS theoretical m/z=447.26. [M+H]+. found 447.3.

Example 131, Compound 98

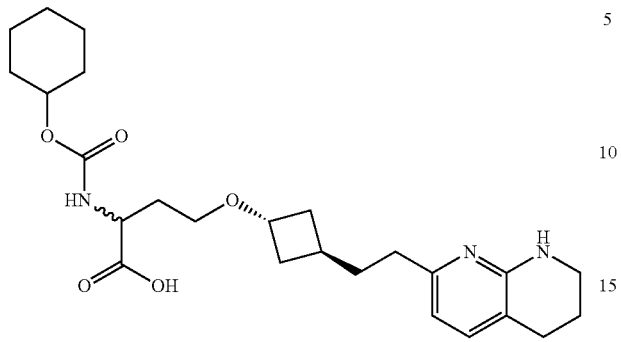

N-((cyclohexyloxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure F with cyclohexyl chloroformate. LCMS theoretical m/z=460.28. [M+H]+. found 460.3.

Example 132, Compound 99

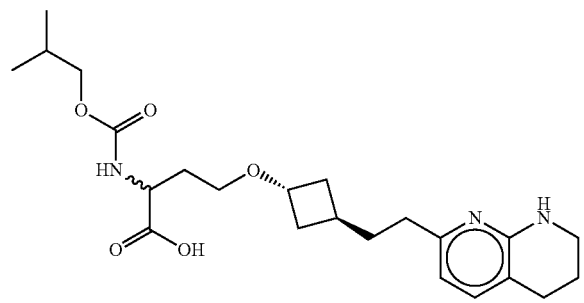

N-(isobutoxycarbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure F with isobutyl chloroformate. LCMS theoretical m/z=434.27. [M+H]+. found 434.3.

Example 133, Compound 100

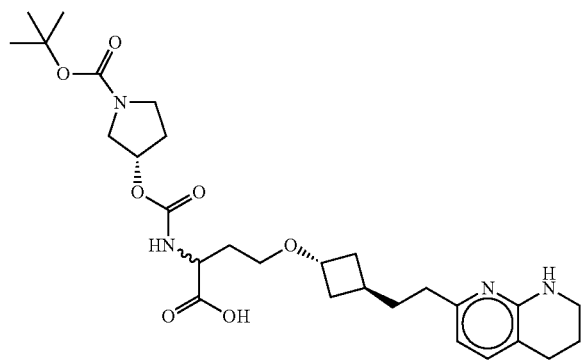

N—((((S)-1-(tert-butoxycarbonyl)pyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-3-((((2,5-dioxopyrrolidin-1-yl)oxy)carbonyl)oxy)pyrrolidine-1-carboxylate (prepared using General Procedure J with tert-butyl (S)-3-hydroxypyrrolidine-1-carboxylate), then General Procedure N. LCMS theoretical m/z=547.31. [M+H]+. found 547.3.

Example 134, Compound 101

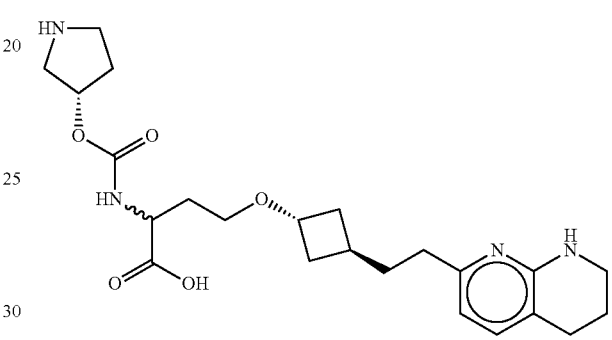

N—((((S)-pyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-3-((((2,5-dioxopyrrolidin-1-yl)oxy)carbonyl)oxy)pyrrolidine-1-carboxylate (prepared using General Procedure J with tert-butyl (S)-3-hydroxypyrrolidine-1-carboxylate), General Procedure D, then General Procedure N. LCMS theoretical m/z=447.26. [M+H]+. found 447.3.

Example 135, Compound 102

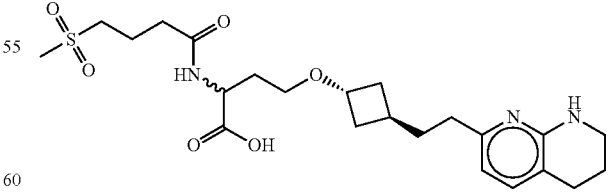

N-(4-(methylsulfonyl)butanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 4-(methylsulfonyl)butanoic acid. LCMS theoretical m/z=482.23. [M+H]+. found 482.2.

Example 136, Compound 103

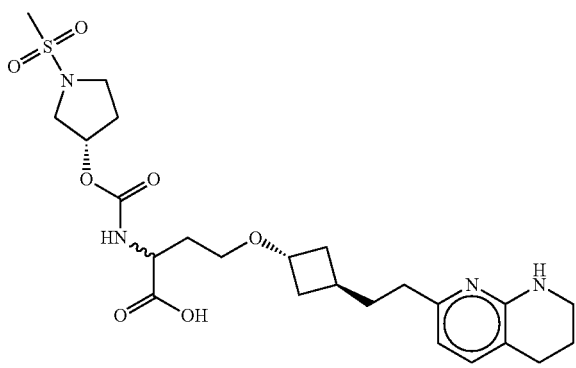

N—((((S)-1-(methylsulfonyl)pyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-3-((((2,5-dioxopyrrolidin-1-yl)oxy)carbonyl)oxy)pyrrolidine-1-carboxylate (prepared using General Procedure J with tert-butyl (S)-3-hydroxypyrrolidine-1-carboxylate), General Procedure D, General Procedure M, then General Procedure N. LCMS theoretical m/z=525.24. [M+H]+. found 525.2.

Example 137, Compound 104

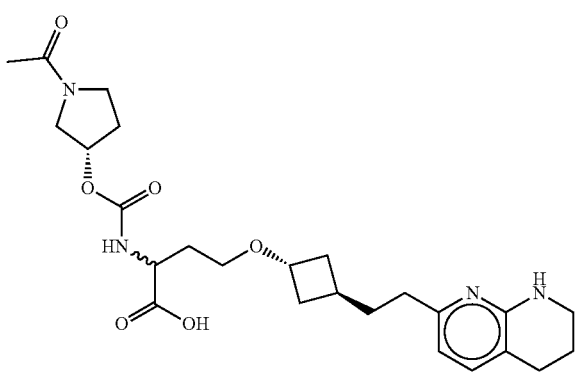

N—((((S)-1-acetylpyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-3-((((2,5-dioxopyrrolidin-1-yl)oxy)carbonyl)oxy)pyrrolidine-1-carboxylate (prepared using General Procedure J with tert-butyl (S)-3-hydroxypyrrolidine-1-carboxylate), General Procedure D, General Procedure L, then General Procedure N. LCMS theoretical m/z=489.27. [M+H]+. found 489.3.

Example 138, Compound 100

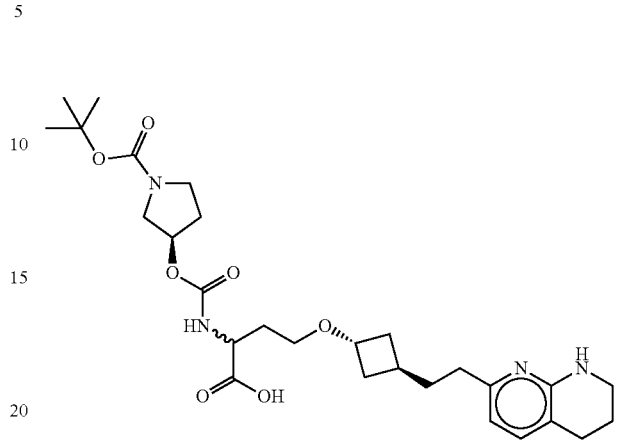

N—((((R)-1-(tert-butoxycarbonyl)pyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (R)-3-((((2,5-dioxopyrrolidin-1-yl)oxy)carbonyl)oxy)pyrrolidine-1-carboxylate (prepared using General Procedure J with tert-butyl (R)-3-hydroxypyrrolidine-1-carboxylate), then General Procedure N. LCMS theoretical m/z=547.31. [M+H]+. found 547.3.

Example 139, Compound 104

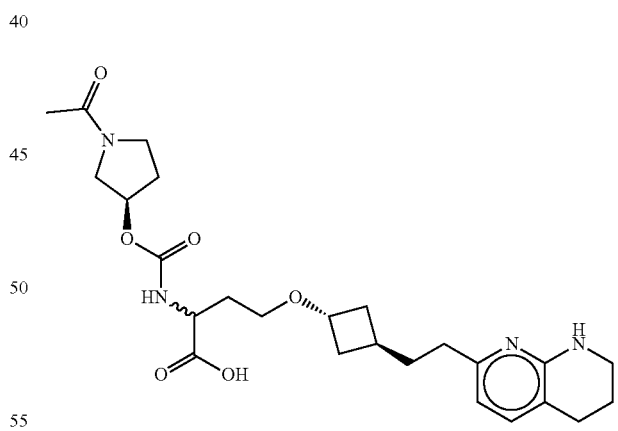

N—((((R)-1-acetylpyrrolidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (R)-3-((((2,5-dioxopyrrolidin-1-yl)oxy)carbonyl)oxy)pyrrolidine-1-carboxylate (prepared using General Procedure J with tert-butyl (R)-3-hydroxypyrrolidine-1-carboxylate), General Procedure D, General Procedure L, then General Procedure N. LCMS theoretical m/z=489.27. [M+H]+. found 489.3.

Example 140, Compound 105

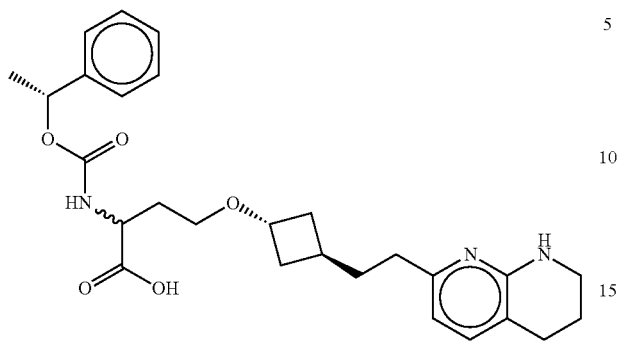

N—(((R)-1-phenylethoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with (R)-2,5-dioxopyrrolidin-1-yl (1-phenylethyl) carbonate (prepared using General Procedure J with (R)-1-phenylethan-1-ol). LCMS theoretical m/z=482.27. [M+H]+. found 482.3.

Example 141, Compound 105

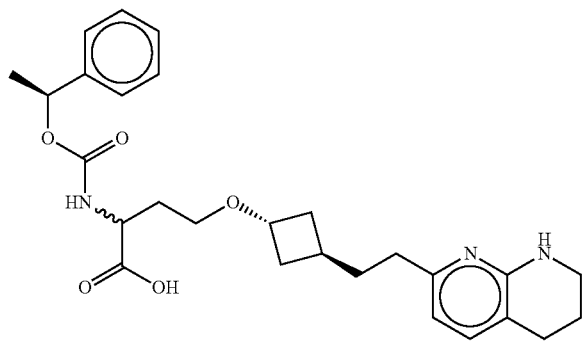

N—(((S)-1-phenylethoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with (S)-2,5-dioxopyrrolidin-1-yl (1-phenylethyl) carbonate (prepared using General Procedure J with (S)-1-phenylethan-1-ol). LCMS theoretical m/z=482.27. [M+H]+. found 482.3.

Example 142, Compound 106

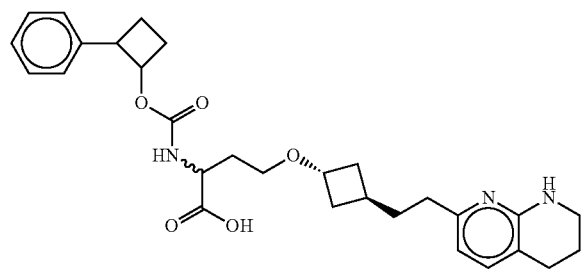

N-((2-phenylcyclobutoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl (2-phenylcyclobutyl) carbonate (prepared using General Procedure J with 2-phenylcyclobutan-1-ol). LCMS theoretical m/z=508.28. [M+H]+. found 508.3.

Example 143, Compound 107

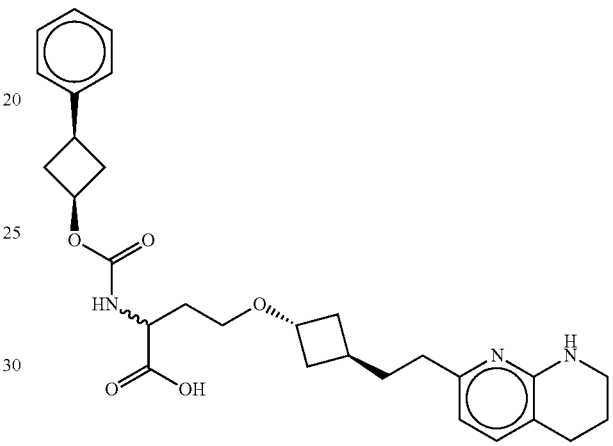

N-((cis-3-phenylcyclobutoxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl ((1s,3s)-3-phenylcyclobutyl) carbonate (prepared using General Procedure J with (1s,3s)-3-phenylcyclobutan-1-ol). LCMS theoretical m/z=508.28. [M+H]+. found 508.3.

Example 144, Compound 108

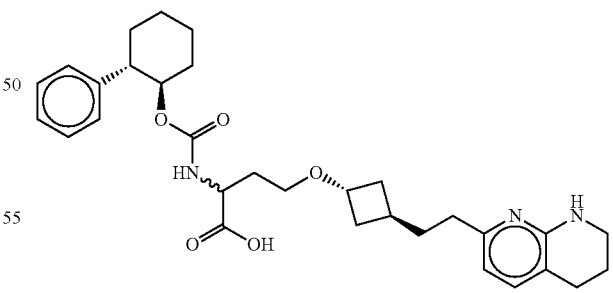

N-((((1R,2S)-2-phenylcyclohexyl)oxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl (((1R,2S)-2-phenylcyclohexyl) carbonate (prepared using General Procedure J with (1R,2S)-2-phenylcyclohexan-1-ol). LCMS theoretical m/z=536.31. [M+H]+. found 536.3.

Example 145, Compound 109

Synthesis of trans-2-((tert-butoxycarbonyl)amino)-3-methyl-4-(trans-3-(2-(5,6,7,8-tetrahydro-1,8-naphthyridin-2-yl)ethyl)cyclobutoxy)butanoic acid and cis-2-((tert-butoxycarbonyl)amino)-3-methyl-4-(trans-3-(2-(5,6,7,8-tetrahydro-1,8-naphthyridin-2-yl)ethyl)cyclobutoxy)butanoic acid (racemate)

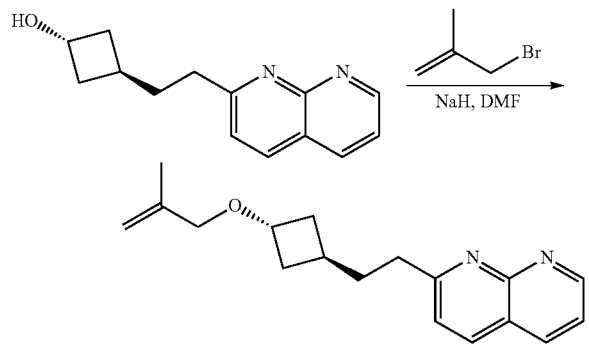

2-(2-((1r,3s)-3-((2-methylallyl)oxy)cyclobutyl)ethyl)-1,8-naphthyridine. To a suspension of sodium hydride (60 wt % dispersion in mineral oil, 64 mg, 1.59 mmol) in DMF (3 mL) at 0° C. was added (1s,3r)-3-(2-(1,8-naphthyridin-2-yl)ethyl)cyclobutan-1-ol (302 mg, 1.32 mmol) in DMF (2 mL) and the resulting mixture was allowed to warm to room temperature and stirred for an additional 30 minutes. To this was then added 3-bromo-2-methylprop-1-ene (357 mg, 2.65 mmol) and the reaction mixture was stirred for 4 hours at room temperature and then diluted with sat. aq. NaHCO$_3$ and extracted with EtOAc. The combined organic extracts were dried over Na$_2$SO$_4$, filtered, and concentrated in vacuo. The crude residue was purified by normal phase silica gel chromatography to give 2-(2-((1r,3s)-3-((2-methylallyl)oxy)cyclobutyl)ethyl)-1,8-naphthyridine.

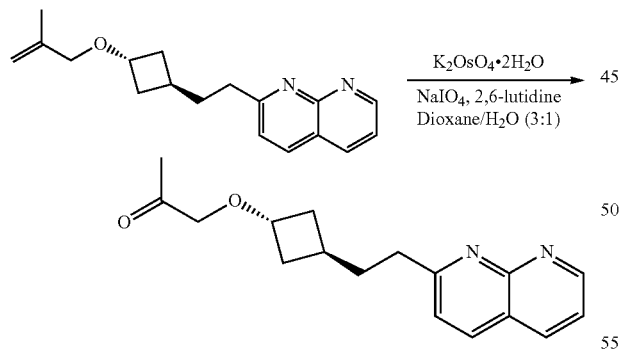

1-((1s,3r)-3-(2-(1,8-naphthyridin-2-yl)ethyl)cyclobutoxy)propan-2-one. To a mixture of 2-(2-((1r,3s)-3-((2-methylallyl)oxy)cyclobutyl)ethyl)-1,8-naphthyridine (174 mg, 0.62 mmol) in 3:1 Dioxane/H$_2$O (3 mL) was added 2,6-lutidine (132 mg, 1.23 mmol), NaIO$_4$ (527 mg, 2.46 mmol), then K$_2$OsO4.2H$_2$O (11 mg, 0.03 mmol) and the resulting mixture was allowed to stir at room temperature for 3 hours. The mixture was filtered and concentrated in vacuo. The crude residue was purified by normal phase silica gel chromatography to give 1-((1s,3r)-3-(2-(1,8-naphthyridin-2-yl)ethyl)cyclobutoxy)propan-2-one.

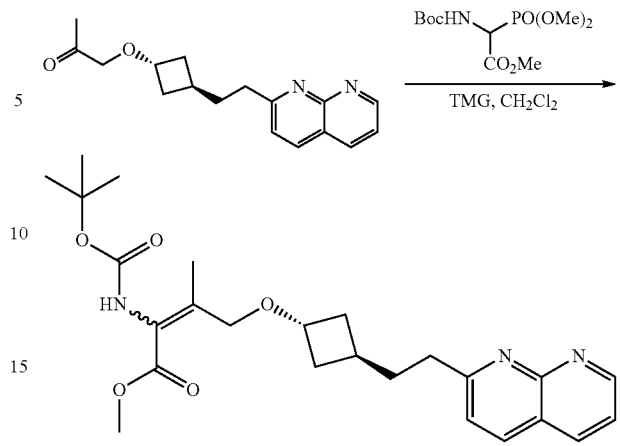

methyl 4-((1s,3r)-3-(2-(1,8-naphthyridin-2-yl)ethyl)cyclobutoxy)-2-((tert-butoxycarbonyl)amino)-3-methylbut-2-enoate. To a solution of 1-((1s,3r)-3-(2-(1,8-naphthyridin-2-yl)ethyl)cyclobutoxy)propan-2-one (175 mg, 0.62 mmol) in CH$_2$Cl$_2$ (2 mL) was added methyl 2-((tert-butoxycarbonyl)amino)-2-(dimethoxyphosphoryl)acetate (366 mg, 1.23 mmol) then 1,1,3,3-tetramethylguanidine (142 mg, 1.23 mmol) and the resulting mixture was heated to 40° C. for 2 days. The reaction mixture was cooled to room temperature and then concentrated in vacuo. The crude residue was purified by normal phase silica gel chromatography to give methyl 4-((1s,3r)-3-(2-(1,8-naphthyridin-2-yl)ethyl)cyclobutoxy)-2-((tert-butoxycarbonyl)amino)-3-methylbut-2-enoate.

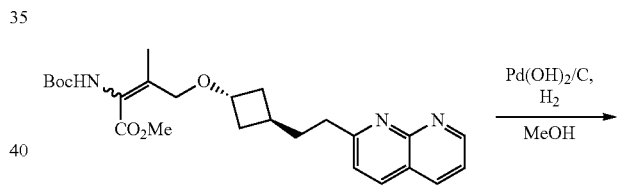

methyl 2-((tert-butoxycarbonyl)amino)-3-methyl-4-((1s,3r)-3-(2-(5,6,7,8-tetrahydro-1,8-naphthyridin-2-yl)ethyl)cyclobutoxy)butanoate. To a flask containing methyl 4-((1s,3r)-3-(2-(1,8-naphthyridin-2-yl)ethyl)cyclobutoxy)-2-((tert-butoxycarbonyl)amino)-3-methylbut-2-enoate (148 mg, 0.32 mmol) was charged Pd(OH)$_2$/C (20 wt % on carbon, 30 mg) and the mixture was evacuated and backfilled with H$_2$ gas for 3 cycles and then stirred under an H$_2$ atmosphere overnight. The mixture was filtered through a pad of Celite and then concentrated in vacuo. The crude residue was purified by normal phase silica gel chromatography to give methyl 2-((tert-butoxycarbonyl)amino)-3-methyl-4-((1s,3r)-3-(2-(5,6,7,8-tetrahydro-1,8-naphthyridin-2-yl)ethyl)cyclobutoxy)butanoate.

Example 145a, Compound 109

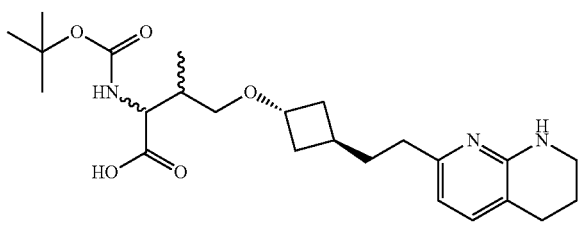 [SMILES: CC(CO[C@H]1C[C@H](CCc2ccc3c(n2)NCCC3)C1)C(NC(=O)OC(C)(C)C)C(=O)O]

2-((tert-butoxycarbonyl)amino)-3-methyl-4-(trans-3-(2-(5,6,7,8-tetrahydro-1,8-naphthyridin-2-yl)ethyl)cyclobutoxy)butanoic acid. Prepared beginning with methyl 2-((tert-butoxycarbonyl)amino)-3-methyl-4-(trans-3-(2-(5,6,7,8-tetrahydro-1,8-naphthyridin-2-yl)ethyl)cyclobutoxy)butanoate then using General Procedure N whereby a racemic mixture of the title compound was isolated as the second eluting isomer by reverse phase preparative HPLC. LCMS theoretical m/z=448.28. [M+H]+. found 448.3. The absolute stereochemistry of the product of Example 145a was subsequently assigned as (2S,3S)-2-((tert-butoxycarbonyl)amino)-3-methyl-4-((1s,3S)-3-(2-(5,6,7,8-tetrahydro-1,8-naphthyridin-2-yl)ethyl)cyclobutoxy)butanoic acid.

Example 145b, Compound 109

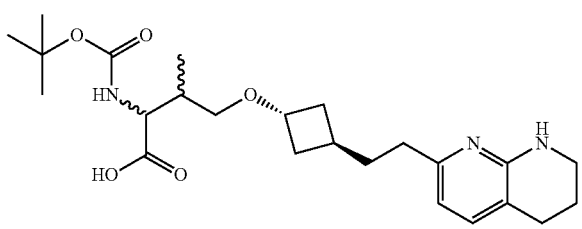 [SMILES: CC(CO[C@H]1C[C@H](CCc2ccc3c(n2)NCCC3)C1)C(NC(=O)OC(C)(C)C)C(=O)O]

2-((tert-butoxycarbonyl)amino)-3-methyl-4-(trans-3-(2-(5,6,7,8-tetrahydro-1,8-naphthyridin-2-yl)ethyl)cyclobutoxy)butanoic acid. Prepared beginning with methyl 2-((tert-butoxycarbonyl)amino)-3-methyl-4-(trans-3-(2-(5,6,7,8-tetrahydro-1,8-naphthyridin-2-yl)ethyl)cyclobutoxy)butanoate then using General Procedure N whereby a racemic mixture of the title compound was isolated as the first eluting peak by reverse phase preparative HPLC. LCMS theoretical m/z=448.28. [M+H]+. found 448.3. The absolute stereochemistry of the product of Example 145b was subsequently assigned as (2S,3R)-2-((tert-butoxycarbonyl)amino)-3-methyl-4-((1s,3R)-3-(2-(5,6,7,8-tetrahydro-1,8-naphthyridin-2-yl)ethyl)cyclobutoxy)butanoic acid (see structure in FIG. 1, Table 2).

Example 146, Compound 108

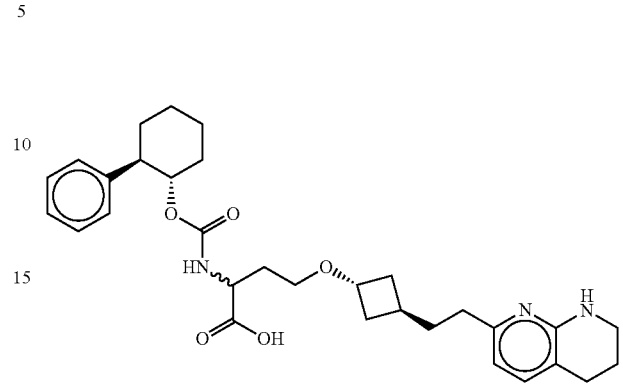

N-((((1S,2R)-2-phenylcyclohexyl)oxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl ((1 S,2R)-2-phenylcyclohexyl) carbonate (prepared using General Procedure J with (1S, 2R)-2-phenylcyclohexan-1-ol). LCMS theoretical m/z=536.31. [M+H]+. found 536.3.

Example 147, Compound 110

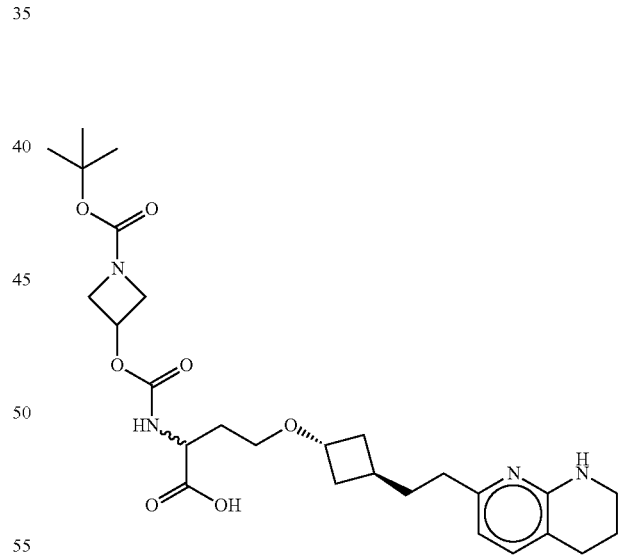

N-(((1-(tert-butoxycarbonyl)azetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)azetidine-1-carboxylate (prepared using General Procedure J with tert-butyl 3-hydroxyazetidine-1-carboxylate), then General Procedure N. LCMS theoretical m/z=533.30. [M+H]+. found 533.3.

Example 148, Compound 111

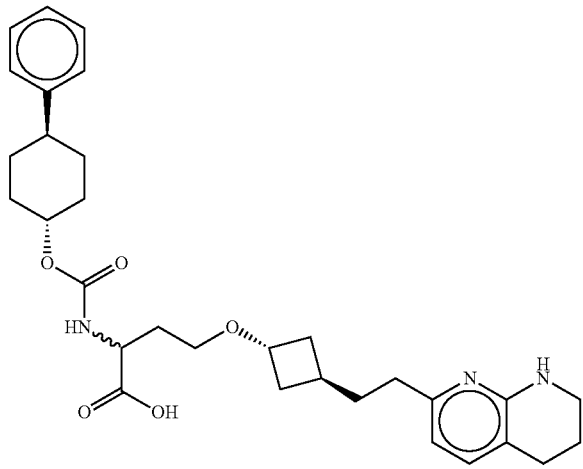

N-(((trans-4-phenylcyclohexyl)oxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl (trans-4-phenylcyclohexyl) carbonate (prepared using General Procedure J with trans-4-phenylcyclohexan-1-ol). LCMS theoretical m/z=536.31. [M+H]+. found 536.3.

Example 149, Compound 111

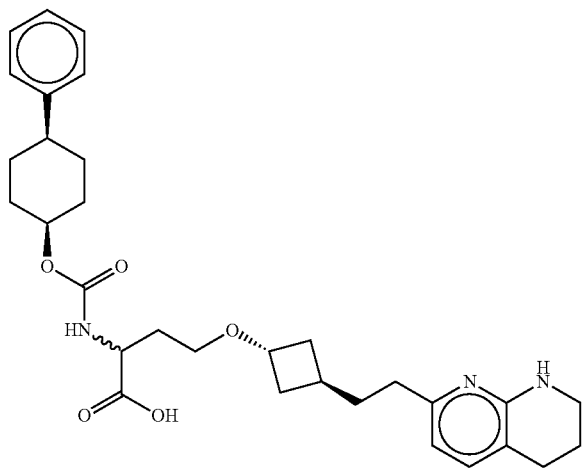

N-(((cis-4-phenylcyclohexyl)oxy)carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure K with 2,5-dioxopyrrolidin-1-yl (cis-4-phenylcyclohexyl) carbonate (prepared using General Procedure J with cis-4-phenylcyclohexan-1-ol). LCMS theoretical m/z=536.31. [M+H]+. found 536.3.

Example 150, Compound 112

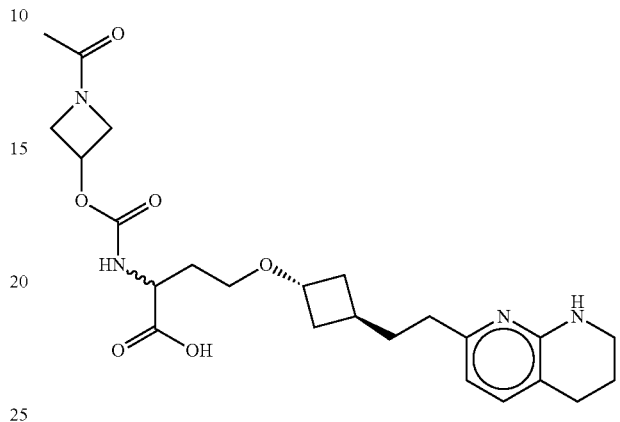

N-(((1-acetylazetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)azetidine-1-carboxylate (prepared using General Procedure J with tert-butyl 3-hydroxyazetidine-1-carboxylate), General Procedure D, General Procedure L, then General Procedure N. LCMS theoretical m/z=475.26. [M+H]+. found 475.3.

Example 151, Compound 113

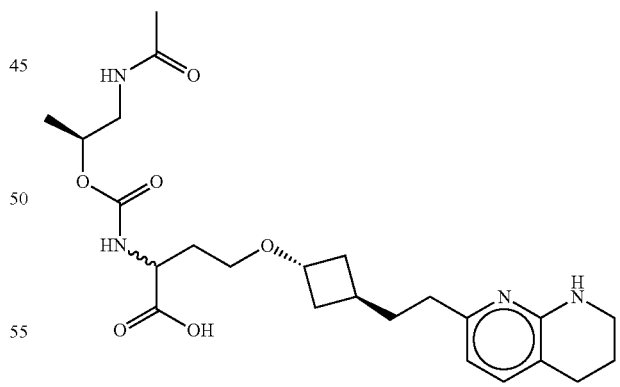

N—((((S)-1-acetamidopropan-2-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-(2-((((2,5-dioxopyrrolidin-1-yl)oxy)carbonyl)oxy)propyl)carbamate (prepared using General Procedure J with tert-butyl (S)-(2-hydroxypropyl)carbamate), General Procedure D, General Procedure L, then General Procedure N. LCMS theoretical m/z=477.27. [M+H]+. found 477.3.

Example 152, Compound 114

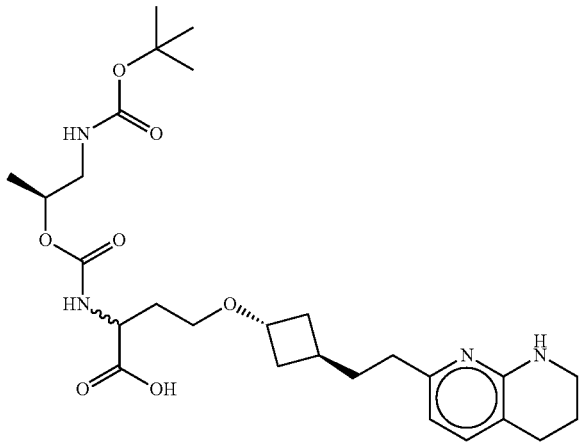

N—((((S)-1-((tert-butoxycarbonyl)amino)propan-2-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (S)-(2-((((2,5-dioxopyrrolidin-1-yl)oxy)carbonyl)oxy)propyl)carbamate (prepared using General Procedure J with tert-butyl (S)-(2-hydroxypropyl)carbamate), then General Procedure N. LCMS theoretical m/z=535.31. [M+H]+. found 535.3.

Example 153

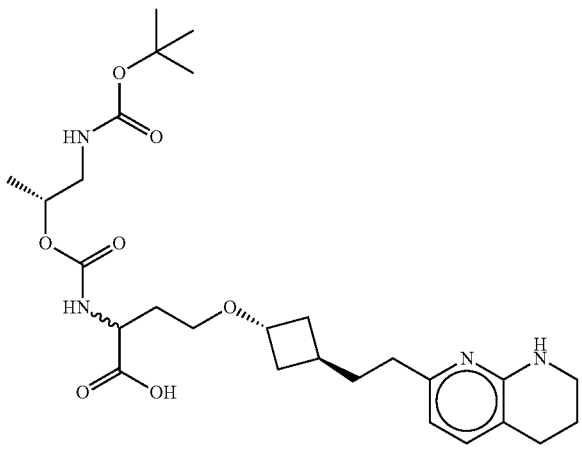

N—((((R)-1-((tert-butoxycarbonyl)amino)propan-2-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (R)-(2-((((2,5-dioxopyrrolidin-1-yl)oxy)carbonyl)oxy)propyl)carbamate (prepared using General Procedure J with tert-butyl (R)-(2-hydroxypropyl)carbamate), then General Procedure N. LCMS theoretical m/z=535.31. [M+H]+. found 535.3.

Example 154, Compound 113

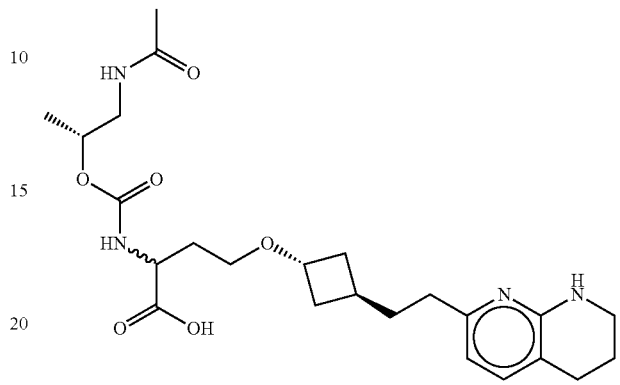

N—((((R)-1-acetamidopropan-2-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl (R)-(2-((((2,5-dioxopyrrolidin-1-yl)oxy)carbonyl)oxy)propyl)carbamate (prepared using General Procedure J with tert-butyl (R)-(2-hydroxypropyl)carbamate), General Procedure D, General Procedure L, then General Procedure N. LCMS theoretical m/z=477.27. [M+H]+. found 447.3.

Example 155a, Compound 115

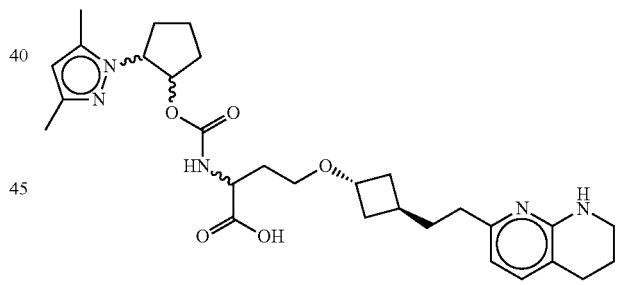

N-((((trans)-2-(3,5-dimethyl-1H-pyrazol-1-yl)cyclopentyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with trans-2-(3,5-dimethyl-1H-pyrazol-1-yl)cyclopentyl (2,5-dioxopyrrolidin-1-yl) carbonate (racemic, prepared using General Procedure J with trans-2-(3,5-dimethyl-1H-pyrazol-1-yl)cyclopentan-1-ol), then General Procedure N followed by preparative HPLC to afford the title compound as the first eluting isomer of unknown absolute stereochemistry at the cyclopentane. LCMS theoretical m/z=540.32. [M+H]+. found 540.3. The absolute stereochemistry of the product of Example 155a was subsequently assigned as N-(((((1R,2R)-2-(3,5-dimethyl-1H-pyrazol-1-yl)cyclopentyl)oxy) carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 155b, Compound 115

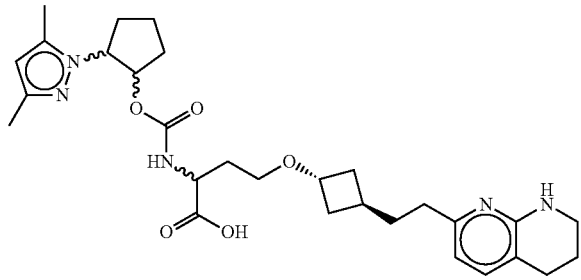

N-((((trans)-2-(3,5-dimethyl-1H-pyrazol-1-yl)cyclopentyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with trans-2-(3,5-dimethyl-1H-pyrazol-1-yl)cyclopentyl (2,5-dioxopyrrolidin-1-yl) carbonate (racemic, prepared using General Procedure J with trans-2-(3,5-dimethyl-1H-pyrazol-1-yl)cyclopentan-1-ol), then General Procedure N followed by preparative HPLC to afford the title compound as the second eluting isomer of unknown absolute stereochemistry at the cyclopentane. LCMS theoretical m/z=540.32. [M+H]+. found 540.3. The absolute stereochemistry of the product of Example 155b was subsequently assigned as N-((((1S,2S)-2-(3,5-dimethyl-1H-pyrazol-1-yl)cyclopentyl)oxy) carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 156a, Compound 116

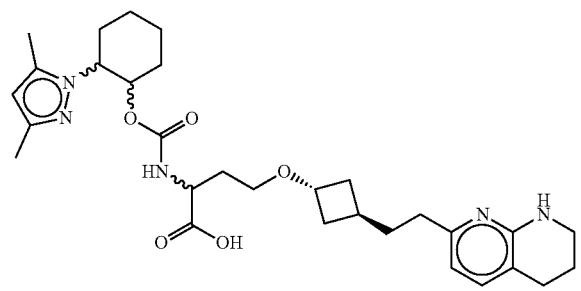

N-((((trans)-2-(3,5-dimethyl-1H-pyrazol-1-yl)cyclohexyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with trans-2-(3,5-dimethyl-1H-pyrazol-1-yl)cyclohexyl (2,5-dioxopyrrolidin-1-yl) carbonate (racemic, prepared using General Procedure J with trans-2-(3,5-dimethyl-1H-pyrazol-1-yl)cyclohexan-1-ol), then General Procedure N followed by preparative HPLC to afford the title compound as the first eluting isomer of unknown absolute stereochemistry at the cyclohexane. LCMS theoretical m/z=554.33. [M+H]+. found 554.4. The absolute stereochemistry of the product of Example 156a was subsequently assigned as N-((((1R,2R)-2-(3,5-dimethyl-1H-pyrazol-1-yl)cyclohexyl)oxy)carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 156b, Compound 116

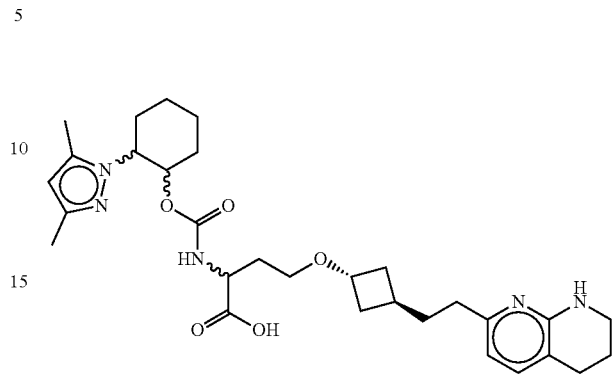

N-((((trans)-2-(3,5-dimethyl-1H-pyrazol-1-yl)cyclohexyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with trans-2-(3,5-dimethyl-1H-pyrazol-1-yl)cyclohexyl (2,5-dioxopyrrolidin-1-yl) carbonate (racemic, prepared using General Procedure J with trans-2-(3,5-dimethyl-1H-pyrazol-1-yl)cyclohexan-1-ol), then General Procedure N followed by preparative HPLC to afford the title compound as the second eluting isomer of unknown absolute stereochemistry at the cyclohexane. LCMS theoretical m/z=554.33. [M+H]+. found 554.4. The absolute stereochemistry of the product of Example 156b was subsequently assigned as N-((((1S,2S)-2-(3,5-dimethyl-1H-pyrazol-1-yl)cyclohexyl)oxy)carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 157, Compound 117

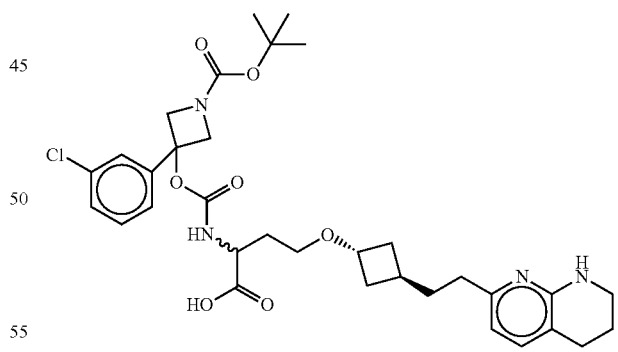

N-(((1-(tert-butoxycarbonyl)-3-(3-chlorophenyl)azetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-(3-chlorophenyl)-3-((((2,5-dioxopyrrolidin-1-yl)oxy)carbonyl)oxy)azetidine-1-carboxylate (prepared using General Procedure J with tert-butyl 3-(3-chlorophenyl)-3-hydroxyazetidine-1-carboxylate), then General Procedure N. LCMS theoretical m/z=643.29. [M+H]+. found 643.3.

Example 158 Compound 118

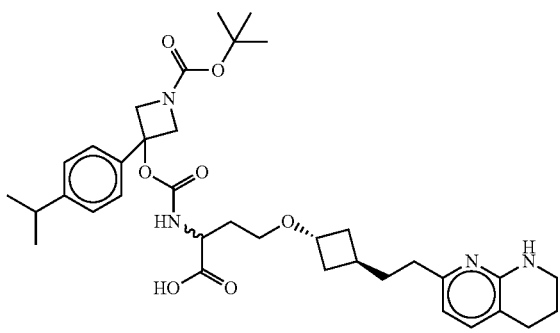

N-(((1-(tert-butoxycarbonyl)-3-(4-isopropylphenyl)azetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)-3-(4-isopropylphenyl)azetidine-1-carboxylate (prepared using General Procedure J with tert-butyl 3-hydroxy-3-(4-isopropylphenyl)azetidine-1-carboxylate), then General Procedure N. LCMS theoretical m/z=651.38. [M+H]+. found 651.4.

Example 159, Compound 119

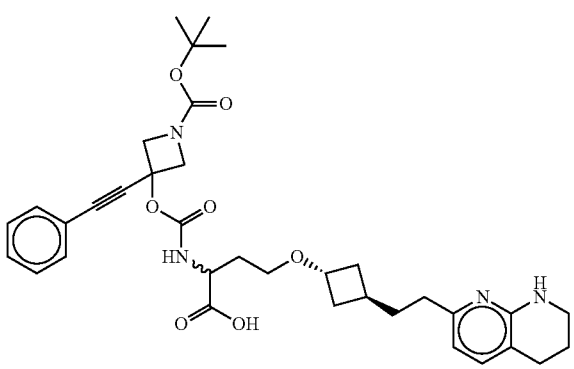

N-(((1-(tert-butoxycarbonyl)-3-(phenylethynyl)azetidin-3-yl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with tert-butyl 3-((((2,5-dioxopyrrolidin-1-yl)oxy)carbonyl)oxy)-3-(phenylethynyl)azetidine-1-carboxylate (prepared using General Procedure J with tert-butyl 3-hydroxy-3-(phenylethynyl)azetidine-1-carboxylate), then General Procedure N. LCMS theoretical m/z=633.33. [M+H]+. found 633.4.

Example 160, Compound 120

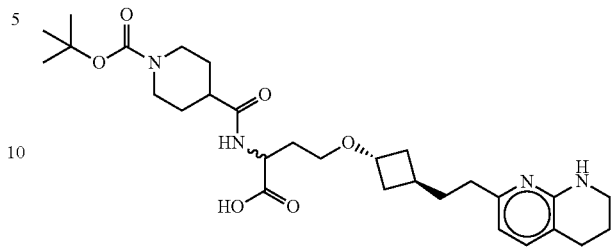

N-(1-(tert-butoxycarbonyl)piperidine-4-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(tert-butoxycarbonyl)piperidine-4-carboxylic acid. LCMS theoretical m/z=545.33. [M+H]+. found 545.3.

Example 161, Compound 121

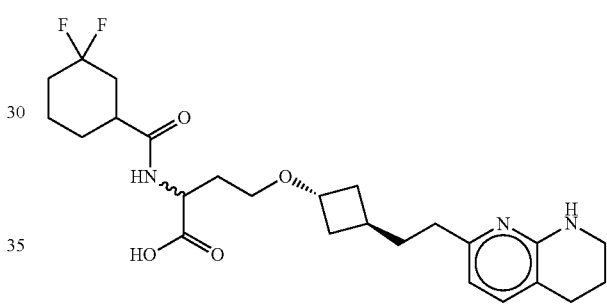

N-(3,3-difluorocyclohexane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 3,3-difluorocyclohexane-1-carboxylic acid. LCMS theoretical m/z=480.27. [M+H]+. found 480.3.

Example 162a, Compound 122

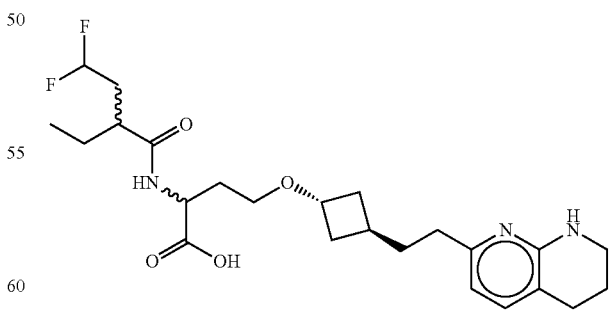

N-(-2-ethyl-4,4-difluorobutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-ethyl-4,4-difluorobutanoic acid, then General Procedure N followed by preparative HPLC to afford the title compound as the first eluting isomer of unknown absolute stereochemistry at the 2-ethyl-4,4-difluorobutanoic amide. LCMS theoretical m/z=468.27. [M+H]+. found 468.3. The absolute stereochemistry of the product of Example 162a was subsequently assigned as N—((S)-2-ethyl-4,4-difluorobutanoyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 162b, Compound 122

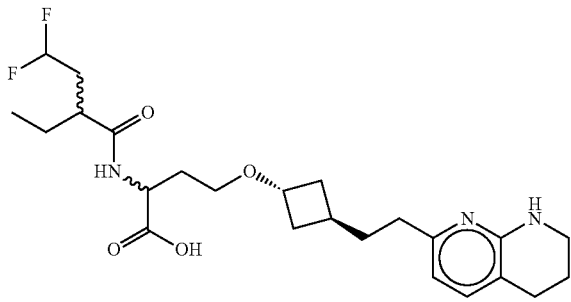

N-(-2-ethyl-4,4-difluorobutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-ethyl-4,4-difluorobutanoic acid, then General Procedure N followed by preparative HPLC to afford the title compound as the second eluting isomer of unknown absolute stereochemistry at the 2-ethyl-4,4-difluorobutanoic amide. LCMS theoretical m/z=468.27. [M+H]+. found 468.3. The absolute stereochemistry of the product of Example 162a was subsequently assigned as N—((R)-2-ethyl-4,4-difluorobutanoyl)-O-((1s,3S)-3-(2-(5,6,7,8-tetrahydro-1,8-naphthyridin-2-yl)ethyl)cyclobutyl)-L-homoserine (see structure in FIG. 1, Table 2).

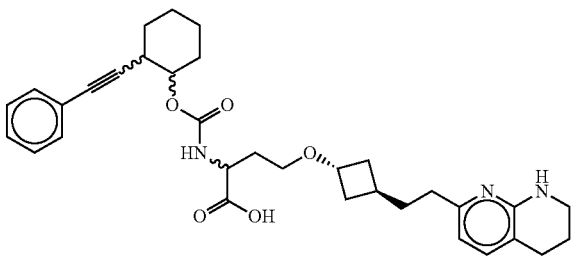

N-(((trans-2-(phenylethynyl)cyclohexyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with 2,5-dioxopyrrolidin-1-yl trans-2-(phenylethynyl)cyclohexyl) carbonate (prepared using General Procedure J with trans-2-(phenylethynyl)cyclohexan-1-ol), and General Procedure N followed by preparative HPLC to afford the title compound as the first eluting isomer of unknown absolute stereochemistry at the cyclohexane. LCMS theoretical m/z=560.31. [M+H]+. found 560.3. The absolute stereochemistry of the product of Example 163a was subsequently assigned as N-((((1R,2S)-2-(phenylethynyl)cyclohexyl)oxy)carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

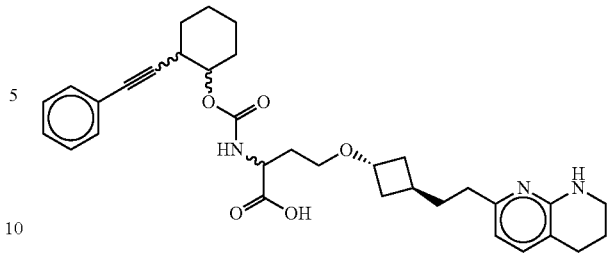

N-(((trans-2-(phenylethynyl)cyclohexyl)oxy)carbonyl)-O-(trans-3-(2-(5,6,7,8-tetrahydro-1,8-naphthyridin-2-yl)ethyl)cyclobutyl)homoserine. Isomer D2 was sequentially used in General Procedure D, General Procedure K with 2,5-dioxopyrrolidin-1-yl trans-2-(phenylethynyl)cyclohexyl) carbonate (prepared using General Procedure J with trans-2-(phenylethynyl)cyclohexan-1-ol), then General Procedure N followed by preparative HPLC to afford the title compound as the second eluting isomer of unknown absolute stereochemistry at the cyclohexane. LCMS theoretical m/z=560.31. [M+H]+. found 560.3. The absolute stereochemistry of the product of Example 163b was subsequently assigned as N-((((1S,2R)-2-(phenylethynyl)cyclohexyl)oxy)carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 164, Compound 124

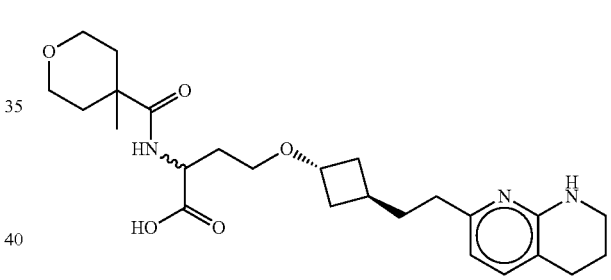

N-(4-methyltetrahydro-2H-pyran-4-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 4-methyltetrahydro-2H-pyran-4-carboxylic acid. LCMS theoretical m/z=460.28. [M+H]+. found 460.3.

Example 165, Compound 125

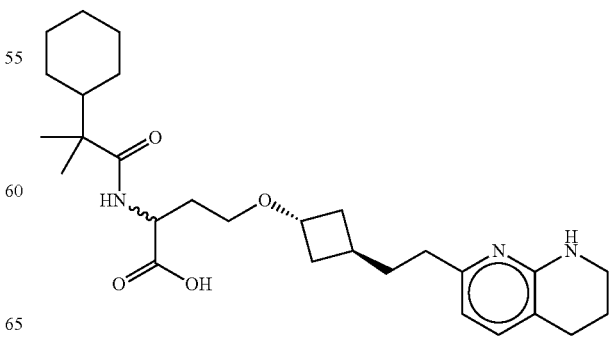

N-(2-cyclohexyl-2-methylpropanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-cyclohexyl-2-methylpropanoic acid. LCMS theoretical m/z=486.33. [M+H]+. found 486.3.

Example 166, Compound 126

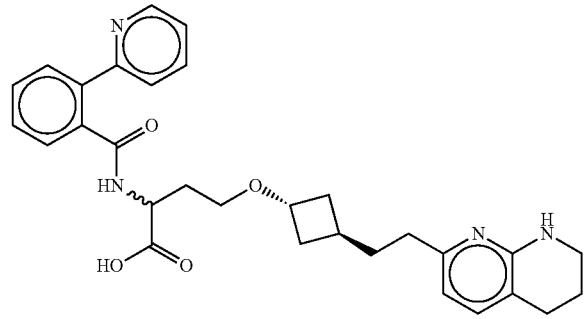

N-(2-(pyridin-2-yl)benzoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(pyridin-2-yl)benzoic acid. LCMS theoretical m/z=515.27. [M+H]+. found 515.3.

Example 167, Compound 127

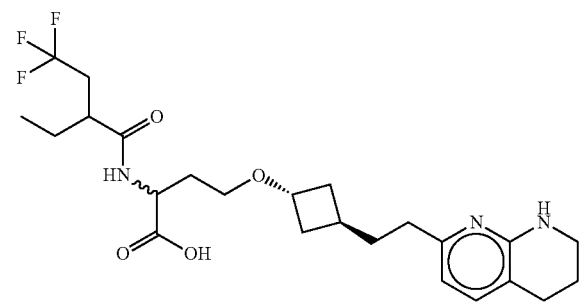

N-(2-ethyl-4,4,4-trifluorobutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-ethyl-4,4,4-trifluorobutanoic acid. LCMS theoretical m/z=486.26. [M+H]+. found 486.3.

Example 168, Compound 128

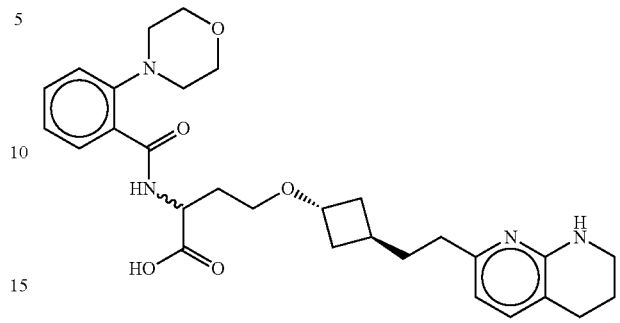

N-(2-morpholinobenzoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-morpholinobenzoic acid. LCMS theoretical m/z=523.29. [M+H]+. found 523.3.

Example 169, Compound 129

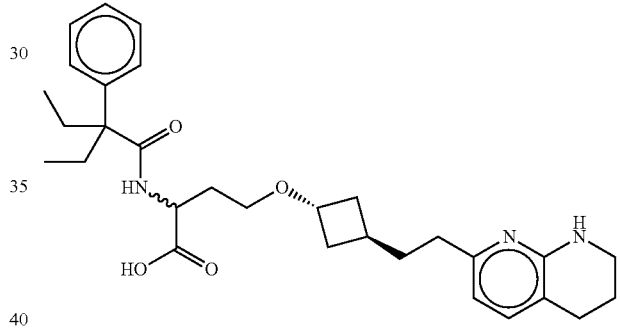

N-(2-ethyl-2-phenylbutanoyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-ethyl-2-phenylbutanoic acid. LCMS theoretical m/z=508.32. [M+H]+. found 508.3.

Example 170, Compound 130

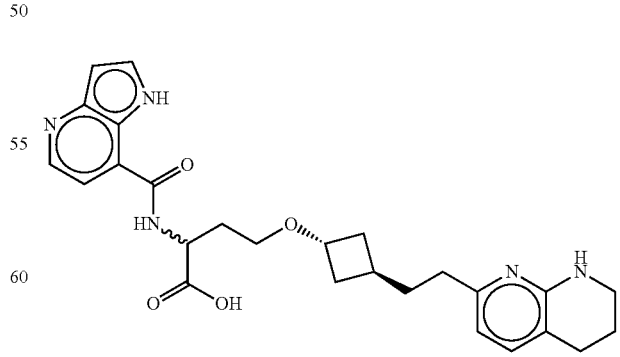

N-(1H-pyrrolo[3,2-b]pyridine-7-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1H-pyrrolo[3,2-b]pyridine-7-carboxylic acid. LCMS theoretical m/z=478.25. [M+H]+. found 478.4.

Example 171, Compound 131

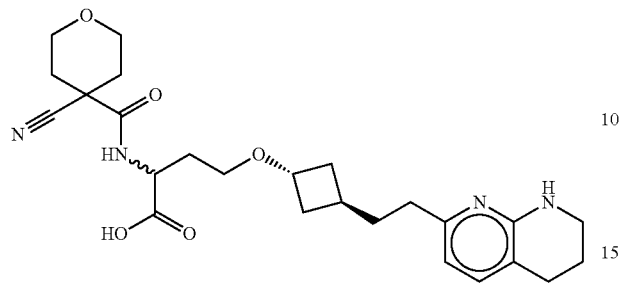

N-(4-cyanotetrahydro-2H-pyran-4-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 4-cyanotetrahydro-2H-pyran-4-carboxylic acid. LCMS theoretical m/z=471.26. [M+H]+. found 471.3.

Example 172, Compound 132

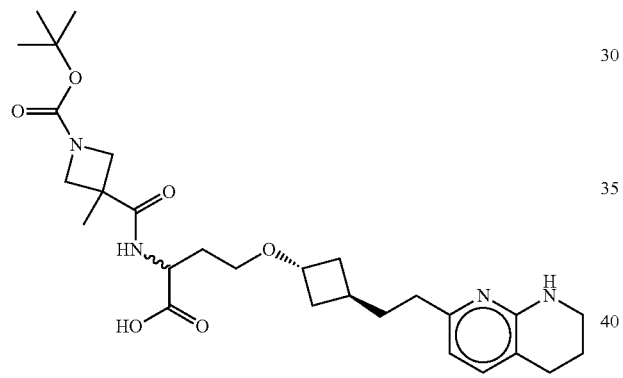

N-(1-(tert-butoxycarbonyl)-3-methylazetidine-3-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(tert-butoxycarbonyl)-3-methylazetidine-3-carboxylic acid. LCMS theoretical m/z=531.32. [M+H]+. found 531.3.

Example 173, Compound 133

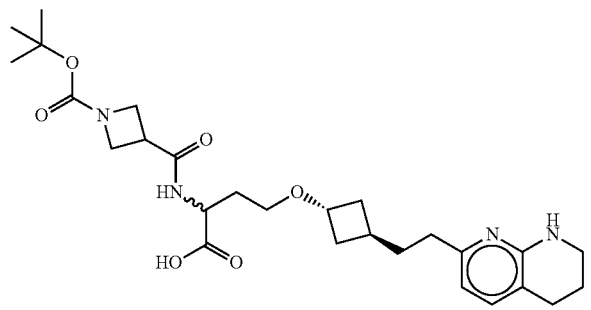

N-(1-(tert-butyxycarbonyl)azetidine-3-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(tert-butoxycarbonyl)azetidine-3-carboxylic acid. LCMS theoretical m/z=517.30. [M+H]+. found 517.3.

Example 174, Compound 134

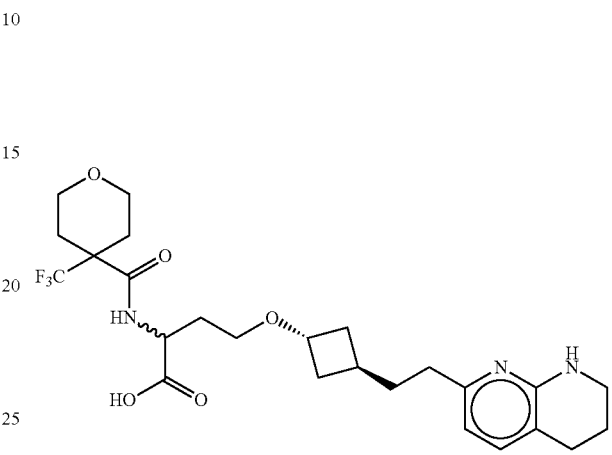

O-(trans-3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine. Isomer D2 was employed in General Scheme D-2 using General Procedure I with 4-(trifluoromethyl)tetrahydro-2H-pyran-4-carboxylic acid, then General Procedure N. LCMS theoretical m/z=514.25. [M+H]+. found 514.3.

Example 175a, Compound 135

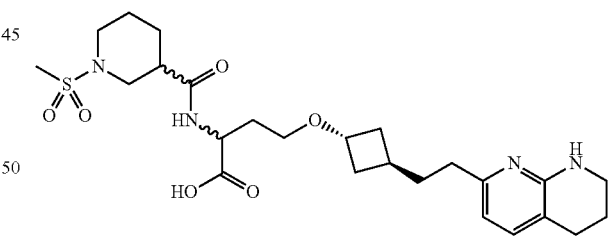

N-(1-(methylsulfonyl)piperidine-3-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(methylsulfonyl)piperidine-3-carboxylic acid, then General Procedure N followed by preparative HPLC to afford the title compound as the first eluting isomer of unknown absolute stereochemistry at the piperidine. LCMS theoretical m/z=523.26. [M+H]+. found 523.3. The absolute stereochemistry of the product of Example 175a was subsequently assigned as N—((R)-1-(methylsulfonyl)piperidine-3-carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 175b, Compound 135

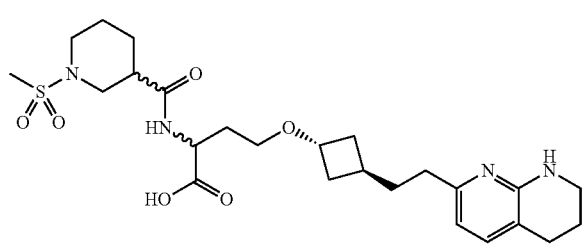 [SMILES: CS(=O)(=O)N1CCCC(C(=O)NC(CCO[C@H]2C[C@H](CCc3ccc4c(n3)NCCC4)C2)C(=O)O)C1]

N-(1-(methylsulfonyl)piperidine-3-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(methylsulfonyl)piperidine-3-carboxylic acid, then General Procedure N followed by preparative HPLC to afford the title compound as the second eluting isomer of unknown absolute stereochemistry at the piperidine. LCMS theoretical m/z=523.26. [M+H]+. found 523.3. The absolute stereochemistry of the product of Example 175b was subsequently assigned as N—((S)-1-(methylsulfonyl)piperidine-3-carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 176a, Compound 136

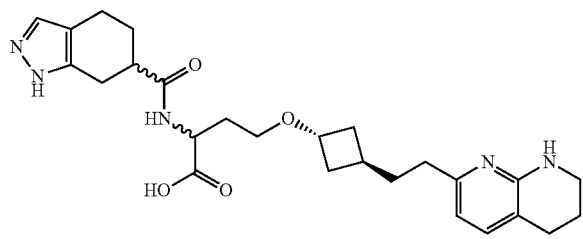 [SMILES: O=C(NC(CCO[C@H]1C[C@H](CCc2ccc3c(n2)NCCC3)C1)C(=O)O)C1CCc2cn[nH]c2C1]

O-(trans-3-(2-(5,6,7,8-tetrahydro-1,8-naphthyridin-2-yl)ethyl)cyclobutyl)-N-(4,5,6,7-tetrahydro-1H-indazole-6-carbonyl)homoserine. Isomer D2 was employed in General Scheme D-2 using General Procedure I with 4,5,6,7-tetrahydro-1H-indazole-6-carboxylic acid, then General Procedure N followed by preparative HPLC to afford the title compound as the first eluting isomer of unknown absolute stereochemistry at the cyclohexylpyrazole. LCMS theoretical m/z=482.28. [M+H]+. found 482.3. The absolute stereochemistry of the product of Example 176a was subsequently assigned as O-((1s,3S)-3-(2-(5,6,7,8-tetrahydro-1,8-naphthyridin-2-yl)ethyl)cyclobutyl)-N—((R)-4,5,6,7-tetrahydro-1H-indazole-6-carbonyl)-L-homoserine (see structure in FIG. 1, Table 2).

Example 176b, Compound 136

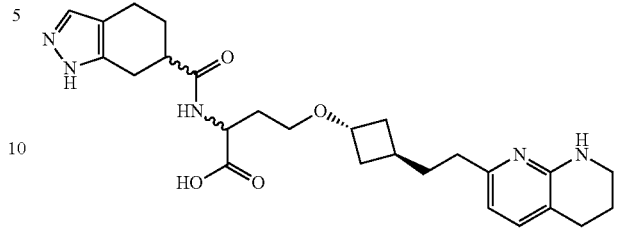

O-(trans-3-(2-(5,6,7,8-tetrahydro-1,8-naphthyridin-2-yl)ethyl)cyclobutyl)-N-(4,5,6,7-tetrahydro-1H-indazole-6-carbonyl)homoserine. Isomer D2 was employed in General Scheme D-2 using General Procedure I with 4,5,6,7-tetrahydro-1H-indazole-6-carboxylic acid, then General Procedure N followed by preparative HPLC to separate the diastereomers as the second eluting isomer of unknown absolute stereochemistry at the cyclohexylpyrazole. LCMS theoretical m/z=482.28. [M+H]+. found 482.3. The absolute stereochemistry of the product of Example 176b was subsequently assigned as O-((1s,3S)-3-(2-(5,6,7,8-tetrahydro-1,8-naphthyridin-2-yl)ethyl)cyclobutyl)-N—((S)-4,5,6,7-tetrahydro-1H-indazole-6-carbonyl)-L-homoserine (see structure in FIG. 1, Table 2).

Example 177, Compound 137

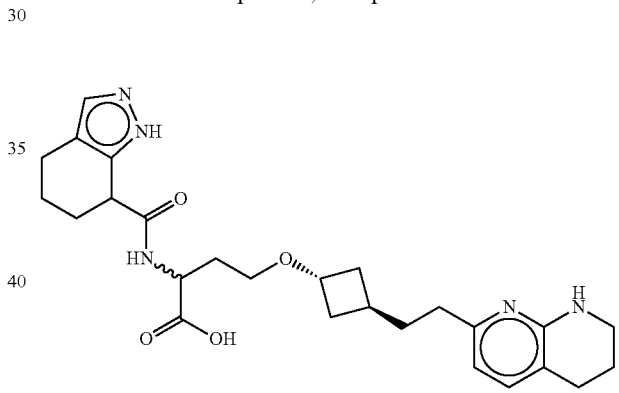

O-(trans-3-(2-(5,6,7,8-tetrahydro-1,8-naphthyridin-2-yl)ethyl)cyclobutyl)-N-(4,5,6,7-tetrahydro-1H-indazole-7-carbonyl)homoserine. Isomer D2 was employed in General Scheme D-2 using General Procedure I with 4,5,6,7-tetrahydro-1H-indazole-7-carboxylic acid. LCMS theoretical m/z=482.28. [M+H]+. found 482.3.

Example 178, Compound 124

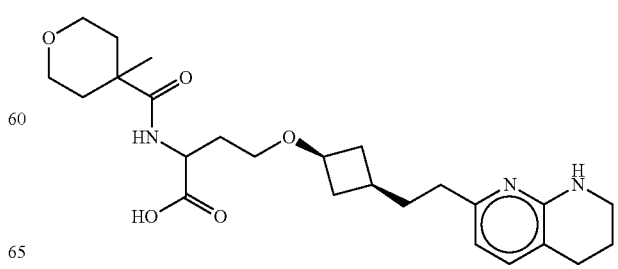

N-(4-methyltetrahydro-2H-pyran-4-carbonyl)-O-(cis-3-(2-(5,6,7,8-tetrahydro-1,8-naphthyridin-2-yl)ethyl)cyclobutyl)homoserine. Prepared according to General Scheme B using General Procedure I with 4-methyltetrahydro-2H-pyran-4-carboxylic acid. LCMS theoretical m/z=460.28. [M+H]+. found 460.3.

Example 179, Compound 124

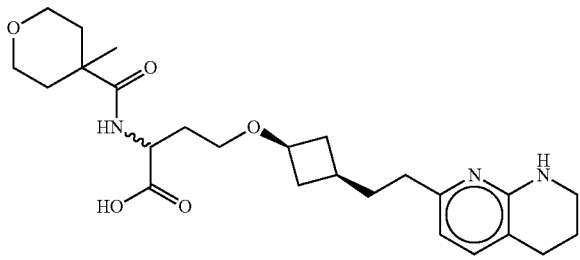

N-(4-methyltetrahydro-2H-pyran-4-carbonyl)-O-(cis-3-(2-(5,6,7,8-tetrahydro-1,8-naphthyridin-2-yl)ethyl)cyclobutyl) homoserine. Isomer E2 was employed in General Scheme E-2 using General Procedure I with 4-methyltetrahydro-2H-pyran-4-carboxylic acid. LCMS theoretical m/z=460.3 [M+H]+. found 460.3.

Example 180a, Compound 138

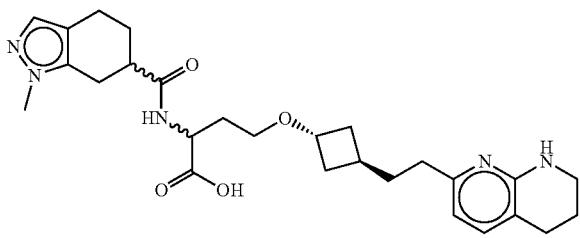

N—((R)-1-methyl-4,5,6,7-tetrahydro-1H-indazole-6-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-methyl-4,5,6,7-tetrahydro-1H-indazole-6-carboxylic acid, then General Procedure N followed by preparative HPLC to afford the first eluting of two diastereomers as a single stereoisomer. LCMS theoretical m/z=496.29. [M+H]+. found 496.3. The absolute stereochemistry of the product of Example 180a was subsequently assigned as N—((R)-1-methyl-4,5,6,7-tetrahydro-1H-indazole-6-carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 180b, Compound 138

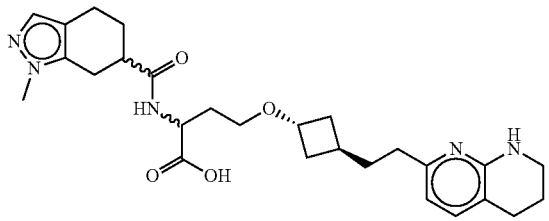

N—((S)-1-methyl-4,5,6,7-tetrahydro-1H-indazole-6-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-methyl-4,5,6,7-tetrahydro-1H-indazole-6-carboxylic acid, then General Procedure N followed by preparative HPLC to afford the second eluting of two diastereomers as a single stereoisomer. LCMS theoretical m/z=496.29. [M+H]+. found 496.3. The absolute stereochemistry of the product of Example 180b was subsequently assigned as N—((S)-1-methyl-4,5,6,7-tetrahydro-1H-indazole-6-carbonyl)-O-((1s,3S)-3-(2-(5,6,7,8-tetrahydro-1,8-naphthyridin-2-yl)ethyl)cyclobutyl)-L-homoserine (see structure in FIG. 1, Table 2).

Example 181, Compound 139

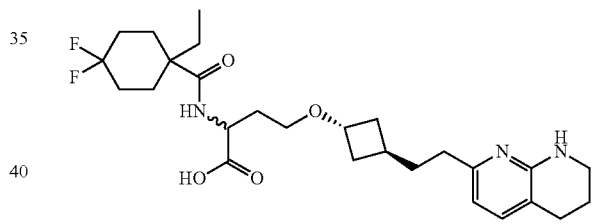

N-(1-ethyl-4,4-difluorocyclohexane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-ethyl-4,4-difluorocyclohexane-1-carboxylic acid. LCMS theoretical m/z=508.3. [M+H]+. found 508.3.

Example 182, Compound 140

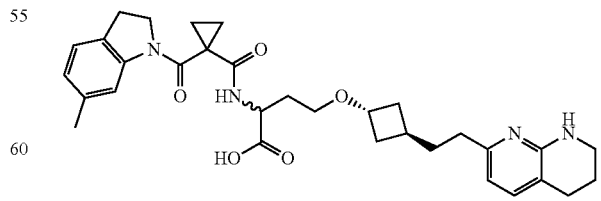

N-(1-(6-methylindoline-1-carbonyl)cyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(6-methylindoline-1-carbonyl)cyclopropane-1-carboxylic acid. LCMS theoretical m/z=561.3. [M+H]+. found 561.3.

Example 183, Compound 134

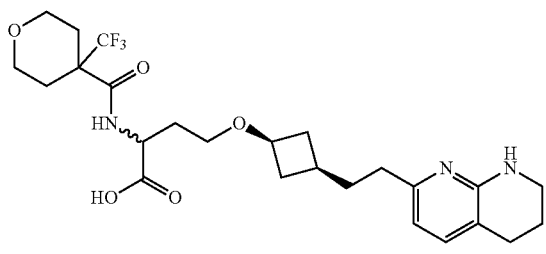 [SMILES: O=C(O)C(CCO[C@H]1C[C@@H](CCc2ccc3c(n2)NCCC3)C1)NC(=O)C1(C(F)(F)F)CCOCC1]

O-(cis-3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine. Isomer E2 was employed in General Scheme E-2 using General Procedure I with 4-trifluoromethyltetrahydro-2H-pyran-4-carboxylic acid. LCMS theoretical m/z=514.2 [M+H]+. found 514.2.

Example 184, Compound 141

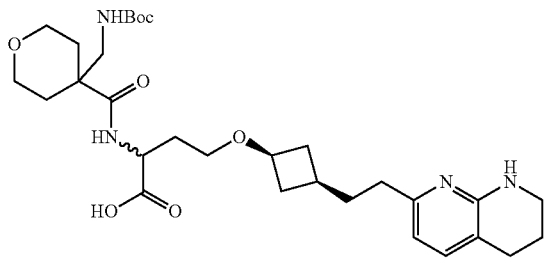 [SMILES: CC(C)(C)OC(=O)NCC1(C(=O)NC(CCO[C@H]2C[C@@H](CCc3ccc4c(n3)NCCC4)C2)C(=O)O)CCOCC1]

N-(4-(((tert-butoxycarbonyl)amino)methyl)tetrahydro-2H-pyran-4-carbonyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 4-(((tert-butoxycarbonyl)amino)methyl)tetrahydro-2H-pyran-4-carboxylic acid. LCMS theoretical m/z=575.3 [M+H]+. found 575.3.

Example 185, Compound 142

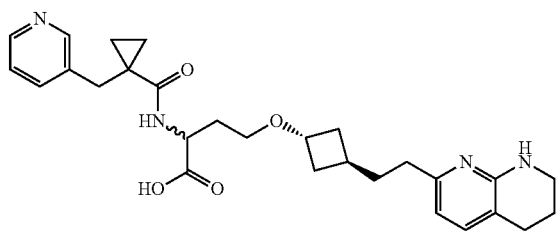 [SMILES: O=C(O)C(CCO[C@H]1C[C@H](CCc2ccc3c(n2)NCCC3)C1)NC(=O)C1(Cc2cccnc2)CC1]

N-(1-(pyridin-3-ylmethyl)cyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(pyridin-3-ylmethyl)cyclopropane-1-carboxylic acid. LCMS theoretical m/z=493.3. [M+H]+. found 493.2.

Example 186, Compound 143

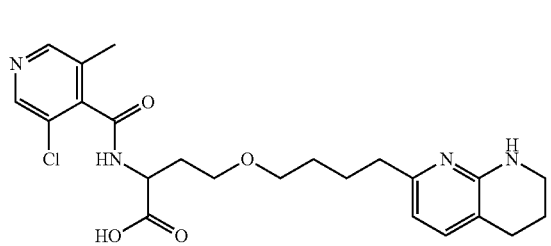 [SMILES: Cc1cncc(Cl)c1C(=O)NC(CCOCCCCc1ccc2c(n1)NCCC2)C(=O)O]

N-(3-chloro-5-methylisonicotinoyl)-O-(4-(5,6,7,8-tetrahydro-1,8-naphthyridin-2-yl)butyl)homoserine. Prepared according to General Scheme C using General Procedure I with 3-chloro-5-methylisonicotinic acid. LCMS theoretical m/z=461.2 [M+H]+. found 461.2.

Example 187, Compound 144

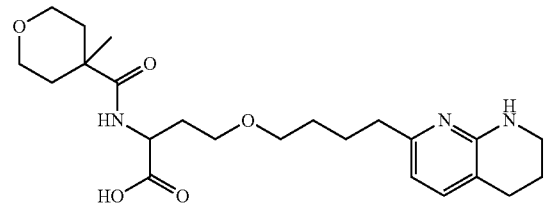 [SMILES: CC1(C(=O)NC(CCOCCCCc2ccc3c(n2)NCCC3)C(=O)O)CCOCC1]

N-(4-methyltetrahydro-2H-pyran-4-carbonyl)-O-(4-(5,6,7,8-tetrahydro-1,8-naphthyridin-2-yl)butyl)homoserine. Prepared according to General Scheme C using General Procedure I with 4-methyltetrahydro-2H-pyran-4-carboxylic acid. LCMS theoretical m/z=434.3 [M+H]+. found 434.3.

Example 188, Compound 145

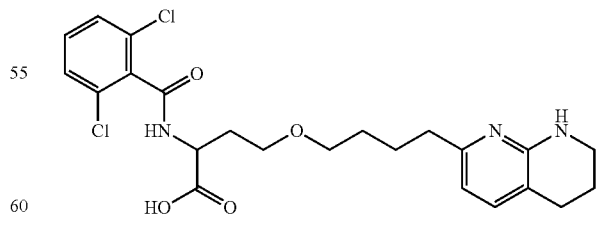

N-(2,6-dichlorobenzoyl)-O-(4-(5,6,7,8-tetrahydro-1,8-naphthyridin-2-yl)butyl)homoserine. Prepared according to General Scheme C using General Procedure I with 2,6-dichlorobenzoic acid. LCMS theoretical m/z=480.1 [M+H]+. found 480.2.

Example 189, Compound 146

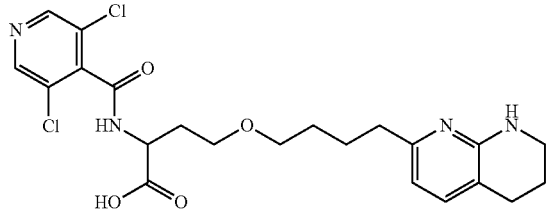 [SMILES: O=C(NC(CCOCCCCc1ccc2c(n1)NCCC2)C(=O)O)c1c(Cl)cncc1Cl]

N-(3,5-dichloroisonicotinoyl)-O-(4-(5,6,7,8-tetrahydro-1,8-naphthyridin-2-yl)butyl)homoserine. Prepared according to General Scheme C using General Procedure I with 3,5-dichloroisonicotinic acid. LCMS theoretical m/z=481.1 [M+H]+. found 481.2.

Example 190, Compound 147

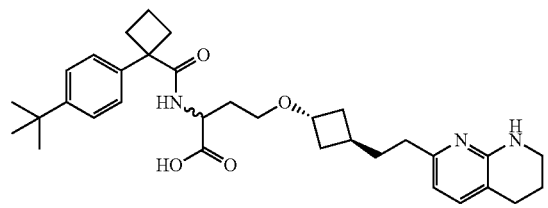 [SMILES: CC(C)(C)c1ccc(C2(C(=O)NC(CCO[C@H]3C[C@H](CCc4ccc5c(n4)NCCC5)C3)C(=O)O)CCC2)cc1]

N-(1-(4-(tert-butyl)phenyl)cyclobutane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(4-(tert-butyl)phenyl)cyclobutane-1-carboxylic acid. LCMS theoretical m/z=548.3. [M+H]+. found 548.3.

Example 191, Compound 124

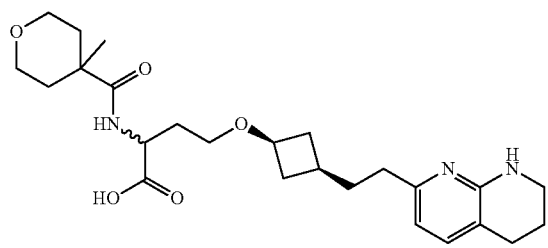 [SMILES: CC1(C(=O)NC(CCO[C@H]2C[C@@H](CCc3ccc4c(n3)NCCC4)C2)C(=O)O)CCOCC1]

N-(4-methyltetrahydro-2H-pyran-4-carbonyl)-O-(cis-3-(2-(5,6,7,8-tetrahydro-1,8-naphthyridin-2-yl)ethyl)cyclobutyl)homoserine. Isomer E1 was employed in General Scheme E-2 using General Procedure I with 4-methyltetrahydro-2H-pyran-4-carboxylic acid. LCMS theoretical m/z=460.3. [M+H]+. found 460.3.

Example 192, Compound 134

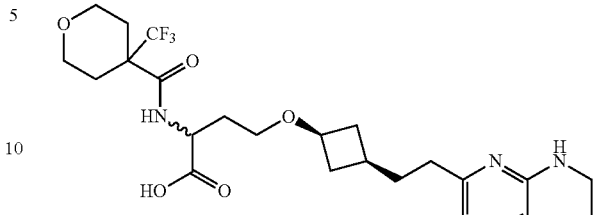

O-(cis-3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine. Isomer E1 was employed in General Scheme E-2 using General Procedure I with 4-(trifluoromethyl)tetrahydro-2H-pyran-4-carboxylic acid. LCMS theoretical m/z=514.3. [M+H]+. found 514.3.

Example 193, Compound 148

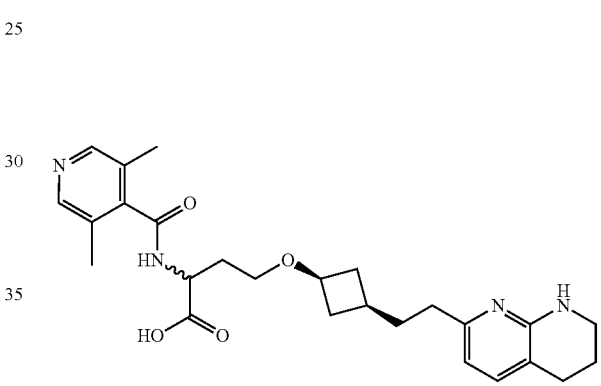

N-(3,5-dimethylisonicotinoyl)-O-(cis-3-(2-(5,6,7,8-tetrahydro-1,8-naphthyridin-2-yl)ethyl)cyclobutyl)homoserine. Isomer E1 was employed in General Scheme E-2 using General Procedure I with 3,5-dimethylisonicotinic acid. LCMS theoretical m/z=467.3. [M+H]+. found 467.3.

Example 194, Compound 149

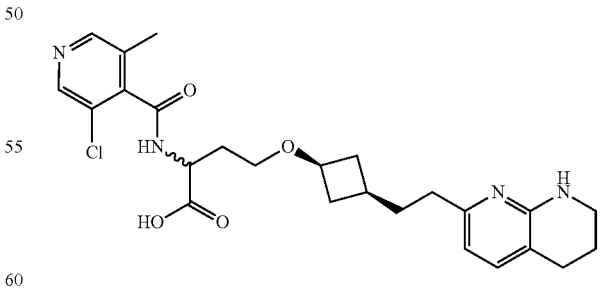

N-(3-chloro-5-methylisonicodnoyl)-O-(cis-3-(2-(5,6,7,8-tetrahydro-1,8-naphthyridin-2-yl)ethyl)cyclobutyl)homoserine. Isomer E1 was employed in General Scheme E-2 using General Procedure I with 3-chloro-5-methylisonicotinic acid. LCMS theoretical m/z=487.2 [M+H]+. found 487.2.

Example 195, Compound 150

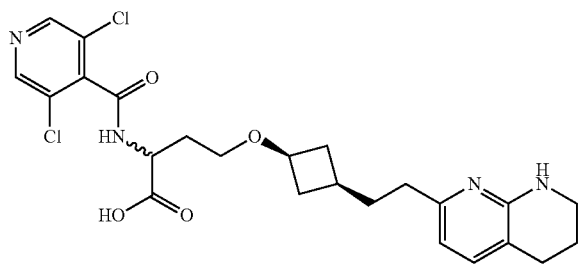 [SMILES: O=C(NC(CCO[C@H]1C[C@@H](CCc2ccc3c(n2)NCCC3)C1)C(=O)O)c1c(Cl)cncc1Cl]

N-(3,5-dichloroisonicotinoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 3,5-dichloroisonicotinic acid. LCMS theoretical m/z=507.1 [M+H]+. found 507.1.

Example 196, Compound 151

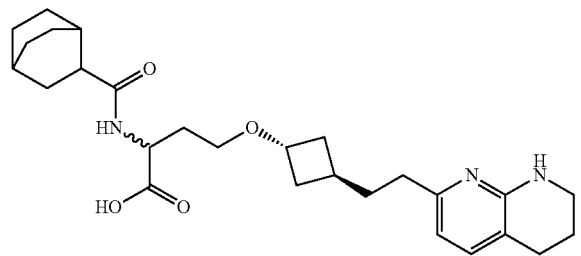 [SMILES: O=C(O)C(CCO[C@H]1C[C@H](CCc2ccc3c(n2)NCCC3)C1)NC(=O)C1CC2CCC1CC2]

N-(bicyclo[2.2.2]octane-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with bicyclo[2.2.2]octane-2-carboxylic acid. LCMS theoretical m/z=470.3. [M+H]+. found 470.3.

Example 197, Compound 152

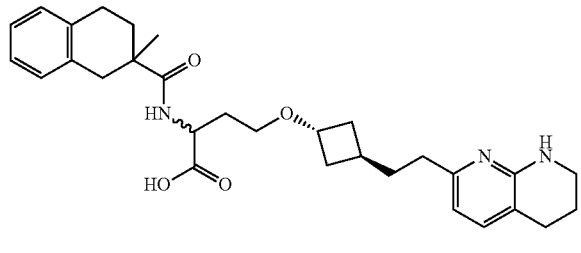 [SMILES: CC1(C(=O)NC(CCO[C@H]2C[C@H](CCc3ccc4c(n3)NCCC4)C2)C(=O)O)CCc2ccccc2C1]

N-(2-methyl-1,2,3,4-tetrahydronaphthalene-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-methyl-1,2,3,4-tetrahydronaphthalene-2-carboxylic acid. LCMS theoretical m/z=430.27. [M+H]+. found 430.3.

Example 198, Compound 153

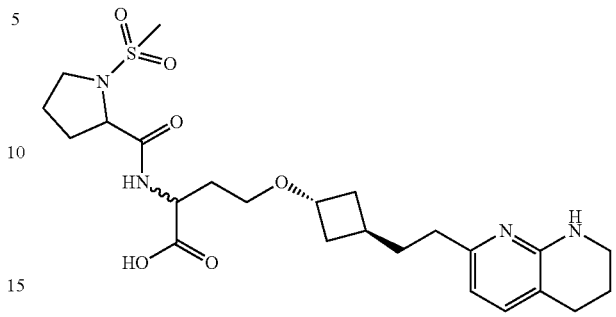

N-((methylsulfonyl)prolyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with (methylsulfonyl)proline. LCMS theoretical m/z=509.2. [M+H]+. found 509.3.

Example 199, Compound 149

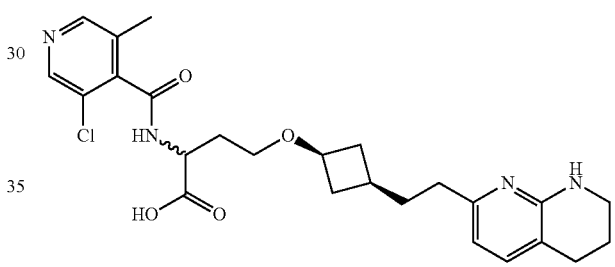

N-(3-chloro-5-methylisonicotinoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 3-chloro-5-methylisonicotinic acid. LCMS theoretical m/z=487.2 [M+H]+. found 487.2.

Example 200, Compound 154

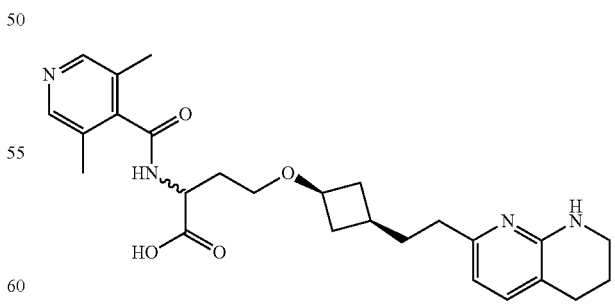

N-(2,4-dimethylnicotinoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 2,4-dimethylnicotinic acid. LCMS theoretical m/z=467.3 [M+H]+. found 467.3.

Example 201, Compound 155

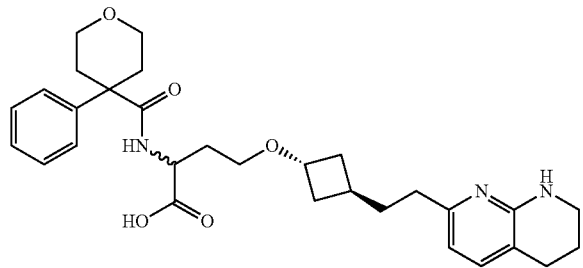 [SMILES: O=C(O)C(CCO[C@H]1C[C@H](CCc2ccc3c(n2)NCCC3)C1)NC(=O)C1(c2ccccc2)CCOCC1]

N-(4-phenyltetrahydro-2H-pyran-4-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 4-phenyltetrahydro-2H-pyran-4-carboxylic acid. LCMS theoretical m/z=522.3. [M+H]+. found 522.2.

Example 202, Compound 156

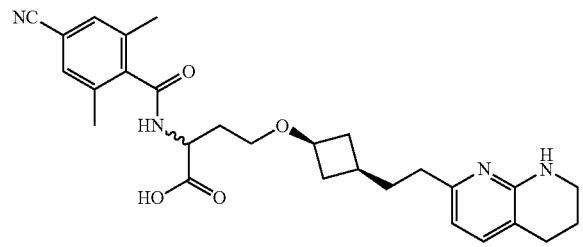 [SMILES: Cc1cc(C#N)cc(C)c1C(=O)NC(CCO[C@H]1C[C@@H](CCc2ccc3c(n2)NCCC3)C1)C(=O)O]

N-(4-cyano-2,6-dimethylbenzoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 4-cyano-2,6-dimethylbenzoic acid. LCMS theoretical m/z=491.3 [M+H]+. found 491.3.

Example 203, Compound 157

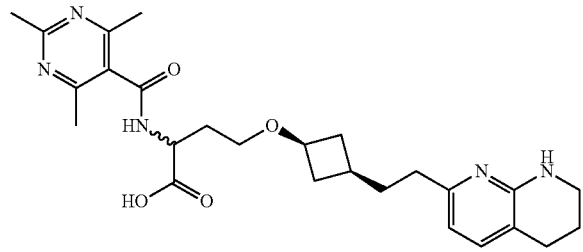 [SMILES: Cc1nc(C)c(C(=O)NC(CCO[C@H]2C[C@@H](CCc3ccc4c(n3)NCCC4)C2)C(=O)O)c(C)n1]

O-(cis-3-(2-(5,6,7,8-tetrahydro-1,8-naphthyridin-2-yl)ethyl)cyclobutyl)-N-(2,4,6-trimethylpyrimidine-5-carbonyl)homoserine. Isomer E2 was employed in General Scheme E-2 using General Procedure I with 2,4,6-trimethylpyrimidine-5-carboxylic acid. LCMS theoretical m/z=482.3 [M+H]+. found 482.2.

Example 204, Compound 158

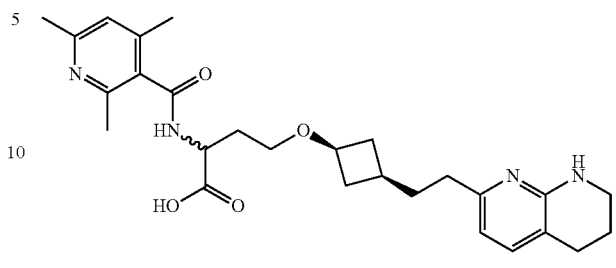

O-(cis-3-(2-(5,6,7,8-tetrahydro-1,8-naphthyridin-2-yl)ethyl)cyclobutyl)-N-(2,4,6-trimethylnicotinoyl)homoserine. Isomer E2 was employed in General Scheme E-2 using General Procedure I with 2,4,6-trimethylnicotinic acid. LCMS theoretical m/z=481.3 [M+H]+. found 481.2.

Example 205, Compound 159

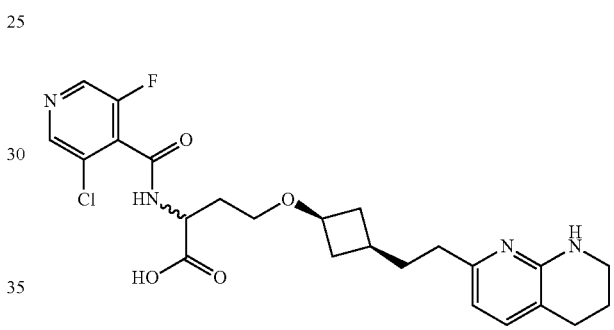

N-(3-chloro-5-fluoroisonicotinoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 3-chloro-5-fluoroisonicotinic acid. LCMS theoretical m/z=491.2 [M+H]+. found 491.1.

Example 206, Compound 160

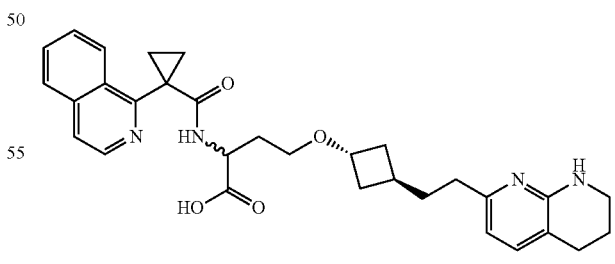

N-(1-(isoquinolin-1-yl)cyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(isoquinolin-1-yl)cyclopropane-1-carboxylic acid. LCMS theoretical m/z=529.3. [M+H]+. found 529.3.

Example 207, Compound 161

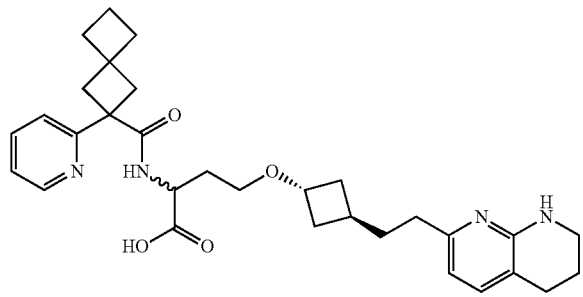 [SMILES: O=C(O)C(CCO[C@H]1C[C@H](CCc2ccc3c(n2)NCCC3)C1)NC(=O)C1(c2ccccn2)CC2(CCC2)C1]

N-(2-(pyridin-2-yl)spiro[3.3]heptane-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(pyridin-2-yl)spiro[3.3]heptane-2-carboxylic acid. LCMS theoretical m/z=533.3. [M+H]+. found 533.3.

Example 208, Compound 162

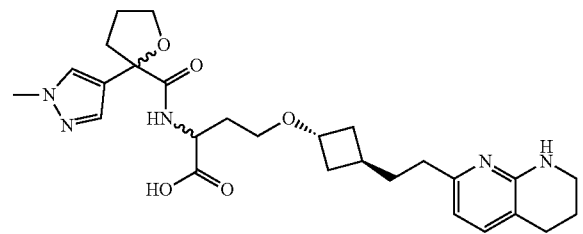 [SMILES: Cn1cc(C2(C(=O)NC(CCO[C@H]3C[C@H](CCc4ccc5c(n4)NCCC5)C3)C(=O)O)CCCO2)cn1]

N-(2-(1-methyl-1H-pyrazol-4-yl)tetrahydrofuran-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(1-methyl-1H-pyrazol-4-yl)tetrahydrofuran-2-carboxylic acid, then General Procedure N followed by preparative HPLC to afford the title compound as the first eluting isomer. LCMS theoretical m/z=512.3. [M+H]+. found 512.3.

Example 209, Compound 162

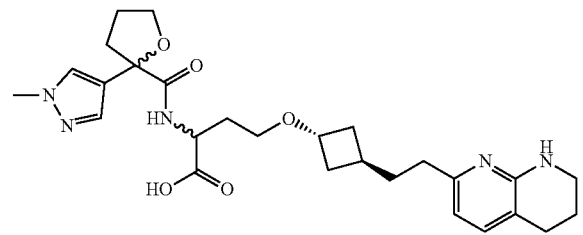 [SMILES: Cn1cc(C2(C(=O)NC(CCO[C@H]3C[C@H](CCc4ccc5c(n4)NCCC5)C3)C(=O)O)CCCO2)cn1]

N-(2-(1-methyl-1H-pyrazol-4-yl)tetrahydrofuran-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2-(1-methyl-1H-pyrazol-4-yl)tetrahydrofuran-2-carboxylic acid, then General Procedure N followed by preparative HPLC to afford the title compound as the second eluting isomer. LCMS theoretical m/z=512.3. [M+H]+. found 512.3.

Example 210, Compound 163

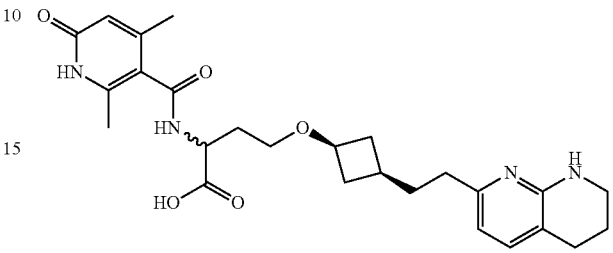

N-(2,4-dimethyl-6-oxo-1,6-dihydropyridine-3-carbonyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 2,4-dimethyl-6-oxo-1,6-dihydropyridine-3-carboxylic acid. LCMS theoretical m/z=491.2 [M+H]+. found 491.1.

Example 211, Compound 164

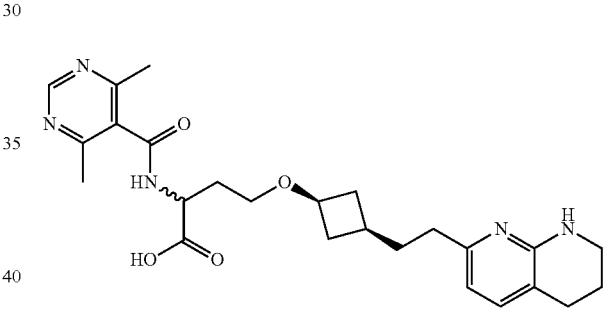

N-(4,6-dimethylpyrimidine-5-carbonyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 4,6-dimethylpyrimidine-5-carboxylic acid. LCMS theoretical m/z=468.3 [M+H]+. found 468.2.

Example 212, Compound 165

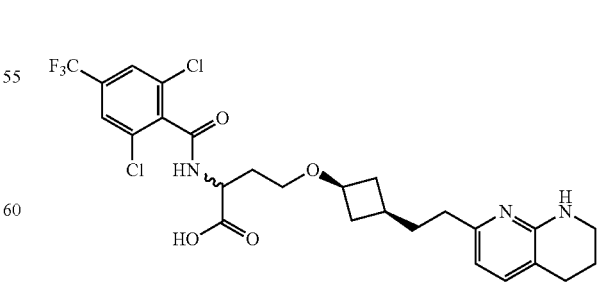

N-(2,6-dichloro-4-(trifluoromethyl)benzoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 2,6-dichloro-4-(trifluoromethyl)benzoic acid. LCMS theoretical m/z=574.1 [M+H]+. found 574.1.

Example 213, Compound 166

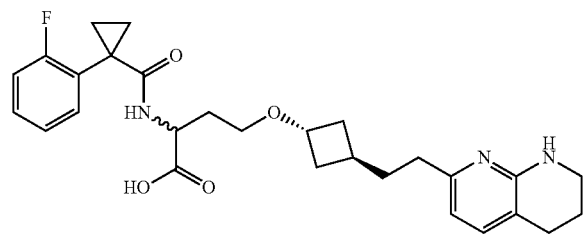 [SMILES: O=C(O)C(CCO[C@H]1C[C@H](CCc2ccc3c(n2)NCCC3)C1)NC(=O)C1(c2ccccc2F)CC1]

N-(1-(2-fluorophenyl)cyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(2-fluorophenyl)cyclopropane-1-carboxylic acid. LCMS theoretical m/z=512.3. [M+H]+. found 512.3.

Example 214, Compound 167

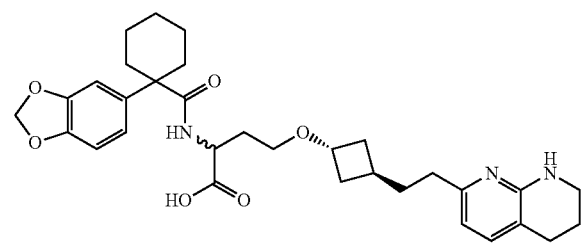 [SMILES: O=C(O)C(CCO[C@H]1C[C@H](CCc2ccc3c(n2)NCCC3)C1)NC(=O)C1(c2ccc3c(c2)OCO3)CCCCC1]

N-(1-(benzo[d][1,3]dioxol-5-yl)cyclohexane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(benzo[d][1,3]dioxol-5-yl)cyclopropane-1-carboxylic acid. LCMS theoretical m/z=564.3. [M+H]+. found 564.3.

Example 215, Compound 168

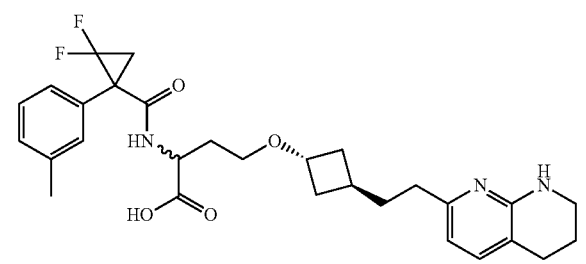 [SMILES: Cc1cccc(C2(C(=O)NC(CCO[C@H]3C[C@H](CCc4ccc5c(n4)NCCC5)C3)C(=O)O)CC2(F)F)c1]

N-(2,2-difluoro-1-(m-tolyl)cyclopropane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,2-difluoro-1-(m-tolyl)cyclopropane-1-carboxylic acid. LCMS theoretical m/z=528.3. [M+H]+. found 528.3.

Example 216, Compound 169

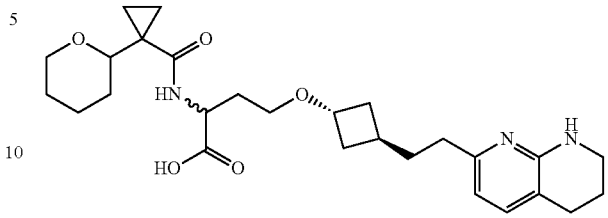

O-(trans-3-(2-(5,6,7,8-tetrahydro-1,8-naphthyridin-2-yl)ethyl)cyclobutyl)-N-(1-(tetrahydro-2H-pyran-2-yl)cyclopropane-1-carbonyl)homoserine. Isomer D2 was employed in General Scheme D-2 using General Procedure I with 1-(tetrahydro-2H-pyran-2-yl)cyclopropane-1-carboxylic acid. LCMS theoretical m/z=486.3. [M+H]+. found 486.3.

Example 217, Compound 170

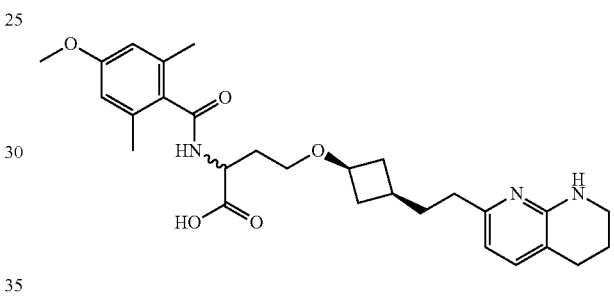

N-(4-methoxy-2,6-dimethylbenzoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 4-methoxy-2,6-dimethylbenzoic acid. LCMS theoretical m/z=496.3 [M+H]+. found 496.2.

Example 218. Compound 171

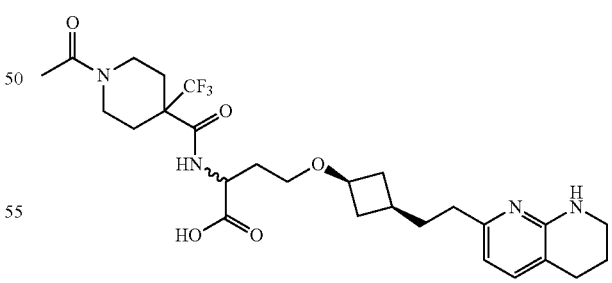

N-(1-acetyl-4-(trifluoromethyl)piperidine-4-carbonyl)-O-(cis-3-(2-(5,6,7,8-tetrahydro-1,8-naphthyridin-2-yl)ethyl)cyclobutyl)homoserine. Isomer E2 was sequentially used in General Procedure D, General Procedure I with 1-(tert-butoxycarbonyl)-4-(trifluoromethyl)piperidine-4-carboxylic acid, General Procedure D, General Procedure L, and General Procedure N. LCMS theoretical m/z=496.3 [M+H]+. found 496.2.

Example 219, Compound 172

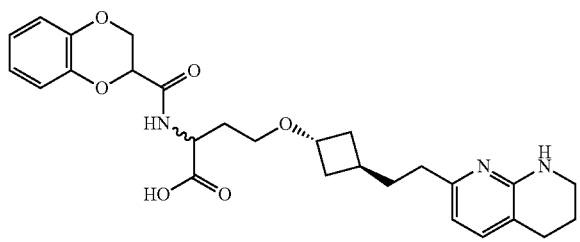 [SMILES: O=C(O)C(CCO[C@H]1C[C@H](CCc2ccc3c(n2)NCCC3)C1)NC(=O)C1COc2ccccc2O1]

N-(2,3-dihydrobenzo[b][1,4]dioxine-2-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 2,3-dihydrobenzo[b][1,4]dioxine-2-carboxylic acid. LCMS theoretical m/z=496.2. [M+H]+. found 496.2.

Example 220, Compound 173

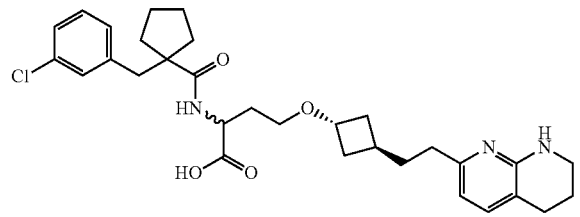 [SMILES: O=C(O)C(CCO[C@H]1C[C@H](CCc2ccc3c(n2)NCCC3)C1)NC(=O)C1(Cc2cccc(Cl)c2)CCCC1]

N-(1-(3-chlorobenzyl)cyclopentane-1-carbonyl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure I with 1-(3-chlorobenzyl)cyclopentane-1-carboxylic acid. LCMS theoretical m/z=554.3. [M+H]+. found 554.3.

Example 221, Compound 174

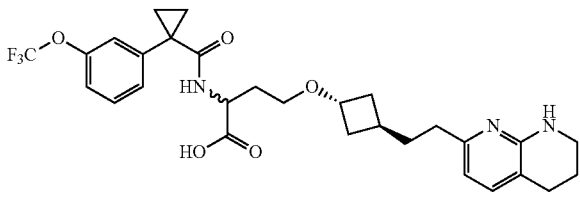 [SMILES: O=C(O)C(CCO[C@H]1C[C@H](CCc2ccc3c(n2)NCCC3)C1)NC(=O)C1(c2cccc(OC(F)(F)F)c2)CC1]

O-(trans-3-(2-(5,6,7,8-tetrahydro-1,8-naphthyridin-2-yl)ethyl)cyclobutyl)-N-(1-(3-(trifluoromethoxy)phenyl)cyclopropane-1-carbonyl)homoserine. Isomer D2 was employed in General Scheme D-2 using General Procedure I with 1-(3-(trifluoromethoxy)phenyl) cyclopropane-1-carboxylic acid. LCMS theoretical m/z=562.2. [M+H]+. found 562.2.

Example 222, Compound 175

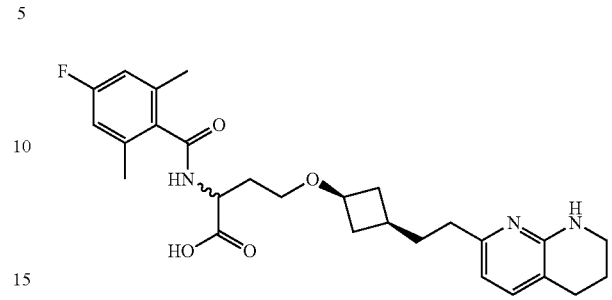

N-(4-fluoro-2,6-dimethylbenzoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 4-fluoro-2,6-dimethylbenzoic acid. LCMS theoretical m/z=484.3 [M+H]+. found 484.2.

Example 223, Compound 148

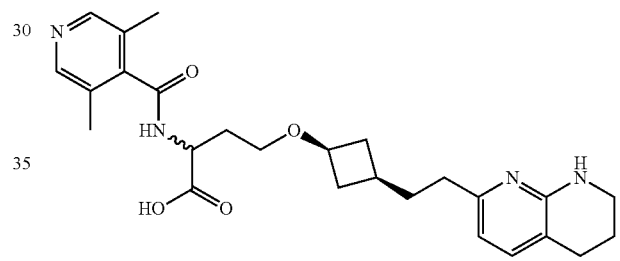

N-(3,5-dimethylisonicotinoyl)-O-(cis-3-(2-(5,6,7,8-tetrahydro-1,8-naphthyridin-2-yl)ethyl)cyclobutyl)homoserine. Isomer E2 was employed in General Scheme E-2 using General Procedure I with 3,5-dimethylisonicotinic acid. LCMS theoretical m/z=467.3 [M+H]+. found 467.2.

Example 224, Compound 178

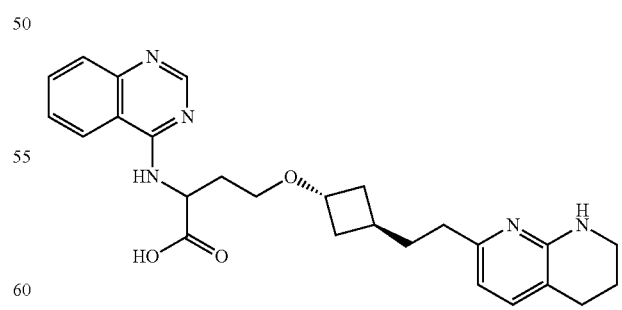

N-(quinazolin-4-yl)-O-(trans-3-(2-(5,6,7,8-tetrahydro-1,8-naphthyridin-2-yl)ethyl)cyclobutyl)homoserine. Prepared according to General Scheme A using General Procedure E with 4-chloroquinazoline. LCMS theoretical m/z=462.3. [M+H]+. found 462.3.

Example 225, Compound 187

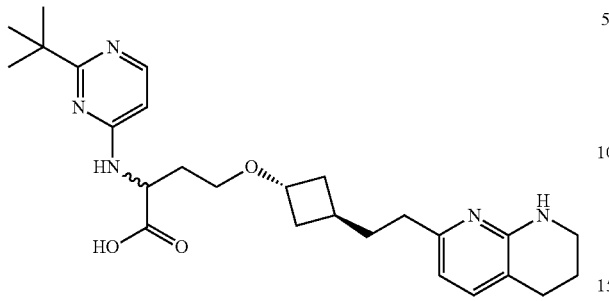

N-(2-(tert-butyl)pyrimidin-4-yl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure E with 2-tert-butyl-4-chloro-pyrimidine. LCMS theoretical m/z=468.3 [M+H]+. found 468.3.

Example 226, Compound 188

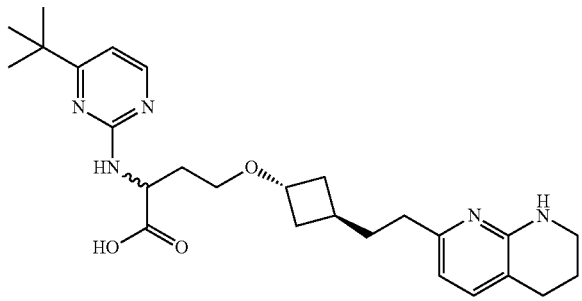 [SMILES: CC(C)(C)c1ccnc(NC(CCO[C@H]2C[C@H](CCc3ccc4c(n3)NCCC4)C2)C(=O)O)n1]

N-(4-(tert-butyl)pyrimidin-2-yl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure E with 4-(tert-butyl)-2-chloropyrimidine. LCMS theoretical m/z=468.3 [M+H]+. found 468.3.

Example 227, Compound 178

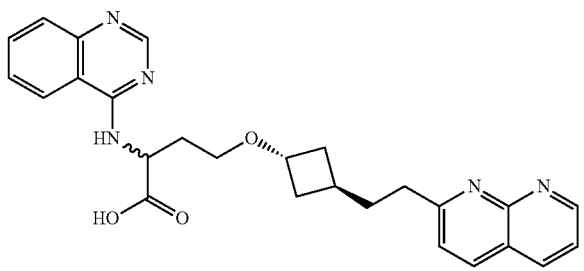 [SMILES: O=C(O)C(CCO[C@H]1C[C@H](CCc2ccc3cccnc3n2)C1)Nc1ncnc2ccccc12]

O-(trans-3-(2-(1,8-naphthyridin-2-yl)ethyl)cyclobutyl)-N-(quinazolin-4-yl)homoserine. Isomer D1 was employed in General Scheme D-2 following General Procedure E with 4-chloroquinazoline. LCMS theoretical m/z=462.3 [M+H]+. found 462.3.

Example 228, Compound 178

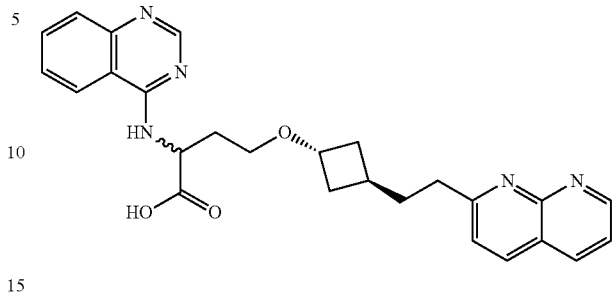

O-(trans-3-(2-(1,8-naphthyridin-2-yl)ethyl)cyclobutyl)-N-(quinazolin-4-yl)homoserine. Isomer D2 was employed in General Scheme D-2 following General Procedure E with 4-chloroquinazoline. LCMS theoretical m/z=462.3 [M+H]+. found 462.3.

Example 229, Compound 186

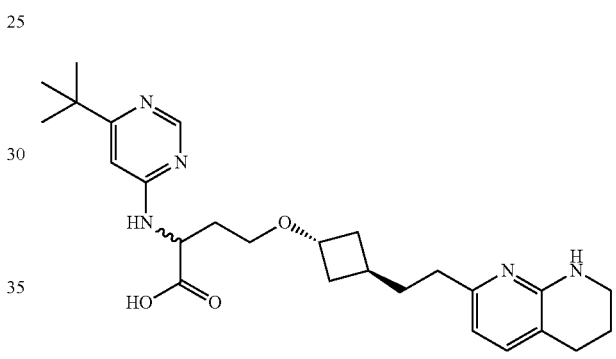

N-(6-(tert-butyl)pyrimidin-4-yl)-O-(trans-3-(2-(5,6,7,8-tetrahydro-1,8-naphthyridin-2-yl)ethyl)cyclobutyl)homoserine. Isomer D2 was employed in General Scheme D-2 using General Procedure E with 4-(tert-butyl)-6-chloropyrimidine. LCMS theoretical m/z=468.3 [M+H]+. found 468.3.

Example 230, Compound 210

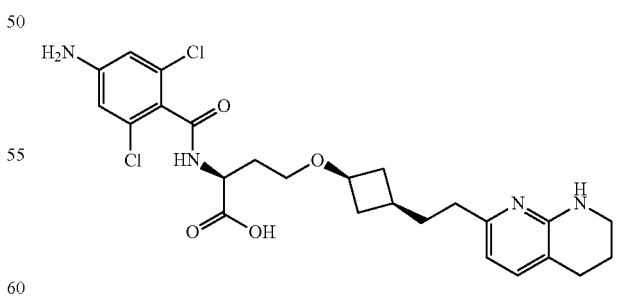

N-(4-amino-2,6-dichlorobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 4-amino-2,6-dichlorobenzoic acid. LCMS theoretical m/z=520.2. [M+H]+. found 521.1.

Example 231, Compound 211

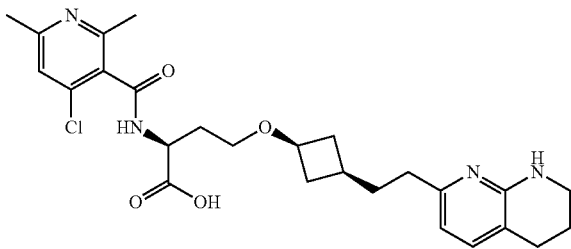 [SMILES: Cc1cc(Cl)c(C(=O)N[C@@H](CCO[C@H]2C[C@@H](CCc3ccc4c(n3)NCCC4)C2)C(=O)O)c(C)n1]

N-(4-chloro-2,6-dimethylnicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 4-chloro-2,6-dimethylnicotinic acid. LCMS theoretical m/z=500.2. [M+H]+. found 501.2.

Example 232. Compound 212

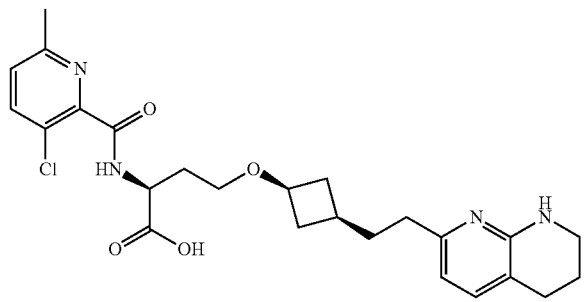 [SMILES: Cc1ccc(Cl)c(C(=O)N[C@@H](CCO[C@H]2C[C@@H](CCc3ccc4c(n3)NCCC4)C2)C(=O)O)n1]

N-(3-chloro-6-methylpicolinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-6-methylpicolinic acid. LCMS theoretical m/z=486.2. [M+H]+. found 487.2.

Example 233, Compound 213

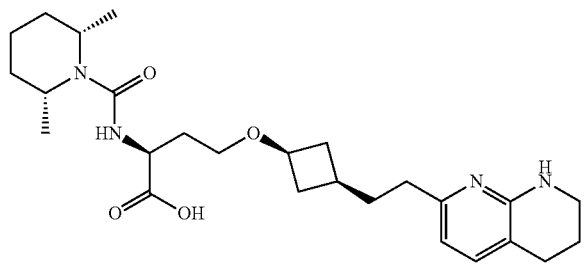 [SMILES: C[C@@H]1CCC[C@H](C)N1C(=O)N[C@@H](CCO[C@H]1C[C@@H](CCc2ccc3c(n2)NCCC3)C1)C(=O)O]

N-((2R,6S)-2,6-dimethylpiperidine-1-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure G with (2R,6S)-2,6-dimethylpiperidine. LCMS theoretical m/z=472.3. [M+H]+. found 473.3.

Example 234, Compound 214

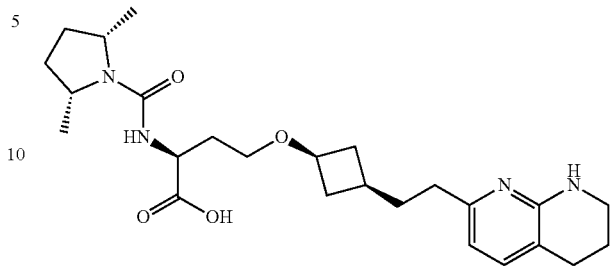

N-((2R,5S)-2,5-dimethylpyrrolidine-1-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure G with (2R,5S)-2,5-dimethylpyrrolidine. LCMS theoretical m/z=458.3. [M+H]+. found 459.3.

Example 235, Compound 215

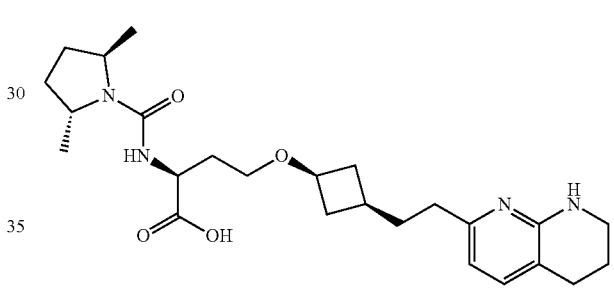

N-((2R,5R)-2,5-dimethylpyrrolidine-1-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure G with (2R,5R)-2,5-dimethylpyrrolidine. LCMS theoretical m/z=458.3. [M+H]+. found 459.3.

Example 236, Compound 216

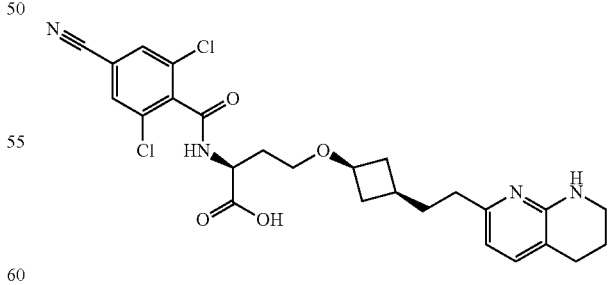

N-(2,6-dichloro-4-cyanobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-dichloro-4-cyanobenzoic acid. LCMS theoretical m/z=530.1. [M+H]+. found 531.1.

Example 237, Compound 217

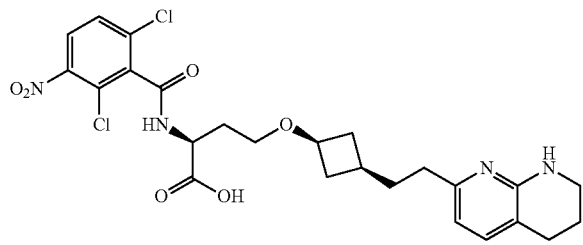 [SMILES: O=C(N[C@@H](CCO[C@H]1C[C@@H](CCc2ccc3c(n2)NCCC3)C1)C(=O)O)c1c(Cl)ccc([N+](=O)[O-])c1Cl]

N-(2,6-dichloro-3-nitrobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-dichloro-3-nitrobenzoic acid. LCMS theoretical m/z=550.2. [M+H]+. found 551.2.

Example 238, Compound 218

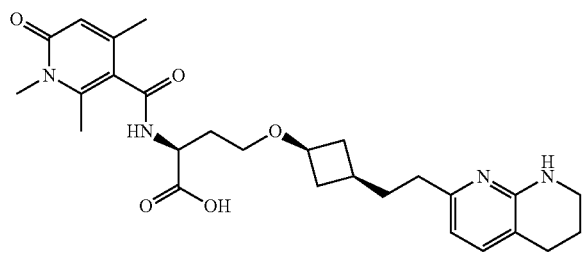 [SMILES: Cc1cc(=O)n(C)c(C)c1C(=O)N[C@@H](CCO[C@H]1C[C@@H](CCc2ccc3c(n2)NCCC3)C1)C(=O)O]

O-((1r,3R)-3-(2-(5,6,7,8-tetrahydro-1,8-naphthyridin-2-yl)ethyl)cyclobutyl)-N-(1,2,4-trimethyl-6-oxo-1,6-dihydropyridine-3-carbonyl)-L-homoserine. Isomer E2 was employed in General Scheme E-2 using General Procedure I with 1,2,4-trimethyl-6-oxo-1,6-dihydropyridine-3-carboxylic acid. LCMS theoretical m/z=496.3. [M+H]+. found 497.3.

Example 239, Compound 219

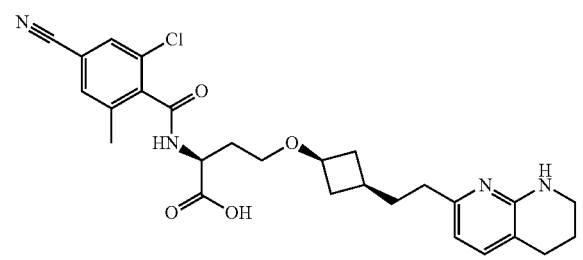 [SMILES: Cc1cc(C#N)cc(Cl)c1C(=O)N[C@@H](CCO[C@H]1C[C@@H](CCc2ccc3c(n2)NCCC3)C1)C(=O)O]

N-(2-chloro-4-cyano-6-methylbenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-chloro-4-cyano-6-methylbenzoic acid. LCMS theoretical m/z=510.2. [M+H]+. found 511.2.

Example 240, Compound 220

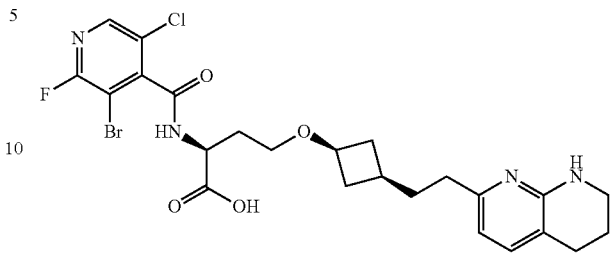

N-(3-bromo-5-chloro-2-fluoroisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-bromo-5-chloro-2-fluoroisonicotinic acid. LCMS theoretical m/z=568.1. [M+H]+. found 569.1.

Example 241, Compound 221

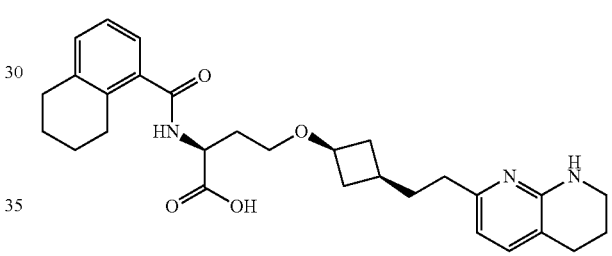

O-((1r,3R)-3-(2-(5,6,7,8-tetrahydro-1,8-naphthyridin-2-yl)ethyl)cyclobutyl)-N-(5,6,7,8-tetrahydronaphthalene-1-carbonyl)-L-homoserine. Isomer E2 was employed in General Scheme E-2 using General Procedure I with 5,6,7,8-tetrahydronaphthalene-1-carboxylic acid. LCMS theoretical m/z=491.3. [M+H]+. found 492.3.

Example 242, Compound 222

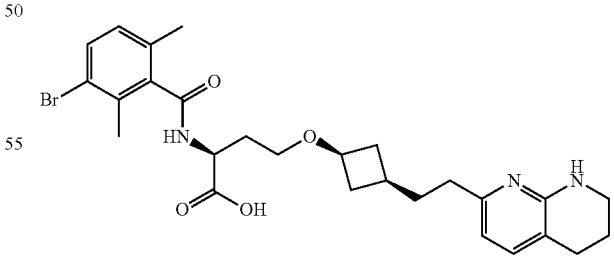

N-(3-bromo-2,6-dimethylbenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-bromo-2,6-dimethylbenzoic acid. LCMS theoretical m/z=543.2. [M+H]+. found 544.2.

Example 243, Compound 223

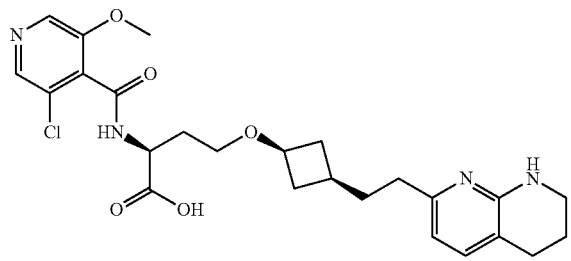 [SMILES: COc1cncc(Cl)c1C(=O)N[C@@H](CCO[C@H]1C[C@@H](CCc2ccc3c(n2)NCCC3)C1)C(=O)O]

N-(3-chloro-5-methoxyisonicotinoyl)-O-((1r,3R)-3-(2-(5,6,7,8-tetrahydro-1,8-naphthyridin-2-yl)ethyl)cyclobutyl)-L-homoserine Isomer E2 was employed in General Scheme E-2 using General Procedure I with 3-chloro-5-methoxyisonicotinic acid. LCMS theoretical m/z=502.2. [M+H]+. found 503.2.

Example 244, Compound 224

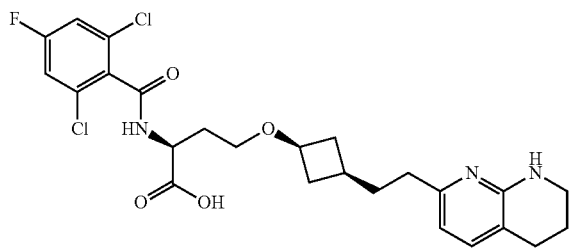 [SMILES: O=C(N[C@@H](CCO[C@H]1C[C@@H](CCc2ccc3c(n2)NCCC3)C1)C(=O)O)c1c(Cl)cc(F)cc1Cl]

N-(2,6-dichloro-4-fluorobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-dichloro-4-fluorobenzoic acid. LCMS theoretical m/z=523.1. [M+H]+. found 524.1.

Example 245, Compound 225

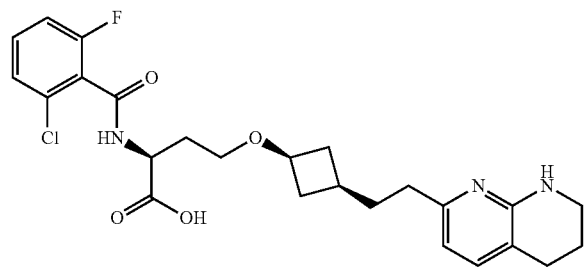 [SMILES: O=C(N[C@@H](CCO[C@H]1C[C@@H](CCc2ccc3c(n2)NCCC3)C1)C(=O)O)c1c(F)cccc1Cl]

N-(2-chloro-6-fluorobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-chloro-6-fluorobenzoic acid. LCMS theoretical m/z=489.2. [M+H]+. found 489.9.

Example 246, Compound 226

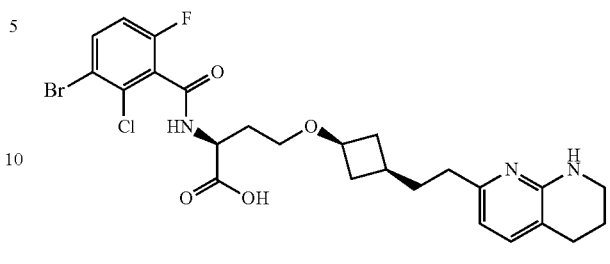

N-(3-bromo-2-chloro-6-fluorobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-bromo-2-chloro-6-fluorobenzoic acid. LCMS theoretical m/z=567.1. [M+H]+. found 568.1.

Example 247, Compound 227

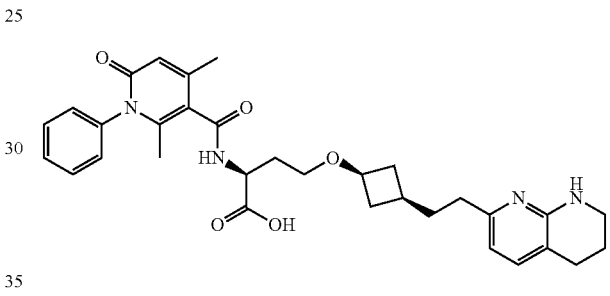

N-(2,4-dimethyl-6-oxo-1-phenyl-1,6-dihydropyridine-3-carbonyl)-O-((1r,3R)-3-(2-(5,6,7,8-tetrahydro-1,8-naphthyridin-2-yl)ethyl)cyclobutyl)-L-homoserine Isomer E2 was employed in General Scheme E-2 using General Procedure I with 2,4-dimethyl-6-oxo-1-phenyl-1,6-dihydropyridine-3-carboxylic acid. LCMS theoretical m/z=558.3. [M+H]+. found 559.3.

Example 248, Compound 228

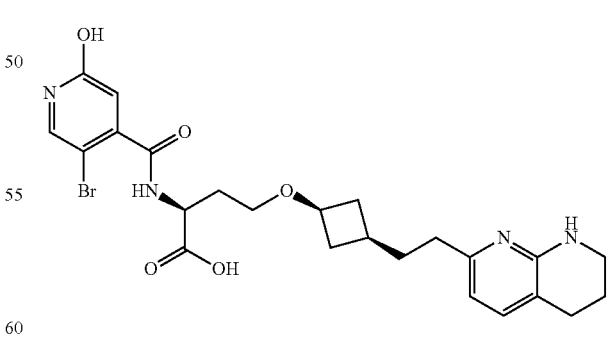

N-(5-bromo-2-hydroxyisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 5-bromo-2-hydroxyisonicotinic acid. LCMS theoretical m/z=532.1. [M+H]+. found 533.1.

Example 249, Compound 229

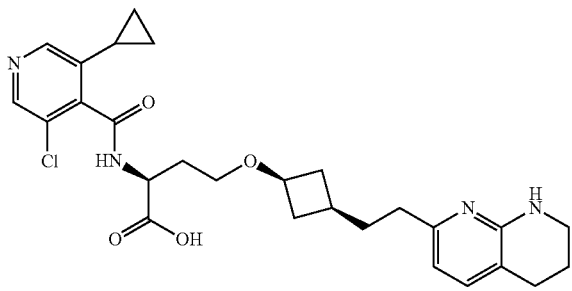 [SMILES: O=C(N[C@@H](CCO[C@H]1C[C@@H](CCc2ccc3c(n2)NCCC3)C1)C(=O)O)c1c(Cl)cncc1C1CC1]

N-(3-chloro-5-cyclopropylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-5-cyclopropylisonicotinic acid. LCMS theoretical m/z=512.2. [M+H]+. found 513.2.

Example 250, Compound 230

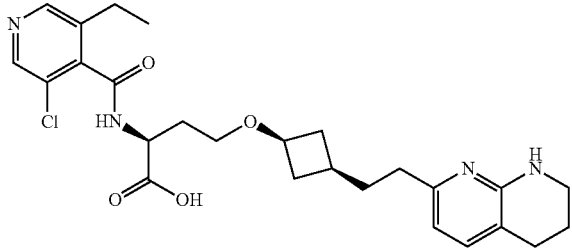 [SMILES: CCc1cncc(Cl)c1C(=O)N[C@@H](CCO[C@H]1C[C@@H](CCc2ccc3c(n2)NCCC3)C1)C(=O)O]

N-(3-chloro-5-ethylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-5-ethylisonicotinic acid. LCMS theoretical m/z=500.2. [M+H]+. found 501.2.

Example 251, Compound 231

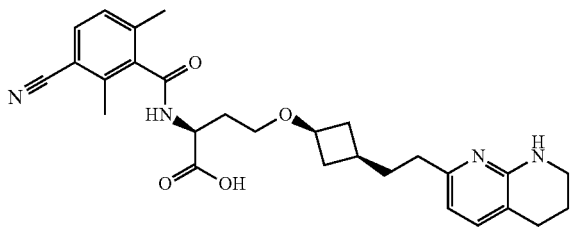 [SMILES: Cc1ccc(C#N)c(C)c1C(=O)N[C@@H](CCO[C@H]1C[C@@H](CCc2ccc3c(n2)NCCC3)C1)C(=O)O]

N-(3-chloro-5-ethylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-cyano-2,6-dimethylbenzoic acid. LCMS theoretical m/z=490.2. [M+H]+. found 491.2.

Example 252, Compound 232

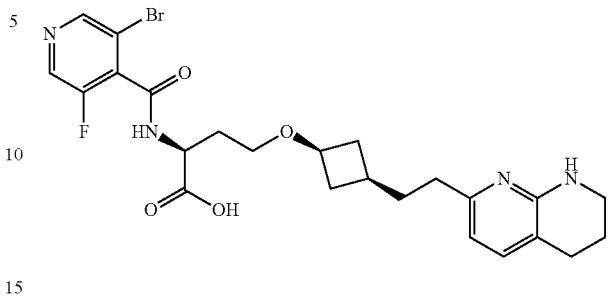

N-(3-bromo-5-fluoroisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-bromo-5-fluoroisonicotinic acid. LCMS theoretical m/z=534.1. [M+H]+. found 535.1.

Example 253, Compound 233

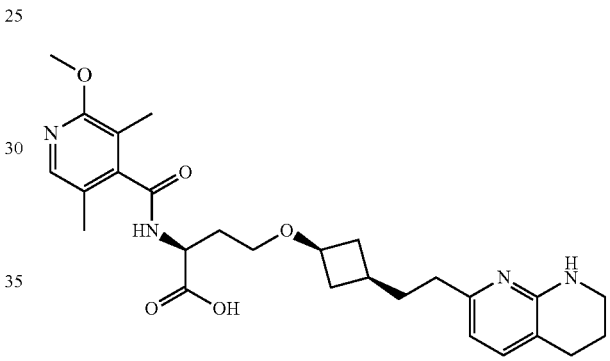

N-(2-methoxy-3,5-dimethylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-methoxy-3,5-dimethylisonicotinic acid. LCMS theoretical m/z=496.2. [M+H]+. found 497.2.

Example 254, Compound 234

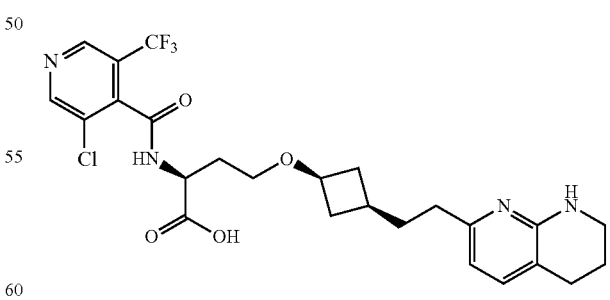

N-(3-chloro-5-(trifluoromethyl)isonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-5-(trifluoromethyl)isonicotinic acid. LCMS theoretical m/z=540.2. [M+H]+. found 541.2.

Example 255, Compound 235

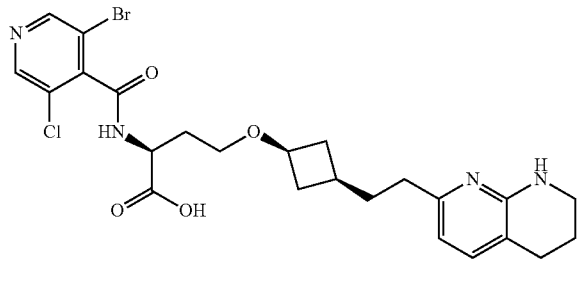 [SMILES: O=C(N[C@@H](CCO[C@H]1C[C@@H](CCc2ccc3c(n2)NCCC3)C1)C(=O)O)c1c(Cl)cncc1Br]

N-(3-bromo-5-chloroisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-bromo-5-chloroisonicotinic acid. LCMS theoretical m/z=550.1. [M+H]+. found 551.1.

Example 256, Compound 236

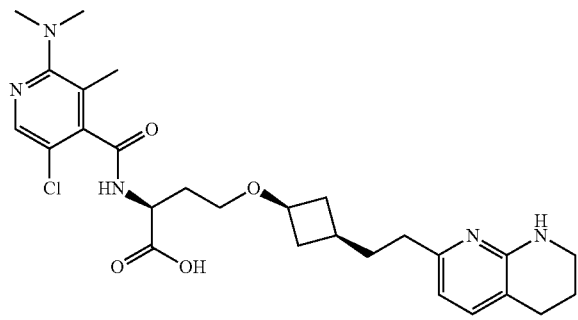 [SMILES: Cc1c(N(C)C)ncc(Cl)c1C(=O)N[C@@H](CCO[C@H]1C[C@@H](CCc2ccc3c(n2)NCCC3)C1)C(=O)O]

N-(5-chloro-2-(dimethylamino)-3-methylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 5-chloro-2-(dimethylamino)-3-methylisonicotinic acid. LCMS theoretical m/z=509.3. [M+H]+. found 510.2.

Example 257, Compound 237

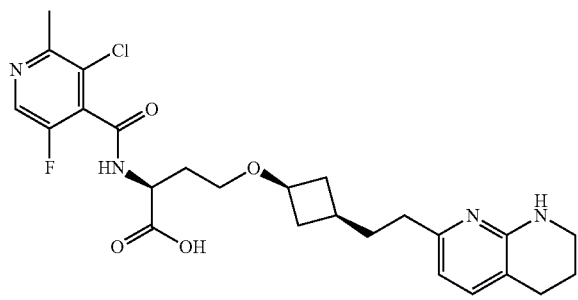 [SMILES: Cc1ncc(F)c(C(=O)N[C@@H](CCO[C@H]2C[C@@H](CCc3ccc4c(n3)NCCC4)C2)C(=O)O)c1Cl]

N-(3-chloro-5-fluoro-2-methylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-5-fluoro-2-methylisonicotinic acid. LCMS theoretical m/z=504.2. [M+H]+. found 505.1.

Example 258, Compound 238

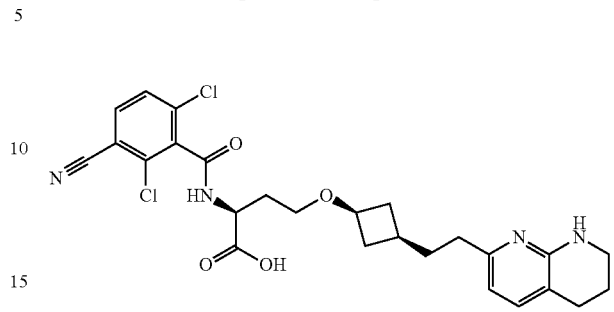

N-(2,6-dichloro-3-cyanobenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-dichloro-3-cyanobenzoic acid. LCMS theoretical m/z=530.1. [M+H]+. found 531.1.

Example 259, Compound 239

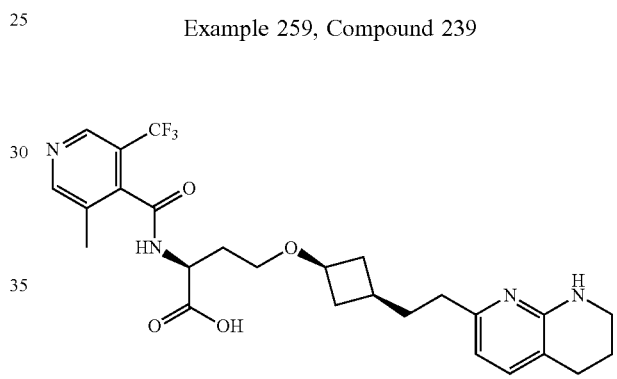

N-(3-methyl-5-(trifluoromethyl)isonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-methyl-5-(trifluoromethyl)isonicotinic acid. LCMS theoretical m/z=520.2. [M+H]+. found 521.2.

Example 260, Compound 240

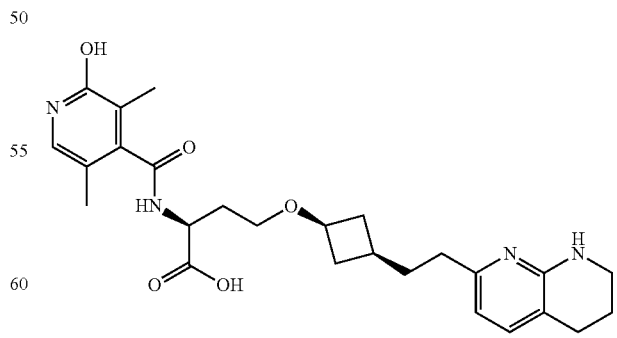

N-(2-hydroxy-3,5-dimethylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-hydroxy- 3,5-dimethylisonicotinic acid. LCMS theoretical m/z=488.2. [M+H]+. found 483.2.

Example 261, Compound 241

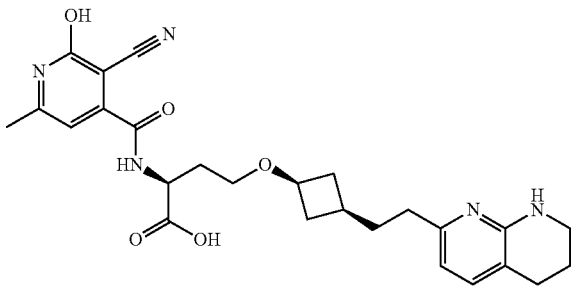 [SMILES: Cc1cc(C(=O)N[C@@H](CCO[C@H]2C[C@@H](CCc3ccc4c(n3)NCCC4)C2)C(=O)O)c(C#N)c(O)n1]

N-(3-cyano-2-hydroxy-6-methylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-cyano-2-hydroxy-6-methylisonicotinic acid. LCMS theoretical m/z=493.2. [M+H]+. found 494.2.

Example 262, Compound 242

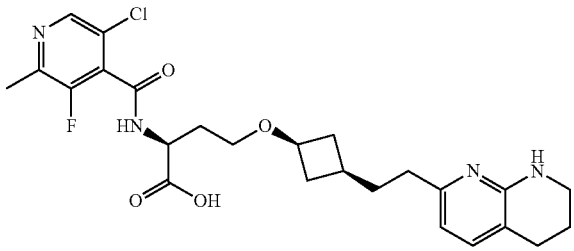 [SMILES: Cc1ncc(Cl)c(C(=O)N[C@@H](CCO[C@H]2C[C@@H](CCc3ccc4c(n3)NCCC4)C2)C(=O)O)c1F]

N—(S-chloro-3-fluoro-2-methylisonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 5-chloro-3-fluoro-2-methylisonicotinic acid. LCMS theoretical m/z=504.2. [M+H]+. found 505.2.

Example 263, Compound 243

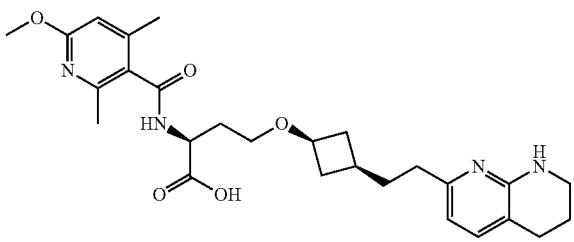 [SMILES: COc1cc(C)c(C(=O)N[C@@H](CCO[C@H]2C[C@@H](CCc3ccc4c(n3)NCCC4)C2)C(=O)O)c(C)n1]

N-(6-methoxy-2,4-dimethylnicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 6-methoxy-2,4-dimethylnicotinic acid. LCMS theoretical m/z=496.2. [M+H]+. found 497.2.

Example 264, Compound 244

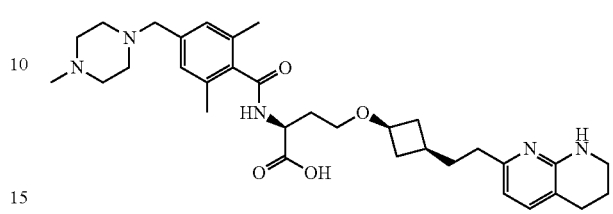

N-(2,6-dimethyl-4-((4-methylpiperazin-1-yl)methyl)benzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-dimethyl-4-((4-methylpiperazin-1-yl)methyl)benzoic acid. LCMS theoretical m/z=577.3. [M+H]+. found 578.3.

Example 265, Compound 245

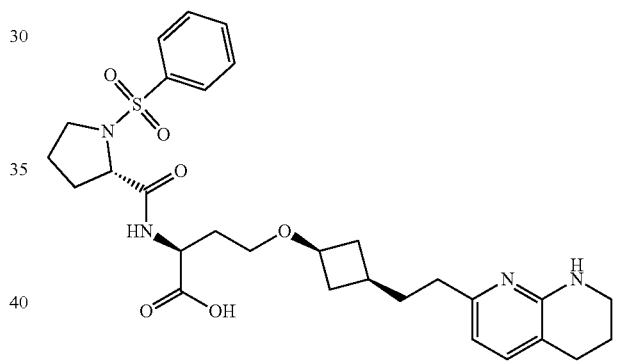

N-((phenylsulfonyl)-L-prolyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with (phenylsulfonyl)-L-proline. LCMS theoretical m/z=570.2. [M+H]+. found 571.2.

Example 266, Compound 246

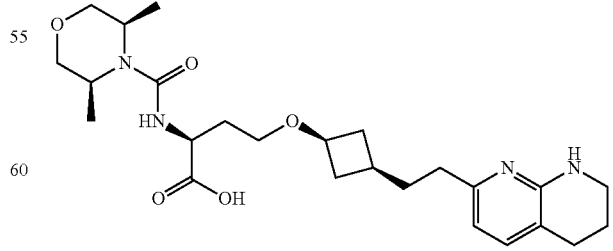

N-((3R,5S)-3,5-dimethylmorpholine-4-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure G with (3R,5S)-3,5-dimethylmorpholine. LCMS theoretical m/z=474.3. [M+H]+. found 475.3.

Example 267, Compound 247

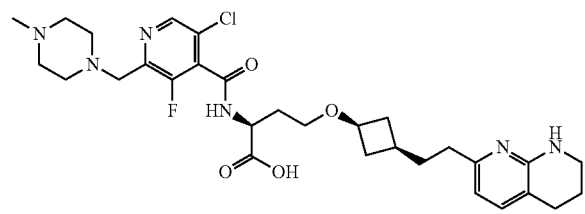 [SMILES: CN1CCN(Cc2ncc(Cl)c(C(=O)N[C@@H](CCO[C@H]3C[C@@H](CCc4ccc5c(n4)NCCC5)C3)C(=O)O)c2F)CC1]

N-(5-chloro-3-fluoro-2-((4-methylpiperazin-1-yl)methyl) isonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 5-chloro-3-fluoro-2-((4-methylpiperazin-1-yl)methyl)isonicotinic acid. LCMS theoretical m/z=602.3. [M+H]+. found 603.3.

Example 268, Compound 248

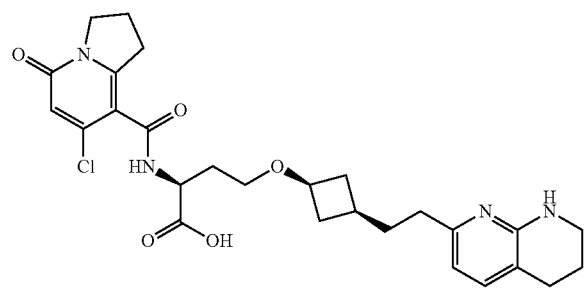 [SMILES: O=C(N[C@@H](CCO[C@H]1C[C@@H](CCc2ccc3c(n2)NCCC3)C1)C(=O)O)c1c(Cl)cc(=O)n2c1CCC2]

N-(7-chloro-5-oxo-1,2,3,5-tetrahydroindolizine-8-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 7-chloro-5-oxo-1,2,3,5-tetrahydroindolizine-8-carboxylic acid. LCMS theoretical m/z=528.2. [M+H]+. found 529.2.

Example 269, Compound 249

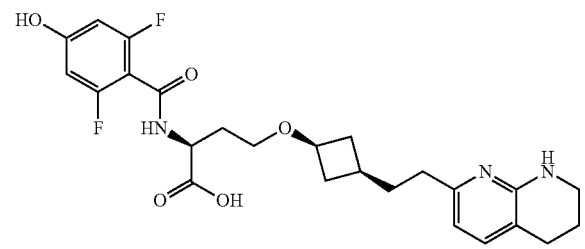 [SMILES: O=C(N[C@@H](CCO[C@H]1C[C@@H](CCc2ccc3c(n2)NCCC3)C1)C(=O)O)c1c(F)cc(O)cc1F]

N-(2,6-difluoro-4-hydroxybenzoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2,6-difluoro-4-hydroxybenzoic acid. LCMS theoretical m/z=489.2. [M+H]+. found 490.2.

Example 270, Compound 250

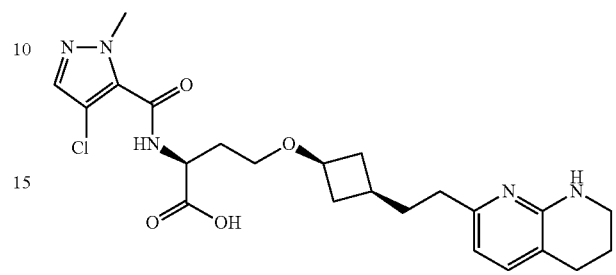

N-(4-chloro-1-methyl-1H-pyrazole-5-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 4-chloro-1-methyl-1H-pyrazole-5-carboxylic acid. LCMS theoretical m/z=475.2. [M+H]+. found 476.2.

Example 271, Compound-251

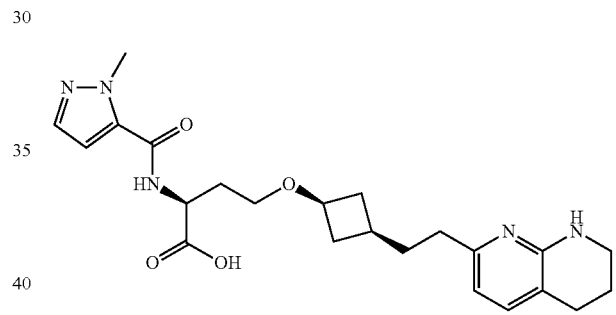

N-(1-methyl-1H-pyrazole-5-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 1-methyl-1H-pyrazole-5-carboxylic acid. LCMS theoretical m/z=441.2. [M+H]+. found 442.2.

Example 272. Compound 252

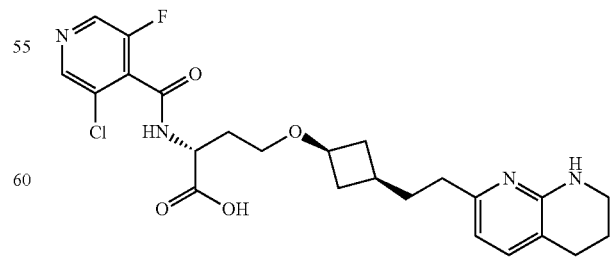

N-(3-chloro-5-fluoroisonicotinoyl)-O-((1r,3S)-3-(2-(5,6,7,8-tetrahydro-1,8-naphthyridin-2-yl)ethyl)cyclobutyl)-D-homoserine. Isomer E1 was employed in General Scheme E-2 using General Procedure I with 3-chloro-5-fluoroisonicotinic acid. LCMS theoretical m/z=490.2. [M+H]+. found 491.2.

Example 273, Compound 253

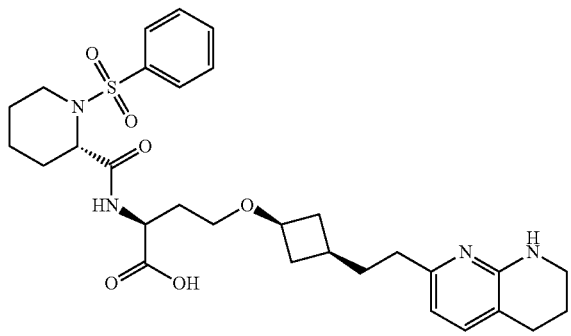 [SMILES: O=C(O)[C@H](CCO[C@H]1C[C@@H](CCc2ccc3c(n2)NCCC3)C1)NC(=O)[C@@H]1CCCCN1S(=O)(=O)c1ccccc1]

N—((S)-1-(phenylsulfonyl)piperidine-2-carbonyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with (S)-1-(phenylsulfonyl)piperidine-2-carboxylic acid. LCMS theoretical m/z=584.3. [M+H]+. found 585.2.

Example 274, Compound 254

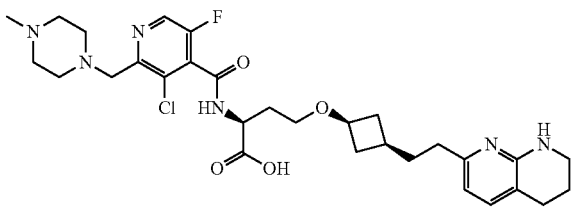 [SMILES: CN1CCN(Cc2ncc(F)c(C(=O)N[C@@H](CCO[C@H]3C[C@@H](CCc4ccc5c(n4)NCCC5)C3)C(=O)O)c2Cl)CC1]

N-(3-chloro-5-fluoro-2-((4-methylpiperazin-1-yl)methyl)isonicotinoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 3-chloro-5-fluoro-2-((4-methylpiperazin-1-yl)methyl)isonicotinic acid. LCMS theoretical m/z=602.3. [M+H]+. found 603.3.

Example 275, Compound 255

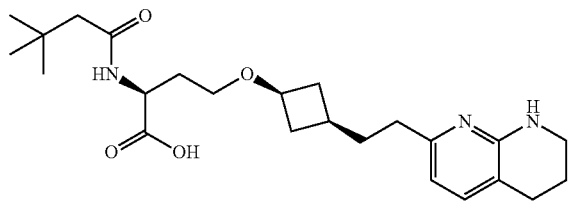 [SMILES: CC(C)(C)CC(=O)N[C@@H](CCO[C@H]1C[C@@H](CCc2ccc3c(n2)NCCC3)C1)C(=O)O]

N-(3,3-dimethylbutanoyl)-O-((1r,3R)-3-(2-(5,6,7,8-tetrahydro-1,8-naphthyridin-2-yl)ethyl)cyclobutyl)-L-homoserine Isomer E2 was employed in General Scheme E-2 using General Procedure I with 3,3-dimethylbutanoic acid. LCMS theoretical m/z=431.3. [M+H]+. found 432.3.

Example 276, Compound 256

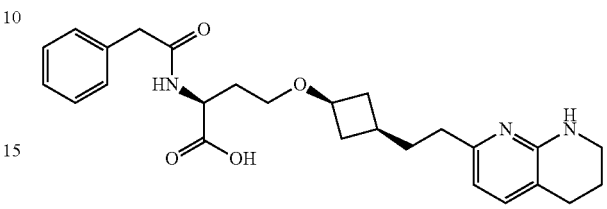

N-(2-phenylacetyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-phenylacetic acid. LCMS theoretical m/z=451.3. [M+H]+. found 452.3.

Example 277, Compound 257

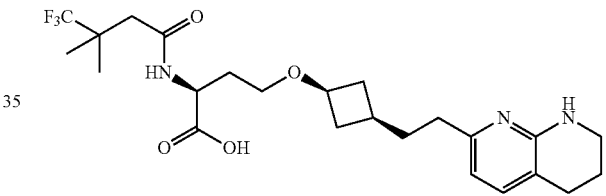

O-((1r,3R)-3-(2-(5,6,7,8-tetrahydro-1,8-naphthyridin-2-yl)ethyl)cyclobutyl)-N-(4,4,4-trifluoro-3,3-dimethylbutanoyl)-L-homoserine. Isomer E2 was employed in General Scheme E-2 using General Procedure I with 4,4,4-trifluoro-3,3-dimethylbutanoic acid. LCMS theoretical m/z=485.3. [M+H]+. found 486.3.

Example 278, Compound 258

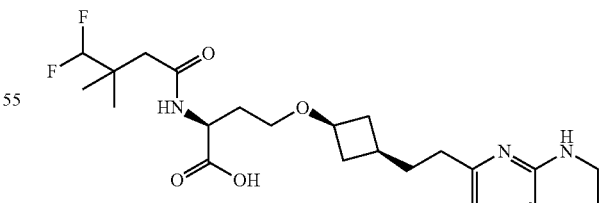

N-(4,4-difluoro-3,3-dimethylbutanoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 4,4-difluoro-3,3-dimethylbutanoic acid. LCMS theoretical m/z=467.3. [M+H]+. found 468.3.

Example 279, Compound 259

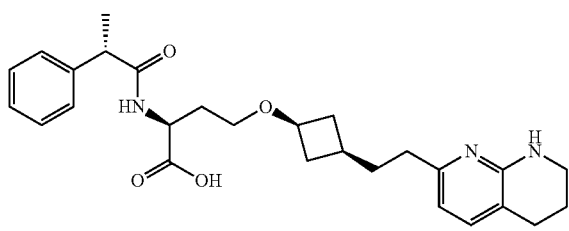 [SMILES: C[C@H](C(=O)N[C@@H](CCO[C@H]1C[C@@H](CCc2ccc3c(n2)NCCC3)C1)C(=O)O)c1ccccc1]

N—((S)-2-phenylpropanoyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with (S)-2-phenylpropanoic acid. LCMS theoretical m/z=465.3. [M+H]+. found 466.3.

Example 280, Compound 260

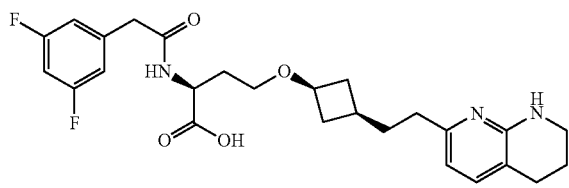 [SMILES: O=C(Cc1cc(F)cc(F)c1)N[C@@H](CCO[C@H]1C[C@@H](CCc2ccc3c(n2)NCCC3)C1)C(=O)O]

N-(2-(3,5-difluorophenyl)acetyl)-O-((1r,3R)-3-(2-(5,6,7,8-tetrahydro-1,8-naphthyridin-2-yl)ethyl)cyclobutyl)-L-homoserine. Isomer E2 was employed in General Scheme E-2 using General Procedure I with 2-(3,5-difluorophenyl)acetic acid. LCMS theoretical m/z=487.2. [M+H]+. found 488.2.

Example 281, Compound 261

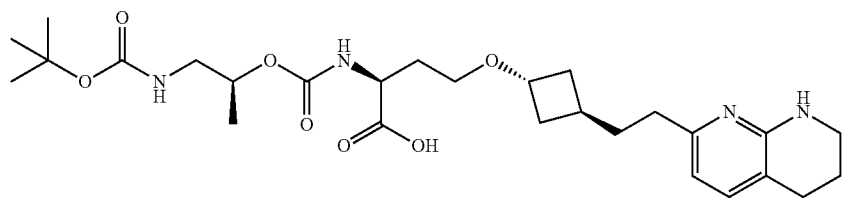 [SMILES: C[C@@H](CNC(=O)OC(C)(C)C)OC(=O)N[C@@H](CCO[C@H]1C[C@H](CCc2ccc3c(n2)NCCC3)C1)C(=O)O]

N—((((S)-1-((tert-butoxycarbonyl)amino)propan-2-yl)oxy)carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with (S)-1-((tert-butoxycarbonyl)amino)propan-2-yl hydrogen carbonate. LCMS theoretical m/z=534.3. [M+H]+. found 535.3.

Example 282, Compound 262

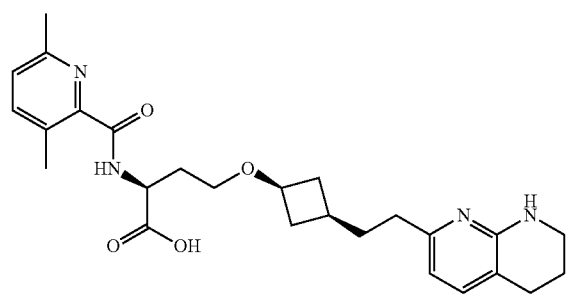 [SMILES: Cc1ccc(C)c(C(=O)N[C@@H](CCO[C@H]2C[C@@H](CCc3ccc4c(n3)NCCC4)C2)C(=O)O)n1]

N-(3,6-dimethylpicolinoyl)-O-((1r,3R)-3-(2-(5,6,7,8-tetrahydro-1,8-naphthyridin-2-yl)ethyl)cyclobutyl)-L-homoserine. Isomer D2 was employed in General Scheme D-2 using General Procedure I with 3,6-dimethylpicolinic acid. LCMS theoretical m/z=466.3. [M+H]+. found 467.3.

Example 283, Compound 263

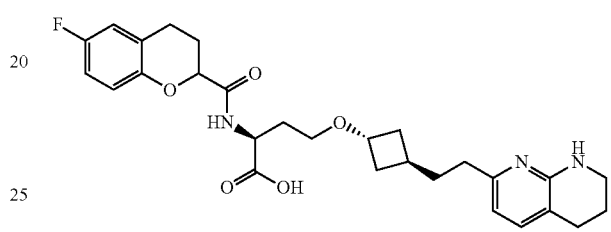

N-(6-fluorochromane-2-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 6-fluorochromane-2-carboxylic acid. LCMS theoretical m/z=511.3. [M+H]+. found 512.3.

Example 284, Compound 264

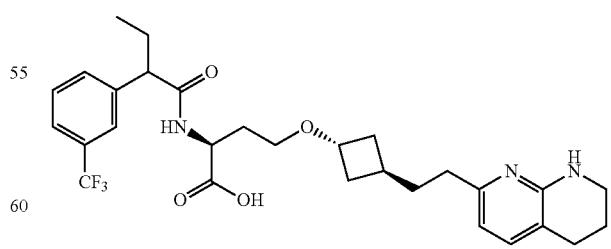

O-((1s,3S)-3-(2-(5,6,7,8-tetrahydro-1,8-naphthyridin-2-yl)ethyl)cyclobutyl)-N-(2-(3-(trifluoromethyl)phenyl)butanoyl)-L-homoserine. Isomer D2 was employed in General Scheme D-2 using General Procedure I with 2-(3-(trifluoromethyl)phenyl)butanoic acid. LCMS theoretical m/z=547.3. [M+H]+. found 548.3.

Example 285, Compound 265

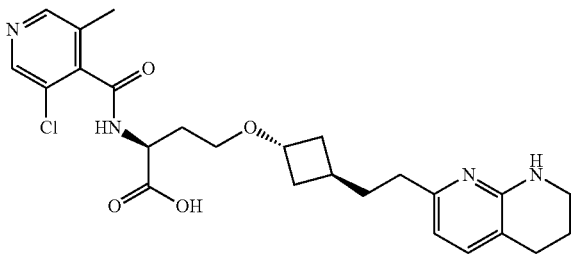 [SMILES: Cc1cncc(Cl)c1C(=O)N[C@@H](CCO[C@H]1C[C@H](CCc2ccc3c(n2)NCCC3)C1)C(=O)O]

N-(3-chloro-5-methylisonicotinoyl)-O-((1s,3S)-3-(2-(5,6,7,8-tetrahydro-1,8-naphthyridin-2-yl)ethyl)cyclobutyl)-1-homoserine. Isomer D2 was employed in General Scheme D-2 using General Procedure I with 3-chloro-5-methylisonicotinic acid. LCMS theoretical m/z=486.2. [M+H]+. found 487.2.

Example 286, Compound 266

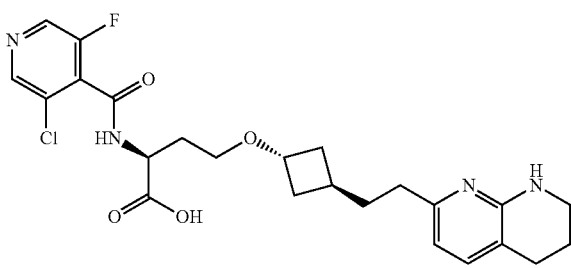 [SMILES: O=C(N[C@@H](CCO[C@H]1C[C@H](CCc2ccc3c(n2)NCCC3)C1)C(=O)O)c1c(F)cncc1Cl]

N-(3-chloro-5 fluoroisonicotinoyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 3-chloro-5-fluoroisonicotinic acid. LCMS theoretical m/z=490.2. [M+H]+. found 491.2.

Example 287, Compound 267

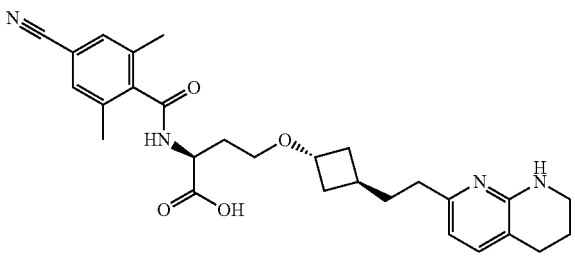 [SMILES: Cc1cc(C#N)cc(C)c1C(=O)N[C@@H](CCO[C@H]1C[C@H](CCc2ccc3c(n2)NCCC3)C1)C(=O)O]

N-(4-cyano-2,6-dimethylbenzoyl)-O-((1s,6,7,8-tetrahydro-1,8-naphthyridin-2-yl)ethyl)cyclobutyl)-L-homoserine. Isomer D2 was employed in General Scheme D-2 using General Procedure I with 4-cyano-2,6-dimethylbenzoic acid. LCMS theoretical m/z=490.3. [M+H]+. found 491.3.

Example 288, Compound 268

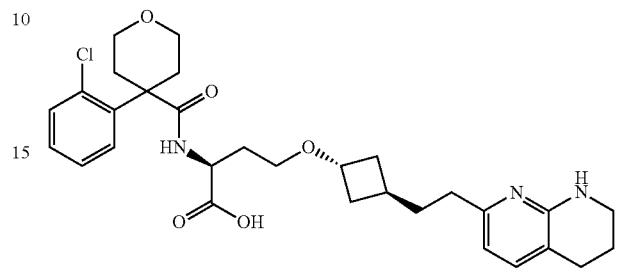

N-(4-(2-chlorophenyl)tetrahydro-2H-pyran-4-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 4-(2-chlorophenyl)tetrahydro-2H-pyran-4-carboxylic acid. LCMS theoretical m/z=555.3. [M+H]+. found 556.3.

Example 289, Compound 269

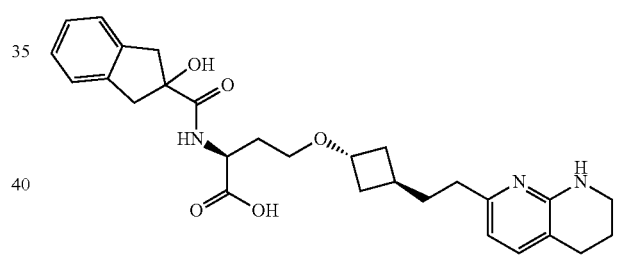

N-(2-hydroxy-2,3-dihydro-JH-indene-2-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 2-hydroxy-2,3-dihydro-1H-indene-2-carboxylic acid. LCMS theoretical m/z=493.3. [M+H]+. found 494.2.

Example 290, Compound 270

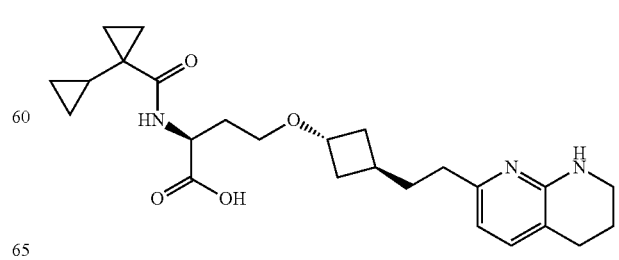

N-([1,1'-bi(cyclopropane)]-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with [1,1'-bi(cyclopropane)]-1-carboxylic acid. LCMS theoretical m/z=441.3. [M+H]+. found 442.3.

Example 291, Compound 271

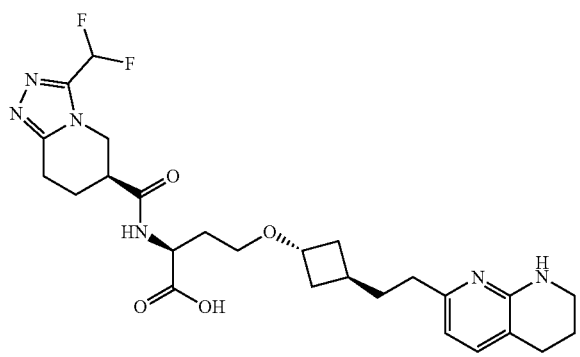 [SMILES: O=C(N[C@@H](CCO[C@H]1C[C@H](CCc2ccc3c(n2)NCCC3)C1)C(=O)O)[C@H]1CCc2nnc(C(F)F)n2C1]

N—((S)-3-(difluoromethyl)-5,6,7,8-tetrahydro-[1,2,4]triazolo[4,3-a]pyridine-6-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 3-(difluoromethyl)-5,6,7,8-tetrahydro-[1,2,4]triazolo[4,3-a]pyridine-6-carboxylic acid. LCMS theoretical m/z=532.3. [M+H]+. found 533.3.

Example 292, Compound 272

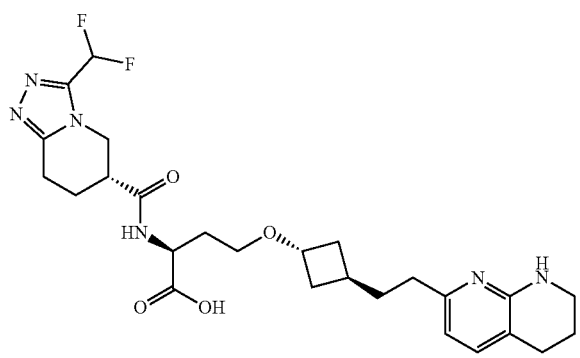 [SMILES: O=C(N[C@@H](CCO[C@H]1C[C@H](CCc2ccc3c(n2)NCCC3)C1)C(=O)O)[C@@H]1CCc2nnc(C(F)F)n2C1]

N—((R)-3-(difluoromethyl)-5,6,7,8-tetrahydro-[1,2,4]triazolo[4,3-a]pyridine-6-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 3-(difluoromethyl)-5,6,7,8-tetrahydro-[1,2,4]triazolo[4,3-a]pyridine-6-carboxylic acid. LCMS theoretical m/z=532.3. [M+H]+. found 533.3.

Example 293, Compound 273

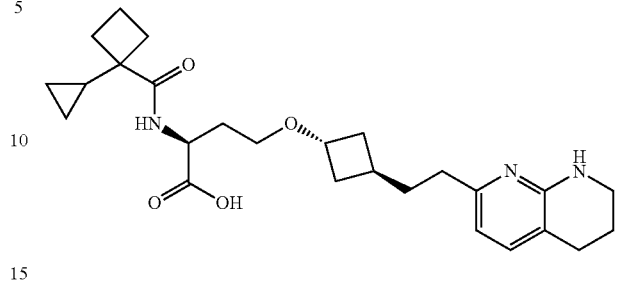

N-(1-cyclopropylcyclobutane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-cyclopropylcyclobutane-1-carboxylic acid. LCMS theoretical m/z=455.3. [M+H]+. found 456.3.

Example 294, Compound 274

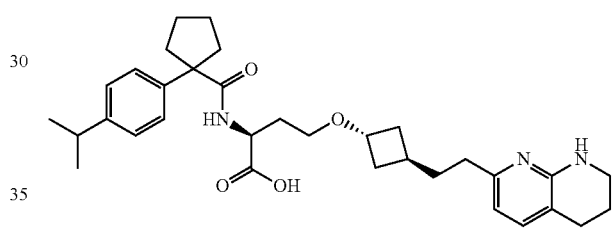

N-(1-(4-isopropylphenyl)cyclopentane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-(4-isopropylphenyl)cyclopentane-1-carboxylic acid. LCMS theoretical m/z=547.3. [M+H]+. found 548.3.

Example 295, Compound 275

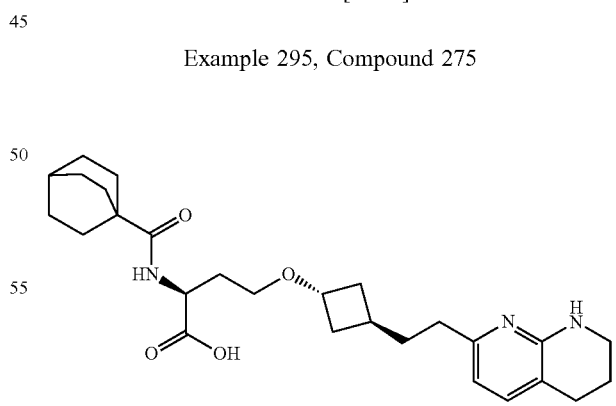

N-(bicyclo[2.2.2]octane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with bicyclo[2.2.2]octane-1-carboxylic acid. LCMS theoretical m/z=469.3. [M+H]+. found 470.3.

Example 296, Compound 276

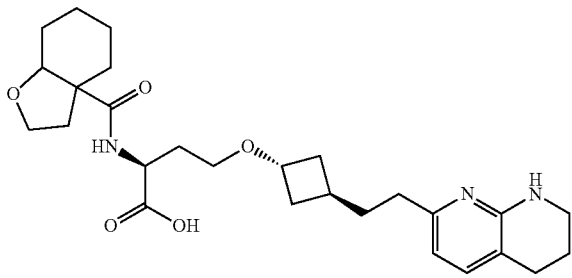 [SMILES: O=C(O)[C@H](CCO[C@H]1C[C@H](CCc2ccc3c(n2)NCCC3)C1)NC(=O)C12CCCCC1OCC2]

N-(octahydrobenzofuran-3a-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with octahydrobenzofuran-4-carboxylic acid. LCMS theoretical m/z=485.3. [M+H]+. found 486.3.

Example 297, Compound 277

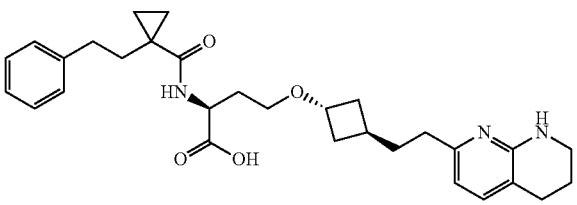 [SMILES: O=C(O)[C@H](CCO[C@H]1C[C@H](CCc2ccc3c(n2)NCCC3)C1)NC(=O)C1(CCc2ccccc2)CC1]

N-(1-phenethylcyclopropane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-phenethylcyclopropane-1-carboxylic acid. LCMS theoretical m/z=505.3. [M+H]+. found 506.3.

Example 298, Compound 278

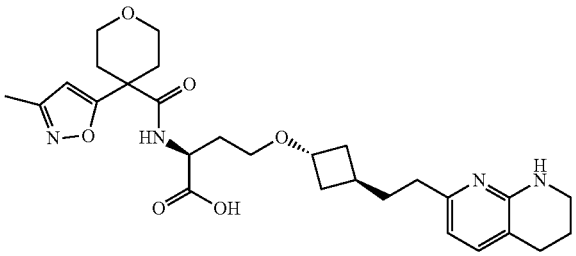 [SMILES: Cc1cc(C2(C(=O)N[C@@H](CCO[C@H]3C[C@H](CCc4ccc5c(n4)NCCC5)C3)C(=O)O)CCOCC2)on1]

N-(4-(3-methylisoxazol-5-yl)tetrahydro-2H-pyran-4-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 4-(3-methylisoxazol-5-yl)tetrahydro-2H-pyran-4-carboxylic acid. LCMS theoretical m/z=526.3. [M+H]+. found 527.1.

Example 299, Compound 279

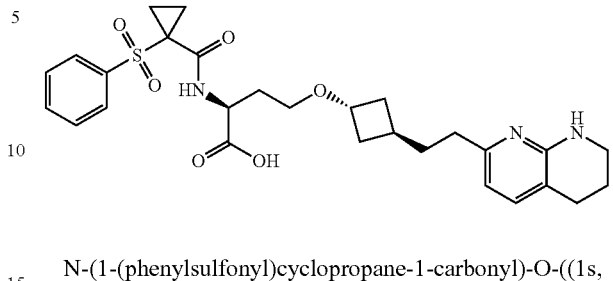

N-(1-(phenylsulfonyl)cyclopropane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-(phenylsulfonyl)cyclopropane-1-carboxylic acid. LCMS theoretical m/z=541.2. [M+H]+. found 542.2.

Example 300, Compound 280

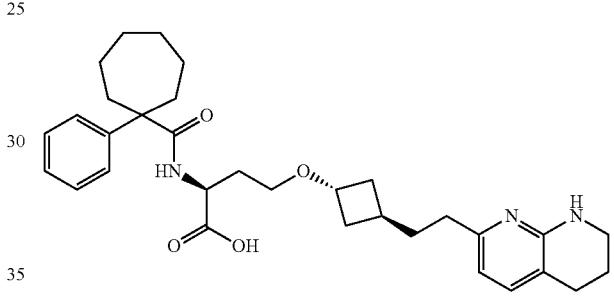

N-(1-phenylcycloheptane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-phenylcycloheptane-1-carboxylic acid. LCMS theoretical m/z=533.3. [M+H]+. found 534.3.

Example 301, Compound 281

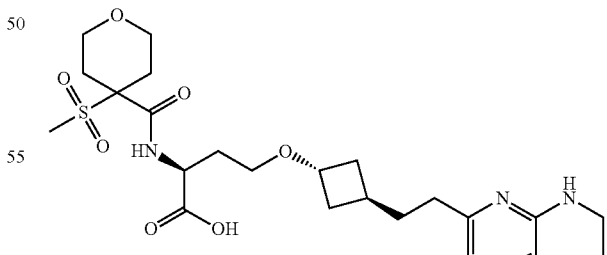

N-(4-(methylsulfonyl)tetrahydro-2H-pyran-4-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 4-(methylsulfonyl)tetrahydro-2H-pyran-4-carboxylic acid. LCMS theoretical m/z=523.2. [M+H]+. found 524.2.

Example 302, Compound 282

Example 303, Compound 283

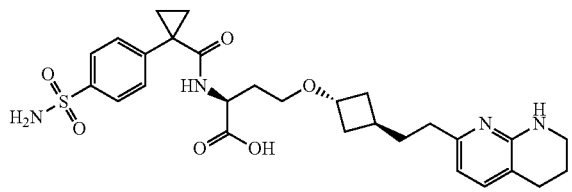 [SMILES: NS(=O)(=O)c1ccc(C2(C(=O)N[C@@H](CCO[C@H]3C[C@H](CCc4ccc5c(n4)NCCC5)C3)C(=O)O)CC2)cc1]

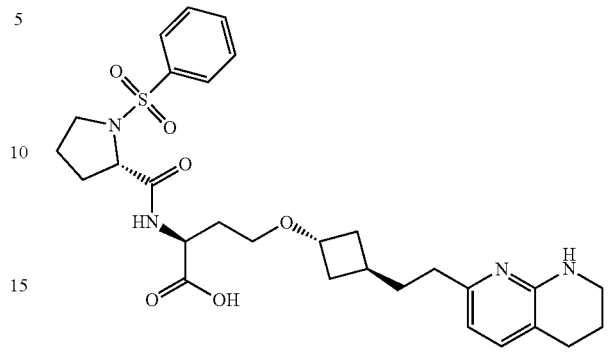

N-(1-(4-sulfamoylphenyl)cyclopropane-1-carbonyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 1-(4-sulfamoylphenyl)cyclopropane-1-carboxylic acid. LCMS theoretical m/z=556.2. [M+H]+. found 557.2.

N-((phenylsulfonyl)-L-prolyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with (phenylsulfonyl)-L-proline. LCMS theoretical m/z=570.2. [M+H]+. found 571.2.

Example 304, Compound 284

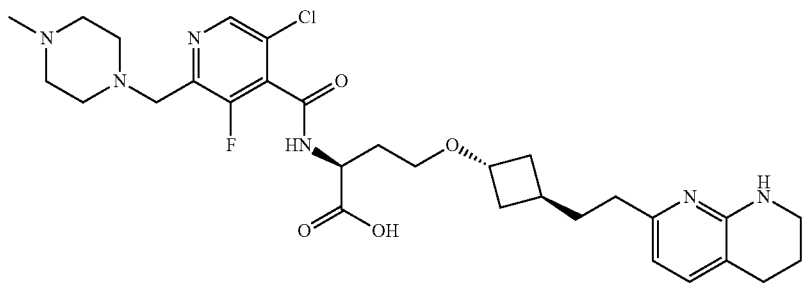 [SMILES: CN1CCN(Cc2ncc(Cl)c(C(=O)N[C@@H](CCO[C@H]3C[C@H](CCc4ccc5c(n4)NCCC5)C3)C(=O)O)c2F)CC1]

N-(5-chloro-3-fluoro-2-((4-methylpiperazin-1-yl)methyl)isonicotinoyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 5-chloro-3-fluoro-2-((4-methylpiperazin-1-yl)methyl)isonicotinic acid. LCMS theoretical m/z=602.3. [M+H]+. found 603.3.

Example 305, Compound 285

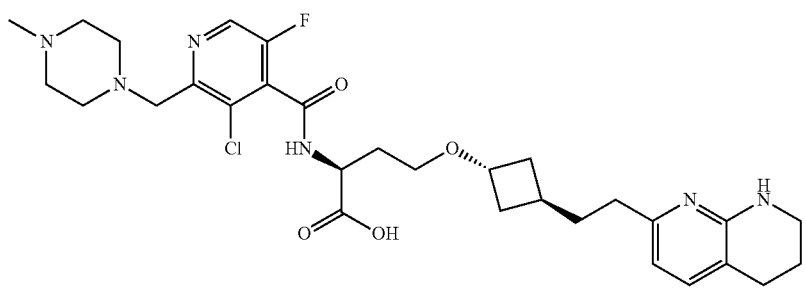 [SMILES: CN1CCN(Cc2ncc(F)c(C(=O)N[C@@H](CCO[C@H]3C[C@H](CCc4ccc5c(n4)NCCC5)C3)C(=O)O)c2Cl)CC1]

N-(3-chloro-5-fluoro-2-((4-methylpiperazin-1-yl)methyl) isonicotinoyl)-O-((1s,3S)-3-(2-(5,6,7,8-tetrahydro-1,8-naphthyridin-2-yl)ethyl)cyclobutyl)-L-homoserine. Isomer D2 was employed in General Scheme D-2 using General Procedure I with 3-chloro-5-fluoro-2-((4-methylpiperazin-1-yl)methyl)isonicotinic acid. LCMS theoretical m/z=602.3. [M+H]+. found 603.3.

Example 306, Compound 286

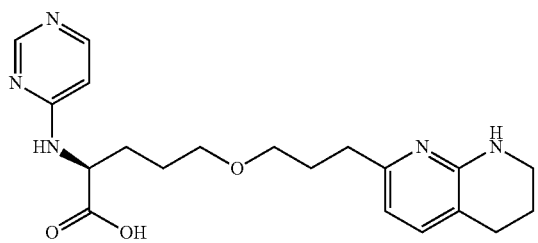 [SMILES: O=C(O)[C@H](CCCOCCCc1ccc2c(n1)NCCC2)Nc1ccncn1]

(S)-2-(pyrimidin-4-ylamino)-5-(3-(5,6,7,8-tetrahydro-1, 8-naphthyridin-2-yl)propoxy)pentanoic acid. Prepared by modifying the reaction with intermediate 2i in Example 2 to replace 2-ethylbutanoic acid with 4-chloropyrimidine and sodium bicarbonate. LCMS theoretical m/z=385.2. [M+H]+. found 386.2.

Example 307, Compound 287

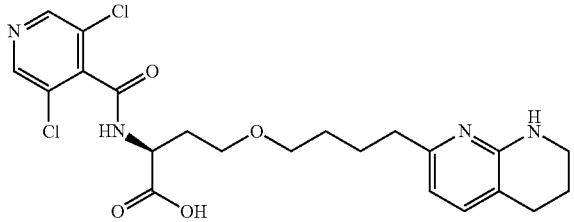 [SMILES: O=C(N[C@@H](CCOCCCCc1ccc2c(n1)NCCC2)C(=O)O)c1c(F)cncc1Cl]

N-(3,5-dichloroisonicofinoyl)-O-(4-(5,6,7,8-tetrahydro-1,8-naphthyridin-2-yl)butyl)-L-homoserine. Isomer F2 was employed in General Scheme F-2 using General Procedure I with 3,5-dichloroisonicotinic acid. LCMS theoretical m/z=480.1. [M+H]+. found 481.1.

Example 308, Compound 288

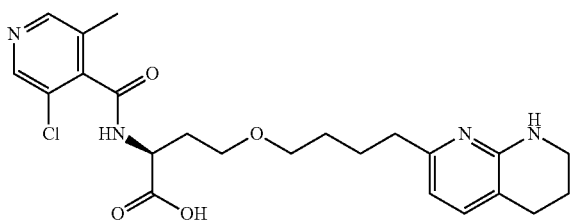

N-(3-chloro-5-methylisonicodnoyl)-O-(4-(5,6,7,8-tetrahydro-1,8-naphthyridin-2-yl)butyl)-L-homoserine. Isomer F2 was employed in General Scheme F-2 using General Procedure I with 3-chloro-5-methylisonicotinic acid. LCMS theoretical m/z=460.2. [M+H]+. found 461.2.

Example 309, Compound 289

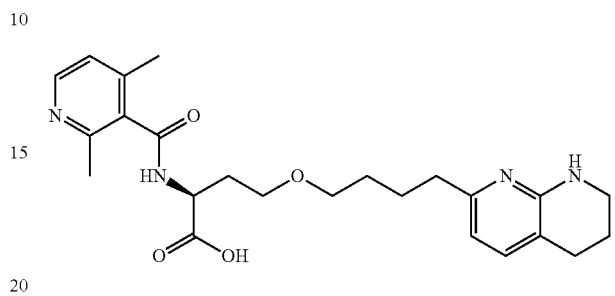

N-(2,4-dimethylnicotinoyl)-O-(4-(5,6,7,8-tetrahydro-1,8-naphthyridin-2-yl)butyl)-L-homoserine. Isomer F2 was employed in General Scheme F-2 using General Procedure I with 2,4-dimethylnicotinic acid. LCMS theoretical m/z=440.2. [M+H]+. found 441.2.

Example 310, Compound 290

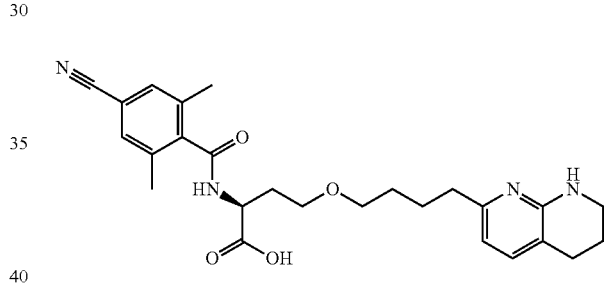

N-(4-cyano-2,6-dimethylbenzoyo-O-(4-(5,6,7,8-tetrahydro-1,8-naphthyridin-2-yl)butyl)-L-homoserine. Isomer F2 was employed in General Scheme F-2 using General Procedure I with 4-cyano-2,6-dimethylbenzoic acid. LCMS theoretical m/z=464.2. [M+H]+. found 465.3.

Example 311, Compound 291

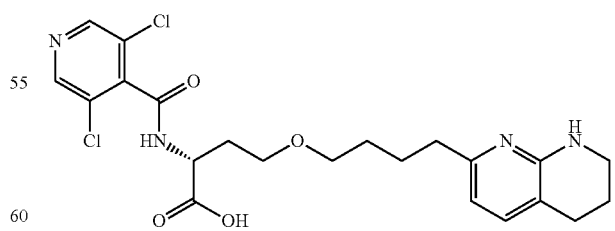

N-(3,5-dichloroisonicotinoyl)-O-(4-(5,6,7,8-tetrahydro-1,8-naphthyridin-2-yl)butyl)-D-homoserine. Isomer F1 was employed in General Scheme F-2 using General Procedure I with 3,5-dichloroisonicotinic acid. LCMS theoretical m/z=480.1. [M+H]+. found 481.1.

Example 312. Compound 292

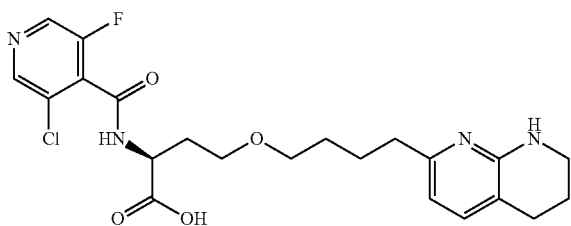

N-(3-chloro-5-fluoroisonicotinoyl)-O-(4-(5,6,7,8-tetrahydro-1,8-naphthyridin-2-yl)butyl)-L-homoserine. Isomer F2 was employed in General Scheme F-2 using General Procedure I with 3-chloro-5-fluoroisonicotinic acid. LCMS theoretical m/z=464.2. [M+H]+. found 465.1.

Example 313, Compound 293

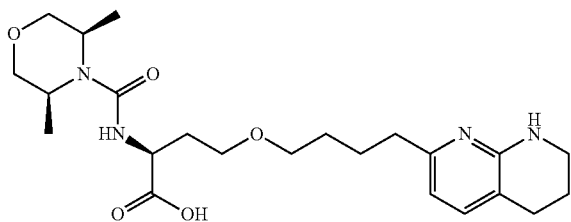 [SMILES: C[C@@H]1COC[C@H](C)N1C(=O)N[C@@H](CCOCCCCc1ccc2c(n1)NCCC2)C(=O)O]

N-((3R,5S)-3,5-dimethylmorpholine-4-carbonyl)-O-(4-(5,6,7,8-tetrahydro-1,8-naphthyridin-2-yl)butyl)-L-homoserine. Isomer F2 was employed in General Scheme F-2 using General Procedure G with (3R,5S)-3,5-dimethylmorpholine. LCMS theoretical m/z=448.3. [M+H]+. found 449.3.

Example 314, Compound 294

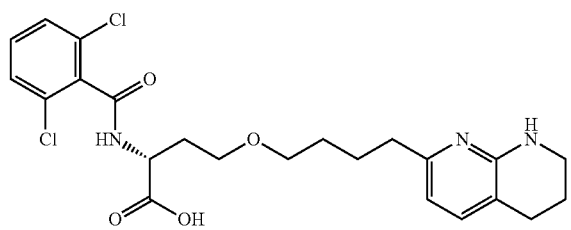 [SMILES: O=C(N[C@H](CCOCCCCc1ccc2c(n1)NCCC2)C(=O)O)c1c(Cl)cccc1Cl]

N-(2,6-dichlorobenzoyl)-O-(4-(5,6,7,8-tetrahydro-1,8-naphthyridin-2-yl)butyl)-D-homoserine. Isomer F1 was employed in General Scheme F-2 using General Procedure I with 2,6-dichlorobenzoic acid. LCMS theoretical m/z=479.1. [M+H]+. found 480.1.

Example 315, Compound 295

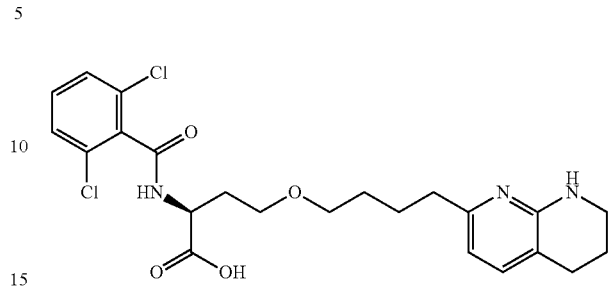

N-(2,6-dichlorobenzoyl)-O-(4-(5,6,7,8-tetrahydro-1,8-naphthyridin-2-yl)butyl)-L-homoserine. Isomer F2 was employed in General Scheme F-2 using General Procedure I with 2,6-dichlorobenzoic acid. LCMS theoretical m/z=479.1. [M+H]+. found 480.1.

Example 316, Compound 296

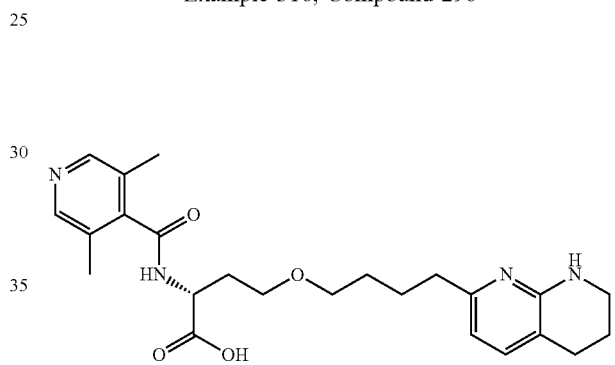

N-(3,5-dimethylisonicotinoyl)-O-(4-(5,6,7,8-tetrahydro-1,8-naphthyridin-2-yl)butyl)-D-homoserine. Isomer F1 was employed in General Scheme F-2 using General Procedure I with 3,5-dimethylisonicotinic acid. LCMS theoretical m/z=440.2. [M+H]+. found 441.2.

Example 317, Compound 297

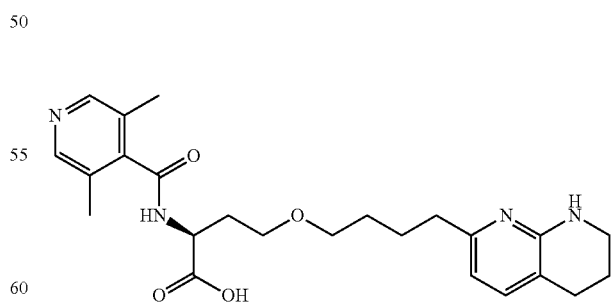

N-(3,5-dimethylisonicotinoyl)-O-(4-(5,6,7,8-tetrahydro-1,8-naphthyridin-2-yl)butyl)-L-homoserine. Isomer F2 was employed in General Scheme F-2 using General Procedure I with 3,5-dimethylisonicotinic acid. LCMS theoretical m/z=440.2. [M+H]+. found 441.2.

Example 318, Compound 298

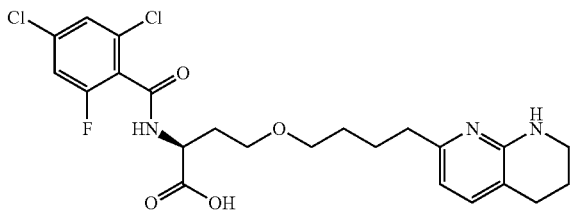 [SMILES: O=C(N[C@@H](CCOCCCCc1ccc2c(n1)NCCC2)C(=O)O)c1c(F)cc(Cl)cc1Cl]

N-(2,4-dichloro-6-fluorobenzoyl)-O-(4-(5,6,7,8-tetrahydro-1,8-naphthyridin-2-yl)butyl)-L-homoserine. Isomer F2 was employed in General Scheme F-2 using General Procedure I with 2,4-dichloro-6-fluorobenzoic acid. LCMS theoretical m/z=497.1 [M+H]+. found 498.1.

Example 319, Compound 299

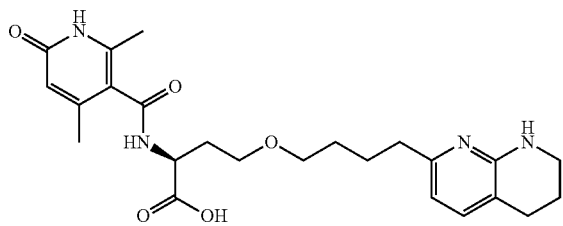 [SMILES: Cc1cc(=O)[nH]c(C)c1C(=O)N[C@@H](CCOCCCCc1ccc2c(n1)NCCC2)C(=O)O]

N-(2,4-dimethyl-6-oxo-1,6-dihydropyridine-3-carbonyl)-O-(4-(5,6,7,8-tetrahydro-1,8-naphthyridin-2-yl)butyl)-L-homoserine. Isomer F2 was employed in General Scheme F-2 using General Procedure I with 2,4-dimethyl-6-oxo-1,6-dihydropyridine-3-carboxylic acid. LCMS theoretical m/z=456.2. [M+H]+. found 457.2.

Example 320, Compound 300

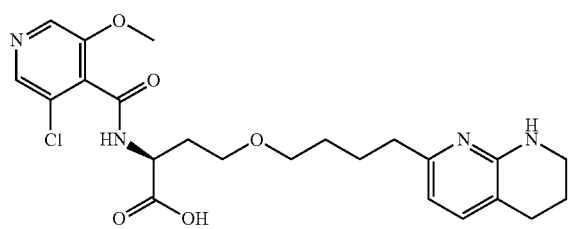 [SMILES: COc1cncc(Cl)c1C(=O)N[C@@H](CCOCCCCc1ccc2c(n1)NCCC2)C(=O)O]

N-(3-chloro-5-methoxyisonicotinoyl)-U-(4-(5,6,7,8-tetrahydro-1,8-naphthyridin-2-yl)butyl)-L-homoserine. Isomer F2 was employed in General Scheme F-2 using General Procedure I with 3-chloro-5-methoxyisonicotinic acid. LCMS theoretical m/z=476.2. [M+H]+. found 477.1.

Example 321, Compound 301

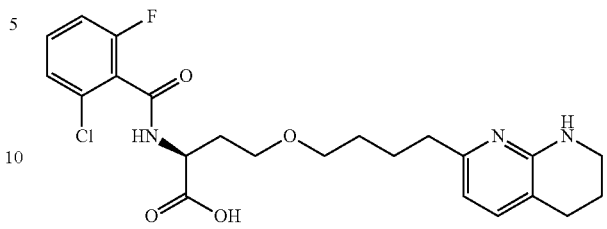

N-(2-chloro-6-fluorobenzoyl)-O-(4-(5,6,7,8-tetrahydro-1,8-naphthyridin-2-yl)butyl)-L-homoserine. Isomer F2 was employed in General Scheme F-2 using General Procedure I with 2-chloro-6-fluorobenzoic acid. LCMS theoretical m/z=463.2. [M+H]+. found 464.2.

Example 322, Compound 302

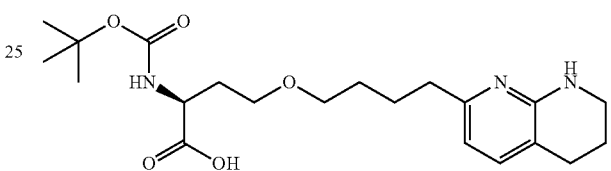

N-(tert-butoxycarbonyl)-O-(4-(5,6,7,8-tetrahydro-1,8-naphthyridin-2-yl)butyl)-L-homoserine. Isomer F2 was employed in General Scheme F-2 using General Procedure N. LCMS theoretical m/z=421.2. [M+H]+. found 422.2.

Example 323, Compound 303

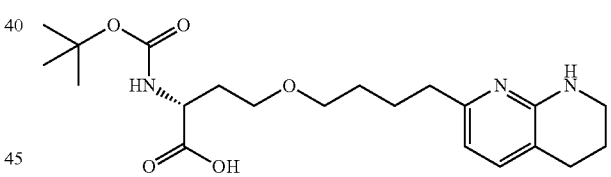

N-(tert-butoxycarbonyl)-O-(4-(5,6,7,8-tetrahydro-1,8-naphthyridin-2-yl)butyl)-D-homoserine. Isomer F1 was employed in General Scheme F-2 using General Procedure N. LCMS theoretical m/z=421.2. [M+H]+. found 422.2.

Example 324. Compound 304

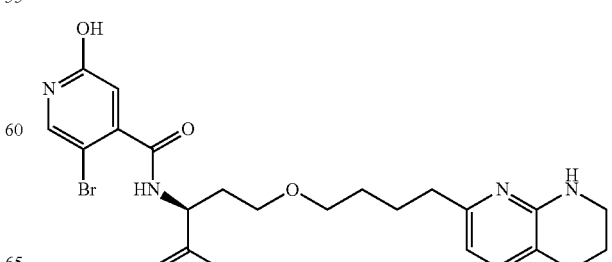

N-(5-bromo-2-hydroxyisonicotinoyl)-O-(4-(5,6,7,8-tetrahydro-1,8-naphthyridin-2-yl)butyl)-L-homoserine. Isomer F2 was employed in General Scheme F-2 using General Procedure I with 5-bromo-2-hydroxyisonicotinic acid. LCMS theoretical m/z=506.1. [M+H]+. found 507.1.

Example 325. Compound 305

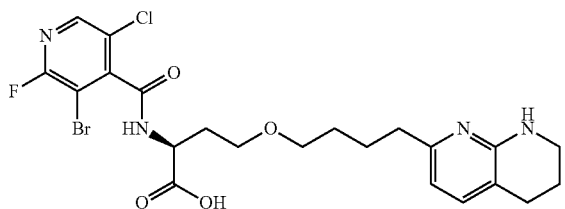 [SMILES: O=C(N[C@@H](CCOCCCCc1ccc2c(n1)NCCC2)C(=O)O)c1c(Cl)cnc(F)c1Br]

N-(3-bromo-5-chloro-2-fluoroisonicotinoyl)-O-(4-(5,6,7,8-tetrahydro-1,8-naphthyridin-2-yl)butyl)-L-homoserine. Isomer F2 was employed in General Scheme F-2 using General Procedure I with 3-bromo-5-chloro-2-fluoroisonicotinic acid. LCMS theoretical m/z=542.1. [M+H]+. found 543.1.

Example 326, Compound 306

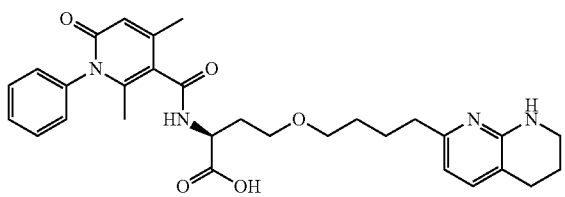 [SMILES: Cc1cc(=O)n(-c2ccccc2)c(C)c1C(=O)N[C@@H](CCOCCCCc1ccc2c(n1)NCCC2)C(=O)O]

N-(2,4-dimethyl-6-oxo-1-phenyl-1,6-dihydropyridine-3-carbonyl)-O-(4-(5,6,7,8-tetrahydro-1,8-naphthyridin-2-yl)butyl)-L-homoserine. Isomer F2 was employed in General Scheme F-2 using General Procedure I with 2,4-dimethyl-6-oxo-1-phenyl-1,6-dihydropyridine-3-carboxylic acid. LCMS theoretical m/z=532.3. [M+H]+. found 533.3.

Example 327, Compound 307

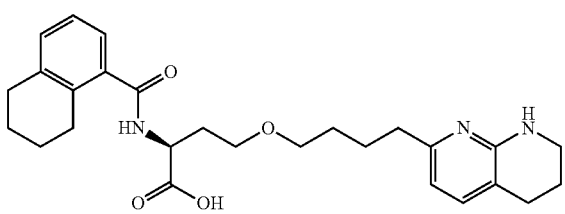 [SMILES: O=C(N[C@@H](CCOCCCCc1ccc2c(n1)NCCC2)C(=O)O)c1cccc2c1CCCC2]

O-(4-(5,6,7,8-tetrahydro-1,8-naphthyridin-2-yl)butyl)-N-(5,6,7,8-tetrahydronaphthalene-1-carbonyl)-L-homoserine. Isomer F2 was employed in General Scheme F-2 using General Procedure I with 5,6,7,8-tetrahydronaphthalene-1-carboxylic acid. LCMS theoretical m/z=465.3. [M+H]+. found 466.2.

Example 328, Compound 308

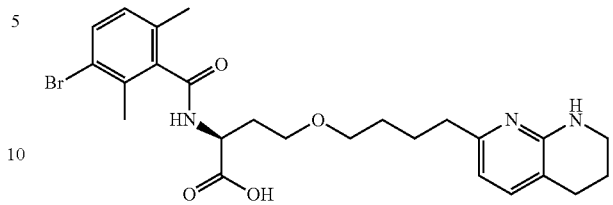

N-(3-bromo-2,6-dimethylbenzoyl)-O-(4-(5,6,7,8-tetrahydro-1,8-naphthyridin-2-yl)butyl)-L-homoserine. Isomer F2 was employed in General Scheme F-2 using General Procedure I with 3-bromo-2,6-dimethylbenzoic acid. LCMS theoretical m/z=517.2. [M+H]+. found 518.2.

Example 329, Compound 309

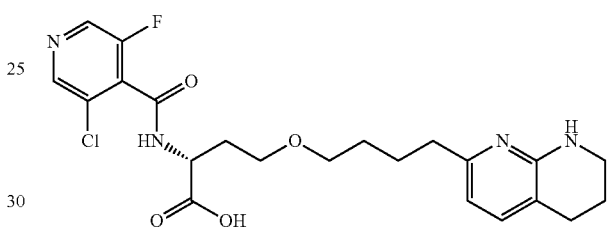

N-(3-chloro-5-fluoroisonicotinoyl)-O-(4-(5,6,7,8-tetrahydro-1,8-naphthyridin-2-yl)butyl)-D-homoserine. Isomer F1 was employed in General Scheme F-2 using General Procedure I with 3-chloro-5-fluoroisonicotinic acid. LCMS theoretical m/z=464.1. [M+H]+. found 465.1.

Example 330, Compound 310

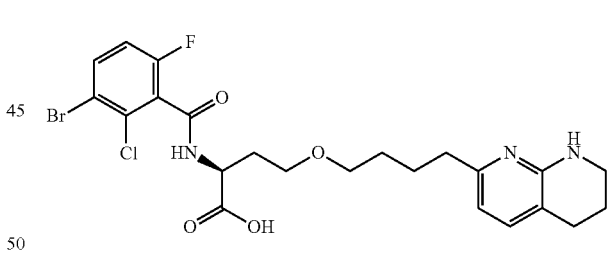

N-(3-bromo-2-chloro-6-fluorobenzoyl)-O-(4-(5,6,7,8-tetrahydro-1,8-naphthyridin-2-yl)butyl)-L-homoserine. Isomer F2 was employed in General Scheme F-2 using General Procedure I with 3-bromo-2-chloro-6-fluorobenzoic acid. LCMS theoretical m/z=541.1. [M+H]+. found 542.1.

General Scheme I

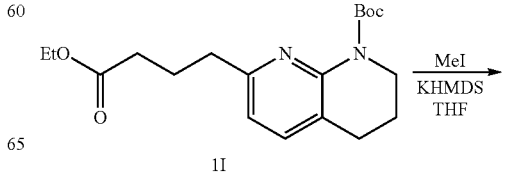

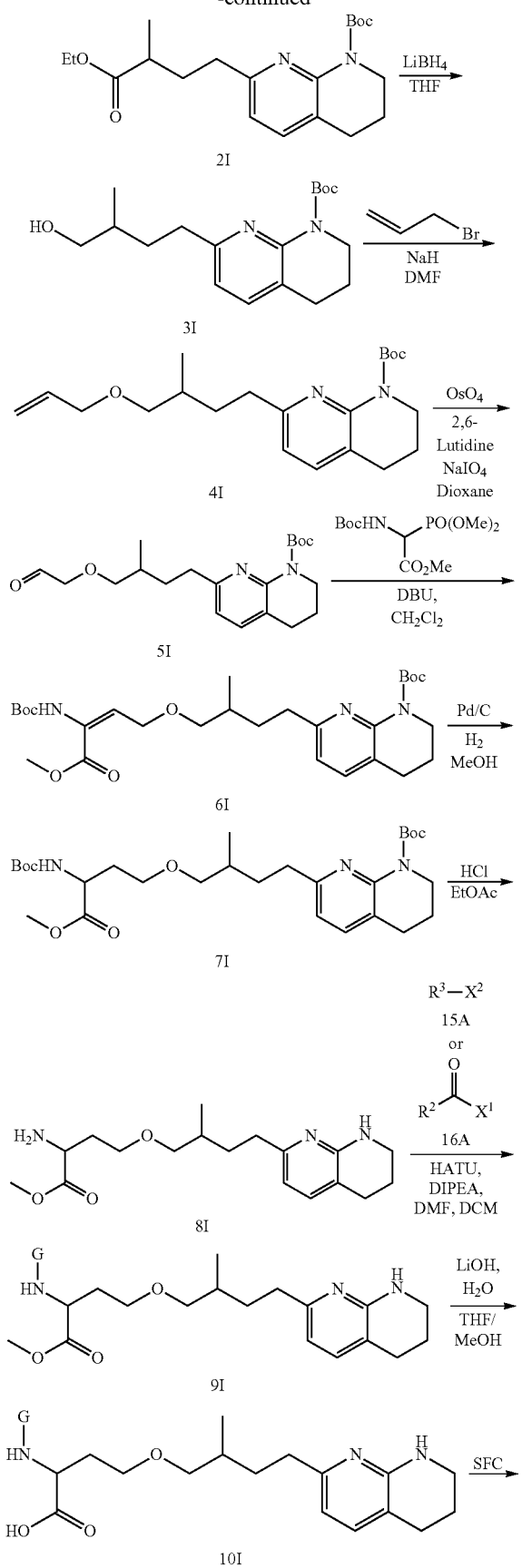

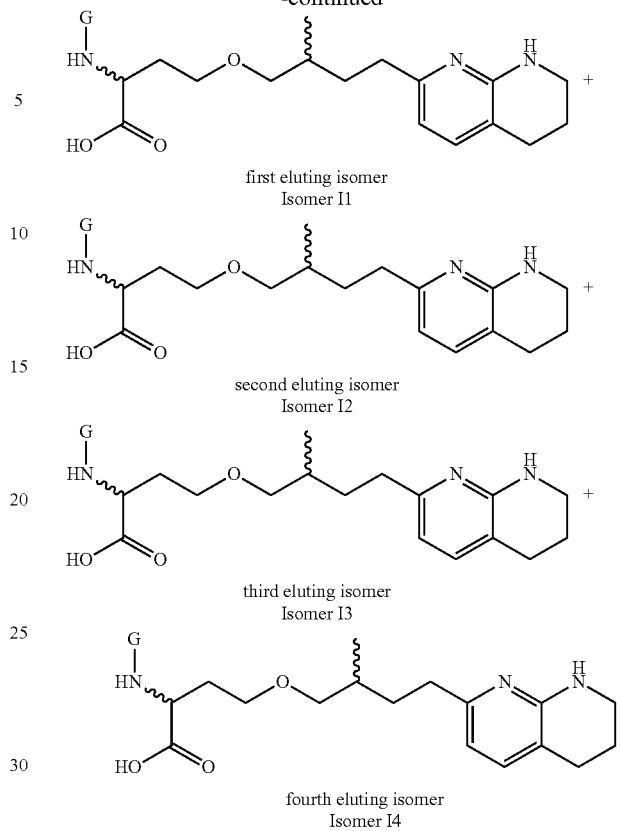

tert-butyl 7-(4-hydroxy-3-methylbutyl)-3,4-dihydro-1,8-naphthyridine-1(2H)-carboxylate (2I in Scheme I). To a solution of tert-butyl 7-(4-ethoxy-4-oxobutyl)-3,4-dihydro-1,8-naphthyridine-1(2H)-carboxylate (1I in Scheme I, 20 g, 57.40 mmol) and MeI (8.15 g, 57.40 mmol) in THF (200 mL) was added KHMDS (1 M, 57.40 mL) dropwise under $N_2$ at −78° C. and the resulting mixture was allowed to stir for 1 h at −78° C. The mixture was then warmed to 0° C. and then to this was slowly added EtOAc (100 mL) followed by a saturated aqueous solution of ammonium chloride (600 mL). The layers were separated and the aqueous layer was extracted with EtOAc. The combined organic extracts were dried over $Na_2SO_4$, filtered, and concentrated in vacuo. The crude residue was purified by normal phase silica gel chromatography to give the title compound. Starting from the title compound, the remainder of the reactions in Scheme I were conducted analogously to the corresponding reactions in Scheme C/General Procedure C to provide the following five compounds.

Example 331, Compound 311

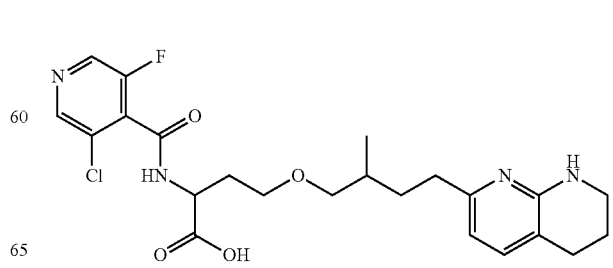

N-(3-chloro-5-fluoroisonicotinoyl)-O-(2-methyl-4-(5,6,7,8-tetrahydro-1,8-naphthyridin-2-yl)butyl)homoserine. Prepared according to General Scheme I using General Procedure N with 3-chloro-5-fluoroisonicotinic acid whereby the title compound was isolated a racemic mixture. LCMS theoretical m/z=478.1. [M+H]+. found 479.1.

Example 332, Compound 312

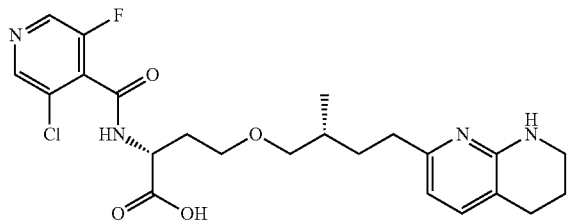 [SMILES: C[C@H](CCc1ccc2c(n1)NCCC2)COCC[C@@H](NC(=O)c1c(F)cncc1Cl)C(=O)O]

N-(3-chloro-5-fluoroisonicotinoyl)-O—((R)-2-methyl-4-(5,6,7,8-tetrahydro-1,8-naphthyridin-2-yl)butyl)-D-homoserine. Prepared according to General Scheme I using General Procedure N with 3-chloro-5-fluoroisonicotinic acid to provide a racemic mixture. The title compound was isolated from the racemic mixture as the fourth eluting isomer by SFC. LCMS theoretical m/z=478.1. [M+H]+. found 479.1.

Example 333, Compound 313

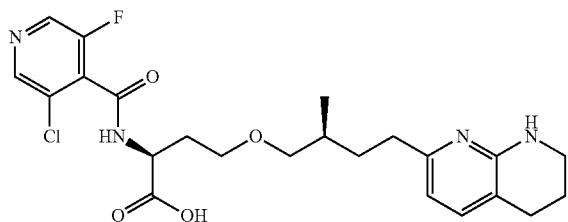 [SMILES: C[C@@H](CCc1ccc2c(n1)NCCC2)COCC[C@H](NC(=O)c1c(F)cncc1Cl)C(=O)O]

N-(3-chloro-5-fluoroisonicotinoyl)-O—((S)-2-methyl-4-(5,6,7,8-tetrahydro-1,8-naphthyridin-2-yl)butyl)-L-homoserine. Prepared according to General Scheme I using General Procedure N with 3-chloro-5-fluoroisonicotinic acid to provide a racemic mixture. The title compound was isolated from the racemic mixture as the first eluting isomer by SFC. LCMS theoretical m/z=478.1. [M+H]+. found 479.1.

Example 334, Compound 314

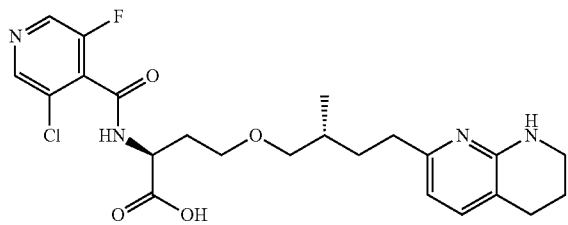 [SMILES: C[C@H](CCc1ccc2c(n1)NCCC2)COCC[C@H](NC(=O)c1c(F)cncc1Cl)C(=O)O]

N-(3-chloro-5-fluoroisonicotinoyl)-O—((R)-2-methyl-4-(5,6,7,8-tetrahydro-1,8-naphthyridin-2-yl)butyl)-L-homoserine. Prepared according to General Scheme I using General Procedure N with 3-chloro-5-fluoroisonicotinic acid to provide a racemic mixture. The title compound was isolated from the racemic mixture as the second eluting isomer by SFC. LCMS theoretical m/z=478.1. [M+H]+. found 479.1.

Example 335, Compound 315

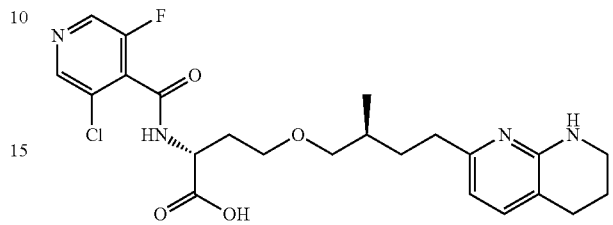

N-(3-chloro-5-fluoroisonicotinoyl)-O—((S)-2-methyl-4-(5,6,7,8-tetrahydro-1,8-naphthyridin-2-yl)butyl)-D-homoserine. Prepared according to General Scheme I using General Procedure N with 3-chloro-5-fluoroisonicotinic acid to provide a racemic mixture. The title compound was isolated from the racemic mixture as the third eluting isomer by SFC. LCMS theoretical m/z=478.1. [M+H]+. found 479.1.

Example 336, Compound 316

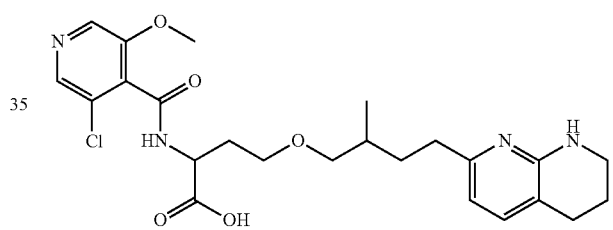

N-(3-chloro-5-methoxyisonicotinoyl)-O-(2-methyl-4-(5,6,7,8-tetrahydro-1,8-naphthyridin-2-yl)butyl)homoserine. Prepared according to General Scheme I using General Procedure N with 3-chloro-5-methoxyisonicotinic acid to provide a racemic mixture. The title compound was isolated from the racemic mixture by preparative reverse phase HPLC. LCMS theoretical m/z=490.2. [M+H]+. found 490.9.

Example 337, Compound 317

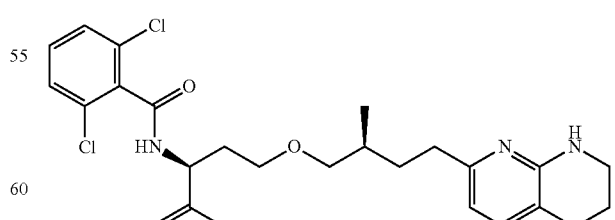

N-(2,6-dichlorobenzoyl)-O—((S)-2-methyl-4-(5,6,7,8-tetrahydro-1,8-naphthyridin-2-yl)butyl)-L-homoserine. Prepared according to General Scheme I using General Procedure N with 2,6-dichlorobenzoic acid. The title compound was isolated as the first eluting isomer by SFC. LCMS theoretical m/z=493.2. [M+H]+. found 494.2.

Example 338, Compound 318

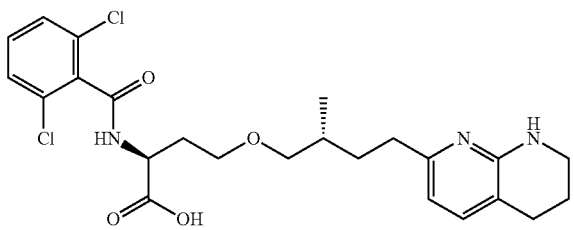 [SMILES: C[C@H](CCc1ccc2c(n1)NCCC2)COCC[C@H](NC(=O)c1c(Cl)cccc1Cl)C(=O)O]

N-(2,6-dichlorobenzoyl)-O—((R)-2-methyl-4-(5,6,7,8-tetrahydro-1,8-naphthyridin-2-yl)butyl)-L-homoserine. Prepared according to General Scheme I using General Procedure N with 2,6-dichlorobenzoic acid. The title compound was isolated as the second eluting isomer by SFC. LCMS theoretical m/z=493.2. [M+H]+. found 494.2.

Example 339, Compound 319

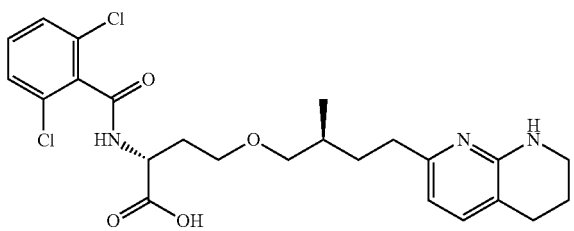 [SMILES: C[C@@H](CCc1ccc2c(n1)NCCC2)COCC[C@@H](NC(=O)c1c(Cl)cccc1Cl)C(=O)O]

N-(2,6-dichlorobenzoyl)-O—((S)-2-methyl-4-(5,6,7,8-tetrahydro-1,8-naphthyridin-2-yl)butyl)-D-homoserine. Prepared according to General Scheme I using General Procedure N with 2,6-dichlorobenzoic acid. The title compound was isolated as the third eluting isomer by SFC. LCMS theoretical m/z=493.2. [M+H]+. found 494.2.

Example 340, Compound 320

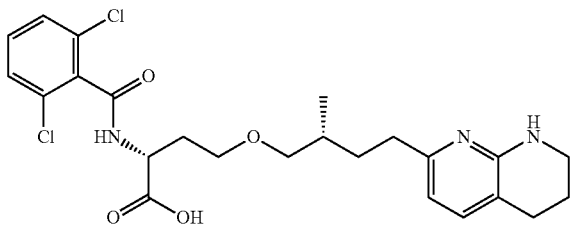 [SMILES: C[C@H](CCc1ccc2c(n1)NCCC2)COCC[C@@H](NC(=O)c1c(Cl)cccc1Cl)C(=O)O]

N-(2,6-dichlorobenzoyl)-O—((R)-2-methyl-4-(5,6,7,8-tetrahydro-1,8-naphthyridin-2-yl)butyl)-D-homoserine. Prepared according to General Scheme I using General Procedure N with 2,6-dichlorobenzoic acid. The title compound was isolated as the fourth eluting isomer by SFC. LCMS theoretical m/z=493.2. [M+H]+. found 494.2.

Example 341, Compound 321

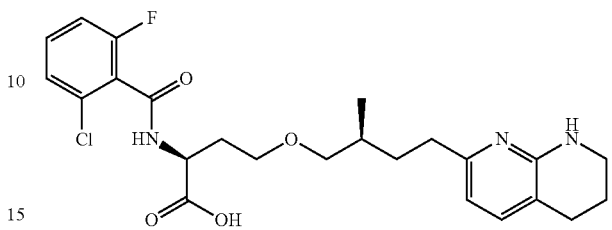

N-(2-chloro-6-fluorobenzoyl)-O—((S)-2-methyl-4-(5,6,7,8-tetrahydro-1,8-naphthyridin-2-yl)butyl)-L-homoserine. Prepared according to General Scheme I using General Procedure N with 2-chloro-6-fluorobenzoic acid. The title compound was isolated as the first eluting isomer by SFC. LCMS theoretical m/z=477.2 [M+H]+. found 478.1.

Example 342. Compound 322

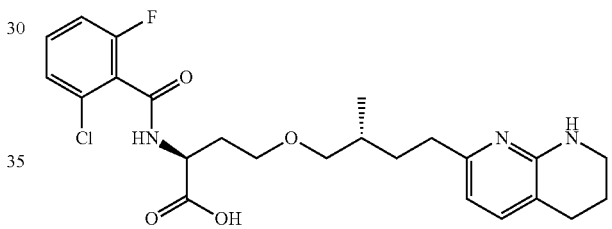

N-(2-chloro-6-fluorobenzoyl)-O—((R)-2-methyl-4-(5,6,7,8-tetrahydro-1,8-naphthyridin-2-yl)butyl)-L-homoserine. Prepared according to General Scheme I using General Procedure N with 2-chloro-6-fluorobenzoic acid. The title compound was isolated as the second eluting isomer by SFC. LCMS theoretical m/z=477.2 [M+H]+. found 478.1.

Example 343, Compound 323

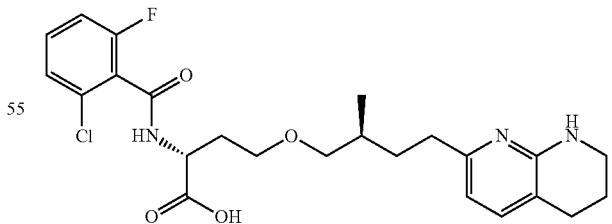

N-(2-chloro-6-fluorobenzoyl)-O—((S)-2-methyl-4-(5,6,7,8-tetrahydro-1,8-naphthyridin-2-yl)butyl)-D-homoserine. Prepared according to General Scheme I using General Procedure N with 2-chloro-6-fluorobenzoic acid. The title compound was isolated as the third eluting isomer by SFC. LCMS theoretical m/z=477.2 [M+H]+. found 478.1.

Example 344, Compound 324

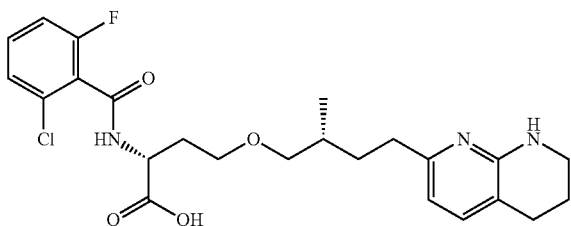 [SMILES: C[C@H](CCc1ccc2c(n1)NCCC2)COCC[C@@H](NC(=O)c1c(F)cccc1Cl)C(=O)O]

N-(2-chloro-6-fluorobenzoyl)-O—((R)-2-methyl-4-(5,6,7,8-tetrahydro-1,8-naphthyridin-2-yl)butyl)-D-homoserine. Prepared according to General Scheme I using General Procedure N with 2-chloro-6-fluorobenzoic acid. The title compound was isolated as the fourth eluting isomer by SFC. LCMS theoretical m/z=477.2 [M+H]+. found 478.1.

Example 345, Compound 325

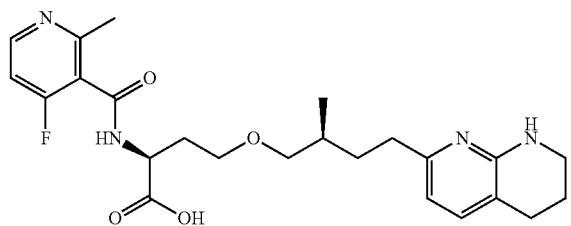 [SMILES: Cc1nccc(F)c1C(=O)N[C@@H](CCOC[C@@H](C)CCc1ccc2c(n1)NCCC2)C(=O)O]

N-(4-fluoro-2-methylnicotinoyl)-O—((S)-2-methyl-4-(5,6,7,8-tetrahydro-1,8-naphthyridin-2-yl)butyl)-L-homoserine. Prepared according to General Scheme I using General Procedure N with 4-fluoro-2-methylnicotinic acid. The title compound was isolated as the first eluting isomer by SFC. LCMS theoretical m/z=458.2 [M+H]+. found 459.2.

Example 346, Compound 326

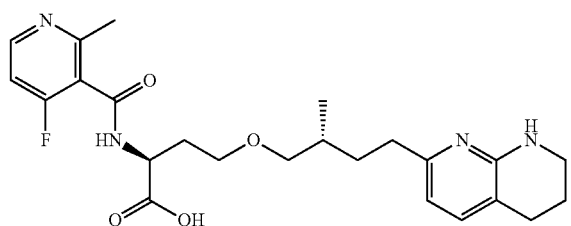 [SMILES: Cc1nccc(F)c1C(=O)N[C@@H](CCOC[C@H](C)CCc1ccc2c(n1)NCCC2)C(=O)O]

N-(4-fluoro-2-methylnicotinoyl)-O—((R)-2-methyl-4-(5,6,7,8-tetrahydro-1,8-naphthyridin-2-yl)butyl)-L-homoserine. Prepared according to General Scheme I using General Procedure N with 4-fluoro-2-methylnicotinic acid. The title compound was isolated as the second eluting isomer by SFC. LCMS theoretical m/z=458.2 [M+H]+. found 459.2.

Example 347, Compound 327

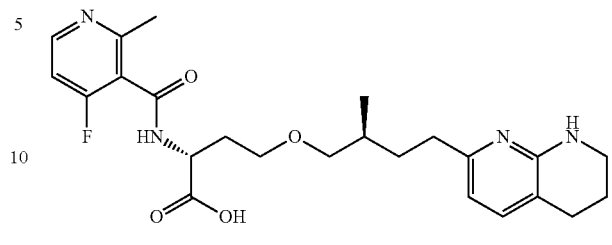

N-(4-fluoro-2-methylnicotinoyl)-O—((S)-2-methyl-4-(5,6,7,8-tetrahydro-1,8-naphthyridin-2-yl)butyl)-D-homoserine. Prepared according to General Scheme I using General Procedure N with 4-fluoro-2-methylnicotinic acid. The title compound was isolated as the third eluting isomer by SFC. LCMS theoretical m/z=458.2. [M+H]+. found 459.2.

Example 348, Compound 328

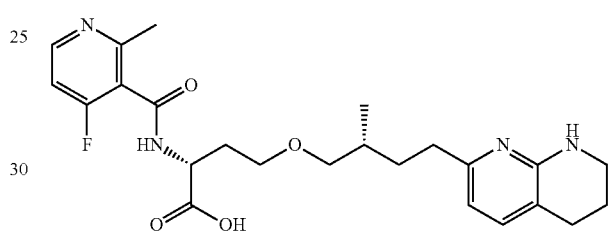

N-(4-fluoro-2-methylnicotinoyl)-O—((R)-2-methyl-4-(5,6,7,8-tetrahydro-1,8-naphthyridin-2-yl)butyl)-D-homoserine. Prepared according to General Scheme I using General Procedure N with 4-fluoro-2-methylnicotinic acid. The title compound was isolated as the fourth eluting isomer by SFC. LCMS theoretical m/z=458.2. [M+H]+. found 459.2.

General Scheme J

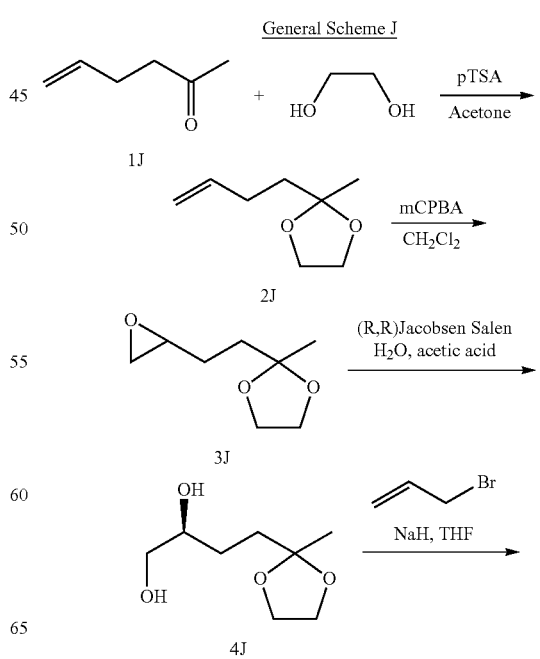

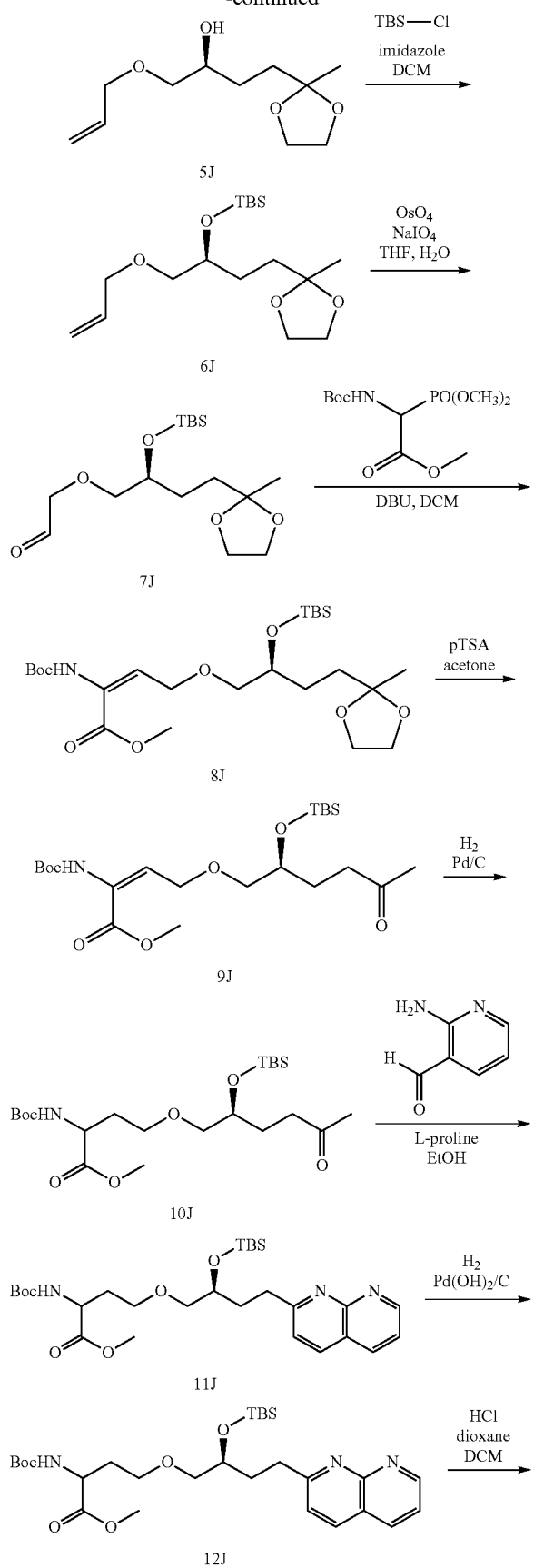

2-(but-3-en-1-yl)-2-methyl-1,3-dioxolane. To a solution of hex-5-en-2-one (18 mL, 155 mmol) in toluene (155 mL) was added ethylene glycol (11.3 mL, 202 mmol) and p-toluenesulfonic acid monohydrate (2.96 g, 15.5 mmol)), and the resulting mixture was stirred at 110° C. overnight and was diluted with water and EtOAc. The layers were separated, and the aqueous layer was extracted with EtOAc. The combined organic layers were washed with water and brine, dried over $Na_2SO_4$, filtered, and concentrated in vacuo to give the title compound, which was used without further purification 2-methyl-2-(2-(oxiran-2-yl)ethyl)-1,3-dioxolane. To a solution of 2-(but-3-en-1-yl)-2-methyl-1,3-dioxolane (15.8 g, 111 mmol) in DCM (200 mL) was added m-chloroperoxybenzoic acid (23 g, 134 mmol), and the resulting mixture was stirred at rt overnight was diluted with water and DCM. The layers were separated, and the aqueous layer was extracted with DCM. The combined organic layers were washed with water and brine, dried over $Na_2SO_4$, filtered, and concentrated in vacuo to give the title compound, which was used without further purification.

(S)-4-(2-methyl-1,3-dioxolan-2-vi)butane-1,2-diol. To a solution of 2-methyl-2-(2-(oxiran-2-yl)ethyl)-1,3-dioxolane (5.3 g, 33 mmol) in toluene (67 mL) was added (R,R)-(−)-N,N"-bis(3,5-di-tertbutylsalicylidene)-1,2-cyclohexanediaminocobalt(II) (40.55 mg, 0.07 mmol), acetic acid (0.04 mL, 0.67 mmol), and water (0.33 mL, 18.5 mmol) and the resulting mixture was allowed to stir at rt overnight rt overnight and then was concentrated in vacuo. The crude residue was purified by silica gel chromatography to give the title compound.

(S)-1-(allyloxy)-4-(2-methyl-1,3-dioxolan-2-yl)butan-2-ol. To a solution of (S)-4-(2-methyl-1,3-dioxolan-2-yl)butane-1,2-diol (1.8 g, 10.2 mmol) in THF (34 mL) was added NaH (410 mg, 10.2 mmol) at 0° C. and the resulting mixture was stirred at rt. After 1 h, allyl bromide (0.9 mL, 10.2 mmol) was added and the resulting mixture was allowed to stir at rt overnight and was concentrated in vacuo. The crude residue was purified by normal phase silica gel chromatography to give the title compound.

(S)-((1-(allyloxy)-4-(2-methyl-1,3-dioxolan-2-yl)butan-2-yl)oxy)(tert-butyl)dimethylsilane. To a solution of (S)-1-(allyloxy)-4-(2-methyl-1,3-dioxolan-2-yl)butan-2-ol (1.00 g, 4.6 mmol) in $CH_2Cl_2$ (9 mL) was added imidazole (1.1 g, 16 mmol) and TBSCl (1.8 mL, 6.9 mmol) and the resulting mixture was allowed to stir at rt for 10 min. The reaction mixture was diluted with saturated sodium bicarbonate and $CH_2Cl_2$. The combined organic layers were washed with water and brine, dried over $Na_2SO_4$, filtered, and concentrated in vacuo. The crude residue was purified by normal phase silica gel chromatography to give the title compound.

(S)-2-(2-((tert-butyldimethylsilyl)oxy)-4-(2-methyl-1,3-dioxolan-2-yl)butoxy)acetaldehyde. To a solution of (S)-((1-(allyloxy)-4-(2-methyl-1,3-dioxolan-2-yl)butan-2-yl)oxy)(tert-butyl)dimethylsilane (1.1 g, 2.4 mmol) in 3:1 THF/$H_2O$ (15 mL) was added $NaIO_4$ (2.1 g, 9.7 mmol) and $OsO_4$ (0.04 mL, 0.121 mmol) and the resulting mixture was allowed to stir at rt for 3 h and was diluted with saturated sodium bicarbonate, saturated sodium thiosulfate, and EtOAc. The layers were separated and the aqueous layer was extracted EtOAc. The combined organic layers were washed with water and brine, dried over $Na_2SO_4$, filtered, and concentrated in vacuo to give the title compound which was used without further purification.

methyl (S,E)-2-((tert-butoxycarbonyl)amino)-4-(2-((tert-butyldimethylsilyl)oxy)-4-(2-methyl-1,3-dioxolan-2-yl)butoxy)but-2-enoate. To a solution of (S)-2-(2-((tert-butyldimethylsilyl)oxy)-4-(2-methyl-1,3-dioxolan-2-yl)butoxy)acetaldehyde (1.1 mg, 2.4 mmol) in $CH_2Cl_2$ (6 mL) was added methyl 2-((tert-butoxycarbonyl)amino)-2-(dimethoxyphosphoryl)acetate (718 mg, 5.3 mmol) and DBU (0.53 mL, 3.50 mmol) and the resulting mixture was allowed to stir at rt for 2 h and then concentrated in vacuo. The crude residue was purified by normal phase column chromatography to give the title compound.

methyl (S,E)-2-((tert-butoxycarbonyl)amino)-4-((2-((tert-butyldimethylsilyl)oxy)-5-oxohexyl)oxy)but-2-enoate. To a solution of methyl (S,E)-2-((tert-butoxycarbonyl)amino)-4-(2-((tert-butyldimethylsilyl)oxy)-4-(2-methyl-1,3-dioxolan-2-yl)butoxy)but-2-enoate (12.4 mg, 0.02 mmol) in $CH_3CN$/$H_2O$ 4:1 (0.5 mL) was added DDQ (0.9 mg, 0.004 mmol) and the resulting mixture was allowed to stir at rt for 2 h and then concentrated in vacuo. The crude residue was purified by normal phase column chromatography to give the title compound.

methyl N-(tert-butoxycarbonyl)-O—((S)-2-((tert-butyldimethylsilyl)oxy)-5-oxohexyl)homoserinate. To a solution of methyl (S,E)-2-((tert-butoxycarbonyl)amino)-4-((2-((tert-butyldimethylsilyl)oxy)-5-oxohexyl)oxy)but-2-enoate (195 mg, 0.334 mmol) in MeOH (2 mL) was added Pd(OH)$_2$/C (20 wt % on carbon, 20 mg) and the resulting mixture was stirred under an $H_2$ atmosphere overnight and was filtered through Celite then concentrated in vacuo to give the title compound which was used without further purification.

methyl N-(tert-butoxycarbonyl)-O—((S)-2-((tert-butyldimethylsilyl)oxy)-4-(1,8-naphthyridin-2-yl)butyl)homoserinate. To a solution of methyl N-(tert-butoxycarbonyl)-O—((S)-2-((tert-butyldimethylsilyl)oxy)-5-oxohexyl)homoserinate (200 mg, 0.341 mmol) in EtOH (1 mL) was added L-proline (27.5 mg, 0.239 mmol) and 2-aminonicotinaldehyde (83.4 mg, 0.683 mmol) and the resulting mixture was stirred at 75° C. overnight and was then concentrated in vacuo. The crude residue was purified by normal phase column chromatography to give the title compound.

methyl N-(tert-butoxycarbonyl)-O—((S)-2-((tert-butyldimethylsilyl)oxy)-4-(1,8-naphthyridin-2-yl)butyl)homoserinate. To a solution of methyl N-(tert-butoxycarbonyl)-O—((S)-2-((tert-butyldimethylsilyl)oxy)-4-(1,8-naphthyridin-2-yl)butyl)homoserinate (67.1 mg, 0.10 mmol) in MeOH (2 mL) was added Pd(OH)$_2$/C (20 wt % on carbon, 20 mg) and the resulting mixture was stirred under an $H_2$ atmosphere overnight and was filtered through Celite then concentrated in vacuo. The crude residue was purified by normal phase silica gel chromatography to the title compound.

methyl O—((S)-2-((tert-butyldimethylsilyl)oxy)-4-(1,8-naphthyridin-2-yl)butyl)homoserinate. To a solution of methyl N-(tert-butoxycarbonyl)-O—((S)-2-((tert-butyldimethylsilyl)oxy)-4-(1,8-naphthyridin-2-yl)butyl)homoserinate (35.0 mg, 0.052 mmol) in DCM (0.1 mL) was added 4 N HCl in 1,4-dioxane (0.06 mL, 0.207 mmol) and the resulting mixture was allowed to stir at rt overnight then was concentrated in vacuo to give the title compound which was used without further purification.

methyl N-(3-chloro-5-fluoroisonicotinoyl)-O—((S)-2-hydroxy-4-(1,8-naphthyridin-2-yl)butyl)homoserinate. To a solution of methyl 4-[(2S)-2-[tert-butyl(diphenyl)silyl]oxy-4-(5,6,7,8-tetrahydro-1,8-naphthyridin-2-yl)butoxy]-2-[(3-chloro-5-fluoro-pyridine-4-carbonyl)amino]butanoate (38.0 mg, 0.0518 mmol) in THF (0.1 mL) was added tetrabutylammonium fluoride (0.06 mL, 0.0622 mmol) and the resulting mixture was allowed to stir at rt for 2 h and was diluted with saturated $NH_4Cl$. The layers were separated and the aqueous layer was extracted $CH_2Cl_2$. The combined organic layers were washed with water and brine, dried over $Na_2SO_4$, filtered, and concentrated in vacuo to give the title compound which was used without further purification.

Example 349, Compound 329

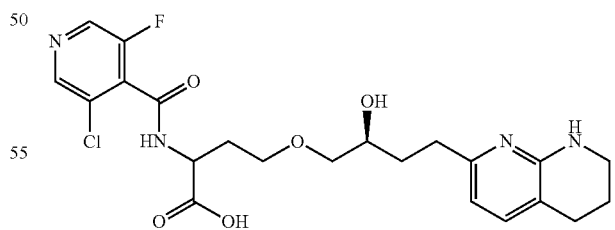

N-(3-chloro-5-fluoroisonicotinoyl)-O—((S)-2-hydroxy-4-(1,8-naphthyridin-2-yl)butyl)homoserine. To a solution of methyl N-(3-chloro-5-fluoroisonicotinoyl)-O—((S)-2-hydroxy-4-(1,8-naphthyridin-2-yl)butyl)homoserinate (25.6 mg, 0.0518 mmol) in THF/MeOH/H2O 3:1:1 was added LiOH (9.9 mg, 0.41 mmol) and the resulting mixture was allowed to stir at rt for 4 h. LCMS showed conversion to product, and the reaction mixture was diluted with water and purified by reverse phase preparative HPLC to afford N-(3-chloro-5-fluoroisonicotinoyl)-O—((S)-2-hydroxy-4-(1,8-naphthyridin-2-yl)butyl)homoserine as a TFA salt.

N-(3-chloro-5-fluoroisonicotinoyl)-O—((S)-2-hydroxy-4-(5,6,7,8-tetrahydro-1,8-naphthyridin-2-yl)butyl)homoserine. (Compound 329, alternate preparation) Prepared according to General Scheme J using General Procedure I with 3-chloro-5-fluoroisonicotinic acid and General Procedure N. The mixture was neutralized with AcOH and then purified by preparative reverse phase HPLC to the title compound as a trifluoroacetic acid salt. LCMS theoretical m/z=480.2. [M+H]+. found 481.1.

Example 350, Compound 10

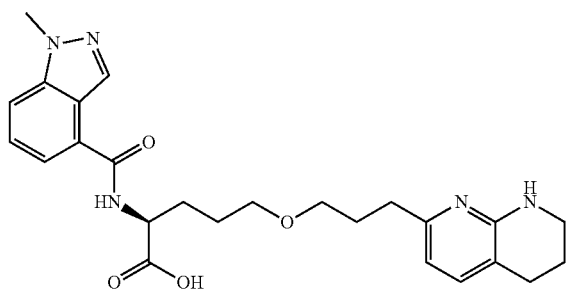 [SMILES: Cn1ncc2c(C(=O)N[C@@H](CCCOCCCc3ccc4c(n3)NCCC4)C(=O)O)cccc21]

(S)-2-(1-methyl-1H-indazole-4-carboxamido)-5-(3-(5,6,7,8-tetrahydro-1,8-naphthyridin-2-yl)propoxy)pentanoic acid. Prepared according to Example 2 with the exception that the acid was replaced by 1-methyl-1H-indazole-4-carboxylic acid in the reaction with intermediate 2i. LCMS theoretical m/z=465.2. [M+H]+. found 466.1.

Example 351, Compound 11

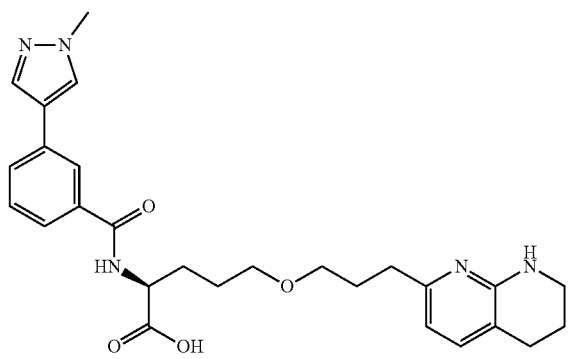

(S)-2-(3-(1-methyl-1H-pyrazol-4-yl)benzamido)-5-(3-(5,6,7,8-tetrahydro-1,8-naphthyridin-2-yl)propoxy)pentanoic acid. Prepared according to Example 2 with the exception that the acid was replaced by 3-(1-methyl-1H-pyrazol-4-yl)benzoic acid in the reaction with intermediate 2i. LCMS theoretical m/z=491.2. [M+H]+. found 492.2.

Example 352, Compound 12

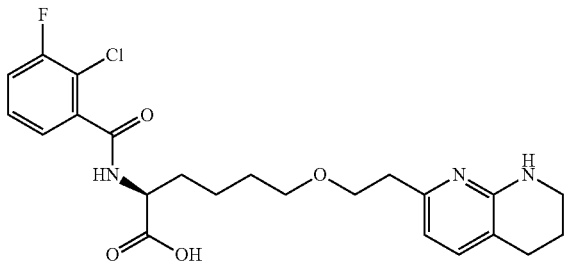 [SMILES: O=C(N[C@@H](CCCCOCCc1ccc2c(n1)NCCC2)C(=O)O)c1cccc(F)c1Cl]

(S)-2-(2-chloro-3-fluorobenzamido)-6-(2-(5,6,7,8-tetrahydro-1,8-naphthyridin-2-yl)ethoxy)hexanoic acid. Prepared according to Example 2 with the exception that the bromide was replaced with 6-bromohex-1-ene in the reaction with intermediate 2d and the acid was replaced by 2-chloro-3-fluorobenzoic acid in the reaction with intermediate 2i. LCMS theoretical m/z=463.2. [M+H]+. found 464.1.

Example 353, Compound 13

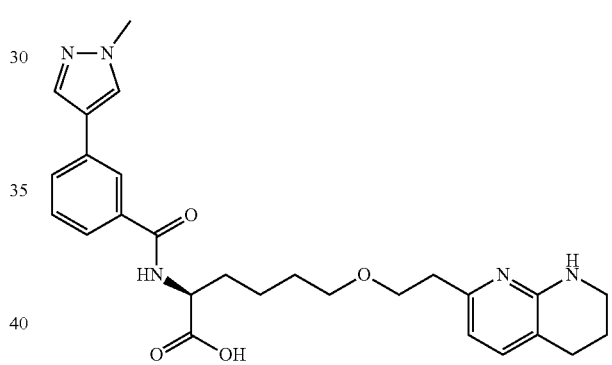

(S)-2-(3-(1-methyl-JH-pyrazol-4-yl)benzamido)-6-(2-(5,6,7,8-tetrahydro-1,8-naphthyridin-2-yl)ethoxy)hexanoic acid prepared according to Example 2 with the exception that the bromide was replaced with 6-bromohex-1-ene in the reaction with intermediate 2d and the acid was replaced by 3-(1-methyl-1H-pyrazol-4-yl)benzoic acid in the reaction with intermediate 2i. LCMS theoretical m/z=491.2. [M+H]+. found 492.2.

Example 354, Compound 16

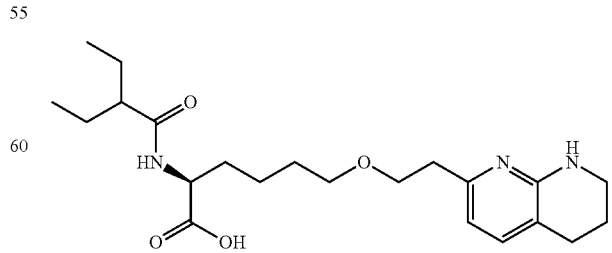

(S)-2-(2-ethylbutanamido)-6-(2-(5,6,7,8-tetrahydro-1,8-naphthyridin-2-yl)ethoxy)hexanoic acid prepared according to Example 2 with the exception that the bromide was replaced with 6-bromohex-1-ene in the reaction with intermediate 2d and the acid was replaced by 2-ethylbutanoic acid in the reaction with intermediate 2i. LCMS theoretical m/z=405.2. [M+H]+. found 406.2.

Example 355, Compound 17

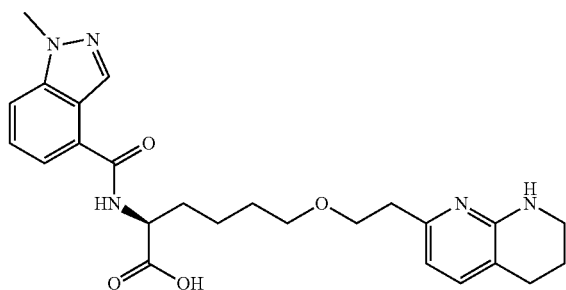 [SMILES: Cn1ncc2c(C(=O)N[C@@H](CCCCOCCc3ccc4c(n3)NCCC4)C(=O)O)cccc21]

(S)-2-(1-methyl-1H-indazole-4-carboxamido)-6-(2-(5,6,7,8-tetrahydro-1,8-naphthyridin-2-yl)ethoxy)hexanoic acid. Prepared according to Example 2 with the exception that the bromide was replaced with 6-bromohex-1-ene in the reaction with intermediate 2d and the acid was replaced by 1-methyl-1H-indazole-4-carboxylic acid in the reaction with intermediate 2i. LCMS theoretical m/z=465.2. [M+H]+. found 466.2.

Example 356, Compound 20

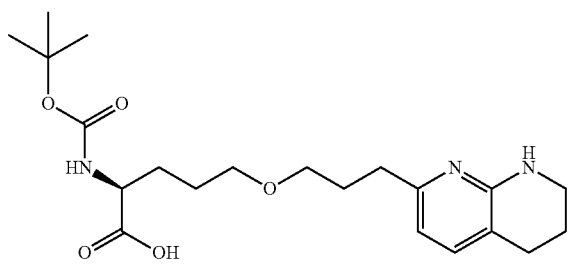 [SMILES: CC(C)(C)OC(=O)N[C@@H](CCCOCCCc1ccc2c(n1)NCCC2)C(=O)O]

(S)-2-((tert-butoxycarbonyl)amino)-5-(3-(5,6,7,8-tetrahydro-1,8-naphthyridin-2-yl)propoxy)pentanoic acid. Prepared according to Example 2 with the exception that the acid was replaced by di-tert-butyl dicarbonate in the reaction with intermediate 2i. LCMS theoretical m/z=407.2. [M+H]+. found 408.2.

Example 357, Compound 21

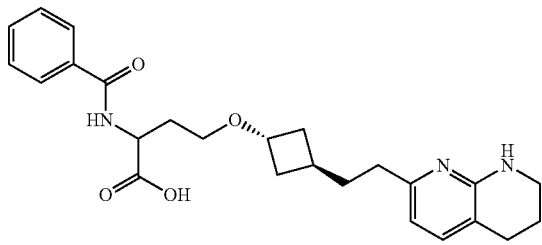 [SMILES: O=C(NC(CCO[C@H]1C[C@H](CCc2ccc3c(n2)NCCC3)C1)C(=O)O)c1ccccc1]

N-benzoyl-O-((1s,3r)-3-(2-(5,6,7,8-tetrahydro-1,8-naphthyridin-2-yl)ethyl)cyclobutyl)homoserine. Isomer D2 was employed in General Scheme D-2 using General Procedure I with benzoic acid. LCMS theoretical m/z=437.2. [M+H]+. found 438.8.

Example 358, Compound 178

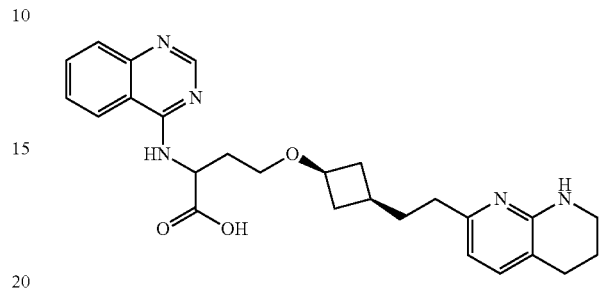

N-(quinazolin-4-yl)-O-((1r,3s)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloroquinazoline. LCMS theoretical m/z=461.2. [M+H]+. found 462.3.

Example 359, Compound 179

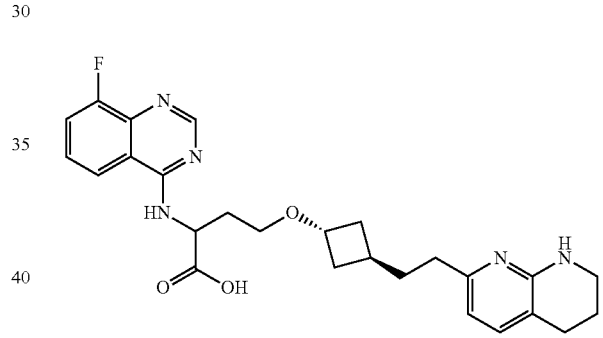

N-(8-fluoroquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-8-fluoroquinazoline. LCMS theoretical m/z=479.2. [M+H]+. found 480.2.

Example 360, Compound 180

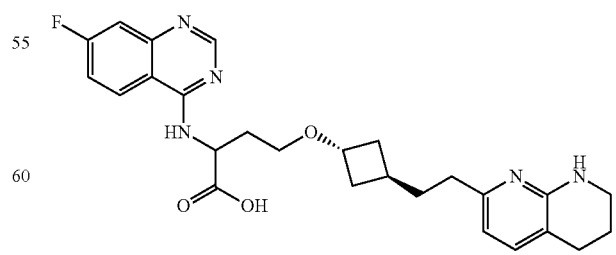

N-(7-fluoroquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-7-fluoroquinazoline. LCMS theoretical m/z=479.2. [M+H]+. found 480.2.

Example 361, Compound 181

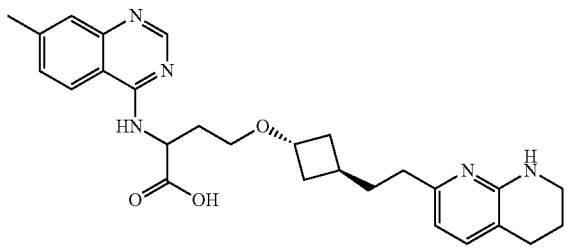 [SMILES: Cc1ccc2c(NC(CCO[C@H]3C[C@H](CCc4ccc5c(n4)NCCC5)C3)C(=O)O)ncnc2c1]

N-(7-methylquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-7-methylquinazoline. LCMS theoretical m/z=475.3. [M+H]+. found 476.3.

Example 362, Compound 182

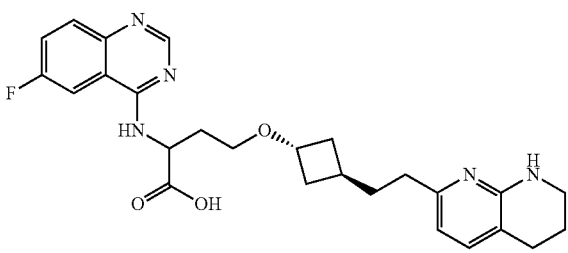 [SMILES: O=C(O)C(CCO[C@H]1C[C@H](CCc2ccc3c(n2)NCCC3)C1)Nc1ncnc2ccc(F)cc12]

N-(6-fluoroquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-6-fluoroquinazoline. LCMS theoretical m/z=479.2. [M+H]+. found 480.2.

Example 363, Compound 183

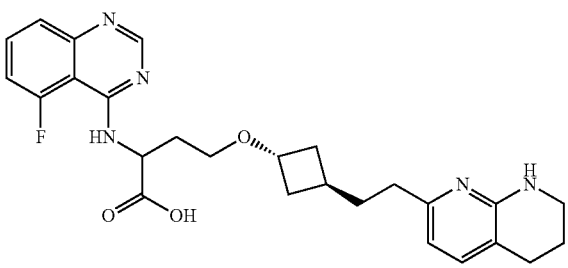 [SMILES: O=C(O)C(CCO[C@H]1C[C@H](CCc2ccc3c(n2)NCCC3)C1)Nc1ncnc2cccc(F)c12]

N-(5-fluoroquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-5-fluoroquinazoline. LCMS theoretical m/z=479.2. [M+H]+. found 480.2.

Example 364, Compound 184

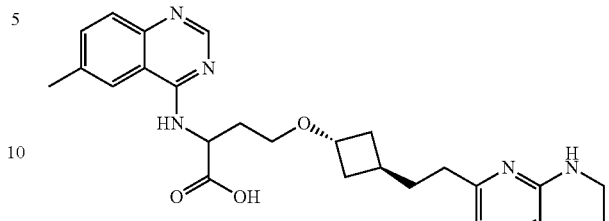

N-(6-methylquinazolin-4-yl)-O-((1s,3r)-3-(2-(5,6,7,8-tetrahydro-1,8-naphthyridin-2-yl)ethyl)cyclobutyl)homoserine. Isomer E2 was employed in General Scheme E-2 using General Procedure E with 4-chloro-6-methylquinazoline. LCMS theoretical m/z=475.3. [M+H]+. found 476.3.

Example 365, Compound 185

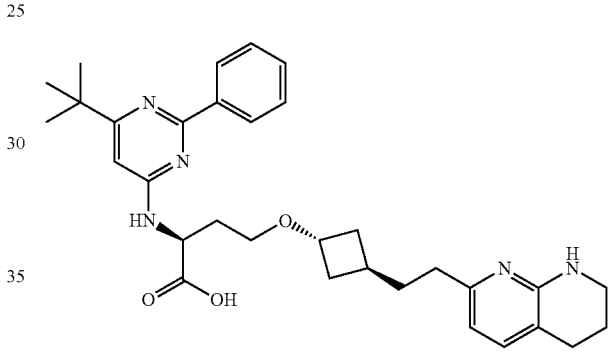

N-(6-(tert-butyl)-2-phenylpyrimidin-4-yl)-O-((1s,3S)-3-(2-(5,6,7,8-tetrahydro-1,8-naphthyridin-2-yl)ethyl)cyclobutyl)-L-homoserine. Isomer E2 was employed in General Scheme E-2 using General Procedure E with 4-(tert-butyl)-6-chloro-2-phenylpyrimidine. LCMS theoretical m/z=543.3. [M+H]+. found 544.3

Example 366, Compound 23

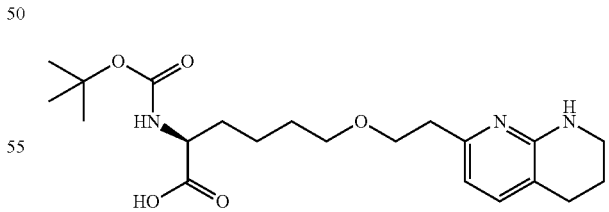

(S)-2-((tert-butoxycarbonyl)amino)-6-(2-(5,6,7,8-tetrahydro-1,8-naphthyridin-2-yl)ethoxy)hexanoic acid. Was prepared by the same procedure used to prepare Example 2 with the exception that the bromide was replaced with 6-bromohex-1-ene in the reaction with intermediate 2d and the acid was replaced by di-tert-butyl dicarbonate in the reaction with intermediate 2i. LCMS theoretical m/z=407.2. [M+H]+. found 408.2.

BIOLOGICAL EXAMPLES

Example B1—Proximity-Based Integrin Receptor Binding Assay for Determining Inhibitor Potency The biochemical potency of compounds was determined using a proximity-based assay (ALPHASCREEN®, Perkin Elmer, Waltham, MA) as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994). To gauge the potency of inhibitors of binding to human integrin $\alpha v \beta_6$, inhibitor compounds and integrin were incubated together with TGF-b1 LAP and biotinylated anti-LAP antibody plus acceptor and donor beads, following the manufacture's recommendations. The donor beads were coated with streptavidin. The acceptor beads had a nitrilotriacetic acid Ni chelator, for binding to a 6×His Tag on human integrin $\alpha v \beta_6$. All incubations occurred at room temperatures in 50 mM Tris-HCl, pH 7.5, 0.1% BSA supplemented with 1 mM each $CaCl_2$) and $MgCl_2$.

The order of reagent addition was as follows:
1. Alpha-v-beta-6 integrin, test inhibitor compound, LAP, biotinylated anti-LAP antibody and acceptor beads were all added together.
2. After 2 hours, donor beads were added. After another 30 minute incubation, samples were then read.

Integrin binding was evaluated by exciting donor beads at 680 nm, and measuring the fluorescent signal produced, between 520-620 nm, using a Biotek Instruments (Winooski, Vt., USA) Synergy Neo2 multimode plate reader. Compound potency was assessed by determining inhibitor concentrations required to reduce fluorescent light output by 50%. Data analysis for $IC_{50}$ determinations was carried out by nonlinear four parameter logistic regression analysis using Dotmatics ELN Software (Core Informatics Inc., Branford, Conn.). $IC_{50}$ values for the compounds in the Examples are provided below in Table B-1 in ranges: below 50 nM; from above 50 nM to 250 nM; from above 250 nM to 1000 nM; and above 1000 nM.

TABLE B-1

| Example No. | IC50 (nM) | Example No. | IC50 (nM) |
|---|---|---|---|
| 1 | <50 | 4 | >1000 |
| 5 | >50-250 | 6 | >250-1000 |
| 7 | >50-250 | 8 | >250-1000 |
| 9 | >50-250 | 10 | >50-250 |
| 11 | >50-250 | 12A | >50-250 |
| 13 | >250-1000 | 14 | <50 |
| 15 | <50 | 16 | <50 |
| 17 | <50 | 18 | >50-250 |
| 19 | <50 | 20 | <50 |
| 21 | <50 | 22 | <50 |
| 23 | <50 | 24 | <50 |
| 25 | <50 | 26 | <50 |
| 27 | <50 | 28 | <50 |
| 29 | <50 | 30 | <50 |
| 31 | <50 | 32 | <50 |
| 33 | <50 | 34 | >50-250 |
| 35 | >50-250 | 36 | <50 |
| 37 | <50 | 38 | >50-250 |
| 39 | >50-250 | 40 | >50-250 |
| 41 | <50 | 42 † | >50-250 |
| 43 †† | >250-1000 | 44 | >50-250 |
| 45 | >50-250 | 46 † | >250-1000 |
| 47 †† | >250-1000 | 48 | >250-1000 |
| 49 | >50-250 | 50 | <50 |
| 51 | <50 | 52 | <50 |
| 53 | >50-250 | 54 | >50-250 |
| 55 | >250-1000 | 56 | >50-250 |
| 57 | >250-1000 | 58* | >1000 |
| 59* | >1000 | 60* | >50-250 |
| 61* | >1000 | 62** | <50 |
| 63** | <50 | 64** | <50 |
| 65** | <50 | 66 | >50-250 |
| 67 | >50-250 | 68 | >250-1000 |
| 69 | >250-1000 | 70 † | >50-250 |
| 71 †† | >1000 | 72 | <50 |
| 73 | >50-250 | 74 † | >1000 |
| 75 †† | >250-1000 | 76 † | >250-1000 |
| 77 †† | >1000 | 78 † | >1000 |
| 79 †† | >50-250 | 80 † | >50-250 |
| 81 †† | >1000 | 82* | >250-1000 |
| 83* | >1000 | 84* | <50 |
| 85* | >250-1000 | 86* | >250-1000 |
| 87* | >250-1000 | 88* | >50-250 |
| 89* | >250-1000 | 90* | >250-1000 |
| 91* | >50-250 | 92* | >250-1000 |
| 93* | >50-250 | 94* | >50-250 |
| 95*, † | >1000 | 96*, †† | >250-1000 |
| 97** | <50 | 98** | <50 |
| 99** | <50 | 100** | >50-250 |
| 101** | <50 | 102** | <50 |
| 103** | <50 | 104** | <50 |
| 105** | <50 | 106** | <50 |
| 107** | <50 | 108** | <50 |
| 109** | <50 | 110**, † | >50-250 |
| 111**, †† | <50 | 112** | >50-250 |
| 113** | <50 | 114** | <50 |
| 115** | <50 | 116** | <50 |
| 117** | <50 | 118** | <50 |
| 119** | >50-250 | 120** | <50 |
| 121** | <50 | 122** | >50-250 |
| 123** | <50 | 124** | <50 |
| 125** | >50-250 | 126** | <50 |
| 127** | <50 | 128** | >50-250 |
| 129** | >50-250 | 130** | >50-250 |
| 131** | <50 | 132** | >50-250 |
| 133** | <50 | 134** | >50-250 |
| 135** | >50-250 | 136** | <50 |
| 137** | >250-1000 | 138** | >50-250 |
| 139** | >1000 | 140** | >250-1000 |
| 141** | <50 | 142** | >50-250 |
| 143** | >250-1000 | 144** | >250-1000 |
| 145A †† | >250-1000 | 145B † | >50-250 |
| 146** | >50-250 | 147** | <50 |
| 148** | >250-1000 | 149** | >50-250 |
| 150** | >250-1000 | 151** | <50 |
| 152** | <50 | 153** | <50 |
| 154** | >250-1000 | 155**, † | <50 |
| 155**, †† | <50 | 157** | <50 |
| 158** | <50 | 159** | <50 |
| 160** | >50-250 | 161** | <50 |
| 162**, †† | <50 | 163**, † | >50-250 |
| 163**, †† | >50-250 | 164** | <50 |
| 165** | <50 | 166** | >50-250 |
| 168** | >50-250 | 169** | >50-250 |
| 170** | <50 | 171** | <50 |
| 172** | <50 | 173** | <50 |
| 174** | <50 | 175** † | <50 |
| 175** †† | <50 | 176** † | <50 |
| 176** †† | >50-250 | 177** | >50-250 |
| 179** | >50-250 | 180** † | <50 |
| 180** †† | >50-250 | 181** | <50 |
| 182** | >50-250 | 183** | >50-250 |
| 184** | <50 | 185** | <50 |
| 187 | >250-1000 | 188 | >50-250 |
| 189 | >50-250 | 190** | <50 |
| 199** | >50-250 | 224 | <50 |
| 225** | >250-1000 | 226** | >250-1000 |
| 227* | >250-1000 | 228** | <50 |
| 229** | >50-250 | | |

*first eluting compound from general synthetic scheme referenced was assayed
**second eluting compound from general synthetic scheme referenced was assayed
† first eluting compound from last chromatography step described in example was assayed
†† second eluting compound from last chromatography step described in example was assayed Example B2—Further Compounds Potently Inhibit αvβ6 in a Proximity-Based Assay The biochemical potency of compounds for inhibiting αvβ6 integrin was determined for a second series of compounds using a proximity-based assay (ALPHASCREEN®, Perkin Elmer, Waltham, MA) as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994). To gauge the potency of inhibitors of binding to human integrin αvβ6, inhibitor compounds and integrin were incubated together with TGF-b1 LAP and biotinylated anti-LAP antibody plus acceptor and donor beads, following the manufacture's recommendations. The donor beads were coated with streptavidin. The acceptor beads had a nitrilotriacetic acid Ni chelator, for binding to a 6×His Tag on human integrin $\alpha_v\beta_6$. All incubations occurred at room temperatures in 50 mM Tris-HCl, pH 7.5, 0.1% BSA supplemented with 1 mM each $CaCl_2$ and $MgCl_2$.

The order of reagent addition was as follows:
1. Alpha-v-beta-6 integrin, test inhibitor compound, LAP, biotinylated anti-LAP antibody and acceptor beads were all added together.
2. After 2 hours, donor beads were added. After another 30 minute incubation, samples were then read.

Integrin binding was evaluated by exciting donor beads at 680 nm, and measuring the fluorescent signal produced, between 520-620 nm, using a Biotek Instruments (Winooski, VT, USA) Synergy Neo2 multimode plate reader. Compound potency was assessed by determining inhibitor concentrations required to reduce fluorescent light output by 50%. Data analysis for $IC_{50}$ determinations was carried out by nonlinear four parameter logistic regression analysis using Dotmatics ELN Software (Core Informatics Inc., Branford, Conn.).

Example B3—The Compounds Potently Inhibit αvβ1 in a Proximity-Based Assay

The biochemical potency of compounds for inhibiting $\alpha_v\beta_1$ integrin was determined using a proximity-based assay (ALPHASCREEN®, Perkin Elmer, Waltham, MA) as described previously (Ullman E F et al., Luminescent oxygen channeling immunoassay: Measurement of particle binding kinetics by chemiluminescence. Proc. Natl. Acad. Sci. USA, Vol. 91, pp. 5426-5430, June 1994). To gauge the potency of inhibitors of binding to human integrin $\alpha_v\beta_1$, inhibitor compounds and integrin were incubated together with TGF-b1 LAP and biotinylated anti-LAP antibody plus acceptor and donor beads, following the manufacture's recommendations. The donor beads were coated with streptavidin. The acceptor beads had a nitrilotriacetic acid Ni chelator, for binding to a 6×His Tag on human integrin $\alpha_v\beta_1$. All incubations occurred at room temperatures in 50 mM Tris-HCl, pH 7.5, 0.1% BSA supplemented with 1 mM each $CaCl_2$ and $MgCl_2$.

The order of reagent addition was as follows:
1. Alpha-v-beta-1 integrin, test inhibitor compound, LAP, biotinylated anti-LAP antibody and acceptor beads were all added together.
2. After 2 hours, donor beads were added. After another 30 minute incubation, samples were then read.

Integrin binding was evaluated by exciting donor beads at 680 nm, and measuring the fluorescent signal produced, between 520-620 nm, using a Biotek Instruments (Winooski, VT, USA) Synergy Neo2 multimode plate reader. Compound potency was assessed by determining inhibitor concentrations required to reduce fluorescent light output by 50%. Data analysis for $IC_{50}$ determinations was carried out by nonlinear four parameter logistic regression analysis using Dotmatics ELN Software (Core Informatics Inc., Branford, Conn.). $IC_{50}$ values for the compounds in the Examples are provided in FIG. 2, Table B-2 in ranges: 50 nM and below; from above 50 nM to 250 nM; from above 250 nM to 1000 nM; and above 1000 nM.

Combined Inhibition Results of Examples B1, B2, and B3

Table B-2, FIG. 2, shows $IC_{50}$ data from Examples B1, B2, and B3 for inhibition of $\alpha v \beta_1$ and $\alpha v \beta_6$ integrin in the solid phase assays and inhibition of human $\alpha v \beta_1$ and $\alpha v \beta_6$ integrin in the proximity-based ALPHASCREEN® assays. The $IC_{50}$ data is shown in four ranges: 50 nM and below; from 50 nM to below 250 nM; from above 250 nM to below 1000 nM; and 1000 nM and above.

What is claimed is:
1. A compound of formula (I):

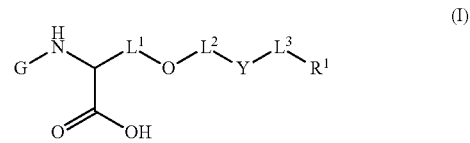

or a pharmaceutically acceptable salt, stereoisomer, or tautomer thereof,
wherein:
G is —C(O)R² or R³;
L¹ is $C_2$-$C_4$ alkylene, wherein the $C_2$-$C_4$ alkylene is optionally substituted by 1 or more independently selected R⁴ substituents;
L² is a bond or $C_1$-$C_3$ alkylene, wherein the $C_1$-$C_3$ alkylene is optionally substituted by 1 or more independently selected R⁴ substituents;
L³ is $C_2$-$C_4$ alkylene, wherein the $C_2$-$C_4$ alkylene is optionally substituted by 1 or more independently selected R⁴ substituents;
Y is a bond or $C_3$-$C_5$ cycloalkylene, wherein the $C_3$-$C_5$ cycloalkylene is optionally substituted by 1 or more independently selected $Y^a$ substituents;
each $Y^a$ is independently =O or R⁴;
R¹ is:

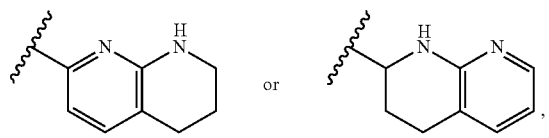

wherein the 5,6,7,8-tetrahydro-1,8-naphthyridin-2-yl or the 1,2,3,4-tetrahydro-1,8-naphthyridin-2-yl is optionally substituted by 1 or more independently selected R⁴ substituents;
R² is $C_1$-$C_6$ alkyl, $NR^{2g}R^{2h}$, $OR^{21}$, $C_3$-$C_8$ cycloalkyl, 3- to 12-membered heterocyclyl, $C_6$-$C_{14}$ aryl, or 5- to 10-membered heteroaryl
wherein the $C_1$-$C_6$ alkyl is optionally substituted by 1 or more independently selected $R^{2a}$ substituents;

wherein the $C_3$-$C_8$ cycloalkyl is optionally substituted by 1 or more independently selected $R^{2b}$ substituents;

wherein the 3- to 12-membered heterocyclyl is optionally substituted by 1 or more independently selected $R^{2c}$ substituents;

wherein the $C_6$-$C_{14}$ aryl is optionally substituted by 1 or more independently selected $R^{2d}$ substituents; and wherein the 5- to 10-membered heteroaryl is optionally substituted by 1 or more independently selected $R^{2e}$ substituents;

each $R^{2a}$ is independently =O or $R^4$;
each $R^{2b}$ is independently =O or $R^4$;
each $R^{2c}$ is independently =O or $R^4$;
each $R^{2d}$ is independently =O or $R^4$;
each $R^{2e}$ is independently =O or $R^4$;

$R^{2f}$ is $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, or 5- to 10-membered heteroaryl is optionally substituted by 1 or more independently selected $R^{2i}$ substituents;

$R^{2g}$ is H, D, $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, or 5- to 10-membered heteroaryl is optionally substituted by 1 or more independently selected $R^{2j}$ substituents;

$R^{2h}$ is H, D, $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, or 5- to 10-membered heteroaryl is optionally substituted by 1 or more independently selected $R^{2j}$ substituents;

each $R^{2i}$ is independently =O or $R^4$;
each $R^{2j}$ is independently =O or $R^4$;

$R^3$ is $C_1$-$C_6$ alkyl, $C_3$-$C_8$ cycloalkyl, 3- to 12-membered heterocyclyl, $C_6$-$C_{14}$ aryl, or 5- to 10-membered heteroaryl;

wherein the $C_1$-$C_6$ alkyl is optionally substituted by 1 or more independently selected $R^{3a}$ substituents;

wherein the $C_3$-$C_8$ cycloalkyl is optionally substituted by 1 or more independently selected $R^{3b}$ substituents;

wherein the 3- to 12-membered heterocyclyl is optionally substituted by 1 or more independently selected $R^{3c}$ substituents;

wherein the $C_6$-$C_{14}$ aryl is optionally substituted by 1 or more independently selected $R^{3d}$ substituents; and wherein the 5- to 10-membered heteroaryl is optionally substituted by 1 or more independently selected $R^{3e}$ substituents;

each $R^{3a}$ is independently =O or $R^4$;
each $R^{3b}$ is independently =O or $R^4$;
each $R^{3c}$ is independently =O or $R^4$;
each $R^{3d}$ is independently =O or $R^4$;
each $R^{3e}$ is independently =O or $R^4$;

each $R^4$ is independently D, halogen, CN, $NO_2$, $C_1$-$C_6$ alkyl, $C_2$-$C_6$ alkenyl, $C_2$-$C_6$ alkynyl, C(NH)$OR^5$, C(O)$R^5$, C(O)$NR^6R^7$, C(O)$OR^5$, P(O)($OR^5$)($OR^6$), $NR^6R^7$, $NR^5C(O)R^6$, $NR^5C(O)NR^6R^7$, $NR^5C(O)OR^6$, $NR^5S(O)R^6$, $NR^5S(O)_2R^6$, $OR^5$, OC(O)$R^5$, $SR^5S(O)R^5$, S(O)$NR^6R^7$, S(O)$_2R^5$, S(O)$_2NR^6R^7$, $C_3$-$C_8$ cycloalkyl, 3- to 12-membered heterocyclyl, $C_6$-$C_{14}$ aryl, or 5- to 10-membered heteroaryl, wherein each $C_1$-$C_6$ alkyl, $C_2$-$C_6$ alkenyl, $C_2$-$C_6$ alkynyl, $C_3$-$C_8$ cycloalkyl, 3- to 12-membered heterocyclyl, $C_6$-$C_{14}$ aryl, and 5- to 10-membered heteroaryl is optionally and independently substituted by 1 or more independently selected $R^{4a}$ substituents;

each $R^{4a}$ is independently D, halogen, CN, $C_1$-$C_6$ alkyl, C(O)$R^8$, C(O)$OR^8$, P(O)($OR^8$)($OR^9$), $NR^8R^9$, $NR^8C(O)OR^{10}$, $OR^8$, =O, —S(O)$R^8$, S(O)$_2R^8$, $C_3$-$C_8$ cycloalkyl, 3- to 12-membered heterocyclyl, $C_6$-$C_{14}$ aryl, or 5- to 10-membered heteroaryl, wherein each $C_1$-$C_6$ alky, 3- to 12-membered heterocyclyl, $C_6$-$C_{14}$ aryl, and 5- to 10-membered heteroaryl is optionally and independently substituted by 1 or more independently selected $R^{4b}$ substituents;

each $R^{4b}$ is independently D, halogen, $C_1$-$C_6$ alkyl, OH, OD, or =O, wherein each $C_1$-$C_6$ alkyl is optionally and independently substituted by 1 or more substituents independently selected from the group consisting of: D, halogen, OH, OD, and =O;

each $R^5$ is independently H, D, $C_1$-$C_6$ alkyl, $C_2$-$C_6$ alkenyl, $C_2$-$C_6$ alkynyl, $C_3$-$C_6$ cycloalkyl, 3- to 10-membered heterocyclyl, $C_6$-$C_{14}$ aryl, or 5- to 10-membered heteroaryl wherein each $C_1$-$C_6$ alkyl, $C_2$-$C_6$ alkenyl, $C_2$-$C_6$ alkynyl, $C_3$-$C_6$ cycloalkyl, 3- to 10-membered heterocyclyl, $C_6$-$C_{14}$ aryl, and 5- to 10-membered heteroaryl is optionally and independently substituted by 1 or more independently selected $R^{5a}$ substituents;

each $R^{5a}$ is independently D, halogen, CN, $C_1$-$C_6$ alkyl, P(O)($OR^{11}$)($OR^{12}$), $NR^{11}R^{12}$, $OR^{10}$, =O, or 3- to 12-membered heterocyclyl, wherein each $C_1$-$C_6$ alkyl is optionally and independently substituted by 1 or more substituents independently selected from the group consisting of: D, halogen, OH, OD, and =O;

each $R^6$ is independently H, D, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$-$C_{14}$ aryl, or 5- to 10-membered heteroaryl, wherein each $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$-$C_{14}$ aryl, and 5- to 10-membered heteroaryl is optionally and independently substituted by 1 or more substituents independently selected from the group consisting of: D, halogen, CN, $C_1$-$C_6$ alkyl, $NR^{11}R^{12}$, $OR^{10}$, and =O; and wherein each $C_1$-$C_6$ alkyl substituent is optionally and independently substituted by 1 or more substituents independently selected from the group consisting of: D, halogen, OH, OD, and =O;

each $R^7$ is independently H, D, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$-$C_{14}$ aryl, or 5- to 10-membered heteroaryl, wherein each $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, $C_6$-$C_{14}$ aryl, and 5- to 10-membered heteroaryl is optionally and independently substituted by 1 or more substituents independently selected from the group consisting of: D, halogen, CN, $C_1$-$C_6$ alkyl, $NR^{11}R^{12}$, OR, and =O; and wherein each $C_1$-$C_6$ alkyl substituent is optionally and independently substituted by 1 or more substituents independently selected from the group consisting of: D, halogen, OH, OD, and =O; or $R^6$ and $R^7$, together with the atom to which they are attached, form a 3- to 10-membered heterocyclyl;

wherein the 3- to 10-membered heterocyclyl is optionally substituted by 1 or more substituents independently selected from the group consisting of: D, halogen, $C_1$-$C_6$ alkyl, $NR^{11}R^{12}$, $OR^{10}$, and =O; and wherein each $C_1$-$C_6$ alkyl substituent is optionally and independently substituted by 1 or more substituents independently selected form the group consisting of: D, halogen, OH, OD, and =O;

each $R^8$ is independently H, D, $C_1$-$C_6$ alkyl, $C_2$-$C_6$ alkenyl, or $C_2$-$C_6$ alkynyl, wherein each $C_1$-$C_6$alkyl, $C_2$-$C_6$ alkenyl, and $C_2$-$C_6$ alkynyl is optionally and independently substituted by 1 or more substituents independently selected from the group consisting of: D, halogen, and =O;

each $R^9$ is independently H, D, $C_1$-$C_6$ alkyl, $C_2$-$C_6$ alkenyl, or $C_2$-$C_6$ alkynyl, wherein each $C_1$-$C_6$alkyl, $C_2$-$C_6$ alkenyl, and $C_2$-$C_6$ alkynyl is optionally and independently substituted by 1 or more substituents independently selected from the group consisting of: D, halogen, and =O;

each $R^{10}$ is independently H, D, $C_1$-$C_6$ alkyl, $C_2$-$C_6$ alkenyl, or $C_2$-$C_6$ alkynyl, wherein each $C_1$-$C_6$alkyl, $C_2$-$C_6$ alkenyl, and $C_2$-$C_6$ alkynyl is optionally and independently substituted by 1 or more substituents independently selected from the group consisting of: D, halogen, and =O;

each $R^{11}$ is independently H, D, $C_1$-$C_6$ alkyl, $C_2$-$C_6$ alkenyl, or $C_2$-$C_6$ alkynyl, wherein each $C_1$-$C_6$ alkyl, $C_2$-$C_6$ alkenyl, and $C_2$-$C_6$ alkynyl is optionally and independently substituted by 1 or more substituents independently selected from the group consisting of: D, halogen, and =O; and each $R^{12}$ is independently H, D, $C_1$-$C_6$ alkyl, $C_2$-$C_6$ alkenyl, or $C_2$-$C_6$ alkynyl, wherein each $C_1$-$C_6$alkyl, $C_2$-$C_6$ alkenyl, and $C_2$-$C_6$ alkynyl is optionally and independently substituted by 1 or more substituents independently selected from the group consisting of: D, halogen, and =O; or $R^{11}$ and $R^{12}$, together with the atom to which they are attached, form a 3- to 6-membered heterocyclyl;
wherein the 3- to 6-membered heterocyclyl is optionally substituted by 1 or more substituents independently selected from the group consisting of: D, halogen, $C_1$-$C_6$ alkyl, and =O; and
wherein the $C_1$-$C_6$ alkyl substituent is optionally and independently substituted by 1 or more substituents independently selected from the group consisting of: D, halogen and =O;

with the provisos that:
(i) if

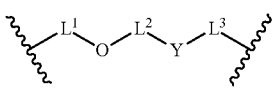

is

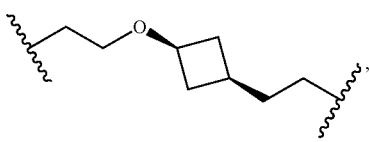 [SMILES: *CCO[C@H]1C[C@@H](CC*)C1]

then $R^2$ is not tetrahydropyranyl;
wherein the tetrahydropyranyl is substituted by 1, 2, or 3 independently selected $R^{2c'}$ substituents;

wherein each $R^{2c'}$ is independently $R^{4'}$;
wherein each $R^{4'}$ is selected from the group consisting of: D, 3- to 12-membered heterocyclyl, $C_6$-$C_{14}$ aryl, and 5- to 10-membered heteroaryl; and
wherein each 3- to 12-membered heterocyclyl, $C_6$-$C_{14}$ aryl, and 5- to 10-membered heteroaryl is optionally and independently substituted by 1 or more independently selected $R^{4a}$ substituents;

(ii) if

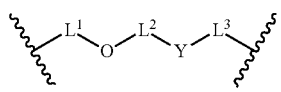

is

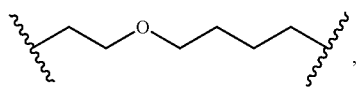 [SMILES: *CCCCOCC*]

then $R^2$ is not phenyl;
wherein the phenyl is substituted by 1, 2, or 3 independently selected $R^{2d'}$ substituents;
wherein each $R^{2c'}$ is independently $R^{4'}$;
wherein each $R^{4'}$ is independently selected from the group consisting of: D, 3- to 12-membered heterocyclyl, $C_6$-$C_{14}$ aryl, and 5- to 10-membered heteroaryl; and
wherein each 3- to 12-membered heterocyclyl, $C_6$-$C_{14}$ aryl, and 5- to 10-membered heteroaryl is optionally and independently substituted by 1 or more independently selected $R^{4a}$ substituents; or (iii) if

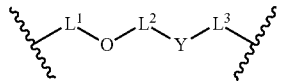

is

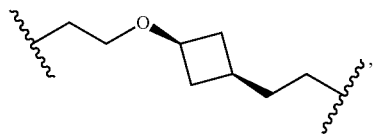 [SMILES: *CCO[C@H]1C[C@@H](CC*)C1]

then $R^2$ is not pyridyl;
wherein the pyridyl is substituted by 1, 2, or 3 independently selected $R^{2e'}$ substituents;
wherein each $R^{2e'}$ is independently $R^{4'}$;
wherein each $R^{4'}$ is independently selected from the group consisting of: D, 3- to 12-membered heterocyclyl, $C_6$-$C_{14}$ aryl, and 5- to 10-membered heteroaryl; and
wherein each 3- to 12-membered heterocyclyl, $C_6$-$C_{14}$ aryl, and 5- to 10-membered heteroaryl is optionally and independently substituted by 1 or more independently selected $R^{4a}$ substituents.

2. The compound of claim 1, or a pharmaceutically acceptable salt, stereoisomer, or tautomer thereof, wherein G is C(O)$R^2$.

3. The compound of claim 2, or a pharmaceutically acceptable salt, stereoisomer, or tautomer thereof, wherein $R^2$ is $C_1$-$C_6$ alkyl, wherein the $C_1$-$C_6$ alkyl is optionally substituted by 1, 2, 3, 4, or 5 independently selected $R^{2a}$ substituents.

4. The compound of claim 3, or a pharmaceutically acceptable salt, stereoisomer, or tautomer thereof, wherein $R^2$ is unsubstituted $C_1$-$C_6$ alkyl.

5. The compound of claim 3, or a pharmaceutically acceptable salt, stereoisomer, or tautomer thereof, wherein $R^2$ is unsubstituted $C_4$-$C_6$ alkyl.

6. The compound of claim 3, or a pharmaceutically acceptable salt, stereoisomer, or tautomer thereof, wherein:
$R^2$ is $C_1$-$C_5$ alkyl, wherein the $C_1$-$C_5$ alkyl is optionally substituted by 1, 2, 3, 4, or 5 independently selected $R^{2a}$ substituents; and
each $R^{2a}$ is halogen, CN, $C_1$-$C_6$ alkyl, $NR^6R^7$, $NR^5C(O)OR^6$, $OR^5$, $S(O)_2R^5$, $C_3$-$C_8$ cycloalkyl, 3- to 12-membered heterocyclyl, $C_6$-$C_{14}$ aryl, or 5- to 10-membered heteroaryl, wherein each $C_1$-$C_6$ alkyl, $C_3$-$C_8$ cycloalkyl, 3- to 12-membered heterocyclyl, $C_6$-$C_{14}$ aryl, and 5- to 10-membered heteroaryl is optionally and independently substituted by 1 or more independently selected $R^{4a}$ substituents.

7. The compound of claim 6, or a pharmaceutically acceptable salt, stereoisomer, or tautomer thereof, wherein:
$R^2$ is $C_2$-$C_5$ alkyl, wherein the $C_2$-$C_5$ alkyl is substituted by 1, 2, 3, 4, or 5 independently selected $R^{2a}$ substituents; and
at least one $R^{2a}$ is a halogen substituent.

8. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is substituted by 1, 2, 3, 4, or 5 independently selected $R^{2a}$ substituents; and
at least one $R^{2a}$ is a $C_3$-$C_8$ cycloalkyl substituent.

9. The compound of claim 6, or a pharmaceutically acceptable salt, stereoisomer, or tautomer thereof, wherein:
$R^2$ is $C_1$-$C_3$ alkyl, wherein the $C_1$-$C_3$ alkyl is substituted by 1 $R^{2a}$ substituent:
$R^{2a}$ is $C_3$-$C_6$ cycloalkyl, wherein the $C_3$-$C_6$ cycloalkyl is optionally substituted by 1, 2, 3, 4, or 5 independently selected $R^{4a}$ substituents; and
each $R^{4a}$ is independently halogen, $C_1$-$C_6$alkyl, or $OR^8$.

10. The compound of claim 6, or a pharmaceutically acceptable salt, stereoisomer, or tautomer thereof, wherein:
$R^2$ is $C_1$-$C_3$ alkyl, wherein the $C_1$-$C_3$ alkyl is substituted by 1 $R^{2a}$ substituent; and
$R^{2a}$ is unsubstituted $C_3$-$C_6$ cycloalkyl.

11. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is substituted by 1, 2, 3, 4, or 5 independently selected $R^{2a}$ substituents; and
at least one $R^{2a}$ is a 3- to 12-membered heterocyclyl substituent.

12. The compound of claim 6, or a pharmaceutically acceptable salt, stereoisomer, or tautomer thereof, wherein:
$R^2$ is $C_1$ alkyl, wherein the $C_1$ alkyl is substituted by 1 $R^{2a}$ substituent; and
$R^{2a}$ is a 6-membered heterocyclyl.

13. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is optionally substituted by 1, 2, 3, 4, or 5 independently selected $R^{2a}$ substituents;
at least one $R^{2a}$ is $C_6$-$C_{14}$ aryl, wherein the $C_6$-$C_{14}$ aryl is optionally substituted by 1, 2, 3, 4, or 5 independently selected $R^{4a}$ substituents;
each $R^{4a}$ is independently halogen or $C_1$-$C_6$ alkyl, wherein each $C_1$-$C_6$ alkyl is optionally and independently substituted by 1, 2, 3, 4, or 5 independently selected $R^{4b}$ substituents; and
each $R^{4b}$ is an independently selected halogen substituent.

14. The compound of claim 13, or a pharmaceutically acceptable salt, stereoisomer, or tautomer thereof, wherein:
at least one $R^{2a}$ is phenyl, wherein the phenyl is optionally substituted by 1, 2, 3, 4, or 5 independently selected $R^{4a}$ substituents; and
each $R^{4a}$ is an independently selected halogen substituent.

15. The compound of claim 6, or a pharmaceutically acceptable salt, stereoisomer, or tautomer thereof, wherein:
$R^2$ is $C_2$-$C_5$ alkyl, wherein the $C_2$-$C_5$ alkyl is substituted by 1, 2, 3, 4, or 5 independently selected $R^{2a}$ substituents; and
at least one $R^{2a}$ is 5- to 10-membered heteroaryl, wherein the 5- to 10-membered heteroaryl is optionally substituted by 1, 2, 3, 4, or 5 independently selected $R^{4a}$ substituents.

16. The compound of claim 15, or a pharmaceutically acceptable salt, stereoisomer, or tautomer thereof, wherein at least one $R^{2a}$ is unsubstituted pyridinyl.

17. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is optionally substituted by 1, 2, 3, 4, or 5 independently selected $R^{2a}$ substituents; and
at least one $R^{2a}$ is $OR^5$; and
each $R^5$ is independently H, $C_1$-$C_6$ alkyl, or $C_6$-$C_{14}$ aryl.

18. The compound of claim 17, or a pharmaceutically acceptable salt, stereoisomer, or tautomer thereof, wherein:
each $R^5$ is independently $C_6$-$C_{14}$ aryl, wherein each $C_6$-$C_{14}$ aryl is optionally and independently substituted by 1, 2, 3, 4, or 5 independently selected $R^{5a}$ substituents; and
each $R^{5a}$ is an independently selected halogen substituent.

19. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is substituted by 1, 2, 3, 4, or 5 independently selected $R^{2a}$ substituents; and
at least one $R^{2a}$ is CN, $NR^6R^7$, $NR^5C(O)OR^6$, or $S(O)_2R^5$.

20. The compound of claim 6, or a pharmaceutically acceptable salt, stereoisomer, or tautomer thereof, wherein:
$R^2$ is $C_1$-$C_5$ alkyl, wherein the $C_1$-$C_5$ alkyl is substituted by 2, 3, 4, or 5 independently selected $R^{2a}$ substituents; and
each $R^{2a}$ is independently halogen, $C_1$-$C_6$ alkyl, $NR^5C(O)OR^6$, $OR^5$, $C_3$-$C_8$ cycloalkyl, $C_6$-$C_{14}$ aryl, or 5- to 10-membered heteroaryl, wherein each $C_6$-$C_{14}$ aryl is optionally and independently substituted by 1 or more independently selected $R^{4a}$ substituents.

21. The compound of claim 20, or a pharmaceutically acceptable salt, stereoisomer, or tautomer thereof, wherein:
$R^2$ is $C_1$-$C_5$ alkyl, wherein the $C_1$-$C_5$ alkyl is substituted by 2, 3, 4, or 5 independently selected $R^{2a}$ substituents;
at least one $R^{2a}$ is $OR^5$:
at least one $R^{2a}$ is phenyl, wherein the phenyl is optionally substituted by 1, 2, 3, 4, or 5 independently selected $R^{4a}$ substituents;
each $R^{4a}$ is an independently selected halogen substituent; and
$R^5$ is H or $C_1$-$C_6$ alkyl.

22. The compound of claim 2, or a pharmaceutically acceptable salt, stereoisomer, or tautomer thereof, wherein $R^2$ is $C_3$-$C_8$ cycloalkyl, and wherein the $C_3$-$C_8$ cycloalkyl is optionally substituted by 1, 2, 3, 4, or 5 independently selected $R^{2b}$ substituents.

23. The compound of claim 22, or a pharmaceutically acceptable salt, stereoisomer, or tautomer thereof, wherein $R^2$ is unsubstituted $C_3$-$C_8$ cycloalkyl.

24. The compound of claim 22, or a pharmaceutically acceptable salt, stereoisomer, or tautomer thereof, wherein:
   $R^2$ is $C_3$-$C_8$ cycloalkyl, wherein the $C_3$-$C_8$ cycloalkyl is substituted by 1, 2, 3, 4, or 5 independently selected $R^{2b}$ substituents; and
   each $R^{2b}$ is independently halogen, $C_1$-$C_6$ alkyl, $OR^5$, 3- to 12-membered heterocyclyl, $C_6$-$C_{14}$ aryl, or 5- to 10-membered heteroaryl, wherein each $C_6$-$C_{14}$ aryl is optionally and independently substituted by 1 or more independently selected $R^{4a}$ substituents.

25. The compound of claim 24, or a pharmaceutically acceptable salt, stereoisomer, or tautomer thereof, wherein:
   $R^2$ is $C_3$-$C_6$ cycloalkyl, wherein the $C_3$-$C_6$ cycloalkyl is substituted by 1, 2, 3, 4, or 5 independently selected $R^{2b}$ substituents; and
   at least one $R^{2b}$ is an independently selected halogen substituent.

26. The compound of claim 24, or a pharmaceutically acceptable salt, stereoisomer, or tautomer thereof, wherein:
   $R^2$ is $C_3$-$C_6$ cycloalkyl, wherein the $C_3$-$C_6$ cycloalkyl is substituted by 1, 2, 3, 4, or 5 independently selected $R^{2b}$ substituents; and
   at least one $R^{2b}$ is an independently selected $C_1$-$C_6$ alkyl substituent, wherein the $C_1$-$C_6$ alkyl substituent is optionally substituted by 1, 2, 3, 4, or 5 independently selected $R^{4a}$ substituents.

27. The compound of claim 24, or a pharmaceutically acceptable salt, stereoisomer, or tautomer thereof, wherein:
   each $R^{2b}$ is independently $C_1$-$C_2$ alkyl, wherein each $C_1$-$C_2$ alkyl is independently substituted by 1, 2, 3, 4, or 5 independently selected 4-5 $R^{4a}$ substituents;
   each $R^{4a}$ is independently phenyl or 6-membered heteroaryl, wherein each phenyl and 6-membered heteroaryl is optionally and independently substituted by 1, 2, 3, 4, or 5 independently selected $R^{4b}$ substituents; and
   each $R^{4b}$ is an independently selected 0-5 halogen substituent.

28. The compound of claim 24, or a pharmaceutically acceptable salt, stereoisomer, or tautomer thereof, wherein:
   $R^2$ is $C_3$-$C_6$ cycloalkyl, wherein the $C_3$-$C_6$ cycloalkyl is substituted by 1, 2, 3, 4, or 5 independently selected $R^{2b}$ substituents; and
   at least one $R^{2b}$ is 3- to 12-membered heterocyclyl.

29. The compound of claim 28, or a pharmaceutically acceptable salt, stereoisomer, or tautomer thereof, wherein at least one $R^{2b}$ is tetrahydro-2H-pyranyl or benzodioxolyl.

30. The compound of claim 24, or a pharmaceutically acceptable salt, stereoisomer, or tautomer thereof, wherein:
   $R^2$ is $C_3$-$C_4$ cycloalkyl, wherein the $C_3$-$C_4$ cycloalkyl is optionally substituted by 1, 2, 3, 4, or 5 independently selected $R^{2b}$ substituents; and
   at least one $R^{2b}$ is $C_6$-$C_{14}$ aryl, wherein the $C_6$-$C_{14}$ aryl is optionally substituted by 1, 2, 3, 4, or 5 independently selected $R^{4a}$ substituents; and
   each $R^{4a}$ is independently halogen, $C_1$-$C_6$ alkyl, and $OR^8$.

31. The compound of claim 24, or a pharmaceutically acceptable salt, stereoisomer, or tautomer thereof, wherein:
   $R^2$ is $C_3$-$C_7$ cycloalkyl, wherein the $C_3$-$C_7$ cycloalkyl is substituted by 1, 2, 3, 4, or 5 independently selected $R^{2b}$ substituents; and
   at least one $R^{2b}$ is 5- to 10-membered heteroaryl.

32. The compound of claim 31, or a pharmaceutically acceptable salt, stereoisomer, or tautomer thereof, wherein at least one $R^{2b}$ is pyridinyl or isoquinolinyl.

33. The compound of claim 24, or a pharmaceutically acceptable salt, stereoisomer, or tautomer thereof, wherein:
   $R^2$ is $C_3$-$C_6$ cycloalkyl, wherein the $C_3$-$C_6$ cycloalkyl is substituted by 2, 3, 4, or 5 independently selected $R^{2b}$ substituents; and
   each $R^{2b}$ is independently halogen, $C_1$-$C_6$ alkyl, OR, or $C_6$-$C_{14}$ aryl, wherein each $C_6$-$C_{14}$ aryl is optionally and independently substituted by 1 or more independently selected $R^{4a}$ substituents.

34. The compound of claim 33, or a pharmaceutically acceptable salt, stereoisomer, or tautomer thereof, wherein:
   at least one $R^{2b}$ is halogen; and
   at least one $R^{2b}$ is phenyl, wherein the phenyl is optionally substituted by 1, 2, 3, 4, or 5 independently selected $R^{4a}$ substituents; and
   each $R^{4a}$ is an independently selected $C_1$-$C_6$ alkyl substituent.

35. The compound of claim 2, or a pharmaceutically acceptable salt, stereoisomer, or tautomer thereof, wherein $R^2$ is 3- to 12-membered heterocyclyl, wherein the 3- to 12-membered heterocyclyl is optionally substituted by 1, 2, 3, 4, or 5 independently selected $R^{2e}$ substituents.

36. The compound of claim 35, or a pharmaceutically acceptable salt, stereoisomer, or tautomer thereof, wherein $R^2$ is unsubstituted 4- to 10-membered heterocyclyl.

37. The compound of claim 35, or a pharmaceutically acceptable salt, stereoisomer, or tautomer thereof, wherein:
   $R^2$ is 3- to 12-membered heterocyclyl, wherein the 3- to 12-membered heterocyclyl is substituted by 1, 2, 3, 4, or 5 independently selected $R^{2c}$ substituents; and
   each $R^{2c}$ is independently halogen, CN, $C_1$-$C_6$ alkyl, $C(O)R^5$, $C(O)OR^5$, $OR^5$, =O, $S(O)_2R^5$, $C_6$-$C_{14}$ aryl, or 5- to 10-membered heteroaryl, wherein each $C_1$-$C_6$ alkyl is optionally and independently substituted by 1 or more independently selected $R^{4a}$ substituents.

38. The compound of claim 37, or a pharmaceutically acceptable salt, stereoisomer, or tautomer thereof, wherein:
   $R^2$ is 4- to 6-membered heterocyclyl, wherein the 4- to 6-membered heterocyclyl is substituted by 1, 2, 3, 4, or 5 independently selected $R^{2c}$ substituents; and
   at least one $R^{2c}$ is $C_1$-$C_6$ alkyl, wherein the $C_1$-$C_6$ alkyl is optionally substituted by 1, 2, 3, 4, or 5 independently selected $R^{4a}$ substituents.

39. The compound of claim 38, or a pharmaceutically acceptable salt, stereoisomer, or tautomer thereof, wherein:
   at least one $R^{2c}$ is $C_1$-$C_2$ alkyl, wherein the $C_1$-$C_2$ alkyl is substituted by 1, 2, 3, 4, or 5 independently selected $R^{4a}$ substituents;
   each $R^{4a}$ is independently halogen, $NR^8C(O)OR^{10}$, phenyl, or 6-membered heteroaryl, wherein each phenyl and 6-membered heteroaryl is optionally and independently substituted by 1, 2, 3, 4, or 5 independently selected $R^{4b}$ substituents; and
   each $R^{4b}$ is an independently selected halogen substituent.

40. The compound of claim 37, or a pharmaceutically acceptable salt, stereoisomer, or tautomer thereof, wherein:
   $R^2$ is 4- to 6-membered heterocyclyl, wherein the 4- to 6-membered heterocyclyl is substituted by 1, 2, 3, 4, or 5 independently selected $R^{2c}$ substituents; and
   at least one $R^{2c}$ is unsubstituted $C_6$-$C_{14}$ aryl.

41. The compound of claim 37, or a pharmaceutically acceptable salt, stereoisomer, or tautomer thereof, wherein:
$R^2$ is 5-membered heterocyclyl, wherein the 5-membered heterocyclyl is substituted by 1, 2, 3, 4, or 5 independently selected $R^{2c}$ substituents:
at least one $R^{2c}$ is 5- to 10-membered heteroaryl, wherein the 5- to 10-membered heteroaryl is optionally substituted by 1, 2, 3, 4, or 5 independently selected $R^{4a}$ substituents; and
each $R^{4a}$ is an independently selected 0-5 $C_1$-$C_6$ alkyl substituent.

42. The compound of claim 37, or a pharmaceutically acceptable salt, stereoisomer, or tautomer thereof, wherein:
$R^2$ is 4- to 6-membered heterocyclyl, wherein the 4- to 6-membered heterocyclyl is substituted by 1, 2, 3, 4, or 5 independently selected $R^{2c}$ substituents;
at least one $R^{2c}$ is $C(O)R^5$, $C(O)OR^5$, or $S(O)_2R^5$; and
each $R^5$ is independently $C_1$-$C_6$ alkyl.

43. The compound of claim 37, or a pharmaceutically acceptable salt, stereoisomer, or tautomer thereof, wherein:
$R^2$ is 4- to 6-membered heterocyclyl, wherein the 4- to 6-membered heterocyclyl is substituted by 1, 2, 3, 4, or 5 independently selected $R^{2c}$ substituents; and
at least one $R^{2c}$ is =O.

44. The compound of claim 37, or a pharmaceutically acceptable salt, stereoisomer, or tautomer thereof, wherein:
$R^2$ is 4- to 6-membered heterocyclyl, wherein the 4- to 6-membered heterocyclyl is substituted by 2, 3, 4, or 5 independently selected $R^{2c}$ substituents; and
each $R^{2c}$ is independently halogen, $C_1$-$C_6$ alkyl, $C(O)R^5$, or $C(O)OR^5$.

45. The compound of claim 4, or a pharmaceutically acceptable salt, stereoisomer, or tautomer thereof, wherein:
$R^2$ is 4- to 6-membered heterocyclyl, wherein the 4- to 6-membered heterocyclyl is substituted by 2, 3, 4, or 5 independently selected $R^{2c}$ substituents;
at least one $R^{2c}$ is $C_1$-$C_6$ alkyl, wherein the $C_1$-$C_6$ alkyl is optionally substituted by 1, 2, 3, 4, or 5 independently selected $R^{4a}$ substituents;
at least one $R^{2c}$ is $C(O)R^5$ or $C(O)OR^5$; and
each $R^{4a}$ is an independently selected halogen substituent.

46. The compound of claim 35, or a pharmaceutically acceptable salt, stereoisomer, or tautomer thereof, wherein $R^2$ is azetidinyl, pyrrolidinyl, piperidinyl, oxetanyl, tetrahydrofuranyl, tetrahydropyranyl, oxabicyclohexanyl, oxabicyclooctanyl, tetrahydro-2H-thiopyranyl, morpholinyl, or benzodioxanyl, wherein the azetidinyl, pyrrolidinyl, piperidinyl, oxetanyl, tetrahydrofuranyl, tetrahydropyranyl, oxabicyclohexanyl, oxabicyclooctanyl, tetrahydro-2H-thiopyranyl, morpholinyl, or benzodioxanyl is optionally substituted by 1, 2, 3, 4, or 5 independently selected $R^{2c}$ substituents.

47. The compound of claim 2, or a pharmaceutically acceptable salt, stereoisomer, or tautomer thereof, wherein $R^2$ is $C_6$-$C_{14}$ aryl, wherein the $C_6$-$C_{14}$ aryl is optionally substituted by 1, 2, 3, 4, or 5 independently selected $R^{2d}$ substituents.

48. The compound of claim 47, or a pharmaceutically acceptable salt, stereoisomer, or tautomer thereof, wherein $R^2$ is unsubstituted $C_6$-$C_{10}$ aryl.

49. The compound of claim 47, or a pharmaceutically acceptable salt, stereoisomer, or tautomer thereof, wherein:
$R^2$ is $C_6$-$C_{10}$ aryl, wherein the $C_6$-$C_{10}$ aryl is optionally substituted by 1, 2, 3, 4, or 5 independently selected $R^{2d}$ substituents:
each $R^{2d}$ is independently halogen, CN, $C_1$-$C_6$ alkyl, $OR^5$, $C_3$-$C_8$ cycloalkyl, 3- to 12-membered heterocyclyl, or 5- to 10-membered heteroaryl, wherein each $C_1$-$C_6$ alkyl, $C_3$-$C_8$ cycloalkyl, 3- to 12-membered heterocyclyl, and 5- to 10-membered heteroaryl is optionally and independently substituted by 1, 2, 3, 4, or 5 independently selected $R^{4a}$ substituents; and
each $R^{4a}$ is independently halogen, $C_1$-$C_6$ alkyl or $OR^8$.

50. The compound of claim 49, or a pharmaceutically acceptable salt, stereoisomer, or tautomer thereof, wherein:
$R^2$ is $C_6$-$C_{10}$ aryl, wherein the $C_6$-$C_{10}$ aryl is optionally substituted by 1, 2, 3, 4, or 5 independently selected $R^{2d}$ substituents; and
at least one $R^{2d}$ is halogen.

51. The compound of claim 49, or a pharmaceutically acceptable salt, stereoisomer, or tautomer thereof, wherein:
$R^2$ is $C_6$-$C_{10}$ aryl, wherein the $C_6$-$C_{10}$ aryl is optionally substituted by 1, 2, 3, 4, or 5 independently selected $R^{2d}$ substituents: wherein
at least one $R^{2d}$ is $C_1$-$C_6$ alkyl, wherein the $C_1$-$C_6$ alkyl is optionally substituted by 1, 2, 3, 4, or 5 independently selected 9-5 $R^{4a}$ substituents; and
each $R^{4a}$ is independently halogen, $C_1$-$C_6$ alkyl or $OR^8$.

52. The compound of claim 51, or a pharmaceutically acceptable salt, stereoisomer, or tautomer thereof, wherein:
$R^2$ is $C_6$-$C_{10}$ aryl, wherein the $C_6$-$C_{10}$ aryl is optionally substituted by 1, 2, 3, 4, or 5 independently selected $R^{2d}$ substituents;
at least one $R^{2d}$ is $C_1$-$C_2$ alkyl, wherein the $C_1$-$C_2$ alkyl is optionally substituted by 1, 2, 3, 4, or 5 independently selected $R^{4a}$ substituents; and
each $R^{4a}$ is independently halogen or $OR^8$.

53. The compound of claim 49, or a pharmaceutically acceptable salt, stereoisomer, or tautomer thereof, wherein:
$R^2$ is phenyl, wherein the phenyl is substituted by 1, 2, 3, 4, or 5 independently selected $R^{2d}$ substituents; and
at least one $R^{2d}$ is $C_3$-$C_6$ cycloalkyl.

54. The compound of claim 49, or a pharmaceutically acceptable salt, stereoisomer, or tautomer thereof, wherein:
$R^2$ is phenyl, wherein the phenyl is substituted by 1, 2, 3, 4, or 5 independently selected $R^{2d}$ substituents; and
at least one $R^{2d}$ is 6-membered heterocyclyl.

55. The compound of claim 49, or a pharmaceutically acceptable salt, stereoisomer, or tautomer thereof, wherein:
$R^2$ is phenyl, wherein the phenyl is substituted by 1, 2, 3, 4, or 5 independently selected $R^{2d}$ substituents;
at least one $R^{2d}$ is 5- or 6-membered heteroaryl, wherein the 5- or 6-membered heteroaryl is optionally substituted by 1, 2, 3, 4, or 5 independently selected $R^{4a}$ substituents; and
each $R^{4a}$ is independently 0-5 $C_1$-$C_6$ alkyl.

56. The compound of claim 49, or a pharmaceutically acceptable salt, stereoisomer, or tautomer thereof, wherein:
$R^2$ is phenyl, wherein the phenyl is substituted by 1, 2, 3, 4, or 5 independently selected $R^{2d}$ substituents; and
at least one $R^{2d}$ is $OR^5$;
$R^5$ is $C_1$-$C_2$ alkyl, wherein the $C_1$-$C_2$ alkyl is optionally substituted by 1, 2, 3, 4, or 5 independently selected $R^{5a}$ substituents; and
each $R^{5a}$ is independently halogen or $OR^{10}$.

57. The compound of claim 49, or a pharmaceutically acceptable salt, stereoisomer, or tautomer thereof, wherein:
$R^2$ is phenyl, wherein the phenyl is substituted by 2, 3, 4, or 5 independently selected $R^{2d}$ substituents; and
each $R^{2d}$ is independently halogen, $C_1$-$C_6$ alkyl, CN, or $OR^5$.

58. The compound of claim 57, or a pharmaceutically acceptable salt, stereoisomer, or tautomer thereof, wherein:
$R^2$ is phenyl, wherein the phenyl is substituted by 2, 3, 4, or 5 independently selected $R^{2d}$ substituents; and at least two $R^{2d}$ are independently selected halogen substituents.

59. The compound of claim 57, or a pharmaceutically acceptable salt, stereoisomer, or tautomer thereof, wherein:
$R^2$ is phenyl, wherein the phenyl is substituted by 2, 3, 4, or 5 independently selected $R^{2d}$ substituents;
at least one $R^{2d}$ is halogen, CN, or $OR^5$; and
at least one $R^{2d}$ is $C_1$-$C_6$ alkyl.

60. The compound of claim 47, or a pharmaceutically acceptable salt, stereoisomer, or tautomer thereof, wherein $R^2$ is phenyl, indanyl, or 1,2,3,4-tetrahydronaphthalenyl, wherein the phenyl, indanyl, or 1,2,3,4-tetrahydronaphthalenyl is optionally substituted by 1, 2, 3, 4, or 5 independently selected $R^{2d}$ substituents.

61. The compound of claim 2, or a pharmaceutically acceptable salt, stereoisomer, or tautomer thereof, wherein $R^2$ is 5- to 10-membered heteroaryl, wherein the 5- to 10-membered heteroaryl is optionally substituted by 1, 2, 3, 4, or 5 independently selected $R^{2e}$ substituents.

62. The compound of claim 61, or a pharmaceutically acceptable salt, stereoisomer, or tautomer thereof, wherein $R^2$ is unsubstituted 5- to 10-membered heteroaryl.

63. The compound of claim 61, or a pharmaceutically acceptable salt, stereoisomer, or tautomer thereof, wherein:
$R^2$ is 5- to 10-membered heteroaryl, wherein the 5- to 10-membered heteroaryl is substituted by 1, 2, 3, 4, or 5 independently selected $R^{2e}$ substituents, and
each $R^{2e}$ is independently halogen, $C_1$-$C_6$ alkyl, or $OR^5$, wherein each $C_1$-$C_6$ alkyl is optionally and independently substituted by 1 or more independently selected $R^{4a}$ substituents.

64. The compound of claim 63, or a pharmaceutically acceptable salt, stereoisomer, or tautomer thereof, wherein at least one $R^{2e}$ is halogen.

65. The compound of claim 63, or a pharmaceutically acceptable salt, stereoisomer, or tautomer thereof, wherein:
at least one $R^{2e}$ is $C_1$-$C_4$ alkyl, wherein the $C_1$-$C_4$ alkyl is optionally substituted by 1, 2, 3, 4, or 5 independently selected $R^{4a}$ substituents; and
each $R^{4a}$ is an independently selected halogen substituent.

66. The compound of claim 61, or a pharmaceutically acceptable salt, stereoisomer, or tautomer thereof, wherein:
$R^2$ is 5- to 10-membered heteroaryl, wherein the 5- to 10-membered heteroaryl is substituted by 2, 3, 4, or 5 independently selected $R^{2e}$ substituents; and
each $R^{2e}$ is independently halogen, $C_1$-$C_6$ alkyl, or CN.

67. The compound of claim 66, or a pharmaceutically acceptable salt, stereoisomer, or tautomer thereof, wherein at least two $R^{2e}$ are independently selected halogen substituents.

68. The compound of claim 66, or a pharmaceutically acceptable salt, stereoisomer, or tautomer thereof, wherein $R^2$ at least two $R^{2e}$ are independently selected $C_1$-$C_6$ alkyl substituents.

69. The compound of claim 66, or a pharmaceutically acceptable salt, stereoisomer, or tautomer thereof, wherein:
$R^2$ is 5- to 10-membered heteroaryl, wherein the 5- to 10-membered heteroaryl is substituted by 3, 4, or 5 independently selected 3-5 $R^{2e}$ substituents; and
each $R^{2e}$ is independently halogen, CN, or $C_1$-$C_6$.

70. The compound of claim 61, or a pharmaceutically acceptable salt, stereoisomer, or tautomer thereof, wherein $R^2$ is pyrazolyl, pyridinyl, pyrimidinyl, indazolyl, pyrrolopyridinyl, quinolinyl, or 4,5,6,7-tetrahydro-indazolyl, wherein the pyrazolyl, pyridinyl, pyrimidinyl, indazolyl, pyrrolopyridinyl, quinolinyl, or 4,5,6,7-tetrahydro-indazolyl is optionally substituted by 1, 2, 3, 4, or 5 independently selected $R^{2e}$ substituents.

71. The compound of claim 2, or a pharmaceutically acceptable salt, stereoisomer, or tautomer thereof, wherein $R^2$ is $OR^{2f}$.

72. The compound of claim 71, or a pharmaceutically acceptable salt, stereoisomer, or tautomer thereof, wherein:
$R^{2f}$ is $C_1$-$C_6$ alkyl, $C_3$-$C_8$ cycloalkyl, 3- to 12-membered heterocyclyl, $C_6$-$C_{14}$ aryl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ aryl, or 5- to 10-membered heteroaryl is optionally substituted by 1 or more independently selected $R^{2i}$ substituents; and
each $R^{2i}$ is optionally and independently substituted by 1 or more independently selected $R^{4a}$ substituents.

73. The compound of claim 72, or a pharmaceutically acceptable salt, stereoisomer, or tautomer thereof, wherein $R^{2f}$ is $C_1$-$C_6$ alkyl, wherein the $C_1$-$C_6$ alkyl is optionally substituted by 1, 2, 3, 4, or 5 independently selected $R^{2i}$ substituents.

74. The compound of claim 73, or a pharmaceutically acceptable salt, stereoisomer, or tautomer thereof, wherein $R^{2f}$ is unsubstituted $C_1$-$C_6$ alkyl.

75. The compound of claim 73, or a pharmaceutically acceptable salt, stereoisomer, or tautomer thereof, wherein:
$R^{2f}$ is $C_1$-$C_6$ alkyl, wherein the $C_1$-$C_6$ alkyl is substituted by 1, 2, 3, 4, or 5 independently selected $R^{2i}$ substituents;
each $R^{2i}$ is independently halogen, $C_1$-$C_6$ alkyl, $NR^5C(O)R^6$, $NR^5C(O)OR^6$, $OR^5$, $C_3$-$C_8$ cycloalkyl, 3- to 12-membered heterocyclyl, $C_6$-$C_{14}$ aryl, or 5- to 10-membered heteroaryl, wherein each $C_1$-$C_6$ alkyl, $C_3$-$C_8$ cycloalkyl, 3- to 12-membered heterocyclyl, $C_6$-$C_{14}$ aryl, and 5- to 10-membered heteroaryl is optionally and independently substituted by 1, 2, 3, 4, or 5 independently selected $R^{4a}$ substituents;
each $R^{4a}$ is independently halogen, CN, $OR^8$, or $C_1$-$C_6$ alkyl, wherein each $C_1$-$C_6$ alkyl substituent is optionally and independently substituted by 1 or more independently selected $R^{4b}$ substituents; and
each $R^{4b}$ is an independently selected halogen substituent.

76. The compound of claim 75, or a pharmaceutically acceptable salt, stereoisomer, or tautomer thereof, wherein at least one $R^{2i}$ is halogen.

77. The compound of claim 75, or a pharmaceutically acceptable salt, stereoisomer, or tautomer thereof, wherein at least one $R^{2i}$ is phenyl.

78. The compound of claim 75, or a pharmaceutically acceptable salt, stereoisomer, or tautomer thereof, wherein:
at least one $R^{2i}$ is $NR^5C(O)OR^6$;
$R^5$ is H; and
$R^6$ is $C_1$-$C_6$ alkyl.

79. The compound of claim 72, or a pharmaceutically acceptable salt, stereoisomer, or tautomer thereof, wherein $R^{2f}$ is $C_3$-$C_8$ cycloalkyl, wherein the $C_3$-$C_8$ cycloalkyl is optionally substituted by 1, 2, 3, 4, or 5 independently selected 0-5 $R^{2i}$ substituents.

80. The compound of claim 79, or a pharmaceutically acceptable salt, stereoisomer, or tautomer thereof, wherein $R^{2f}$ is unsubstituted $C_3$-$C_8$ cycloalkyl.

81. The compound of claim 79, or a pharmaceutically acceptable salt, stereoisomer, or tautomer thereof, wherein:
$R^{2f}$ is $C_3$-$C_8$ cycloalkyl, wherein the $C_3$-$C_8$ cycloalkyl is substituted by 1, 2, 3, 4, or 5 independently selected $R^{2i}$ substituents; and each $R^{2i}$ is independently halogen, $C_1$-$C_6$ alkyl, $C_2$-$C_6$ alkynyl, $C_6$-$C_{14}$ aryl, or 5- to 10-membered heteroaryl, wherein each $C_1$-$C_6$ alkyl, $C_2$-$C_6$ alkynyl, $C_6$-$C_{14}$ aryl, and 5- to 10-membered heteroaryl is optionally and independently substituted by 1, 2, 3, 4, or 5 independently selected $R^{4a}$ substituents; and each $R^{4a}$ is $C_1$-$C_6$ alkyl or $C_6$-$C_{14}$ aryl.

82. The compound of claim 81, or a pharmaceutically acceptable salt, stereoisomer, or tautomer thereof, wherein:
$R^{2f}$ is $C_3$-$C_6$ cycloalkyl, wherein the $C_3$-$C_6$ cycloalkyl is substituted by 1, 2, 3, 4, or 5 independently selected $R^{21}$ substituents; and at least one $R^{2i}$ is $C_1$ alkyl.

83. The compound of claim 1, or a pharmaceutically acceptable salt, stereoisomer, or tautomer thereof, wherein:
$R^{2f}$ is $C_3$-$C_6$ cycloalkyl, wherein the $C_3$-$C_6$ cycloalkyl is substituted by 1, 2, 3, 4, or 5 independently selected $R^{21}$ substituents; and at least one $R^{2i}$ is $C_2$ alkynyl, wherein the $C_2$ alkynyl is optionally substituted by 1 $R^{4a}$ substituent; and $R^{4a}$ is phenyl.

84. The compound of claim 81, or a pharmaceutically acceptable salt, stereoisomer, or tautomer thereof, wherein:
$R^{2f}$ is $C_3$-$C_6$ cycloalkyl, wherein the $C_3$-$C_6$ cycloalkyl is substituted by 1, 2, 3, 4, or 5 independently selected $R^{2i}$ substituents; and at least one $R^{2i}$ is phenyl and pyrazolyl, wherein the phenyl or pyrazolyl is optionally substituted by 1, 2, or 3 independently selected $R^{4a}$ substituents; and each $R^{4a}$ is $C_1$-$C_6$ alkyl.

85. The compound of claim 72, or a pharmaceutically acceptable salt, stereoisomer, or tautomer thereof, wherein:
$R^{2f}$ is 3- to 12-membered heterocyclyl, wherein the 3- to 12-membered heterocyclyl is optionally substituted by 1, 2, 3, 4, or 5 independently selected $R^{2i}$ substituents; and each $R^{2i}$ is optionally and independently substituted by 1 or more independently selected $R^{4a}$ substituents.

86. The compound of claim 85, or a pharmaceutically acceptable salt, stereoisomer, or tautomer thereof, wherein $R^{2f}$ is unsubstituted 3- to 12-membered heterocyclyl.

87. The compound of claim 85, or a pharmaceutically acceptable salt, stereoisomer, or tautomer thereof, wherein:
$R^{2f}$ is 3- to 12-membered heterocyclyl, wherein the 3- to 12-membered heterocyclyl is substituted by 1, 2, 3, 4, or 5 independently selected $R^{2i}$ substituents; and each $R^{2i}$ is independently $C_1$-$C_6$ alkyl, $C_2$-$C_6$ alkynyl, $C_6$-$C_{14}$ aryl, $C(O)R^5$, $C(O)OR^5$, or $S(O)_2R^5$ wherein each $C_1$-$C_6$ alkyl, $C_2$-$C_6$ alkynyl, and $C_6$-$C_{14}$ aryl is optionally and independently substituted by 1 or more independently selected $R^{4a}$ substituents.

88. The compound of claim 87, or a pharmaceutically acceptable salt, stereoisomer, or tautomer thereof, wherein:
at least one $R^{2i}$ is $C_1$-$C_6$ alkyl or $C_2$-$C_6$ alkynyl, wherein the $C_1$-$C_6$ alkyl or $C_2$-$C_6$ alkynyl is optionally substituted by 1 $R^{4a}$ substituent; and $R^{4a}$ is phenyl.

89. The compound of claim 87, or a pharmaceutically acceptable salt, stereoisomer, or tautomer thereof, wherein:
at least one $R^{2i}$ is $C_6$-$C_{14}$ aryl, wherein the $C_6$-$C_{14}$ aryl is optionally substituted by 1, 2, 3, 4, or 5 independently selected $R^{4a}$ substituents; and each $R^{4a}$ is independently halogen or $C_1$-$C_6$ alkyl.

90. The compound of claim 87, or a pharmaceutically acceptable salt, stereoisomer, or tautomer thereof, wherein:
at least one $R^{2i}$ is C(O)RN; and $R^5$ is $C_1$-$C_6$ alkyl.

91. The compound of claim 87, or a pharmaceutically acceptable salt, stereoisomer, or tautomer thereof, wherein:
at least one $R^{2i}$ is $C(O)OR^5$; and $R^5$ is $C_1$-$C_6$ alkyl.

92. The compound of claim 87, or a pharmaceutically acceptable salt, stereoisomer, or tautomer thereof, wherein:
at least one $R^{2i}$ is $S(O)_2R^5$; and $R^5$ is $C_1$-$C_6$ alkyl.

93. The compound of claim 87, or a pharmaceutically acceptable salt, stereoisomer, or tautomer thereof, wherein:
$R^{2f}$ is 3- to 12-membered heterocyclyl, wherein the 3- to 12-membered heterocyclyl is substituted by 2, 3, 4, or 5 independently selected $R^{2i}$ substituents; and at least one $R^{2i}$ is $C(O)R^5$, $C(O)OR^5$, or $S(O)_2R^5$; and $R^5$ is $C_1$-$C_6$ alkyl.

94. The compound of claim 85, or a pharmaceutically acceptable salt, stereoisomer, or tautomer thereof, wherein $R^{2f}$ is azetidinyl, pyrrolidinyl, or tetrahydropyranyl, and wherein the azetidinyl, pyrrolidinyl, or tetrahydropyranyl is optionally substituted by 1, 2, 3, 4, or 5 independently selected $R^{2i}$ substituents.

95. The compound of claim 72, or a pharmaceutically acceptable salt, stereoisomer, or tautomer thereof, wherein $R^{2f}$ is $C_6$-$C_{14}$ aryl, wherein the $C_6$-$C_{14}$ aryl is optionally substituted by 1, 2, 3, 4, or 5 independently selected $R^{2i}$ substituents.

96. The compound of claim 95, or a pharmaceutically acceptable salt, stereoisomer, or tautomer thereof, wherein $R^{2f}$ is unsubstituted $C_6$-$C_{14}$ aryl.

97. The compound of claim 2, or a pharmaceutically acceptable salt, stereoisomer, or tautomer thereof, wherein $R^2$ is $NR^{2g}R^{2h}$.

98. The compound of claim 97, or a pharmaceutically acceptable salt, stereoisomer, or tautomer thereof, wherein:
$R^{2g}$ is H; and $R^{2h}$ is $C_1$-$C_6$ alkyl, wherein the $C_1$-$C_6$ alkyl is optionally substituted by 1, 2, 3, 4, or 5 independently selected $R^{2j}$ substituents; and each $R^{2j}$ is an independently selected halogen substituent.

99. The compound of claim 97, or a pharmaceutically acceptable salt, stereoisomer, or tautomer thereof, wherein:
$R^{2g}$ is $C_1$-$C_6$ alkyl, wherein the $C_1$-$C_6$ alkyl is optionally substituted by 1, 2, 3, 4, or 5 independently selected $R^{2j}$ substituents:

$R^{2h}$ is $C_1$-$C_6$ alkyl, wherein the $C_1$-$C_6$ alkyl is optionally substituted by 1, 2, 3, 4, or 5 independently selected $R^{2j}$ substituents; and each $R^{2j}$ is an independently selected halogen substituent.

100. The compound of claim 1, or a pharmaceutically acceptable salt, stereoisomer, or tautomer thereof, wherein G is —$C(O)R^2$ and $R^2$ is selected from the group consisting of:

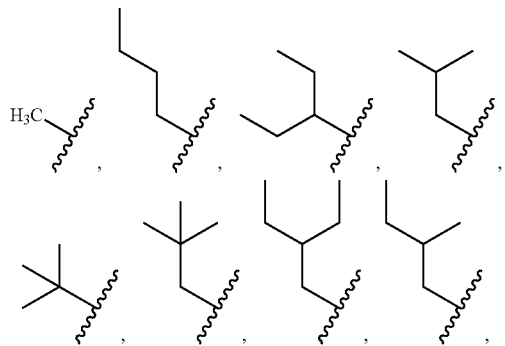

409
-continued
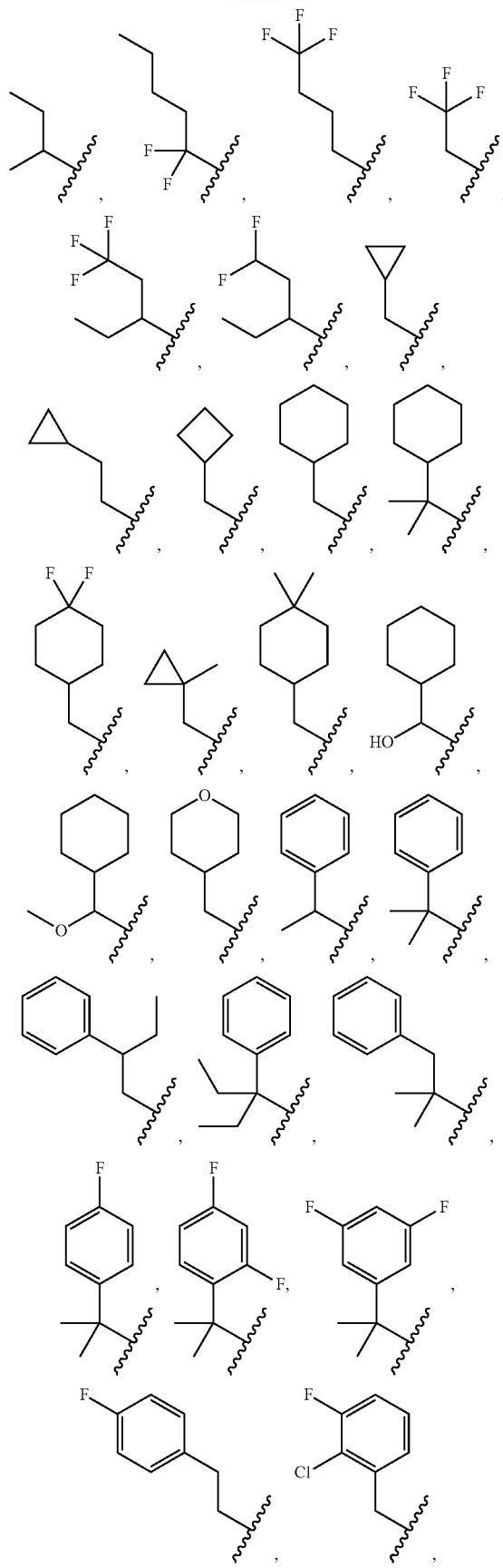
410
-continued
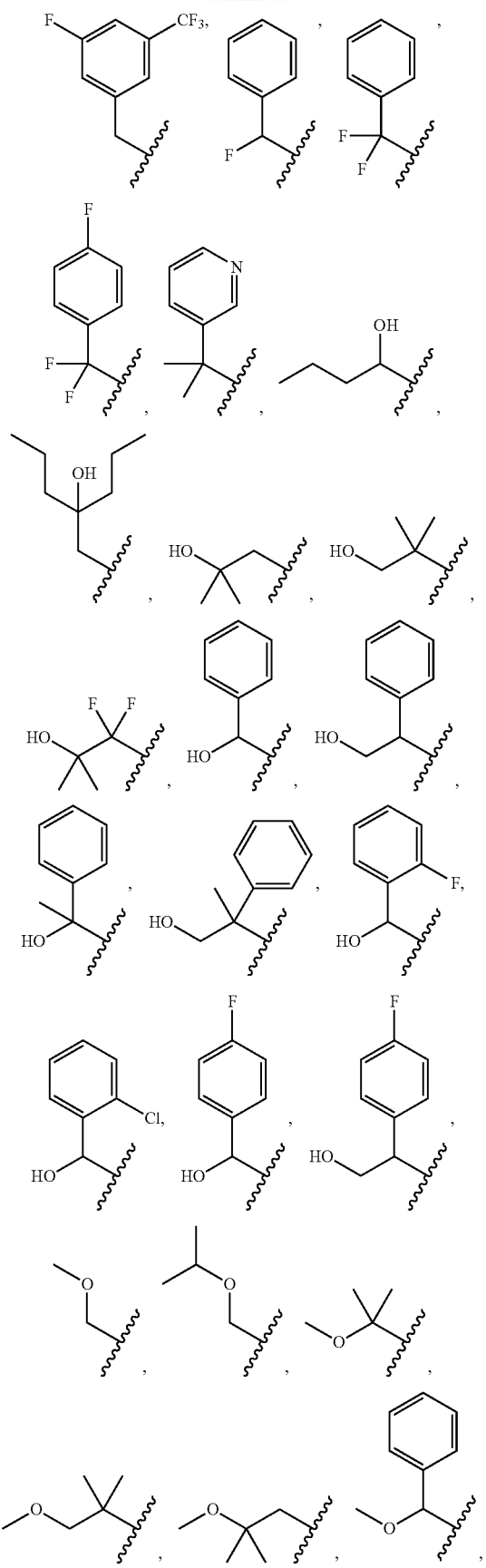

411
-continued
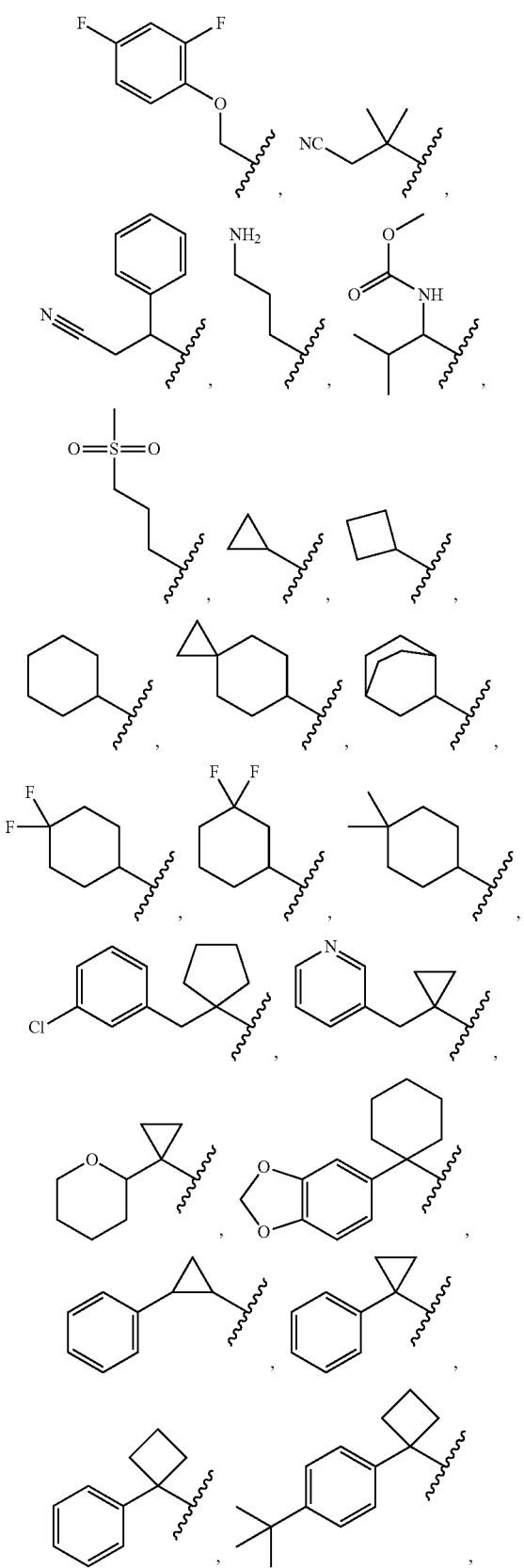
412
-continued
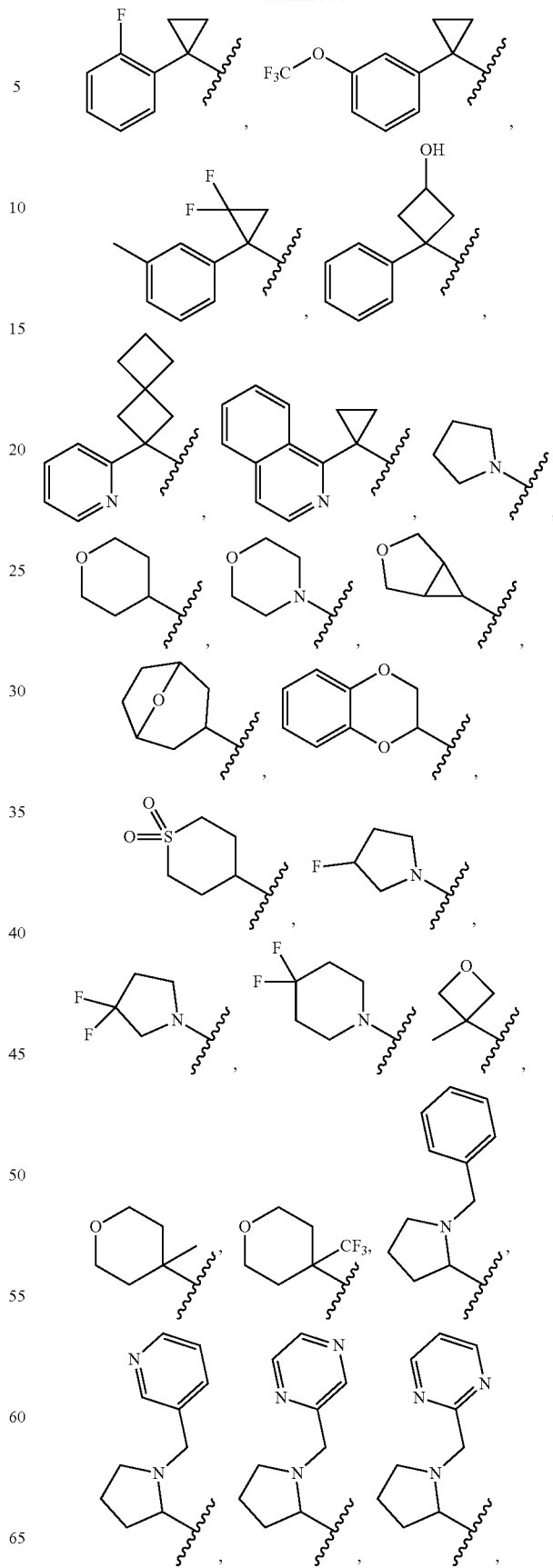

413
-continued
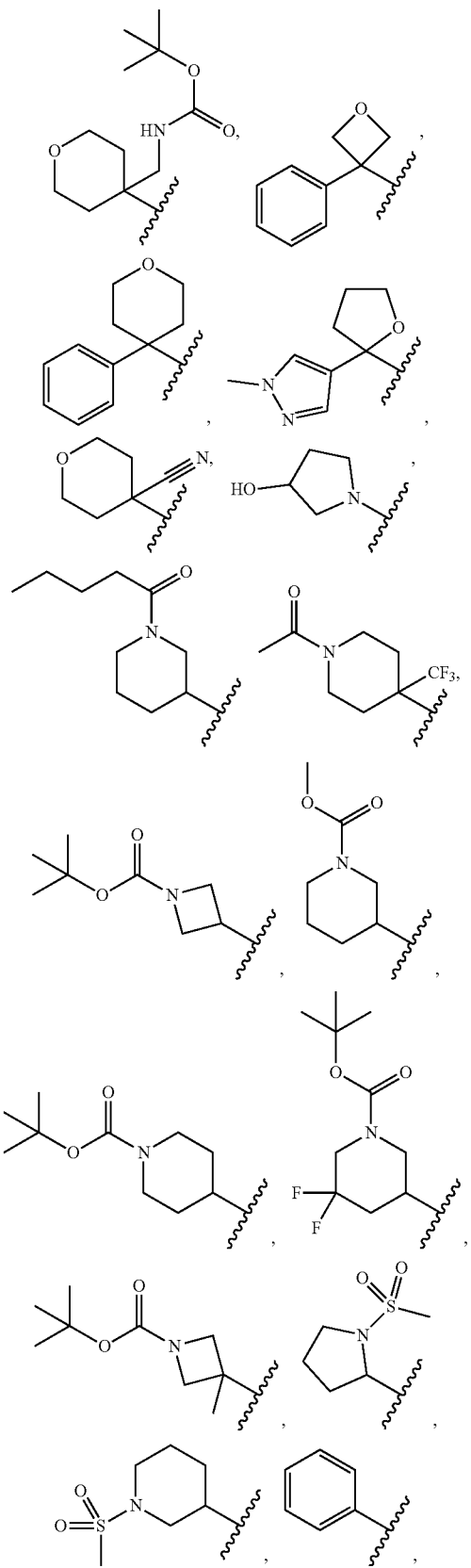
414
-continued
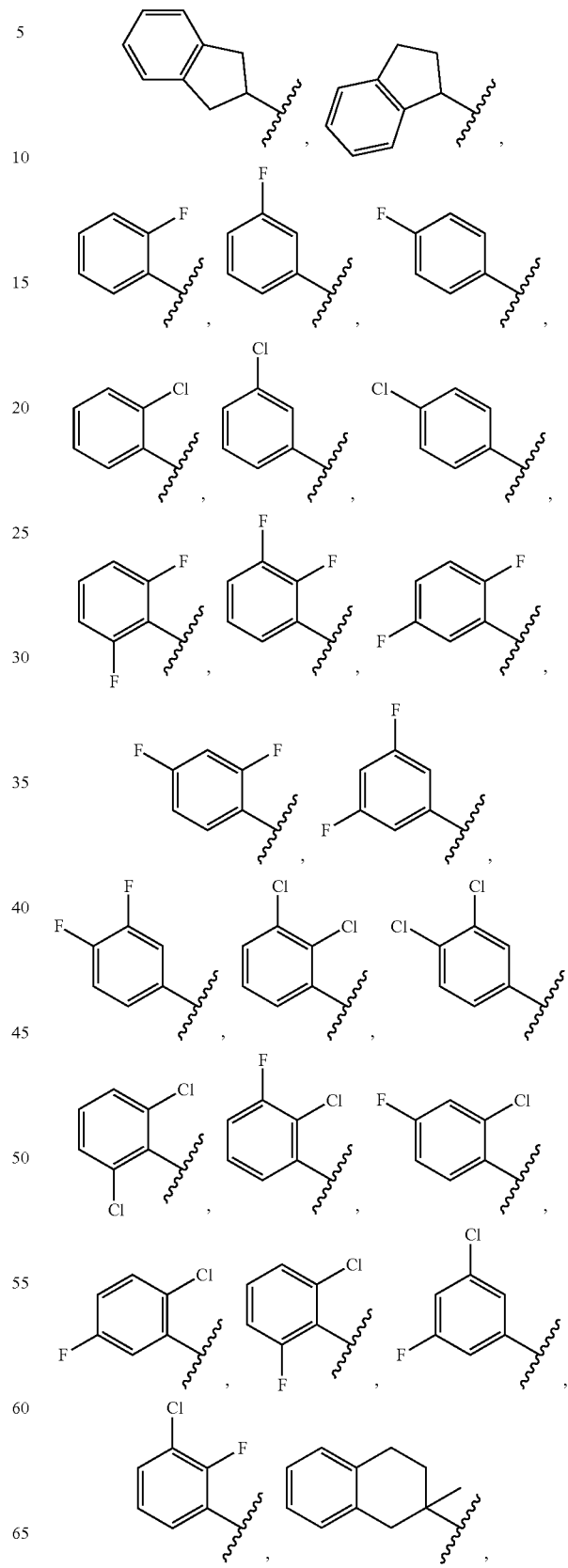

415
-continued
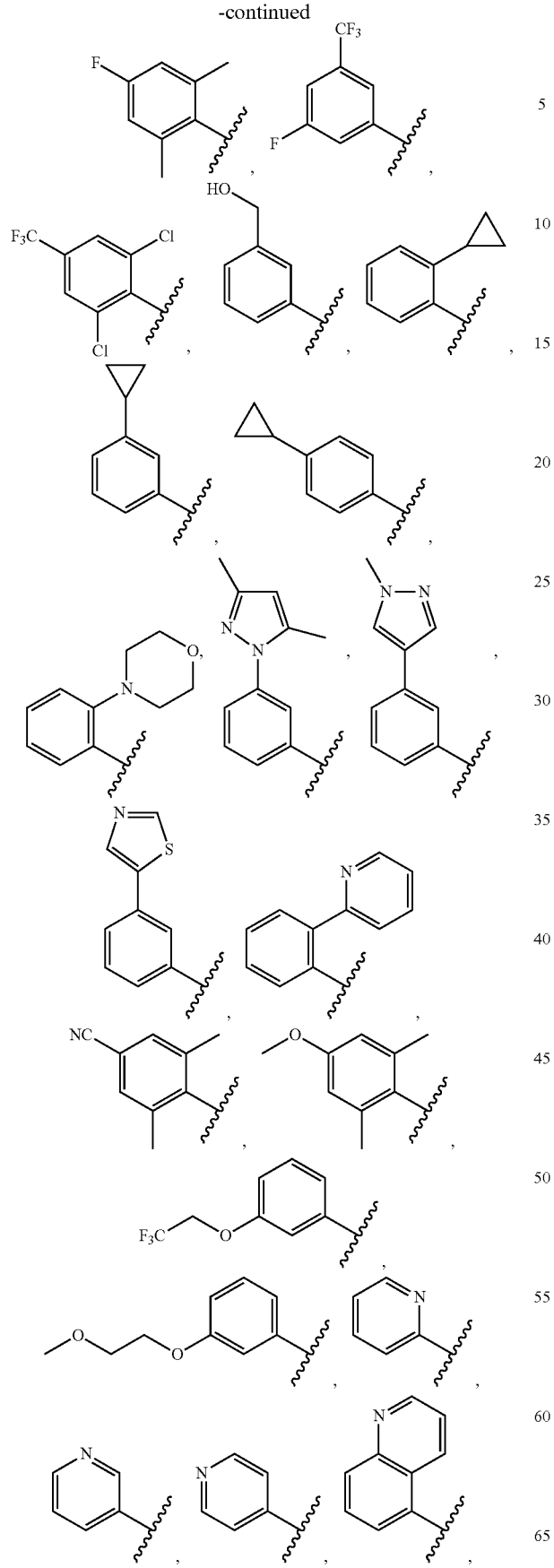
416
-continued
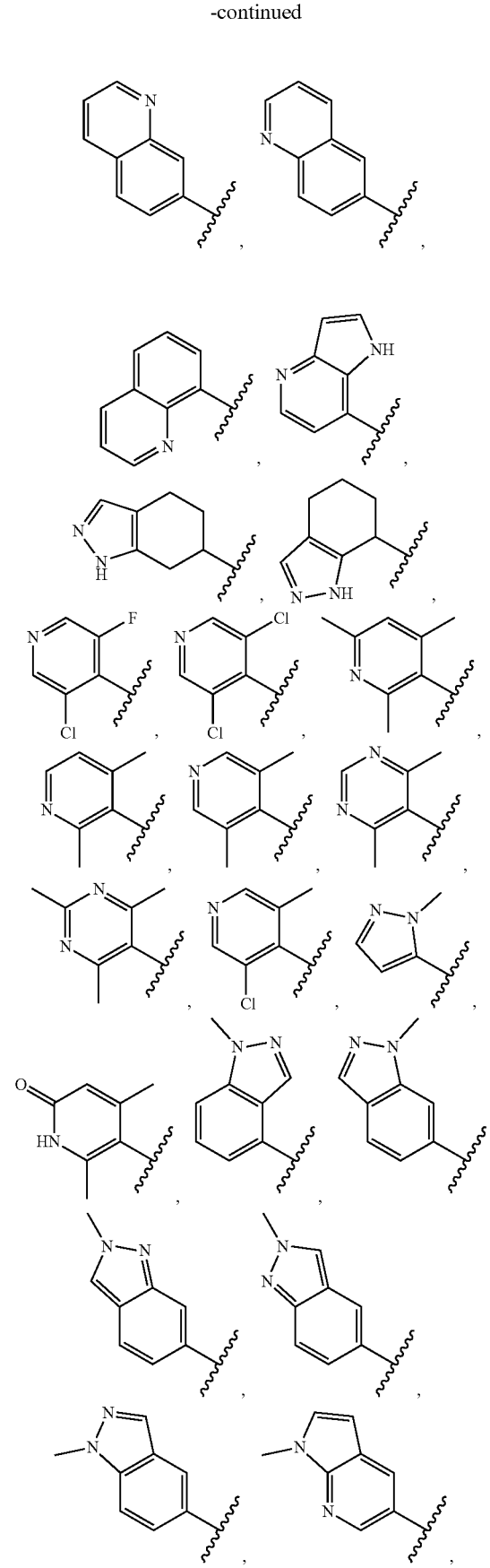

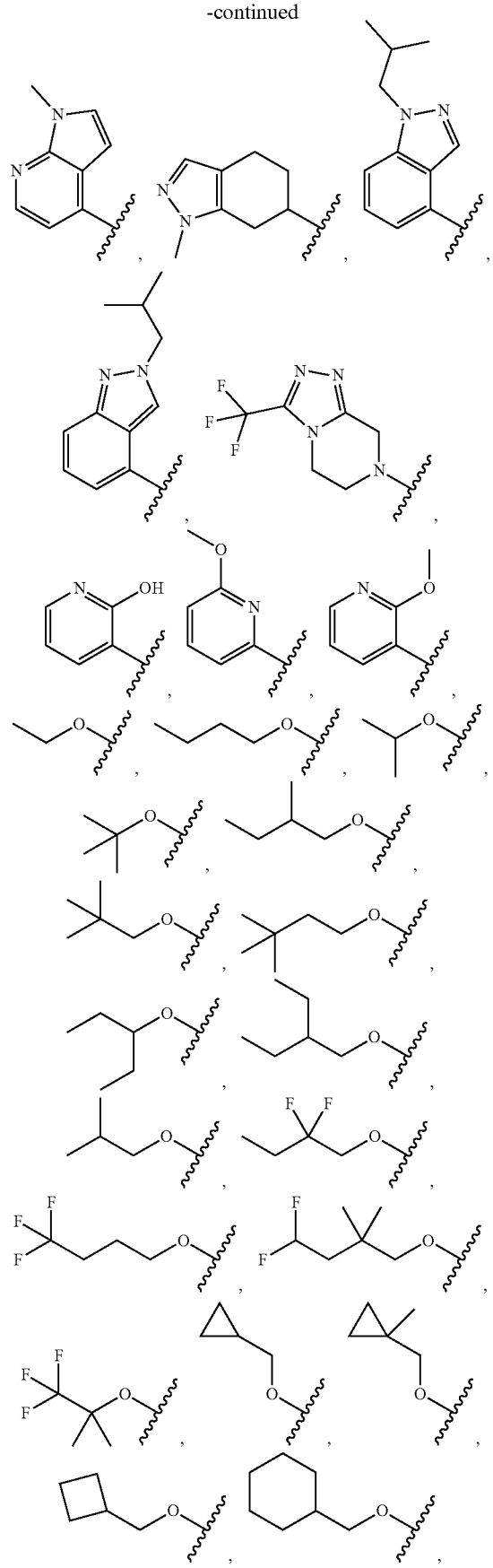
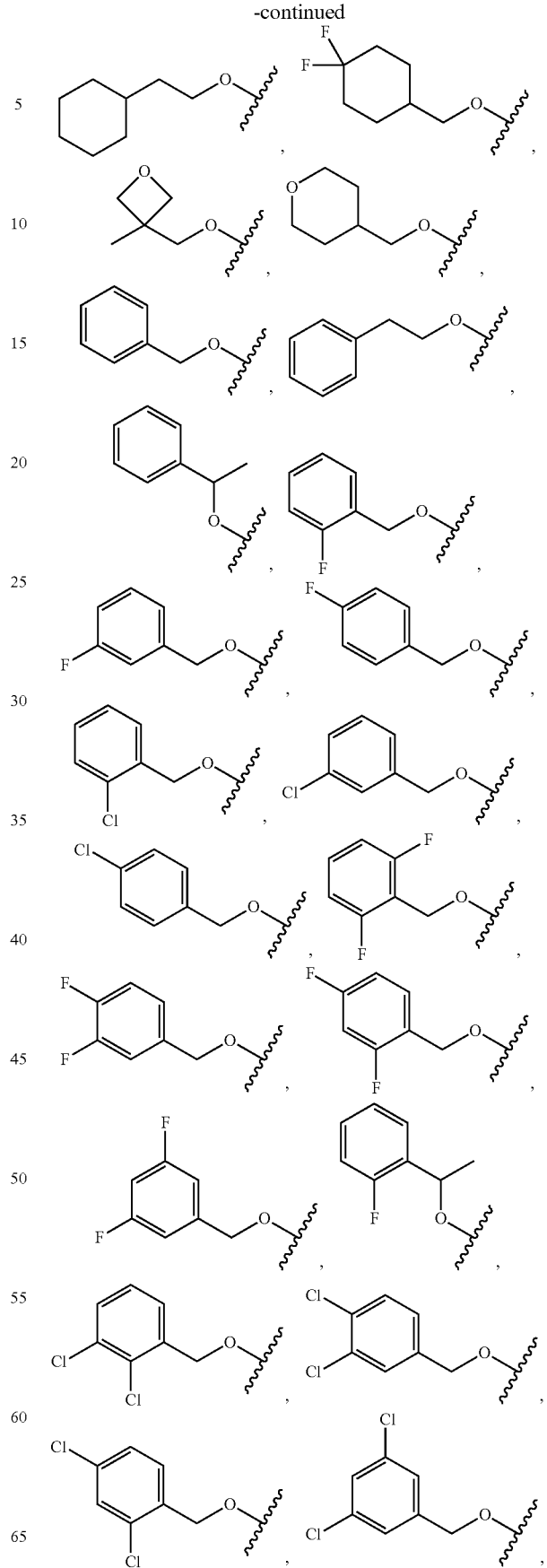

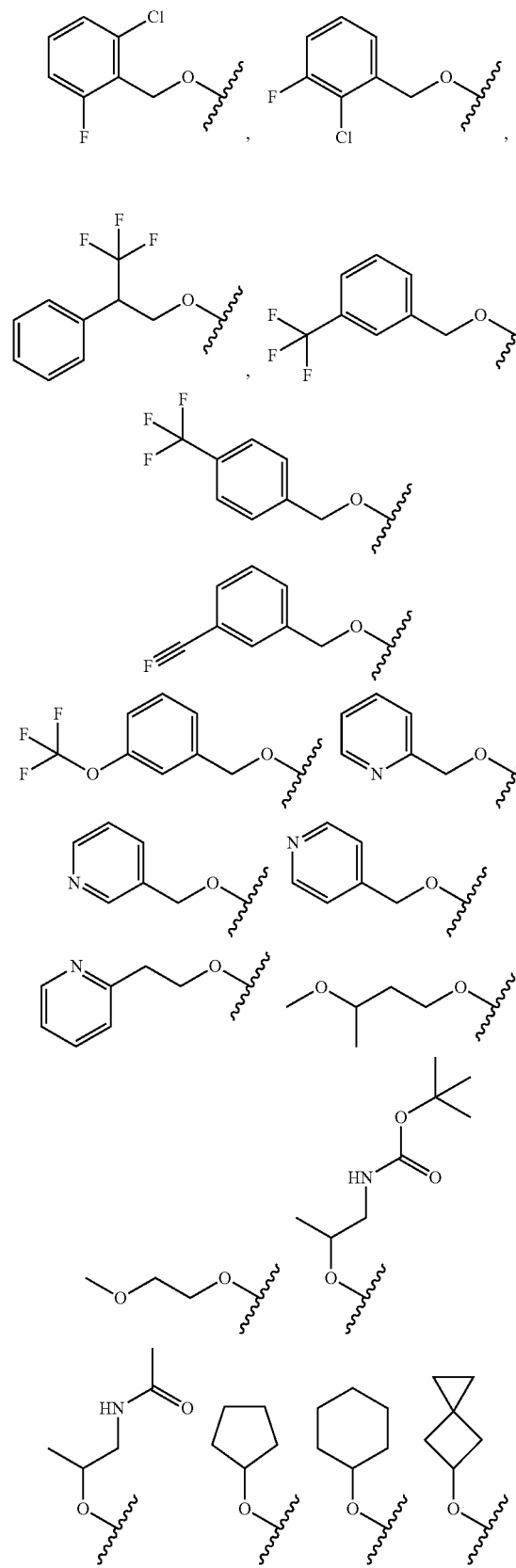
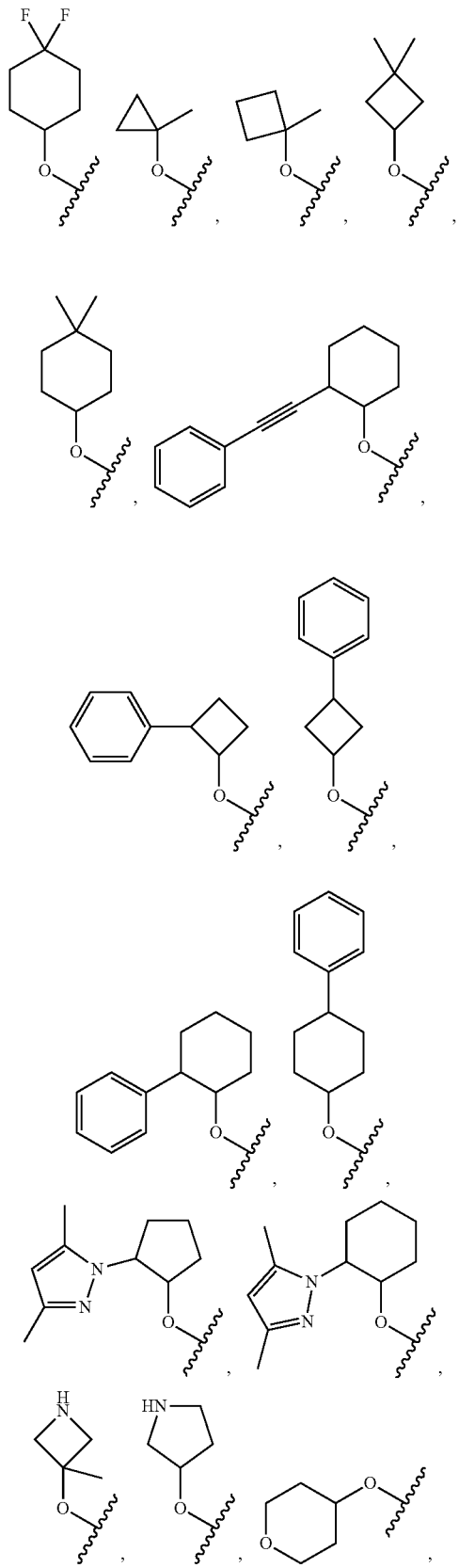

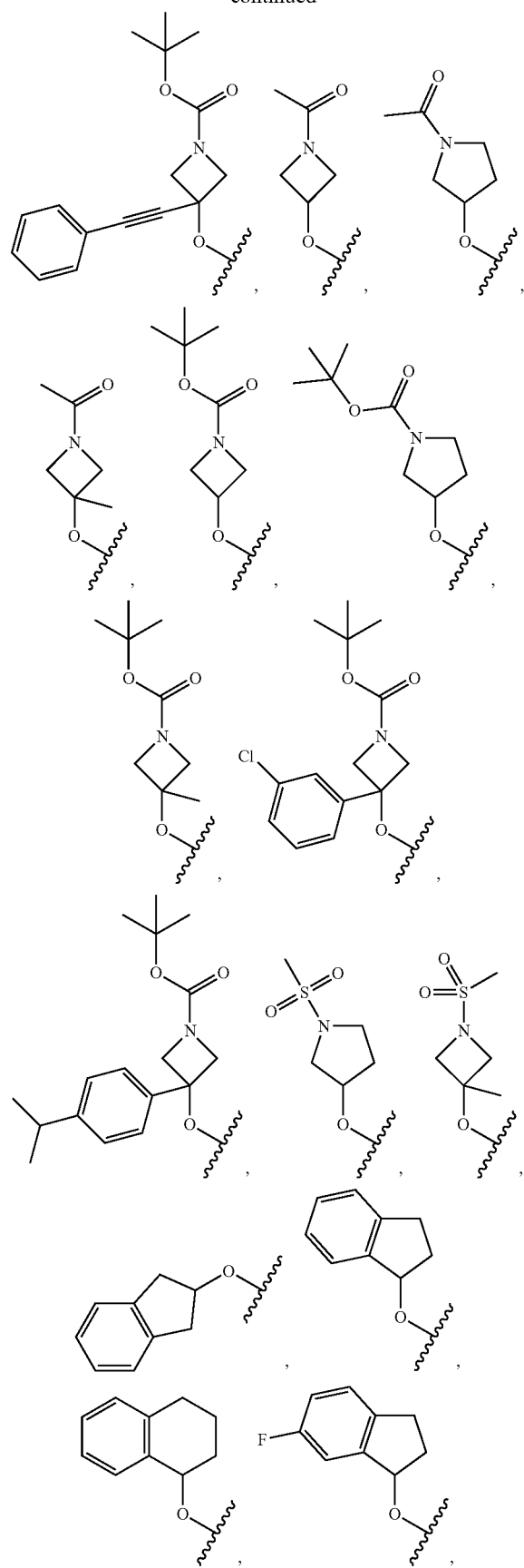
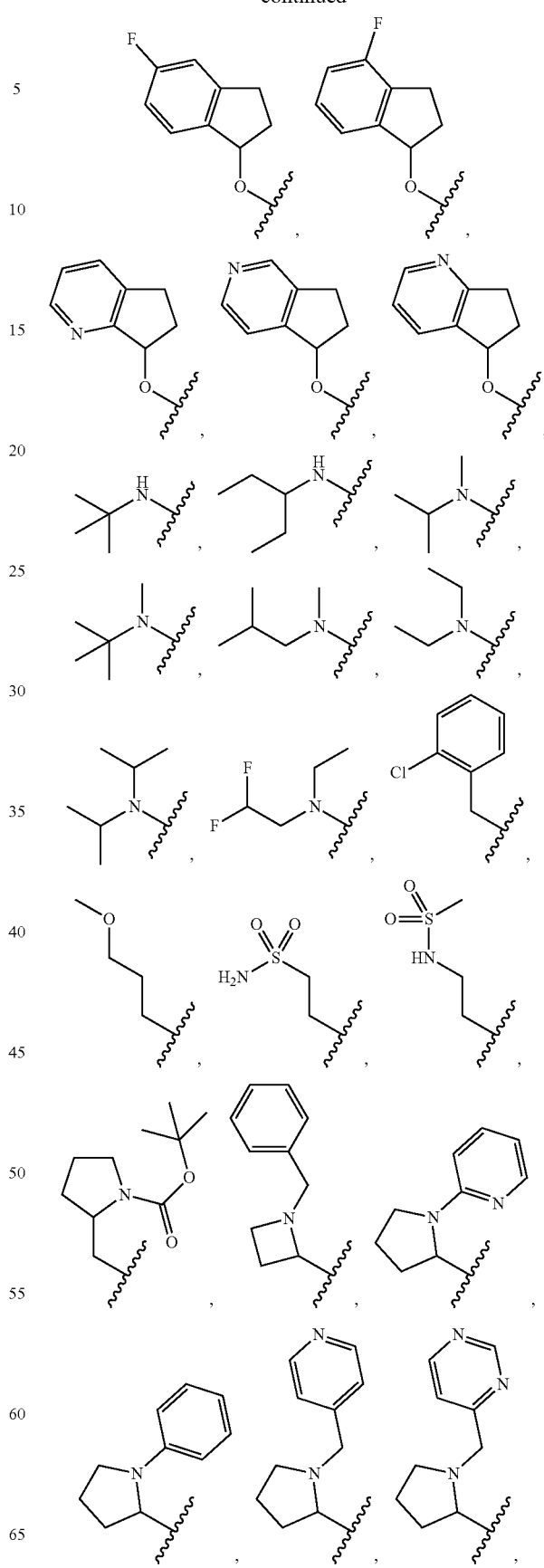

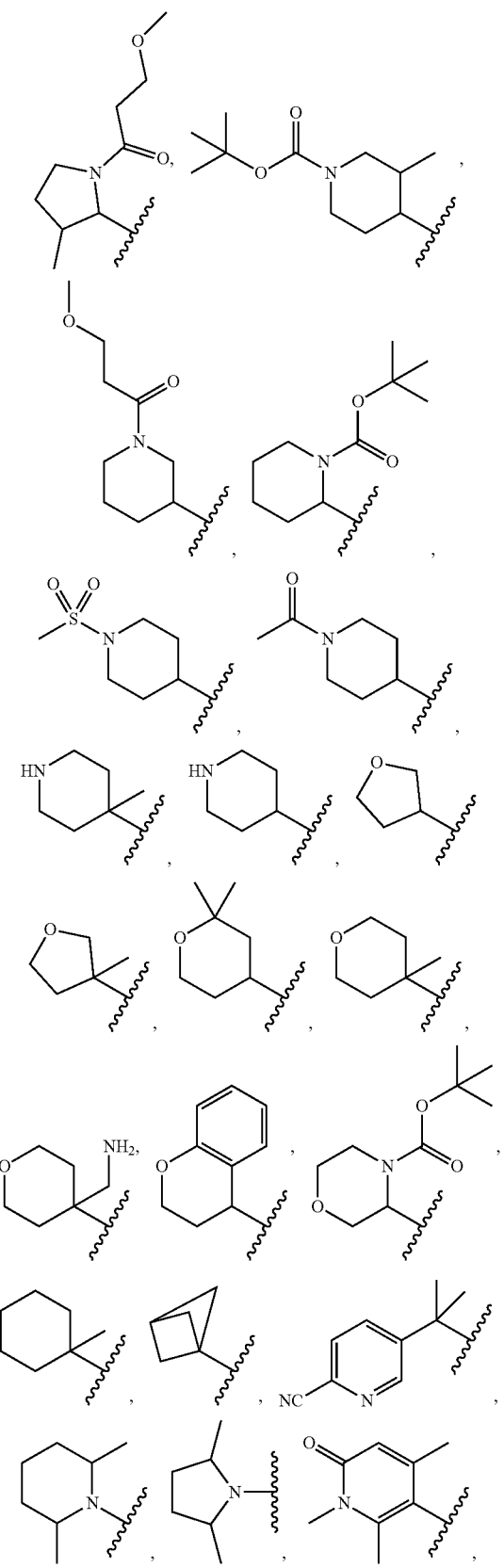
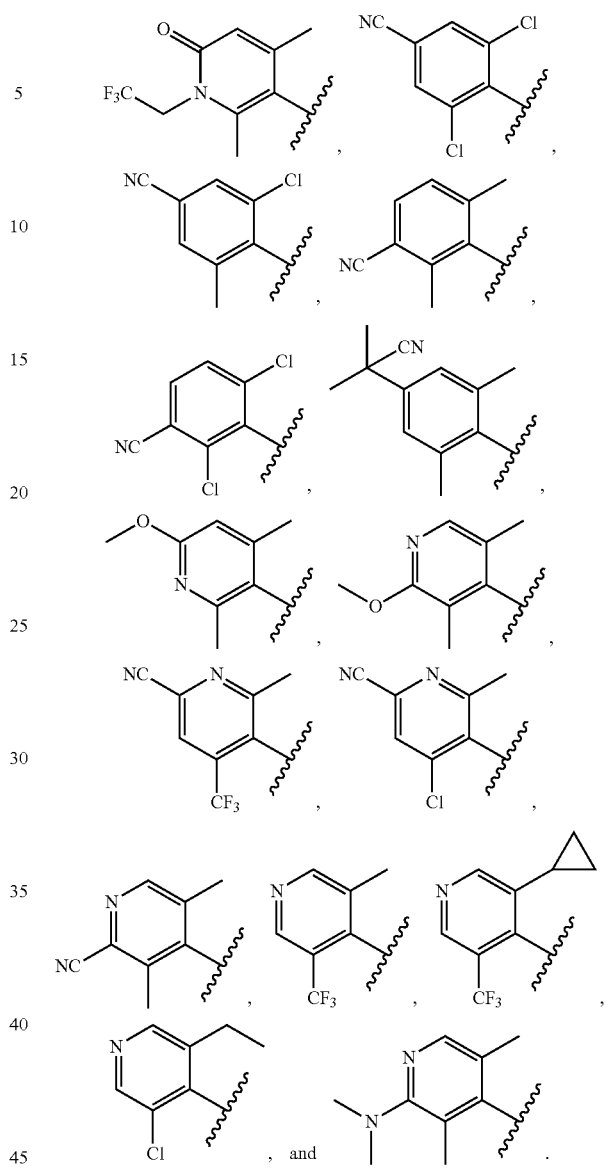
101. The compound of claim 1, or a pharmaceutically acceptable salt, stereoisomer, or tautomer thereof, wherein G is —C(O)R² and R² is selected from the group consisting of:
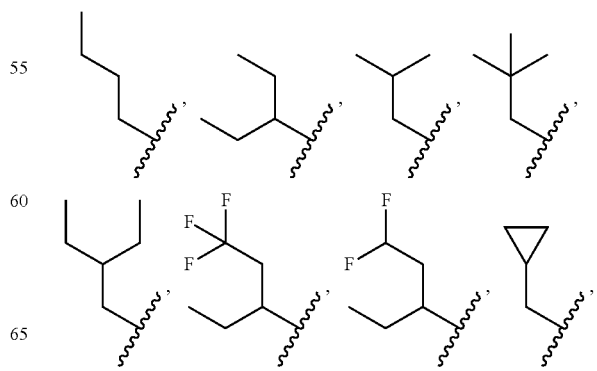

425
-continued
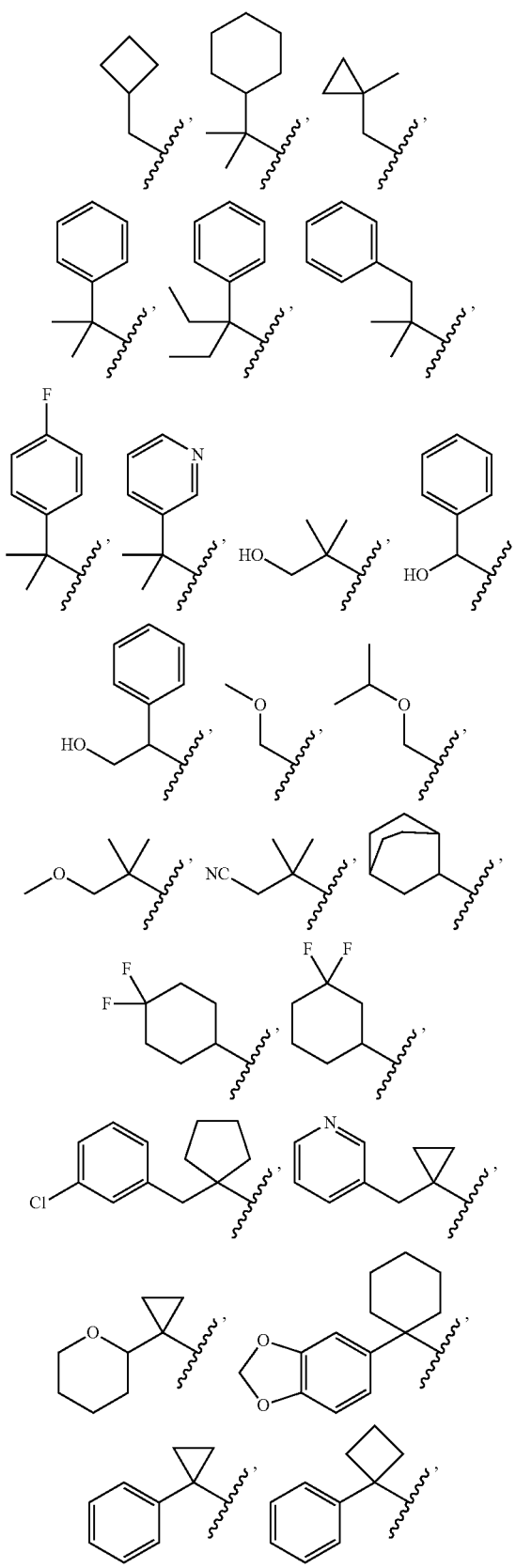
426
-continued
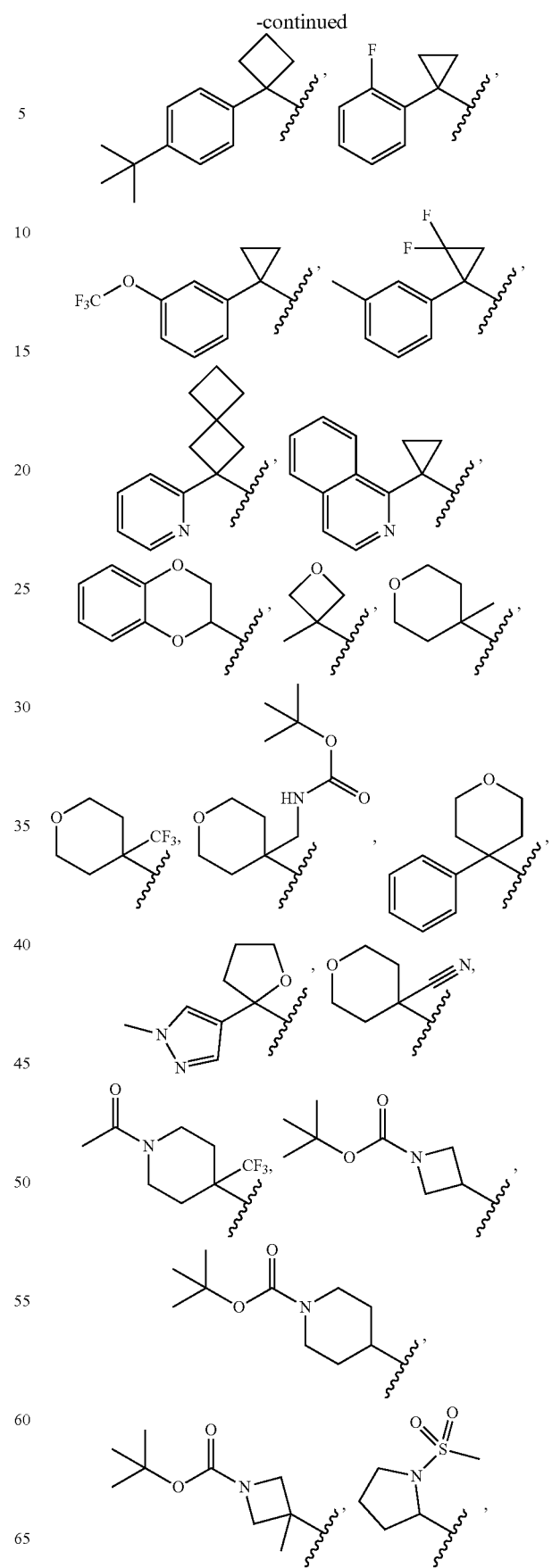

-continued
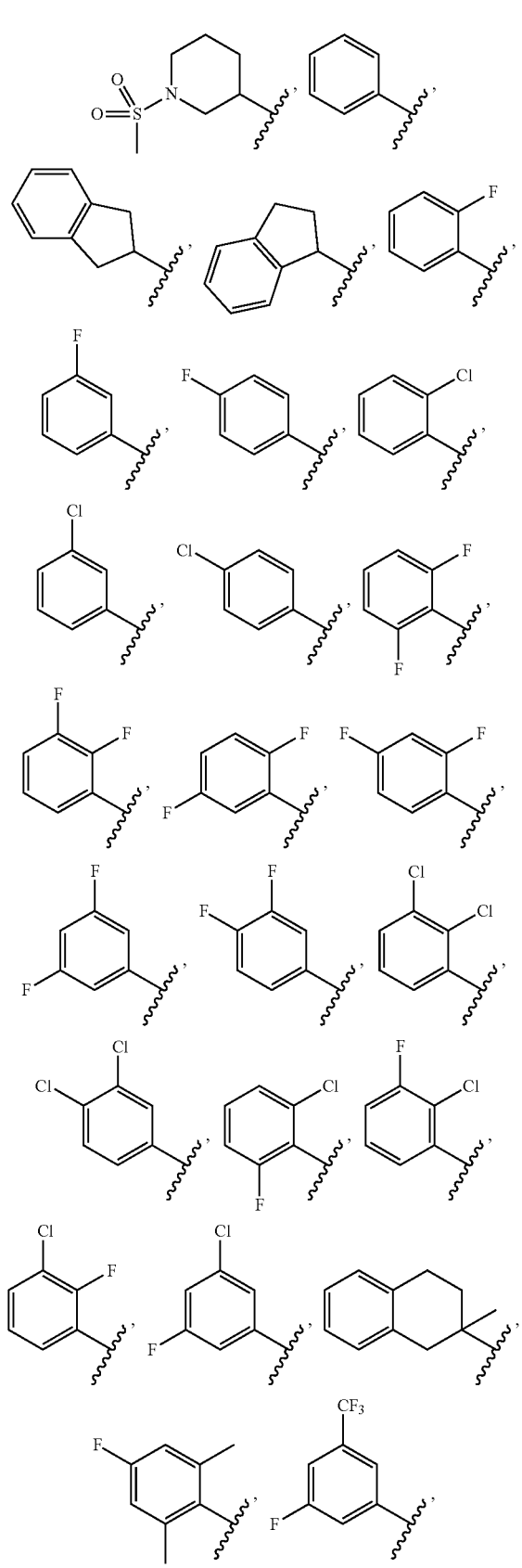
-continued
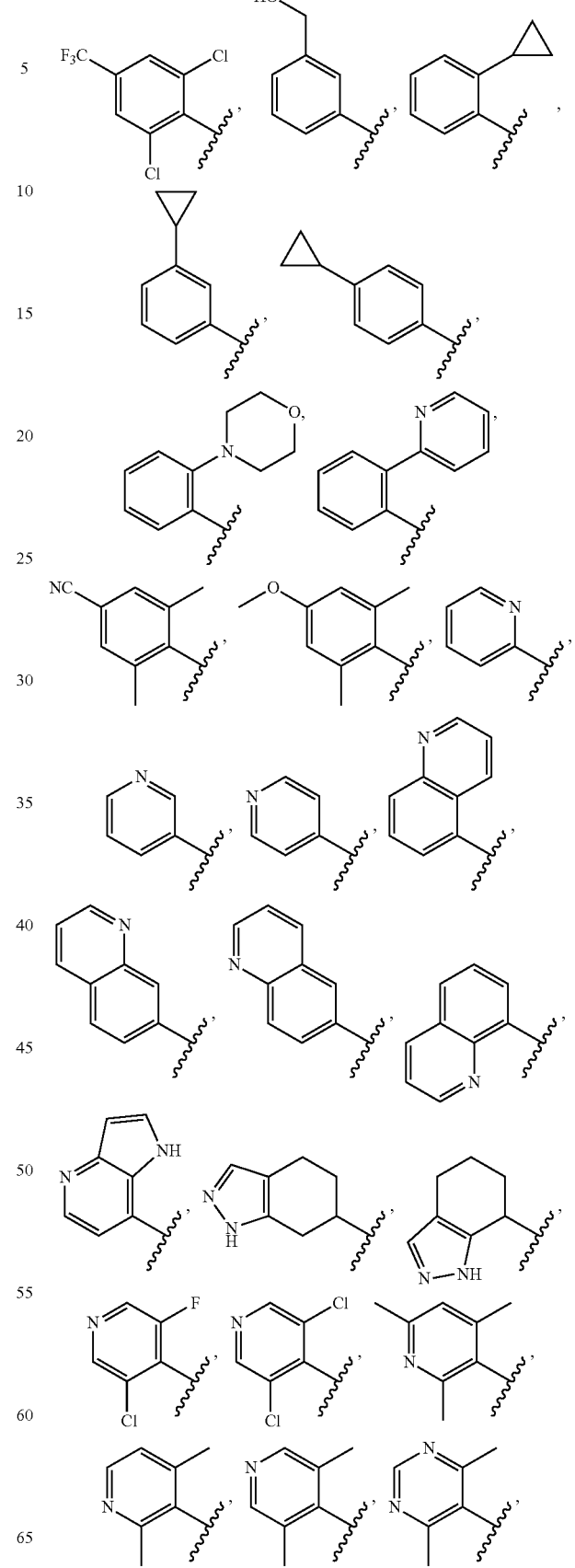

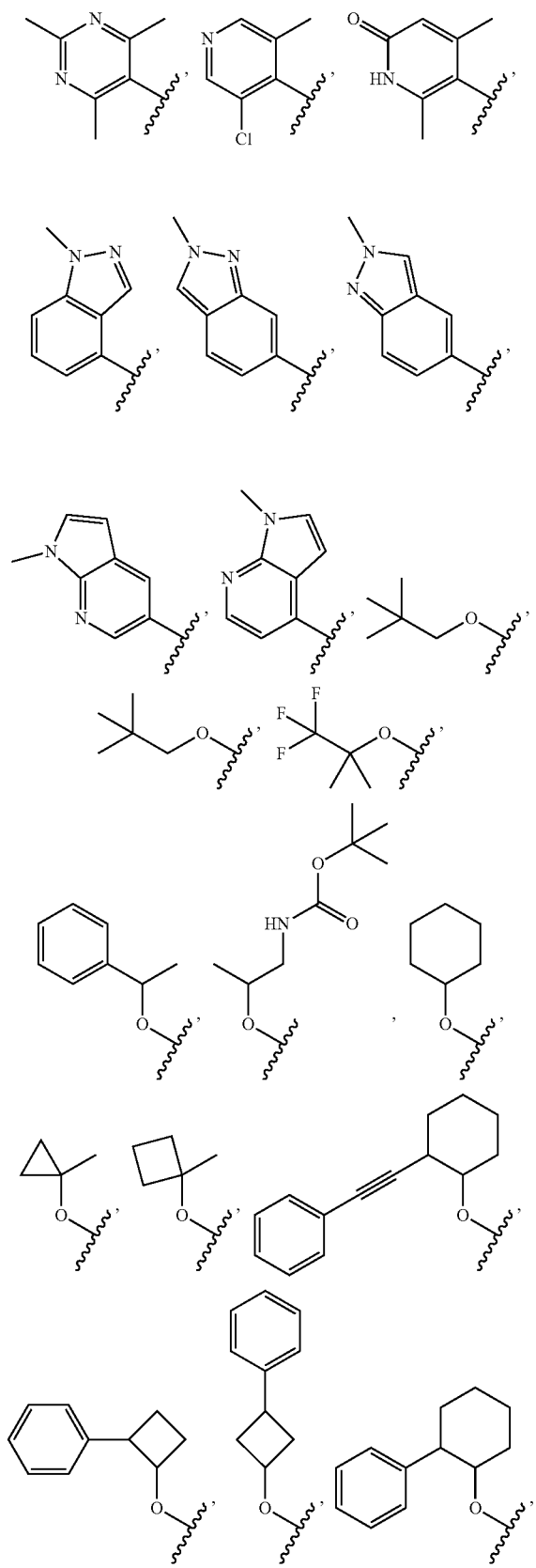
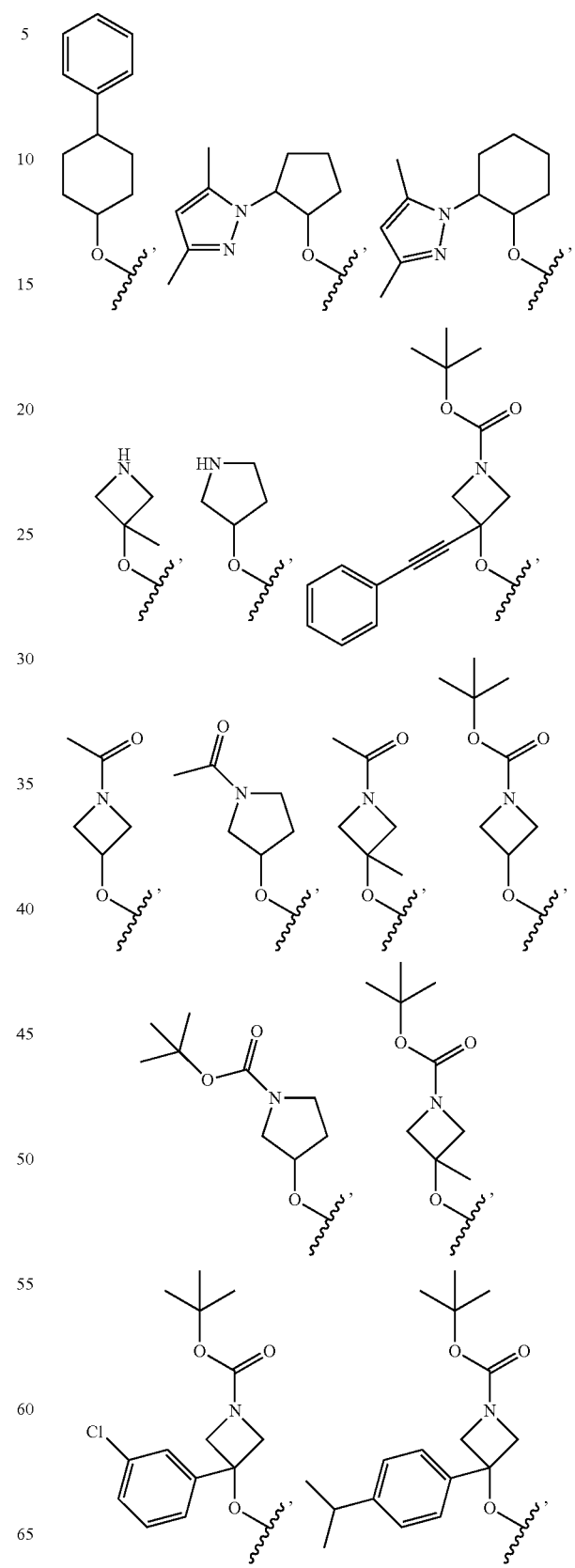

-continued

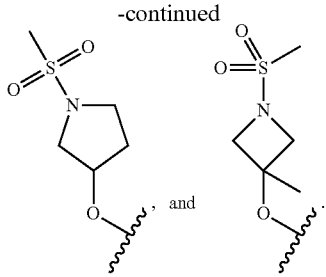

102. The compound of claim 1, or a pharmaceutically acceptable salt, stereoisomer, or tautomer thereof, wherein G is $R^3$.

103. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is optionally substituted by 1, 2, 3, 4, or 5 independently selected 0-5 $R^{3e}$ substituents; and
   each $R^{3e}$ is independently halogen, $C_1$-$C_6$ alkyl, $OC_1$-$C_6$ alkyl, or 5- to 10-membered heteroaryl, wherein each $C_1$-$C_6$ alkyl is optionally and independently substituted by 1 or more independently selected halogen substituents, and further wherein each 5- to 10-membered heteroaryl is optionally and independently substituted by 1 or more independently selected from the group consisting of halogen and $C_1$-$C_6$ alkyl.

104. The compound of claim 102, or a pharmaceutically acceptable salt, stereoisomer, or tautomer thereof, wherein $R^3$ is unsubstituted 5- to 10-membered heteroaryl.

105. The compound of claim 102, or a pharmaceutically acceptable salt, stereoisomer, or tautomer thereof, wherein $R^3$ is pyrimidinyl or quinazolinyl.

106. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is substituted by 1, 2, 3, 4, or 5 independently selected $R^{3e}$ substituents; and
   each $R^{3e}$ is independently halogen, $C_1$-$C_6$ alkyl, or $C_6$-$C_{14}$ aryl.

107. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is substituted by 1, 2, 3, 4, or 5 independently selected $R^{3o}$ substituents; and
   at least one $R^{3c}$ is halogen.

108. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is substituted by 1, 2, 3, 4, or 5 independently selected $R^{3e}$ substituents; and
   at least one $R^{3e}$ is $C_1$-$C_4$ alkyl.

109. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is substituted by 1, 2, 3, 4, or 5 independently selected $R^{3c}$ substituents; and
   at least one $R^{3e}$ is phenyl.

110. The compound of claim 102, or a pharmaceutically acceptable salt, stereoisomer, or tautomer thereof, wherein:
   $R^3$ is 5- to 10-membered heteroaryl, wherein the 5- to 10-membered heteroaryl is substituted by 2, 3, 4, or 5 independently selected $R^{3c}$ substituents:
   at least one $R^{3e}$ is $C_1$-$C_6$ alkyl; and
   at least one $R^{3e}$ is $C_6$-$C_{14}$ aryl.

111. The compound of claim 102, or a pharmaceutically acceptable salt, stereoisomer, or tautomer thereof, wherein $R^3$ is selected from the group consisting of:

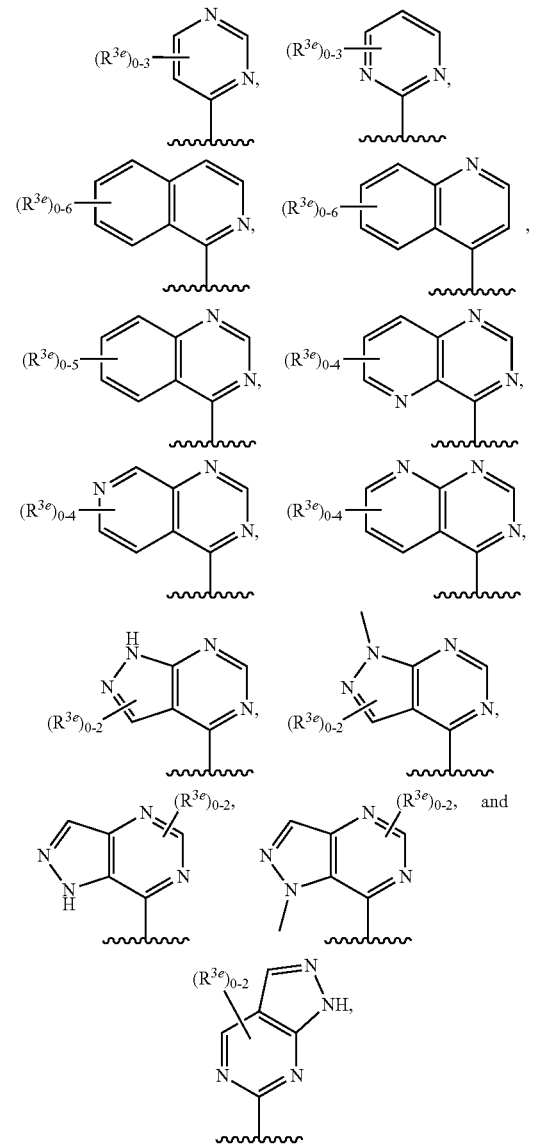

and wherein each $R^{3e}$ is independently $R^4$.

112. The compound of claim 102, or a pharmaceutically acceptable salt, stereoisomer, or tautomer thereof, wherein $R^3$ is selected from the group consisting of:

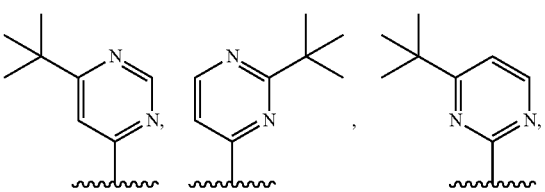

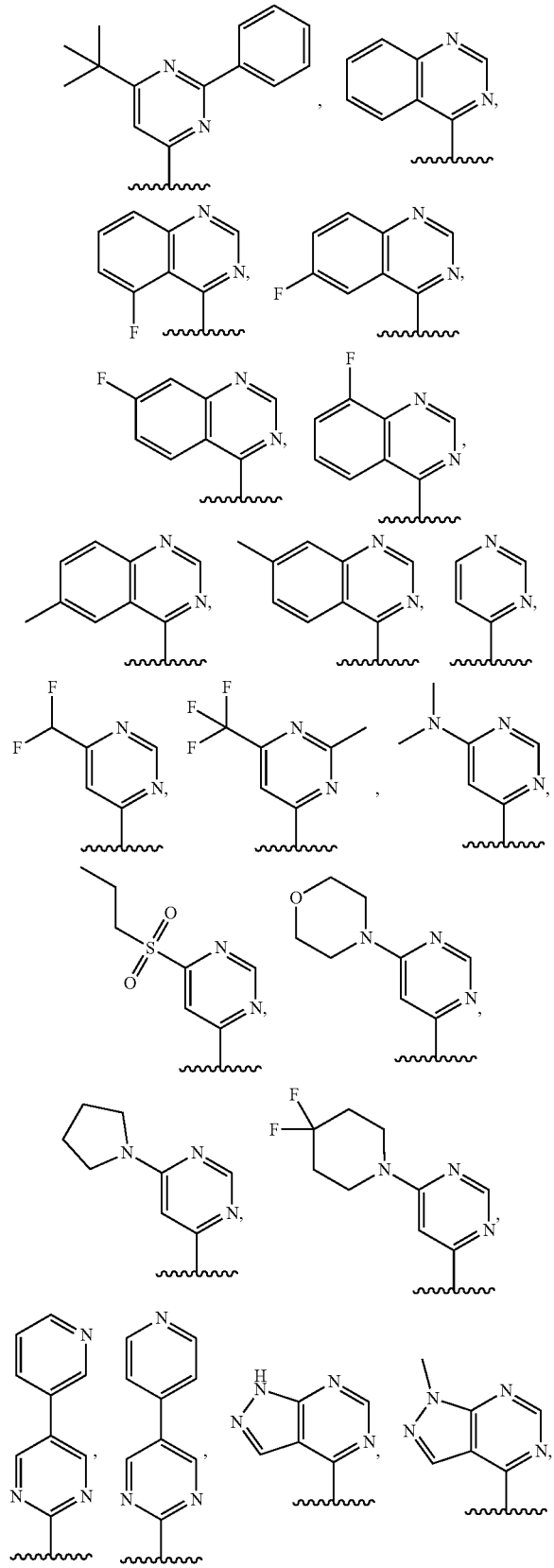
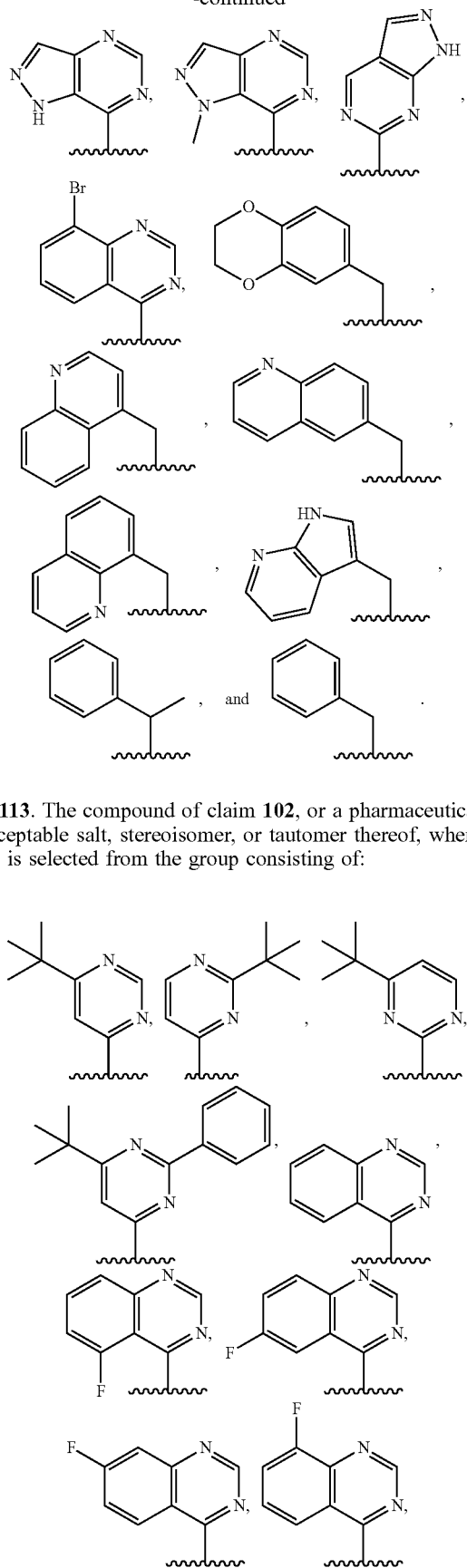
113. The compound of claim 102, or a pharmaceutically acceptable salt, stereoisomer, or tautomer thereof, wherein $R^3$ is selected from the group consisting of:

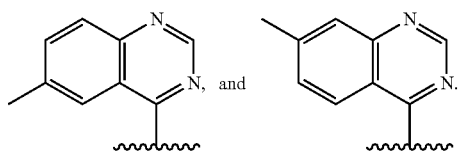
114. The compound of claim 1, or a pharmaceutically acceptable salt, stereoisomer, or tautomer thereof, wherein G is —C(O)R$^2$ and R$^2$ is selected from the group consisting of:
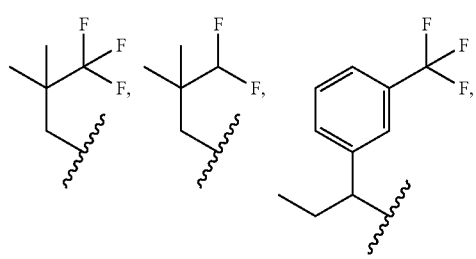
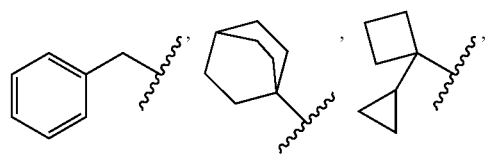
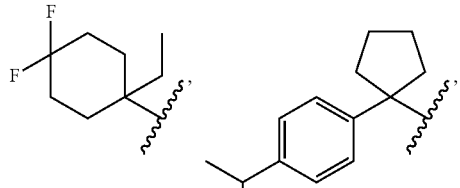
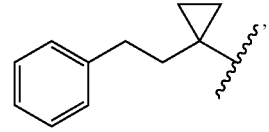
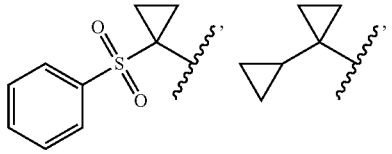
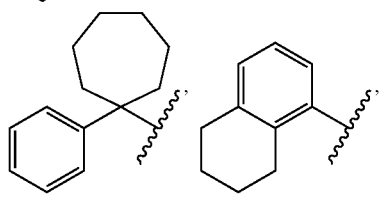
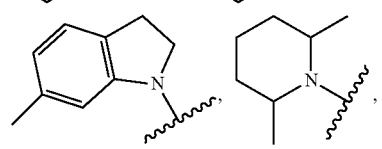
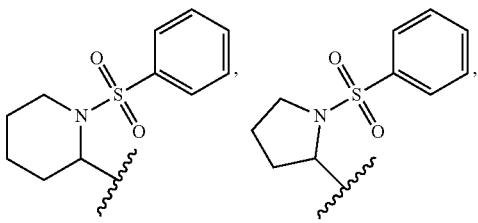
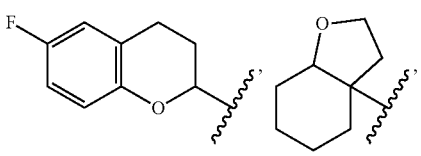
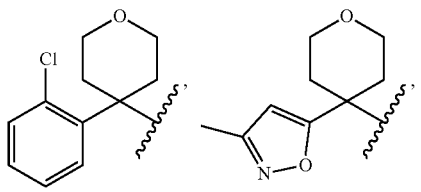
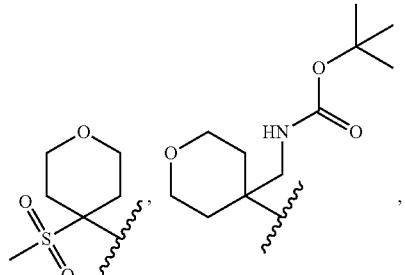
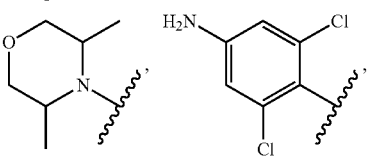
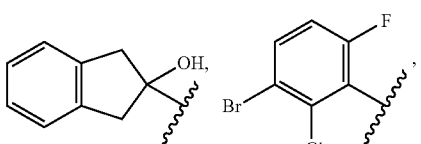
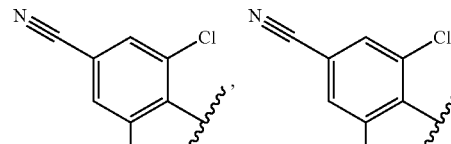
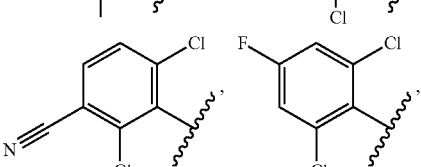
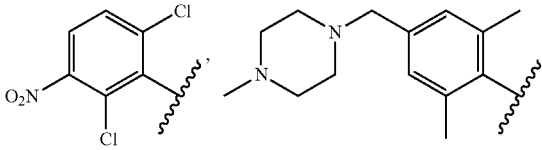

-continued

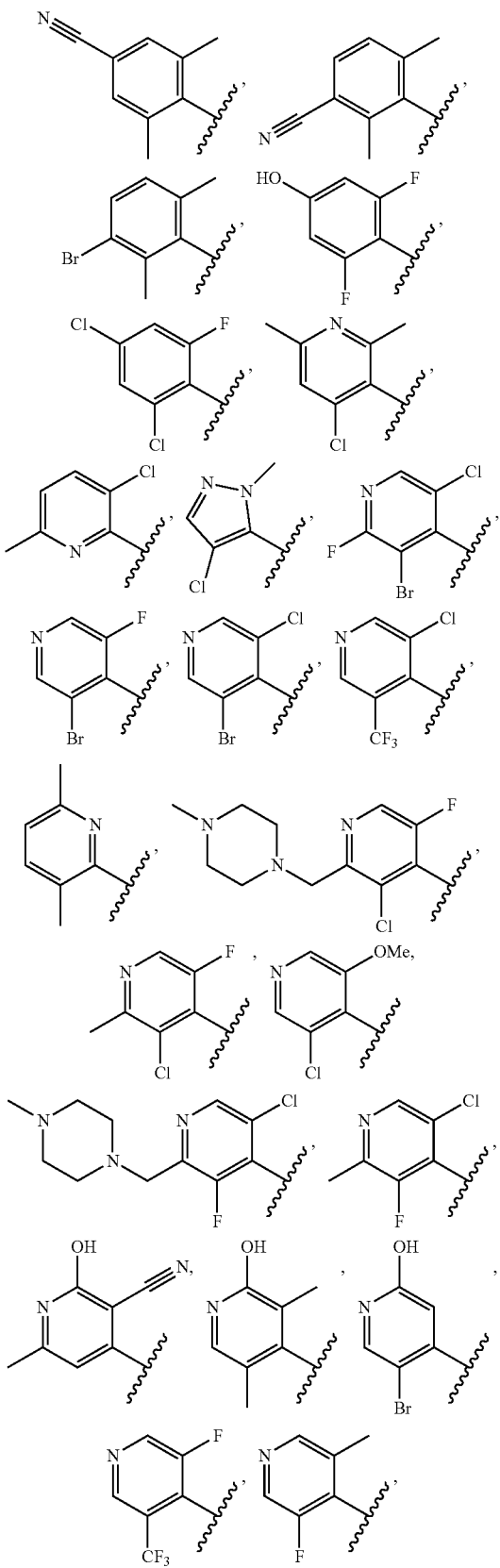

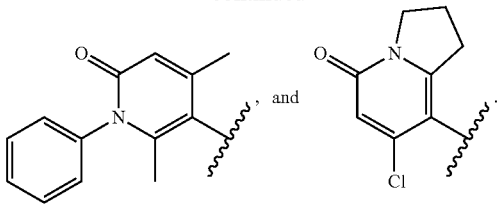, and

115. The compound of claim 1, or a pharmaceutically acceptable salt, stereoisomer, or tautomer thereof, wherein $L^1$ is $C_2$ alkylene, wherein the $C_2$ alkylene is optionally substituted by 1 or more independently selected $R^4$ substituents.

116. The compound of claim 115, or a pharmaceutically acceptable salt, stereoisomer, or tautomer thereof, wherein $L^1$ is —$CH_2CH_2$—.

117. The compound of claim 1, or a pharmaceutically acceptable salt, stereoisomer, or tautomer thereof, wherein at least one of $Y^a$, $R^{2a}$, $R^{2b}$, $R^{2c}$, $R^{2d}$, $R^{2e}$, $R^{2g}$, $R^{2h}$, $R^{2i}$, $R^{2j}$, $R^{3a}$, $R^{3b}$, $R^{3c}$, $R^{3d}$, $R^{3e}$, $R^{4a}$, $R^{4b}$, $R^5$, $R^{5a}$, $R^6$, $R^7$, $R^8$, $R^9$, $R^{10}$, $R^{11}$, or $R^{12}$ is D.

118. The compound of claim 1, or a pharmaceutically acceptable salt, stereoisomer, or tautomer thereof, wherein -$L^1$-O-$L^2$-Y-$L^3$- is selected from the group consisting of:

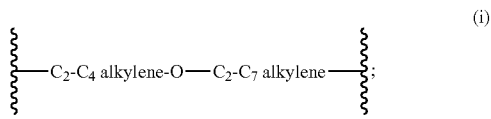 (i)

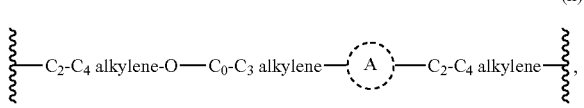 (ii)

wherein

is a $C_3$-$C_5$ cycloalkylene optionally substituted by 1 or more independently selected $Y^a$ substituents; and

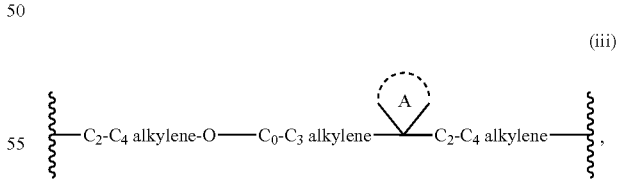 (iii)

wherein

is a $C_3$-$C_5$ cycloalkylene optionally substituted by 1 or more independently selected $Y^a$ substituents.

119. The compound of claim 118, or a pharmaceutically acceptable salt, stereoisomer, or tautomer thereof, wherein -L$^1$-O-L$^2$-Y-L$^3$- is selected from the group consisting of:

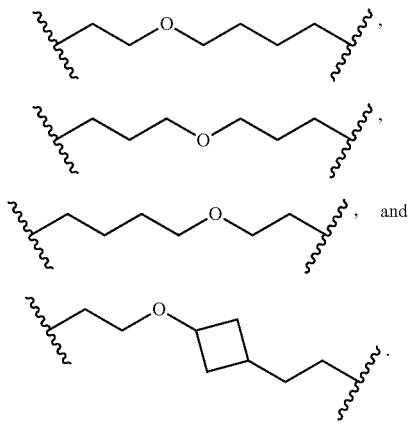

120. The compound of claim 118, or a pharmaceutically acceptable salt, stereoisomer, or tautomer thereof, wherein -L$^1$-O-L$^2$-Y-L$^3$- is selected from the group consisting of:

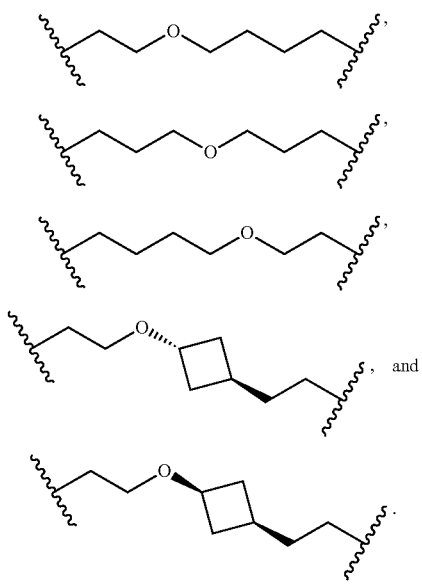

121. The compound of claim 118, or a pharmaceutically acceptable salt, stereoisomer, or tautomer thereof, wherein -L$^1$-O-L$^2$-Y-L$^3$- is selected from the group consisting of:

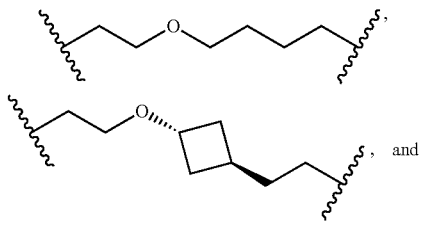

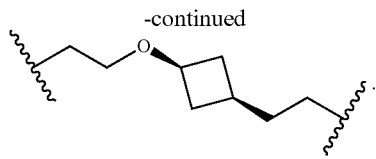

122. The compound of claim 1, or a pharmaceutically acceptable salt, stereoisomer, or tautomer thereof, wherein R$^1$ is:

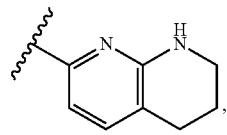

wherein the 5,6,7,8-tetrahydro-1,8-naphthyridin-2-yl is optionally substituted by 1 or more independently selected R$^4$ substituents.

123. The compound of claim 1, wherein the compound is of any one of the following formulas:

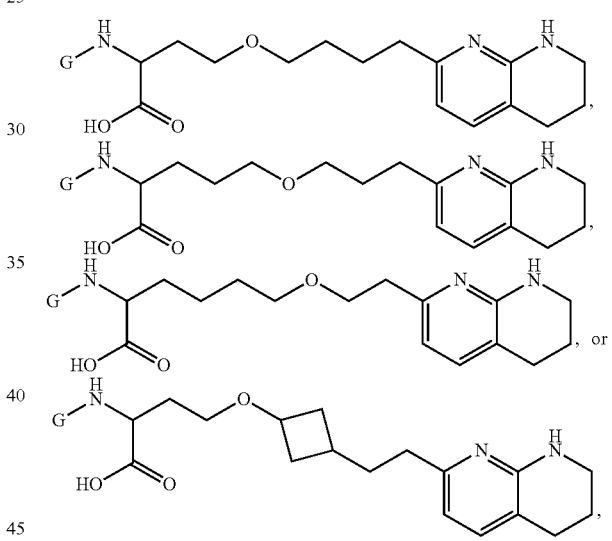

or a pharmaceutically acceptable salt, stereoisomer, or tautomer thereof.

124. The compound of claim 1, wherein the compound is of any one of the following formulas:

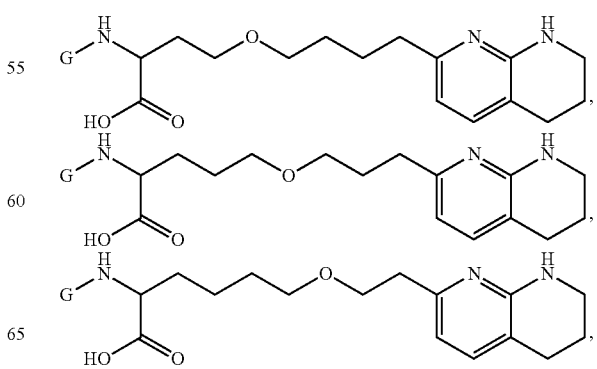

-continued

[structure]

, or

[structure]

, or a pharmaceutically acceptable salt, stereoisomer, or tautomer thereof.

125. The compound of claim 1, wherein the compound is of formula (II-A-1) or formula (II-A-2):

(II-A-1)

[structure]

or (II-A-2)

[structure]

, or a pharmaceutically acceptable salt, stereoisomer, or tautomer thereof,
wherein:
(i) j is 2; and
k is 4; or
(ii) j is 3; and
k is 3; or
(iii) j is 4; and
k is 2.

126. The compound of claim 125, wherein the compound is of formula (II-A-1):

(II-A-1)

[structure]

or a pharmaceutically acceptable salt, stereoisomer, or tautomer thereof,
wherein:
$R^2$ is $C_1$-$C_6$ alkyl, $OR^{2f}$, or cyclohexyl:
wherein the $C_1$-$C_6$ alkyl is optionally substituted by 1, 2, 3, or 4 independently selected $R^{2a}$ substituents; and wherein the cyclohexyl is optionally substituted by 1, 2, 3, or 4 independently selected $R^{2b}$ substituents; and
$R^{2f}$ is $C_1$-$C_6$ alkyl, wherein the $C_1$-$C_6$ alkyl is optionally substituted by 1, 2, 3, or 4 independently selected $R^{2i}$ substituents.

127. The compound of claim 125, wherein the compound is of formula (II-A-1):

(II-A-1)

[structure]

or a pharmaceutically acceptable salt, stereoisomer, or tautomer thereof,
wherein:
$R^2$ is phenyl, 1,2,3,4-tetrahydronaphthalen-5-yl, 1,2,3,4-tetrahydronaphthalen-6-yl, 1,2,3,4-tetrahydronaphthalen-7-yl, or 1,2,3,4-tetrahydronaphthalen-8-yl; and
wherein the phenyl, 1,2,3,4-tetrahydronaphthalen-5-yl, 1,2,3,4-tetrahydronaphthalen-6-yl, 1,2,3,4-tetrahydronaphthalen-7-yl, or 1,2,3,4-tetrahydronaphthalen-8-yl is optionally substituted by 1, 2, 3, or 4 independently selected $R^{2d}$ substituents.

128. The compound of claim 125, wherein the compound is of formula (II-A-1):

(II-A-1)

[structure]

or a pharmaceutically acceptable salt, stereoisomer, or tautomer thereof,
wherein:
$R^2$ is tetrahydropyranyl or morpholinyl:
wherein the tetrahydropyranyl or morpholinyl is optionally substituted by 1, 2, 3, or 4 independently selected $R^{2e}$ substituents.

129. The compound of claim 125, wherein the compound is of formula (II-A-1):

(II-A-1)

[structure]

or a pharmaceutically acceptable salt, stereoisomer, or tautomer thereof,
wherein:
$R^2$ is pyridin-2(1H)-onyl, pyridinyl, indazol-4-yl, indazol-5-yl, indazol-6-yl, or indazol-7-yl;
wherein the pyridin-2(1H)-onyl is optionally substituted by 1, 2, or 3 independently selected $R^{2c}$ substituents; and wherein the pyridinyl, indazol-4-yl, indazol-5-yl, indazol-6-yl, or indazol-7-yl is optionally substituted by 1, 2, 3, or 4 independently selected $R^{2e}$ substituents.

130. The compound of claim 125, wherein the compound is of formula (II-A-2):

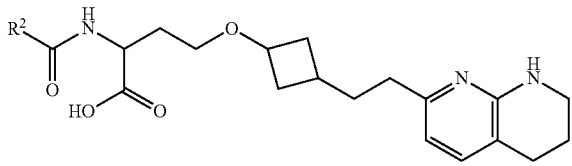

(II-A-2)

or a pharmaceutically acceptable salt, stereoisomer, or tautomer thereof,
wherein:
$R^2$ is $C_1$-$C_6$ alkyl, $OR^{2f}$, or $C_3$-$C_8$ cycloalkyl:
wherein the $C_1$-$C_6$ alkyl is optionally substituted by 1, 2, 3, or 4 independently selected $R^{2a}$ substituents; and
wherein the $C_3$-$C_8$ alkyl is optionally substituted by 1, 2, 3, or 4 independently selected $R^{2b}$ substituents; and
$R^{2f}$ is $C_1$-$C_6$ alkyl or $C_3$-$C_8$ cycloalkyl, wherein the $C_1$-$C_6$ alkyl or $C_3$-$C_8$ cycloalkyl is optionally substituted by 1, 2, 3, or 4 independently selected $R^{2i}$ substituents.

131. The compound of claim 125, wherein the compound is of formula (II-A-2):

(II-A-2)

or a pharmaceutically acceptable salt, stereoisomer, or tautomer thereof,
wherein:
$R^2$ is $NR^{2g}R^{2h}$;
$R^{2g}$ is H, D, $C_1$-$C_6$ alkyl, $C_3$-$C_8$ cycloalkyl, 3- to 12-membered heterocyclyl, $C_6$-$C_{14}$ alkyl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ alkyl, or 5- to 10-membered heteroaryl is optionally substituted by 1, 2, 3, or 4 independently selected $R^{2j}$ substituents; and
$R^{2h}$ is H, D, $C_1$-$C_6$ alkyl, $C_3$-$C_8$ cycloalkyl, 3- to 12-membered heterocyclyl, $C_6$-$C_{14}$ alkyl, or 5- to 10-membered heteroaryl, wherein the $C_1$-$C_6$ alkyl, $C_3$-$C_8$ cycloalkyl, 3- to 12-membered heterocyclyl, $C_6$-$C_{14}$ alkyl, or 5- to 10-membered heteroaryl is optionally substituted by 1, 2, 3, or 4 independently selected $R^{2j}$ substituents.

132. The compound of claim 131, wherein:
$R^{2g}$ is $C_1$-$C_6$ alkyl; and
$R^{2h}$ is $C_1$-$C_6$ alkyl.

133. The compound of claim 125, wherein the compound is of formula (II-A-2):

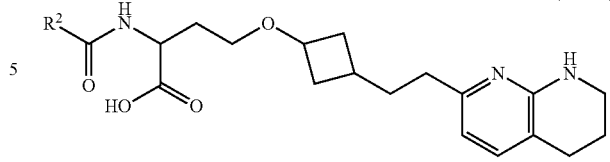

(II-A-2)

or a pharmaceutically acceptable salt, stereoisomer, or tautomer thereof,
wherein:
$R^2$ is phenyl, 2,3-dihydro-1H-inden-4-yl, 2,3-dihydro-1H-inden-5-yl, 2,3-dihydro-1H-inden-6-yl, 2,3-dihydro-1H-inden-7-yl, 1H-inden-4-yl, 1H-inden-5-yl, 1H-inden-6-yl, 1H-inden-7-yl, 1,2,3,4-tetrahydronaphthalen-5-yl, 1,2,3,4-tetrahydronaphthalen-6-yl, 1,2,3,4-tetrahydronaphthalen-7-yl, or 1,2,3,4-tetrahydronaphthalen-8-yl;
wherein the phenyl, 2,3-dihydro-1H-inden-4-yl, 2,3-dihydro-1H-inden-5-yl, 2,3-dihydro-1H-inden-6-yl, 2,3-dihydro-1H-inden-7-yl, 1H-inden-4-yl, 1H-inden-5-yl, 1H-inden-6-yl, 1H-inden-7-yl, 1,2,3,4-tetrahydronaphthalen-5-yl, 1,2,3,4-tetrahydronaphthalen-6-yl, 1,2,3,4-tetrahydronaphthalen-7-yl, or 1,2,3,4-tetrahydronaphthalen-8-yl is optionally substituted by 1, 2, 3, or 4 independently selected $R^{2d}$ substituents.

134. The compound of claim 125, wherein the compound is of formula (II-A-2):

(II-A-2)

or a pharmaceutically acceptable salt, stereoisomer, or tautomer thereof,
wherein:
$R^2$ is oxetanyl, tetrahydrofuranyl, tetrahydropyranyl, octahydrobenzofuran-4-yl, octahydrobenzofuran-5-yl, octahydrobenzofuran-6-yl, or octahydrobenzofuran-7-yl, chroman-5-yl, chroman-6-yl, chroman-7-yl, chroman-8-yl, 2,3-dihydrobenzo[b][1,4]dioxin-5-yl, 2,3-dihydrobenzo[b][1,4]dioxin-6-yl, 2,3-dihydrobenzo[b][1,4]dioxin-7-yl, or 2,3-dihydrobenzo[b][1,4]dioxin-8-yl:
wherein the oxetanyl, tetrahydrofuranyl, tetrahydropyranyl, octahydrobenzofuran-4-yl, octahydrobenzofuran-5-yl, octahydrobenzofuran-6-yl, or octahydrobenzofuran-7-yl, chroman-5-yl, chroman-6-yl, chroman-7-yl, chroman-8-yl, 2,3-dihydrobenzo[b][1,4]dioxin-5-yl, 2,3-dihydrobenzo[b][1,4]dioxin-6-yl, 2,3-dihydrobenzo[b][1,4]dioxin-7-yl, or 2,3-dihydrobenzo[b][1,4]dioxin-8-yl is optionally substituted by 1, 2, 3, or 4 independently selected $R^{2e}$ substituents.

135. The compound of claim 125, wherein the compound is of formula (II-A-2):

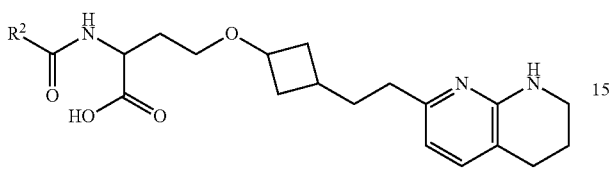

(II-A-2)

or a pharmaceutically acceptable salt, stereoisomer, or tautomer thereof,
wherein:
$R^2$ is $OR^{2f}$, azetidinyl, pyrrolidinyl, piperidinyl, morpholinyl, indolin-4-yl, indolin-5-yl, indolin-6-yl, or indolin-7-yl:
  wherein the azetidinyl, pyrrolidinyl, piperidinyl, morpholinyl, indolin-4-yl, indolin-5-yl, indolin-6-yl, or indolin-7-yl is optionally substituted by 1, 2, 3, or 4 independently selected $R^{2e}$ substituents; and
$R^{2f}$ is azetidinyl, pyrrolidinyl, or piperidinyl, wherein the azetidinyl, pyrrolidinyl, or piperidinyl is optionally substituted by 1, 2, 3, or 4 independently selected $R^{2i}$ substituents.

136. The compound of claim 125, wherein the compound is of formula (II-A-2):

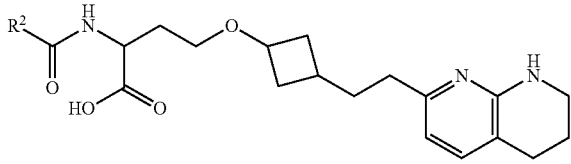

(II-A-2)

or a pharmaceutically acceptable salt, stereoisomer, or tautomer thereof,
wherein:
$R^2$ is pyridin-2(1H)-onyl, 4,5,6,7-tetrahydro-1H-indazol-4-yl, 4,5,6,7-tetrahydro-1H-indazol-5-yl, 4,5,6,7-tetrahydro-1H-indazol-6-yl, 4,5,6,7-tetrahydro-1H-indazol-7-yl, 5,6,7,8-tetrahydro-[1,2,4]triazolo[4,3-a]pyridin-5-yl, 5,6,7,8-tetrahydro-[1,2,4]triazolo[4,3-a]pyridin-6-yl, 5,6,7,8-tetrahydro-[1,2,4]triazolo[4,3-a]pyridin-7-yl, 5,6,7,8-tetrahydro-[1,2,4]triazolo[4,3-a]pyridin-8-yl, pyrazolyl, pyridinyl, pyrimidinyl, 1Hindazol-4-yl, 1H-indazol-5-yl, 1H-indazol-6-yl, 1H-indazol-7-yl, quinolin-5-yl, quinolin-6-yl, quinolin-7-yl, quinolin-8-yl, 1H-pyrrolo[3,2-b]pyridin-5-yl, 1H-pyrrolo[3,2-b]pyridin-6-yl, 1H-pyrrolo[3,2-b]pyridin-7-yl, 1H-pyrrolo[2,3-b]pyridin-4-yl, 1H-pyrrolo[2,3-b]pyridin-5-yl, or 1H-pyrrolo[2,3-b]pyridin-6-yl:
  wherein the pyridin-2(1H)-onyl, 4,5,6,7-tetrahydro-1H-indazol-4-yl, 4,5,6,7-tetrahydro-1H-indazol-5-yl, 4,5,6,7-tetrahydro-1H-indazol-6-yl, 4,5,6,7-tetrahydro-1H-indazol-7-yl, 5,6,7,8-tetrahydro-[1,2,4]triazolo[4,3-a]pyridin-5-yl, 5,6,7,8-tetrahydro-[1,2,4]triazolo[4,3-a]pyridin-6-yl, 5,6,7,8-tetrahydro-[1,2,4]triazolo[4,3-a]pyridin-7-yl, 5,6,7,8-tetrahydro-[1,2,4]triazolo[4,3-a]pyridin-8-yl is optionally substituted by 1, 2, 3, or 4 independently selected $R^{2c}$ substituents; and
  wherein the pyrazolyl, pyridinyl, pyrimidinyl, 1H-indazol-4-yl, 1H-indazol-5-yl, 1H-indazol-6-yl, 1H-indazol-7-yl, quinolin-5-yl, quinolin-6-yl, quinolin-7-yl, quinolin-8-yl, 1H-pyrrolo[3,2-b]pyridin-5-yl, 1H-pyrrolo[3,2-b]pyridin-6-yl, 1H-pyrrolo[3,2-b]pyridin-7-yl, 1H-pyrrolo[2,3-b]pyridin-4-yl, 1H-pyrrolo[2,3-b]pyridin-5-yl, or 1H-pyrrolo[2,3-b]pyridin-6-yl is optionally substituted by 1, 2, 3, or 4 independently selected $R^{2e}$ substituents.

137. The compound of claim 125, wherein the compound of formula (II-A-2) is of formula (II-A-2i) or formula (II-A-2ii):

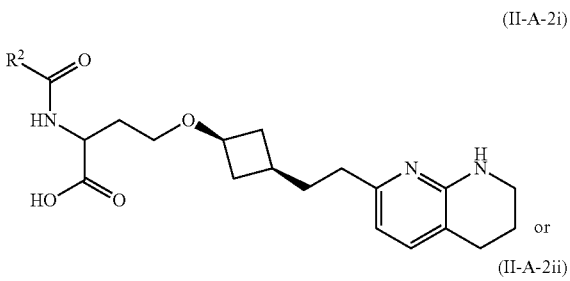

(II-A-2i)

or

(II-A-2ii)

or a pharmaceutically acceptable salt, stereoisomer, or tautomer thereof.

138. The compound of claim 1, wherein the compound is of formula (II-B-1), formula (II-B-2), or formula (II-B-3):

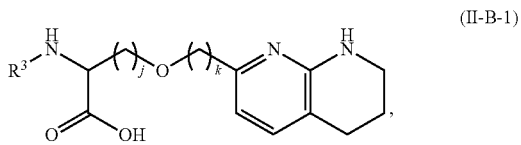

(II-B-1)

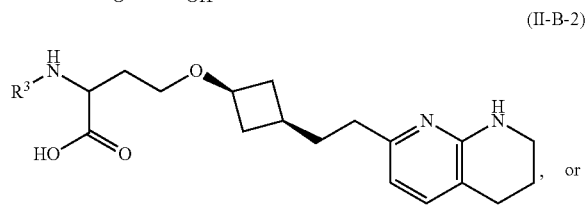

(II-B-2)

or

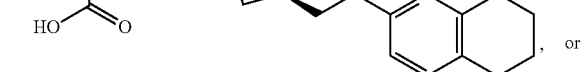

-continued (II-B-3)

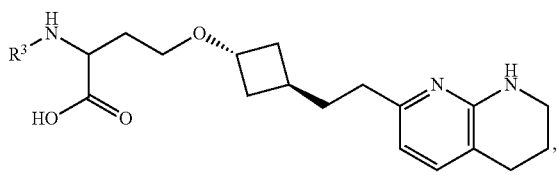

or a pharmaceutically acceptable salt, stereoisomer, or tautomer thereof,
wherein:
(i) j is 2; and
k is 4; or
(ii) j is 3; and
k is 3; or
(iii) j is 4; and
k is 2.

139. The compound of claim 138, wherein the compound is of formula (II-B-1):

(II-B-1)

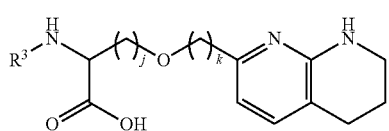

or a pharmaceutically acceptable salt, stereoisomer, or tautomer thereof,
wherein:
$R^3$ is pyrimidinyl:
wherein the pyrimidinyl is optionally substituted by 1, 2, or 3 independently selected $R^{3e}$ substituents.

140. The compound of claim 138, wherein the compound is of formula (II-B-2) or formula (II-B-3):

(II-B-2)

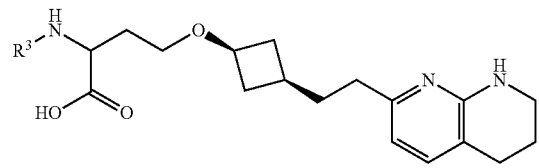

or (II-B-3)

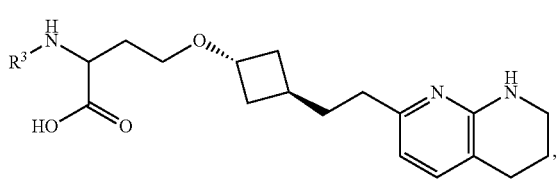

or a pharmaceutically acceptable salt, stereoisomer, or tautomer thereof,
wherein:
$R^3$ is pyrimidinyl, quinazolin-5-yl, quinazolin-6-yl, quinazolin-7-yl, or quinazolin-8-yl:
wherein the pyrimidinyl is optionally substituted by 1, 2, or 3 independently selected $R^{3e}$ substituents; and wherein the quinazolin-5-yl, quinazolin-6-yl, quinazolin-7-yl, or quinazolin-8-yl is optionally substituted by 1, 2, 3, or 4 independently selected $R^{3e}$ substituents.

141. The compound of claim 1, wherein the compound is selected from the group consisting of:

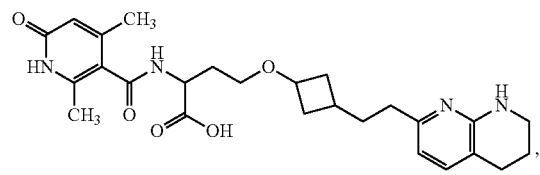

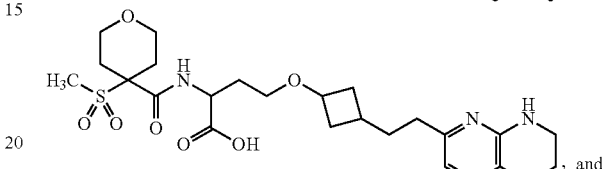

, and

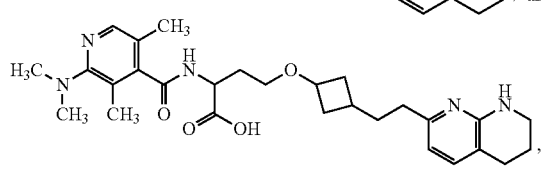

, or a pharmaceutically acceptable salt, stereoisomer, or tautomer thereof.

142. The compound of claim 141, wherein the compound is selected from the group consisting of:

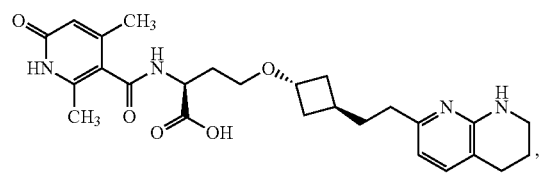

,

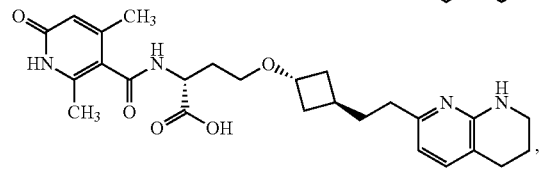

,

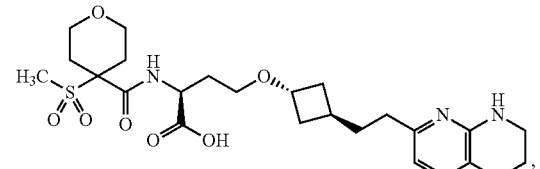

,

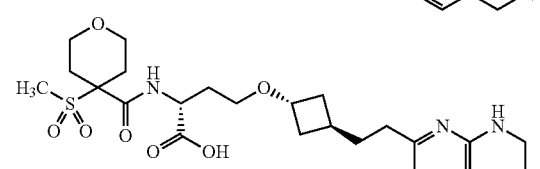

,

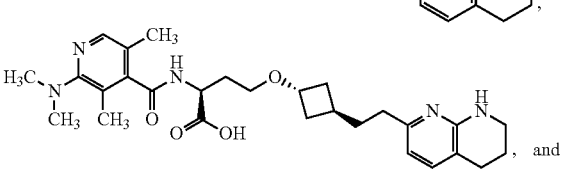

, and

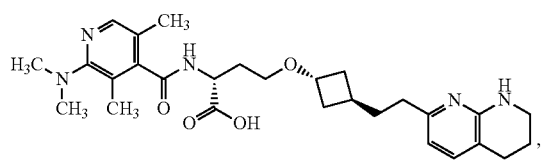
or a pharmaceutically acceptable salt or tautomer thereof.
143. The compound of claim 1, wherein the compound is selected from the group consisting of:
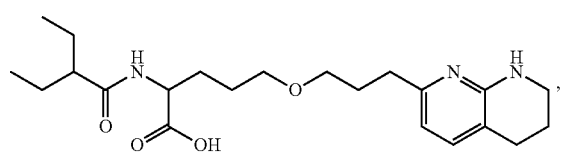
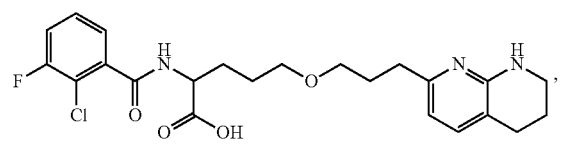
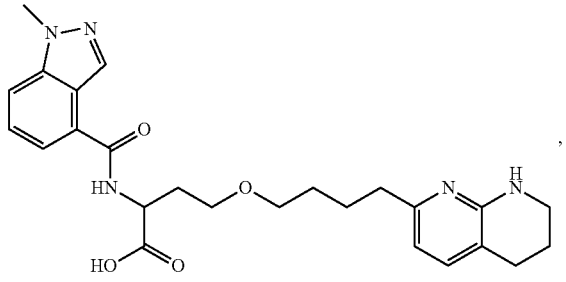
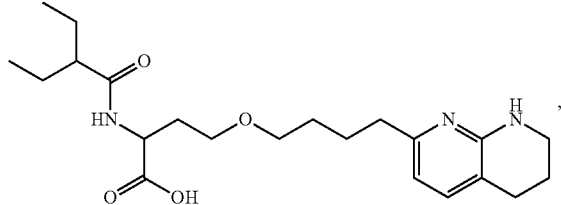
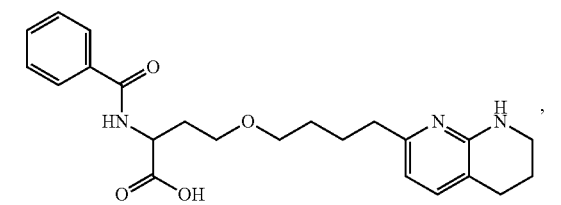
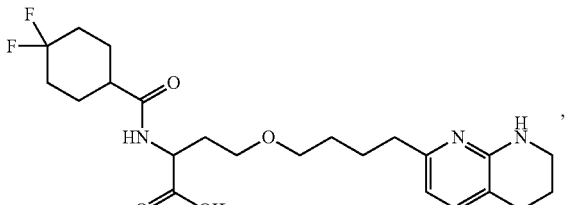
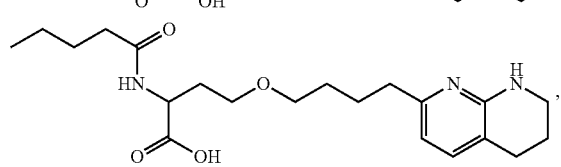
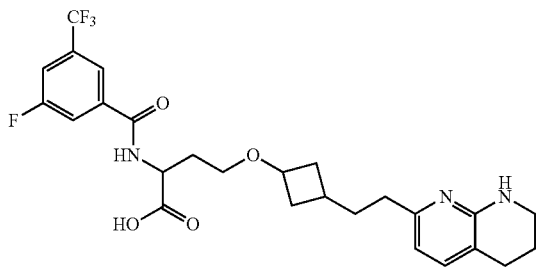
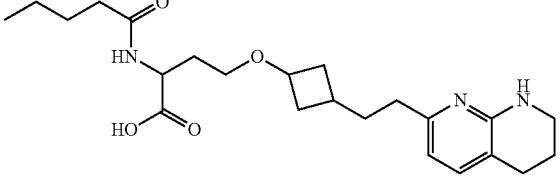
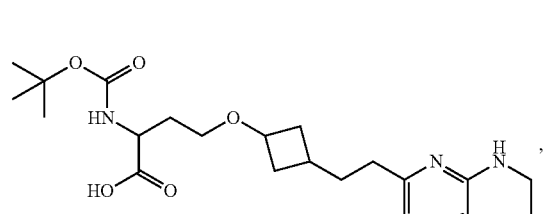
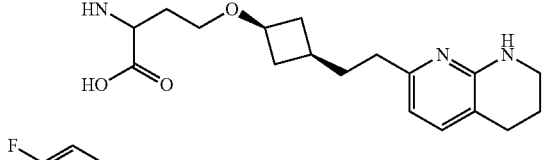
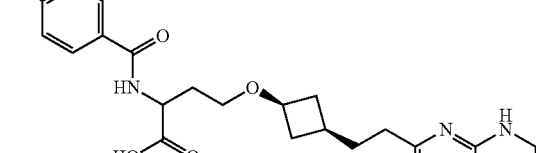

-continued
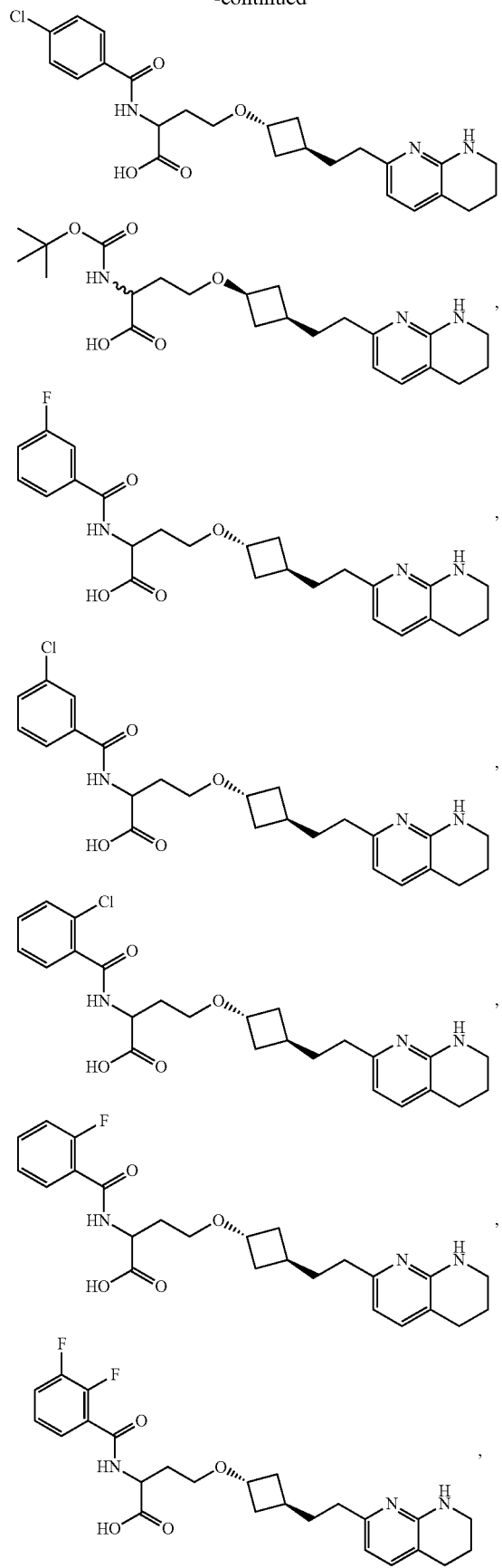
-continued
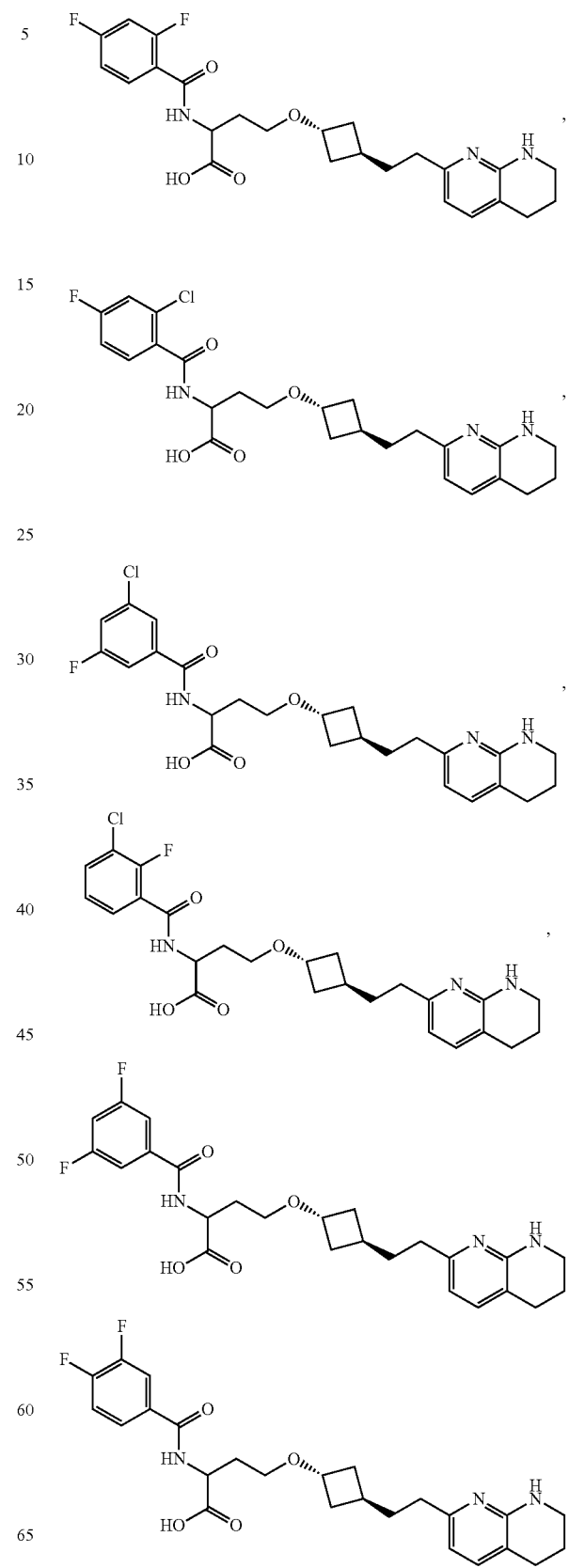

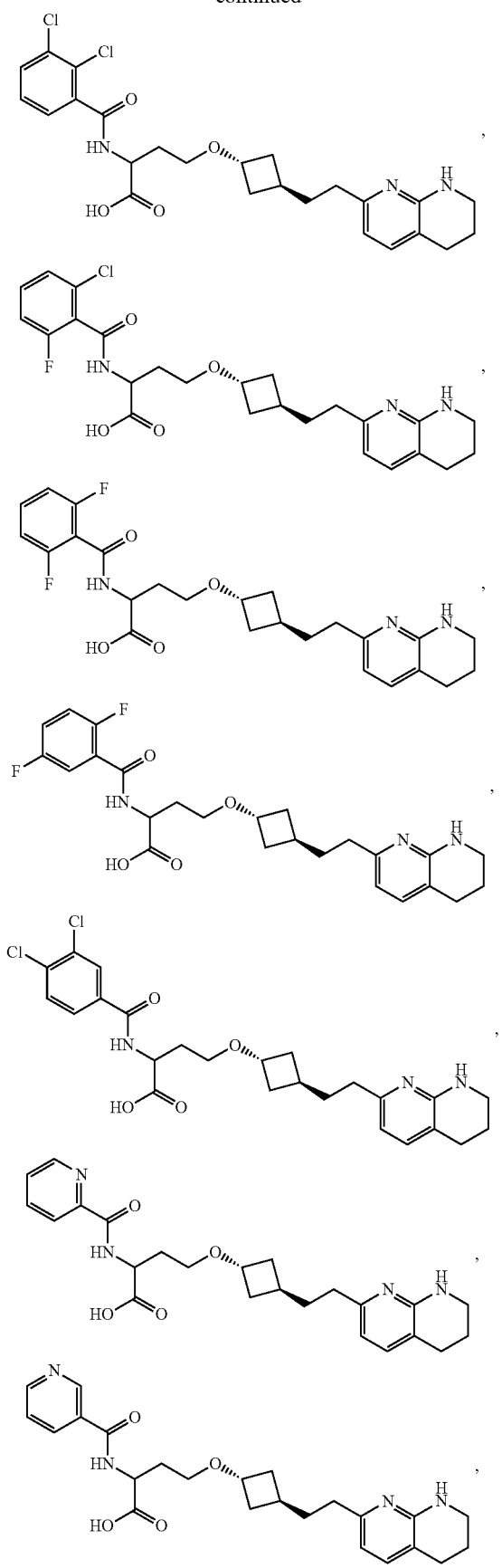
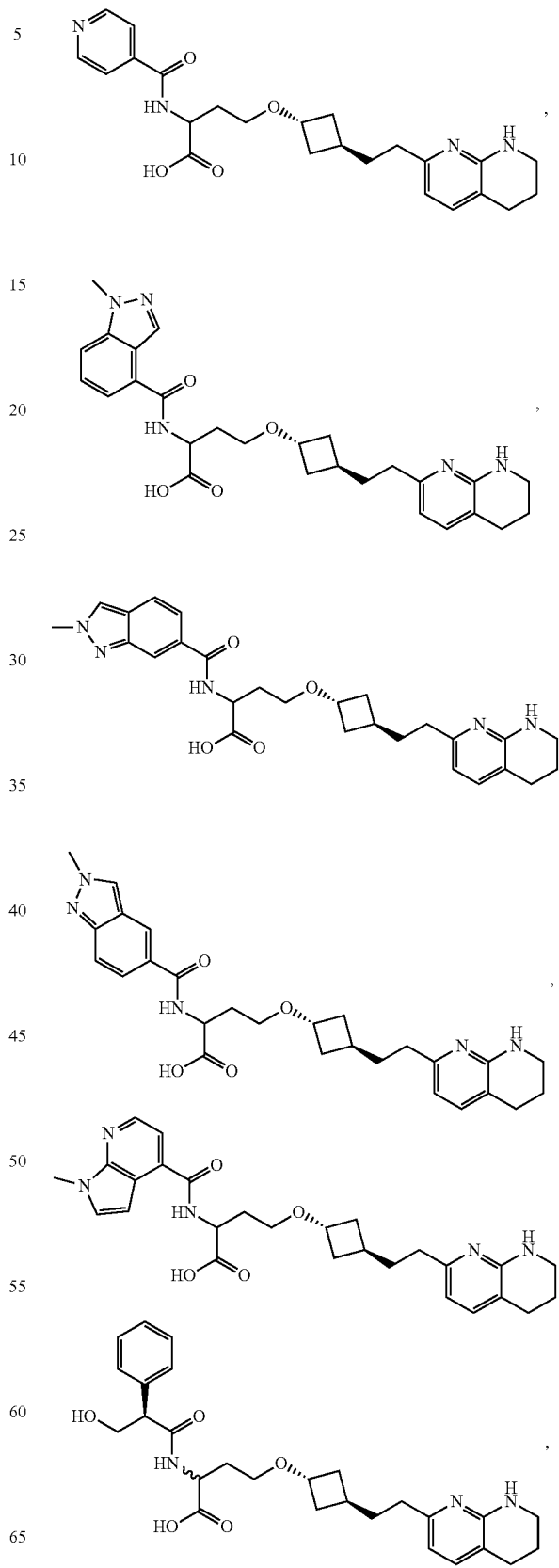

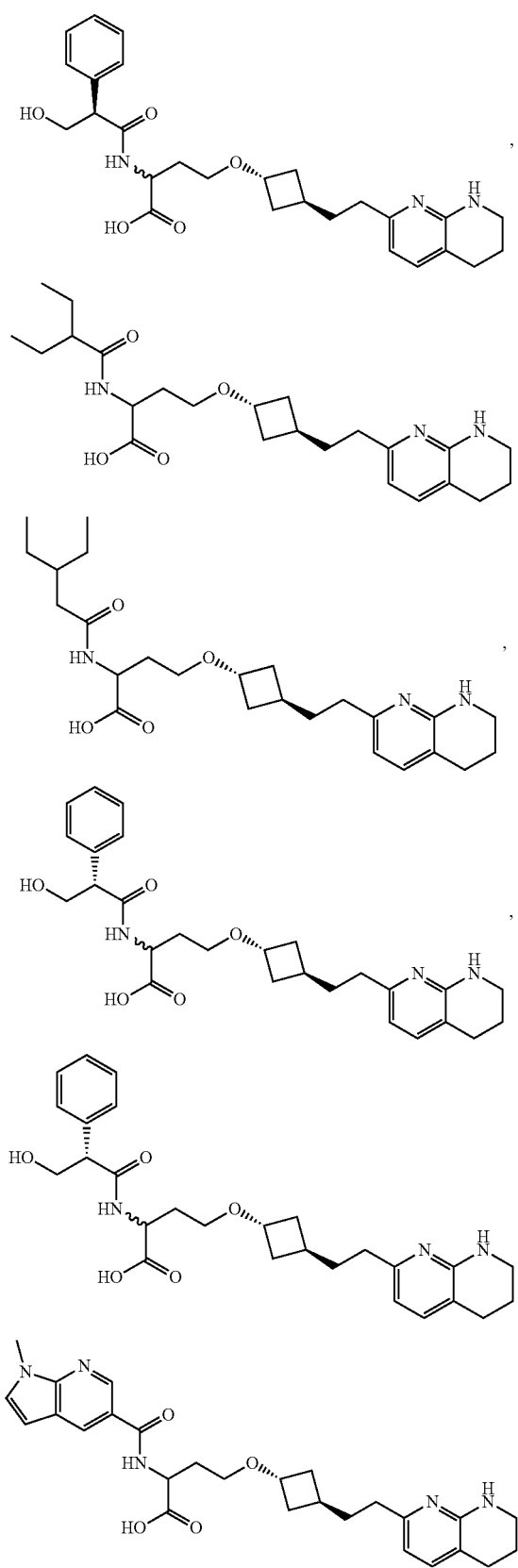
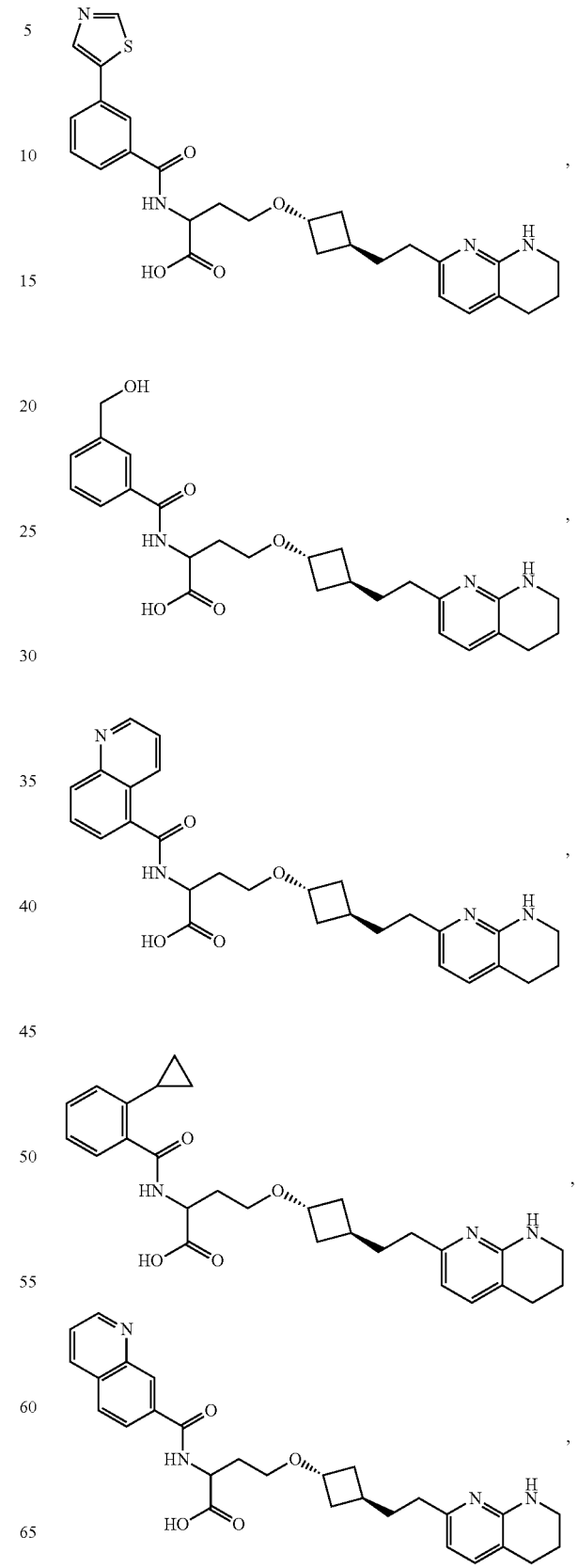

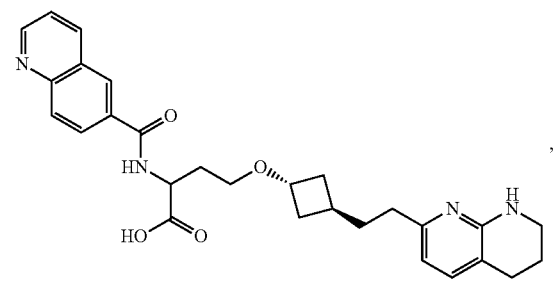
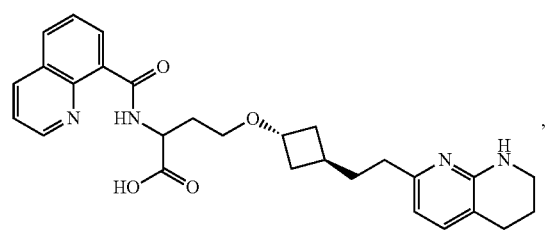
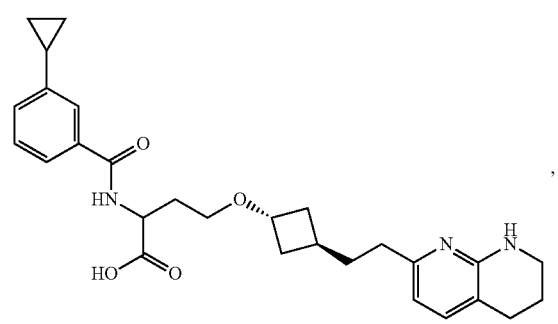
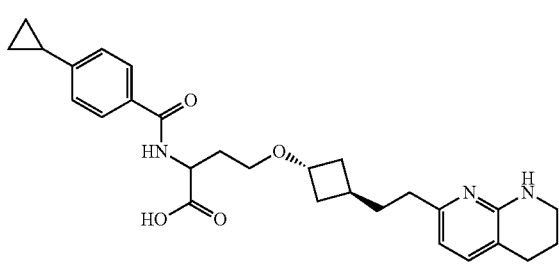
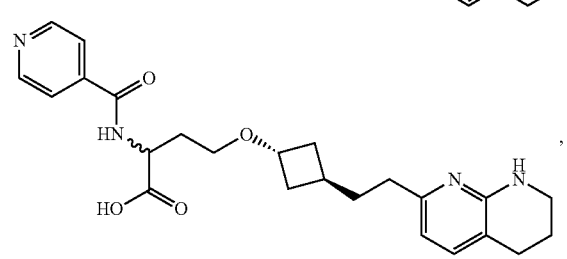
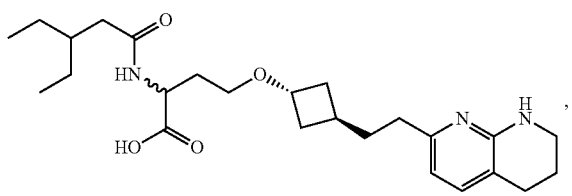
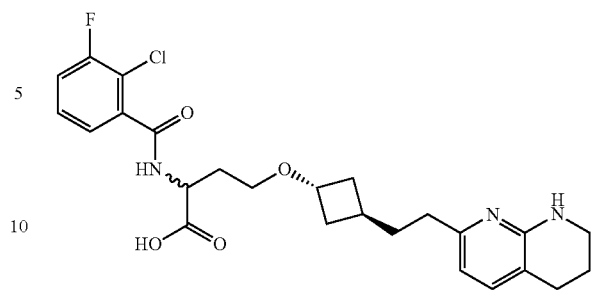
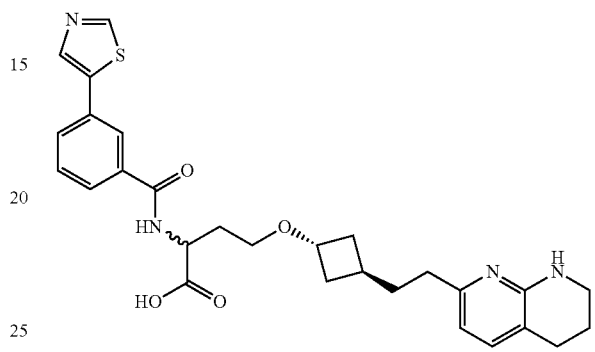
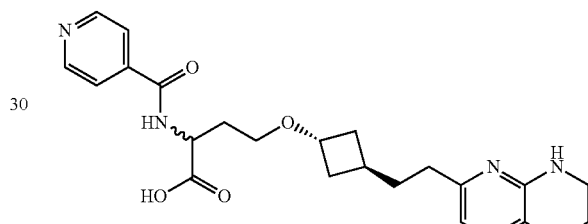
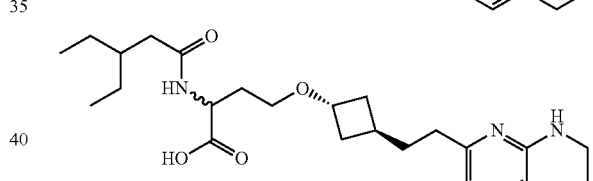
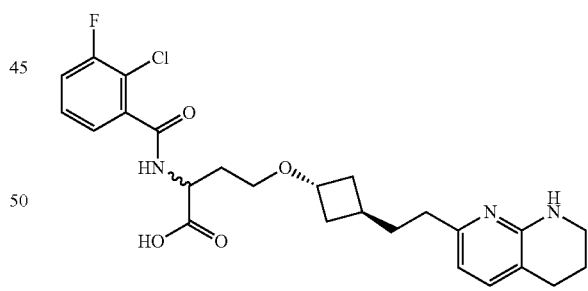
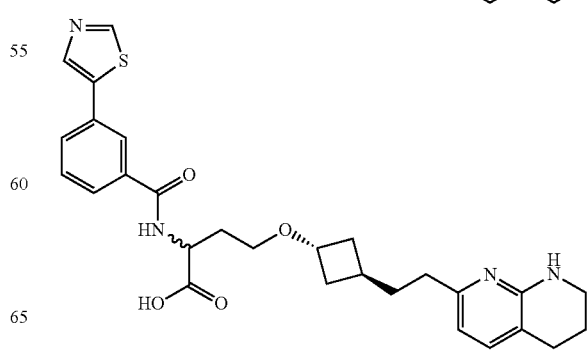

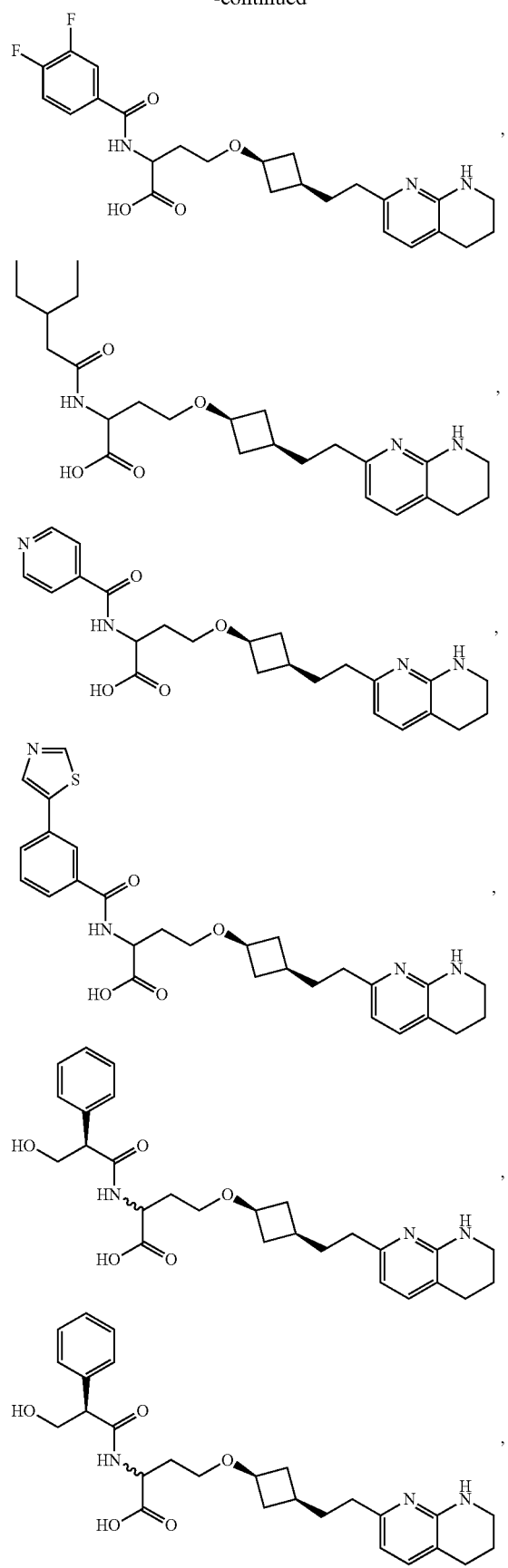
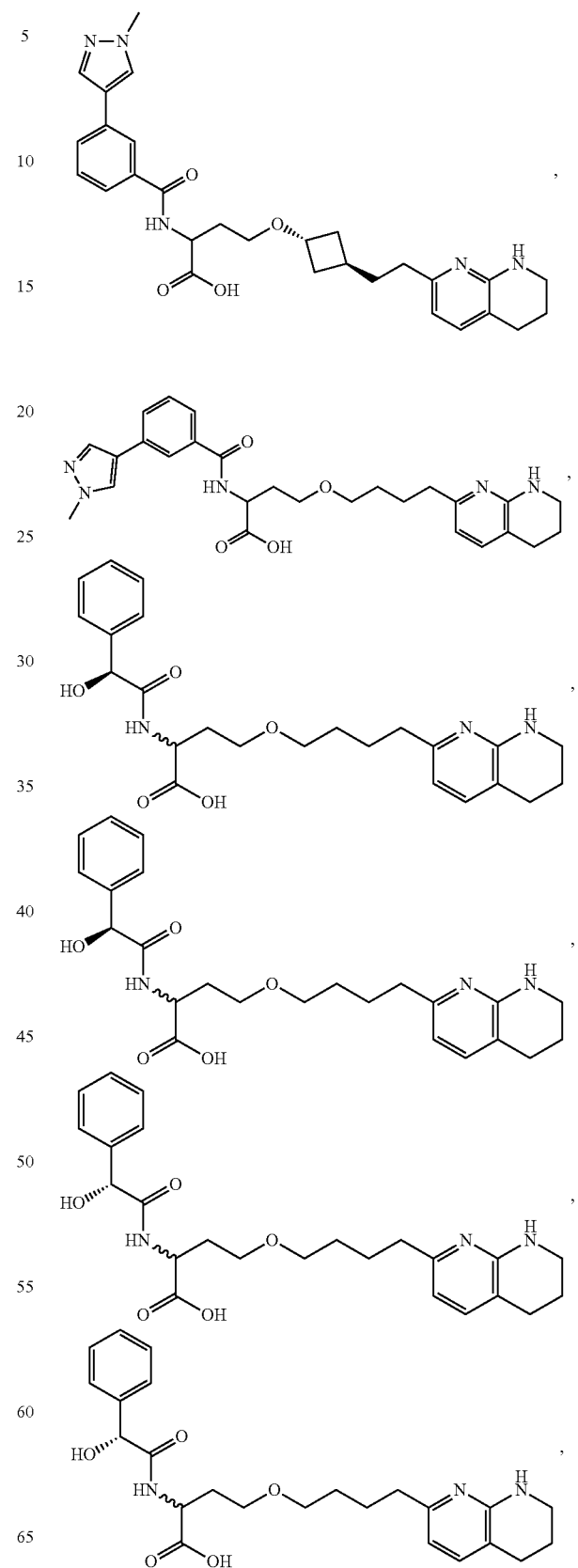

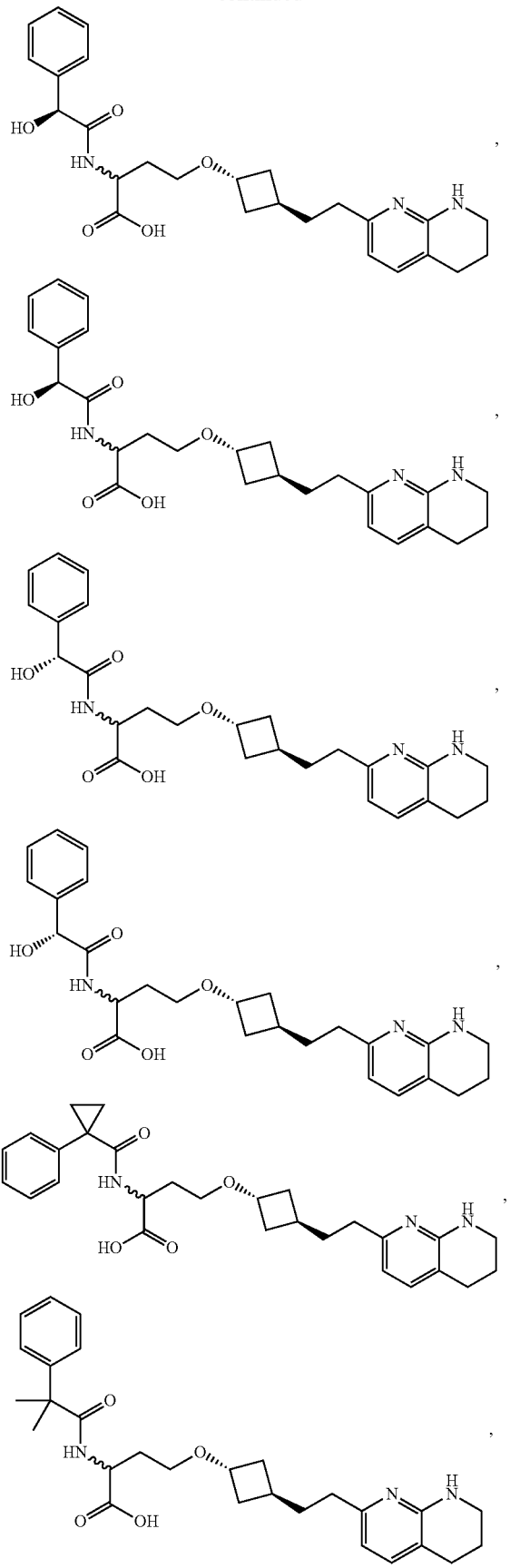
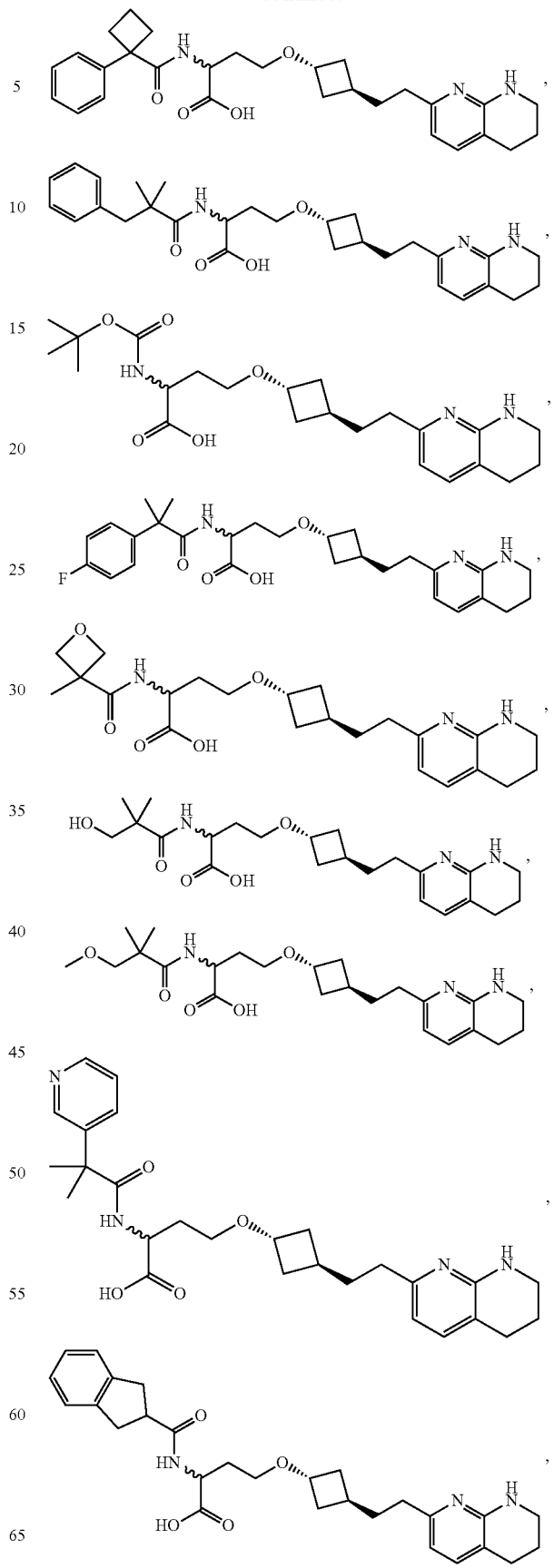

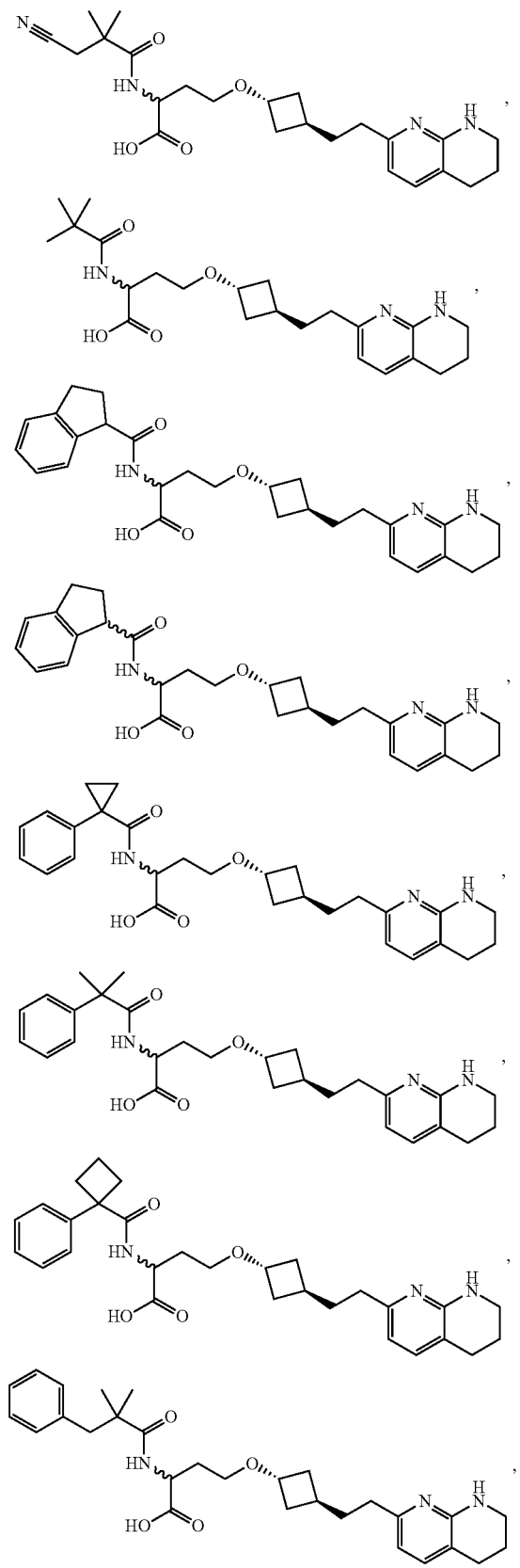
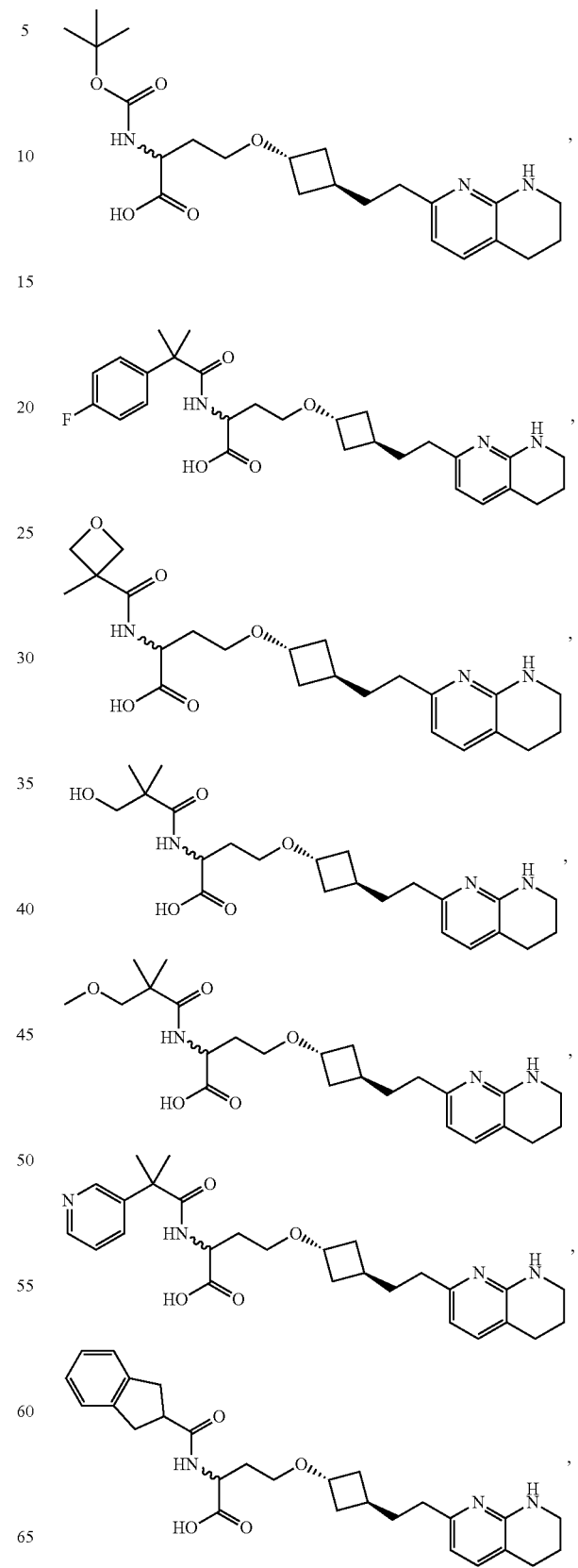

465
-continued
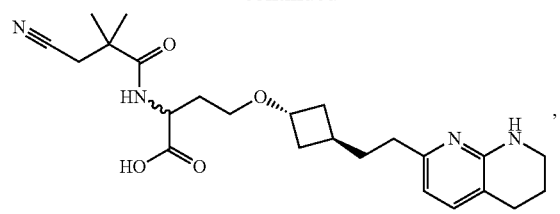,
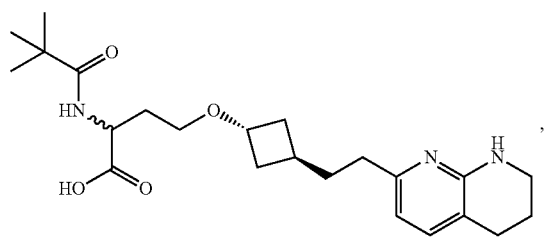,
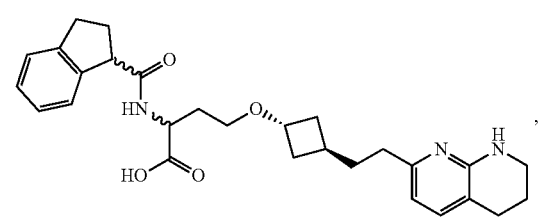,
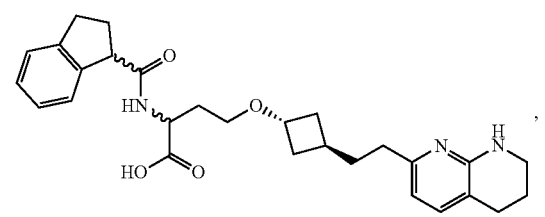,
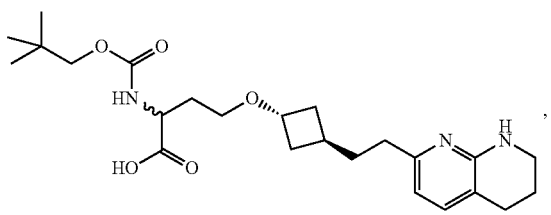,
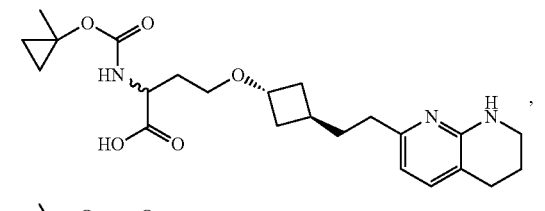,
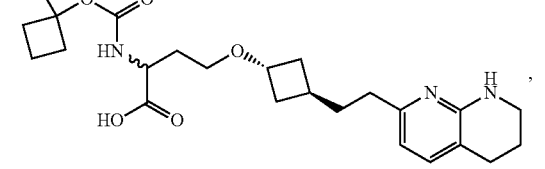,
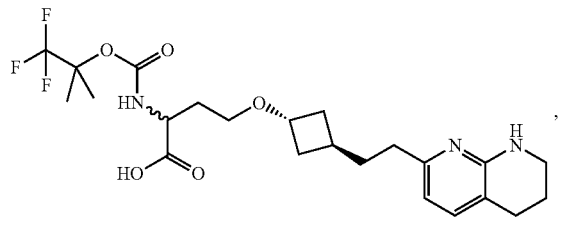,
466
-continued
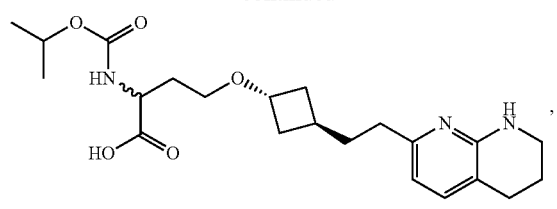,
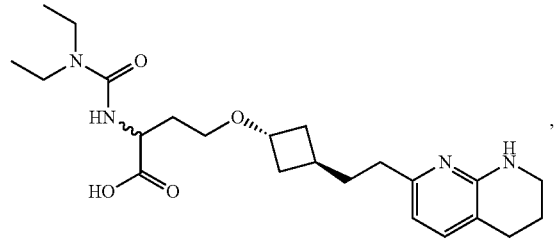,
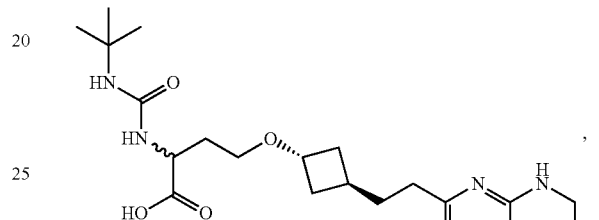,
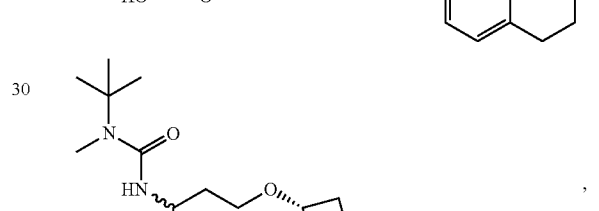,
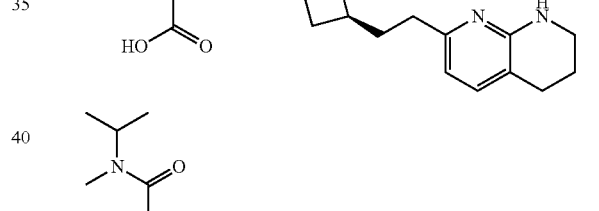,
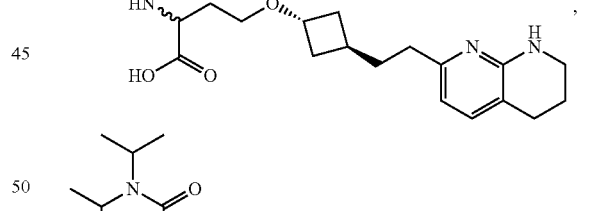,
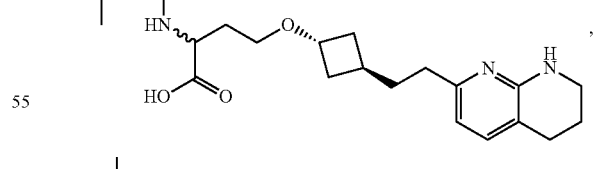,
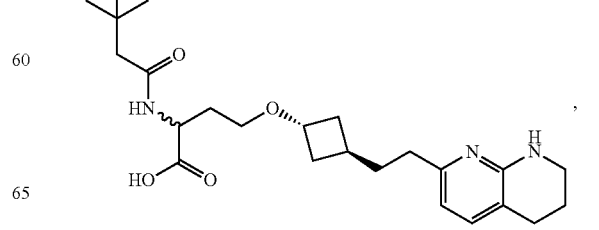, 467
-continued
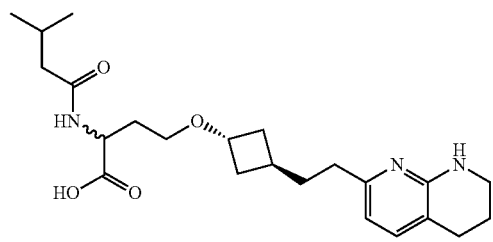,
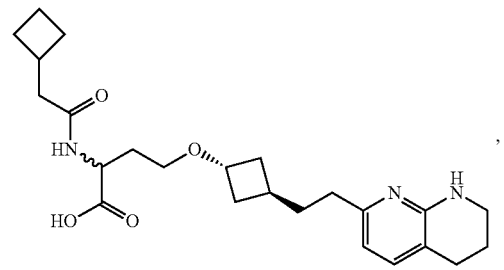,
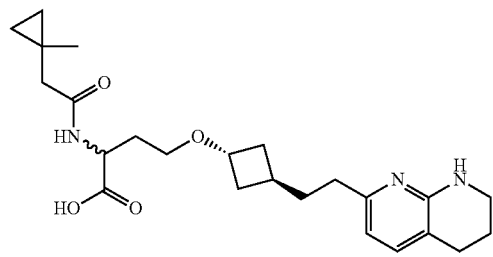,
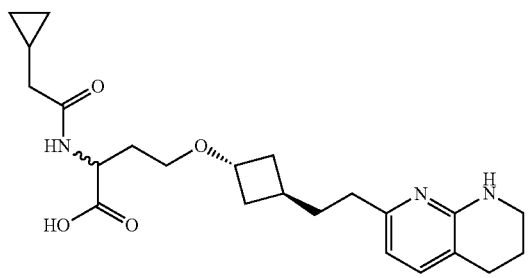,
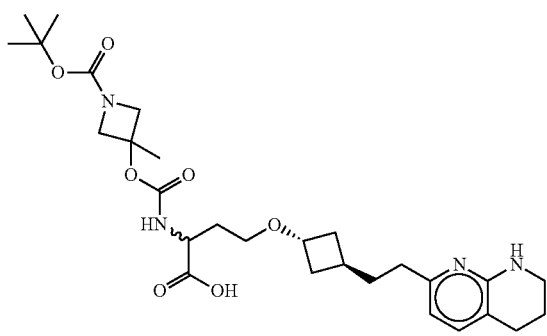,
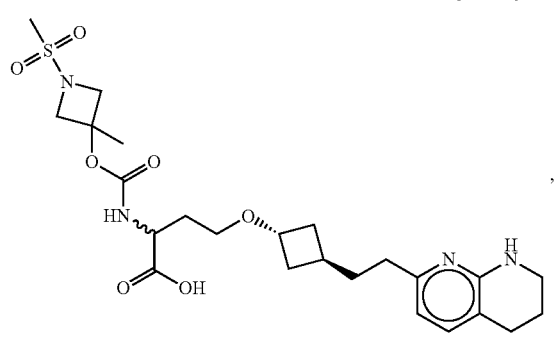,
468
-continued
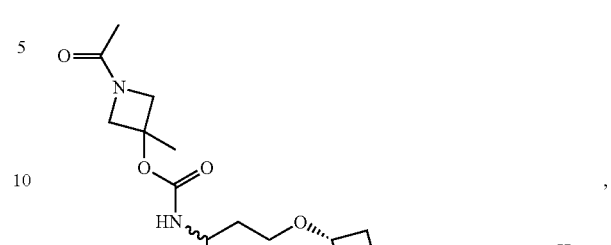,
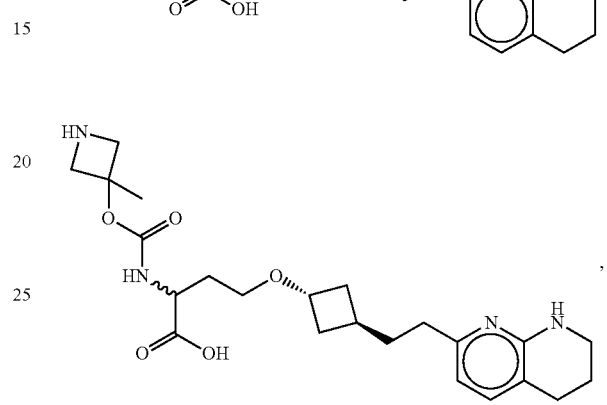,
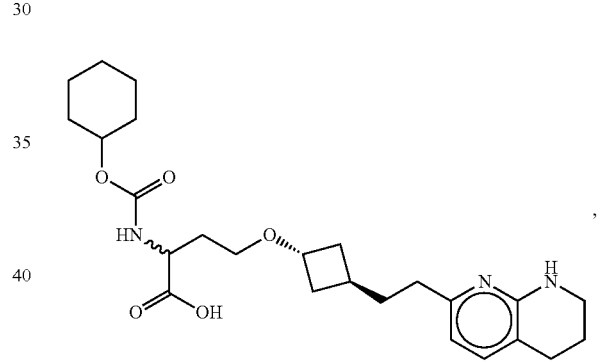,
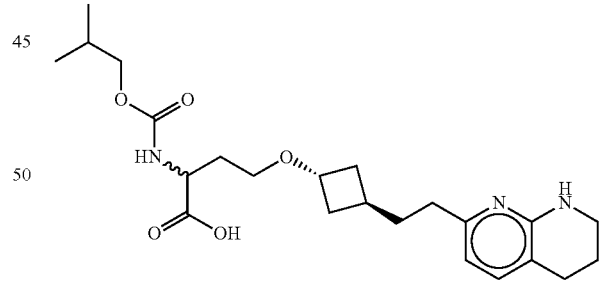,
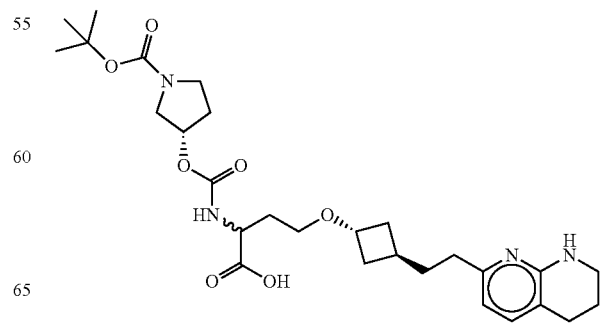, 469
-continued
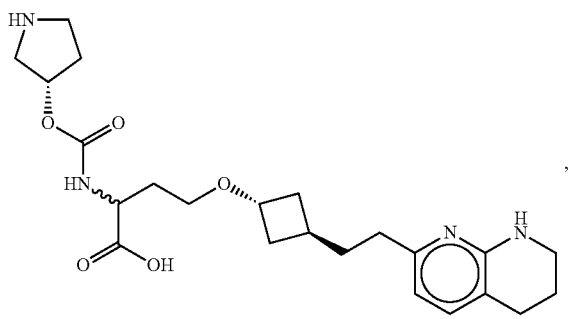
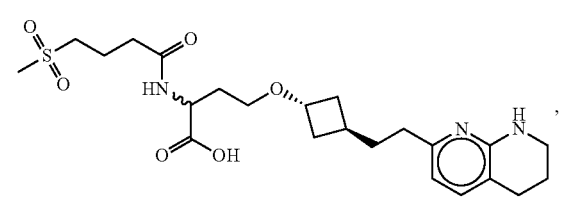
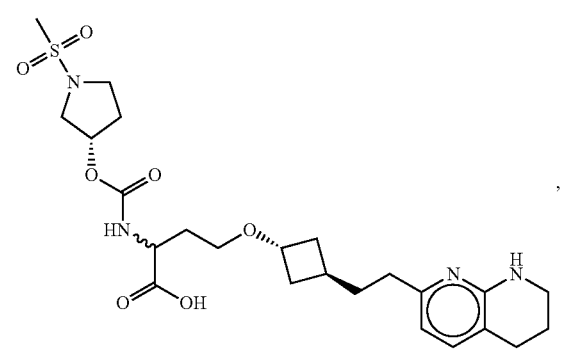
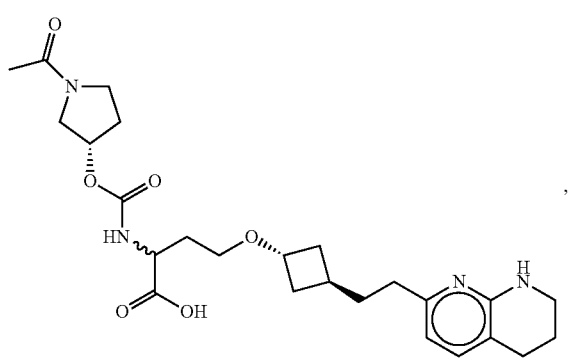
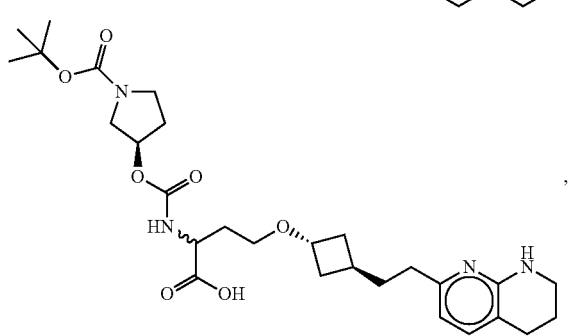
470
-continued
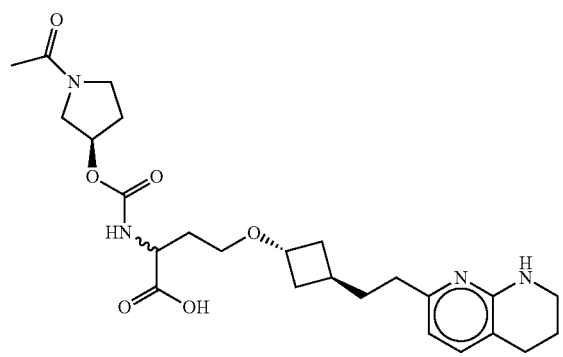
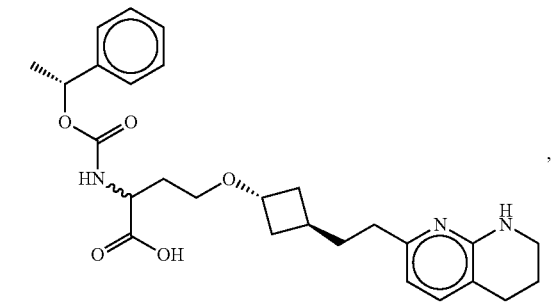
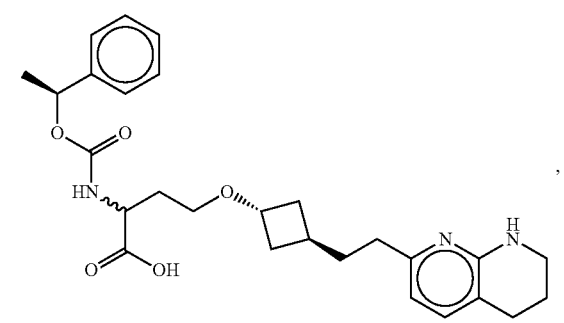
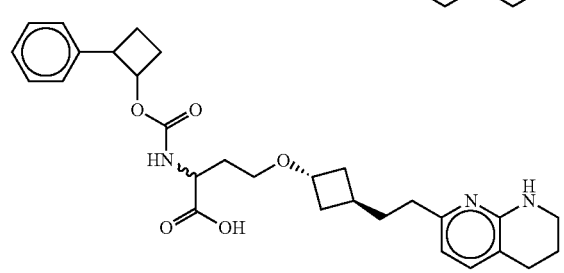
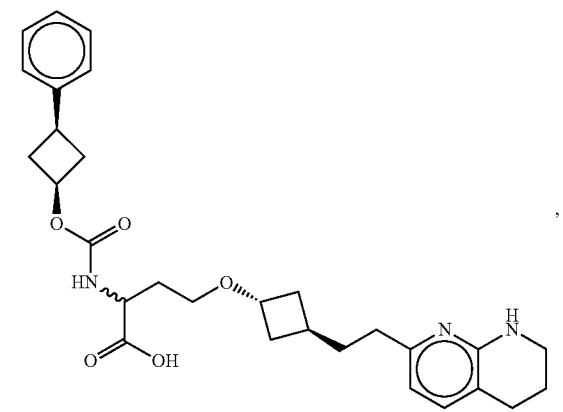

471
-continued
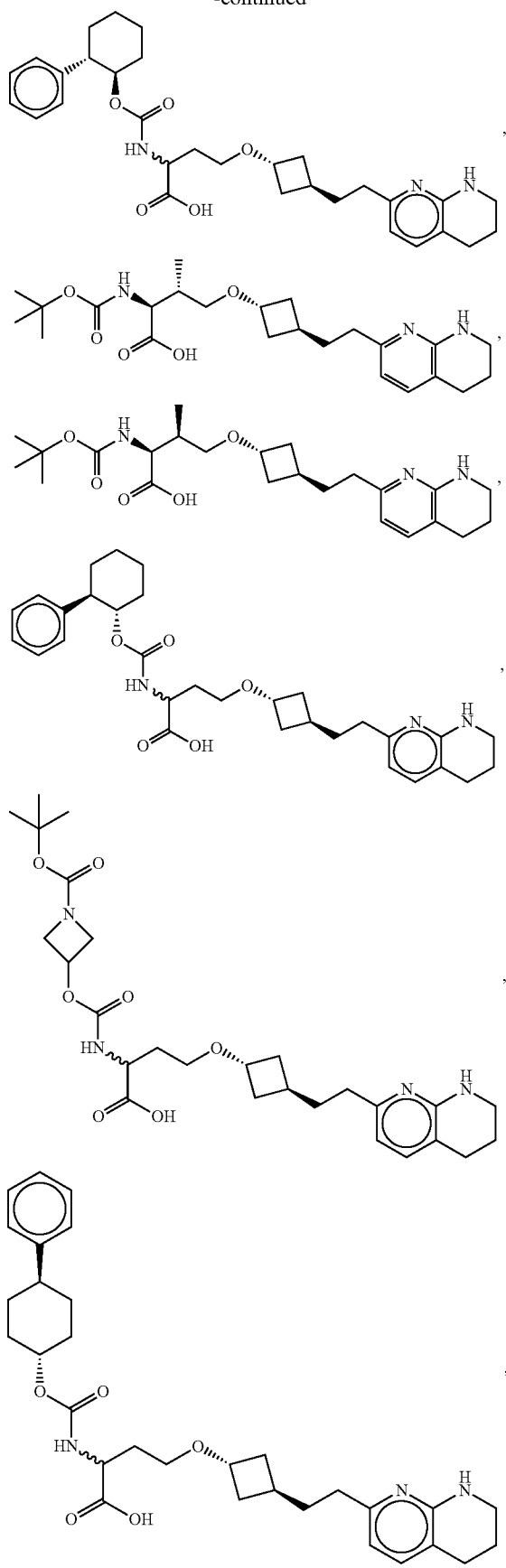
472
-continued
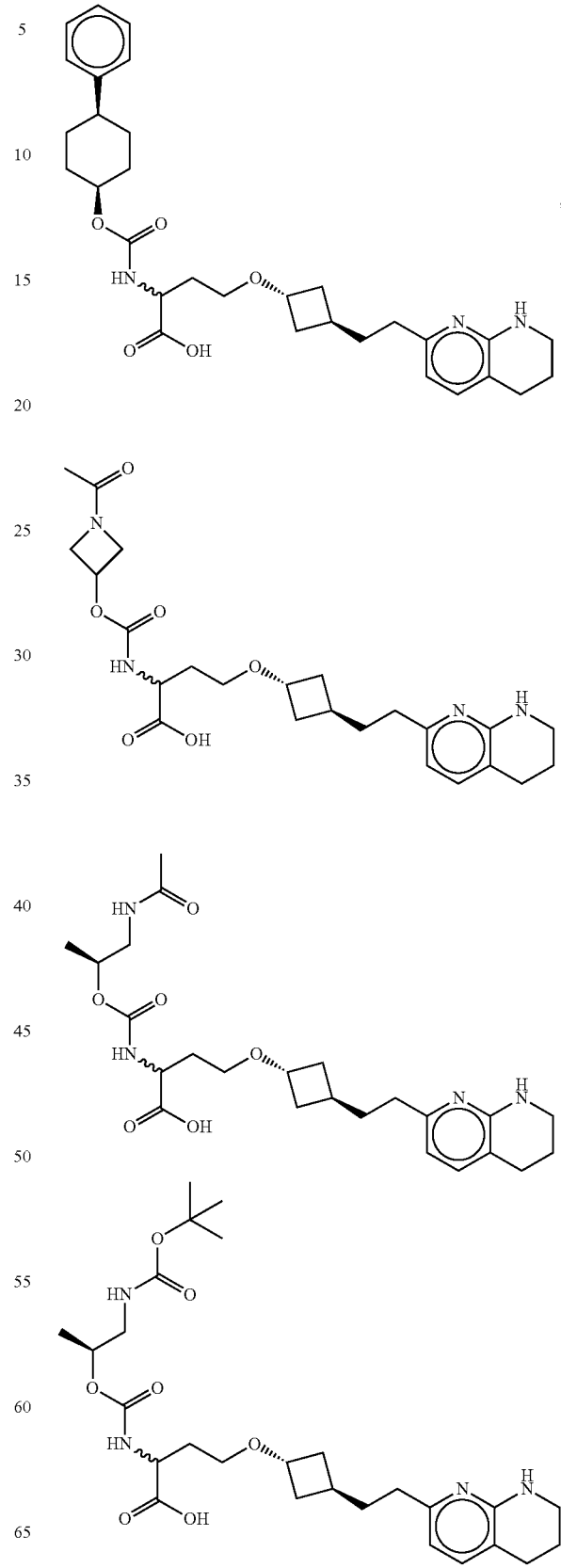

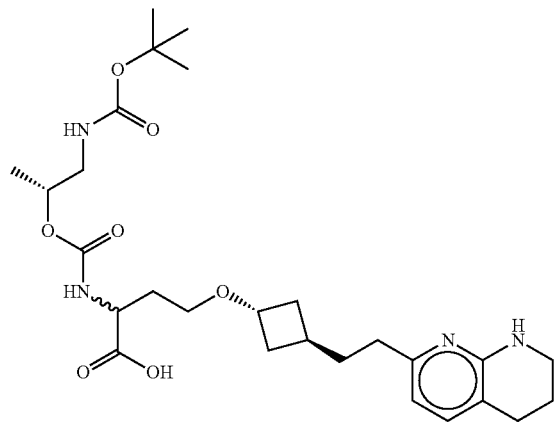
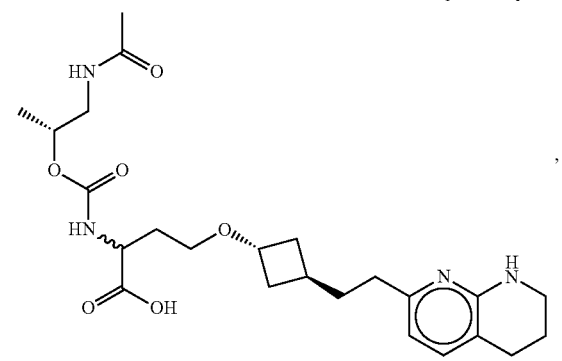
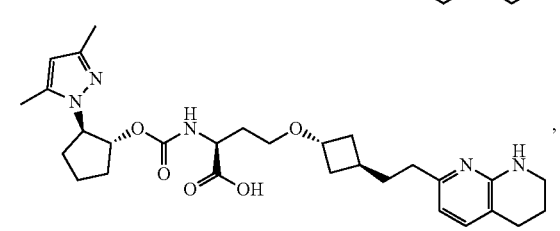
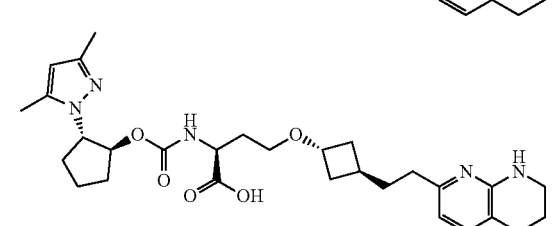
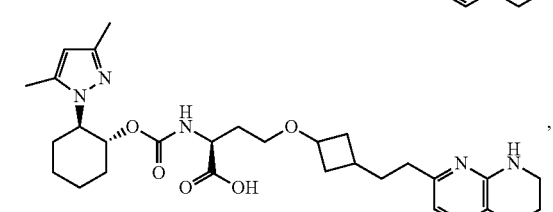
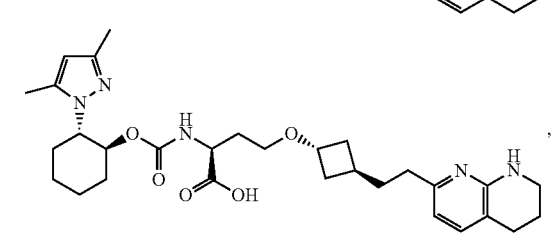
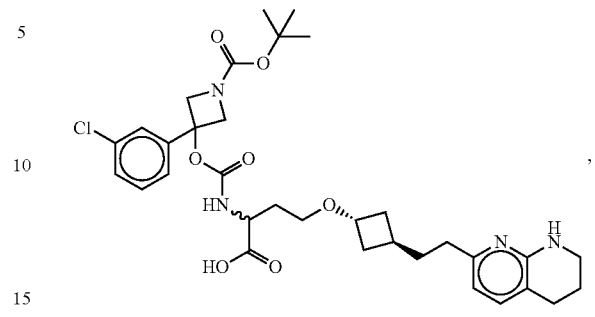
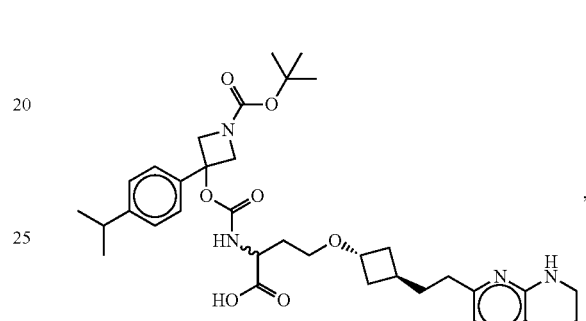
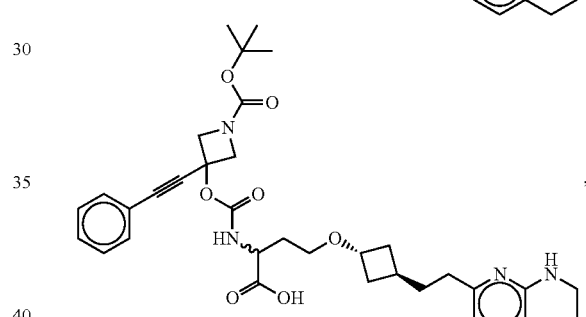
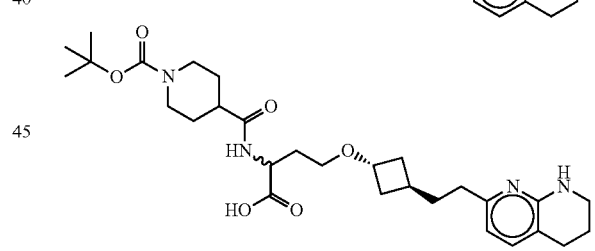
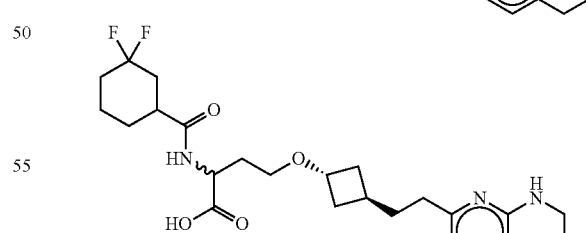
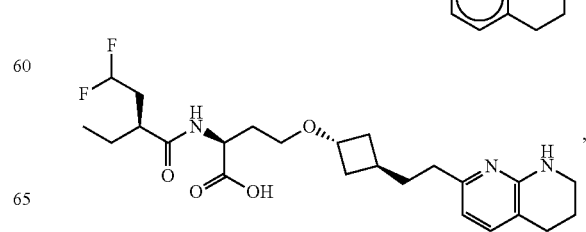

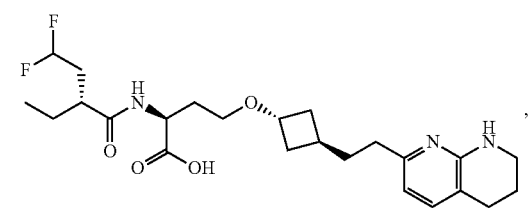,
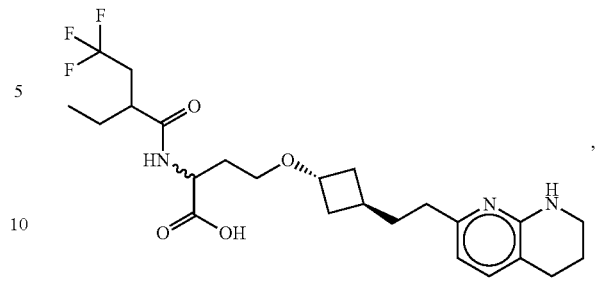,
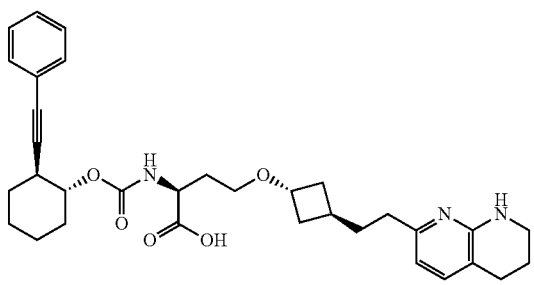,
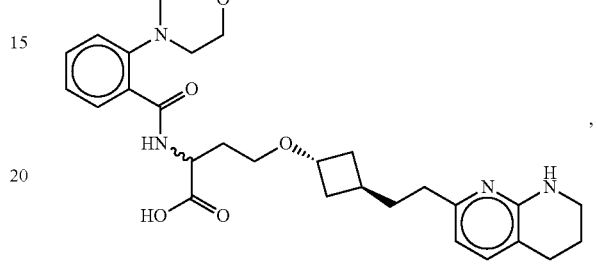,
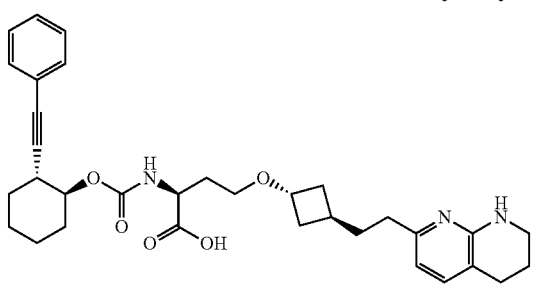,
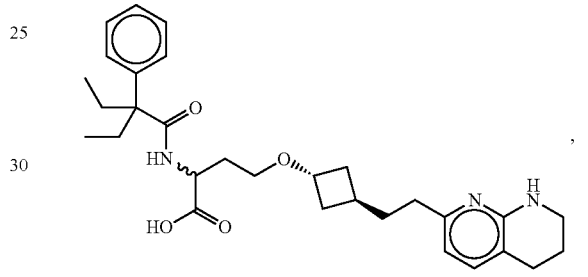,
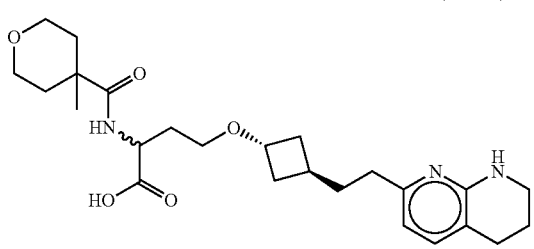,
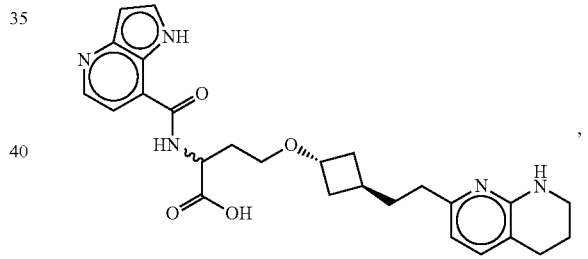,
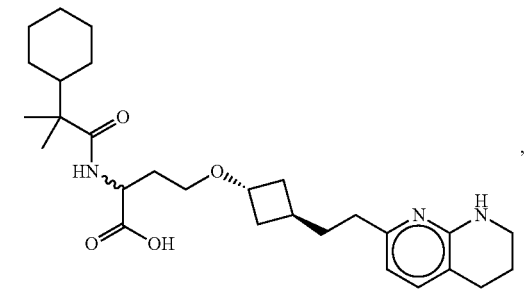,
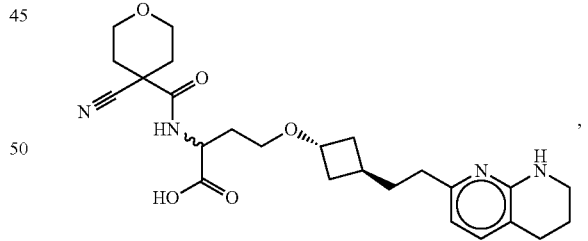,
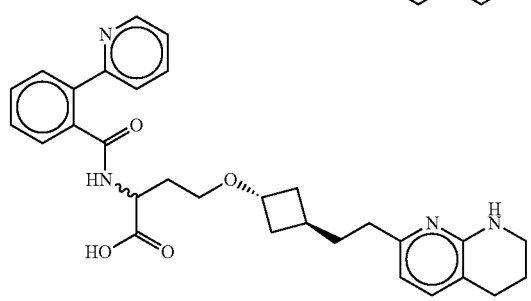,
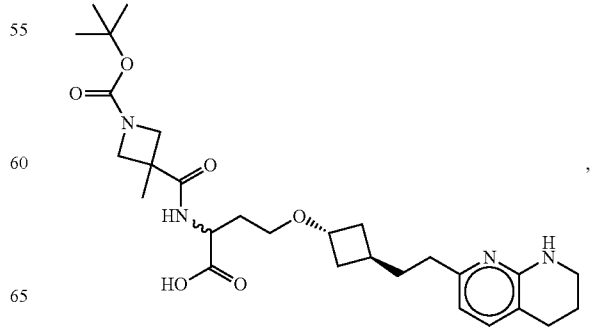,

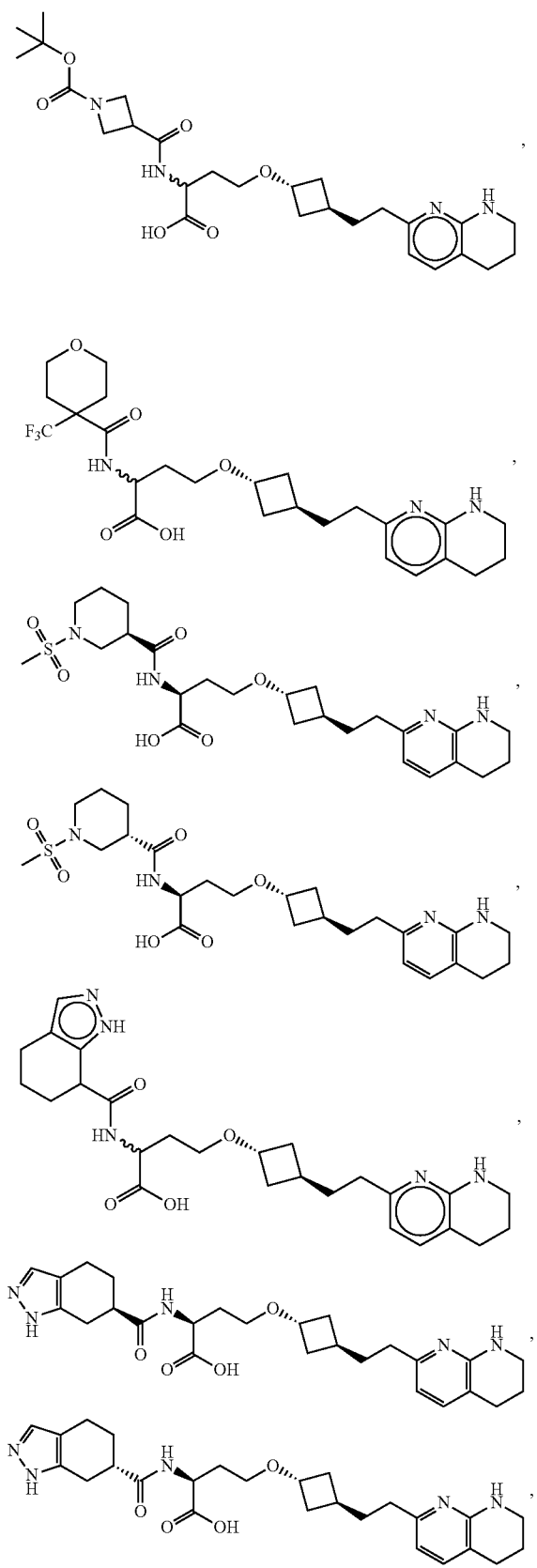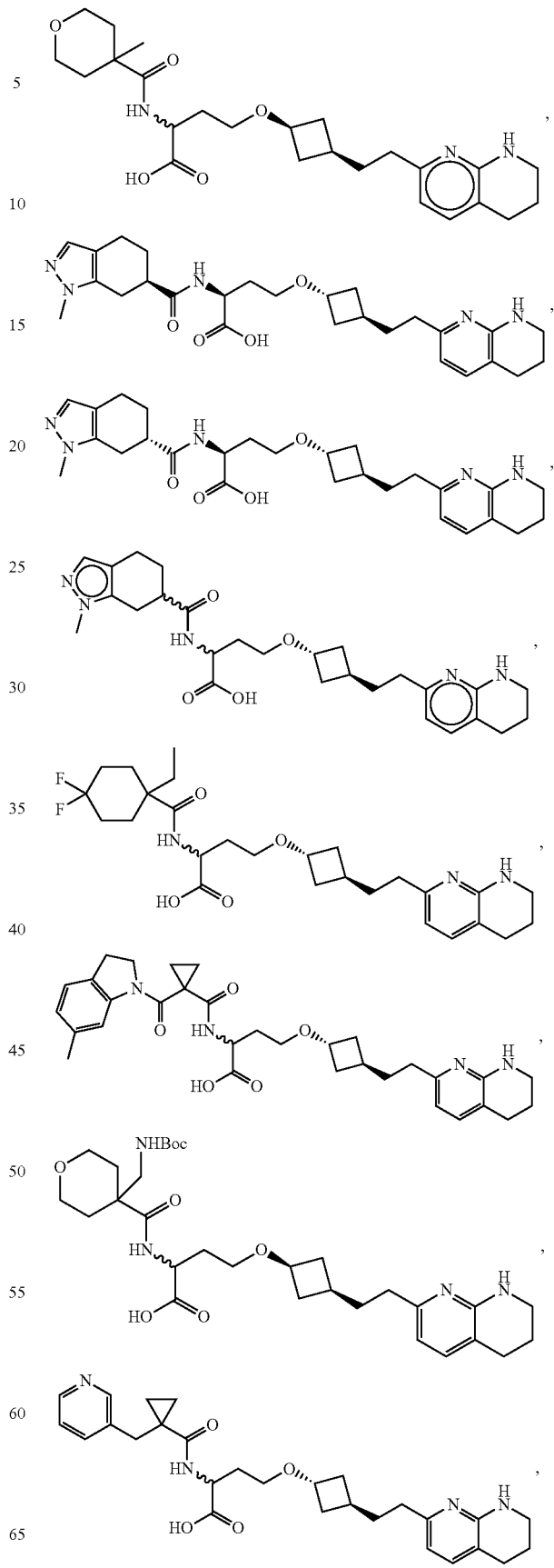

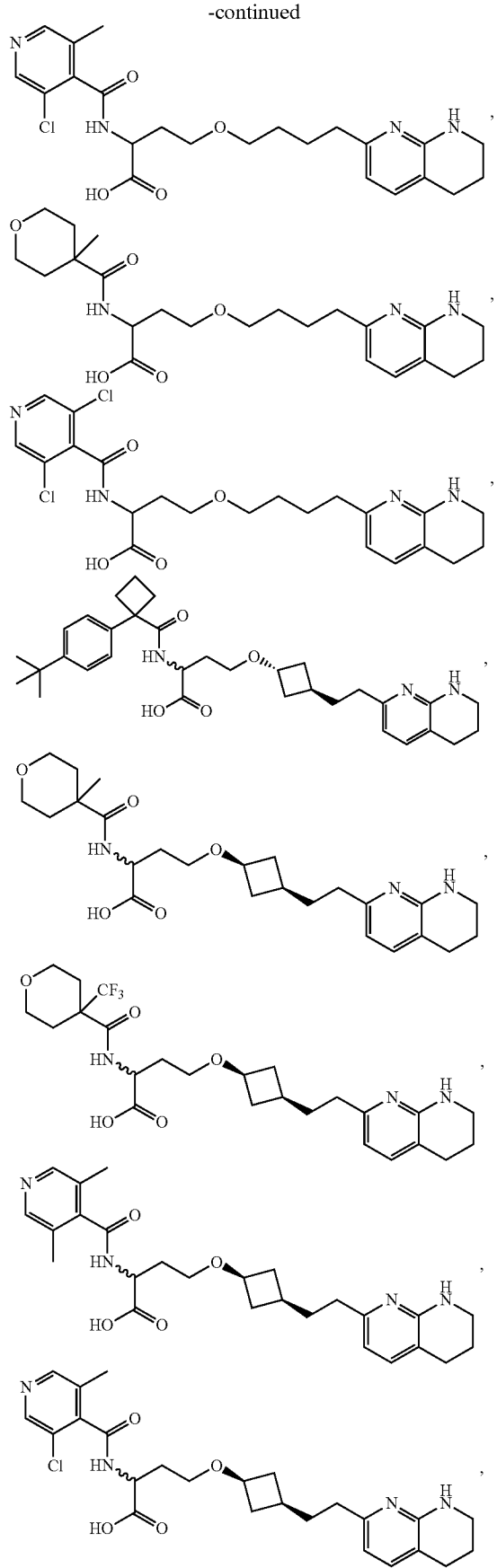
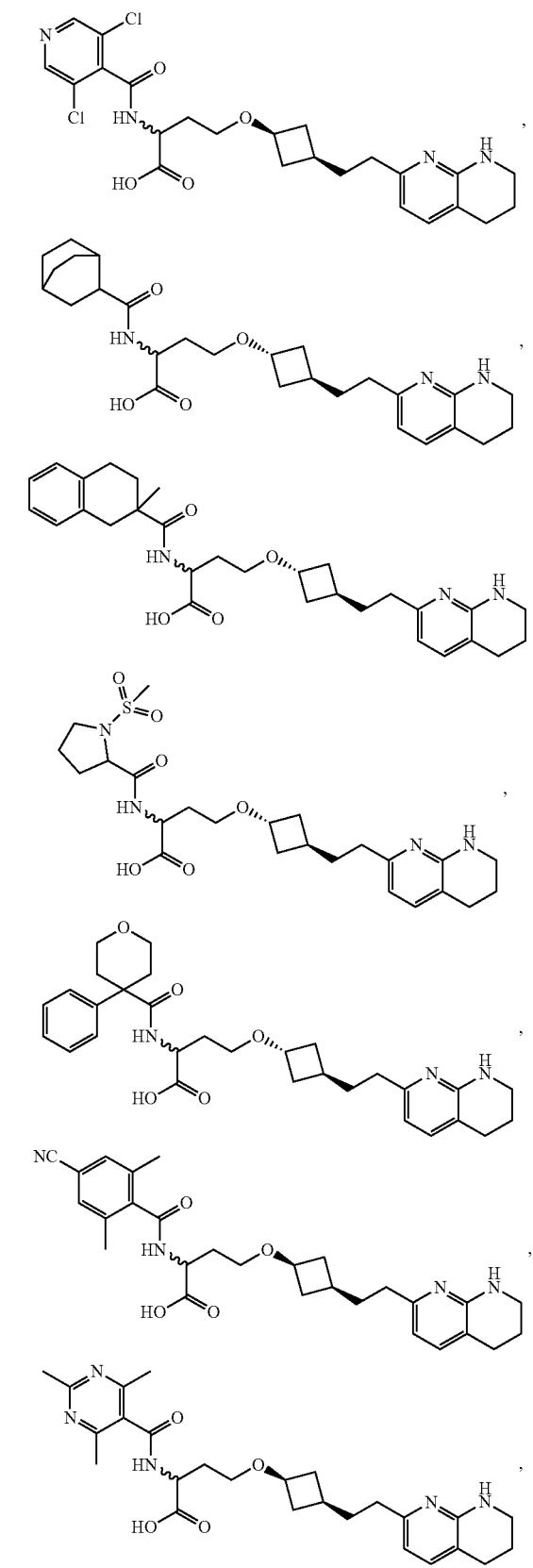

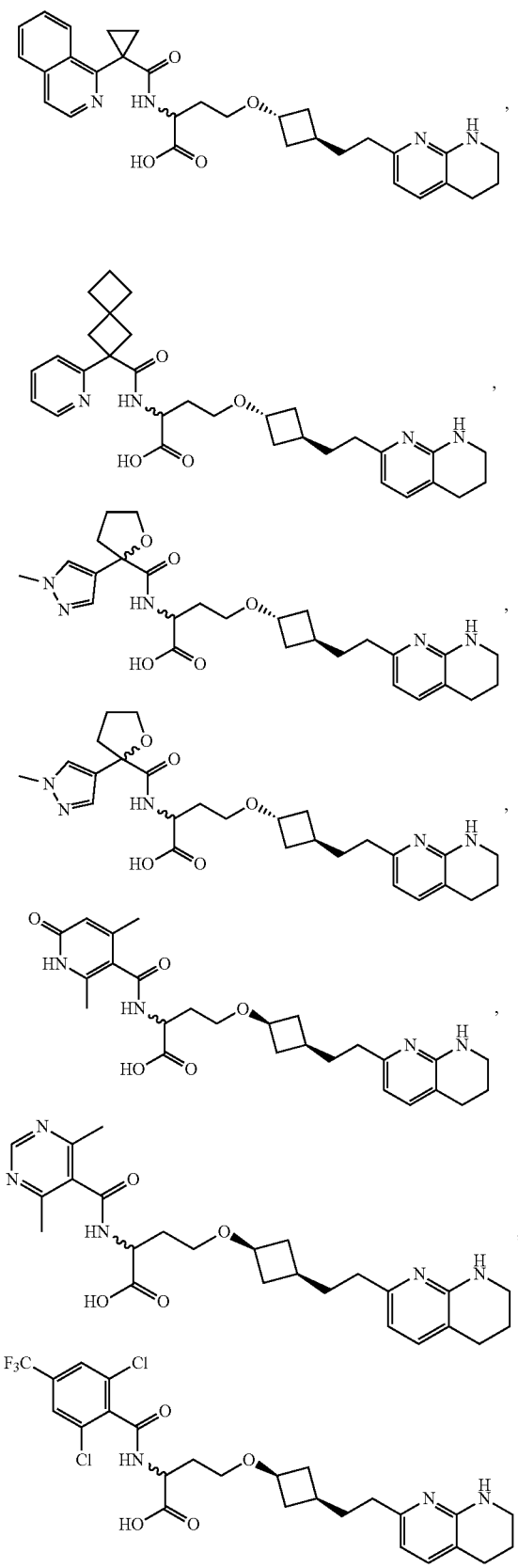
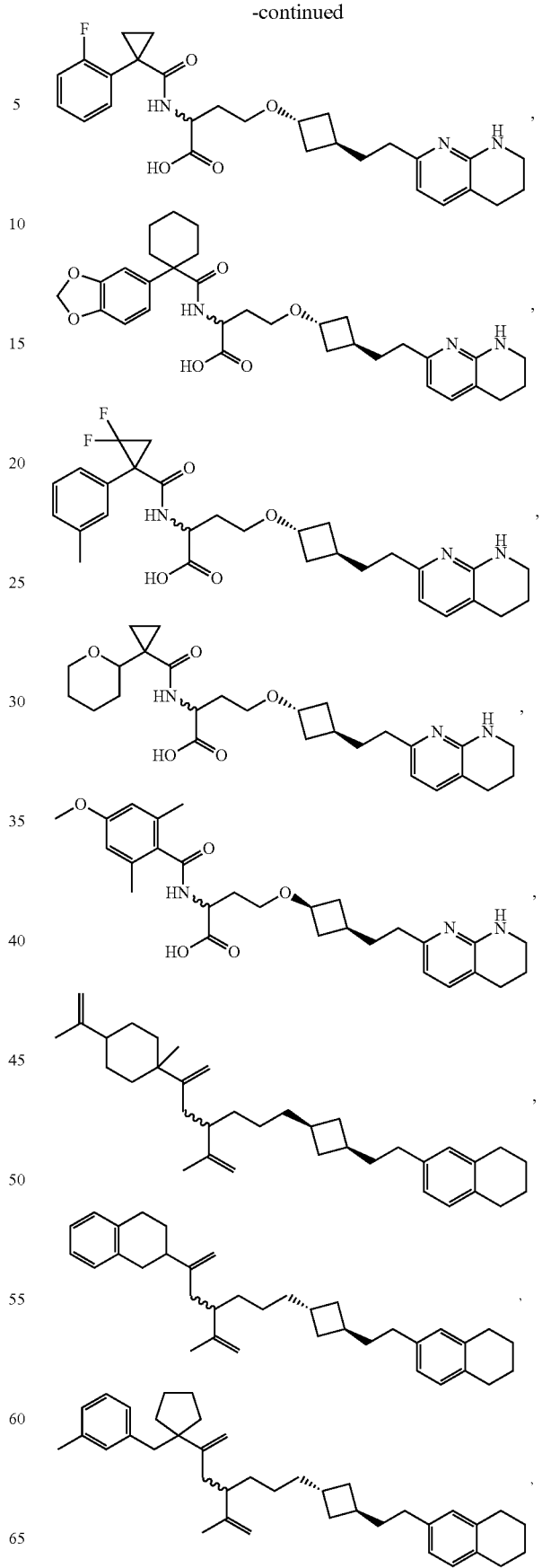

483
-continued
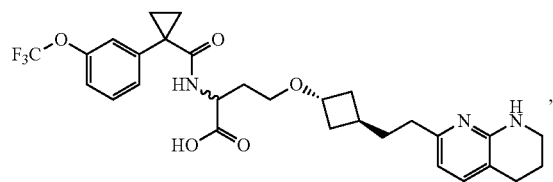,
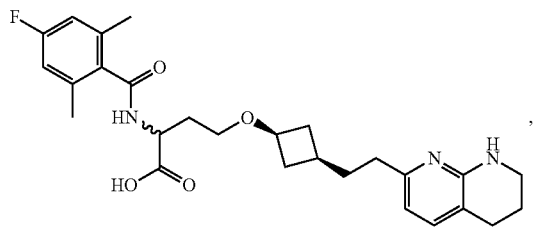,
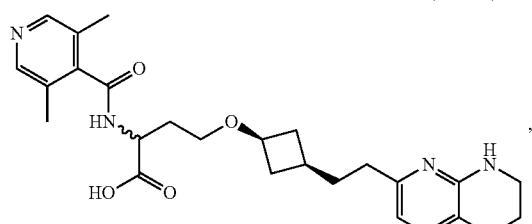,
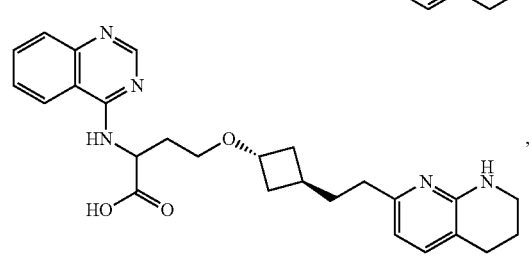,
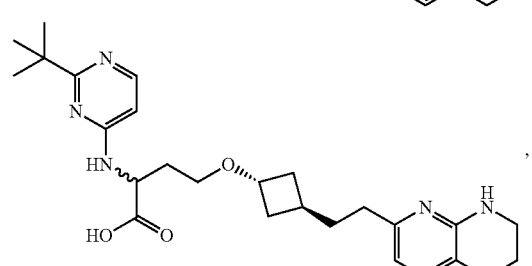,
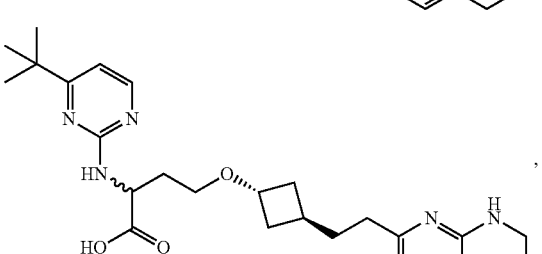,
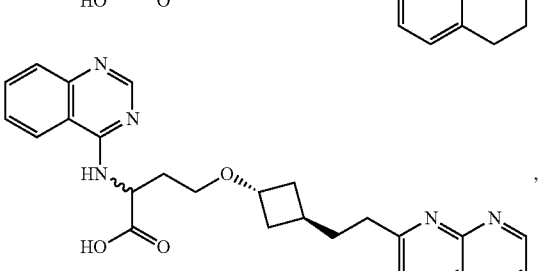,
484
-continued
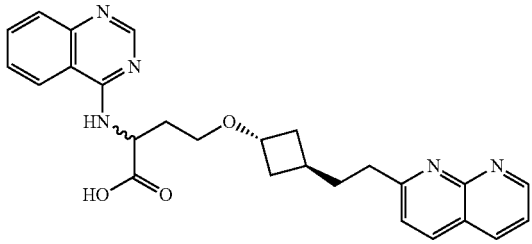,
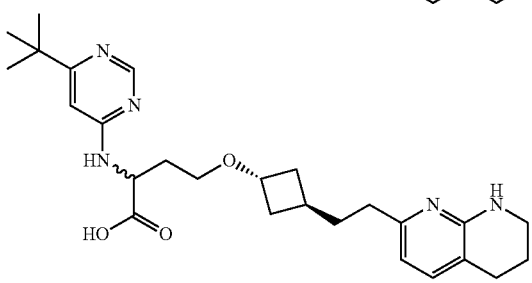,
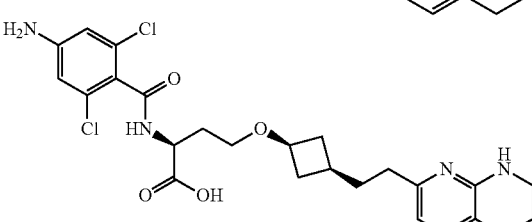,
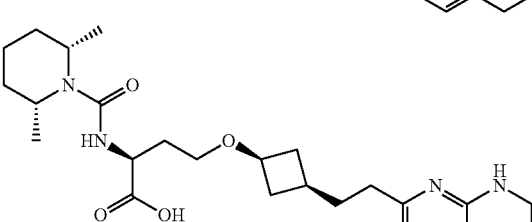,
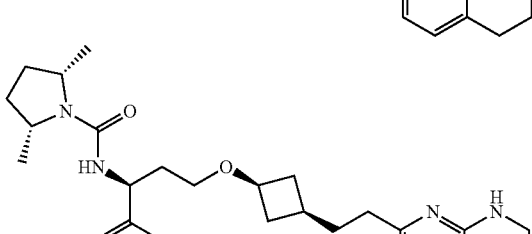,
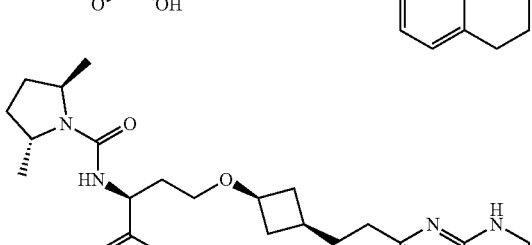,
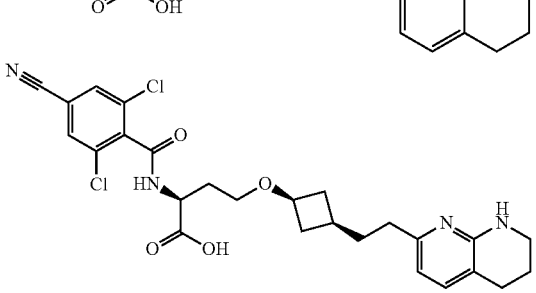,

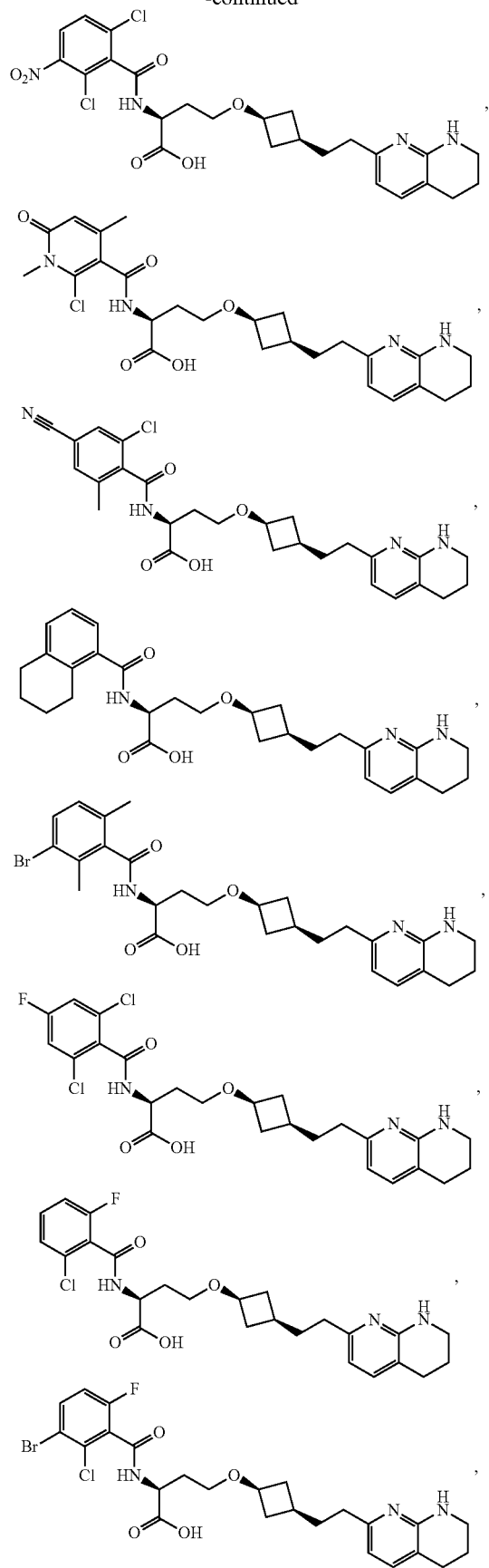
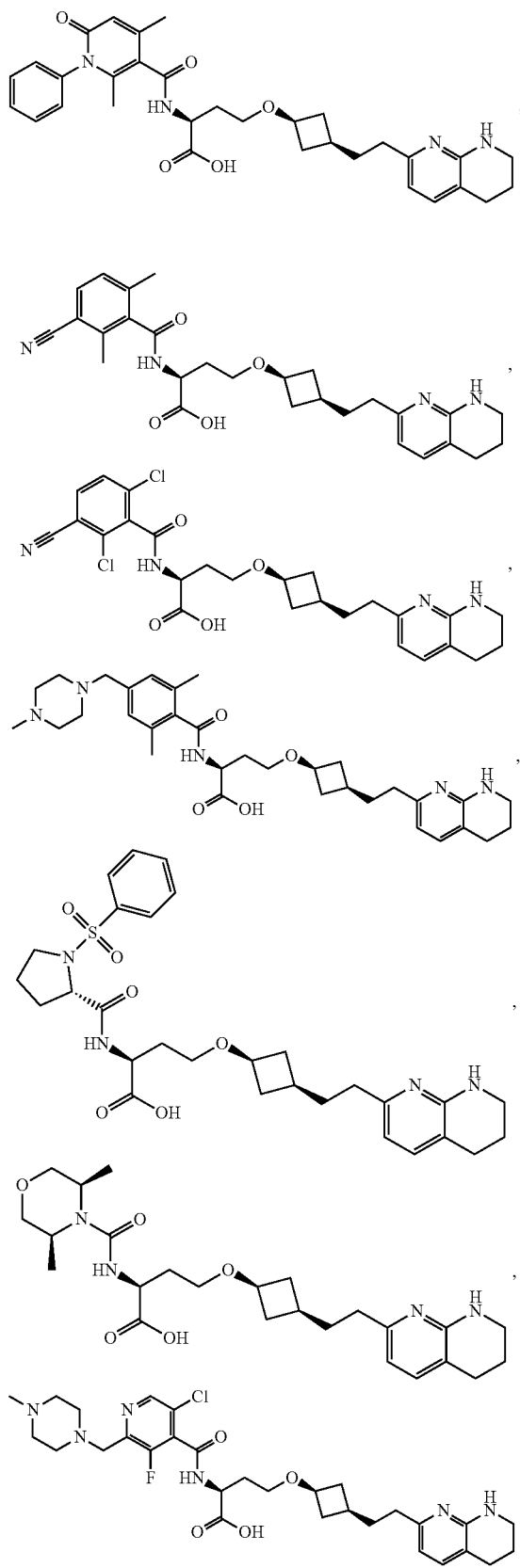

487
-continued
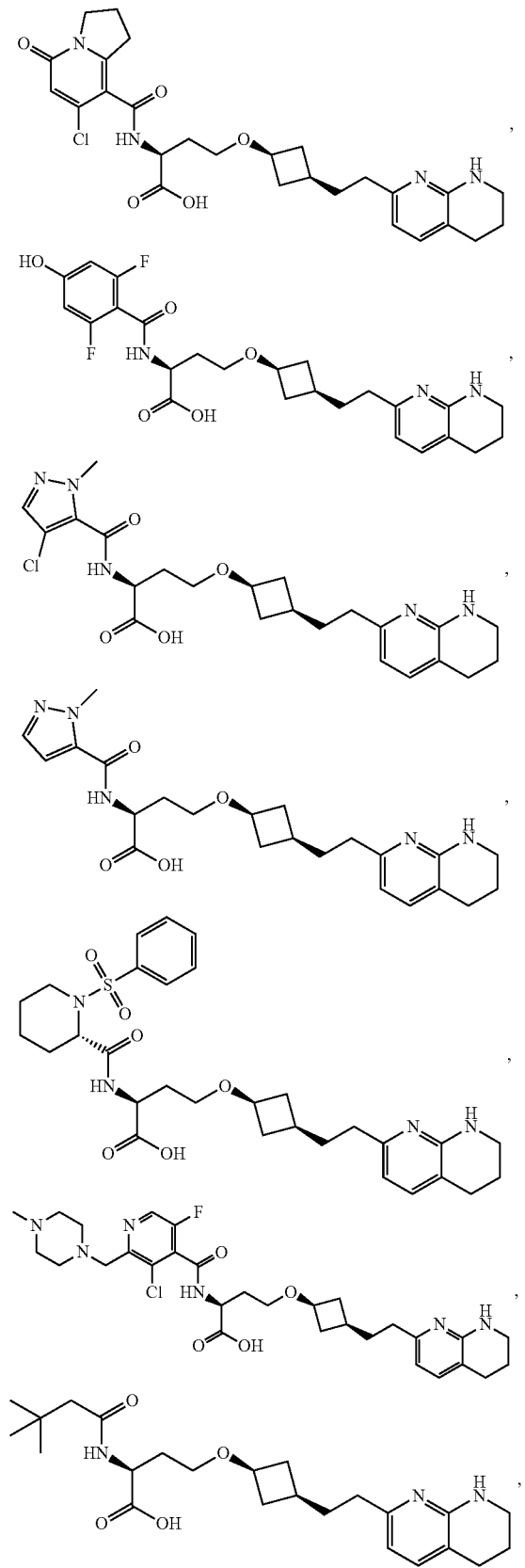
488
-continued
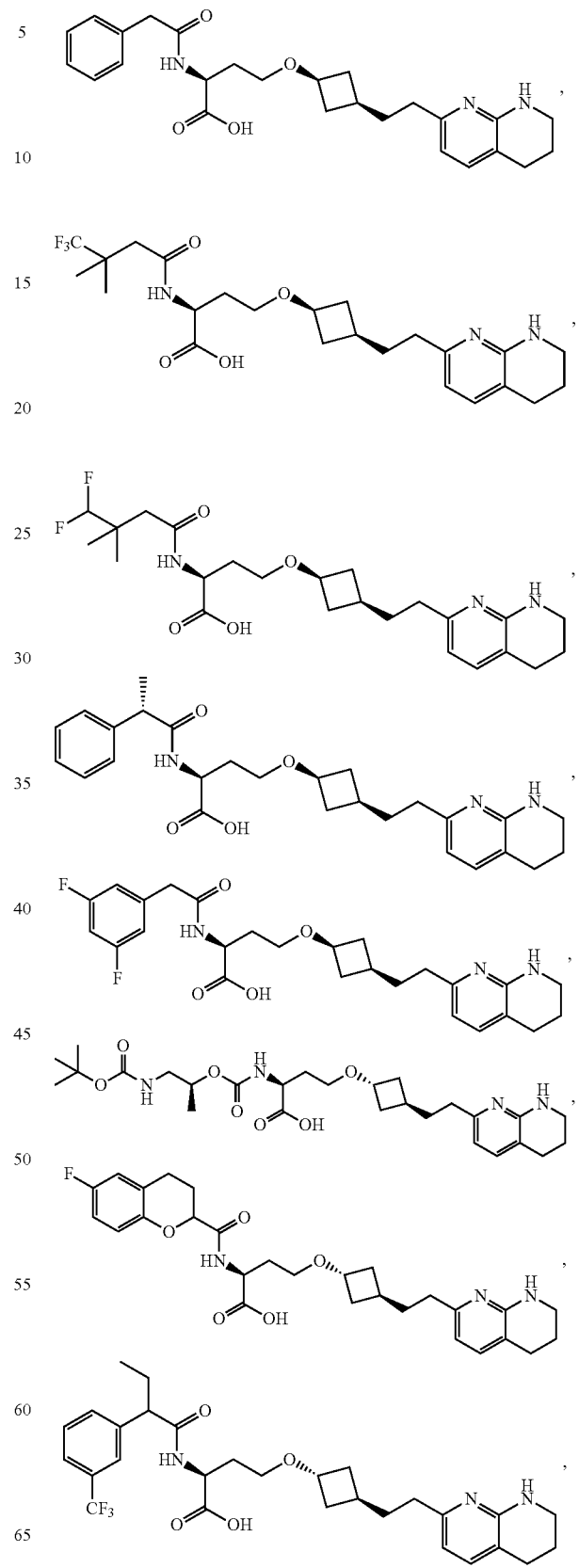

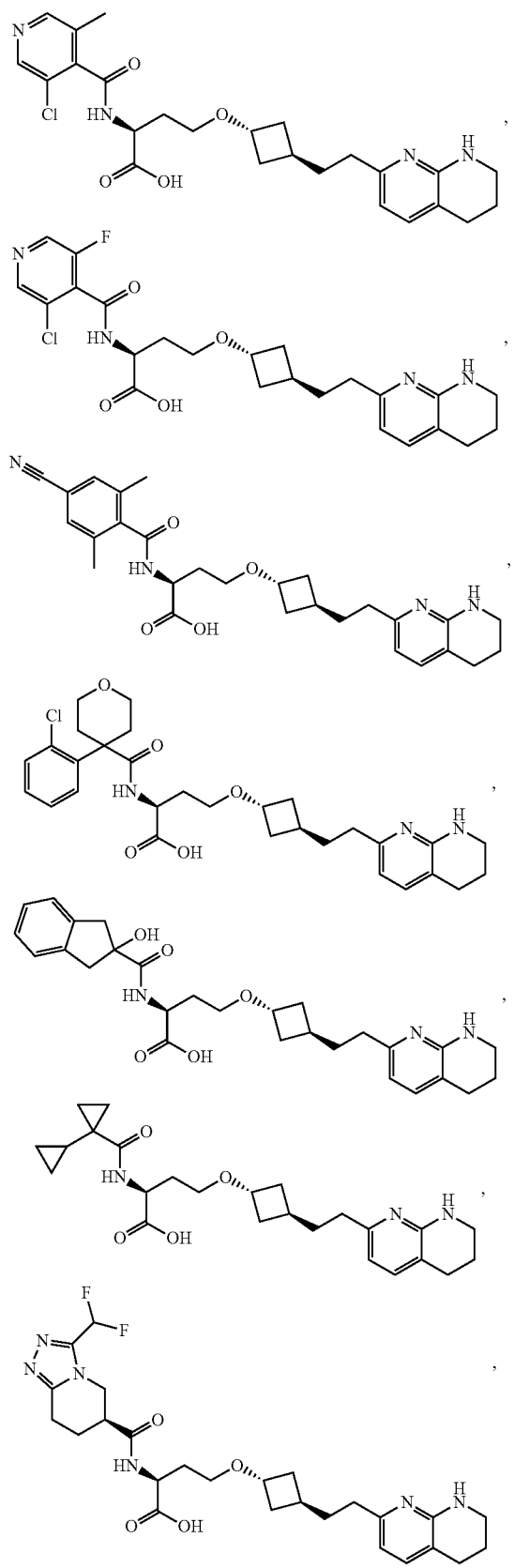
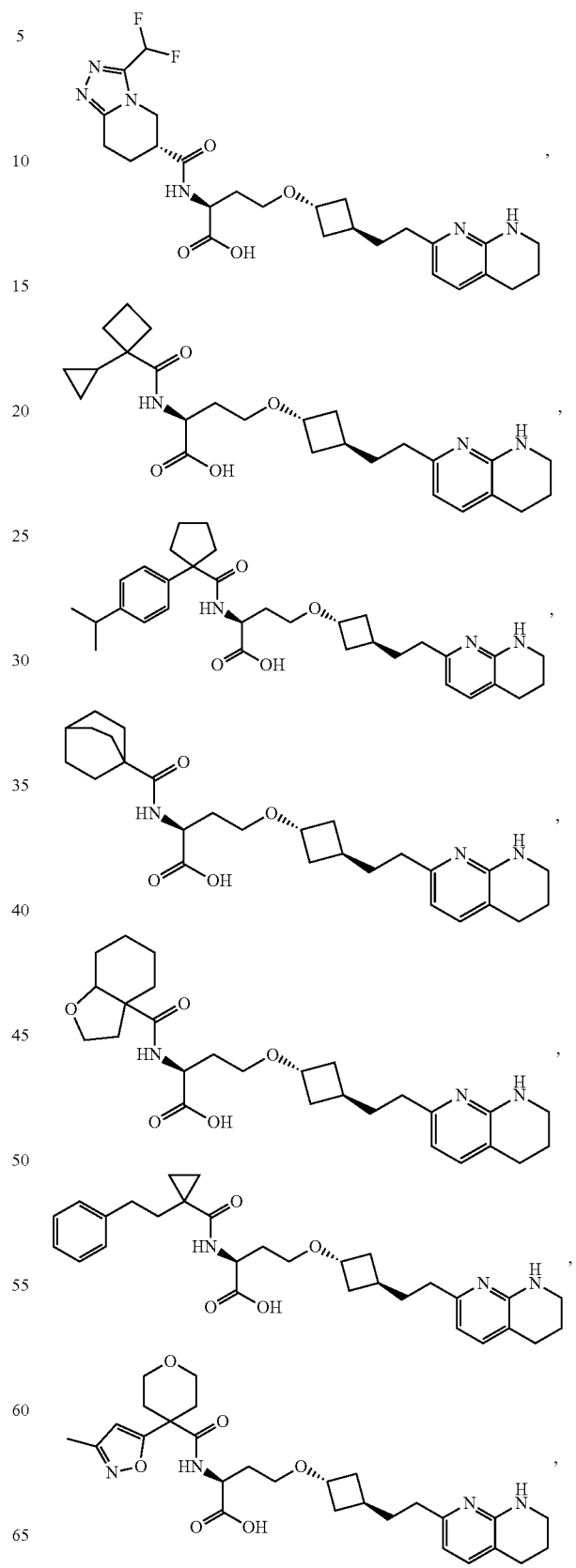

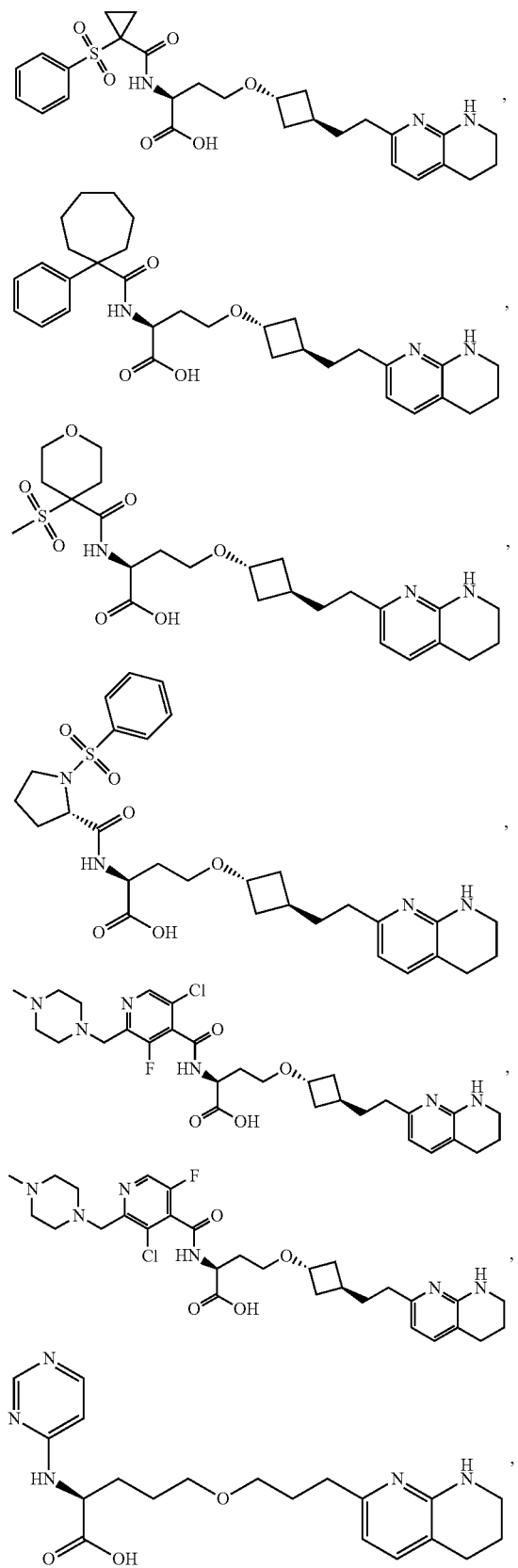
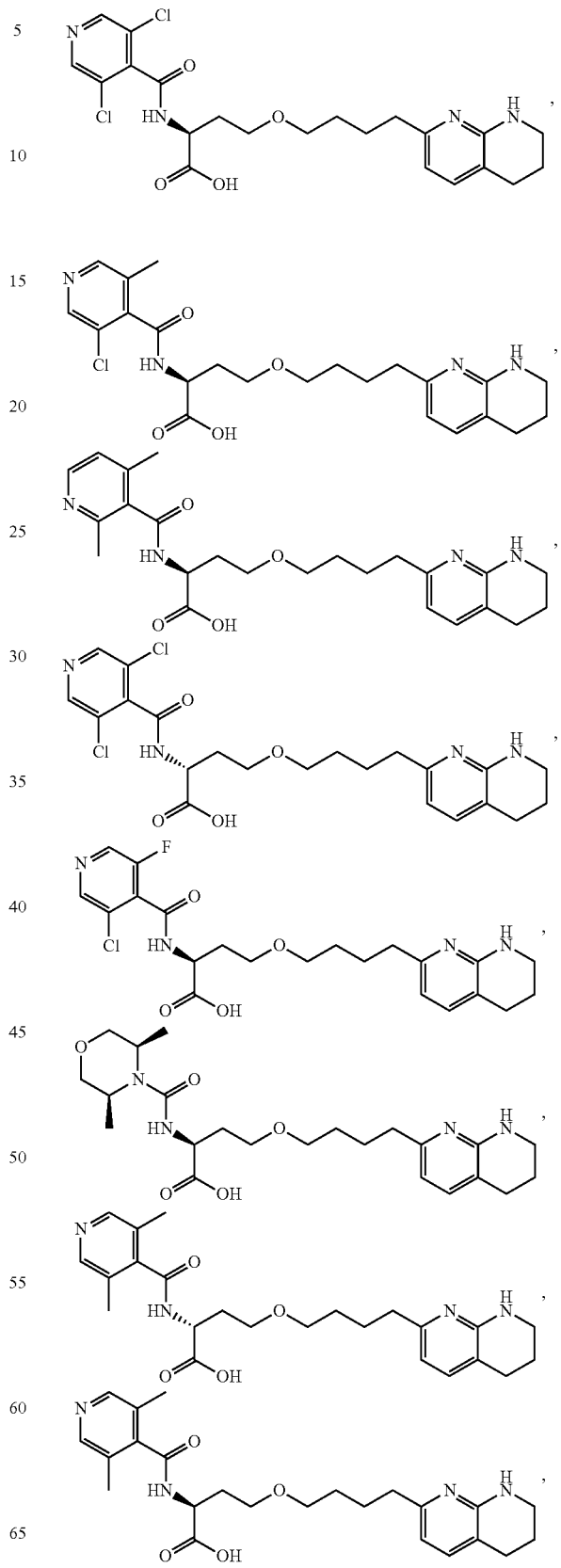

493
-continued
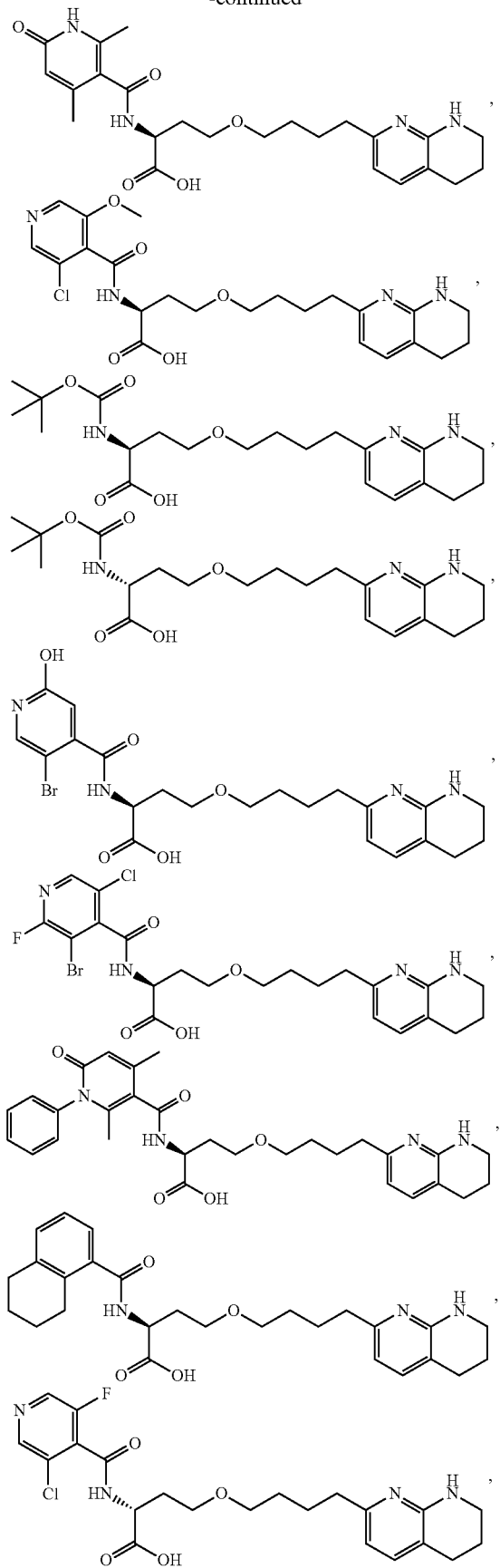
494
-continued
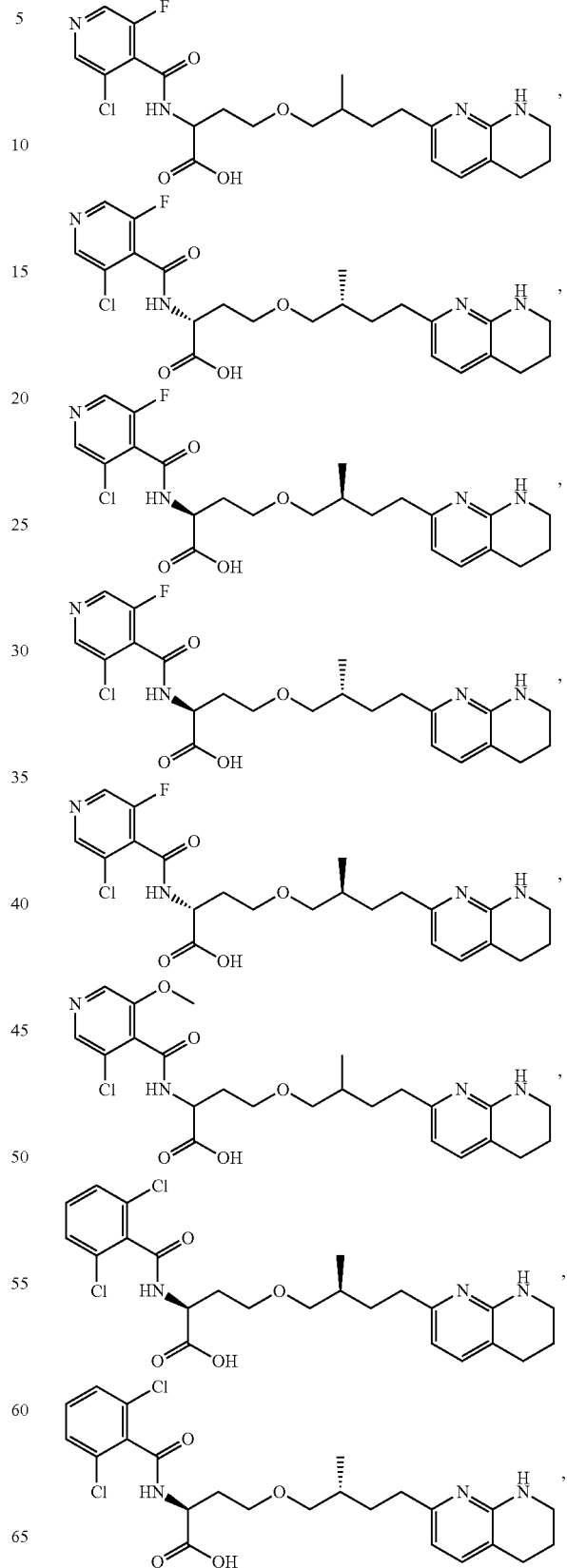

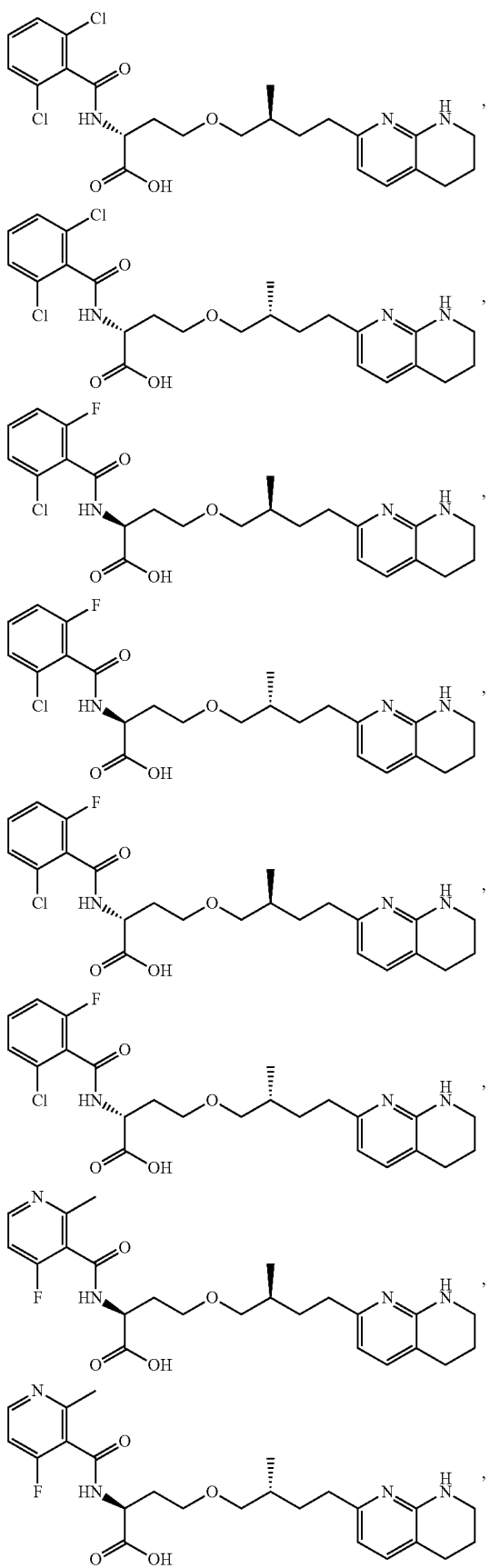
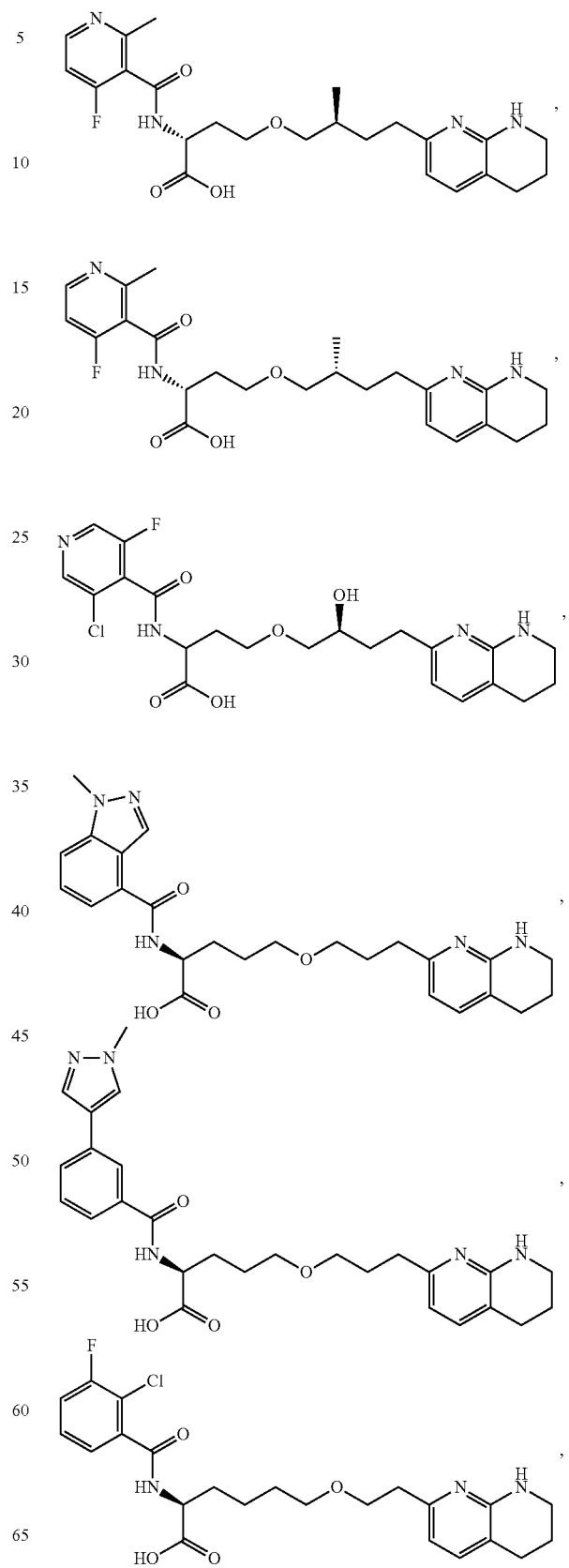

497
-continued
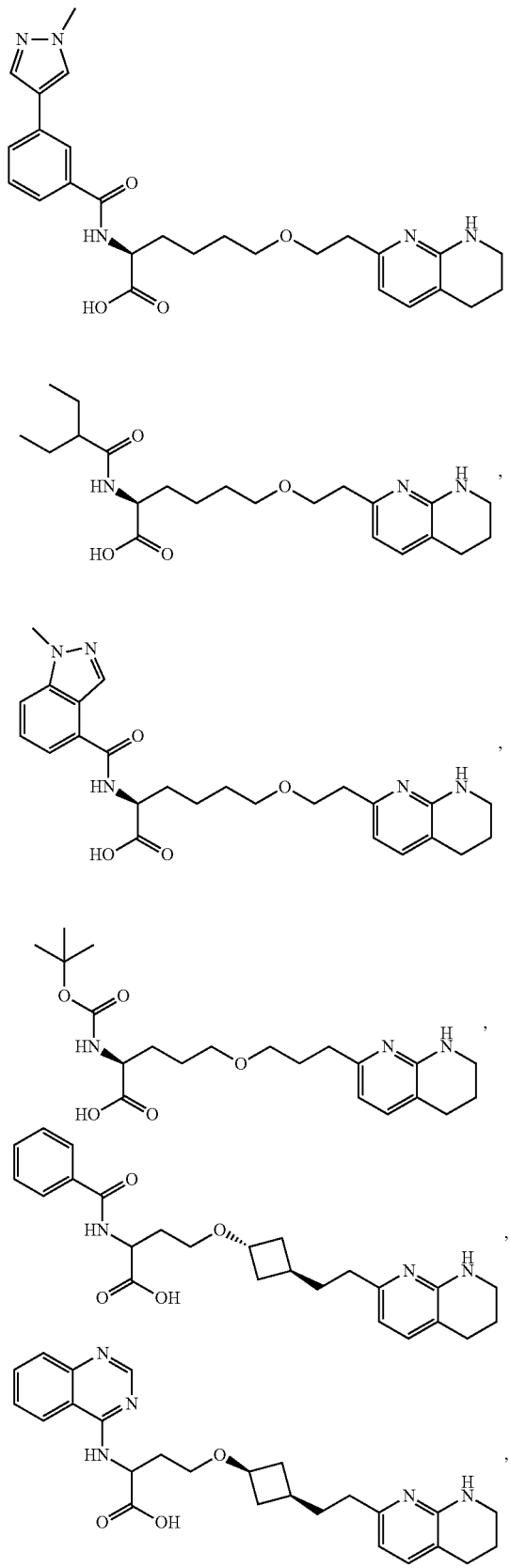
498
-continued
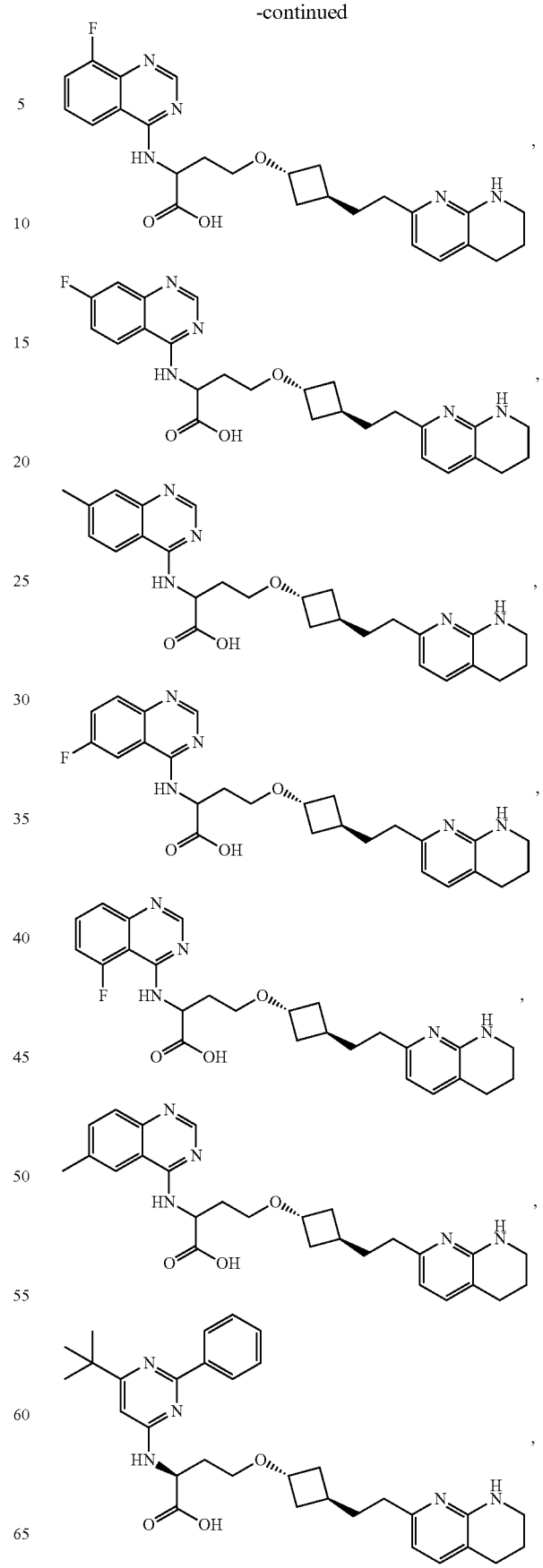

-continued
and

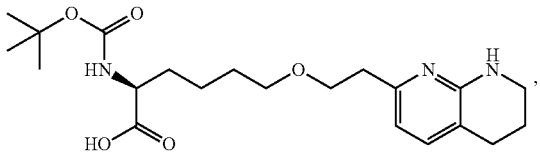

or a pharmaceutically acceptable salt or tautomer thereof.

144. The compound of claim 1, wherein the compound is selected from the group consisting of:
N-(1-methyl-1H-indazole-4-carbonyl)-O-(4-(5,6,7,8-tetrahydro-1,8-naphthyridin-2-yl)butyl)homoserine;
N-(4,4-difluorocyclohexane-1-carbonyl)-O-(4-(5,6,7,8-tetrahydro-1,8-naphthyridin-2-yl)butyl)homoserine;
N-pentanoyl-O-(4-(5,6,7,8-tetrahydro-1,8-naphthyridin-2-yl)butyl)homoserine;
N-(3-fluoro-5-(trifluoromethyl)benzoyl)-O-(3-(2-(5,6,7,8-tetrahydro-1,8-naphthyridin-2-yl)ethyl)cyclobutyl)homoserine;
N-pentanoyl-O-(3-(2-(5,6,7,8-tetrahydro-1,8-naphthyridin-2-yl)ethyl)cyclobutyl)homoserine;
N-(tert-butoxycarbonyl)-O-(4-(5,6,7,8-tetrahydro-1,8-naphthyridin-2-yl)butyl)homoserine;
N-(4-fluorobenzoyl)-O-(3-(2-(5,6,7,8-tetrahydro-1,8-naphthyridin-2-yl)ethyl)cyclobutyl)homoserine;
N-(4-chlorobenzoyl)-O-(3-(2-(5,6,7,8-tetrahydro-1,8-naphthyridin-2-yl)ethyl)cyclobutyl)homoserine;
N-(3-fluorobenzoyl)-O-(3-(2-(5,6,7,8-tetrahydro-1,8-naphthyridin-2-yl)ethyl)cyclobutyl)homoserine;
N-(3-chlorobenzoyl)-O-(3-(2-(5,6,7,8-tetrahydro-1,8-naphthyridin-2-yl)ethyl)cyclobutyl)homoserine;
N-(2-chlorobenzoyl)-O-(3-(2-(5,6,7,8-tetrahydro-1,8-naphthyridin-2-yl)ethyl)cyclobutyl)homoserine;
N-(2-fluorobenzoyl)-O-(3-(2-(5,6,7,8-tetrahydro-1,8-naphthyridin-2-yl)ethyl)cyclobutyl)homoserine;
N-(2,3-difluorobenzoyl)-O-(3-(2-(5,6,7,8-tetrahydro-1,8-naphthyridin-2-yl)ethyl)cyclobutyl)homoserine;
N-(2,4-difluorobenzoyl)-O-(3-(2-(5,6,7,8-tetrahydro-1,8-naphthyridin-2-yl)ethyl)cyclobutyl)homoserine;
N-(2-chloro-4-fluorobenzoyl)-O-(3-(2-(5,6,7,8-tetrahydro-1,8-naphthyridin-2-yl)ethyl)cyclobutyl)homoserine;
N-(3-chloro-5-fluorobenzoyl)-O-(3-(2-(5,6,7,8-tetrahydro-1,8-naphthyridin-2-yl)ethyl)cyclobutyl)homoserine;
N-(3-chloro-2-fluorobenzoyl)-O-(3-(2-(5,6,7,8-tetrahydro-1,8-naphthyridin-2-yl)ethyl)cyclobutyl)homoserine;
N-(3,5-difluorobenzoyl)-O-(3-(2-(5,6,7,8-tetrahydro-1,8-naphthyridin-2-yl)ethyl)cyclobutyl)homoserine;
N-(2,3-dichlorobenzoyl)-O-(3-(2-(5,6,7,8-tetrahydro-1,8-naphthyridin-2-yl)ethyl)cyclobutyl)homoserine;
N-(2-chloro-6-fluorobenzoyl)-O-(3-(2-(5,6,7,8-tetrahydro-1,8-naphthyridin-2-yl)ethyl)cyclobutyl)homoserine;
N-(2,6-difluorobenzoyl)-O-(3-(2-(5,6,7,8-tetrahydro-1,8-naphthyridin-2-yl)ethyl)cyclobutyl)homoserine;
N-(2,5-difluorobenzoyl)-O-(3-(2-(5,6,7,8-tetrahydro-1,8-naphthyridin-2-yl)ethyl)cyclobutyl)homoserine;
N-(3,4-dichlorobenzoyl)-O-(3-(2-(5,6,7,8-tetrahydro-1,8-naphthyridin-2-yl)ethyl)cyclobutyl)homoserine;
N-picolinoyl-O-(3-(2-(5,6,7,8-tetrahydro-1,8-naphthyridin-2-yl)ethyl)cyclobutyl)homoserine;
N-nicotinoyl-O-(3-(2-(5,6,7,8-tetrahydro-1,8-naphthyridin-2-yl)ethyl)cyclobutyl)homoserine;
N-(1-methyl-1H-indazole-4-carbonyl)-O-(3-(2-(5,6,7,8-tetrahydro-1,8-naphthyridin-2-yl)ethyl)cyclobutyl)homoserine;
N-(2-methyl-2H-indazole-6-carbonyl)-O-(3-(2-(5,6,7,8-tetrahydro-1,8-naphthyridin-2-yl)ethyl)cyclobutyl)homoserine;
N-(2-methyl-2H-indazole-5-carbonyl)-O-(3-(2-(5,6,7,8-tetrahydro-1,8-naphthyridin-2-yl)ethyl)cyclobutyl)homoserine;
N-(1-methyl-1H-pyrrolo[2,3-b]pyridine-4-carbonyl)-O-(3-(2-(5,6,7,8-tetrahydro-1,8-naphthyridin-2-yl)ethyl)cyclobutyl)homoserine;
N-(2-ethylbutanoyl)-O-(3-(2-(5,6,7,8-tetrahydro-1,8-naphthyridin-2-yl)ethyl)cyclobutyl)homoserine;
N-(1-methyl-1H-pyrrolo[2,3-b]pyridine-5-carbonyl)-O-(3-(2-(5,6,7,8-tetrahydro-1,8-naphthyridin-2-yl)ethyl)cyclobutyl)homoserine;
N-(3-(hydroxymethyl)benzoyl)-O-(3-(2-(5,6,7,8-tetrahydro-1,8-naphthyridin-2-yl)ethyl)cyclobutyl)homoserine;
N-(quinoline-5-carbonyl)-O-(3-(2-(5,6,7,8-tetrahydro-1,8-naphthyridin-2-yl)ethyl)cyclobutyl)homoserine;
N-(2-cyclopropylbenzoyl)-O-(3-(2-(5,6,7,8-tetrahydro-1,8-naphthyridin-2-yl)ethyl)cyclobutyl)homoserine;
N-(quinoline-7-carbonyl)-O-(3-(2-(5,6,7,8-tetrahydro-1,8-naphthyridin-2-yl)ethyl)cyclobutyl)homoserine;
N-(quinoline-6-carbonyl)-O-(3-(2-(5,6,7,8-tetrahydro-1,8-naphthyridin-2-yl)ethyl)cyclobutyl)homoserine;
N-(quinoline-8-carbonyl)-O-(3-(2-(5,6,7,8-tetrahydro-1,8-naphthyridin-2-yl)ethyl)cyclobutyl)homoserine;
N-(3-cyclopropylbenzoyl)-O-(3-(2-(5,6,7,8-tetrahydro-1,8-naphthyridin-2-yl)ethyl)cyclobutyl)homoserine;
N-(4-cyclopropylbenzoyl)-O-(3-(2-(5,6,7,8-tetrahydro-1,8-naphthyridin-2-yl)ethyl)cyclobutyl)homoserine;
N-isonicotinoyl-O-(3-(2-(5,6,7,8-tetrahydro-1,8-naphthyridin-2-yl)ethyl)cyclobutyl)homoserine;
N-(3-ethylpentanoyl)-O-(3-(2-(5,6,7,8-tetrahydro-1,8-naphthyridin-2-yl)ethyl)cyclobutyl)homoserine;
N-(2-chloro-3-fluorobenzoyl)-O-(3-(2-(5,6,7,8-tetrahydro-1,8-naphthyridin-2-yl)ethyl)cyclobutyl)homoserine;
N-(3,4-difluorobenzoyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(3-(thiazol-5-yl)benzoyl)homoserine;
N-(3-hydroxy-2-phenylpropanoyl)-O-(3-(2-(5,6,7,8-tetrahydro-1,8-naphthyridin-2-yl)ethyl)cyclobutyl)homoserine;
N-(3-(1-methyl-1H-pyrazol-4-yl)benzoyl)-O-(3-(4-(5,6,7,8-tetrahydro-1,8-naphthyridin-2-yl)butyl)cyclobutyl)homoserine;
N-(3-(1-methyl-1H-pyrazol-4-yl)benzoyl)-O-(4-(5,6,7,8-tetrahydro-1,8-naphthyridin-2-yl)butyl)homoserine;
N-(2-hydroxy-2-phenylacetyl)-O-(4-(5,6,7,8-tetrahydro-1,8-naphthyridin-2-yl)butyl)homoserine;
N-(2-hydroxy-2-phenylacetyl)-O-(3-(2-(5,6,7,8-tetrahydro-1,8-naphthyridin-2-yl)ethyl)cyclobutyl)homoserine;
N-(1-phenylcyclopropane-1-carbonyl)-O-(3-(2-(5,6,7,8-tetrahydro-1,8-naphthyridin-2-yl)ethyl)cyclobutyl)homoserine;
N-(2-methyl-2-phenylpropanoyl)-O-(3-(2-(5,6,7,8-tetrahydro-1,8-naphthyridin-2-yl)ethyl)cyclobutyl)homoserine;

N-(1-phenylcyclobutane-1-carbonyl)-O-(3-(2-(5,6,7,8-tetrahydro-1,8-naphthyridin-2-yl)ethyl)cyclobutyl)homoserine;

N-(2,2-dimethyl-3-phenylpropanoyl)-O-(3-(2-(5,6,7,8-tetrahydro-1,8-naphthyridin-2-yl)ethyl)cyclobutyl)homoserine;

N-(tert-butoxycarbonyl)-O-(3-(2-(5,6,7,8-tetrahydro-1,8-naphthyridin-2-yl)ethyl)cyclobutyl)homoserine;

N-(2-(4-fluorophenyl)-2-methylpropanoyl)-O-(3-(2-(5,6,7,8-tetrahydro-1,8-naphthyridin-2-yl)ethyl)cyclobutyl)homoserine;

N-(3-methyloxetane-3-carbonyl)-O-(3-(2-(5,6,7,8-tetrahydro-1,8-naphthyridin-2-yl)ethyl)cyclobutyl)homoserine;

N-(3-hydroxy-2,2-dimethylpropanoyl)-O-(3-(2-(5,6,7,8-tetrahydro-1,8-naphthyridin-2-yl)ethyl)cyclobutyl)homoserine;

N-(3-methoxy-2,2-dimethylpropanoyl)-O-(3-(2-(5,6,7,8-tetrahydro-1,8-naphthyridin-2-yl)ethyl)cyclobutyl)homoserine;

N-(2-methyl-2-(pyridin-3-yl)propanoyl)-O-(3-(2-(5,6,7,8-tetrahydro-1,8-naphthyridin-2-yl)ethyl)cyclobutyl)homoserine;

N-(2,3-dihydro-1H-indene-2-carbonyl)-O-(3-(2-(5,6,7,8-tetrahydro-1,8-naphthyridin-2-yl)ethyl)cyclobutyl)homoserine;

N-(3-cyano-2,2-dimethylpropanoyl)-O-(3-(2-(5,6,7,8-tetrahydro-1,8-naphthyridin-2-yl)ethyl)cyclobutyl)homoserine;

N-pivaloyl-O-(3-(2-(5,6,7,8-tetrahydro-1,8-naphthyridin-2-yl)ethyl)cyclobutyl)homoserine;

N-(2,3-dihydro-1H-indene-1-carbonyl)-O-(3-(2-(5,6,7,8-tetrahydro-1,8-naphthyridin-2-yl)ethyl)cyclobutyl)homoserine;

N-((neopentyloxy)carbonyl)-O-(3-(2-(5,6,7,8-tetrahydro-1,8-naphthyridin-2-yl)ethyl)cyclobutyl)homoserine;

N-((1-methylcyclopropoxy)carbonyl)-O-(3-(2-(5,6,7,8-tetrahydro-1,8-naphthyridin-2-yl)ethyl)cyclobutyl)homoserine;

N-((1-methylcyclobutoxy)carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(((1,1,1-trifluoro-2-methylpropan-2-yl)oxy)carbonyl)homoserine;

N-(isopropoxycarbonyl)-O-(3-(2-(5,6,7,8-tetrahydro-1,8-naphthyridin-2-yl)ethyl)cyclobutyl)homoserine;

N-(diethylcarbamoyl)-O-(3-(2-(5,6,7,8-tetrahydro-1,8-naphthyridin-2-yl)ethyl)cyclobutyl)homoserine;

N-(tert-butylcarbamoyl)-O-(3-(2-(5,6,7,8-tetrahydro-1,8-naphthyridin-2-yl)ethyl)cyclobutyl)homoserine;

N-(tert-butyl(methyl)carbamoyl)-O-(3-(2-(5,6,7,8-tetrahydro-1,8-naphthyridin-2-yl)ethyl)cyclobutyl)homoserine;

N-(isopropyl(methyl)carbamoyl)-O-(3-(2-(5,6,7,8-tetrahydro-1,8-naphthyridin-2-yl)ethyl)cyclobutyl)homoserine;

N-(diisopropylcarbamoyl)-O-(3-(2-(5,6,7,8-tetrahydro-1,8-naphthyridin-2-yl)ethyl)cyclobutyl)homoserine;

N-(3,3-dimethylbutanoyl)-O-(3-(2-(5,6,7,8-tetrahydro-1,8-naphthyridin-2-yl)ethyl)cyclobutyl)homoserine;

N-(3-methylbutanoyl)-O-(3-(2-(5,6,7,8-tetrahydro-1,8-naphthyridin-2-yl)ethyl)cyclobutyl)homoserine;

N-(2-cyclobutylacetyl)-O-(3-(2-(5,6,7,8-tetrahydro-1,8-naphthyridin-2-yl)ethyl)cyclobutyl)homoserine;

N-(2-(1-methylcyclopropyl)acetyl)-O-(3-(2-(5,6,7,8-tetrahydro-1,8-naphthyridin-2-yl)ethyl)cyclobutyl)homoserine;

N-(2-cyclopropylacetyl)-O-(3-(2-(5,6,7,8-tetrahydro-1,8-naphthyridin-2-yl)ethyl)cyclobutyl)homoserine;

N-(((1-(tert-butoxycarbonyl)-3-methylazetidin-3-yl)oxy)carbonyl)-O-(3-(2-(5,6,7,8-tetrahydro-1,8-naphthyridin-2-yl)ethyl)cyclobutyl)homoserine;

N-(((3-methyl-1-(methylsulfonyl)azetidin-3-yl)oxy)carbonyl)-O-(3-(2-(5,6,7,8-tetrahydro-1,8-naphthyridin-2-yl)ethyl)cyclobutyl)homoserine;

N-(((1-acetyl-3-methylazetidin-3-yl)oxy)carbonyl)-O-(3-(2-(5,6,7,8-tetrahydro-1,8-naphthyridin-2-yl)ethyl)cyclobutyl)homoserine;

N-(((3-methylazetidin-3-yl)oxy)carbonyl)-O-(3-(2-(5,6,7,8-tetrahydro-1,8-naphthyridin-2-yl)ethyl)cyclobutyl)homoserine;

N-((cyclohexyloxy)carbonyl)-O-(3-(2-(5,6,7,8-tetrahydro-1,8-naphthyridin-2-yl)ethyl)cyclobutyl)homoserine;

N-(isobutoxycarbonyl)-O-(3-(2-(5,6,7,8-tetrahydro-1,8-naphthyridin-2-yl)ethyl)cyclobutyl)homoserine;

N-(((pyrrolidin-3-yl)oxy)carbonyl)-O-(3-(2-(5,6,7,8-tetrahydro-1,8-naphthyridin-2-yl)ethyl)cyclobutyl)homoserine;

N-(4-(methylsulfonyl)butanoyl)-O-(3-(2-(5,6,7,8-tetrahydro-1,8-naphthyridin-2-yl)ethyl)cyclobutyl)homoserine;

N-(((1-(methylsulfonyl)pyrrolidin-3-yl)oxy)carbonyl)-O-(3-(2-(5,6,7,8-tetrahydro-1,8-naphthyridin-2-yl)ethyl)cyclobutyl)homoserine;

N-(((1-(tert-butoxycarbonyl)pyrrolidin-3-yl)oxy)carbonyl)-O-(3-(2-(5,6,7,8-tetrahydro-1,8-naphthyridin-2-yl)ethyl)cyclobutyl)homoserine;

N-(((1-acetylpyrrolidin-3-yl)oxy)carbonyl)-O-(3-(2-(5,6,7,8-tetrahydro-1,8-naphthyridin-2-yl)ethyl)cyclobutyl)homoserine;

N-((1-phenylethoxy)carbonyl)-O-(3-(2-(5,6,7,8-tetrahydro-1,8-naphthyridin-2-yl)ethyl)cyclobutyl)homoserine;

N-((2-phenylcyclobutoxy)carbonyl)-O-(3-(2-(5,6,7,8-tetrahydro-1,8-naphthyridin-2-yl)ethyl)cyclobutyl)homoserine;

N-((3-phenylcyclobutoxy)carbonyl)-O-(3-(2-(5,6,7,8-tetrahydro-1,8-naphthyridin-2-yl)ethyl)cyclobutyl)homoserine;

2-((tert-butoxycarbonyl)amino)-3-methyl-4-(3-(2-(5,6,7,8-tetrahydro-1,8-naphthyridin-2-yl)ethyl)cyclobutoxy)butanoic acid;

N-(((2-phenylcyclohexyl)oxy)carbonyl)-O-(3-(2-(5,6,7,8-tetrahydro-1,8-naphthyridin-2-yl)ethyl)cyclobutyl)homoserine;

N-(((1-(tert-butoxycarbonyl)azetidin-3-yl)oxy)carbonyl)-O-(3-(2-(5,6,7,8-tetrahydro-1,8-naphthyridin-2-yl)ethyl)cyclobutyl)homoserine;

N-(((4-phenylcyclohexyl)oxy)carbonyl)-O-(3-(2-(5,6,7,8-tetrahydro-1,8-naphthyridin-2-yl)ethyl)cyclobutyl)homoserine;

N-(((1-acetylazetidin-3-yl)oxy)carbonyl)-O-(3-(2-(5,6,7,8-tetrahydro-1,8-naphthyridin-2-yl)ethyl)cyclobutyl)homoserine;

N-(((1-((tert-butoxycarbonyl)amino)propan-2-yl)oxy)carbonyl)-O-(3-(2-(5,6,7,8-tetrahydro-1,8-naphthyridin-2-yl)ethyl)cyclobutyl)homoserine;

N-(((1-acetamidopropan-2-yl)oxy)carbonyl)-O-(3-(2-(5,6,7,8-tetrahydro-1,8-naphthyridin-2-yl)ethyl)cyclobutyl)homoserine;

N-(((2-(3,5-dimethyl-1H-pyrazol-1-yl)cyclopentyl)oxy)carbonyl)-O-(3-(2-(5,6,7,8-tetrahydro-1,8-naphthyridin-2-yl)ethyl)cyclobutyl)homoserine;
N-(((2-(3,5-dimethyl-1H-pyrazol-1-yl)cyclohexyl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(3-chlorophenyl)azetidin-3-yl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(4-isopropylphenyl)azetidin-3-yl)oxy)carbonyl)-O-(3-(2-(5,6,7,8-tetrahydro-1,8-naphthyridin-2-yl)ethyl)cyclobutyl)homoserine;
N-(((1-(tert-butoxycarbonyl)-3-(phenylethynyl)azetidin-3-yl)oxy)carbonyl)-O-(3-(2-(5,6,7,8-tetrahydro-1,8-naphthyridin-2-yl)ethyl)cyclobutyl)homoserine;
N-(1-(tert-butoxycarbonyl)piperidine-4-carbonyl)-O-(3-(2-(5,6,7,8-tetrahydro-1,8-naphthyridin-2-yl)ethyl)cyclobutyl)homoserine;
N-(3,3-difluorocyclohexane-1-carbonyl)-O-(3-(2-(5,6,7,8-tetrahydro-1,8-naphthyridin-2-yl)ethyl)cyclobutyl)homoserine;
N-(2-ethyl-4,4-difluorobutanoyl)-O-(3-(2-(5,6,7,8-tetrahydro-1,8-naphthyridin-2-yl)ethyl)cyclobutyl)homoserine;
N-(((2-(phenylethynyl)cyclohexyl)oxy)carbonyl)-O-(3-(2-(5,6,7,8-tetrahydro-1,8-naphthyridin-2-yl)ethyl)cyclobutyl)homoserine;
N-(2-cyclohexyl-2-methylpropanoyl)-O-(3-(2-(5,6,7,8-tetrahydro-1,8-naphthyridin-2-yl)ethyl)cyclobutyl)homoserine;
N-(2-(pyridin-2-yl)benzoyl)-O-(3-(2-(5,6,7,8-tetrahydro-1,8-naphthyridin-2-yl)ethyl)cyclobutyl)homoserine;
N-(2-ethyl-4,4,4-trifluorobutanoyl)-O-(3-(2-(5,6,7,8-tetrahydro-1,8-naphthyridin-2-yl)ethyl)cyclobutyl)homoserine;
N-(2-morpholinobenzoyl)-O-(3-(2-(5,6,7,8-tetrahydro-1,8-naphthyridin-2-yl)ethyl)cyclobutyl)homoserine;
N-(2-ethyl-2-phenylbutanoyl)-O-(3-(2-(5,6,7,8-tetrahydro-1,8-naphthyridin-2-yl)ethyl)cyclobutyl)homoserine;
N-(1H-pyrrolo[3,2-b]pyridine-7-carbonyl)-O-(3-(2-(5,6,7,8-tetrahydro-1,8-naphthyridin-2-yl)ethyl)cyclobutyl)homoserine;
N-(4-cyanotetrahydro-2H-pyran-4-carbonyl)-O-(3-(2-(5,6,7,8-tetrahydro-1,8-naphthyridin-2-yl)ethyl)cyclobutyl)homoserine;
N-(1-(tert-butoxycarbonyl)-3-methylazetidine-3-carbonyl)-O-(3-(2-(5,6,7,8-tetrahydro-1,8-naphthyridin-2-yl)ethyl)cyclobutyl)homoserine;
N-(1-(tert-butoxycarbonyl)azetidine-3-carbonyl)-O-(3-(2-(5,6,7,8-tetrahydro-1,8-naphthyridin-2-yl)ethyl)cyclobutyl)homoserine;
N-(1-(methylsulfonyl)piperidine-3-carbonyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(4,5,6,7-tetrahydro-1H-indazole-6-carbonyl)homoserine;
O-(3-(2-(5,6,7,8-tetrahydro-1,8-naphthyridin-2-yl)ethyl)cyclobutyl)-N-(4,5,6,7-tetrahydro-1H-indazole-7-carbonyl)homoserine;
N-(1-methyl-4,5,6,7-tetrahydro-1H-indazole-6-carbonyl)-O-(3-(2-(5,6,7,8-tetrahydro-1,8-naphthyridin-2-yl)ethyl)cyclobutyl)homoserine;
N-(1-ethyl-4,4-difluorocyclohexane-1-carbonyl)-O-(3-(2-(5,6,7,8-tetrahydro-1,8-naphthyridin-2-yl)ethyl)cyclobutyl)homoserine;
N-(1-(6-methylindoline-1-carbonyl)cyclopropane-1-carbonyl)-O-(3-(2-(5,6,7,8-tetrahydro-1,8-naphthyridin-2-yl)ethyl)cyclobutyl)homoserine;
N-(4-(((tert-butoxycarbonyl)amino)methyl)tetrahydro-2H-pyran-4-carbonyl)-O-(3-(2-(5,6,7,8-tetrahydro-1,8-naphthyridin-2-yl)ethyl)cyclobutyl)homoserine;
N-(1-(pyridin-3-ylmethyl)cyclopropane-1-carbonyl)-O-(3-(2-(5,6,7,8-tetrahydro-1,8-naphthyridin-2-yl)ethyl)cyclobutyl)homoserine;
N-(3-chloro-5-methylisonicotinoyl)-O-(4-(5,6,7,8-tetrahydro-1,8-naphthyridin-2-yl)butyl)homoserine;
N-(4-methyltetrahydro-2H-pyran-4-carbonyl)-O-(4-(5,6,7,8-tetrahydro-1,8-naphthyridin-2-yl)butyl)homoserine;
N-(3,5-dichloroisonicotinoyl)-O-(4-(5,6,7,8-tetrahydro-1,8-naphthyridin-2-yl)butyl)homoserine;
N-(1-(4-(tert-butyl)phenyl)cyclobutane-1-carbonyl)-O-(3-(2-(5,6,7,8-tetrahydro-1,8-naphthyridin-2-yl)ethyl)cyclobutyl)homoserine;
N-(4-methyltetrahydro-2H-pyran-4-carbonyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(4-(trifluoromethyl)tetrahydro-2H-pyran-4-carbonyl)homoserine;
N-(3-chloro-5-methylisonicotinoyl)-O-(3-(2-(5,6,7,8-tetrahydro-1,8-naphthyridin-2-yl)ethyl)cyclobutyl)homoserine;
N-(3,5-dichloroisonicotinoyl)-O-(3-(2-(5,6,7,8-tetrahydro-1,8-naphthyridin-2-yl)ethyl)cyclobutyl)homoserine;
N-(bicyclo[2.2.2]octane-2-carbonyl)-O-(3-(2-(5,6,7,8-tetrahydro-1,8-naphthyridin-2-yl)ethyl)cyclobutyl)homoserine;
N-(2-methyl-1,2,3,4-tetrahydronaphthalene-2-carbonyl)-O-(3-(2-(5,6,7,8-tetrahydro-1,8-naphthyridin-2-yl)ethyl)cyclobutyl)homoserine;
N-((methylsulfonyl)prolyl)-O-(3-(2-(5,6,7,8-tetrahydro-1,8-naphthyridin-2-yl)ethyl)cyclobutyl)homoserine;
N-(2,4-dimethylnicotinoyl)-O-(3-(2-(5,6,7,8-tetrahydro-1,8-naphthyridin-2-yl)ethyl)cyclobutyl)homoserine;
N-(4-phenyltetrahydro-2H-pyran-4-carbonyl)-O-(3-(2-(5,6,7,8-tetrahydro-1,8-naphthyridin-2-yl)ethyl)cyclobutyl)homoserine;
N-(4-cyano-2,6-dimethylbenzoyl)-O-(3-(2-(5,6,7,8-tetrahydro-1,8-naphthyridin-2-yl)ethyl)cyclobutyl)homoserine;
O-(3-(2-(5,6,7,8-tetrahydro-1,8-naphthyridin-2-yl)ethyl)cyclobutyl)-N-(2,4,6-trimethylpyrimidine-5-carbonyl)homoserine;
O-(3-(2-(5,6,7,8-tetrahydro-1,8-naphthyridin-2-yl)ethyl)cyclobutyl)-N-(2,4,6-trimethylnicotinoyl)homoserine;
N-(3-chloro-5-fluoroisonicotinoyl)-O-(3-(2-(5,6,7,8-tetrahydro-1,8-naphthyridin-2-yl)ethyl)cyclobutyl)homoserine;
N-(1-(isoquinolin-1-yl)cyclopropane-1-carbonyl)-O-(3-(2-(5,6,7,8-tetrahydro-1,8-naphthyridin-2-yl)ethyl)cyclobutyl)homoserine;
N-(2-(pyridin-2-yl)spiro[3.3]heptane-2-carbonyl)-O-(3-(2-(5,6,7,8-tetrahydro-1,8-naphthyridin-2-yl)ethyl)cyclobutyl)homoserine;
N-(2-(1-methyl-1H-pyrazol-4-yl)tetrahydrofuran-2-carbonyl)-O-(3-(2-(5,6,7,8-tetrahydro-1,8-naphthyridin-2-yl)ethyl)cyclobutyl)homoserine;
N-(4,6-dimethylpyrimidine-5-carbonyl)-O-(3-(2-(5,6,7,8-tetrahydro-1,8-naphthyridin-2-yl)ethyl)cyclobutyl)homoserine;

N-(2,6-dichloro-4-(trifluoromethyl)benzoyl)-O-(3-(2-(5,6,7,8-tetrahydro-1,8-naphthyridin-2-yl)ethyl)cyclobutyl)homoserine;

N-(1-(2-fluorophenyl)cyclopropane-1-carbonyl)-O-(3-(2-(5,6,7,8-tetrahydro-1,8-naphthyridin-2-yl)ethyl)cyclobutyl)homoserine;

N-(1-(benzo[d][1,3]dioxol-5-yl)cyclohexane-1-carbonyl)-O-(3-(2-(5,6,7,8-tetrahydro-1,8-naphthyridin-2-yl)ethyl)cyclobutyl)homoserine;

N-(2,2-difluoro-1-(m-tolyl)cyclopropane-1-carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(1-(tetrahydro-2H-pyran-2-yl)cyclopropane-1-carbonyl)homoserine;

N-(4-methoxy-2,6-dimethylbenzoyl)-O-(3-(2-(5,6,7,8-tetrahydro-1,8-naphthyridin-2-yl)ethyl)cyclobutyl)homoserine;

N-(1-acetyl-4-(trifluoromethyl)piperidine-4-carbonyl)-O-(3-(2-(5,6,7,8-tetrahydro-1,8-naphthyridin-2-yl)ethyl)cyclobutyl)homoserine;

N-(2,3-dihydrobenzo[b][1,4]dioxine-2-carbonyl)-O-(3-(2-(5,6,7,8-tetrahydro-1,8-naphthyridin-2-yl)ethyl)cyclobutyl)homoserine;

N-(1-(3-chlorobenzyl)cyclopentane-1-carbonyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(1-(3-(trifluoromethoxy)phenyl)cyclopropane-1-carbonyl)homoserine;

N-(4-fluoro-2,6-dimethylbenzoyl)-O-(3-(2-(5,6,7,8-tetrahydro-1,8-naphthyridin-2-yl)ethyl)cyclobutyl)homoserine;

N-(3,5-dimethylisonicotinoyl)-O-(3-(2-(5,6,7,8-tetrahydro-1,8-naphthyridin-2-yl)ethyl)cyclobutyl)homoserine;

N-(2-(tert-butyl)pyrimidin-4-yl)-O-(3-(2-(5,6,7,8-tetrahydro-1,8-naphthyridin-2-yl)ethyl)cyclobutyl)homoserine;

N-(4-(tert-butyl)pyrimidin-2-yl)-O-(3-(2-(5,6,7,8-tetrahydro-1,8-naphthyridin-2-yl)ethyl)cyclobutyl)homoserine;

O-(3-(2-(1,8-naphthyridin-2-yl)ethyl)cyclobutyl)-N-(quinazolin-4-yl)homoserine;

N-(6-(tert-butyl)pyrimidin-4-yl)-O-(3-(2-(5,6,7,8-tetrahydro-1,8-naphthyridin-2-yl)ethyl)cyclobutyl)homoserine;

2-[(4-amino-2,6-dichloro-benzoyl)amino]-4-[3-[2-(5,6,7,8-tetrahydro-1,8-naphthyridin-2-yl)ethyl]cyclobutoxy]butanoic acid;

N-(4-chloro-2,6-dimethylnicotinoyl)-O-(3-(2-(5,6,7,8-tetrahydro-1,8-naphthyridin-2-yl)ethyl)cyclobutyl)homoserine;

2-[(3-chloro-6-methyl-pyridine-2-carbonyl)amino]-4-[3-[2-(5,6,7,8-tetrahydro-1,8-naphthyridin-2-yl)ethyl]cyclobutoxy]butanoic acid;

N-(2,6-dimethylpiperidine-1-carbonyl)-O-(3-(2-(5,6,7,8-tetrahydro-1,8-naphthyridin-2-yl)ethyl)cyclobutyl)homoserine;

N-(2,5-dimethylpyrrolidine-1-carbonyl)-O-(3-(2-(5,6,7,8-tetrahydro-1,8-naphthyridin-2-yl)ethyl)cyclobutyl)homoserine;

N-(2,6-dichloro-4-cyanobenzoyl)-O-(3-(2-(5,6,7,8-tetrahydro-1,8-naphthyridin-2-yl)ethyl)cyclobutyl)homoserine;

N-(2,6-dichloro-3-nitrobenzoyl)-O-(3-(2-(5,6,7,8-tetrahydro-1,8-naphthyridin-2-yl)ethyl)cyclobutyl)homoserine;

4-[3-[2-(5,6,7,8-tetrahydro-1,8-naphthyridin-2-yl)ethyl]cyclobutoxy]-2-[(1,2,4-trimethyl-6-oxo-pyridine-3-carbonyl)amino]butanoic acid;

N-(2-chloro-4-cyano-6-methylbenzoyl)-O-(3-(2-(5,6,7,8-tetrahydro-1,8-naphthyridin-2-yl)ethyl)cyclobutyl)homoserine;

N-(3-bromo-5-chloro-2-fluoroisonicotinoyl)-O-(3-(2-(5,6,7,8-tetrahydro-1,8-naphthyridin-2-yl)ethyl)cyclobutyl)homoserine;

O-(3-(2-(5,6,7,8-tetrahydro-1,8-naphthyridin-2-yl)ethyl)cyclobutyl)-N-(5,6,7,8-tetrahydronaphthalene-1-carbonyl)homoserine;

N-(3-bromo-2,6-dimethylbenzoyl)-O-(3-(2-(5,6,7,8-tetrahydro-1,8-naphthyridin-2-yl)ethyl)cyclobutyl)homoserine;

2-[(3-chloro-5-methoxy-pyridine-4-carbonyl)amino]-4-[3-[2-(5,6,7,8-tetrahydro-1,8-naphthyridin-2-yl)ethyl]cyclobutoxy]butanoic acid;

2-[(2,6-dichloro-4-fluoro-benzoyl)amino]-4-[3-[2-(5,6,7,8-tetrahydro-1,8-naphthyridin-2-yl)ethyl]cyclobutoxy]butanoic acid;

2-[(2-chloro-6-fluoro-benzoyl)amino]-4-[3-[2-(5,6,7,8-tetrahydro-1,8-naphthyridin-2-yl)ethyl]cyclobutoxy]butanoic acid;

N-(3-bromo-2-chloro-6-fluorobenzoyl)-O-(3-(2-(5,6,7,8-tetrahydro-1,8-naphthyridin-2-yl)ethyl)cyclobutyl)homoserine;

N-(2,4-dimethyl-6-oxo-1-phenyl-1,6-dihydropyridine-3-carbonyl)-O-(3-(2-(5,6,7,8-tetrahydro-1,8-naphthyridin-2-yl)ethyl)cyclobutyl)homoserine;

N-(5-bromo-2-hydroxyisonicotinoyl)-O-(3-(2-(5,6,7,8-tetrahydro-1,8-naphthyridin-2-yl)ethyl)cyclobutyl)homoserine;

N-(3-chloro-5-cyclopropylisonicotinoyl)-O-(3-(2-(5,6,7,8-tetrahydro-1,8-naphthyridin-2-yl)ethyl)cyclobutyl)homoserine;

N-(3-chloro-5-ethylisonicotinoyl)-O-(3-(2-(5,6,7,8-tetrahydro-1,8-naphthyridin-2-yl)ethyl)cyclobutyl)homoserine;

N-(3-cyano-2,6-dimethylbenzoyl)-O-(3-(2-(5,6,7,8-tetrahydro-1,8-naphthyridin-2-yl)ethyl)cyclobutyl)homoserine;

N-(3-bromo-5-fluoroisonicotinoyl)-O-(3-(2-(5,6,7,8-tetrahydro-1,8-naphthyridin-2-yl)ethyl)cyclobutyl)homoserine;

N-(2-methoxy-3,5-dimethylisonicotinoyl)-O-(3-(2-(5,6,7,8-tetrahydro-1,8-naphthyridin-2-yl)ethyl)cyclobutyl)homoserine;

N-(3-chloro-5-(trifluoromethyl)isonicotinoyl)-O-(3-(2-(5,6,7,8-tetrahydro-1,8-naphthyridin-2-yl)ethyl)cyclobutyl)homoserine;

N-(3-bromo-5-chloroisonicotinoyl)-O-(3-(2-(5,6,7,8-tetrahydro-1,8-naphthyridin-2-yl)ethyl)cyclobutyl)homoserine;

N-(3-chloro-5-fluoro-2-methylisonicotinoyl)-O-(3-(2-(5,6,7,8-tetrahydro-1,8-naphthyridin-2-yl)ethyl)cyclobutyl)homoserine;

N-(2,6-dichloro-3-cyanobenzoyl)-O-(3-(2-(5,6,7,8-tetrahydro-1,8-naphthyridin-2-yl)ethyl)cyclobutyl)homoserine;

N-(3-methyl-5-(trifluoromethyl)isonicotinoyl)-O-(3-(2-(5,6,7,8-tetrahydro-1,8-naphthyridin-2-yl)ethyl)cyclobutyl)homoserine;

N-(2-hydroxy-3,5-dimethylisonicotinoyl)-O-(3-(2-(5,6,7,8-tetrahydro-1,8-naphthyridin-2-yl)ethyl)cyclobutyl)homoserine;

N-(3-cyano-2-hydroxy-6-methylisonicotinoyl)-O-(3-(2-(5,6,7,8-tetrahydro-1,8-naphthyridin-2-yl)ethyl)cyclobutyl)homoserine;

N-(5-chloro-3-fluoro-2-methylisonicotinoyl)-O-(3-(2-(5,6,7,8-tetrahydro-1,8-naphthyridin-2-yl)ethyl)cyclobutyl)homoserine;

2-[(6-methoxy-2,4-dimethyl-pyridine-3-carbonyl)amino]-4-[3-[2-(5,6,7,8-tetrahydro-1,8-naphthyridin-2-yl)ethyl]cyclobutoxy]butanoic acid;

2-[[2,6-dimethyl-4-[(4-methylpiperazin-1-yl)methyl]benzoyl]amino]-4-[3-[2-(5,6,7,8-tetrahydro-1,8-naphthyridin-2-yl)ethyl]cyclobutoxy]butanoic acid;

N-(3,5-dimethylmorpholine-4-carbonyl)-O-(3-(2-(5,6,7,8-tetrahydro-1,8-naphthyridin-2-yl)ethyl)cyclobutyl)homoserine;

2-[[5-chloro-3-fluoro-2-[(4-methylpiperazin-1-yl)methyl]pyridine-4-carbonyl]amino]-4-[3-[2-(5,6,7,8-tetrahydro-1,8-naphthyridin-2-yl)ethyl]cyclobutoxy]butanoic acid;

methyl 2-[(7-chloro-5-oxo-2,3-dihydro-1H-indolizine-8-carbonyl)amino]-4-[3-[2-(5,6,7,8-tetrahydro-1,8-naphthyridin-2-yl)ethyl]cyclobutoxy]butanoate;

2-[(2,6-difluoro-4-hydroxy-benzoyl)amino]-4-[3-[2-(5,6,7,8-tetrahydro-1,8-naphthyridin-2-yl)ethyl]cyclobutoxy]butanoic acid;

2-[(4-chloro-2-methyl-pyrazole-3-carbonyl)amino]-4-[3-[2-(5,6,7,8-tetrahydro-1,8-naphthyridin-2-yl)ethyl]cyclobutoxy]butanoic acid;

2-[(2-methylpyrazole-3-carbonyl)amino]-4-[3-[2-(5,6,7,8-tetrahydro-1,8-naphthyridin-2-yl)ethyl]cyclobutoxy]butanoic acid;

N-(1-(phenylsulfonyl)piperidine-2-carbonyl)-O-(3-(2-(5,6,7,8-tetrahydro-1,8-naphthyridin-2-yl)ethyl)cyclobutyl)homoserine;

2-(3,3-dimethylbutanoylamino)-4-[3-[2-(5,6,7,8-tetrahydro-1,8-naphthyridin-2-yl)ethyl]cyclobutoxy]butanoic acid;

2-[(2-phenylacetyl)amino]-4-[3-[2-(5,6,7,8-tetrahydro-1,8-naphthyridin-2-yl)ethyl]cyclobutoxy]butanoic acid;

4-[3-[2-(5,6,7,8-tetrahydro-1,8-naphthyridin-2-yl)ethyl]cyclobutoxy]-2-[(4,4,4-trifluoro-3,3-dimethyl-butanoyl)amino]butanoic acid;

2-[(4,4-difluoro-3,3-dimethyl-butanoyl)amino]-4-[3-[2-(5,6,7,8-tetrahydro-1,8-naphthyridin-2-yl)ethyl]cyclobutoxy]butanoic acid;

2-[[2-phenylpropanoyl]amino]-4-[3-[2-(5,6,7,8-tetrahydro-1,8-naphthyridin-2-yl)ethyl]cyclobutoxy]butanoic acid;

2-[[2-(3,5-difluorophenyl)acetyl]amino]-4-[3-[2-(5,6,7,8-tetrahydro-1,8-naphthyridin-2-yl)ethyl]cyclobutoxy]butanoic acid;

2-[[2-(tert-butoxycarbonylamino)-1-methyl-ethoxy]carbonylamino]-4-[3-[2-(5,6,7,8-tetrahydro-1,8-naphthyridin-2-yl)ethyl]cyclobutoxy]butanoic acid;

2-[(3,6-dimethylpyridine-2-carbonyl)amino]-4-[3-[2-(5,6,7,8-tetrahydro-1,8-naphthyridin-2-yl)ethyl]cyclobutoxy]butanoic acid;

2-[(6-fluorochromane-2-carbonyl)amino]-4-[3-[2-(5,6,7,8-tetrahydro-1,8-naphthyridin-2-yl)ethyl]cyclobutoxy]butanoic acid;

4-[3-[2-(5,6,7,8-tetrahydro-1,8-naphthyridin-2-yl)ethyl]cyclobutoxy]-2-[2-[3-(trifluoromethyl)phenyl]butanoylamino]butanoic acid;

2-[(3-chloro-5-methyl-pyridine-4-carbonyl)amino]-4-[3-[2-(5,6,7,8-tetrahydro-1,8-naphthyridin-2-yl)ethyl]cyclobutoxy]butanoic acid;

2-[(3-chloro-5-fluoro-pyridine-4-carbonyl)amino]-4-[3-[2-(5,6,7,8-tetrahydro-1,8-naphthyridin-2-yl)ethyl]cyclobutoxy]butanoic acid;

2-[(4-cyano-2,6-dimethyl-benzoyl)amino]-4-[3-[2-(5,6,7,8-tetrahydro-1,8-naphthyridin-2-yl)ethyl]cyclobutoxy]butanoic acid;

2-[[4-(2-chlorophenyl)tetrahydropyran-4-[3-[2-(5,6,7,8-tetrahydro-1,8-naphthyridin-2-yl)ethyl]cyclobutoxy]butanoic acid;

2-[(2-hydroxyindane-2-carbonyl)amino]-4-[3-[2-(5,6,7,8-tetrahydro-1,8-naphthyridin-2-yl)ethyl]cyclobutoxy]butanoic acid;

2-[(1-cyclopropylcyclopropanecarbonyl)amino]-4-[3-[2-(5,6,7,8-tetrahydro-1,8-naphthyridin-2-yl)ethyl]cyclobutoxy]butanoic acid;

2-[[3-(difluoromethyl)-5,6,7,8-tetrahydro-[1,2,4]-triazolo[4,3-a]pyridine-6-carbonyl]amino]-4-[3-[2-(5,6,7,8-tetrahydro-1,8-naphthyridin-2-yl)ethyl]cyclobutoxy]butanoic acid;

2-[(1-cyclopropylcyclobutanecarbonyl)amino]-4-[3-[2-(5,6,7,8-tetrahydro-1,8-naphthyridin-2-yl)ethyl]cyclobutoxy]butanoic acid;

2-[[1-(4-isopropylphenyl)cyclopentanecarbonyl]amino]-4-[3-[2-(5,6,7,8-tetrahydro-1,8-naphthyridin-2-yl)ethyl]cyclobutoxy]butanoic acid;

2-(bicyclo[2.2.2]octane-4-carbonylamino)-4-[3-[2-(5,6,7,8-tetrahydro-1,8-naphthyridin-2-yl)ethyl]cyclobutoxy]butanoic acid;

2-(3,4,5,6,7,7a-hexahydro-2H-benzofuran-3a-carbonylamino)-4-[3-[2-(5,6,7,8-tetrahydro-1,8-naphthyridin-2-yl)ethyl]cyclobutoxy]butanoic acid;

2-[[1-(2-phenylethyl)cyclopropanecarbonyl]amino]-4-[3-[2-(5,6,7,8-tetrahydro-1,8-naphthyridin-2-yl)ethyl]cyclobutoxy]butanoic acid;

2-[[4-(3-methylisoxazol-5-yl)tetrahydropyran-4-carbonyl]amino]-4-[3-[2-(5,6,7,8-tetrahydro-1,8-naphthyridin-2-yl)ethyl]cyclobutoxy]butanoic acid;

2-[[1-(benzenesulfonyl)cyclopropanecarbonyl]amino]-4-[3-[2-(5,6,7,8-tetrahydro-1,8-naphthyridin-2-yl)ethyl]cyclobutoxy]butanoic acid;

2-[(1-phenylcycloheptanecarbonyl)amino]-4-[3-[2-(5,6,7,8-tetrahydro-1,8-naphthyridin-2-yl)ethyl]cyclobutoxy]butanoic acid;

N-((phenylsulfonyl)prolyl)-O-(3-(2-(5,6,7,8-tetrahydro-1,8-naphthyridin-2-yl)ethyl)cyclobutyl)homoserine;

N-(5-chloro-3-fluoro-2-((4-methylpiperazin-1-yl)methyl)isonicotinoyl)-O-(3-(2-(5,6,7,8-tetrahydro-1,8-naphthyridin-2-yl)ethyl)cyclobutyl)homoserine;

N-(3-chloro-5-fluoro-2-((4-methylpiperazin-1-yl)methyl)isonicotinoyl)-O-(3-(2-(5,6,7,8-tetrahydro-1,8-naphthyridin-2-yl)ethyl)cyclobutyl)homoserine;

2-(pyrimidin-4-ylamino)-5-(3-(5,6,7,8-tetrahydro-1,8-naphthyridin-2-yl)propoxy)pentanoic acid;

2-[(3-chloro-5-methyl-pyridine-4-carbonyl)amino]-4-[4-(5,6,7,8-tetrahydro-1,8-naphthyridin-2-yl)butoxy]butanoic acid;

2-[(2,4-dimethylpyridine-3-carbonyl)amino]-4-[4-(5,6,7,8-tetrahydro-1,8-naphthyridin-2-yl)butoxy]butanoic acid;

2-[(3,5-dichloropyridine-4-carbonyl)amino]-4-[4-(5,6,7,8-tetrahydro-1,8-naphthyridin-2-yl)butoxy]butanoic acid;

2-[(3-chloro-5-fluoro-pyridine-4-carbonyl)amino]-4-[4-(5,6,7,8-tetrahydro-1,8-naphthyridin-2-yl)butoxy]butanoic acid;
N-(3,5-dimethylmorpholine-4-carbonyl)-O-(4-(5,6,7,8-tetrahydro-1,8-naphthyridin-2-yl)butyl)homoserine;
N-(3,5-dimethylisonicotinoyl)-O-(4-(5,6,7,8-tetrahydro-1,8-naphthyridin-2-yl)butyl)homoserine;
2-[(2,4-dimethyl-6-oxo-1H-pyridine-3-carbonyl)amino]-4-[4-(5,6,7,8-tetrahydro-1,8-naphthyridin-2-yl)butoxy]butanoic acid;
N-(3-chloro-5-methoxyisonicotinoyl)-O-(4-(5,6,7,8-tetrahydro-1,8-naphthyridin-2-yl)butyl)homoserine;
N-(5-bromo-2-hydroxyisonicotinoyl)-O-(4-(5,6,7,8-tetrahydro-1,8-naphthyridin-2-yl)butyl)homoserine;
N-(3-bromo-5-chloro-2-fluoroisonicotinoyl)-O-(4-(5,6,7,8-tetrahydro-1,8-naphthyridin-2-yl)butyl)homoserine;
N-(2,4-dimethyl-6-oxo-1-phenyl-1,6-dihydropyridine-3-carbonyl)-O-(4-(5,6,7,8-tetrahydro-1,8-naphthyridin-2-yl)butyl)homoserine;
O-(4-(5,6,7,8-tetrahydro-1,8-naphthyridin-2-yl)butyl)-N-(5,6,7,8-tetrahydronaphthalene-1-carbonyl)homoserine;
N-(3-chloro-5-fluoroisonicotinoyl)-O-(4-(5,6,7,8-tetrahydro-1,8-naphthyridin-2-yl)butyl)homoserine;
2-[(3-chloro-5-methoxy-pyridine-4-carbonyl)amino]-4-[2-methyl-4-(5,6,7,8-tetrahydro-1,8-naphthyridin-2-yl)butoxy]butanoic acid;
2-[(3-chloro-5-fluoro-pyridine-4-carbonyl)amino]-4-[2-methyl-4-(5,6,7,8-tetrahydro-1,8-naphthyridin-2-yl)butoxy]butanoic acid;
N-(3-chloro-5-fluoroisonicotinoyl)-O-(2-methyl-4-(5,6,7,8-tetrahydro-1,8-naphthyridin-2-yl)butyl)homoserine;
N-(2,6-dichlorobenzoyl)-O-(2-methyl-4-(5,6,7,8-tetrahydro-1,8-naphthyridin-2-yl)butyl)homoserine;
N-(2-chloro-6-fluorobenzoyl)-O-(2-methyl-4-(5,6,7,8-tetrahydro-1,8-naphthyridin-2-yl)butyl)homoserine;
N-(4-fluoro-2-methylnicotinoyl)-O-(2-methyl-4-(5,6,7,8-tetrahydro-1,8-naphthyridin-2-yl)butyl)homoserine;
2-[(3-chloro-5-fluoro-pyridine-4-carbonyl)amino]-4-[2-hydroxy-4-(5,6,7,8-tetrahydro-1,8-naphthyridin-2-yl)butoxy]butanoic acid;
2-(1-methyl-1H-indazole-4-carboxamido)-5-(3-(5,6,7,8-tetrahydro-1,8-naphthyridin-2-yl)propoxy)pentanoic acid;
2-(3-(1-methyl-1H-pyrazol-4-yl)benzamido)-5-(3-(5,6,7,8-tetrahydro-1,8-naphthyridin-2-yl)propoxy)pentanoic acid;
2-(2-chloro-3-fluorobenzamido)-6-(2-(5,6,7,8-tetrahydro-1,8-naphthyridin-2-yl)ethoxy)hexanoic acid;
2-(3-(1-methyl-1H-pyrazol-4-yl)benzamido)-6-(2-(5,6,7,8-tetrahydro-1,8-naphthyridin-2-yl)ethoxy)hexanoic acid;
2-(2-ethylbutanamido)-6-(2-(5,6,7,8-tetrahydro-1,8-naphthyridin-2-yl)ethoxy)hexanoic acid; 2-(1-methyl-1H-indazole-4-carboxamido)-6-(2-(5,6,7,8-tetrahydro-1,8-naphthyridin-2-yl)ethoxy)hexanoic acid;
2-((tert-butoxycarbonyl)amino)-5-(3-(5,6,7,8-tetrahydro-1,8-naphthyridin-2-yl)propoxy)pentanoic acid;
N-benzoyl-O-(3-(2-(5,6,7,8-tetrahydro-1,8-naphthyridin-2-yl)ethyl)cyclobutyl)homoserine;
N-(quinazolin-4-yl)-O-(3-(2-(5,6,7,8-tetrahydro-1,8-naphthyridin-2-yl)ethyl)cyclobutyl)homoserine;
N-(8-fluoroquinazolin-4-yl)-O-(3-(2-(5,6,7,8-tetrahydro-1,8-naphthyridin-2-yl)ethyl)cyclobutyl)homoserine;
N-(7-fluoroquinazolin-4-yl)-O-(3-(2-(5,6,7,8-tetrahydro-1,8-naphthyridin-2-yl)ethyl)cyclobutyl)homoserine;
N-(7-methylquinazolin-4-yl)-O-(3-(2-(5,6,7,8-tetrahydro-1,8-naphthyridin-2-yl)ethyl)cyclobutyl)homoserine; N-(6-fluoroquinazolin-4-yl)-O-(3-(2-(5,6,7,8-tetrahydro-1,8-naphthyridin-2-yl)ethyl)cyclobutyl)homoserine;
N-(5-fluoroquinazolin-4-yl)-O-(3-(2-(5,6,7,8-tetrahydro-1,8-naphthyridin-2-yl)ethyl)cyclobutyl)homoserine;
N-(6-methylquinazolin-4-yl)-O-(3-(2-(5,6,7,8-tetrahydro-1,8-naphthyridin-2-yl)ethyl)cyclobutyl)homoserine;
N-(6-(tert-butyl)-2-phenylpyrimidin-4-yl)-O-(3-(2-(5,6,7,8-tetrahydro-1,8-naphthyridin-2-yl)ethyl)cyclobutyl)homoserine;
N-(2-ethylbutanoyl)-O-(4-(5,6,7,8-tetrahydro-1,8-naphthyridin-2-yl)butyl)homoserine;
N-benzoyl-O-(4-(5,6,7,8-tetrahydro-1,8-naphthyridin-2-yl)butyl)homoserine;
2-(2-ethylbutanamido)-5-(3-(5,6,7,8-tetrahydro-1,8-naphthyridin-2-yl)propoxy)pentanoic acid; 2-(2-chloro-3-fluorobenzamido)-5-(3-(5,6,7,8-tetrahydro-1,8-naphthyridin-2-yl)propoxy)pentanoic acid;
2-((tert-butoxycarbonyl)amino)-6-(2-(5,6,7,8-tetrahydro-1,8-naphthyridin-2-yl)ethoxy)hexanoic acid;
N-(3-(1-methyl-1H-pyrazol-4-yl)benzoyl)-O-(3-(2-(5,6,7,8-tetrahydro-1,8-naphthyridin-2-yl)ethyl)cyclobutyl)homoserine;
N-((pyrrolidin-3-yloxy)carbonyl)-O-(3-(2-(5,6,7,8-tetrahydro-1,8-naphthyridin-2-yl)ethyl)cyclobutyl)homoserine;
N-(4-cyanotetrahydro-2H-pyran-4-carbonyl)-O-(4-(5,6,7,8-tetrahydro-1,8-naphthyridin-2-yl)butyl)homoserine;
O-(4-(5,6,7,8-tetrahydro-1,8-naphthyridin-2-yl)butyl)-N-(4-(trifluoromethyl)tetrahydro-2H-pyran-4-carbonyl)homoserine;
N-(8-oxabicyclo[3.2.1]octane-3-carbonyl)-O-(4-(5,6,7,8-tetrahydro-1,8-naphthyridin-2-yl)butyl)homoserine;
N-(2-(dimethylamino)-3,5-dimethylisonicotinoyl)-O-(4-(5,6,7,8-tetrahydro-1,8-naphthyridin-2-yl)butyl)homoserine;
N-(5-chloro-2-(dimethylamino)-3-methylisonicotinoyl)-O-(4-(5,6,7,8-tetrahydro-1,8-naphthyridin-2-yl)butyl)homoserine;
N-(3-cyclopropyl-5-fluoroisonicotinoyl)-O-(4-(5,6,7,8-tetrahydro-1,8-naphthyridin-2-yl)butyl)homoserine;
N-(5-chloro-2-methoxy-3-methylisonicotinoyl)-O-(4-(5,6,7,8-tetrahydro-1,8-naphthyridin-2-yl)butyl)homoserine;
N-(3-ethyl-5-fluoroisonicotinoyl)-O-(4-(5,6,7,8-tetrahydro-1,8-naphthyridin-2-yl)butyl)homoserine;
N-(5-fluoro-3-methylpyridazine-4-carbonyl)-O-(4-(5,6,7,8-tetrahydro-1,8-naphthyridin-2-yl)butyl)homoserine;
N-(2,4-dimethyl-6-oxo-1,6-dihydropyridine-3-carbonyl)-O-(4-(5,6,7,8-tetrahydro-1,8-naphthyridin-2-yl)butyl)homoserine;
N-(2,4-dimethyl-6-oxo-1-(2,2,2-trifluoroethyl)-1,6-dihydropyridine-3-carbonyl)-O-(4-(5,6,7,8-tetrahydro-1,8-naphthyridin-2-yl)butyl)homoserine;
N-(3,5-dimethylpyridazine-4-carbonyl)-O-(4-(5,6,7,8-tetrahydro-1,8-naphthyridin-2-yl)butyl)homoserine;
O-(4-(5,6,7,8-tetrahydro-1,8-naphthyridin-2-yl)butyl)-N-(1,2,4-trimethyl-6-oxo-1,6-dihydropyridine-3-carbonyl)homoserine;
N-(5-chloro-3-methylpyridazine-4-carbonyl)-O-(4-(5,6,7,8-tetrahydro-1,8-naphthyridin-2-yl)butyl)homoserine;

N-(6-methoxy-2,4-dimethylnicotinoyl)-O-(4-(5,6,7,8-tetrahydro-1,8-naphthyridin-2-yl)butyl)homoserine;

N-(4-((1,3-dimethyl-1H-pyrazol-5-yl)methyl)-2,6-dimethylbenzoyl)-O-(4-(5,6,7,8-tetrahydro-1,8-naphthyridin-2-yl)butyl)homoserine; and N-(4-((1,3-dimethyl-1H-pyrazol-5-yl)methyl)-2-fluoro-6-methylbenzoyl)-O-(4-(5,6,7,8-tetrahydro-1,8-naphthyridin-2-yl)butyl)homoserine, or a pharmaceutically acceptable salt, stereoisomer, or tautomer thereof.

145. A pharmaceutical composition comprising a pharmaceutically acceptable carrier or excipient and a compound of claim 1, or a pharmaceutically acceptable salt, stereoisomer, or tautomer thereof.

146. A kit comprising a compound of claim 1, or a pharmaceutically acceptable salt, stereoisomer, or tautomer thereof.

147. The kit of claim 146, wherein the kit further comprises instructions for the treatment of a fibrotic disease.

148. A method for modulating the activity of at least one integrin comprising an αv subunit in an individual in need thereof, wherein the method comprises administering to the individual a therapeutically effective amount of a compound of claim 1, or a pharmaceutically acceptable salt, stereoisomer, or tautomer thereof.

149. The method of claim 148, wherein modulating the activity of at least one integrin comprising an αv subunit in the individual in need thereof is inhibiting the activity of at least one integrin comprising an αv subunit in the individual in need thereof.

150. The method of claim 148, wherein the at least one integrin is at least one αvβ1 integrin or at least one αvβ6 integrin.

151. The method of claim 148, wherein:
(i) modulating the activity of at least one integrin is inhibiting the activity of αvβ1 integrin; or
(ii) modulating the activity of at least one integrin is inhibiting the activity of αvβ6 integrin; or
(iii) modulating the activity of at least one integrin is inhibiting the activity of both αvβ1 integrin and αvβ6 integrin; and
(iv) the individual has or is at risk of having a fibrotic disease or fibrotic condition selected from the group consisting of alcoholic liver disease induced fibrosis, Alport syndrome, biliary atresia, chronic kidney disease, Crohn's disease, diabetic kidney disease, diabetic nephropathy, focal segmental glomerulosclerosis, idiopathic pulmonary fibrosis (IPF), interstitial lung disease, nonalcoholic fatty liver disease (NAFLD), nonalcoholic steatohepatitis (NASH), primary biliary cholangitis, primary sclerosing cholangitis (PSC), radiation-induced pulmonary fibrosis, scleroderma, and systemic sclerosis associated interstitial lung disease.

152. The method of claim 151, wherein the individual has or is at risk of having nonalcoholic steatohepatitis (NASH).

153. The method of claim 151, wherein the individual has or is at risk of having idiopathic pulmonary fibrosis (IPF).

154. The method of claim 151, wherein the individual has or is at risk of having primary sclerosing cholangitis (PSC).

155. A method for inhibiting αvβ6 integrin activity in an individual in need thereof, wherein the method comprises administering to the individual a therapeutically effective amount of a compound of claim 1, or a pharmaceutically acceptable salt, stereoisomer, or tautomer thereof.

156. A method for modulating transforming growth factor beta (TGFβ) activation in a cell, wherein the method comprises contacting the cell with an effective amount of a compound of claim 1, or a pharmaceutically acceptable salt, stereoisomer, or tautomer thereof.

157. The method of claim 156, wherein modulating the activation of transforming growth factor beta (TGFβ) in the cell is inhibiting the activation of transforming growth factor beta (TGFβ) in the cell.

158. The method of claim 156, wherein the activation of transforming growth factor beta (TGFβ) in the cell is mediated in the cell by at least one αvβ1 integrin or at least one αvβ6 integrin.

159. A method for treating an individual having one or more tissues in need of therapy, wherein the method comprises administering to the individual in need thereof a therapeutically effective amount of a compound of claim 1, or a pharmaceutically acceptable salt, stereoisomer, or tautomer thereof;
wherein when compared to a healthy state of the one or more tissues, the one or more tissues have at least one elevated level of:
(a) transforming growth factor beta (TGFβ) activation; or
(b) transforming growth factor beta (TGFβ) expression; or
(c) both transforming growth factor beta (TGFβ) activation and transforming growth factor beta (TGFβ) expression; or
(d) αvβ1 integrin activity; or
(e) αvβ1 integrin expression; or
(f) both αvβ1 integrin activity and αvβ1 integrin expression; or
(g) αvβ6 integrin activity; or
(h) αvβ6 integrin expression; or
(i) both αvβ6 integrin activity and αvβ6 integrin expression.

160. The method of claim 159, wherein:
(a) the method selectively inhibits αvβ1 integrin activity compared to αvβ6 integrin activity in the individual; or
(b) the method selectively inhibits αvβ1 integrin expression compared to αvβ6 integrin expression in the individual.

161. The method of claim 159, wherein:
(a) the method selectively inhibits αvβ6 integrin activity compared to αvβ1 integrin activity in the individual; or
(b) the method selectively inhibits αvβ6 integrin expression compared to αvβ1 integrin expression in the individual.

162. The method of claim 159, wherein:
(a) the method selectively inhibits both αvβ1 integrin activity and αvβ6 integrin activity in the individual; or
(b) the method selectively inhibits both αvβ1 integrin expression and αvβ6 integrin expression in the individual.

163. The method of claim 159, wherein:
(a) the method selectively inhibits both αvβ1 integrin activity and αvβ6 integrin activity compared to the activity of at least one other αv-containing integrin in the individual; or
(b) the method selectively inhibits both αvβ1 integrin expression and αvβ6 integrin expression compared to the expression of at least one other αv-containing integrin in the individual.

164. The method of claim 159, wherein the αvβ1 integrin activity or αvβ1 integrin expression is inhibited in one or more fibroblasts in the individual.

165. The method of claim 159, wherein the αvβ6 integrin activity or αvβ1 integrin expression is inhibited in one or more epithelial cells in the individual.

166. The method of claim 159, wherein the one or more tissues in the individual are selected from the group consisting of bile duct tissue, cardiac tissue, gallbladder tissue, gastrointestinal tissue, kidney tissue, liver tissue, lung tissue, and skin tissue, or a combination thereof.

167. A method for inhibiting transforming growth factor beta (TGFβ) activation in a cell, wherein the method comprises contacting the cell with an effective amount of a compound of claim 1, or a pharmaceutically acceptable salt, stereoisomer, or tautomer thereof.

168. A method for modulating transforming growth factor beta (TGFβ) activation in a cell, wherein the method comprises contacting the cell with an effective amount of the pharmaceutical composition of claim 145.

169. The method of claim 168, wherein modulating the activation of transforming growth factor beta (TGFβ) in the cell is inhibiting the activation of transforming growth factor beta (TGFβ) in the cell.

170. The method of claim 168, wherein the activation of transforming growth factor beta (TGFβ) in the cell is mediated in the cell by at least one αvβ1 integrin or at least one αvβ6 integrin.

171. A method for treating a fibrotic disease or fibrotic condition in an individual in need thereof, wherein the method comprises administering to the individual a therapeutically effective amount of a compound of claim 1, or a pharmaceutically acceptable salt, stereoisomer, or tautomer thereof.

172. The method of claim 142, wherein the fibrotic disease or fibrotic condition is selected from the group consisting of biliary fibrosis, cardiac fibrosis, gastrointestinal fibrosis, kidney fibrosis, liver fibrosis, primary sclerosing cholangitis (PSC), pulmonary fibrosis, and skin fibrosis.

* * * * *